(12) United States Patent
Rousso et al.

(10) Patent No.: US 8,606,349 B2
(45) Date of Patent: Dec. 10, 2013

(54) RADIOIMAGING USING LOW DOSE ISOTOPE

(75) Inventors: Benny Rousso, Rishon-LeZion (IL);
Shlomo Ben-Haim, London (GB);
Michael Nagler, Tel-Aviv (IL); Omer Ziv, Rechovot (IL); Ran Ravhon, Kiryat-Motzkin (IL); Dalia Dickman, Moshav Manof Doar-Na Misgav (IL);
Yoel Zilberstein, Haifa (IL); Eli Dichterman, Haifa (IL); Simona Ben-Haim, Caesarea (IL); Shankar Vallabhajosula, Larchmont, NY (US);
Daniel Berman, Valley Village, CA (US); Zohar Bronshtine, Talmey ElAzar (IL); Ziv Popper, Zikhron-Yaakov (IL);
Nir Weissberg, Haifa (IL); Nathaniel Roth, Herzlia Pituach (IL); Haim Melman, Kfar-Saba (IL)

(73) Assignee: Biosensors International Group, Ltd., HaMilton (BM)

( * ) Notice: Subject to any disclaimer, the term of this patent is extended or adjusted under 35 U.S.C. 154(b) by 1236 days.

(21) Appl. No.: 11/980,653

(22) Filed: Oct. 31, 2007

(65) Prior Publication Data

US 2008/0128626 A1 Jun. 5, 2008

Related U.S. Application Data

(66) Continuation of application No. 11/798,017, filed on May 9, 2007, which is a continuation-in-part of

(60) Provisional application No. 60/648,690, filed on Feb. 2, 2005, provisional application No. 60/648,385, filed on Feb. 1, 2005, provisional application No. 60/640,215, filed on Jan. 3, 2005, provisional

(30) Foreign Application Priority Data

Oct. 10, 2005 (IL) .......................... 171346

(51) Int. Cl.
*A61B 6/00* (2006.01)

(52) U.S. Cl.
USPC .......................... 600/436; 424/9.1

(58) Field of Classification Search
USPC ............... 250/362–365; 424/1.11–1.89, 9.1;
382/128, 131–133; 600/407, 425–429,
600/431, 436
See application file for complete search history.

(56) References Cited

U.S. PATENT DOCUMENTS

| 630,611 A | 8/1899 | Knapp et al. |
| 2,776,377 A | 1/1957 | Anger |

(Continued)

FOREIGN PATENT DOCUMENTS

| DE | 1516429 | 12/1969 |
| DE | 19814199 | 10/1999 |

(Continued)

OTHER PUBLICATIONS

Official Action Dated Dec. 8, 2010 From the US Patent and Trademark Office Re.: U.S. Appl. No. 11/980,690.

(Continued)

*Primary Examiner* — Parikha Mehta

(57) ABSTRACT

A method of imaging, comprising:
(a) providing an isotope at a low dosage in a body of a patient;
(b) receiving radiation generated by said isotope from said body using a radiation camera; and
(c) reconstructing a 3D distribution of said isotope from said received radiation,
wherein the dosage is less than $\frac{1}{3}$ of a standard dose set forth in Table 5.

66 Claims, 220 Drawing Sheets

Related U.S. Application Data

(66) application No. PCT/IL2005/001173, filed on Nov. 9, 2005, which is a continuation-in-part of application No. PCT/IL2005/000572, filed on Jun. 1, 2005, and a continuation-in-part of application No. PCT/IL2005/000575, filed on Jun. 1, 2005, and a continuation-in-part of application No. PCT/IL2005/000048, filed on Jan. 13, 2005, Substitute for application No. 60/632,515, filed on Dec. 3, 2004.

(60) application No. 60/636,088, filed on Dec. 16, 2004, provisional application No. 60/635,630, filed on Dec. 14, 2004, provisional application No. 60/632,236, filed on Dec. 2, 2004, provisional application No. 60/630,561, filed on Nov. 26, 2004, provisional application No. 60/625,971, filed on Nov. 9, 2004, provisional application No. 60/720,541, filed on Sep. 27, 2005, provisional application No. 60/720,652, filed on Sep. 27, 2005, provisional application No. 60/720,034, filed on Sep. 26, 2005, provisional application No. 60/702,979, filed on Jul. 28, 2005, provisional application No. 60/700,753, filed on Jul. 20, 2005, provisional application No. 60/700,752, filed on Jul. 20, 2005, provisional application No. 60/700,318, filed on Jul. 19, 2005, provisional application No. 60/700,317, filed on Jul. 19, 2005, provisional application No. 60/700,299, filed on Jul. 19, 2005, provisional application No. 60/691,780, filed on Jun. 20, 2005, provisional application No. 60/675,892, filed on Apr. 29, 2005, provisional application No. 60/628,105, filed on Nov. 17, 2004, provisional application No. 60/800,845, filed on May 17, 2006.

(56) References Cited

U.S. PATENT DOCUMENTS

| | | |
|---|---|---|
| 3,340,866 A | 9/1967 | Nöller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluzhnikov et al. |
| 3,719,183 A | 3/1973 | Schwartz |
| 3,739,279 A | 6/1973 | Hollis |
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledley |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A | 2/1995 | Nunn et al. |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hogrefe et al. |
| 5,431,161 A | 7/1995 | Ryals et al. |

(56) References Cited

U.S. PATENT DOCUMENTS

| | | |
|---|---|---|
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misic et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | DeVito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |
| 5,800,355 A | 9/1998 | Hasegawa |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,742 A | 9/1998 | Pearlman |
| 5,811,814 A | 9/1998 | Leone et al. |
| 5,813,985 A | 9/1998 | Carroll |
| 5,818,050 A | 10/1998 | Dilmanian et al. |
| 5,821,541 A | 10/1998 | Tümer |
| 5,825,031 A | 10/1998 | Wong et al. |
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A | 6/1999 | Judd et al. |
| 5,911,252 A | 6/1999 | Cassel |
| 5,916,167 A | 6/1999 | Kramer et al. |
| 5,916,197 A | 6/1999 | Reilly et al. |
| 5,920,054 A | 7/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber, III et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |

(56) References Cited

U.S. PATENT DOCUMENTS

| | | | |
|---|---|---|---|
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,172,362 B1 | 1/2001 | Lingren et al. |
| 6,173,201 B1 | 1/2001 | Front |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 | 3/2001 | Torchilin et al. |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Tumer |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito |
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 * | 4/2002 | Iwanczyk et al. ............ 600/425 |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tuemer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Cowan et al. |
| 6,657,200 B2 | 12/2003 | Nygard et al. |
| 6,662,036 B2 | 12/2003 | Cosman |
| 6,664,542 B2 | 12/2003 | Ye et al. |

(56) References Cited

U.S. PATENT DOCUMENTS

| | | |
|---|---|---|
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,813,868 B2 | 11/2004 | Baldwin et al. |
| 6,821,013 B2 | 11/2004 | Reilly et al. |
| 6,822,237 B2 | 11/2004 | Jimbo et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,906,330 B2 | 6/2005 | Blevis et al. |
| D507,832 S | 7/2005 | Yanniello et al. |
| 6,915,170 B2 | 7/2005 | Engleson et al. |
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Turner |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |
| 6,974,443 B2 | 12/2005 | Reilly et al. |
| 6,976,349 B2 | 12/2005 | Baldwin et al. |
| 6,984,222 B1 | 1/2006 | Hitchins et al. |
| 6,985,870 B2 | 1/2006 | Martucci et al. |
| 6,988,981 B2 | 1/2006 | Hamazaki |
| 6,994,249 B2 | 2/2006 | Peterka et al. |
| 7,009,183 B2 | 3/2006 | Wainer et al. |
| 7,011,814 B2 | 3/2006 | Suddarth et al. |
| 7,012,430 B2 | 3/2006 | Misic |
| 7,017,622 B2 | 3/2006 | Osborne et al. |
| 7,018,363 B2 | 3/2006 | Cowan et al. |
| 7,019,783 B2 | 3/2006 | Kindem et al. |
| 7,025,757 B2 | 4/2006 | Reilly et al. |
| 7,026,623 B2 | 4/2006 | Oaknin et al. |
| 7,043,063 B1 | 5/2006 | Noble et al. |
| 7,102,138 B2 | 9/2006 | Belvis et al. |
| 7,103,204 B1 | 9/2006 | Celler et al. |
| 7,127,026 B2 | 10/2006 | Amemiya et al. |
| 7,142,634 B2 | 11/2006 | Engler et al. |
| 7,145,986 B2 | 12/2006 | Wear et al. |
| 7,147,372 B2 | 12/2006 | Nelson et al. |
| 7,164,130 B2 | 1/2007 | Welsh et al. |
| 7,176,466 B2 | 2/2007 | Rousso et al. |
| 7,187,790 B2 | 3/2007 | Sabol et al. |
| 7,217,953 B2 | 5/2007 | Carlson |
| 7,256,386 B2 | 8/2007 | Carlson et al. |
| 7,327,822 B2 | 2/2008 | Sauer et al. |
| 7,359,535 B2 | 4/2008 | Salla et al. |
| 7,373,197 B2 | 5/2008 | Daighighian et al. |
| 7,394,923 B2 | 7/2008 | Zou et al. |
| 7,444,010 B2 | 10/2008 | De Man |
| 7,468,513 B2 | 12/2008 | Charron et al. |
| 7,470,896 B2 | 12/2008 | Pawlak et al. |
| 7,490,085 B2 | 2/2009 | Walker et al. |
| 7,495,225 B2 | 2/2009 | Hefetz et al. |
| 7,502,499 B2 | 3/2009 | Grady |
| 7,570,732 B2 | 8/2009 | Stanton et al. |
| 7,592,597 B2 | 9/2009 | Hefetz et al. |
| 7,620,444 B2 | 11/2009 | Le et al. |
| 7,627,084 B2 | 12/2009 | Jabri et al. |
| 7,652,259 B2 | 1/2010 | Kimchy et al. |
| 7,671,331 B2 | 3/2010 | Hefetz |
| 7,672,491 B2 | 3/2010 | Krishnan et al. |
| 7,680,240 B2 | 3/2010 | Manjeshwar et al. |
| 7,705,316 B2 | 4/2010 | Rousso et al. |
| 7,734,331 B2 | 6/2010 | Dhawale et al. |
| 7,826,889 B2 | 11/2010 | David et al. |
| 7,831,024 B2 | 11/2010 | Metzler et al. |
| 7,835,927 B2 | 11/2010 | Schlotterbeck et al. |
| 7,872,235 B2 | 1/2011 | Rousso et al. |
| 7,894,650 B2 | 2/2011 | Weng et al. |
| 7,968,851 B2 | 6/2011 | Rousso et al. |
| 8,013,308 B2 | 9/2011 | Guerin et al. |
| 8,055,329 B2 | 11/2011 | Kimchy et al. |
| 8,111,886 B2 | 2/2012 | Rousso et al. |
| 8,158,951 B2 | 4/2012 | Bal et al. |
| 8,204,500 B2 | 6/2012 | Weintraub et al. |
| 8,338,788 B2 | 12/2012 | Zilberstein et al. |
| 2001/0016029 A1 | 8/2001 | Tumer |
| 2001/0020131 A1 | 9/2001 | Kawagishi et al. |
| 2001/0035902 A1 | 11/2001 | Iddan et al. |
| 2001/0049608 A1 | 12/2001 | Hochman |
| 2002/0068864 A1 | 6/2002 | Bishop et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0099310 A1 | 7/2002 | Kimchy et al. |
| 2002/0099334 A1 | 7/2002 | Hanson et al. |
| 2002/0103429 A1 | 8/2002 | DeCharms |
| 2002/0103431 A1 | 8/2002 | Toker et al. |
| 2002/0145114 A1 | 10/2002 | Inoue et al. |
| 2002/0148970 A1 | 10/2002 | Wong et al. |
| 2002/0165491 A1 | 11/2002 | Reilly |
| 2002/0168094 A1 | 11/2002 | Kaushikkar et al. |
| 2002/0168317 A1 | 11/2002 | Daighighian et al. |
| 2002/0172405 A1 | 11/2002 | Schultz |
| 2002/0179843 A1 | 12/2002 | Tanaka et al. |
| 2002/0183645 A1 | 12/2002 | Nachaliel |

(56) References Cited

U.S. PATENT DOCUMENTS

| | | |
|---|---|---|
| 2002/0188197 A1 | 12/2002 | Bishop et al. |
| 2002/0198738 A1 | 12/2002 | Osborne |
| 2003/0001098 A1 | 1/2003 | Stoddart et al. |
| 2003/0001837 A1 | 1/2003 | Baumberg |
| 2003/0006376 A1 | 1/2003 | Tumer |
| 2003/0013950 A1 | 1/2003 | Rollo et al. |
| 2003/0013966 A1 | 1/2003 | Barnes et al. |
| 2003/0038240 A1 | 2/2003 | Weinberg |
| 2003/0055685 A1 | 3/2003 | Cobb et al. |
| 2003/0063787 A1 | 4/2003 | Natanzon et al. |
| 2003/0071219 A1 | 4/2003 | Motomura et al. |
| 2003/0081716 A1 | 5/2003 | Tumer |
| 2003/0135388 A1 | 7/2003 | Martucci et al. |
| 2003/0136912 A1 | 7/2003 | Juni |
| 2003/0139661 A1 | 7/2003 | Kimchy et al. |
| 2003/0144322 A1 | 7/2003 | Kozikowski et al. |
| 2003/0147887 A1 | 8/2003 | Wang et al. |
| 2003/0158481 A1 | 8/2003 | Stotzka et al. |
| 2003/0183226 A1 | 10/2003 | Brand et al. |
| 2003/0189174 A1 | 10/2003 | Tanaka et al. |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215122 A1 | 11/2003 | Tanaka |
| 2003/0215124 A1 | 11/2003 | Li |
| 2003/0216631 A1 | 11/2003 | Bloch et al. |
| 2003/0219149 A1 | 11/2003 | Vailaya et al. |
| 2004/0003001 A1 | 1/2004 | Shimura |
| 2004/0010397 A1 | 1/2004 | Barbour et al. |
| 2004/0015075 A1 | 1/2004 | Kimchy et al. |
| 2004/0021065 A1 | 2/2004 | Weber |
| 2004/0044282 A1 | 3/2004 | Mixon et al. |
| 2004/0051368 A1 | 3/2004 | Caputo et al. |
| 2004/0054248 A1 | 3/2004 | Kimchy et al. |
| 2004/0054278 A1 | 3/2004 | Kimchy et al. |
| 2004/0065838 A1 | 4/2004 | Tumer |
| 2004/0075058 A1 | 4/2004 | Blevis et al. |
| 2004/0081623 A1 | 4/2004 | Eriksen et al. |
| 2004/0082918 A1 | 4/2004 | Evans et al. |
| 2004/0084340 A1 | 5/2004 | Morelle et al. |
| 2004/0086437 A1 | 5/2004 | Jackson |
| 2004/0101176 A1 | 5/2004 | Mendonca et al. |
| 2004/0101177 A1 | 5/2004 | Zahlmann et al. |
| 2004/0116807 A1 | 6/2004 | Amrami et al. |
| 2004/0120557 A1 | 6/2004 | Sabol et al. |
| 2004/0122311 A1 | 6/2004 | Cosman |
| 2004/0125918 A1 | 7/2004 | Shanmugaval et al. |
| 2004/0138557 A1 | 7/2004 | Le et al. |
| 2004/0143449 A1 | 7/2004 | Behrenbruch et al. |
| 2004/0144925 A1 | 7/2004 | Stoddart et al. |
| 2004/0153128 A1 | 8/2004 | Suresh et al. |
| 2004/0162492 A1 | 8/2004 | Kobayashi |
| 2004/0171924 A1 | 9/2004 | Mire et al. |
| 2004/0183022 A1 | 9/2004 | Weinberg |
| 2004/0184644 A1 | 9/2004 | Leichter et al. |
| 2004/0193453 A1 | 9/2004 | Butterfield et al. |
| 2004/0195512 A1 | 10/2004 | Crosetto |
| 2004/0204646 A1 | 10/2004 | Nagler et al. |
| 2004/0205343 A1 | 10/2004 | Forth et al. |
| 2004/0210126 A1 | 10/2004 | Hajaj et al. |
| 2004/0238743 A1 | 12/2004 | Gravrand et al. |
| 2004/0251419 A1 | 12/2004 | Nelson et al. |
| 2004/0253177 A1 | 12/2004 | Elmaleh et al. |
| 2004/0263865 A1 | 12/2004 | Pawlak et al. |
| 2005/0001170 A1 | 1/2005 | Juni |
| 2005/0006589 A1 | 1/2005 | Joung et al. |
| 2005/0020898 A1 | 1/2005 | Vosniak et al. |
| 2005/0020915 A1 | 1/2005 | Belardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1 | 4/2005 | Cagnolini et al. |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0121505 A1 | 6/2005 | Metz et al. |
| 2005/0131270 A1 | 6/2005 | Weil et al. |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0173643 A1 | 8/2005 | Tumer |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0211909 A1 | 9/2005 | Smith |
| 2005/0215889 A1 | 9/2005 | Patterson, II |
| 2005/0234424 A1 | 10/2005 | Besing et al. |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1 | 1/2006 | Charron et al. |
| 2006/0033028 A1 | 2/2006 | Juni |
| 2006/0036157 A1 | 2/2006 | Tumer |
| 2006/0072799 A1 | 4/2006 | McLain |
| 2006/0074290 A1 | 4/2006 | Chen et al. |
| 2006/0104519 A1 | 5/2006 | Stoeckel et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0188136 A1 | 8/2006 | Ritt et al. |
| 2006/0214097 A1 | 9/2006 | Wang et al. |
| 2006/0237652 A1 | 10/2006 | Kimchy et al. |
| 2006/0257012 A1 | 11/2006 | Kaufman et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0001090 A1 | 1/2008 | Ben-Haim et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0137938 A1 | 6/2008 | Zahniser |
| 2008/0230702 A1 | 9/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260580 A1 | 10/2008 | Helle et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2009/0304582 A1 | 12/2009 | Rousso et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0140483 A1 | 6/2010 | Rousso et al. |
| 2010/0202664 A1 | 8/2010 | Busch et al. |

(56) References Cited

U.S. PATENT DOCUMENTS

| | | |
|---|---|---|
| 2010/0245354 A1 | 9/2010 | Rousso et al. |
| 2012/0106820 A1 | 5/2012 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |
| 2013/0114792 A1 | 5/2013 | Zilberstein et al. |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 6-109848 | 4/1994 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/25268 | 5/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Official Action Dated Nov. 10, 2010 From the US Patent and Trademark Office Re.: U.S. Appl. No. 10/616,307.

Official Action Dated Nov. 10, 2010 From the US Patent and Trademark Office Re.: U.S. Appl. No. 10/836,223.

Official Action Dated Nov. 23, 2010 From the US Patent and Trademark Office Re.: U.S. Appl. No. 11/656,548.

Response Dated Nov. 18, 2010 to Official Action of Jul. 19, 2010 From the US Patent and Trademark Office Re.: U.S. Appl. No. 11/607,075.

Official Action Dated Dec. 15, 2011 From the US Patent and Trademark Office Re.: U.S. Appl. No. 10/343,792.

Official Action Dated Dec. 20, 2011 From the US Patent and Trademark Office Re. U.S. Appl. No. 12/309,479.

Response Dated Dec. 29, 2011 to Office Action of Jul. 17, 2007 From the Israeli Patent Office Re.: Application No. 154323.

Berman et al. "Dual-Isotope Myocardial Perfusion SPECT With Rest Thallium-201 and Stress Tc-99m Sestamibi", Cardiology Clinics, 12(2): 261-270, May 1994.

DeGrado et al. "Topics in Integrated Systems Physiology. Tracer Kinetic Modeling in Nuclear Cardiology", Journal of Nuclear Cardiology, 7: 686-700, 2000.

Links "Advances in SPECT and PET Imaging", Annals in Nuclear Medical Science, 13(2): 107-120, Jun. 2000.

Notice of Allowance Dated Dec. 17, 2010 From the US Patent and Trademark Office Re. U.S. Appl. No. 11/980,617.

Official Action Dated Dec. 8, 2010 From the US Patent and Trademark Office Re.: U.S. Appl. No. 09/641,973.

Official Action Dated Dec. 28, 2010 From the US Patent and Trademark Office Re.: U.S. Appl. No. 11/607,075.

Response Dated Dec. 15, 2010 to Official Action of Jul. 19, 2010 From the US Patent and Trademark Office Re.: U.S. Appl. No. 11/656,548.

Official Action Dated Oct. 7, 2011 From the US Patent and Trademark Office Re. U.S. Appl. No. 11/750,057.

Official Action Dated Oct. 7, 2011 From the US Patent and Trademark Office Re. U.S. Appl. No. 11/932,872.

Communication Pursuant to Article 94(3) EPC Dated Oct. 21, 2009 From the European Patent Office Re.: Application No. 02716285.8.

Notice of Allowance Dated Sep. 17, 2009 From the US Patent and Trademark Office Re.: U.S. Appl. No. 10/533,568.

Official Action Dated Sep. 1, 2009 From the US Patent and Trademark Office Re.: U.S. Appl. No. 11/794,799.

Official Action Dated Sep. 2, 2009 From the US Patent and Trademark Office Re.: U.S. Appl. No. 10/343,792.

Official Action Dated Aug. 11, 2009 From the US Patent and Trademark Office Re.: U.S. Appl. No. 09/641,973.

Official Action Dated Sep. 15, 2009 From the US Patent and Trademark Office Re.: U.S. Appl. No. 10/616,307.

Official Action Dated Sep. 15, 2009 From the US Patent and Trademark Office Re.: U.S. Appl. No. 10/836,223.

Official Action Dated Sep. 16, 2009 From the US Patent and Trademark Office Re.: U.S. Appl. No. 09/727,464.

Official Action Dated Sep. 21, 2009 From the US Patent and Trademark Office Re.: U.S. Appl. No. 11/798,017.

Official Action Dated Aug. 28, 2009 From the US Patent and Trademark Office Re.: U.S. Appl. No. 10/240,239.

Official Action Dated Oct. 30, 2009 From the US Patent and Trademark Office Re.: U.S. Appl. No. 11/980,690.

Response Dated Dec. 10, 2009 to Official Action of Aug. 11, 2009 From the US Patent and Trademark Office Re.: U.S. Appl. No. 09/641,973.

Response Dated Oct. 12, 2009 to Notice of Allowance of Jul. 16, 2009 From the US Patent and Trademark Office Re.: U.S. Appl. No. 12/084,559.

Response Dated Oct. 14, 2009 to Official Action of May 14, 2009 From the US Patent and Trademark Office Re.: U.S. Appl. No. 11/656,548.

Response Dated Nov. 16, 2009 to Official Action of Jul. 15, 2009 From the US Patent and Trademark Office Re.: U.S. Appl. No. 10/616,301.

(56) References Cited

OTHER PUBLICATIONS

Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Official Action Dated Jan. 19, 2012 From the US Patent and Trademark Office Re. U.S. Appl. No. 11/667,793.
Official Action Dated Jan. 23, 2012 From the US Patent and Trademark Office Re. U.S. Appl. No. 12/087,150.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Toennies et al. "Scatter Segmentation in Dynamic SPECT Images Using Principal Component Analysis", Progress in Biomedical Optics and Imaging, 4(23): 507-516, 2003.
Communication Pursuant to Article 94(3) EPC Dated Sep. 23, 2011 From the European Patent Office Re.: Application No. 06832278.3.
Written Opinion Dated Nov. 1, 2007 from the International Searching Authority of the Patent Cooperation Treaty Re.: Application No. PCT/IL06/00840.
Written Opinion Dated Jul. 11, 2008 from the International Searching Authority of the Patent Cooperation Treaty Re.: Application No. PCT/IL06/01511.
Official Action Dated Jan. 31, 2011 From the US Patent and Trademark Office Re. U.S. Appl. No. 11/667,793.
Communication Relating to the Results of the Partial International Search Dated Apr. 18, 2007 From the International Searching Authority of the Patent Cooperation Treaty Re.: Application No. PCT/IL2006/001291.
Official Action Dated Jun. 25, 2008 From the US Patent and Trademark Office Re.: U.S. Appl. No. 10/616,301.
Supplementary Partial European Search Report Dated Nov. 11, 2008 From the European Patent Office Re.: Application No. 01951883.6.
Written Opinion Dated Jul. 25, 2008 From the International Searching Authority of the Patent Cooperation Treaty Re.: Application No. PCT/IL05/001173.
Gugnin et al "Radiocapsule for Recording the Ionizing Radiation in the Gastrointestinal Tract", UDC 615.417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Notice of Allowance Dated Feb. 2, 2012 From the US Patent and Trademark Office Re. U.S. Appl. No. 11/628,074.
Communication Pursuant to Article 94(3) EPC Dated Mar. 2, 2011 From the European Patent Office Re.: Application No. 06756259.5.
Notice of Allowance Dated Nov. 15, 2010 From the US Patent and Trademark Office Re. U.S. Appl. No. 10/616,301.
Notice of Non-Compliant Amendment Dated Feb. 14, 2011 From the US Patent and Trademark Office Re.: U.S. Appl. No. 10/616,307.
Response Dated Feb. 10, 2011 to Notice of Allowance of Nov. 15, 2010 From the US Patent and Trademark Office Re. U.S. Appl. No. 10/616,301.
Mettler et al. "Legal Requirements and Radiation Safety", Essentials of Nuclear Medicine Imaging, 2nd Ed., Chap.13: 323-331, 1985.
Notice of Panel Decision From Pre-Appeal Brief Review Dated Feb. 29, 2012 From the US Patent and Trademark Office Re.: U.S. Appl. No. 10/836,223.
Official Action Dated Mar. 1, 2012 From the US Patent and Trademark Office Re.: U.S. Appl. No. 10/616,307.
Official Action Dated Dec. 22, 2011 From the US Patent and Trademark Office Re. U.S. Appl. No. 12/514,785.
Official Action Dated Feb. 28, 2012 From the US Patent and Trademark Office Re.: U.S. Appl. No. 09/641,973.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Relating to the Results of the Partial International Search Dated May 21, 2008 From the international Searching Authority of the Patent Cooperation Treaty Re.: Application No. PCT/IL2007/001588.
International Search Report Dated Oct. 10, 2006 From the International Searching Authority of the Patent Cooperation Treaty Re.: Application No. PCT/IL06/00059.
International Search Report Dated Jul. 11, 2008 From the International Searching Authority of the Patent Cooperation Treaty Re.: Application No. PCT/IL06/01511.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Office Action Dated Dec. 2, 2007 From the Israeli Patent Office Re.: Application No. 158442.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated May 3, 2007 From the US Patent and Trademark Office Re.: U.S. Appl. No. 10/240,239.

(56) References Cited

OTHER PUBLICATIONS

Official Action Dated Sep. 4, 2008 From the US Patent and Trademark Office Re.: U.S. Appl. No. 10/533,568.
Official Action Dated Oct. 7, 2008 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/765,316.
Official Action Dated Jan. 17, 2006 From the United States Patent and Trademark Office Re.: U.S. Appl. No. 11/034,007.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.
Official Action Dated Jun. 23, 2006 From the United States Patent and Trademark Office Re.: U.S. Appl. No. 09/727,464.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Response Dated Mar. 8, 2011 to Official Action of Dec. 8, 2010 From the US Patent and Trademark Office Re.: U.S. Appl. No. 11/980,690.
Supplementary European Search Report Dated Dec. 12, 2005 From the European Patent Office Re.: Application No. 03810570.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Written Opinion Dated Oct. 10, 2006 From the International Searching Authority of the Patent Cooperation Treaty Re.: Application No. PCT/IL06/00059.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Mar. 26, 2007 From the International Searching Authority of the Patent Cooperation Treaty Re.: Application No. PCT/IL05/00394.
Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Annual Meeting, Chicago, Illinois, 2000.
Lavall?e et al. "Building a Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Response Dated Mar. 24, 2011 to Official Action of Dec. 8, 2010 From the US Patent and Trademark Office Re.: U.S. Appl. No. 09/641,973.
Official Action Dated Mar. 6, 2012 From the US Patent and Trademark Office Re. U.S. Appl. No. 12/792,856.
Restriction Official Action Dated Mar. 9, 2012 From the US Patent and Trademark Office Re. U.S. Appl. No. 11/976,852.
Office Action Dated Jul. 17, 2007 From the Israeli Patent Office Re.: Application No. 154323 and Its Translation Into English.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. Application No. U.S Appl. No. 11/667,793.
Response Dated Apr. 5, 2011 to Official Action of Nov. 10, 2010 From the US Patent and Trademark Office Re.: Application No. U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Interview Summary Dated Mar. 25, 2011 From the US Patent and Trademark Office Re.: Application No. U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Restriction Official Action Dated Apr. 13, 2012 From the US Patent and Trademark Office Re. U.S. Appl. No. 11/989,223.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 94(3) EPC Dated Mar. 8, 2010 From the European Patent Office Re.: U.S. Appl. No. 06832278.3.
Communication Pursuant to Article 94(3) EPC Dated Jul. 22, 2009 From the European Patent Office Re.: Application No. 06809851.6.
Notice of Allowance Dated Jul. 16, 2009 From the US Patent and Trademark Office Re.: U.S. Appl. No. 12/084,559.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Jul. 7, 2009 From the US Patent and Trademark Office Re.: U.S. Appl. No. 10/533,568.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 11, 2010 From the US Patent and Trademark Office Re.: U.S. Appl. No. 11/607,075.
Official Action Dated Jul. 15, 2009 From the US Patent and Trademark Office Re.: U.S. Appl. No. 10/616,301.
Official Action Dated Mar. 19, 2010 From the US Patent and Trademark Office Re.: U.S. Appl. No. 10/240,239.

(56) References Cited

OTHER PUBLICATIONS

Official Action Dated Jul. 20, 2009 From the US Patent and Trademark Office Re.: U.S. Appl. No. 11/980,617.
Official Action Dated Feb. 23, 2010 From the US Patent and Trademark Office Re.: U.S. Appl. No. 09/641,973.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Official Action Dated Apr. 9, 2010 From the US Patent and Trademark Office Re.: U.S. Appl. No. 11/798,017.
Response Dated Mar. 3, 2011 to Notice of Non-Compliant Amendment of Feb. 14, 2011 From the US Patent and Trademark Office Re. : U.S. Appl. No. 10/616,307.
Official Action Dated Apr. 16, 2012 From the US Patent and Trademark Office Re.: U.S. Appl. No. 10/836,223.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Official Action Dated Apr. 20, 2011 From the US Patent and Trademark Office Re. : U.S. Appl. No. 11/798,017.
Official Action Dated Apr. 27, 2011 From the US Patent and Trademark Office Re.: U.S. Appl. No. 10/836,223.

Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Bromiley et al. "Attenuation Correction in PET Using Consistency Conditions and a Three-Dimensional Template", IEEE Transactions on Nuclear Science, 48(4): 1371-1377, 2001. p. 1376, Col.2, § 2.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Hassan et al. "A Radiotelemetry Pill for the Measurement of Ionising Radiation Using a Mercuric Iodide Detector", Physics in Medicine and Biology, 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry 89(3-4): 349-352, 2000.
Jessup "Tumor Markers—Prognostic and Therapeutic Implications for Colorectal Carcinoma", Surgical Oncology, 7: 139-151, 1998.
Kojima et al. "Quantitative Planar Imaging Method for Measurement of Renal Activity by Using a Conjugate-Emission Image and Transmission Data", Medical Physics, 27(3): 608-615, 2000. p. 608.
Lavallée et al. "Building a Hybrid Patient's Model for Augmented Reality in Surgery: A Registration Problem", Computing in Biological Medicine, 25(2): 149-64, 1995.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Mori et al. "Overexpression of Matrix Metalloproteinase-7mRNA in Human Colon Carcinomas", Cancer, 75: 1516-1519, 1995.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Piperno et al. "Breast Cancer Screening by Impedance Measurements", Frontiers Med. Biol. Engng., 2(2): 11-17, 1990.
Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedance Monitoring During CT-Guided Stereotactic Surgery: Relative Value in Cystic and Solid Lesions", British Journal of Neurosurgery, 6: 439-444, 1992.
Reutter et al. "Direct Least Squares Estimation of Spatiotemporal Distributions From Dynamic SPECT Projections Using a Spatial Segmentation and Temporal B- Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Zhang et al. "An Innovative High Efficiency and High Resolution Probe for Prostate Imaging", The Journal of Nuclear Medicine, 68: 18, 2000. Abstract.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.

(56) References Cited

OTHER PUBLICATIONS

Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Communication Pursuant to Article 94(3) EPC Dated May 12, 2010 From the European Patent Office Re. Application No. 06809851.6.
International Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Search Report Dated Jul. 1, 2008 From the International Searching Authority Re. Application No. PCT/IL2006/000834.
International Search Report. Dated Jul. 2, 2007 From the International Searching Authority Re. Application No. PCT/IL2006/001291.
International Search Report Dated Aug. 3, 2006 From the International Searching Authority Re. Application No. PCT/IL2005/001173. International Search Report Dated Oct. 15, 2008 From the International Searching Authority Re. Application No. PCT/2007/000918.
Official Action Dated Nov. 1, 2010 From the US Patent and Trademark Office Re. Application No. 12/728,383.
Official Action Dated Mar. 2, 2010 From the US Patent and Trademark Office Re. U.S. Appl. No. 11/980,617.
Official Action Dated Dec. 8, 2010 From the US Patent and Trademark Office Re. U.S. Appl. No. 11/980,690.
Official Action Dated Apr. 9, 2010 From the US Patent and Trademark Office Re. U.S. Appl. No. 11/798,017.
Official Action Dated Aug. 13, 2008 From the US Patent and Trademark Office Re. U.S. Appl. No. 11/769,826.
Official Action Dated Feb. 16, 2012 From the US Patent and Trademark Office Re. U.S. Appl. No. 11/747,378.
Official Action Dated May 18, 2012 From the US Patent and Trademark Office Re. U.S. Appl. No. 11/989,223.
Official Action Dated Apr. 20, 2011 From the US Patent and Trademark Office Re. U.S. Appl. No. 11/798,017.
Official Action Dated Sep. 21, 2009 From the US Patent and Trademark Office Re. U.S. Appl. No. 11/798,017.
Official Action Dated May 23, 2011 From the US Patent and Trademark Office Re. U.S. Appl. No. 11/980,690.
Official Action Dated Sep. 30, 2010 From the US Patent and Trademark Office Re. U.S. Appl. No. 11/798,017.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Referen Bracco Diagnostics "Techneplex®: Kit for the Preparation of Technetium Tc 99m Pentetate Injection. Diagnostic—for Intravenous Use", Bracco Diagnostics™, Product Sheet 5 P., 1995.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Mallinckrodt "Kit for the Preparation of Technetium Tc 99m Sestamibi Injection", Mallinckrodt Inc., Product Sheet, 2 P., Sep. 8, 2008.

Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.
Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.
Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Chengazi et al. "Imaging Prostate Cancer With Technetium-99m-7E11-C5.3 CYT-351)", Journal of Nuclear Medicine, 38: 675-682, 1997.
McJilton et al. "Protein Kinase Cε Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Communication Pursuant to Article 94(3) EPC Dated May 29, 2012 From the European Patent Office Re. Application No. 05803689.8.
Communication Under Rule 71(3) EPC Dated May 30, 2012 From the European Patent Office Re.: Application No. 02716285.8.
Interview Summary Dated May 31, 2011 From the US Patent and Trademark Office Re. U.S. Appl. No. 10/616,301.
Communication Pursuant to Article 94(3) EPC Dated Jun. 11, 2012 From the European Patent Office Re.: Application No. 06756259.5.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Dillman "Radiolabeled Anti-CD20 Monoclonal Antibodies for the Treatment of B-Cell Lymphoma", Journal of Clinical Oncology, 20(16): 3545-3557, Aug. 15, 2002.
Sands et al. "Methods for the Study of the Metabolism of Radiolabeled Monoclonal Antibodies by Liver and Tumor", The Journal of Nuclear Medicine, 28: 390-398, 1987.
Official Action Dated Jun. 21, 2012 From the US Patent and Trademark Office Re. U.S. Appl. No. 12/309,479.
Notice of Allowance Dated Jun. 23, 2011 From the US Patent and Trademark Office Re. : U.S. Appl. No. 10/616,301.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Advisory Action Before the Filing of an Appeal Brief Dated Jul. 12, 2012 From the US Patent and Trademark Office Re. U.S. Appl. No. 11/667,793.
Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.

(56) References Cited

OTHER PUBLICATIONS

Official Action Dated Apr. 23, 2012 From the US Patent and Trademark Office Re. U.S. Appl. No. 11/932,987.
Official Action Dated Jun. 28, 2011 From the US Patent and Trademark Office Re. U.S. Appl. No. 11/628,074.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Communication Pursuant to Article 94(3) EPC of Mar. 8, 2010 From the European Patent Office Re.: Application No. 06832278.3.
Response Dated Jul. 8, 2010 to Official Action of Apr. 9, 2010 From the US Patent and Trademark Office Re.: U.S. Appl. No. 11/798,017.
Response Dated Jun. 23, 2010 to Official Action of Feb. 23, 2010 From the US Patent and Trademark Office Re.: U.S. Appl. No. 09/641,973.
Examination Report Dated Jun. 22, 2011 From the Government of India, Patent Office, Intellectual Property Building Re. Application No. 2963/CHENP/2006.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Response Dated Jun. 28, 2011 to Official Action of Dec. 28, 2010 From the US Patent and Trademark Office Re.: U.S. Appl. No. 11/607,075.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Official Action Dated Jul. 12, 2011 From the US Patent and Trademark Office Re.: U.S. Appl. No. 09/641,973.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Notice of Allowance Dated Jul. 22, 2010 From the US Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Official Action Dated Jan. 7, 2009 From the US Patent and Trademark Office Re.: U.S. Appl. No. 10/616,307.
Summons to Attend Oral Proceedings Pursuant to Rule 115(1) EPC Dated Jan. 16, 2009 From the European Patent Office Re.: Application No. 03810570.6.
Supplementary Partial European Search Report Dated Nov. 20, 2007 From the European Patent Office Re.: Application No. 02716285.8.
Kinahan et al. "Attenuation Correction for a Combined 3D PET/CT Scanner", Medical Physics, 25(10): 2046-2053, Oct. 1998.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Response Dated Aug. 25, 2010 to Official Action of Jul. 27, 2010 From the US Patent and Trademark Office Re.: U.S. Appl. No. 10/616,307.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Official Action Dated Sep. 12, 2011 From the US Patent and Trademark Office Re. U.S. Appl. No. 12/087,150.
Response Dated Sep. 12, 2011 to Official Action of Jul. 11, 2011 From the US Patent and Trademark Office Re.: U.S. Appl. No. 11/980,683.
Response Dated Sep. 20, 2011 to Official Action of Apr. 20, 2011 From the US Patent and Trademark Office Re.: U.S. Appl. No. 11/798,017.
Communication Pursuant to Article 94(3) EPC Dated Sep. 22, 2011 From the European Patent Office Re. Application No. 06756258.7.
Notice of Allowance Dated Sep. 16, 2011 From the US Patent and Trademark Office Re.: U.S. Appl. No. 11/607,075.
Official Action Dated Sep. 13, 2011 From the US Patent and Trademark Office Re. U.S. Appl. No. 11/976,852.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With a Triple Camera SPECT System", IEEE Transactions on Nuclear Science, NP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.

(56) References Cited

OTHER PUBLICATIONS

International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 15, 2008 From the International Searching Authority Re.: Application No. PCT/IL07/00918.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Office Action Dated Jan. 2, 2006 From the Israeli Patent Office Re.: Application No. 154323.
Office Action Dated Sep. 4, 2007 From the Israeli Patent Office Re.: Application No. 157007.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Dec. 16, 2008 From the US Patent and Trademark Office Re.: U.S. Appl. No. 10/343,792.
Official Action Dated Dec. 23, 2008 From the US Patent and Trademark Office Re.: U.S. Appl. No. 09/727,464.
Official Action Dated Nov. 26, 2008 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Nov. 25, 2005 to Office Action of May 13, 2005 From the Patent Office of the People's Republic of China Re.: Application No. 1817689.5.
Response Dated Oct. 13, 2007 to Official Action of Jul. 12, 2007 From the US Patent and Trademark Office Re.: U.S. Appl. No. 10/616,301.
Response Dated Apr. 7, 2009 to Official Action of Oct. 7, 2008 From the US Patent and Trademark Office Re.: U.S. Appl. No. 10/616,301.
Response to the International Search Report and the Written Opinion of Oct. 10, 2006 From the International Searching Authority Re.: Appliction No. PCT/IL06/00059.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Translation of Office Action Dated May 13, 2005 From the Patent Office of the People's Republic of China Re.: Application No. 01817689.5.
Written Opinion Dated Oct. 15, 2008 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Kinahan et al. "Attenuation Correction for a Combined 3D PET/CT Scanner", Medical Physics, 25(10): 2046-2053, Oct. 1998.
Response dated Sep. 1, 2010 to Official Action of Aug. 3, 2010 From the US Patent and Trademark Office Re.: U.S. Appl. No. 11/980,690.
Response Dated Oct. 14, 2011 to Supplementary European Search Report and the European Search Opinion of Mar. 16, 2011 From the European Patent Office Re. Application No. 05803689.8.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.
Del Guerra et al. "An Integrated PET-SPECT Small Animal Imager: Preliminary Results", Nuclear Science Symposium, IEEE Records, 1: 541-544, 1999.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Supplemental Notice of Allowability Dated Oct. 24, 2011 From the US Patent and Trademark Office Re.: U.S. Appl. No. 11/607,075.
Official Action Dated Sep. 4, 2008 From the US Patent Office Re.: U.S. Appl. No. 10/533,568.
Official Action Dated Oct. 7, 2008 From the US Patent Office Re.: U.S. Appl. No. 10/616,301.
Official Action Dated Jul. 12, 2007 From the US Patent Office Re.: U.S. Appl. No. 10/616,301.
Official Action Dated Dec. 13, 2007 From the US Patent Office Re.: U.S. Appl. No. 10/616,301.
Official Action Dated Mar. 21, 2008 From the US Patent Office Re.: U.S. Appl. No. 10/533,568.
Official Action Dated Jun. 25, 2008 From the US Patent Office Re.: U.S. Appl. No. 10/616,301.
Official Action Dated Sep. 25, 2006 From the US Patent Office Re.: U.S. Appl. No. 10/616,301.
Official Action Dated Sep. 30, 2008 From the US Patent Office Re.: U.S. Appl. No. 10/616,301.
Official Action Dated Dec. 2, 2007 from the Israeli Patent Office Re.: Application No. 158442.
Official Action Dated Jul. 17, 2007 from the Israeli Patent Office Re.: Application No. 154323.
International Search Report May 24, 2007 from the International Searching Authority of the Patent Cooperation Treaty Re.: Application No. PCT/IL05/00575.
Official Action Dated Apr. 15, 2008 from the United States Patent and Trademark Office Re.: U.S. Appl. No. 09/641,973.
Official Action Dated Jul. 15, 2008 from the United States Patent and Trademark Office Re.: U.S. Appl. No. 09/641,973.
Official Action Dated May 3, 2007 from the United States Patent and Trademark Office Re.: No. U.S. Appl. No. 10/240,239.
Official Action Dated Jun. 1, 2006 from the United States Patent and Trademark Office Re.: U.S. Appl. No. 10/686,536.
Official Action Dated Aug. 10, 2007 from the United States Patent and Trademark Office Re.: U.S. Appl. No. 10/836,223.
Official Action Dated Mar. 15, 2004 from the United States Patent and Trademark Office Re.: U.S. Appl. No. 09/725,316.
Official Action Dated Feb. 15, 2008 from the United States Patent and Trademark Office Re.: U.S. Appl. No. 10/343,792.
Notice of Allowance Dated Oct. 11, 2011 From the US Patent and Trademark Office Re. U.S. Appl. No. 11/988,926.
Response Dated Oct. 14, 2011 to Communication Pursuant to Rules 70(2) and 70a(2) EPC of Apr. 4, 2011 From the European Patent Office Re. Application No. 05803689.8.
Communication Pursuant to Article 93(3) EPC Dated Mar. 8, 2010 From the European Patent Office Re.: Application No. 06832278.3.
International Search Report Dated Sep. 12, 2002 From the International Searching Authority of the Patent Cooperation Treaty Re: Application No. PCT/IL02/00057.

(56) References Cited

OTHER PUBLICATIONS

International Search Report Dated Mar. 18, 2004 From the International Searching Authority of the Patent Cooperation Treaty Re.: Application No. PCT/IL03/00917.
Official Action Dated Jul. 2, 2004 From the US Patent and Trademark Office Re.: U.S. Appl. No. 09/641,973.
Official Action Dated Sep. 5, 2002 From the US Patent and Trademark Office Re.: U.S. Appl. No. 12/084,559.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Supplementary Partial European Search Report Dated Sep. 4, 2007 From the European Patent Office Re.: Application No. 0 2716285.8.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Lavallée et al. "Building a Hybrid Patient's Model for Augmented Reality in Surgery: A Registration Problem", Computing in Biological Medicine, 25(2): 149-164, 1995.
Restriction Official Action Dated Nov. 8, 2011 From the US Patent and Trademark Office Re. U.S. Appl. No. 12/309,479.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Response Dated Oct. 24, 2011 to Official Action of May 23, 2011 From the US Patent and Trademark Office Re. U.S Appl. No. 11/667,793.
Restriction Official Action Dated Nov. 15, 2011 From the US Patent and Trademark Office Re. U.S. Appl. No. 11/980,683.
Communication Pursuant to Article 94(3) EPC Dated Nov. 18, 2011 From the European Patent Office Re. Application No. 05803689.8.
Response Dated Nov. 14, 2011 to Official Action of Jul. 12, 2011 From the US Patent and Trademark Office Re.: U.S. Appl. No. 09/641,973.
Response Dated Nov. 23, 2011 to Official Action of May 23, 2011 From the US Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.
Response Dated Nov. 28, 2011 to Official Action of Jun. 28, 2011 From the US Patent and Trademark Office Re. U.S. Appl. No. 11/628,074.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Response Dated Dec. 8, 2011 to Restriction Official Action of Nov. 8, 2011 From the US Patent and Trademark Office Re. U.S. Appl. No. 12/309,479.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniformity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Official Action Dated Dec. 19, 2012 From the US Patent and Trademark Office Re. U.S. Appl. No. 12/448,473.
Notice of Allowance Dated Dec. 26, 2012 From the US Patent and Trademark Office Re.: U.S. Appl. No. 11/980,690.
Official Action Dated Dec. 28, 2012 From the US Patent and Trademark Office Re.: U.S. Appl. No. 10/343,792.
Charland et al. "The Use of Deconvolution and Total Least Squares in Recovering a Radiation Detector Line Spread Function", Medical Physics, 25(2): 152-160, Feb. 1998. Abstract Only!
Official Action Dated Jul. 30, 2012 From the US Patent and Trademark Office Re.: U.S. Appl. No. 11/980,683.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Official Action Dated Aug. 2, 2012 From the US Patent and Trademark Office Re. U.S. Appl. No. 12/087,150.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Restriction Official Action Dated Aug. 16, 2012 From the US Patent and Trademark Office Re. U.S. Appl. No. 12/448,473.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Notice of Allowance Dated Sep. 28, 2012 From the US Patent and Trademark Office Re. U.S. Appl. No. 12/792,856.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Lange et al. "EM Reconstruction Algorithms for Emission and Transmission Tomography", Journal of Computer Assisted Tomography, 8(2): 306-316, Apr. 1984.
Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.
Rockmore et al. "A Maximum Likelihood Approach to Emission Image Reconstruction From Projections", IEEE Transactions on Nuclear Science, 23(4): 1428-1432, Aug. 1976.
Shepp et al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Solanki "The Use of Automation in Radiopharmacy", Hospital Pharmacist, 7(4): 94-98, Apr. 2000.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Official Action Dated Oct. 11, 2012 From the US Patent and Trademark Office Re. U.S. Appl. No. 11/976,852.
Official Action Dated Oct. 10, 2012 From the US Patent and Trademark Office Re. U.S. Appl. No. 11/798,017.
Communication Pursuant to Article 94(3) EPC Dated Oct. 26, 2012 From the European Patent Office Re. Application No. 05803689.8.
Communication Pursuant to Article 94(3) EPC Dated Nov. 12, 2012 From the European Patent Office Re. Application No. 06756258.7.
Notice of Allowance Dated Nov. 15, 2012 From the US Patent and Trademark Office Re.: U.S. Appl. No. 11/980,683.

(56) References Cited

OTHER PUBLICATIONS

Summons to Attend Oral Proceedings Pursuant to Rule 115(1) EPC Dated Nov. 29, 2012 From the European Patent Office Re. Application No. 06756259.5.
Supplementary European Search Report and the European Search Opinion Dated Nov. 13, 2012 From the European Patent Office Re. Application No. 06728347.3.
Notice of Allowance Dated Oct. 26, 2012 From the US Patent and Trademark Office Re. U.S. Appl. No. 12/514,785.
Official Action Dated Nov. 30, 2012 From the US Patent and Trademark Office Re. U.S. Appl. No. 12/514,785.
Advisory Action Before the Filing of an Appeal Brief Dated Feb. 26, 2013 From the US Patent and Trademark Office Re. U.S. Appl. No. 11/989,223.
Applicant-Initiated Interview Summary Dated Jan. 28, 2013 From the US Patent and Trademark Office Re.: U.S. Appl. No. 11/798,017.
Communication Under Rule 71(3) EPC Dated Feb. 26, 2013 From the European Patent Office Re. Application No. 06756259.5.
Notice of Allowance Dated Mar. 7, 2013 From the US Patent and Trademark Office Re. U.S. Appl. No. 13/726,316.
Notice of Allowance Dated Mar. 14, 2013 From the US Patent and Trademark Office Re.: U.S. Appl. No. 11/798,017.
Notice of Allowance Dated Feb. 25, 2013 From the US Patent and Trademark Office Re.: U.S. Appl. No. 09/641,973.
Notice of Allowance Dated Feb. 27, 2013 From the US Patent and Trademark Office Re. U.S. Appl. No. 12/514,785.
Official Action Dated Mar. 11, 2013 From the US Patent and Trademark Office Re. U.S. Appl. No. 13/345,719.
Official Action Dated Feb. 22, 2013 From the US Patent and Trademark Office Re.: U.S. Appl. No. 10/616,307.
Sluden "Compton Camera With Position-Sensitive Silicon Detectors", Doctoral Thesis, University of Ljubljana, Faculty of Mathematics and Physics, 36 P.
Applicant-Initiated Interview Summary Dated May 1, 2013 From the US Patent and Trademark Office Re. U.S. Appl. No. 10/343,792.
Applicant-Initiated Interview Summary Dated May 1, 2013 From the US Patent and Trademark Office Re. U.S. Appl. No. 11/980,653.
Applicant-Initiated Interview Summary Dated May 9, 2013 From the US Patent and Trademark Office Re. U.S. Appl. No. 12/448,473.
Official Action Dated Nov. 30, 2012 From the US Patent and Trademark Office Re. U.S. Appl. No. 11/989,223.
Notice of Allowance Dated Jun. 14, 2013 From the US Patent and Trademark Office Re. U.S. Appl. No. 10/616,307.
Notice of Allowance Dated Jul. 15, 2013 From the US Patent and Trademark Office Re. U.S. Appl. No. 11/932,987.
Notice of Allowance Dated Jul. 19, 2013 From the US Patent and Trademark Office Re. U.S. Appl. No. 11/989,223.
Notice of Allowance Dated 25 Jul. 25, 2013 From the US Patent and Trademark Office Re. U.S. Appl. No. 13/345,719.
Official Action Dated Aug. 5, 013 From the US Patent and Trademark Office Re. U.S. Appl. No. 12/309,479.
Official Action Dated Jul. 5, 2013 From the US Patent and Trademark Office Re.: U.S. Appl. No. 11/656,548.
Official Action Dated Jun. 12, 2013 From the US Patent and Trademark Office Re. U.S. Appl. No. 12/087,150.
Official Action Dated Aug. 14, 2013 From the US Patent and Trademark Office Re. U.S. Appl. No. 12/448,473.
Official Action Dated Jul. 30, 2013 From the US Patent and Trademark Office Re. U.S. Appl. No. 10/343,792.
Official Action Dated Jul. 31, 2013 From the US Patent and Trademark Office Re. U.S. Appl. No. 11/667,793.
Bacharach et al. "Attenuation Correction in Cardiac Positron Emission Tomography and Single-Photon Emission Computed Tomography", Journal of Nucelar Cardiology, 2(3): 246-255, 1995.
Berman et al. "D-SPECT: A Novel Camera for High Speed Quantitative Molecular Imaging: Initial Clinical Results", The Journal of Nuclear Medicine, 47(Suppl.1): 131P, 2006.
Berman et al. "Myocardial Perfusion Imaging With Technetium-99m-Sestamibi: Comparative Analysis of Available Imaging Protocols", The Journal of Nuclear Medicine, 35: 681-688, 1994.
Borges-Neto et al. "Perfusion and Function at Rest and Treadmill Exercise Using Technetium-99m-Sestamibi: Comparison of One- and Two-Day Protocols in Normal Volunteers", The Journal of Nuclear Medicine, 31(7): 1128-1132, Jul. 1990.
Kwok et al. "Feasability of Simultaneous Dual-Isotope Myocardial Perfusion Acquisition Using a Lower Dose of Sestamibi", European Journal of Nuclear Medicine, 24(3): 281-285, Mar. 1997.
Patton et al. "D-SPECT: A New Solid State Camera for High Speed Molecular Imaging", The Journal of Nuclear Medicine, 47(Suppl.1): 189P, 2006.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.

\* cited by examiner

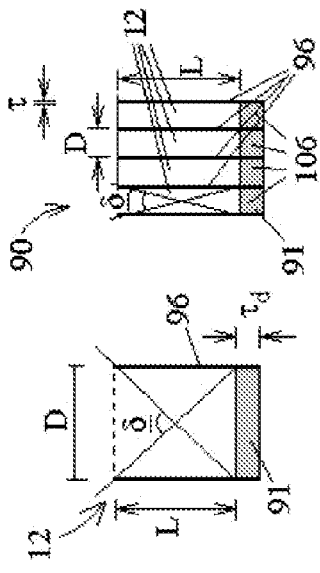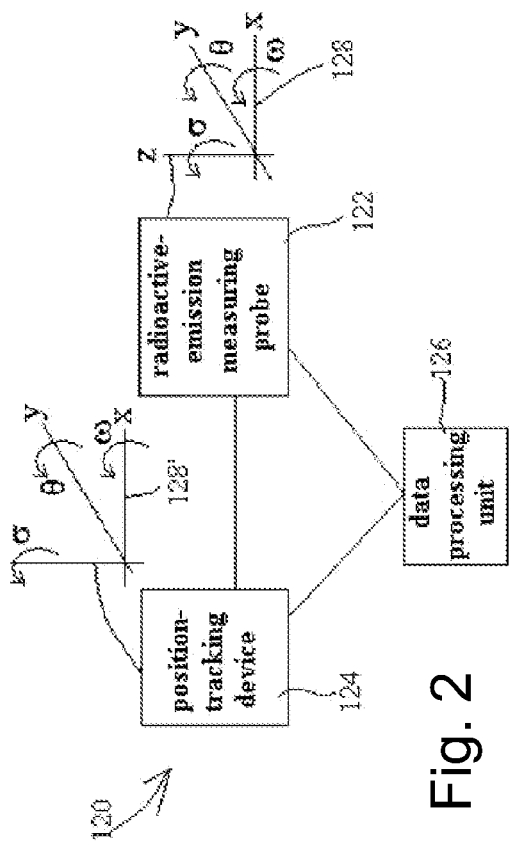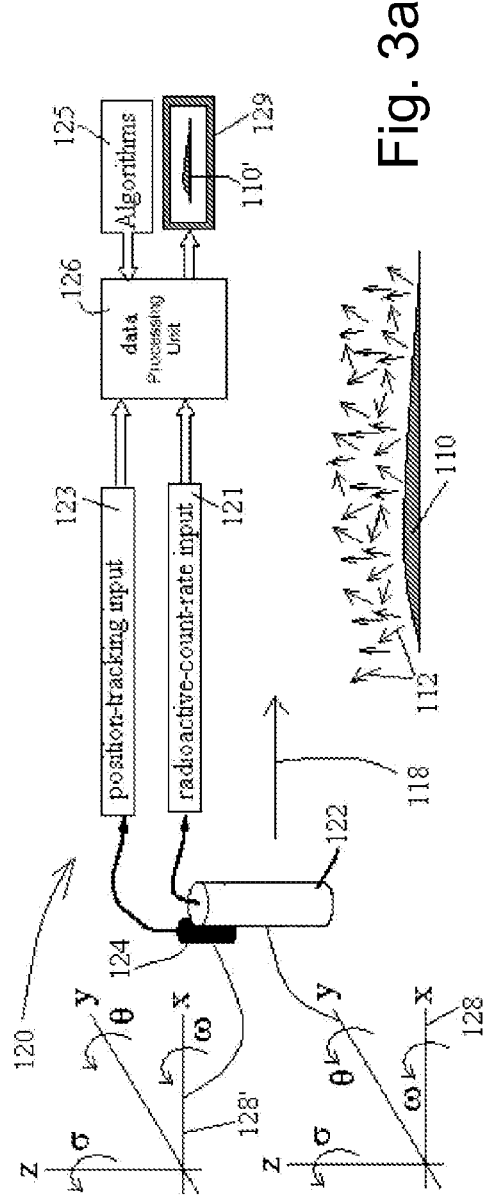

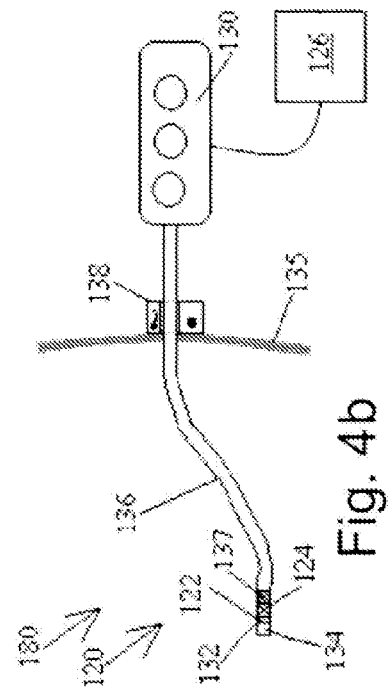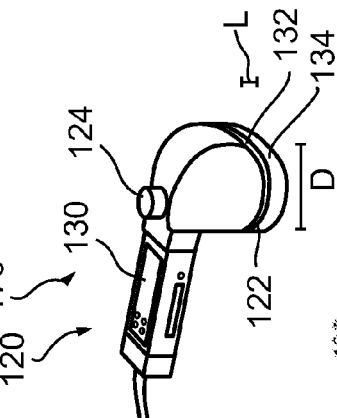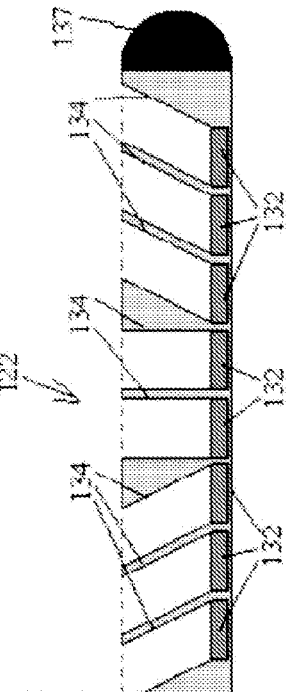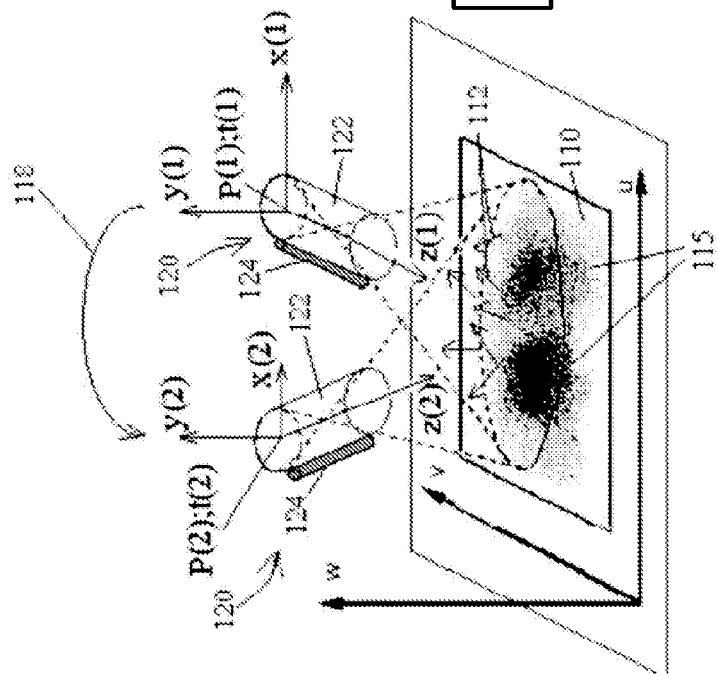
Fig. 4a
Fig. 4b
Fig. 4c
Fig. 3b

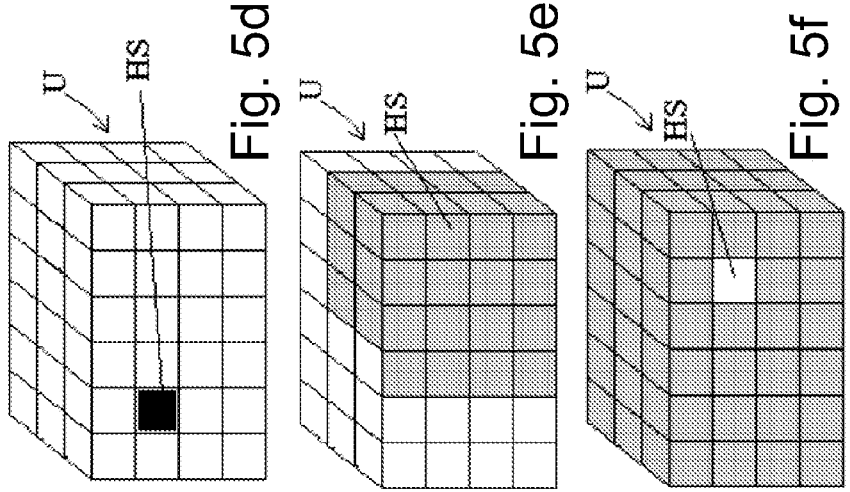
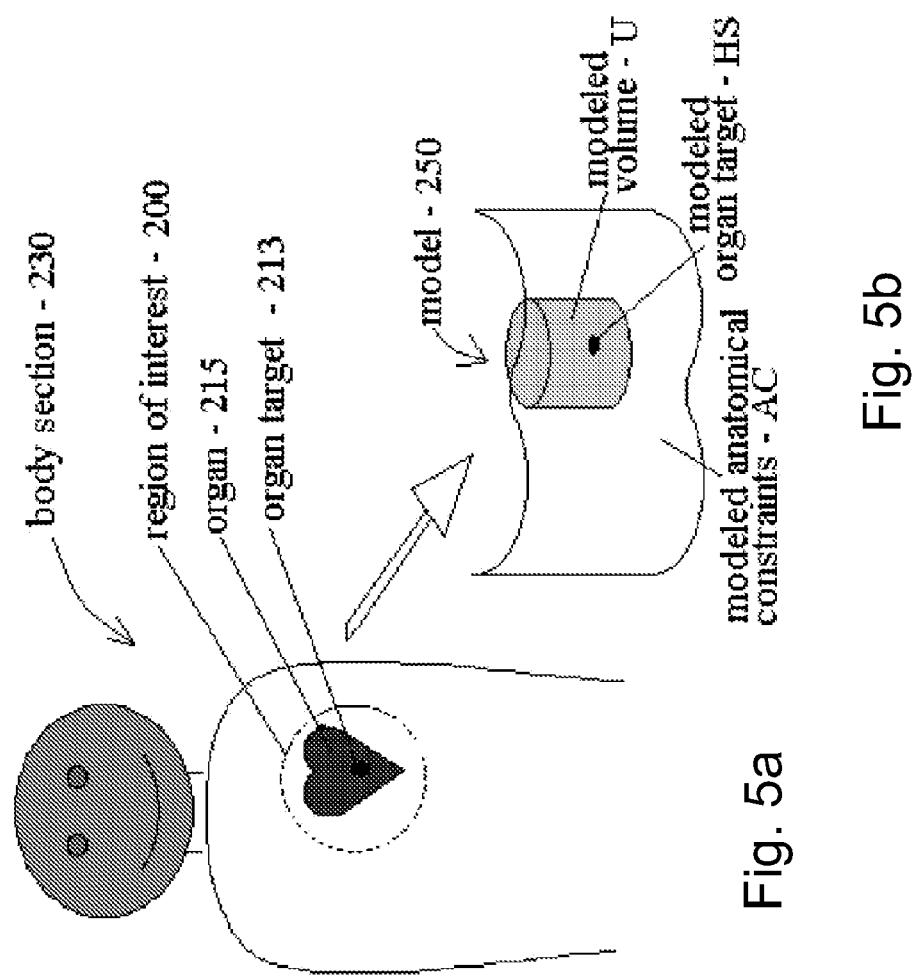

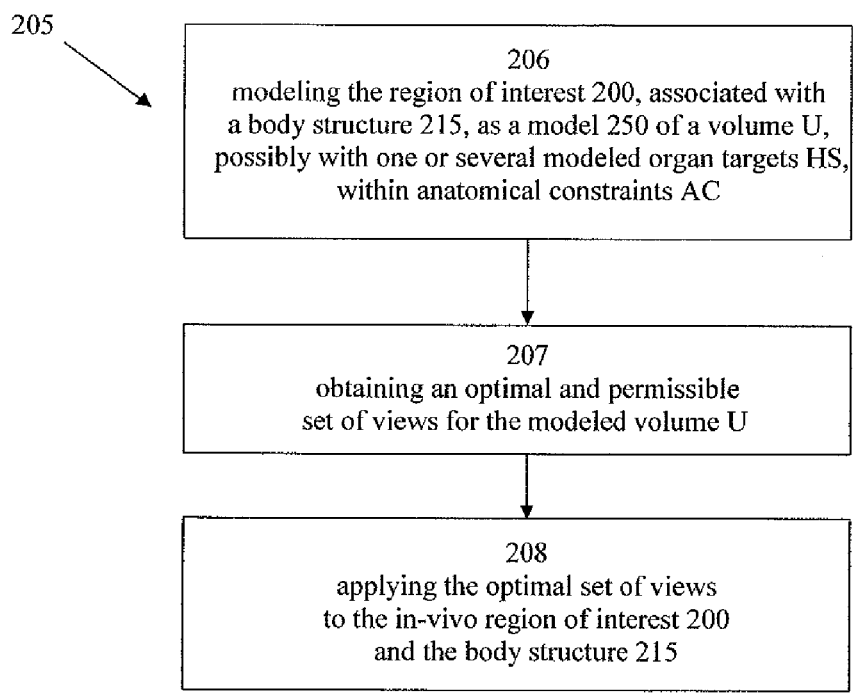

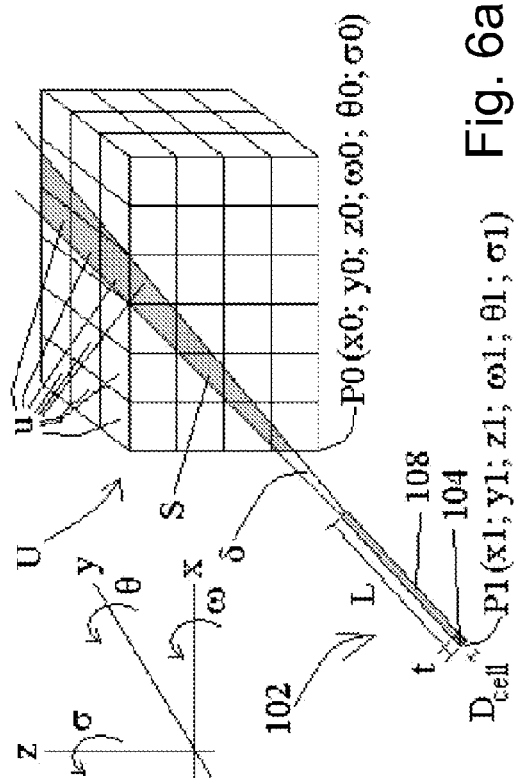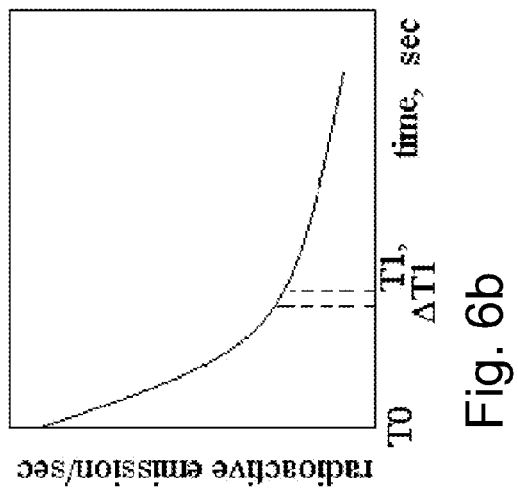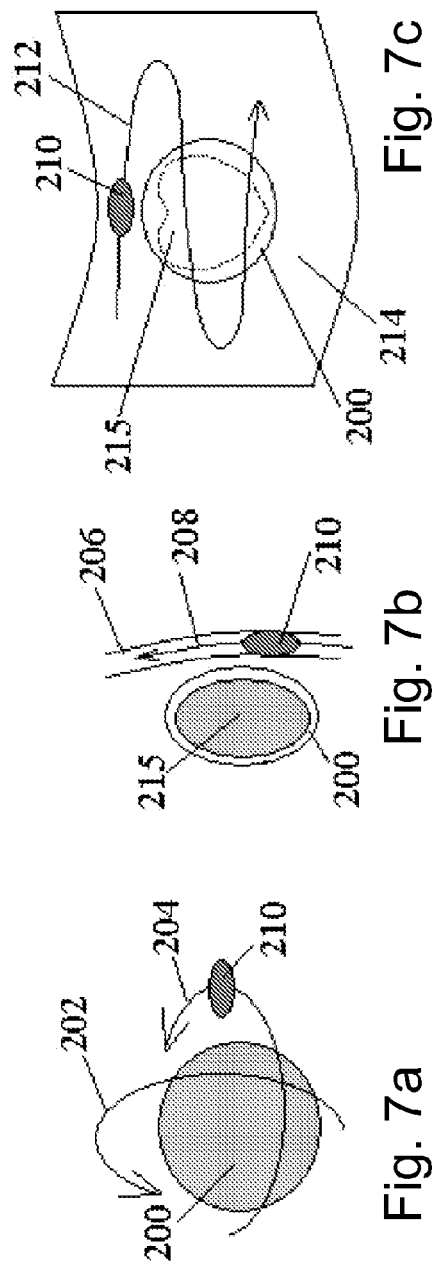

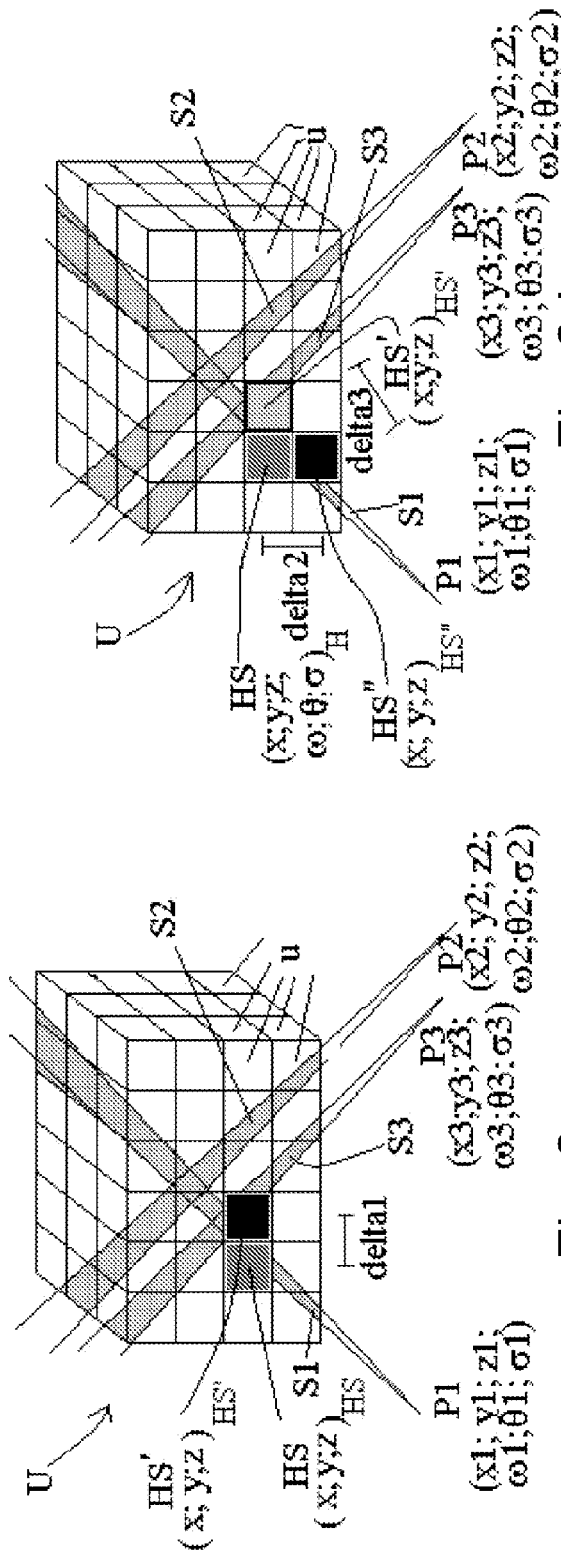
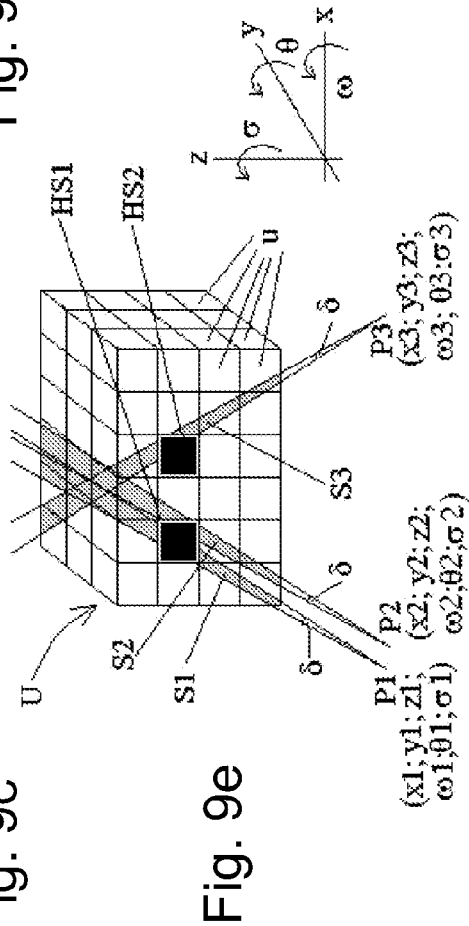
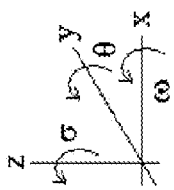
Fig. 9c
Fig. 9d
Fig. 9e

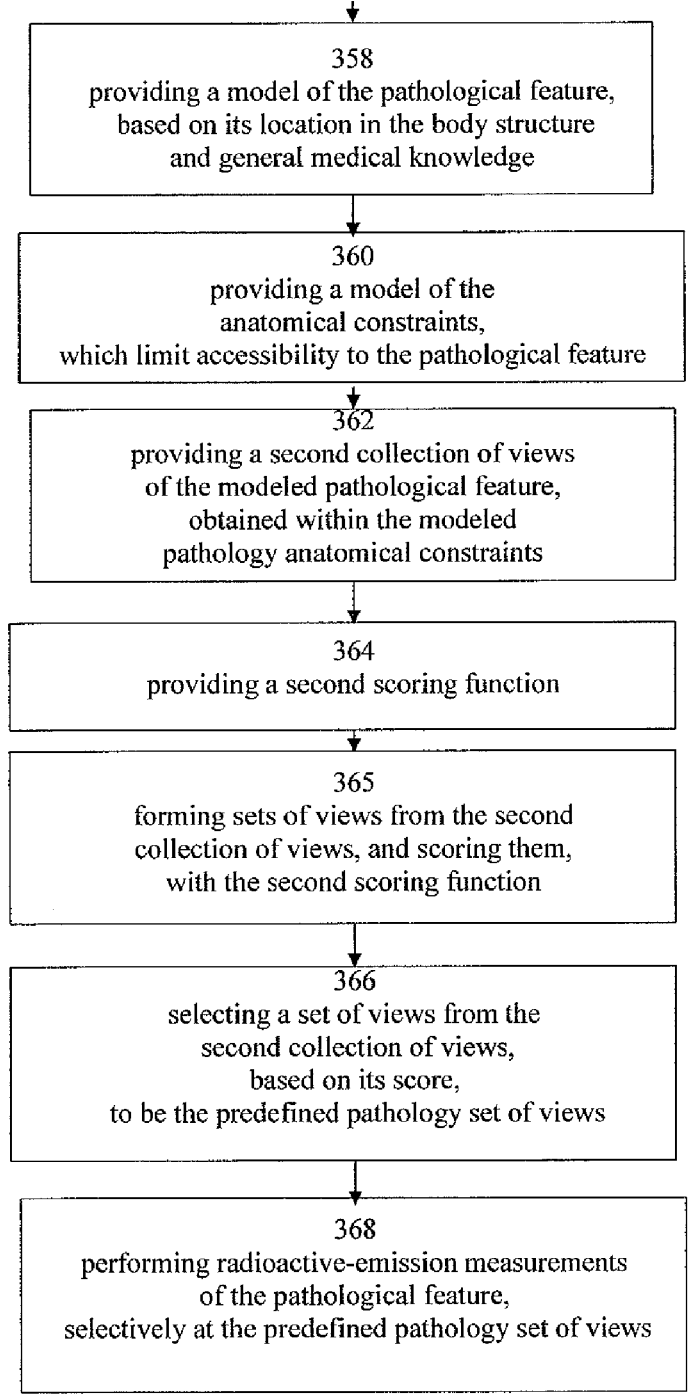

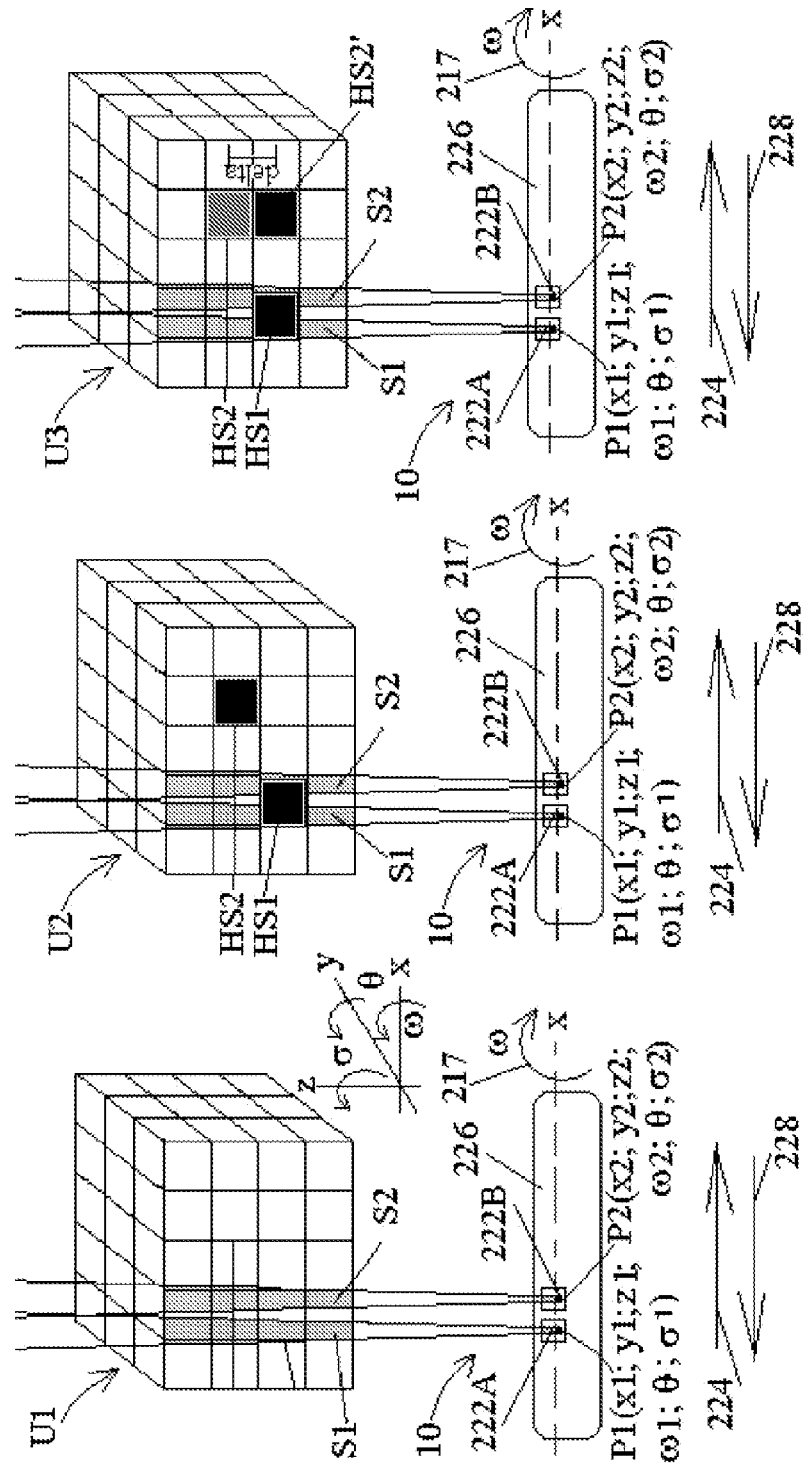

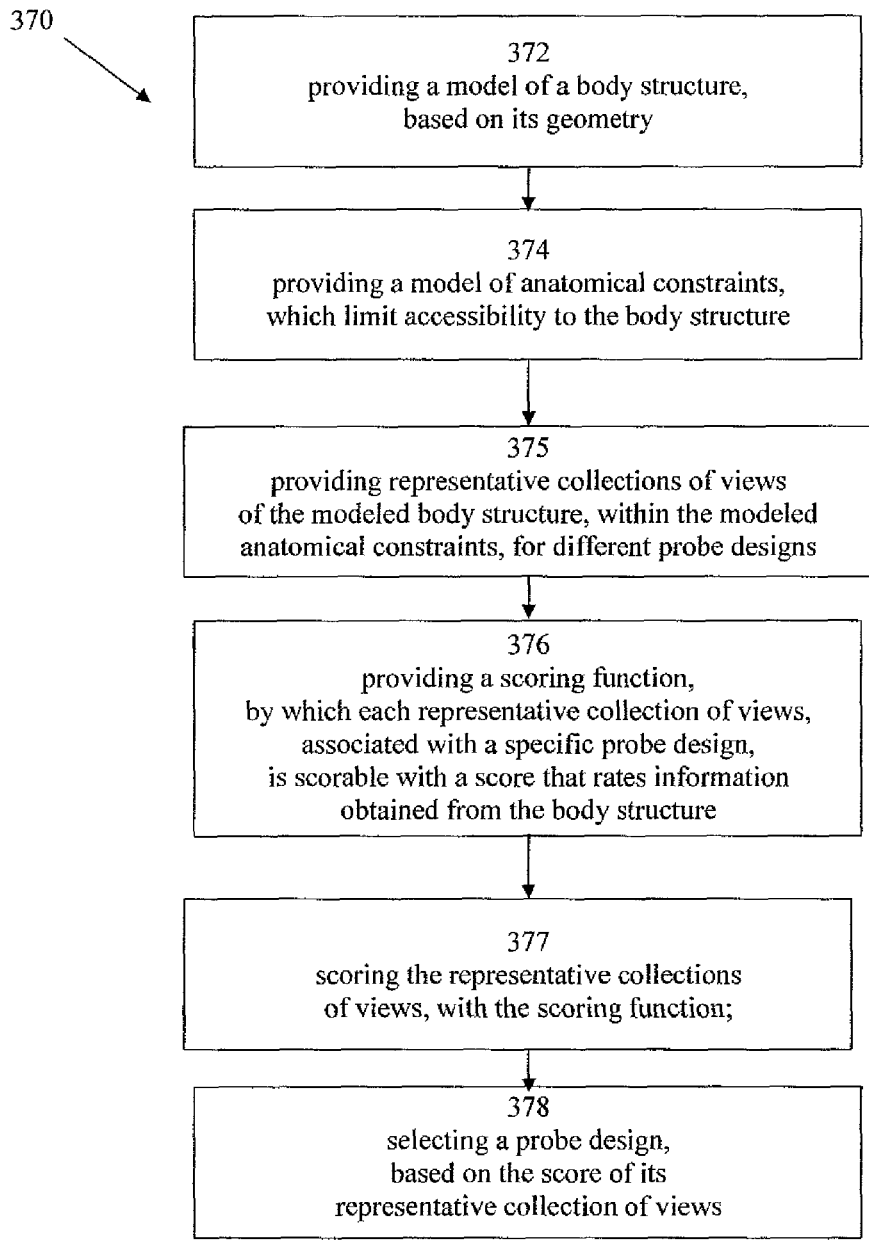

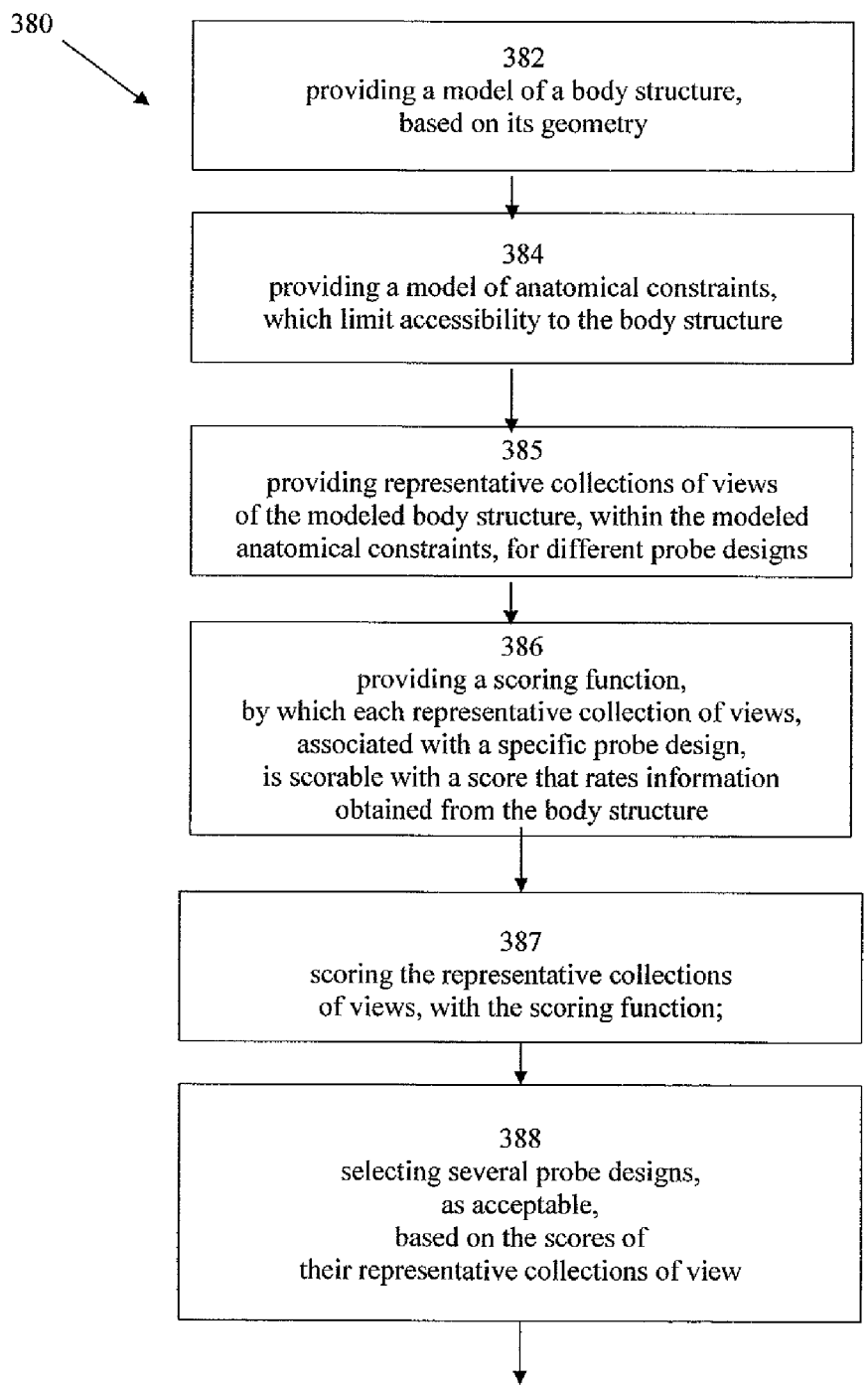

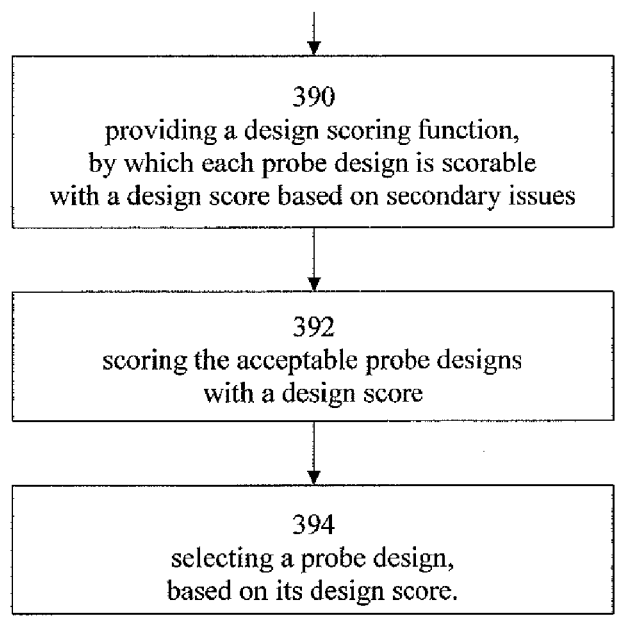

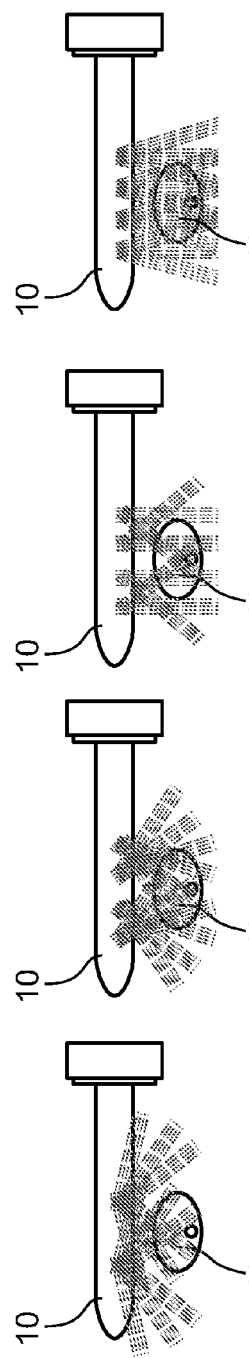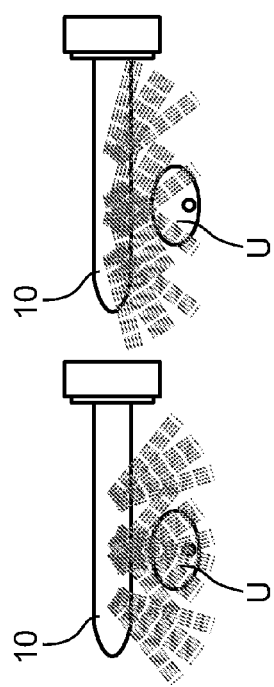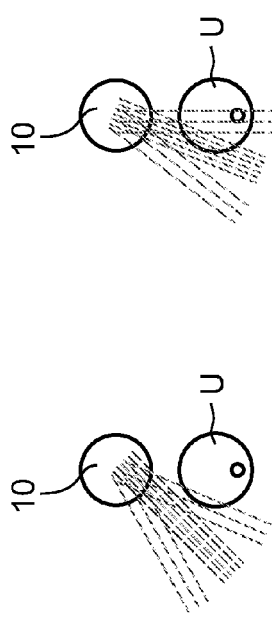
Fig. 16A  Fig. 16B  Fig. 16C  Fig. 16D  Fig. 16E  Fig. 16F  Fig. 16G  Fig. 16H  Fig. 16I  Fig. 16J  Fig. 16K

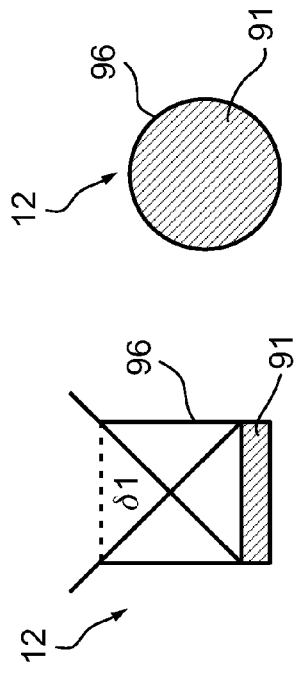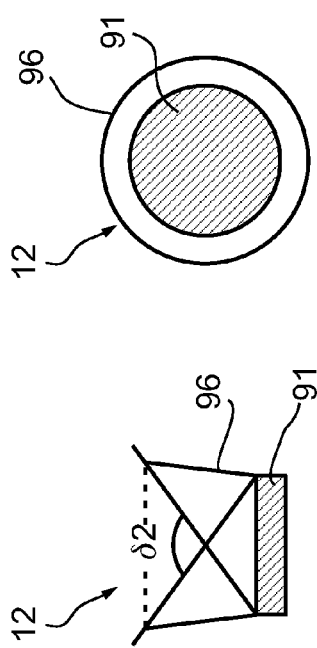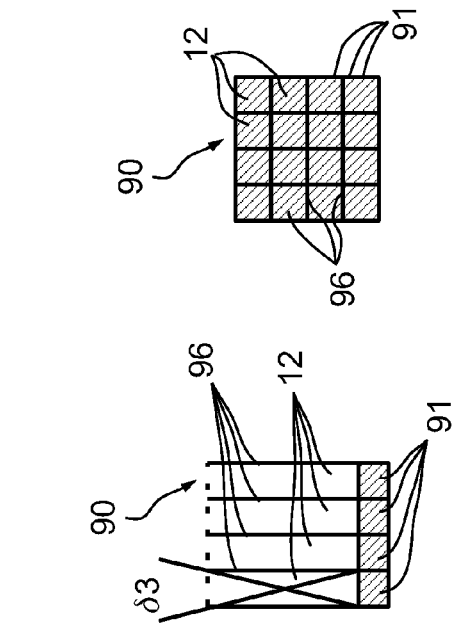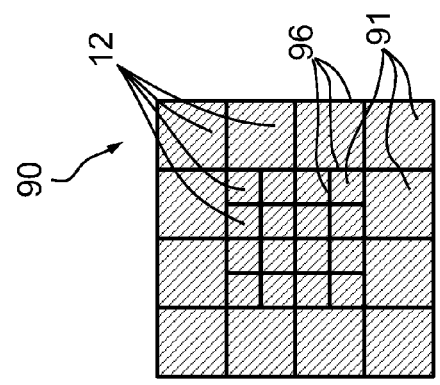
Fig. 17a Fig. 17b Fig. 17c Fig. 17d Fig. 17e Fig. 17f Fig. 17g Fig. 17h

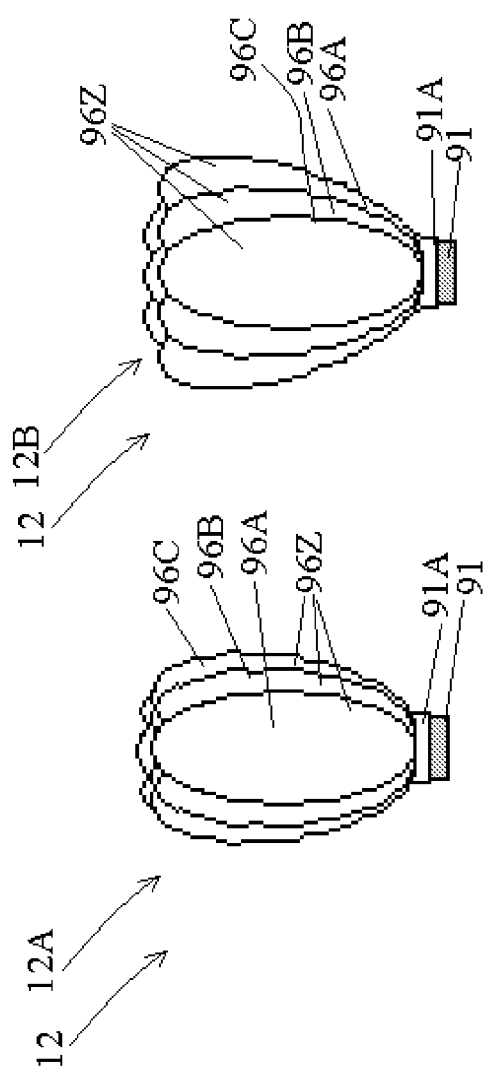

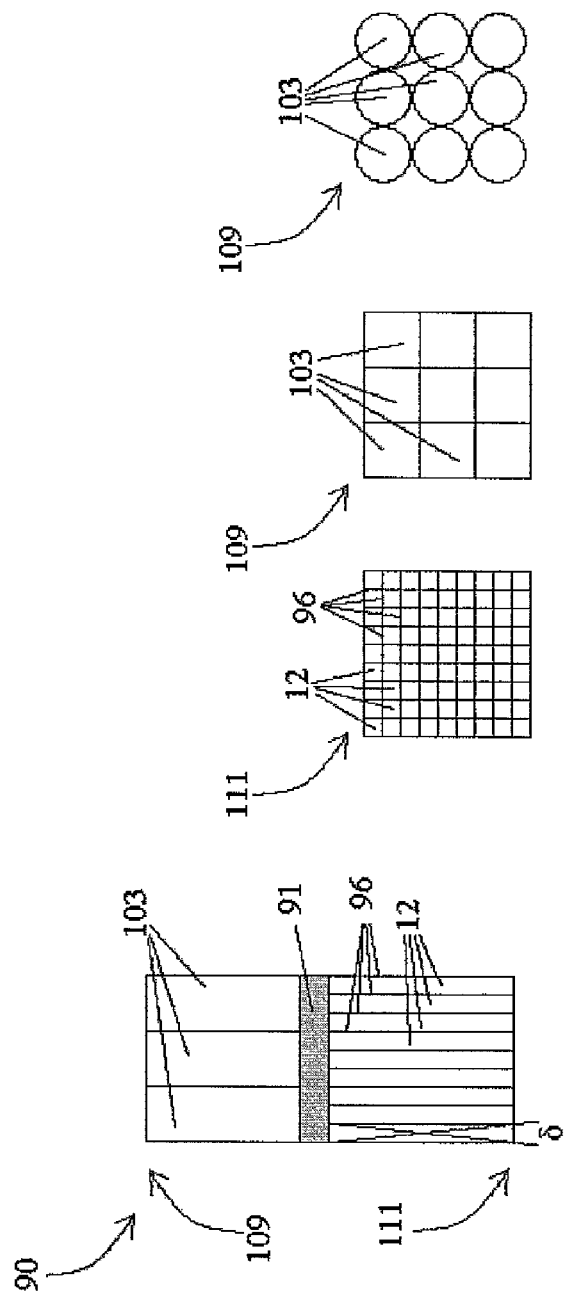

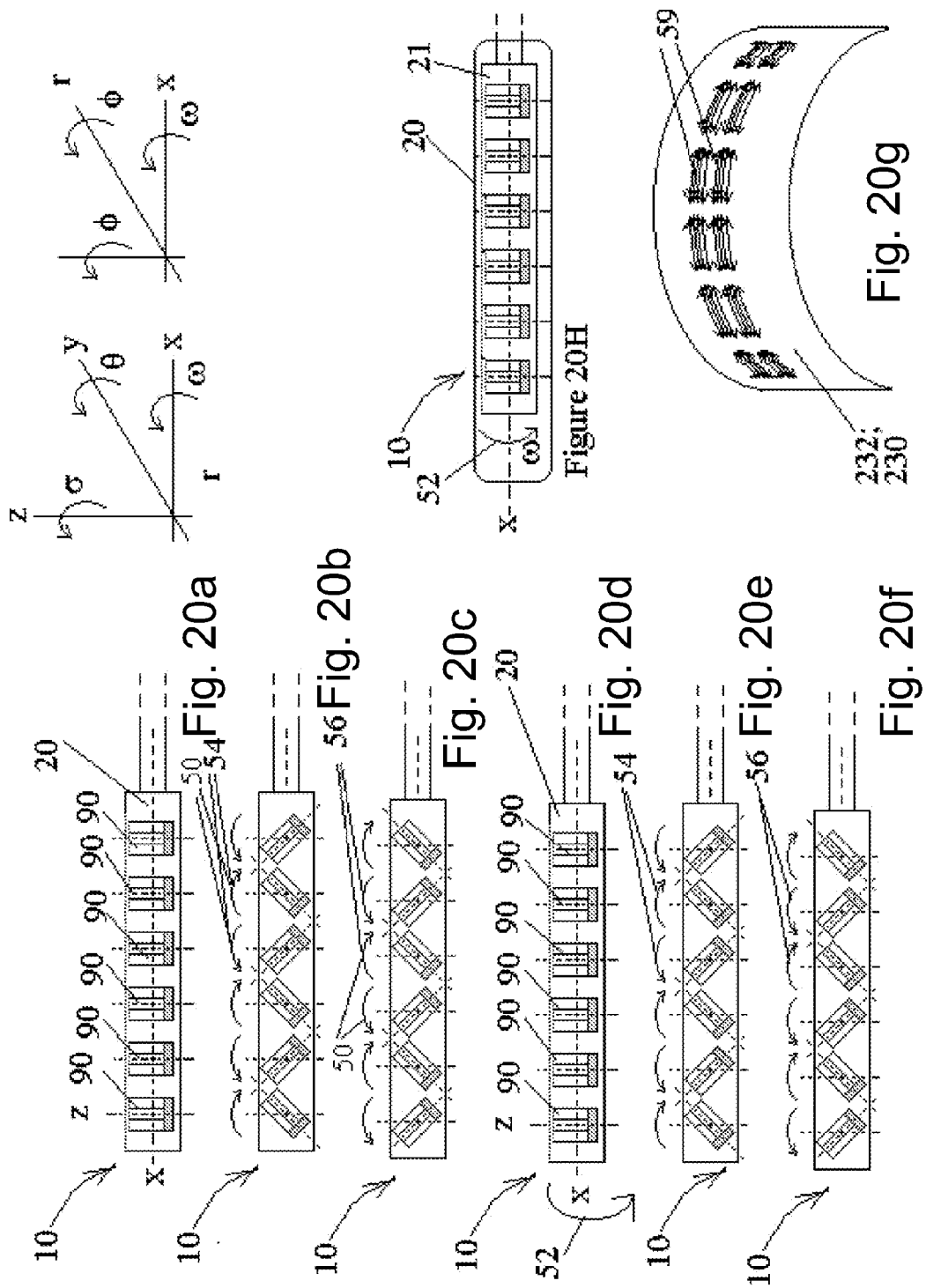

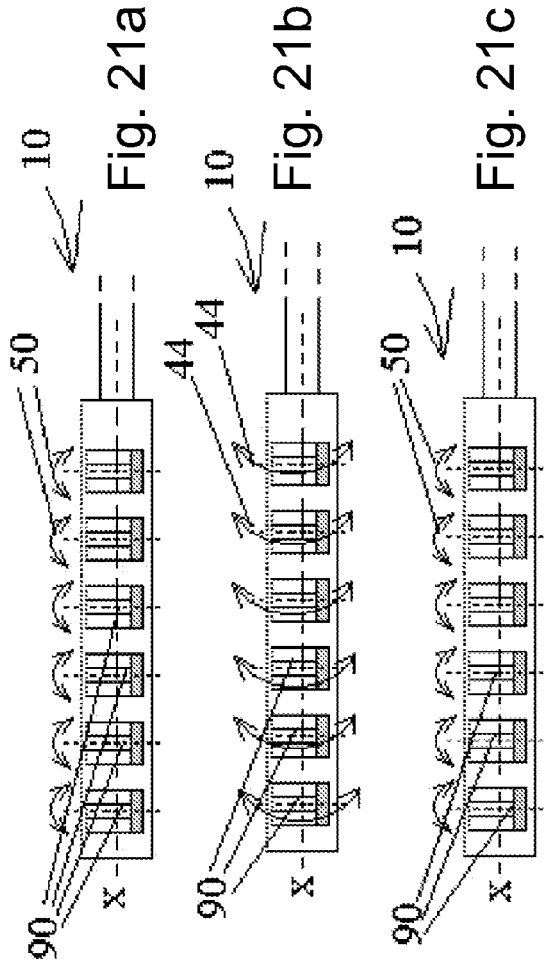
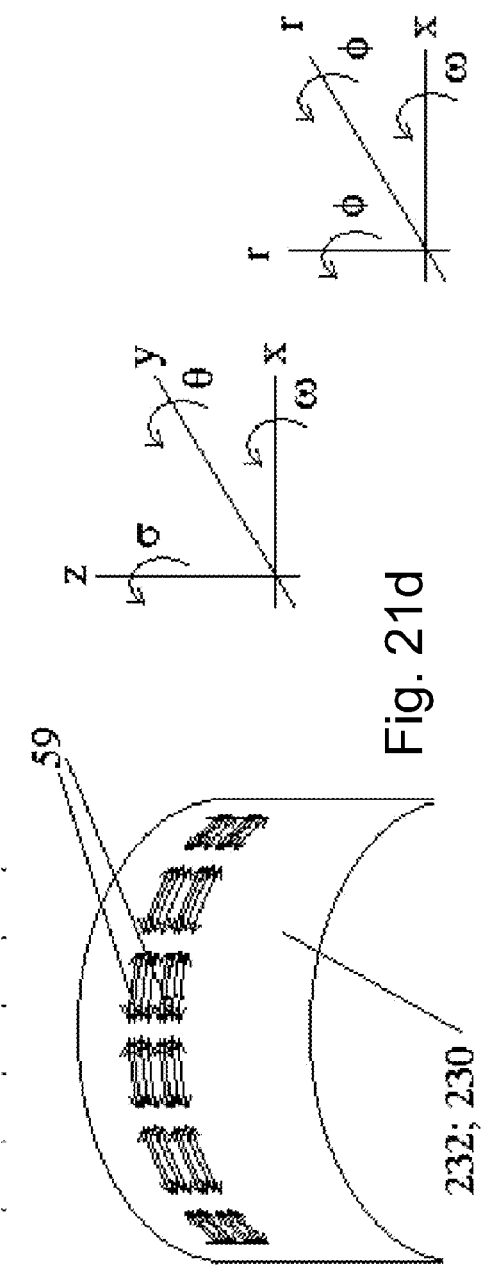
Fig. 21a
Fig. 21b
Fig. 21c
Fig. 21d

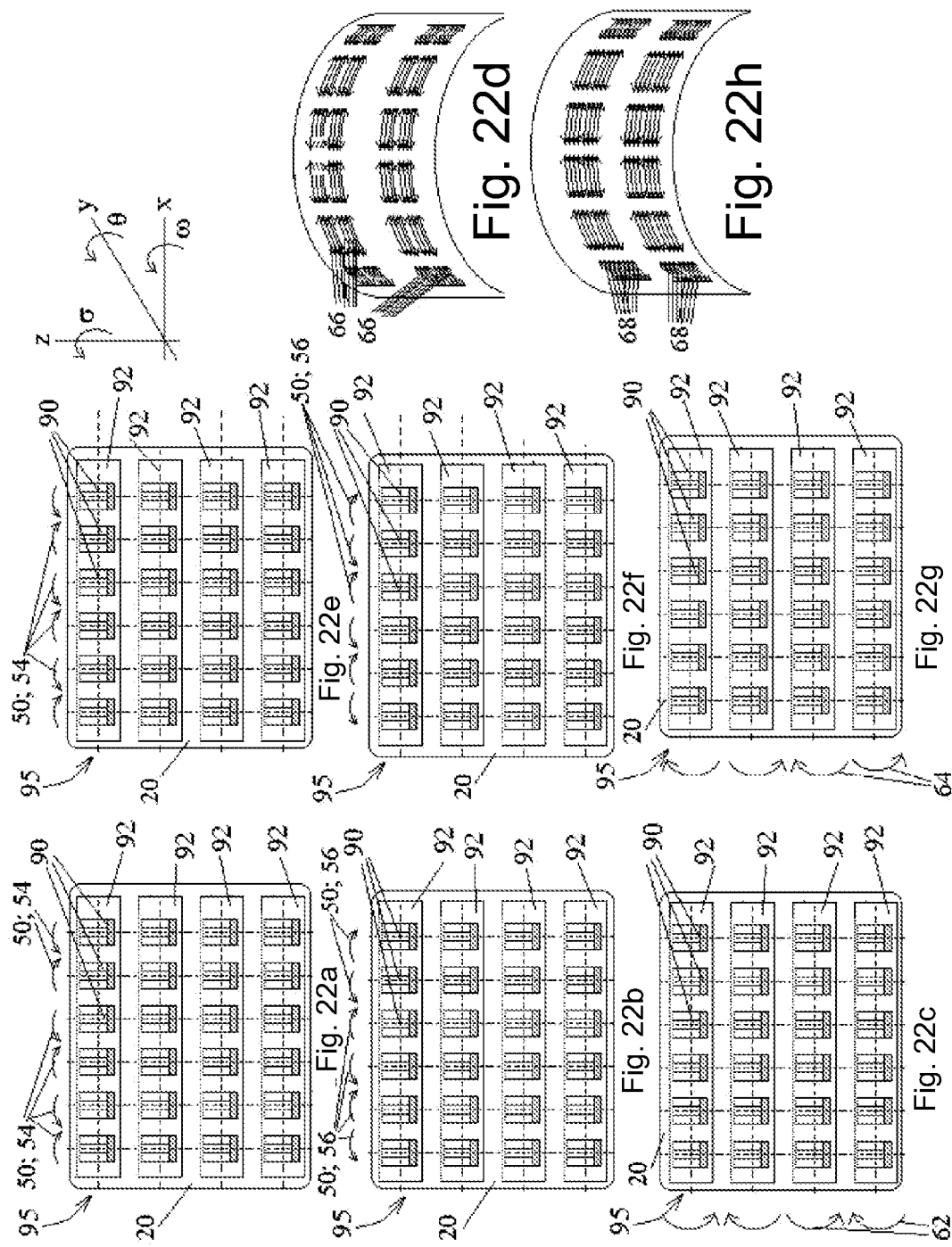

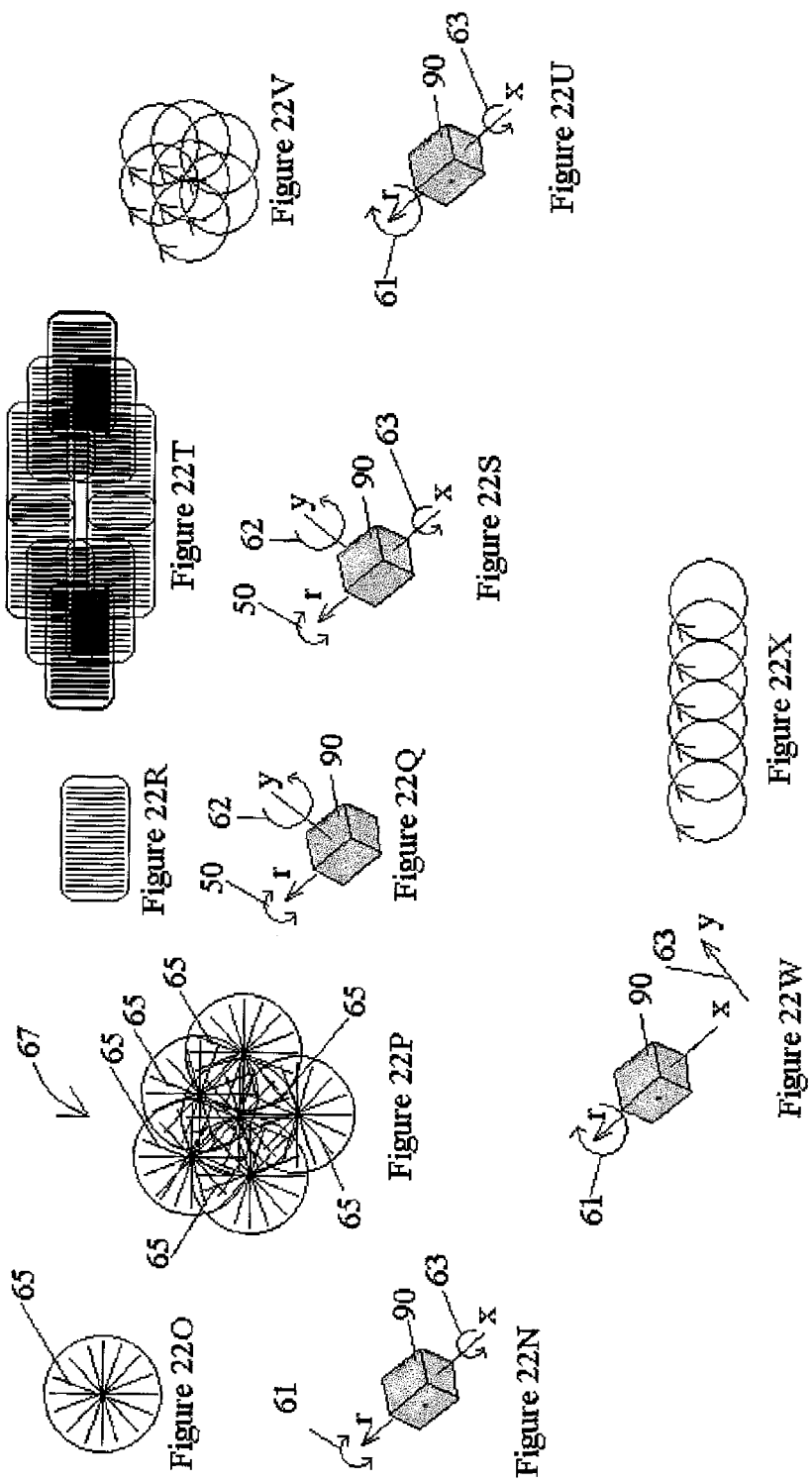

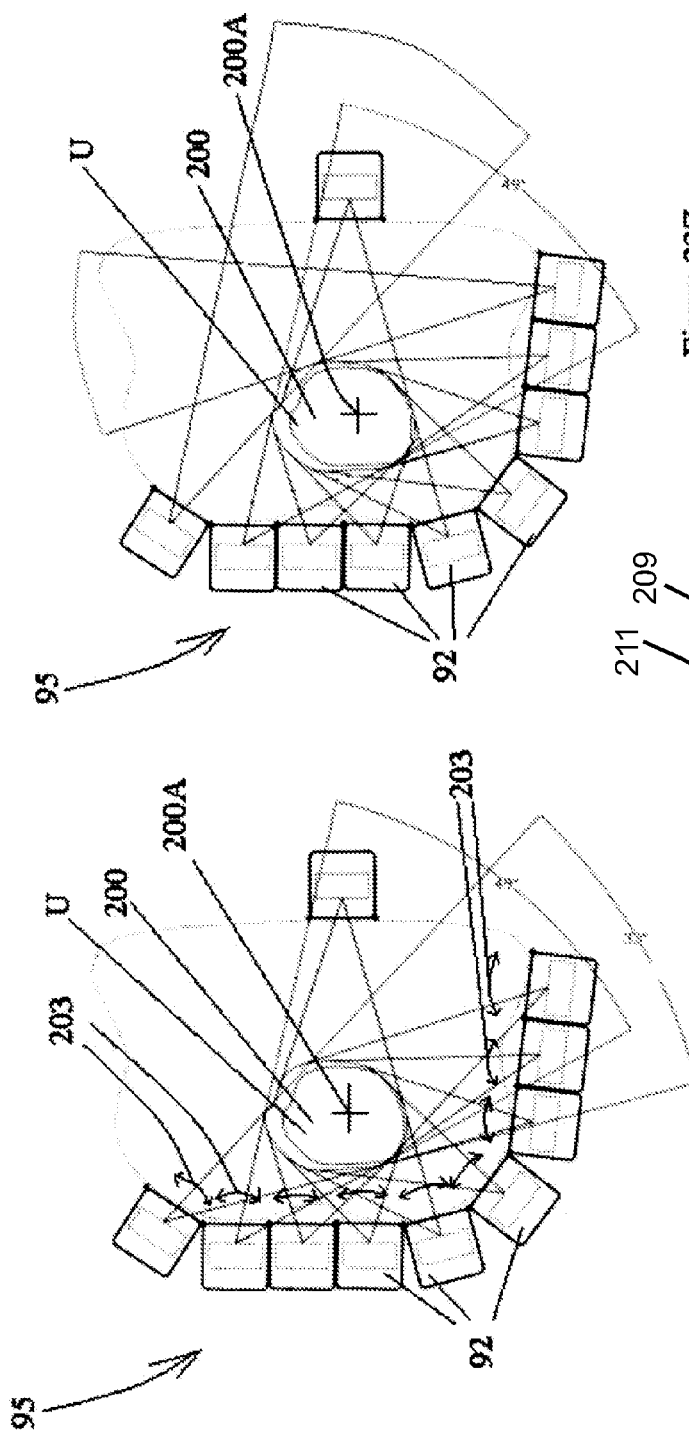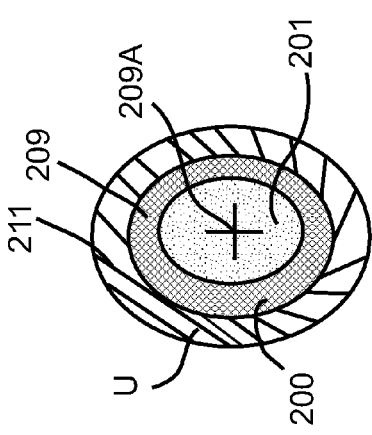

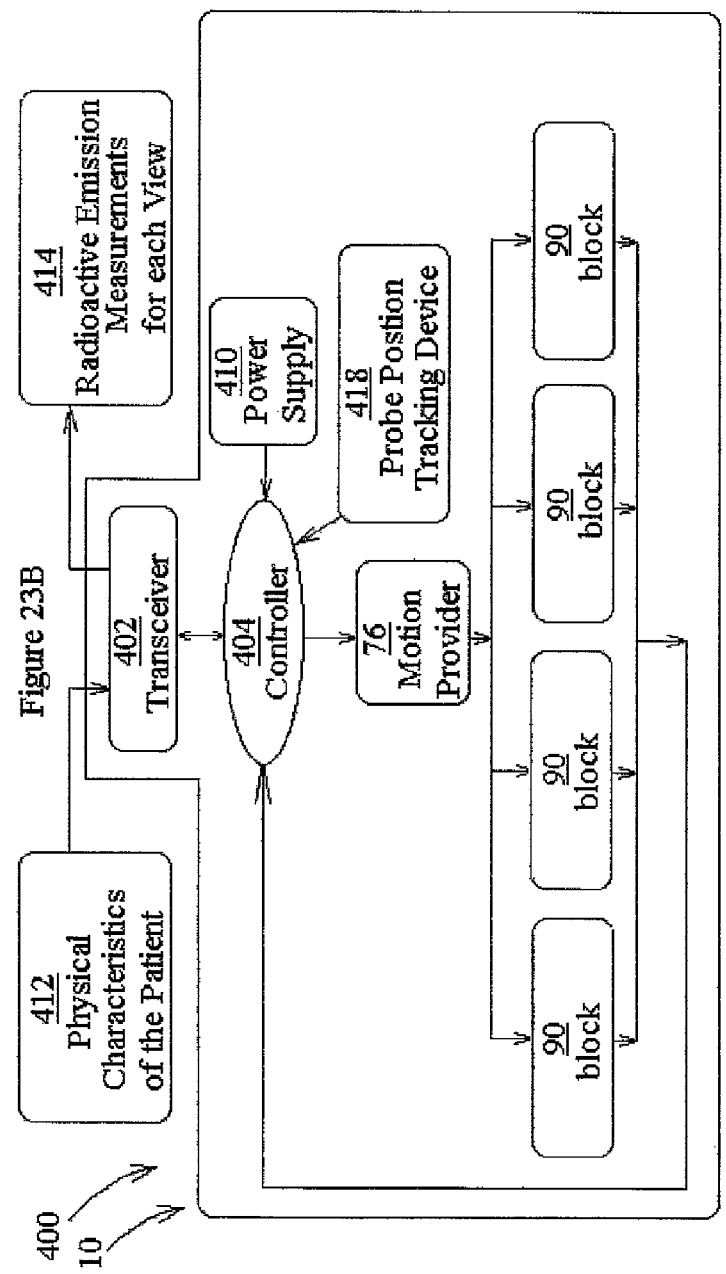

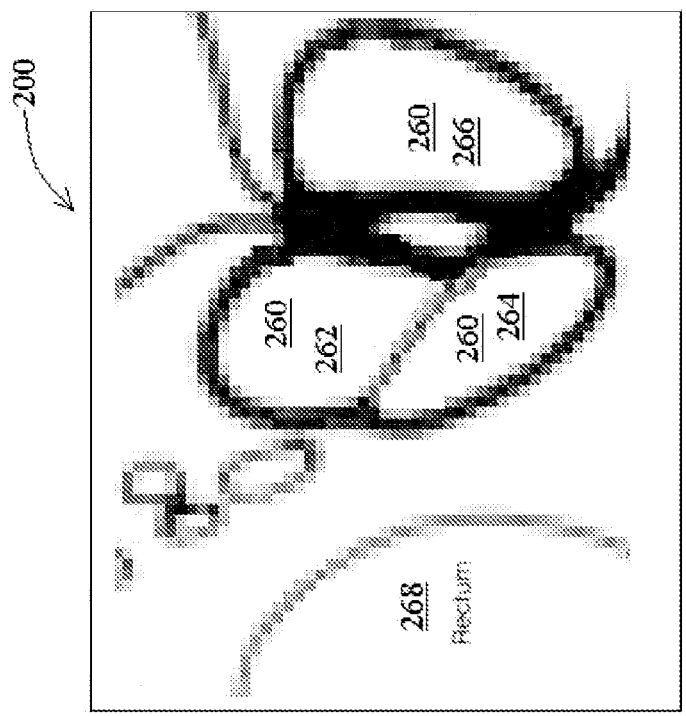
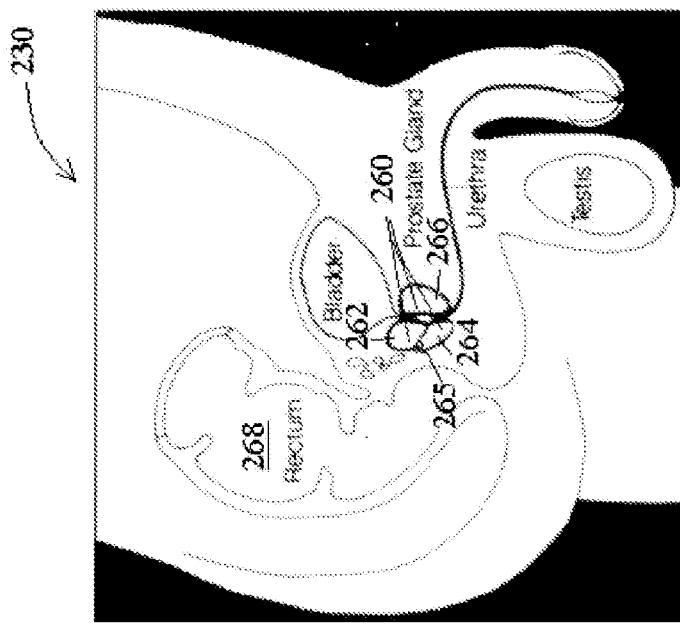
Fig. 24B
Fig. 24A

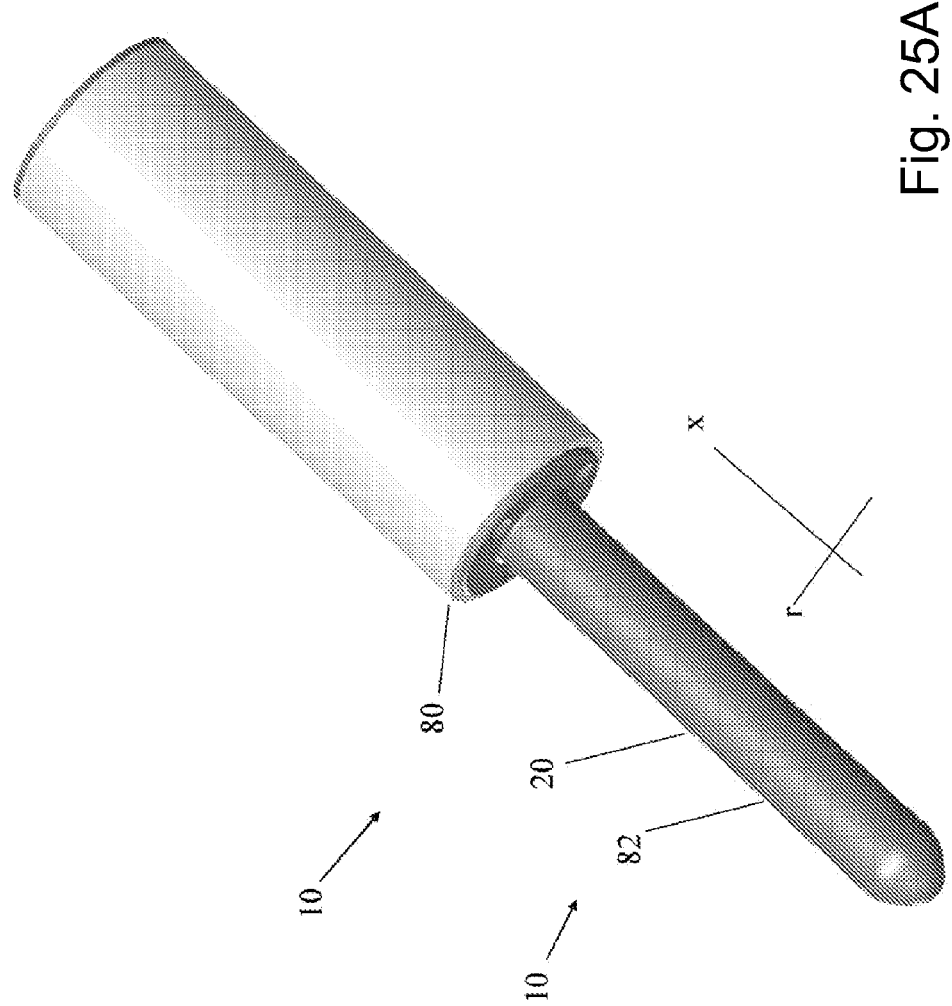

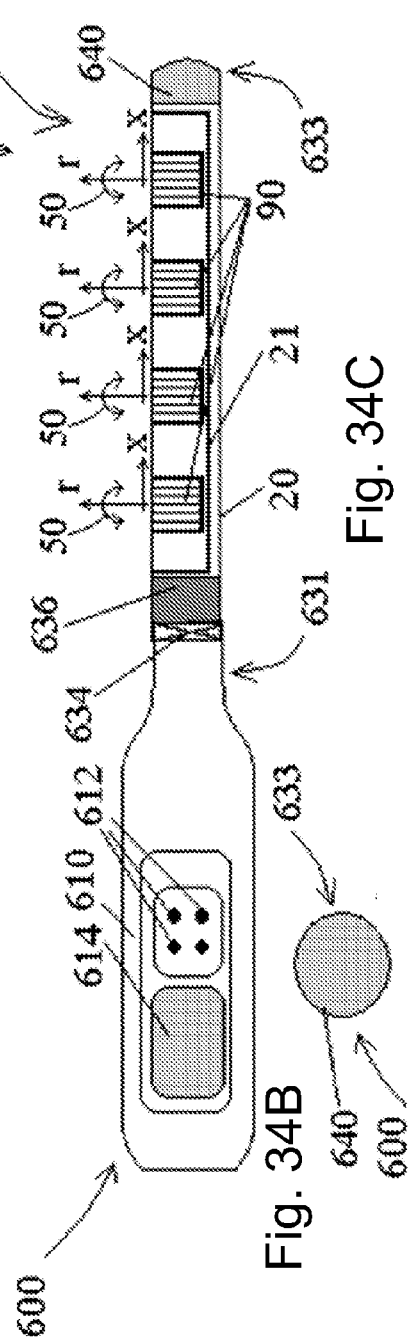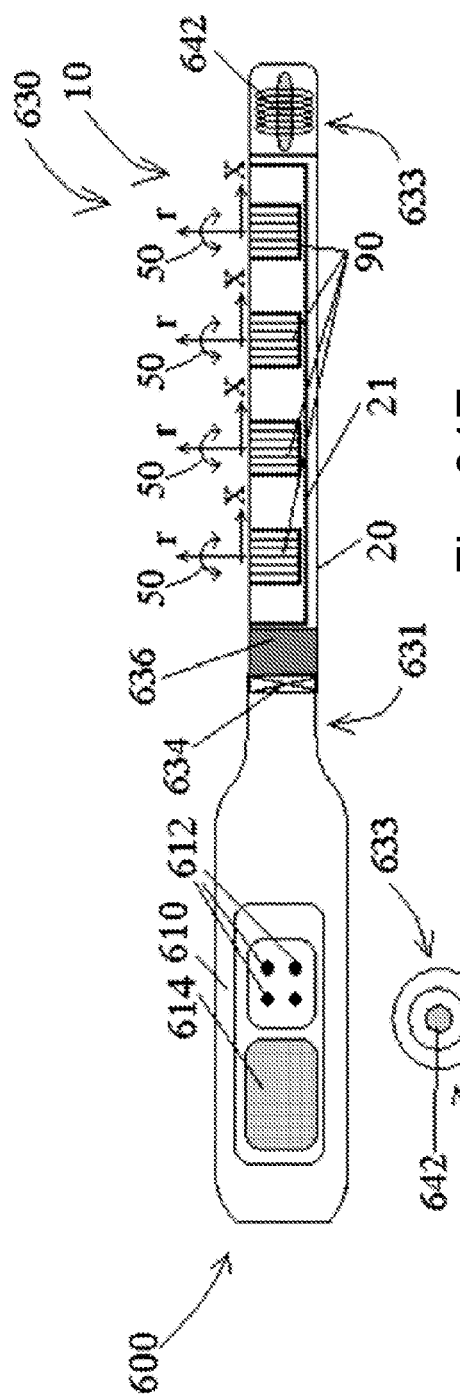

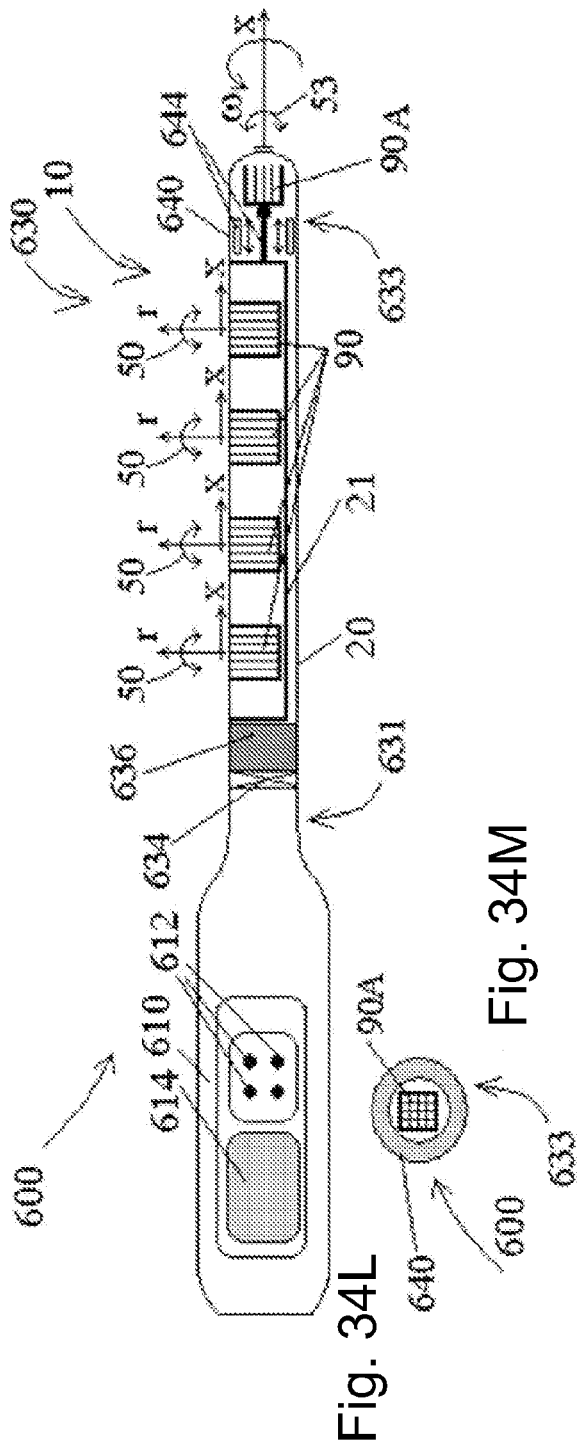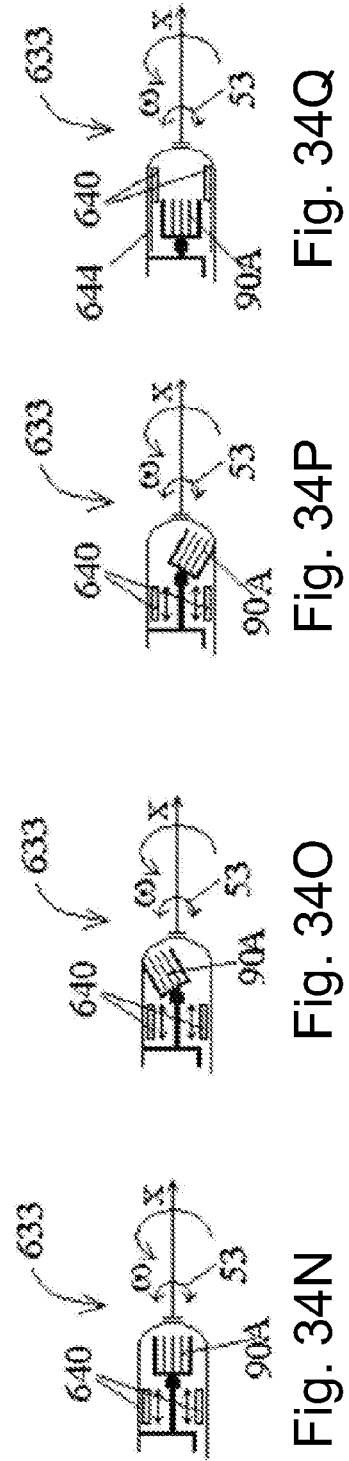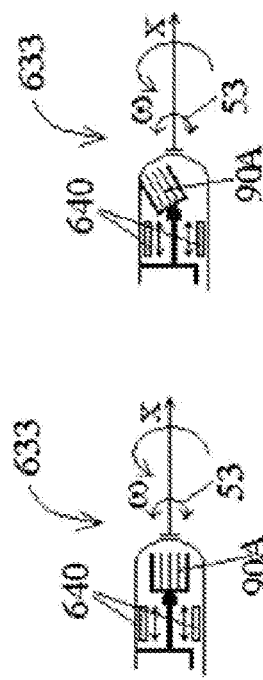

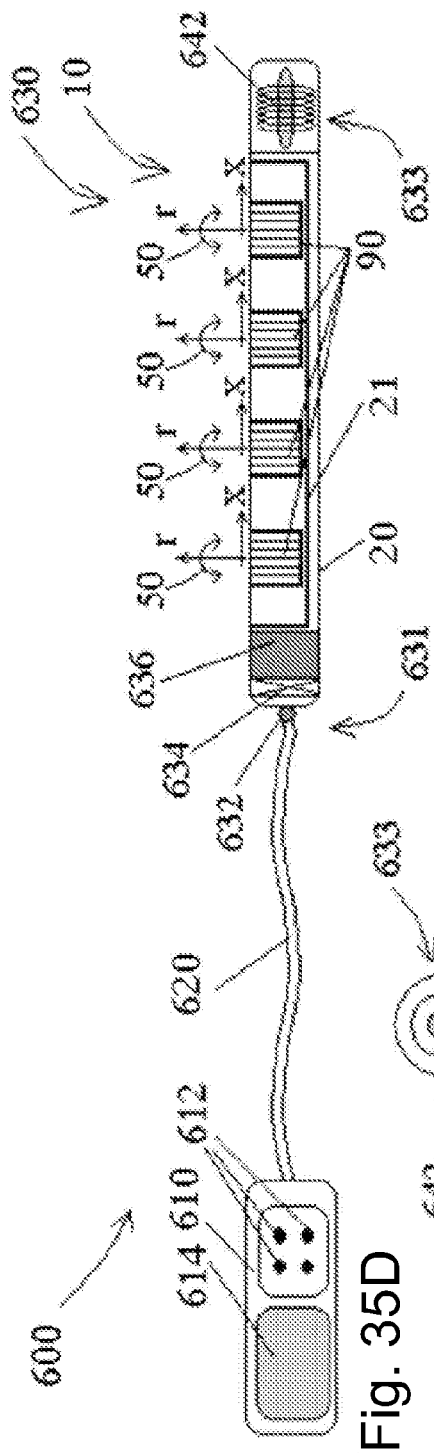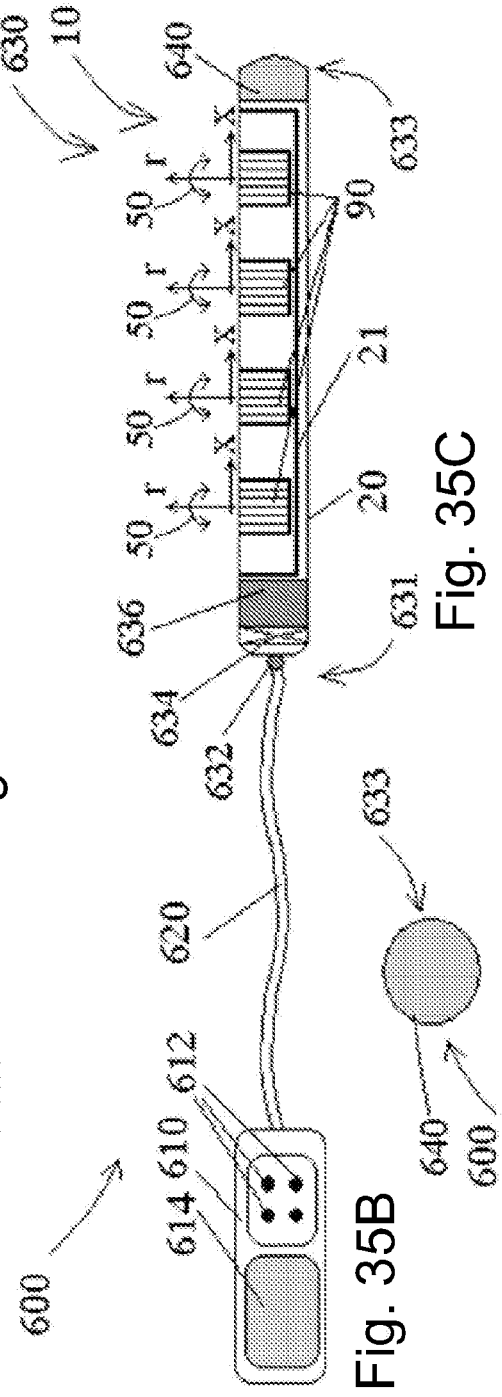

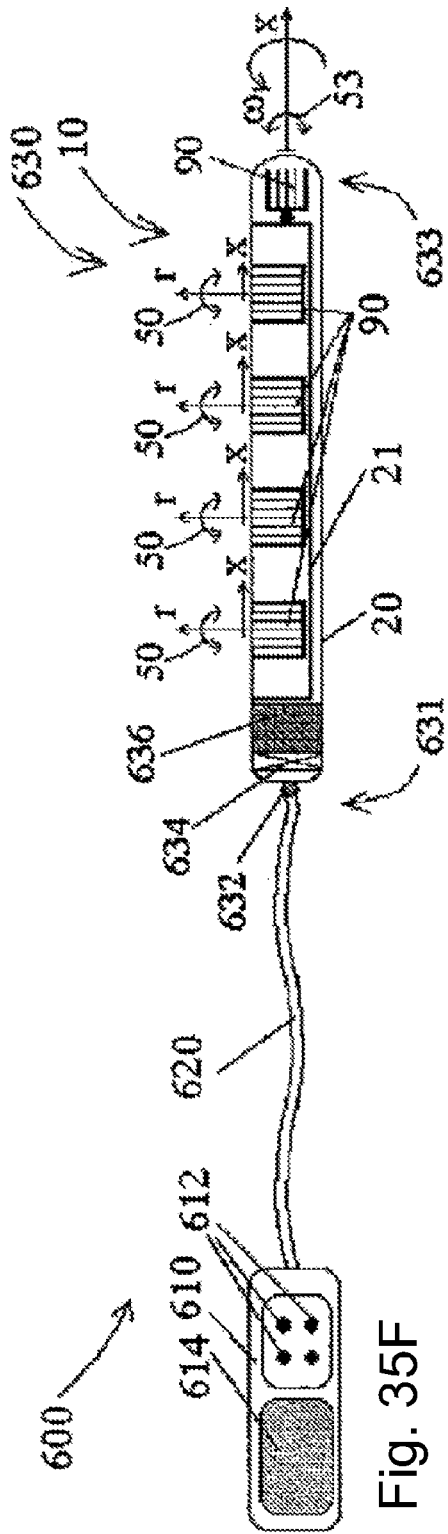
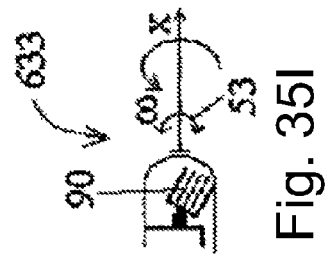
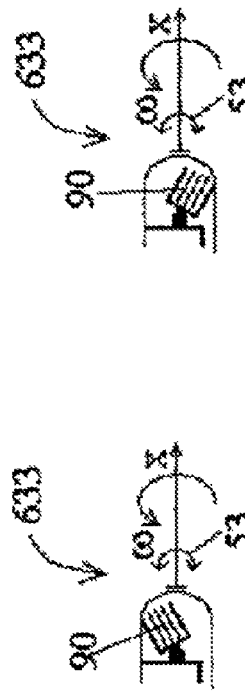
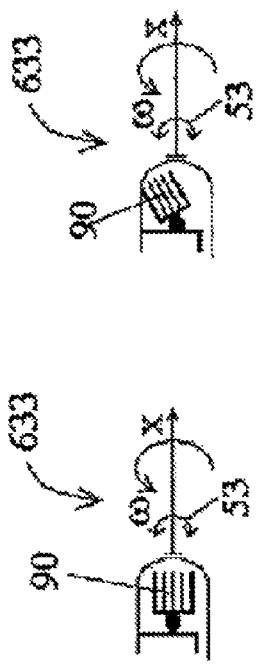
Fig. 35F
Fig. 35G
Fig. 35H
Fig. 35I

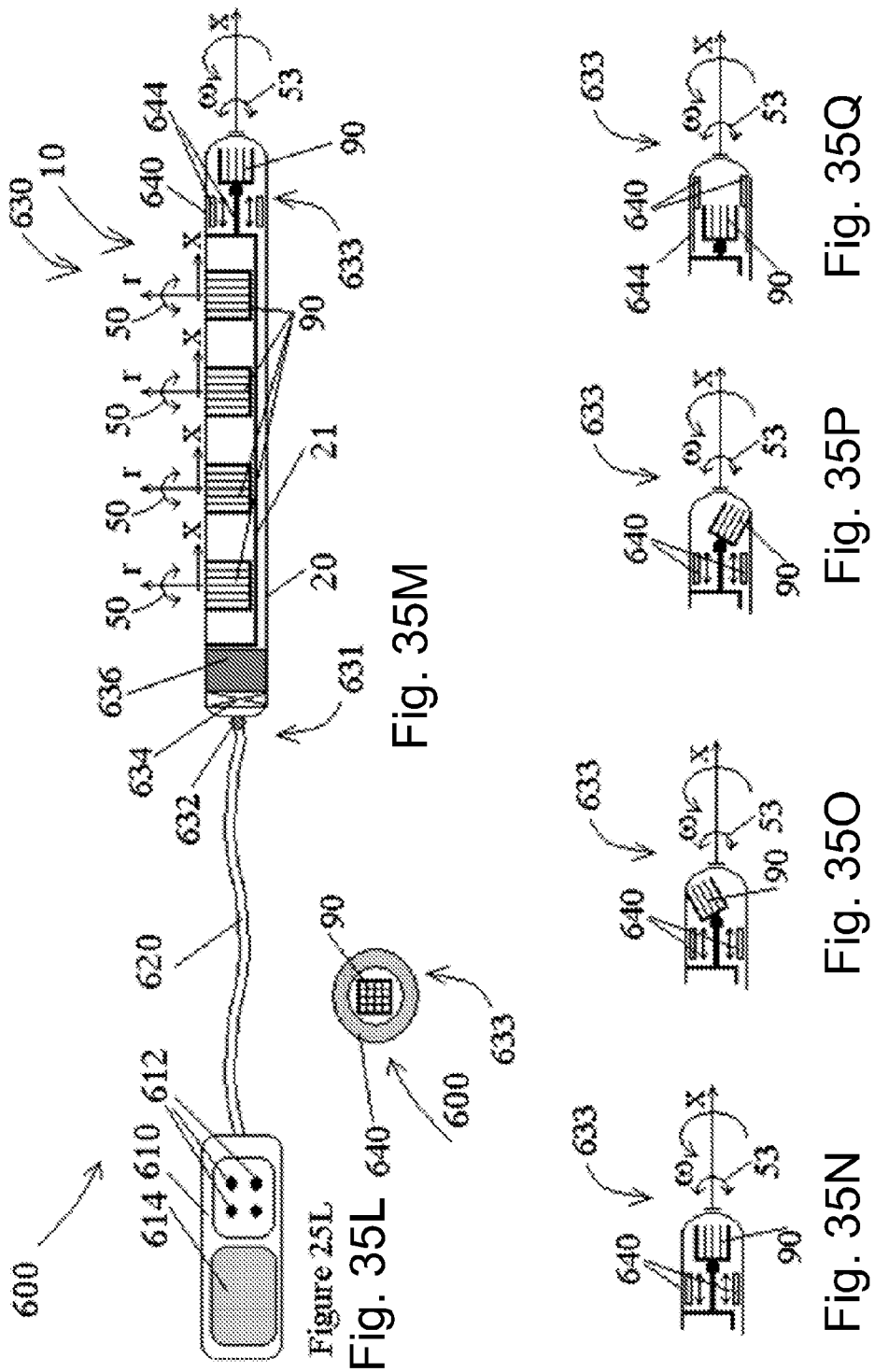

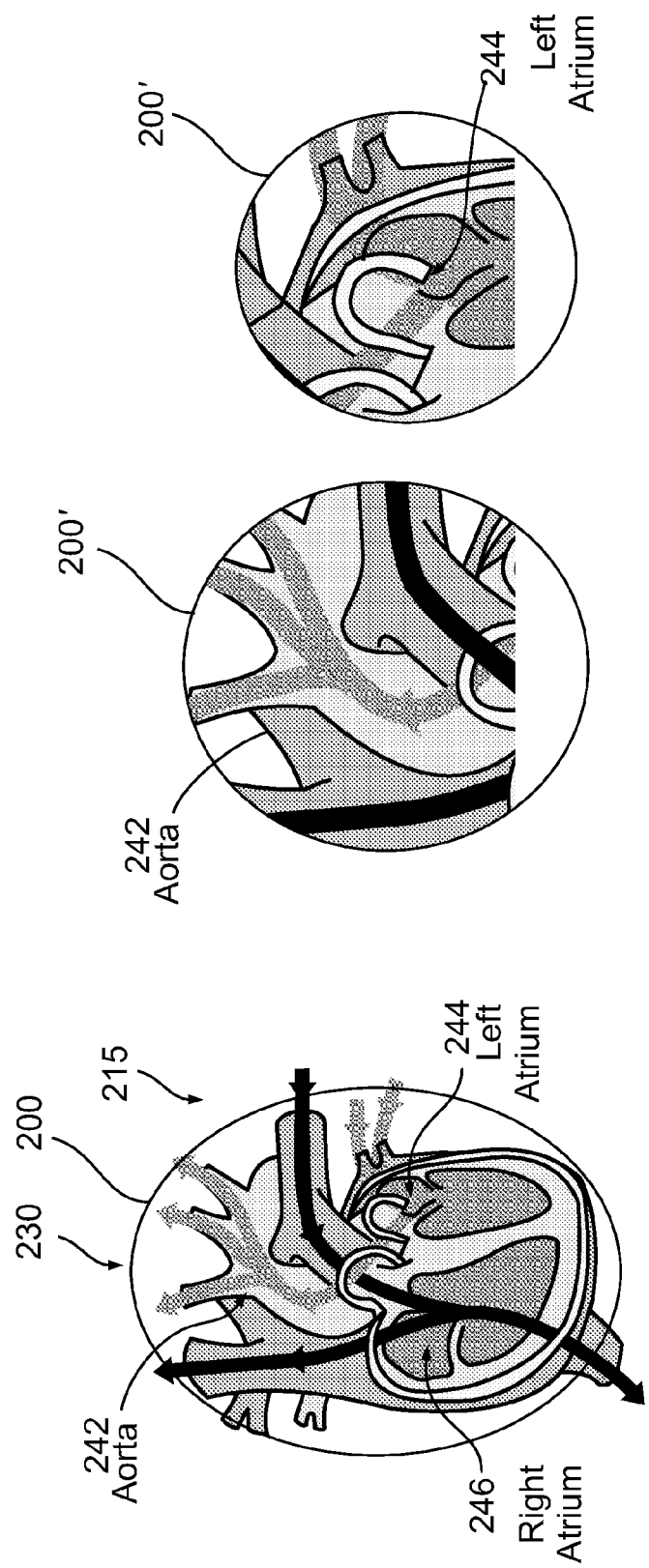

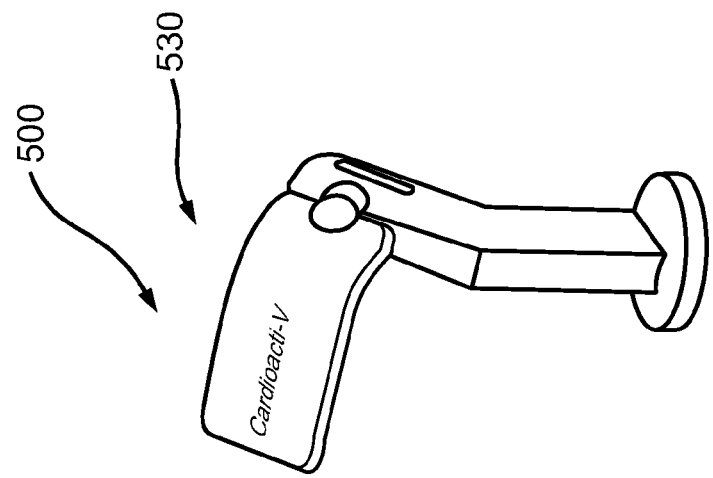
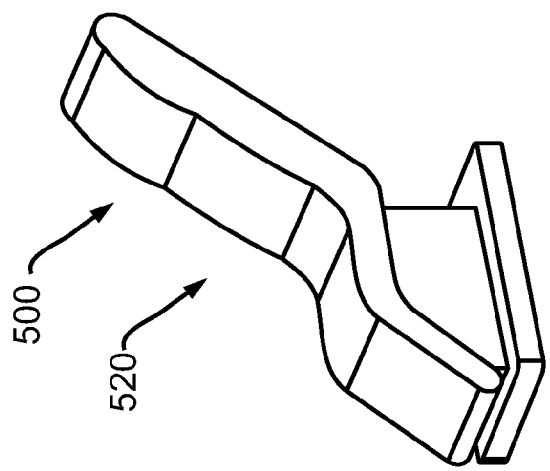
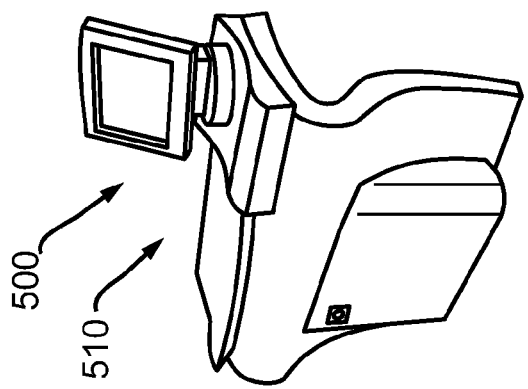
Fig. 42
Fig. 41
Fig. 40

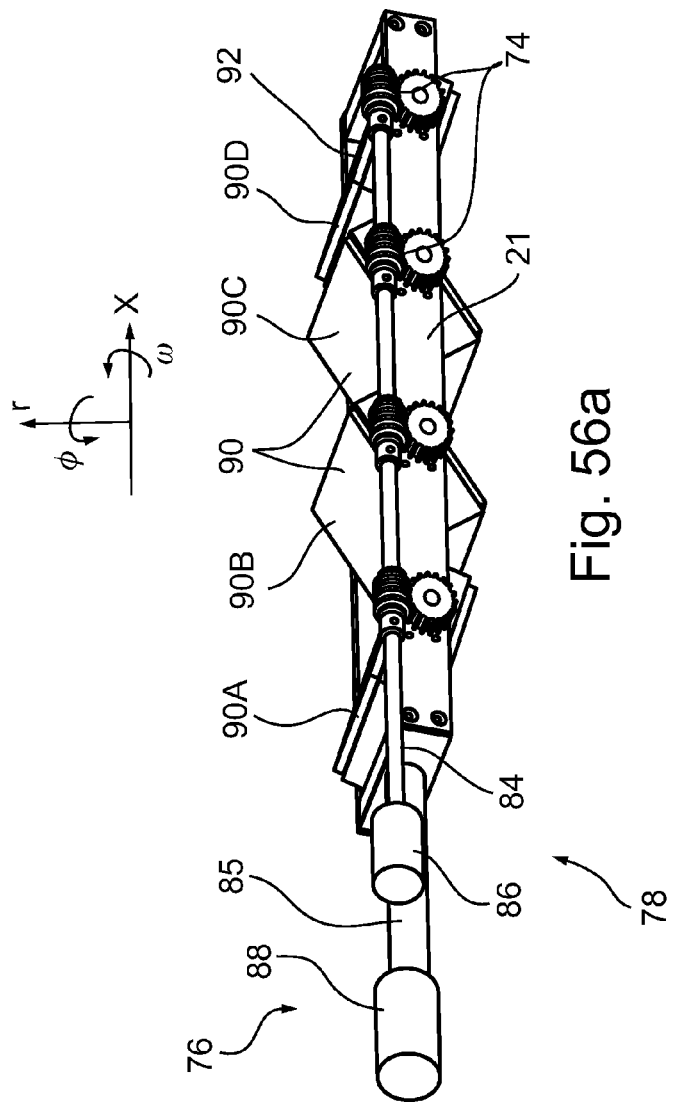
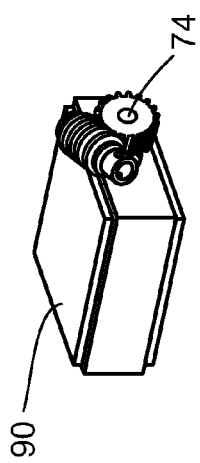
Fig. 56a
Fig. 56b

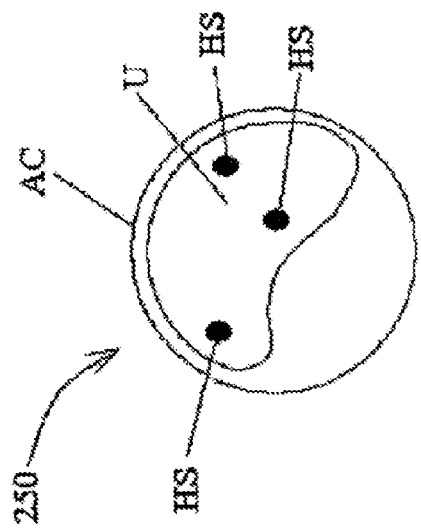
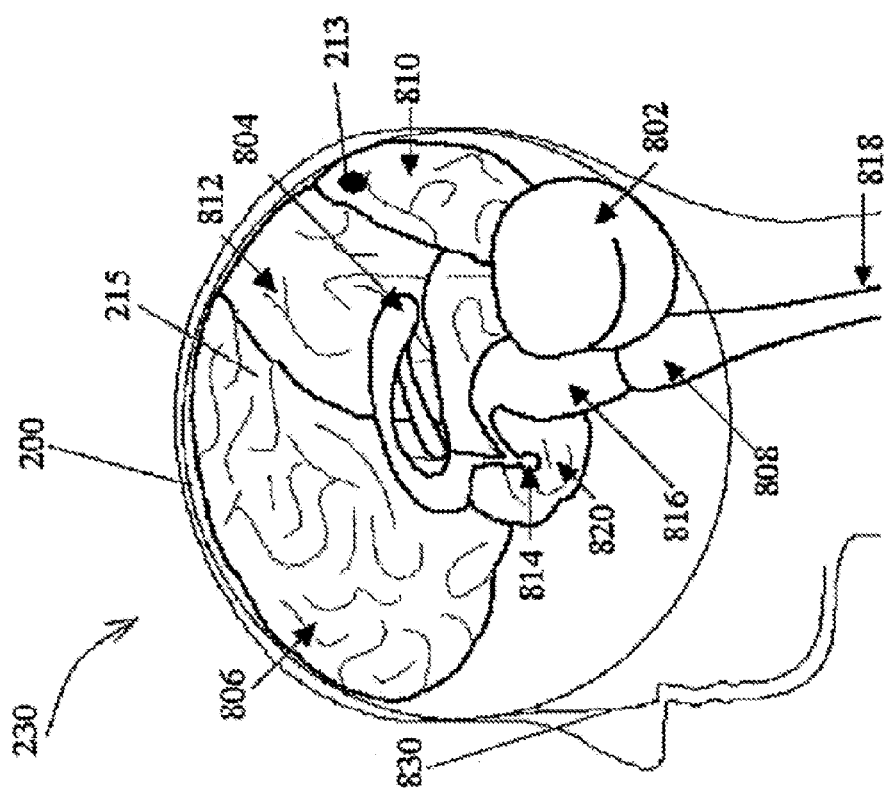
Fig. 57B
Fig. 57A

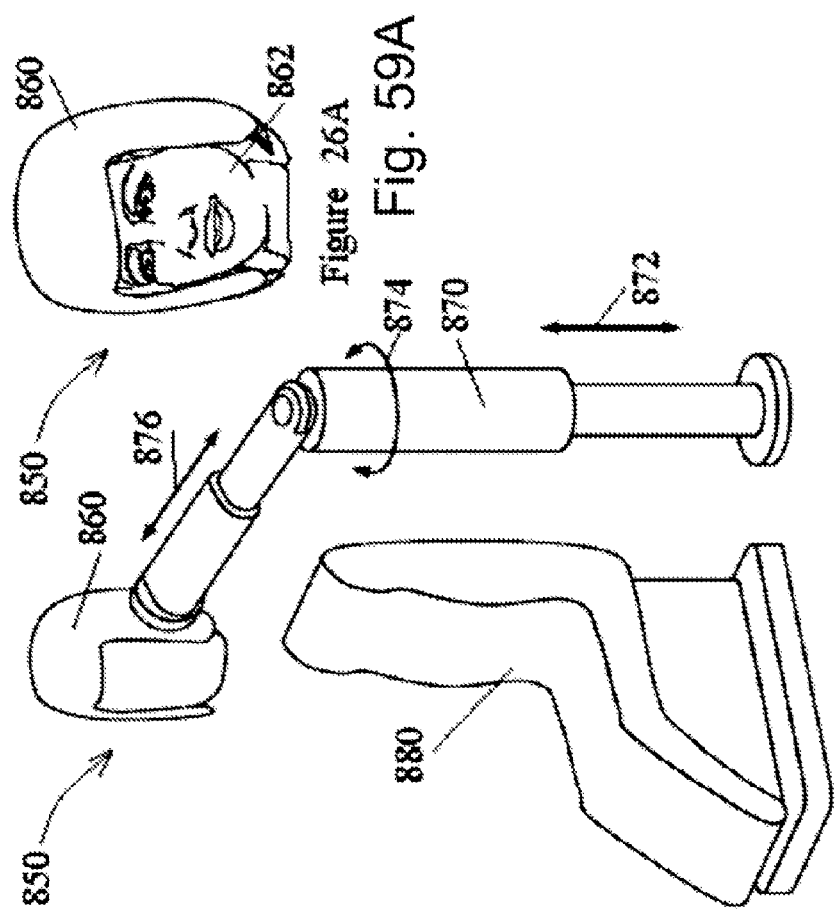
Fig. 59A
Fig. 59B
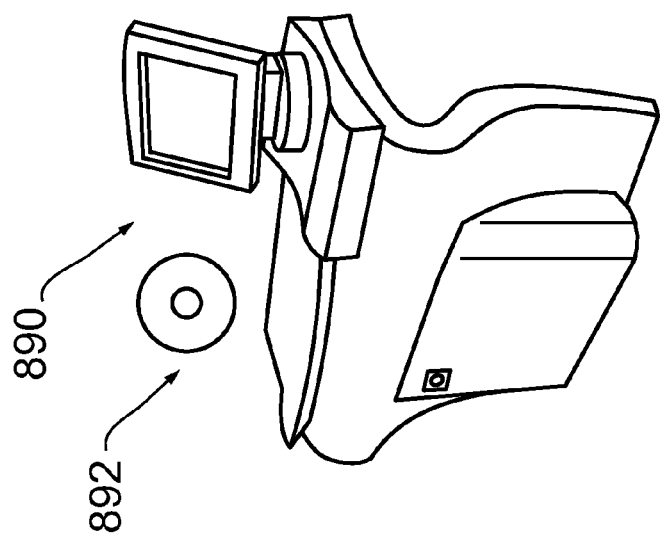
Fig. 59C

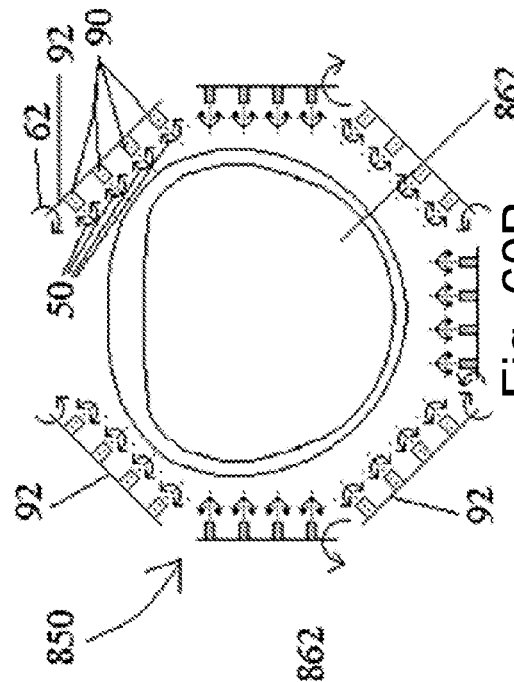
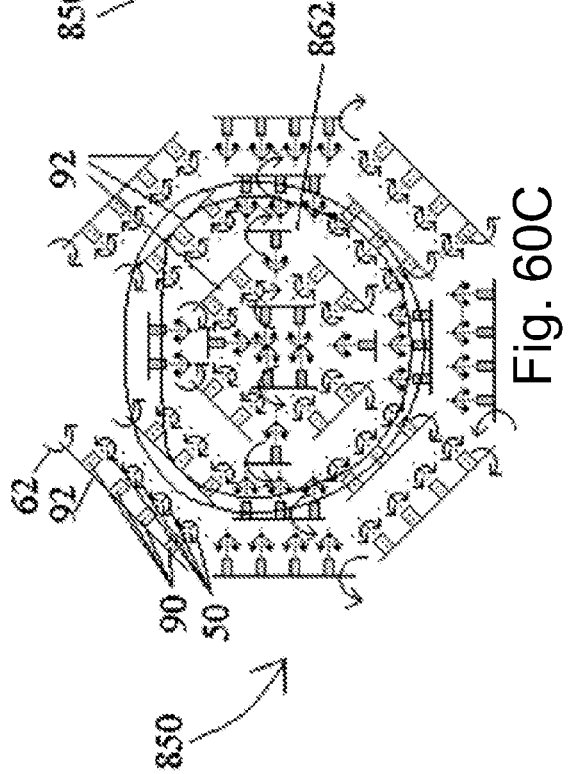
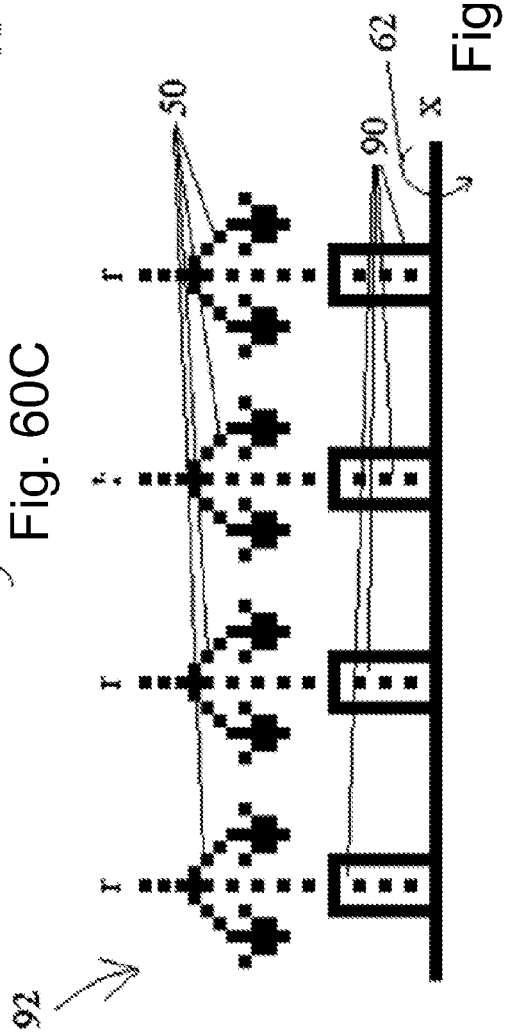
Fig. 60A
Fig. 60B
Fig. 60C

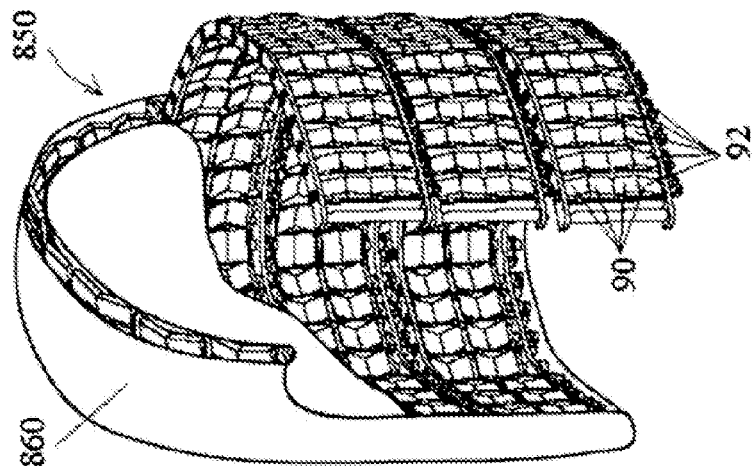
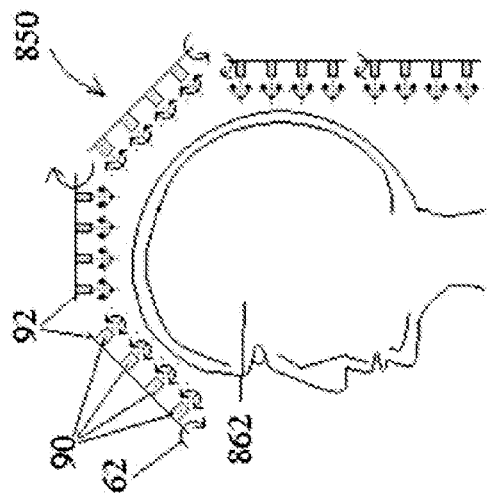
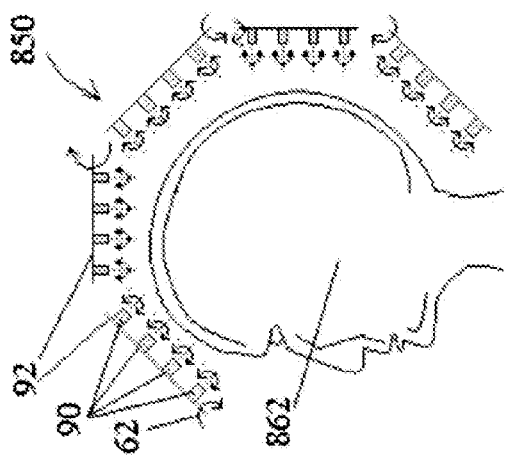
Fig. 60F
Fig. 60E
Fig. 60D

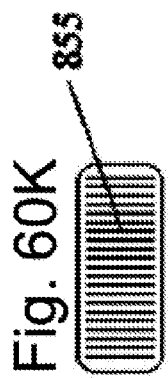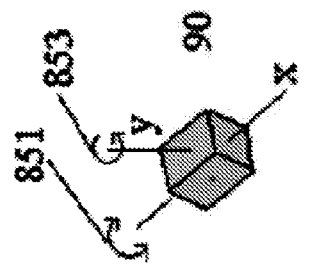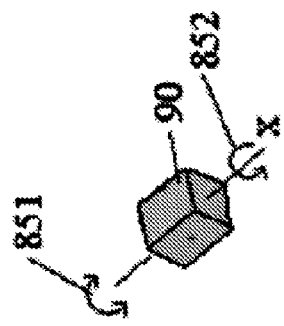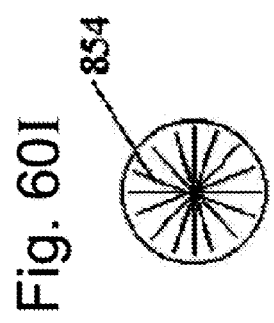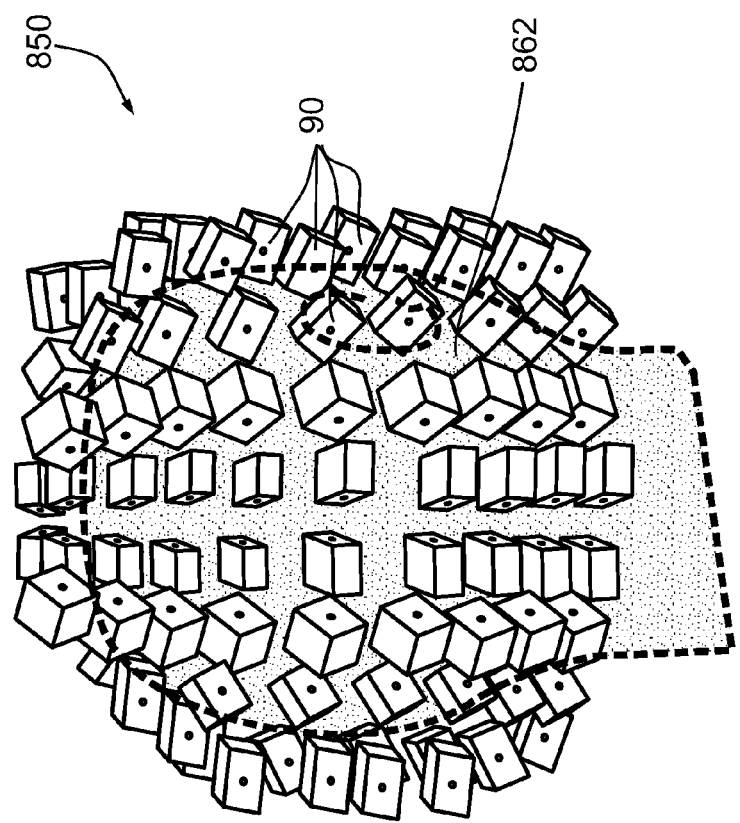

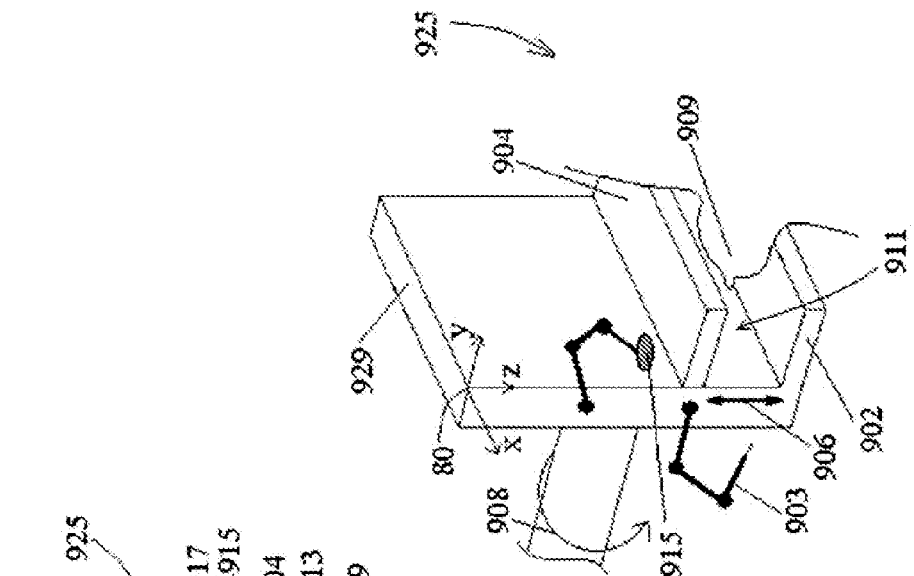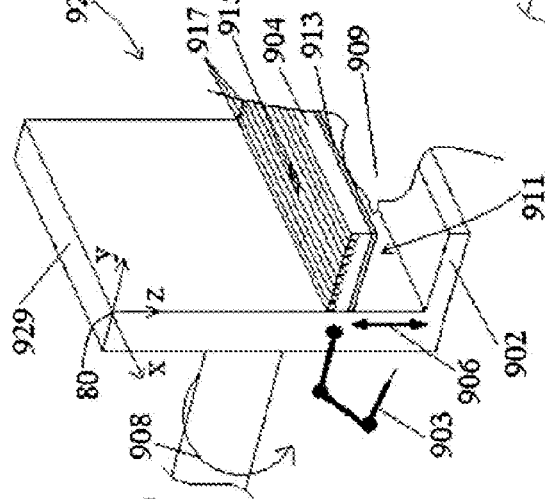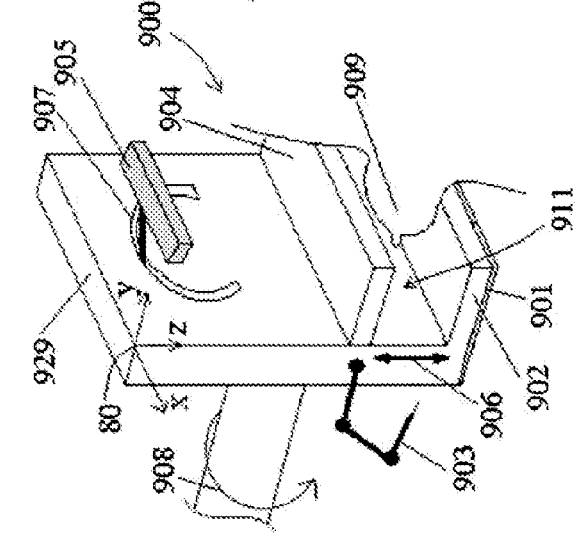

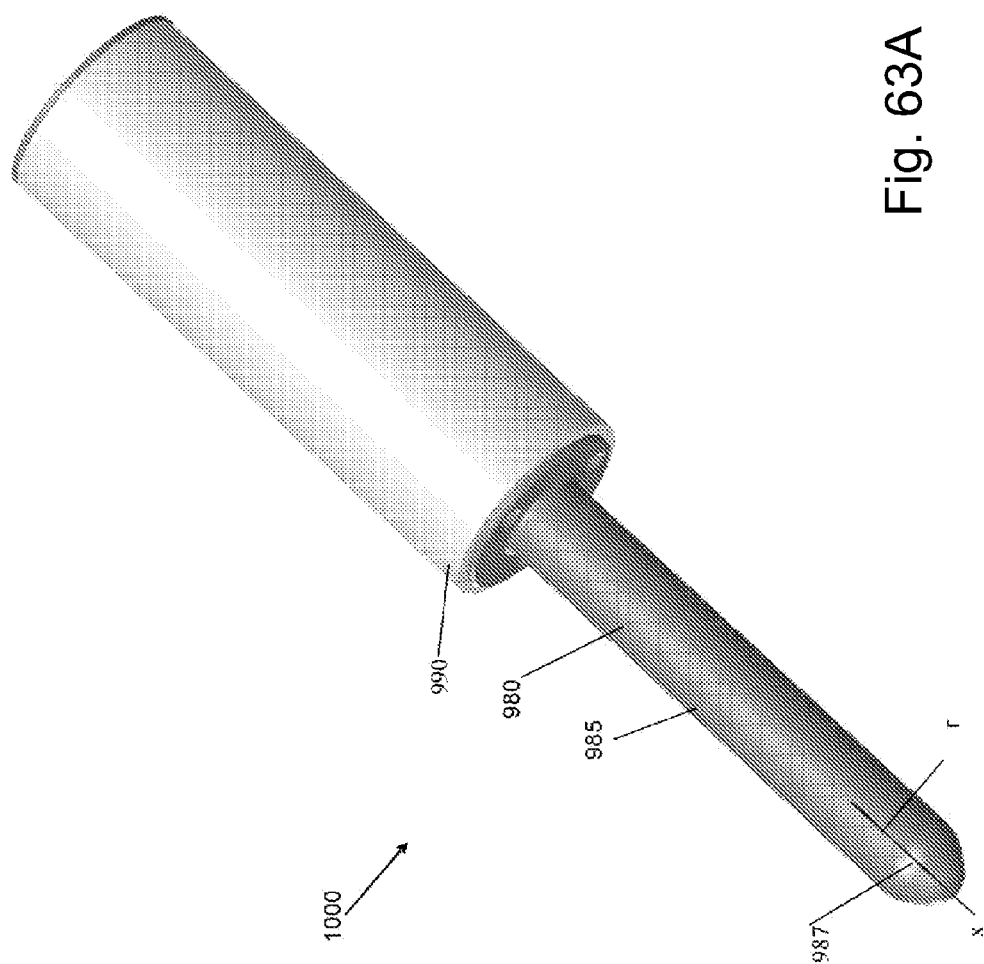

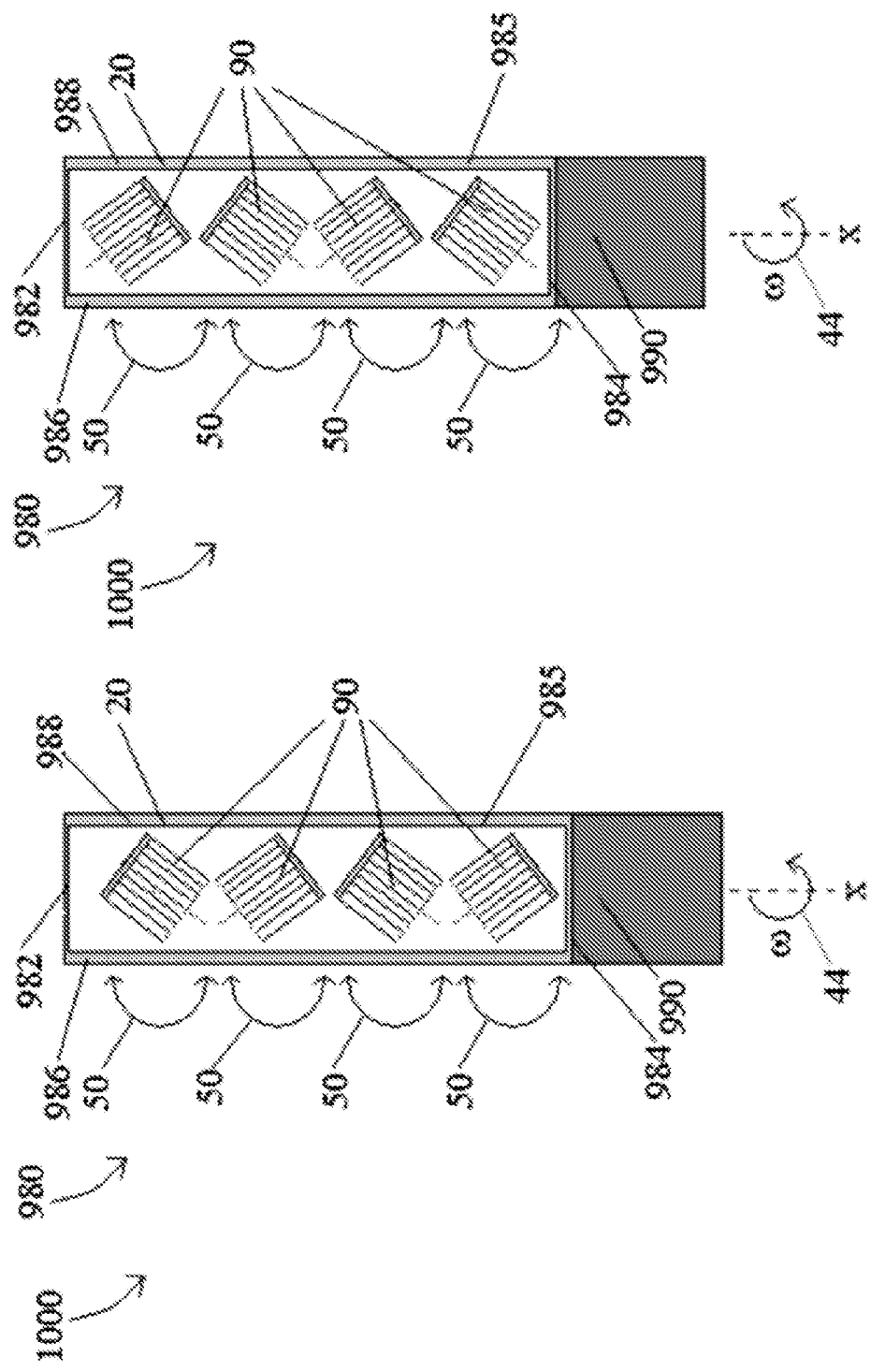

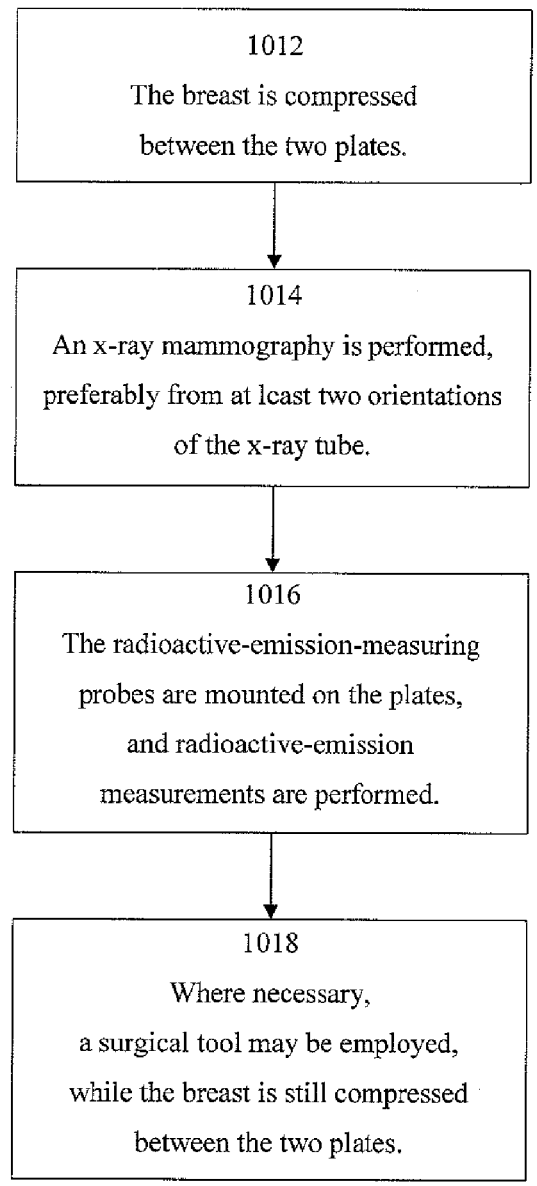

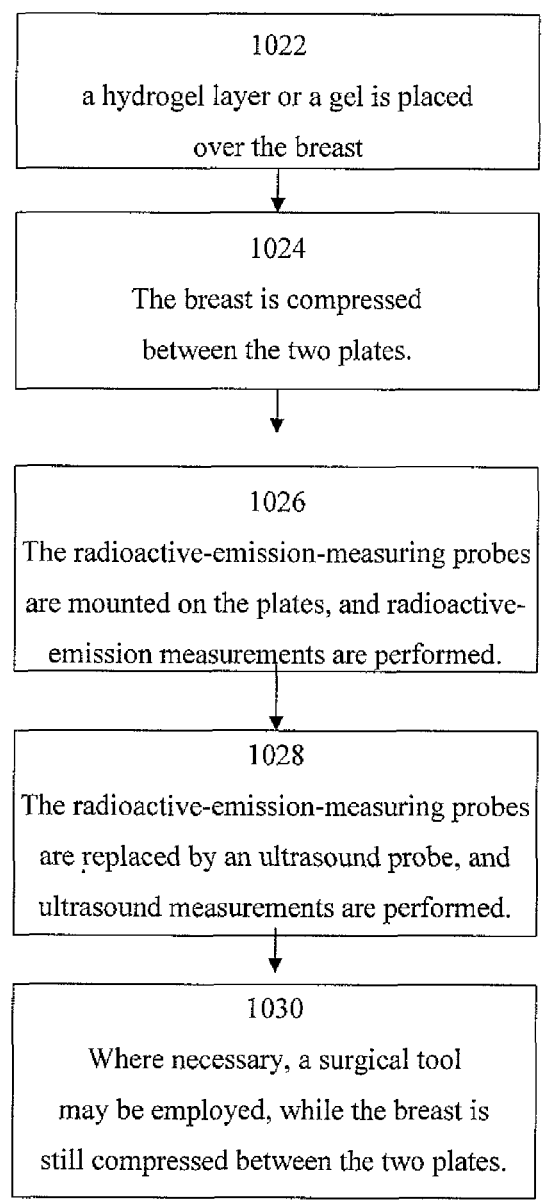

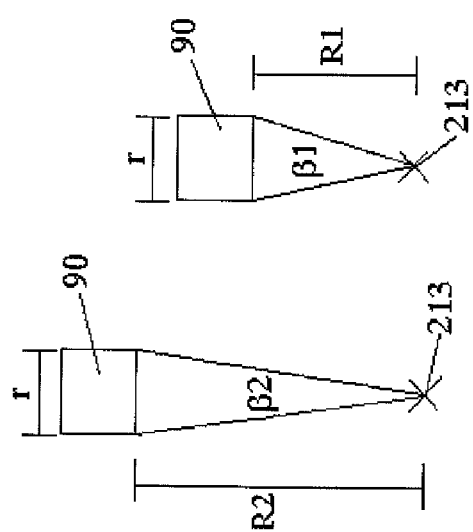

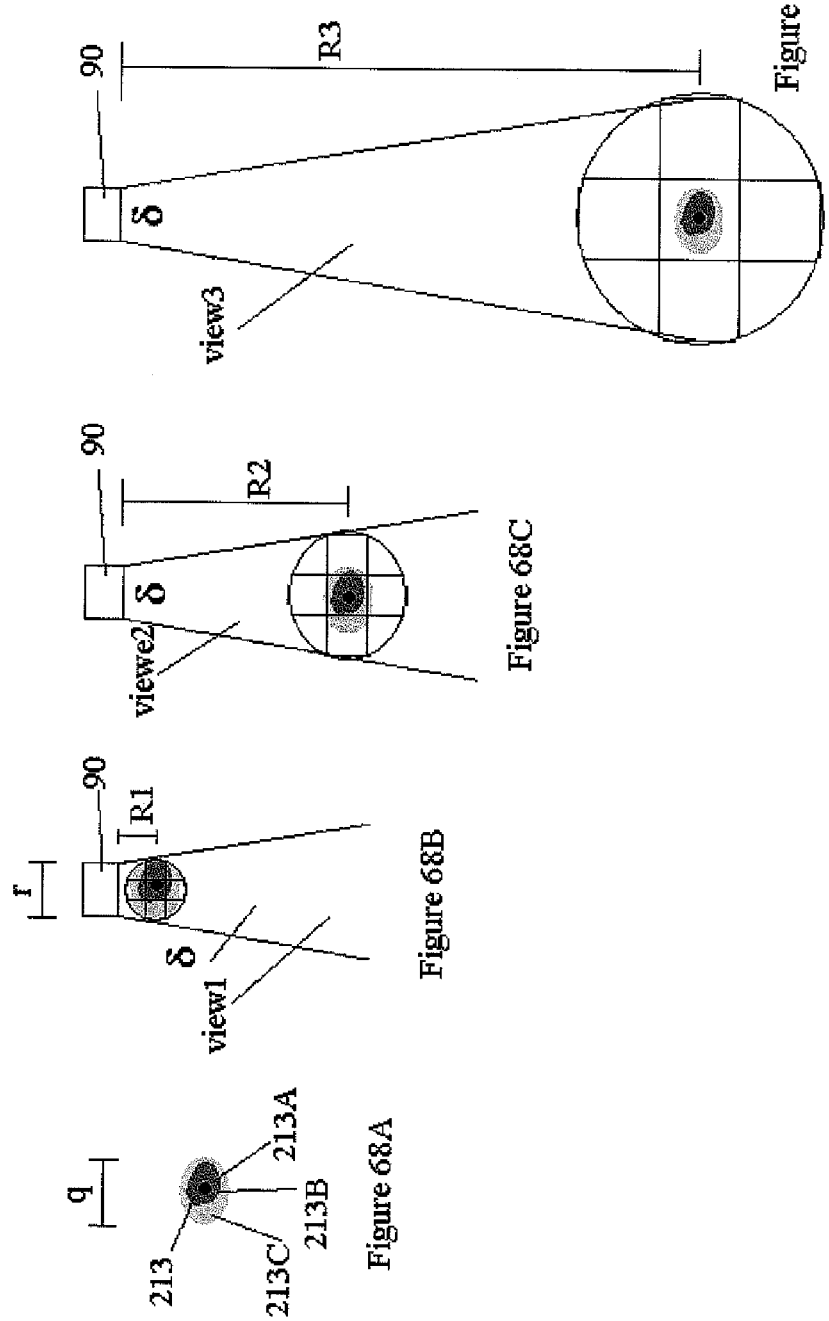

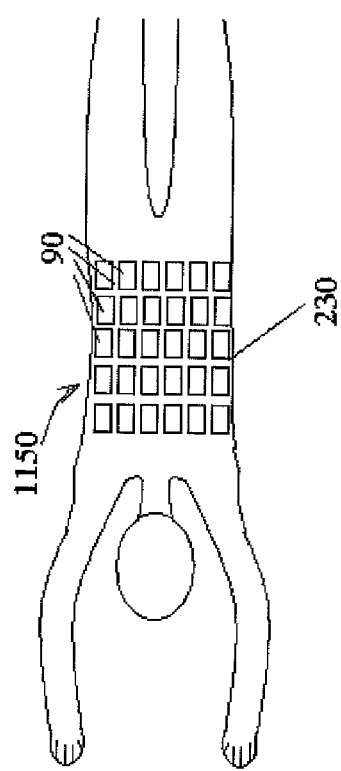

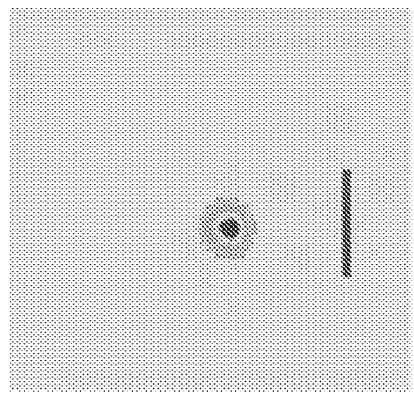 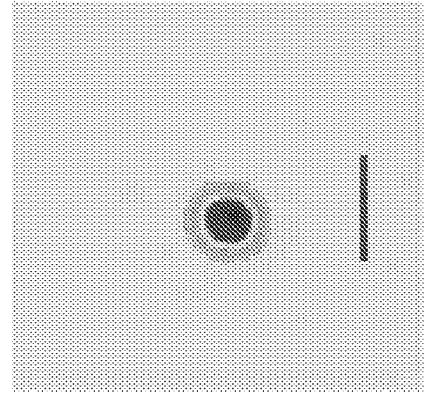
Figure 76A    Figure 76B
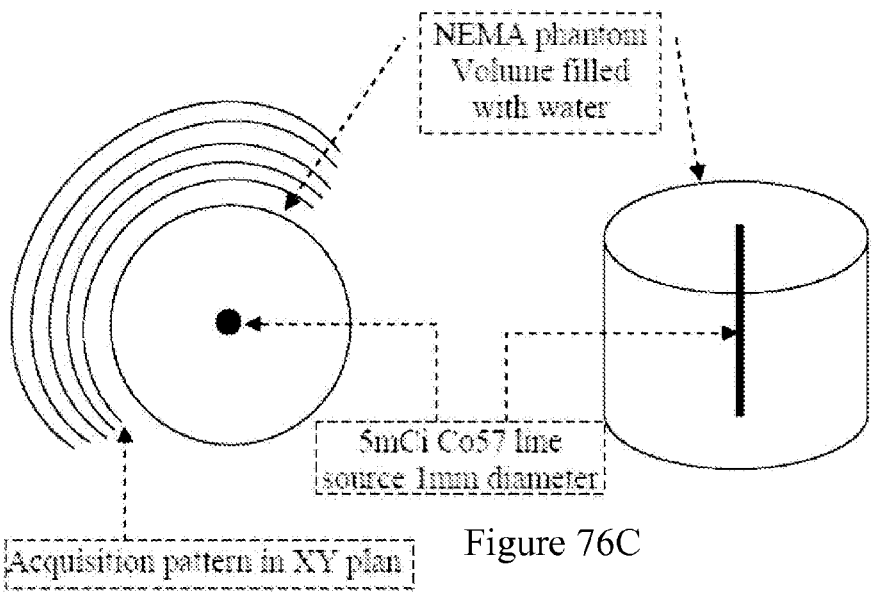
Figure 76C

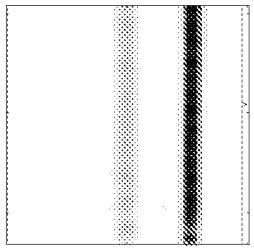
Figure 77B
x-z plane
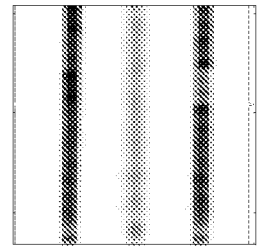
Figure 77C
y-z plane
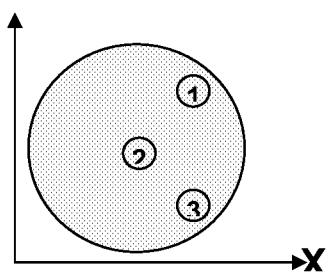
Figure 77A
Geometry
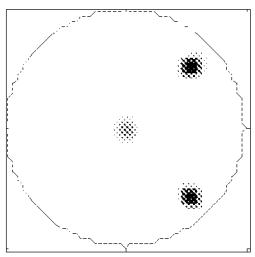
Figure 77D
x-y plane
reconstruction, without attenuation correction or smoothing.
Figures 77E of x-z plane    77F of y-z plane
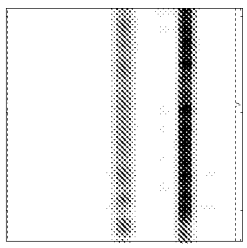 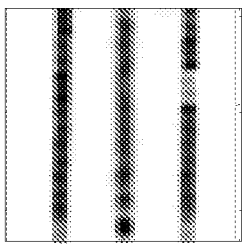
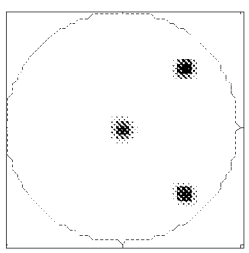
77G of x-y plane

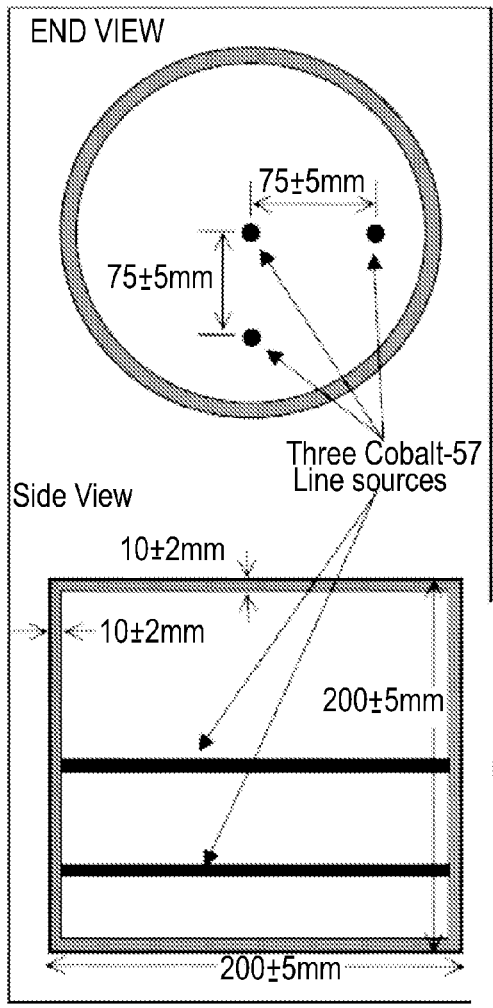
Fig. 78B
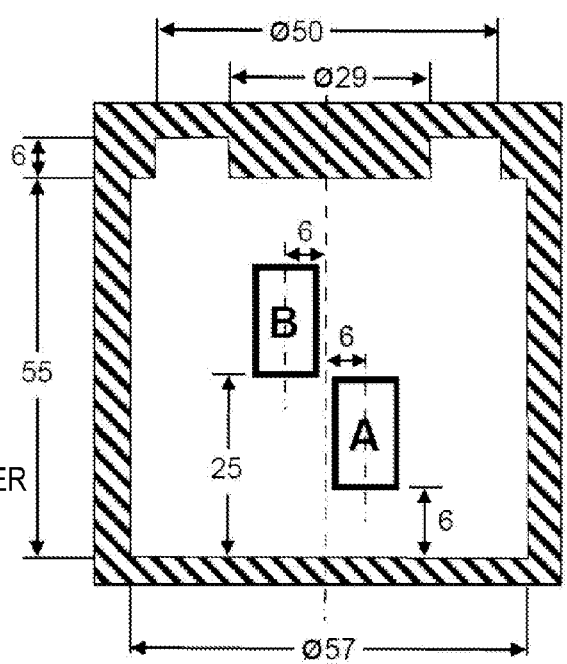
Fig. 78A
Fig. 78C
A,B: ø10 h=15
Target volume: 1.17cc
Background volume: 158cc Figure 79A of x-z plane
Figure 79B of y-z plane
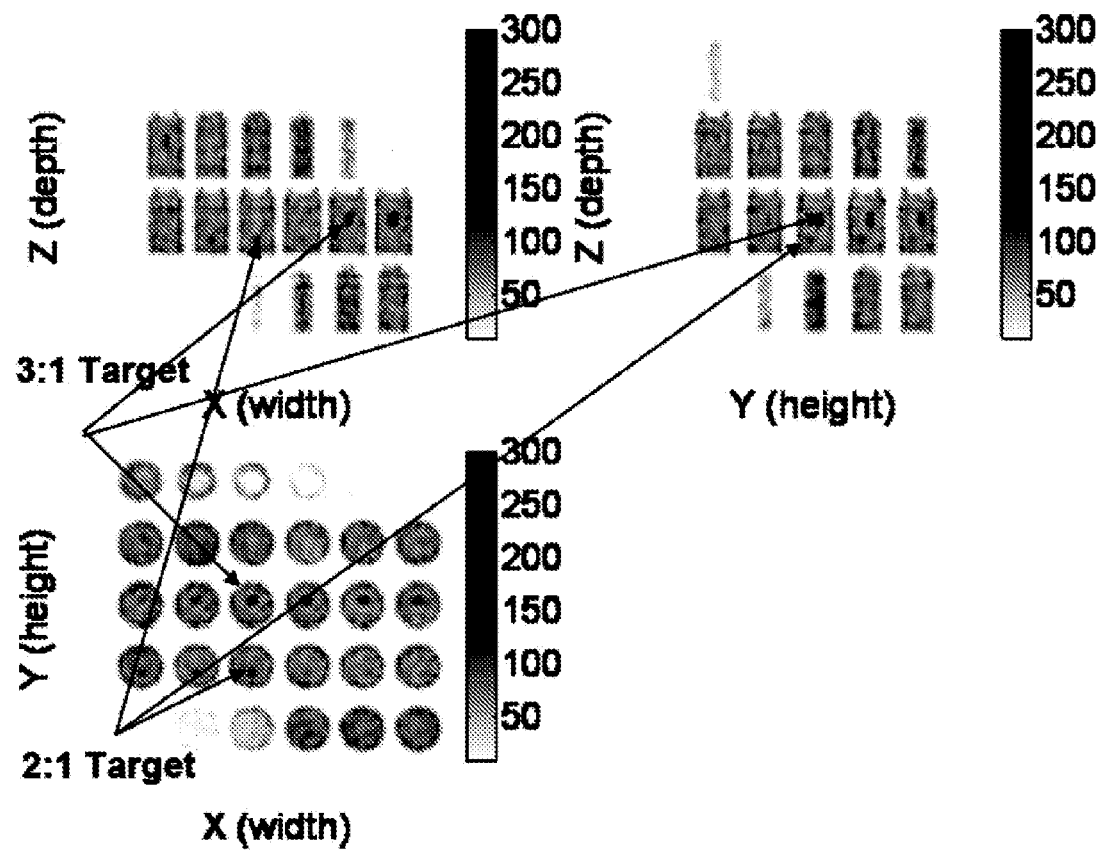
Figure 79C of x-y plane

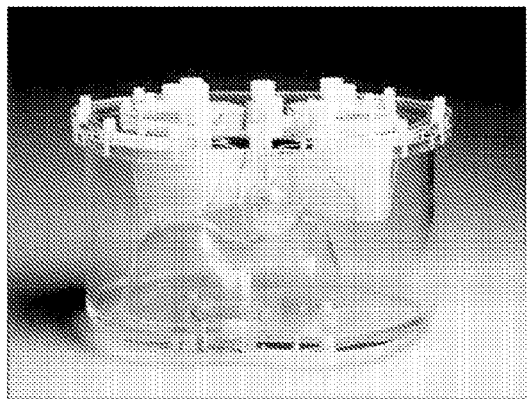
Anthropomorphic Torso Phantom
Model ECT/TOR/P
Produced by Data Spectrum
Corporation, USA
Figure 80A
The resulting reconstructions as compared to that performed by the conventional camera are shown below (keeping the same brightness and spatial scale):
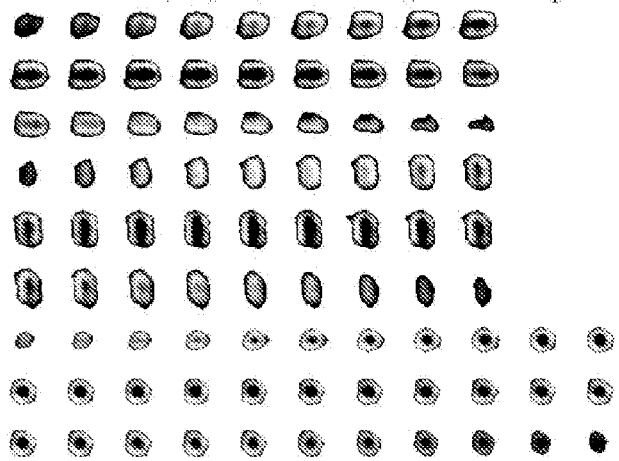
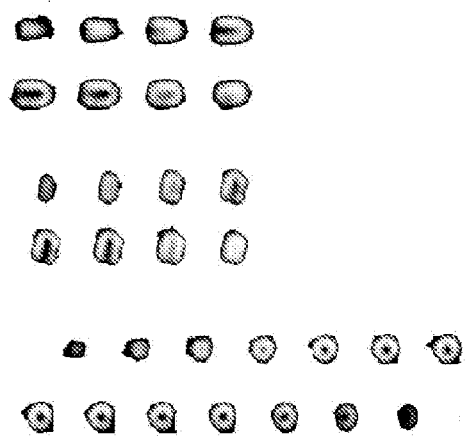
Figure 80B
probe of the present invention
Net Acquisition time = 1.25min
Figure 80C
Conventional Camera
Net Acquisition time= 12.5min

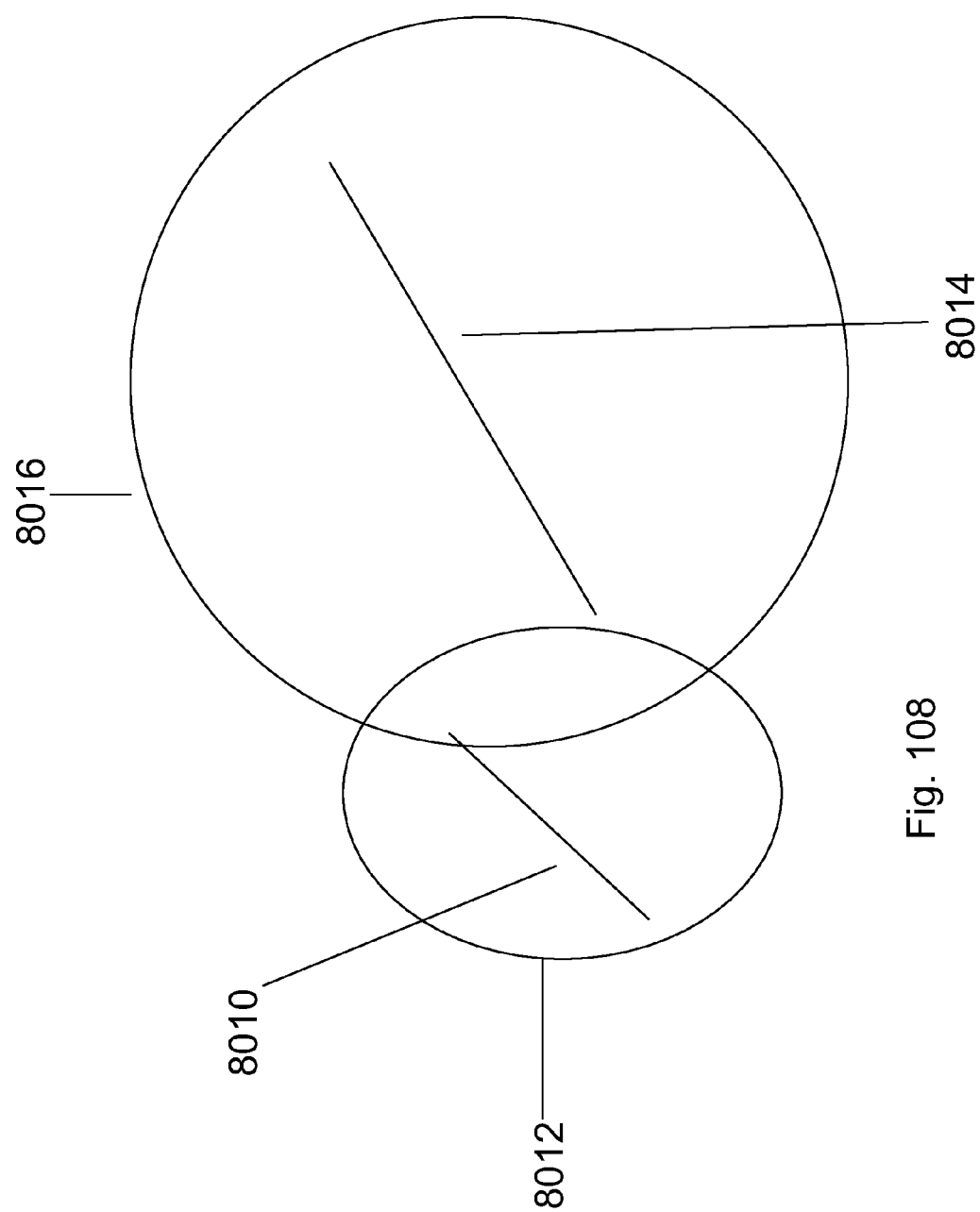

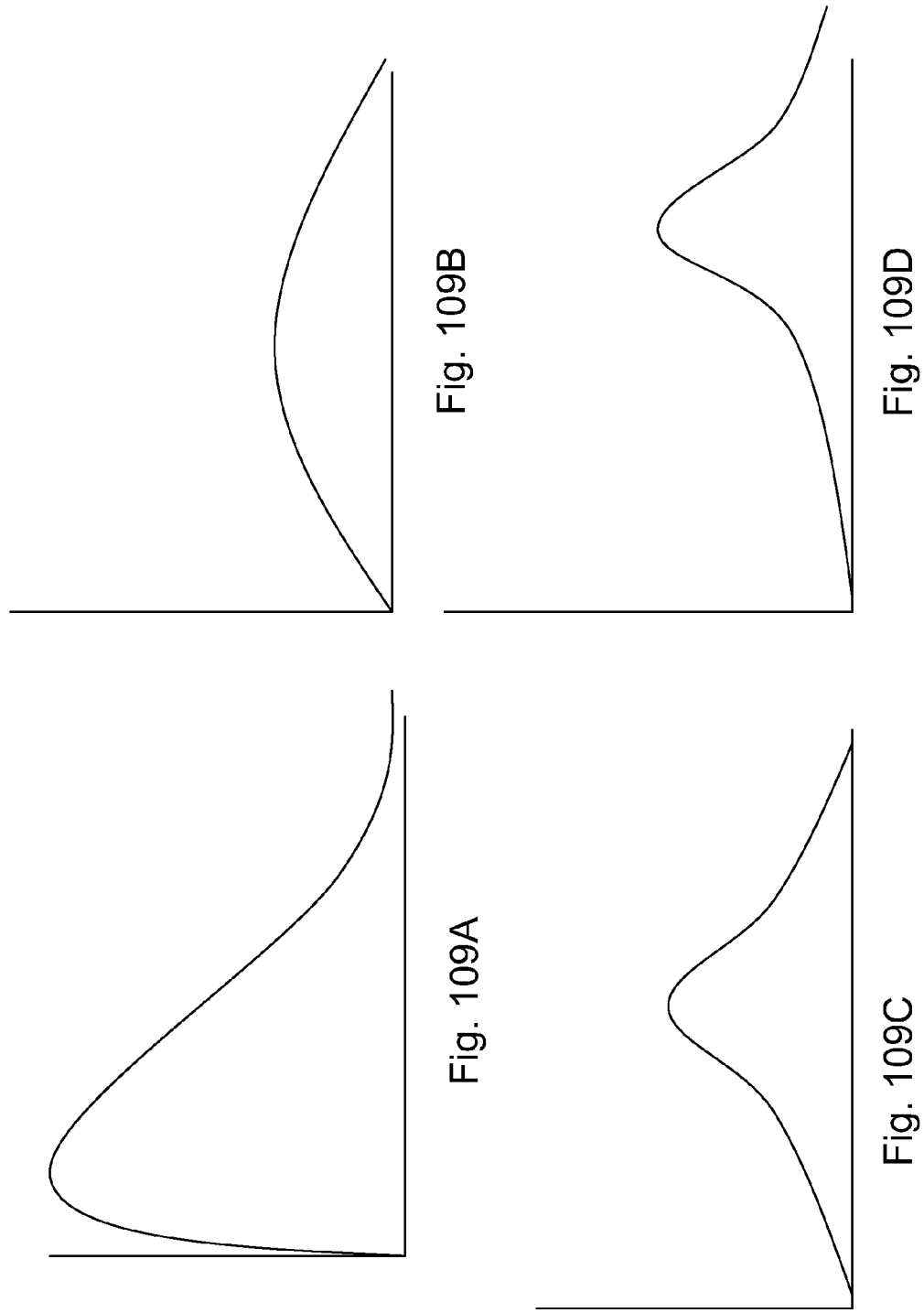

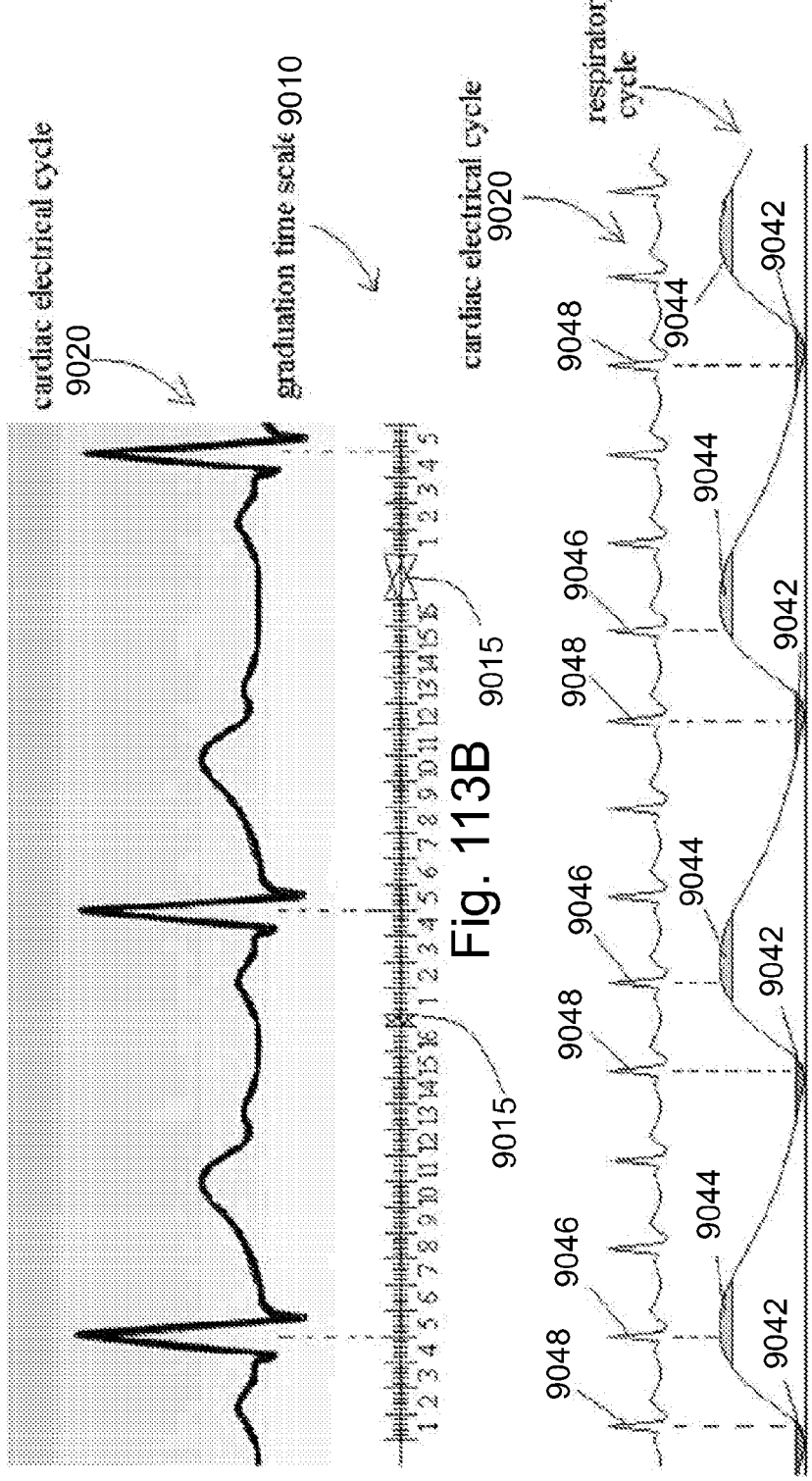

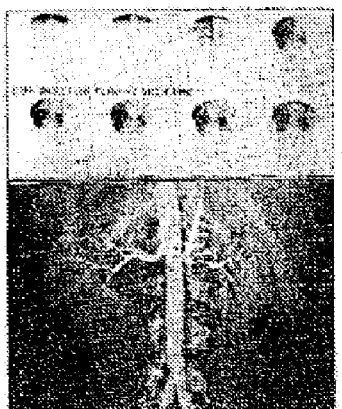

- Differential Diagnosis includes Vascular, Parenchymal, Urinary Obstructive Disease, infectious process
- TODAY: work-up involves multiple steps using multiple imaging modalities

- Nuclear/Functional Imaging:
  - 99Tc DMSA and/or DTPA nuclear scan
- Anatomic Imaging:
  - CT and/or US
  - Urography (Iodine contrast)

Spectrum Dynamics 1-step simultaneous imaging:

1. 99Tc DMSA : glomerular filtration
2. 67Ga : inflammation/infection
3. CT/US concomitantly

Spectrum Dynamics 1-step simultaneous imaging PLUS concomitant CT/Echo:

| Graft Patency: 99Tc Sestamibi myocardial perfusion | Osteomyelitis: 99TcHDP-bone scan | Mediastinitis: 67Ga-inflammation |

 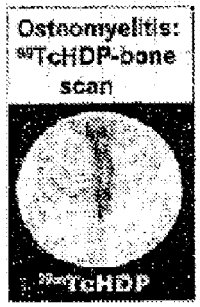 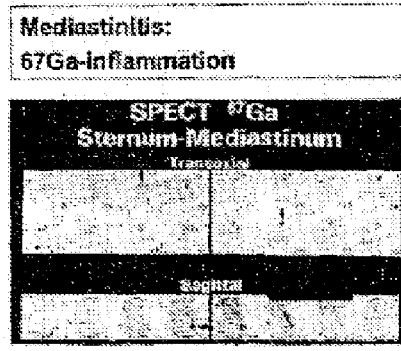

Fig. 138

| Indication | compound #1 compound detects | admin | compound #2 compound detects | admin | compound #3 compound detects | admin | compound #4 compound detects | admin | compound #5 compound detects | admin | compound #6 compound detects | admin |
|---|---|---|---|---|---|---|---|---|---|---|---|---|
| liver-SOL/spleen | Tc colloid texture | + t0-4mCi | Tc-RBC vascularity ==> | t0 low-dose | Ga67 | 2d-20mCi >10min inject >4h image | Inflamation/tumor low % cases | 1d-8mCi | | | | |
| hemagioma | | | | | | | | | | | | |
| tumor | | | | | | | | | | | | |
| abcess | | | | | | | | | | | | |
| bone scan | Tc MDP Abnormality | ==> t0-25 | Ga67 | | Inflammation inject after Tc, image 6h after imaging, typically 24h maybe can bind to residuals of bacteria | | | | | | | |
| infection | | | In+WBC | ==> | few hr after injection, map 24 hr later inflamation | | | | | | | |
| morco fractures/trauma | | | HIG | | | | | | | | | |
| tumors | | can add | FDG F18 for SOL and for bone scan | | | | | | | | | |
| arthritis | | | F18 tumors in bone marrow | | | | | | | | | |
| | | | FDG tumors /infection in bone narrow | | | | | | | | | |
| cardio | Tc | 30-60 min rest | Tc | | 30-60 after stress inject during stress | | | | | | | |
| | Thallium stress first | | Thallium rest | | | | | | | | | |
| cardio | Mibi+Tc/Th rest/stress | t0 rest | MIBG | | automatic OR b-adrenalin receptors? 10 | BMIPP | heart failure | to | FDG | viability to | | |
| | Mibi+FDG concurrent | | (Sandler?) did it in SPECT, thus less efficiency | | | | | | | | | |
| lymphoscintigraphy | Colloid+Tc mapping sentinel node | FDG | tumor | | 5-10mCi | | | | | | | |
| determining if the snetinel lymph node is | t0-0.8mCi | | | | | | | | | | | |
| has a tumor | intraoperative as well | Mibi+Tc | tumor | | 20mCi | | | | | | | |

Today can not be simultaneous due to technical limitations
True for all Tc+F18

Fig. 139A

FDG+Tc

Tc first
every tumor and mapping the metastasis
FDG secondary

Tumor - FDG
Lung, colon, melanoma, lymphoma mapping of tumor vascularization ???          Albumin Tc macroaggregates FDG also for brain or Cardiac. Other indication usually lead to whole body scan

Fig. 139B

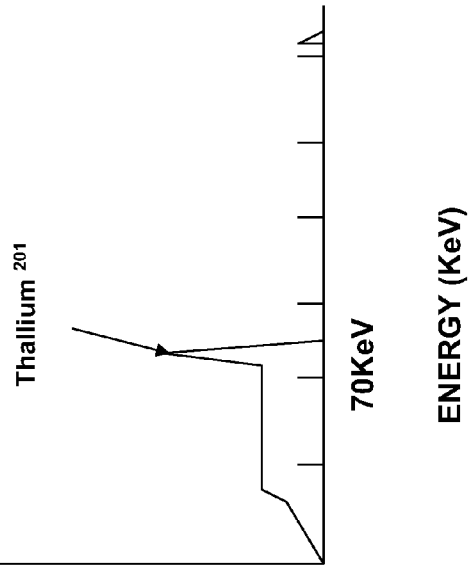
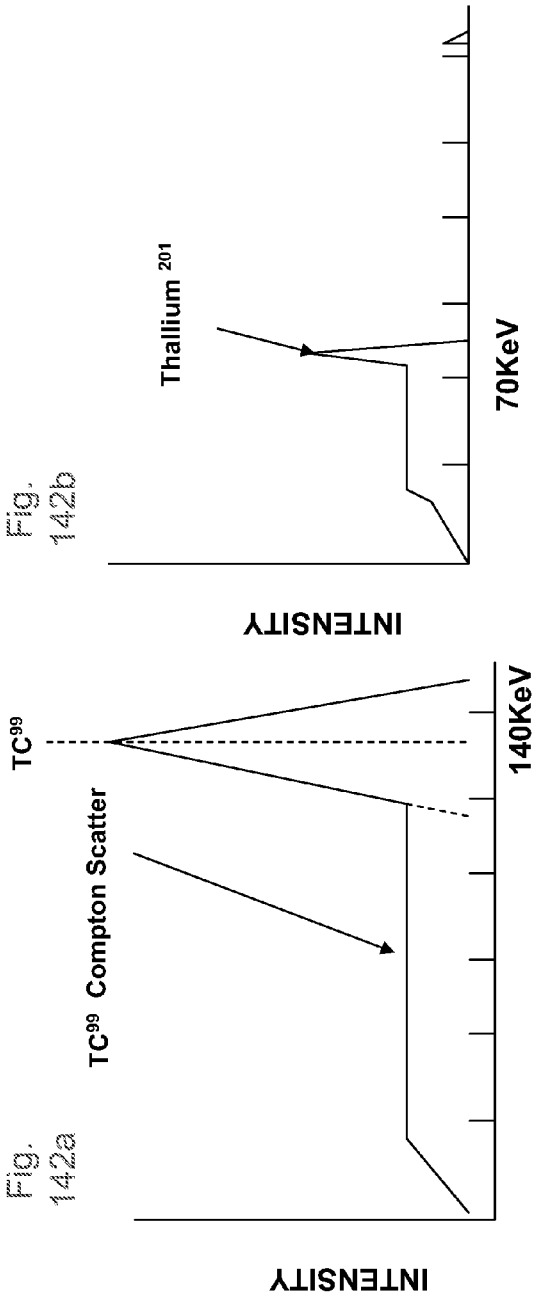
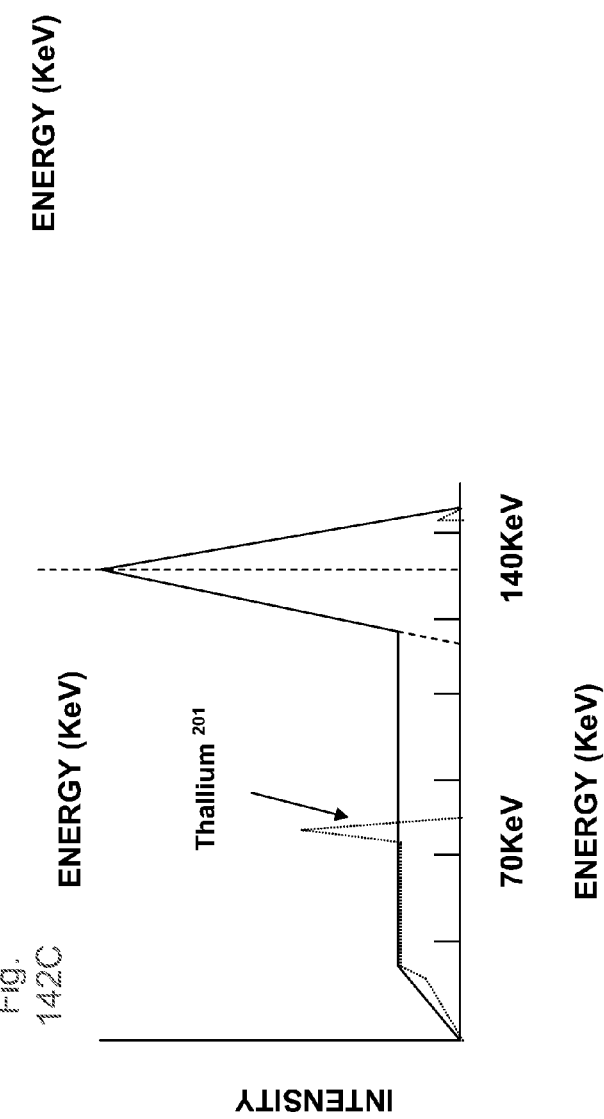

| Protocol | Rest injection | | Waiting time | Rest imaging | Stress |
|---|---|---|---|---|---|
| Standard protocol-dual isotope-fast imaging | Tl | 3mCi | 10-15 min | 2 min | treadmill |
| Standard protocol-single isotope-fast imaging | Tc-MIBI | 8-10mCi | 30 min | 2 min | treadmill |
| Ultra-Fast dual-isotope Protocol | Tl | 3mCi | 2 min | 2 min | pharma |
| Ultra-Fast Single Isotope Protocol | Tc-MIBI | 8-10mCi | 0 | 2min | pharma |
| Simultaneous dual-isotope | Tl | 3mCi | | | treadmill |
| Thallium stress perfusion | Tc-MIBI | 3mCi | 30 min | 2 min | treadmill |
| Fast Thallium stress perfusion | Tc-MIBI | 3mCi | 30 min | 2min | pharma |
| Ultra-Fast Thallium stress perfusion | Tc-MIBI | 3mCi | 0 | 2min | pharma |
| Simultaneous Thallium stress perfusion | Tc-MIBI | 3mCi | 30 min | | exercise/pharma |
| Teboroxime | Teboroxime | 8-10mCi | 0 | 2min- then wait 10 min | pharma |

\*\*\*\*ALL STUDIES ARE GATED

Fig. 148A

| Stress injection | | Waiting time | stress gated imaging | Total Camera Time | Total Patient Time | Benefit | D-SPECT Requirements |
|---|---|---|---|---|---|---|---|
| Tc-MIBI | 20-30mCi | 30 - 60 min | 2 min | 4 min | 60-90 min | rapid imaging (better resolution) | |
| Tc-MIBI | 20-30mCi | 30 - 60 min | 2 min | 4 min | 90 min | rapid imaging (better resolution) | |
| Tc-MIBI | 20-30mCi | immediate | 2 min | 4 min | 20-30 min | rapid imaging; less blinding by liver | of stress; all injections while positioned |
| Tc-MIBI | 20-30mCi | immediate | 2 min | 4 min | 20-30 min | rapid imaging; less blinding by liver | of stress; all injections while positioned |
| Tc-MIBI | 20-30mCi | 30-60 min | 2 min | 2 min | 60-90 min | better registration of images-shortened overall imaging time | |
| Tl | 3 mCi | 10-15 min | 4min | 6min | 45-60 min | better flow linearity; ability to detect smaller lesions; viability | |
| Tl | 3 mCi | immediate | 4min | 6min | 20-30 min | better flow linearity, ability to detect smaller lesions; viability | of stress; all injections while positioned |
| Tl | 3 mCi | | 0 4 min | 6 min | 10-20min | better flow linearity, ability to detect smaller lesions; viability | not effected by liver uptakepharmacologicol stress; |
| Tl | 3 mCi | 2min | 4 min | 6 min | 10-20min | linearity; ability to detect smaller lesions; viabilityone | |
| Teboroxime | 20-30mCi | | 0 2min | | | | |

Fig. 148B

| Protocol | Clinical Significance | Radioisotope | Radiopharmaceutical |
|---|---|---|---|
| Brain Perfusion - Perfusion Mapping | Perfusion described by quantative parameters (ml/min/gr); Cerebral Flow Reserve in stress protocols using pharmacological stress agents); parametric quantitation; disease signature (Alzheimer's, depression, schizophrenia, etc. ...) | Tc-99m I-123 | HMPAO ECD (neurolite) IMP (spectamine) |
| Hepatobiliary - Tc99m sulfur colloid | routinely is done to look a the liver structure (hemangiomas, abcesses, liver enlargement, | Tc-99m I-123 | choletec |
| Lung v/P DTPA aerosol and macro-aggregated albumin (lung perfusion agent) | Perfusion described by quantitative parameters (ml/min/gr); | Tc-99m I-123 | |
| MDP-bone scan-whole body scan | routinely performed to look for bone tumors or inflammatory processes of the bone (e.g. osteomyelitis) | Tc-99m | MDP |
| Kidney- Renal Function-Dynamic FlowStudy 111 in DTPA & 99mTc-MAG3 | Assessment of filtration and tubular secretion; Perfusion described by quantitative parameters(ml(min/gr) parametric quantitation | Tc-99 In-III | DTPA MAG3 |
| Kidney- Renal Function-Dynamic FlowStudy 111 in DTPA & Hippuran 1-123 | Assessment of filtration and tubular secretion; Perfusion described by quantitative parameters(ml/min/gr) parametric quantitation | Tc-99 I-123 | DTPA Hippuran |

Fig. 148C

| Total Injected Dose | Time to acquisition | Acquisition protocol | Acquisition Time | Benefit |
|---|---|---|---|---|
| up to 3mCi for Tc-99m labeled up to 0.5mCi for I-123 | wait up to one hour after injection | energy window- anywhere between 3-15% | 0-30 min | can show stroke at early stages<br>Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| up to 0.5mCi | immediate acquisition | energy window- anywhere between 3-15% | 0-30 min | |
| MAA up to 0.5mCi (up to 1M particles) | immediate acquisition immediately after DTPA, MAA in injected and the immediate acquisition | energy window- anywhere between 3-15% | 0-30 min | fast |
| 2-3mCi | 0-60 min | energy window- anywhere between 3-15% | up to 60 min | fast |
| 0.2mCi In-111<br>up to 1mCi Tc-99m | 0 or before | energy window- anywhere between 3-15% | up to 30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |
| 0.3mCi In-123<br>up to 1mCi Tc-99m | | energy window- anywhere between 3-15% | up to 30 min | Study:<br>o Fluid flow<br>o Tracer rate of uptake (passive or active)<br>o Tracer accumulation/redistribution<br>o Tracer metabolism<br>o Tracer/metabolites secretion and/or washout (active or passive) |

Fig. 148D

Table 7-A

| Protocol | Clinical Significance |
|---|---|
| vulnerable plaque-III in Annexin and/or 99m Tc-Acu Tcc | 99mTc-AcuTec attaches to activated platelets and shows thrombus, the Annexin attaches to apoptotic cells |
| Prostascint | imaging of prostate metastasis and possibly primary cancer |
| Octreoide 99m Tc-P829, Neotec® | In III-Ostreoide (tumor imaging agent for SST-receptor expressing tumors) Neuroendicrine tumors (Somatostatin receptors) |
| 99m Tc-P280, Acutect® | Thrombus detection; DVT and intrarerial thrombus in coronary and carotid arteries (GP IIb/IIIa receptors on platelets). |
| 123 I-MIBG (meta-iodo benzyl guanidine) | Tumor imaging (Pheochromocytoma) and or Myocardial failure; Adrenergic tissue uptake; Presynaptic adrenergic receptors |

Fig. 148E

Table 10-B

| Radiopharmaceutical | Total injected dose | Time to acquisition |
|---|---|---|
| Thallous chloride | up to 1mCi Tl-201 | |
| pertechnetate | up to 15mCi Tc-99m | 10 min |
| Sestamibi | up to 15mCi Tc-99m | |
| Iodide | up to 100microCi I-123 | 10 min |
| Iodide | up to 4mCi I-131 | |
| MDP | up to 10mCi MDP/RBC | up to 2 hours |
| Octeroide | up to 3mCi In-III | up to 3 days after In-III injection but not more than 2 |
| MDP | up to 15mCi Tc-99m | hours after MDP injection |
| Prostascint | up to 3mCi In-III | up to 3 days after In-III injection but not more than 2 |
| Tc-99m-RBC | up to 15mCi Tc-99m | hours after RBC injection |
| Colloid | up to 3mCi In-III | up to 3 days after In-III injection but not more than 2 |
| In-III WBC | up to 15mCi Tc-99m | hours after colloid injection?? |
| Thallous chloride | up to 2mCi Tl-201 | |
| MDP | up to 15mCi for MDP | up to 2 hours |
| Thallous chloride | up to 1mCi for Tl-201 | |
| MIBI | up to 10mCi for MIBI | |
| In-III WBC | up to 2mCi I-III WBC | up to 24 hours |
| Thallous chloride | up to 1mCi for Tl-201 | |
| MDP | up to 10mCi for MDP | |
| In-III WBC | up to 2mCi I-III WBC | up to 24 hours |
| Thallous chloride | up to 1mCi for Tl-201 | |
| MIBI | up to 10mCi for MIBI or teboroxine | |
| BMIPP | up to 2mCi I-123 WBC | up to 48 hours |
| NeutroSpect Tc-99m; | up to 15mCi Tc-99m | |
| WBC-In-III | up to 2mCi I-III | up to 24 hours |
| 123I-IBZM; Ceretec | up to 2mCi 123I; up to 15 mCi Ceretec | up to 48 hours |
| | up to 2mCi | |
| | up to 2mCi In-III ab | |
| | up to 10mCi Te | |
| In-III ab Tc-MIBI/CEA Tl | up to 1mCi Tl | up to 24 hours |
| | up to 2mCi IIIa- | |
| IIIIn DTPA & 99mTc-MAG3 | up to 15mCi 99mTc- | up to 24 hours |
| 201Tl or 99mTc-Teboroxinne & | up to 1mCI 201Tl or up to 15 mCi 99m Tc teboroxine | |
| 99mTcMIBI | OR | |
| | 99mTc MIBI | up to 1 hour |
| | up to 15mCi 99mTc-sulfor colloid | |
| 99mTc-sulfor colloid & III In-WBC | up to 2mCi III-WBC | up to 24 hours |
| 99mTc-MDP & III In-WBC | up to 15mCi 99mTc-MDP | |
| | up to 2mCi IIIIn-WBC | up to 24 hours |
| | up to 5mCi Ga67 | |
| Ga67 & III In-WBC | up to 2mCi IIIn | up to 72 hours |
| 99mTc-Teboroxinne/Or Tl | up to 2mCi IIIn- | |
| III In Annexin | up to 15mCi 99mTc- | up to 24 hours |
| 201Tl 99m Tc-PYP | up to 2mi Tl-201 | |
| | up to 15mCi 99mTc- | up to 1 hour |

Fig. 148F

| Acquisition protocol | Acquisition Time | Benefit |
|---|---|---|
| energy window anywhere between 2-10% | 5min? | simultaneous acqusition saves time; no problems with registration: no questions of anatomical location |
| energy window anywhere between 2-10% | 5min? | simultaneous acqusition saves time; no problems with registration: no questions of anatomical location |
| energy window anywhere between 2-10% | up to 30 min | |
| energy window anywhere between 2-10% | up to 30 min | |
| energy window anywhere between 2-10% | up to 30 min | |
| energy window anywhere between 2-10% | up to 30 min | |
| energy window anywhere between 2-10% | up to 30 min | |
| energy window anywhere between 2-10% | up to 30 min | non-invasive biopsy; one-stop diagnosis--many pathologies may be identified and charachterized by a single scan |
| energy window anywhere between 2-10% | up to 30 min | non-invasive biopsy; one-stop diagnosis--many pathologies may be identified and charachterized by a single scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |
| energy window anywhere between 2-10% | up to 30 min | comprehensive differential diagnosis in one step/one scan |

Fig. 148G

Table 6

| Protocol | Clinical significance | Radioisotope | Radiopharmaceutical | Total injected dose | Time to acquisition | Acquixition protocol | Acquixition time | Benefit |
|---|---|---|---|---|---|---|---|---|
| Dual phase gastric emptying | solid food: To99m-S-colloid labeled liquid food; In-III-DTPA labeled...???? | Tc-99m 1u-111 | Tc-Colloid DTPA | | | | | |
| o Ventricular function (ejection fraction w/*smart gating for DV/DT* | | | | see all cardiac protocols | see all cardiac protocols | see all cardiac protocols | see all cardiac protocols | see all cardiac protocols |

Fig. 148H

Table 7-A

| Protocol | Clinical Significance |
|---|---|
| vulnerable plaque-I IIIIn-Annexin and/or 99mTc-AcuTee | 99mTc-AcuTec attaches to activated platelets and shows thrombus, the Annexin attaches to apoptotic cells |
| Prostascint | imaging of prostate metastasis and possibly primary cancer. |
| Octeotide 99mTc-P829, Neotec®) | In-III-Octreotide tumor imaging agent for SST-eceptor expressing tumors) Neuroendocrine tumors) (Somatosta in receptors) |
| 99mTc-P280, Acutect®) | Thrombus detection; DVT and intraterelal thrombus in coronary and carotid arteries (GP IIb/IIIa receptors on platelets) |
| 123I-MIBG (meta-iodo benzyl guanidine) | Tumor imaging (Pheochromocytoma) and or Myocardial failure; Adrenergic tissue uptake; Presynaptic adrenergic receptors) |

Fig. 148I

| Radioisotope | Radiopharmaceutical | Total injected dose | Time to acquisition | Acquisition protocol | Acquisition time | Benefit |
|---|---|---|---|---|---|---|
| In-III | Annexin | up to 5mCi | | | | |
| Tc-99m | Accutec | up to 5mCi | | | | |
| In-III | Prostascint | up to 5mCi | | | | |
| In-III | Octreotide | up to 20mCi | | | | |
| | Neotec | | | | | |
| Tc-99m | Acutect | up to 20mCi | | | | |
| Tc-99m | MIBG | up to 5mCi | | | | |
| I-I23 | | | | | | |

Fig. 148J

Table 8

Table 8-A

| Protocol | Clinical Significance | Radioisotope | Radiopharmaceutical |
|---|---|---|---|
| Gated Cardiac study during pharmacological stress | this will be a dynamic study to investigate the effects of stress (adenosine-ice-water-etc..... Vasodilation) on the flow kinetics with thallium | SEE ALL THALLIUM STUDIES IN CARDIAC SECTION | SEE ALL THALLIUM STUDIES IN CARDIAC SECTION |
| Kidney function | this will be a dynamic study to investigate the effects of stress (captopril; fusides etc....) on the flow kinetics with MA3 | | |
| Gallbladder | Cholesystochinin is administered when gallbladder shows activity but cannot empty-this is for differential diagnosis stimulate the | | |
| CNS | brain (rapid blinking; flashlights) and study blood flow; epilepsy; etc... | | |

These should be standard protocols as performed today or in fast or low-dose protocols. What is important here is that this will be analyzed in a quantitative manner to study the response of tissue to pharmacologic, mechanic or any other type of stress or stimulus to characterize the physiological response of the tissue in a dynamic and quantitative manner. This information will be used to identify disease signature, personalize patient therapy.

Fig. 148K

Table 9

| Protocol | Clinical Significance | Radioisotope | Radiopharmaceutical | Total injected dose | Time to acquisition | Acquisition protocol | Acquisition time | Benefit |
|---|---|---|---|---|---|---|---|---|
| | | | | SEE ALL THALLIUM STUDIES IN CARDIAC SECTION | SEE ALL THALLIUM STUDIES IN CARDIAC SECTION | SEE ALL THALLIUM STUDIES IN CARDIAC SECTION | SEE ALL THALLIUM STUDIES IN CARDIAC SECTION | SEE ALL THALLIUM STUDIES IN CARDIAC SECTION |
| Bexaar dosimetry | determine the dose required to inject in order to administer an effective dose of 75 REM | I-131 | Bexaar | 5mCi/35mg protein | 3 acquisition during the week to produce a graph of metabolism | energy window- anywhere between 3-15% | each scan up to 5 min | |

Table 3-A

| Protocol | Rest injection | | Waiting time | Rest Imaging | Stress | Stress injection | |
|---|---|---|---|---|---|---|---|
| Cardiac Standard protocol- dual isotope-low dose | Tl | 0.3mCi | 10-15 min | 15 min | treadmill | Tc-MIBI | 3mCi |
| Cardiac Standard protocol- single isotope-low dose | Tc MIBI | 0.3mCi | 30 min | 15 min | treadmill | Tc-MIBI | 3mCi |
| Cardiac simultaneous dual-isotope-low dose | Tl | 0.3mCi | | | treadmill/pharma | Tc-MIBI | 3-5mCi |
| Cardiac fast dual-isotope Protocol-low dose | Tl | 0.3mCi | 2 min | 15 min | pharma | Tc-MIBI | 20-30mCi |
| Cardiac fast Single Isotope Protocol-low-dose | MIBI | 0.3mCi | | 0 15 min | pharma | Tc-MIBI | 3mCi |

Fig. 148N

Table 3-B

| Post-stress gated imaging | Acquisition protocol | Benefit |
|---|---|---|
| 15 min | energy window-anywhere between 3-15% | low dose (better resolution) |
| 15 min | energy window-anywhere between 3-15% | low dose (better resolution) one acquisition; low dose- better registration of images- shortened overall imaging time |
| 5-15 min | energy window-anywhere between 3-15% | |
| 2 min | energy window-anywhere between 3-15% | pharmacological stress; all injections while positioned under the camera rapid imaging; less blinding by liver |
| 15 min | energy window-anywhere between 3-15% | pharmacological stress; all injections while positioned under the camera rapid imaging; less blinding by liver |

Fig. 148O

Table 2-A

| Protocol | Clinical Significance | Radioisotope | Radiopharmaceutical |
|---|---|---|---|
| Lung V/P-DTPA aerosol and macro-aggregated albumin (lung perfusion agent) | Perfusion described by quantitative parameters (ml/min/gr); | Tc-99m I-123 | |
| MDP-bone scan-whole body scan | routinely performed to look for bone tumors or inflammatory processes of the bone (e.g. osteomyelitis) | Tc-99m | MDP |

Fig. 148P

Table 2-B

| Total injected dose | Time to acquisition | Acquisition protocol | Acquisition time | Benefit |
|---|---|---|---|---|
| MAA up to 5mCi (up to 1M particles) | immediate acquisition immediately after DTPA; MAA in injected and the immediate acquisition | energy window-anywhere between 3-15% | up to 6 min | fast |
| 20-30mCi | 0-60 min | energy window-anywhere between 3-15% | up to 6 min | fast |

Table 2-B

| Protocol | Clinical Significance | Radioisotope | Radiopharma-ceutical | Total injected | Time to acquisition | Acquisition protocol | Acquisition time | Benefit |
|---|---|---|---|---|---|---|---|---|
| Cardiac-Perfusion 1 (Thallium stress) | Perfusion described by quantitative parameters (ml/min/gr) Coronary flow reserve; parametric quantitation | Tl-201 | Thallous-Chloride-201 | up to 4mCi | 0 or before | energy window- anywhere between 3-15% | 2-20 minutes | Study: Fluid flow Tracer rate of uptake (passive or active) Tracer accumulation/redistribution Tracer metabolism Tracer/metabolites secretion and/or washout (active or passive) |
| Cardiac-Perfusion 2 (Thallium stress) | Perfusion described by quantitative parameters (ml/min/gr) Coronary flow reserve; parametric quantitation | Tl-201 | Thallous-Chloride-201 | up to 4mCi | 0 or before | energy window- anywhere between 3-15% | 2-20 minutes | Study: Fluid flow Tracer rate of uptake (passive or active) Tracer accumulation/redistribution Tracer metabolism Tracer/metabolites secretion and/or washout (active or passive) |
| Cardiac-Perfusion 3 (Teboroxine stress) | Perfusion described by quantitative parameters (ml/min/gr) Coronary flow reserve; parametric quantitation | Tc-99m | Teboroxine | up to 30 mCi | 0 or before | energy window- anywhere between 3-15% | 0-15 minutes | Study: Fluid flow Tracer rate of uptake (passive or active) Tracer accumulation/redistribution Tracer metabolism Tracer/metabolites secretion and/or washout (active or passive) |
| Cardiac-Perfusion 4 (Teboroxine stress) | Perfusion described by quantitative parameters (ml/min/gr) Coronary flow reserve; parametric quantitation | Tc-99m | Teboroxine | up to 30 mCi | 0 or before | energy window- anywhere between 3-15% | 0-15 minutes | Study: Fluid flow Tracer rate of uptake (passive or active) Tracer accumulation/redistribution Tracer metabolism Tracer/metabolites secretion and/or washout (active or passive) |
| Cardiac-Perfusion 5 (Sestamibi stress) | Perfusion described by quantitative parameters (ml/min/gr) Coronary flow reserve; parametric quantitation | Tc-99m | Sestamibi | up to 30 mCi | 0 or before | energy window- anywhere between 3-15% | 0-15 minutes | Study: Fluid flow Tracer rate of uptake (passive or active) Tracer accumulation/redistribution Tracer metabolism Tracer/metabolites secretion and/or washout (active or passive) |
| Cardiac-Perfusion 6 (Sestamibi stress) | Perfusion described by quantitative parameters (ml/min/gr) Coronary flow reserve; parametric quantitation | Tc-99m | Sestamibi | up to 30 mCi | 0 or before | energy window- anywhere between 3-15% | 0-15 minutes | Study: Fluid flow Tracer rate of uptake (passive or active) Tracer accumulation/redistribution Tracer metabolism Tracer/metabolites secretion and/or washout (active or passive) |

Fig. 148R₁

| Study | Description | Tracer | Dose | Energy window | Study parameters |
|---|---|---|---|---|---|
| Cardiac-Perfusion 5 (Tetrofosmin rest) | Perfusion described by quantitative parameters(ml/min/gr) Coronary flow reserve; parametric quantitation | Tc-99m tetrofosmine | up to 30 mCi 0 or before | energy window-anywhere between 3-15% | Study: Fluid flow Tracer rate of uptake (passive or active) Tracer accumulation/redistribution Tracer metabolism Tracer/metabolities secretion and/or washout (active or passive) |
| Cardiac-Perfusion 6 (Tetrofosmin stress) | Perfusion described by quantitative parameters(ml/min/gr) Coronary flow reserve; parametric quantitation | Tc-99m tetrofosmine | up to 30 mCi 0 or before | energy window-anywhere between 3-15% 0-15 minutes | Study: Fluid flow Tracer rate of uptake (passive or active) Tracer accumulation/redistribution Tracer metabolism Tracer/metabolities secretion and/or washout (active or passive) |
| Cardiac-Perfusion 5 (Te-99m-phosfurunine rest) | Perfusion described by quantitative parameters(ml/min/gr) Coronary flow reserve; parametric quantitation | Tc-99m | up to 30 mCi 0 or before | energy window-anywhere between 3-15% 0-15 minutes | Study: Fluid flow Tracer rate of uptake (passive or active) Tracer accumulation/redistribution Tracer metabolism Tracer/metabolities secretion and/or washout (active or passive) |
| Cardiac-Perfusion 6 (Te-99m-phosfurunine stress) | Perfusion described by quantitative parameters(ml/min/gr) Coronary flow reserve; parametric quantitation | Tc-99m | up to 30 mCi 0 or before | energy window-anywhere between 3-15% 0-15 minutes | Study: Fluid flow Tracer rate of uptake (passive or active) Tracer accumulation/redistribution Tracer metabolism Tracer/metabolities secretion and/or washout (active or passive) |
| BMIPP rest | Perfusion described by quantitative parameters(ml/min/gr) Coronary flow reserve; parametric quantitation; myocardial fatty acid metabolition | Tc-99m | up to 30 mCi 0 or before | energy window-anywhere between 3-15% | Study: Fluid flow Tracer rate of uptake (passive or active) Tracer accumulation/redistribution Tracer metabolism Tracer/metabolities secretion and/or washout (active or passive) |
| BMIPP stress | Perfusion described by quantitative parameters(ml/min/gr) Coronary flow reserve; parametric quantitation | Tc-99m | 0 or before | energy window-anywhere between 3-15% | Study: Fluid flow Tracer rate of uptake (passive or active) Tracer accumulation/redistribution Tracer metabolism Tracer/metabolities secretion and/or washout (active or passive) |

Fig. 148R$_2$

Table 5-B

| | | | | Study: Fluid flow Tracer rate of uptake (passive or archive) Tracer accumulation/redistribution Tracer metabolism Tracer/metabolities secretion and/or washout (active or passive) |
|---|---|---|---|---|
| Any one of the above combinations of rest and stress protocols | Perfusion described by quantitative parameters(ml/min/gr) Coronary flow reserve; parametric quantitation | | 0 or before | energy window- anywhere between 3-15% 0-15 minutes |
| All PET radiopharmaceuticals within the currently used PET protocols used with our SPECT camera | Perfusion described by quantitative parameters(ml/min/gr) Coronary flow reserve; parametric quantitation | | 0 or before | energy window- anywhere between 3-15% | Study: Fluid flow Tracer rate of uptake (passive or archive) Tracer accumulation/redistribution Tracer metabolism Tracer/metabolities secretion and/or washout (active or passive) |
| Cancer-Tumor Perfusion evaluation of tumors by single isotope (need to expand on breast) SPECT with TeboroxineTc99m or 99mTc-MIBI or TI-201 | Image tumor blood supply w/201Il in combination with MIBI uptake and washout which is affected by the MDR complex showing therapeutic response to chemo. Perfusion escribed by quantitative parameters (ml/min/gr); | Tc-99m Sestamibi | up to 30mCi for MIBI 0 or before | energy window- anywhere between 3-15% | Study: Fluid flow Tracer rate of uptake (passive or archive) Tracer accumulation/redistribution Tracer metabolism Tracer/metabolities secretion and/or washout (active or passive) |
| Cancer-Tumor Perfusion evaluation by simultaneous duak isotope SPECT with TI-201 chloride and 99mTc-MIBI | Tumor imaging: image tumor blood supply w/201II in combination with MIBI uptakeand washout which is affected by the MDR complex showing therapeutic response to chemo. Perfusion escribed by quantitative parameters (ml/min/gr); parametric quantitation | Tc-201 thallous chloride Tc-99m sestamibi | up to 4mCi for TI-201 up to 30mCi for MIBI simultaneous injection 0 or before | energy window- anywhere between 3-15% | Study: Fluid flow Tracer rate of uptake (passive or archive) Tracer accumulation/redistribution Tracer metabolism Tracer/metabolities secretion and/or washout (active or passive) |
| Kidney- Renal Function-Dynamic flow study III In- DTPA&99mTcMAG3 | Assessment of filtration and tubular secretion; Perfusion described by quantitative parameters (ml/min/gr) parametric quantitation | Tc-99 DTPA In-III MAG3 | 0.23mCi- mCi-In-III up to 10mCi 0 or before | energy window- anywhere between 3-15% |

| | | | | | Study: |
|---|---|---|---|---|---|
| Kidney-Renal Function-Dynamic flow study III In-DTPA& Hippuraun I-123 | Assessment of filtration and tubular secretion; Perfusion described by quantitative parameters (ml/min/gr) parametric quantitation | Tc-99 I-123 | DTPA Hippuran | 0.3mCi-1mCi-I-123 up to 10mCi | Fluid flow Tracer rate of uptake (passive or archive) Tracer accumulation/redistribution Tracer metabolism Tracer/metabolites secretion and/or washout (active or passive) |
| Brain-perfusion-perfusion mapping | Perfusion described by quantitative parameters(ml/min/gr) Cerebral flow reserve (in stress protocols using pharmacological stress agents); parametric quantitation; disease signature (Alzheimer's, depression, schizophrenia, etc....) | Tc-99m I-123 | HMPAO ECD(neurolite) IMP(spectamine) | up to 20mCi for Tc-99m labeled up to 5mCi for I-123 | Study: Fluid flow Tracer rate of uptake (passive or archive) Tracer accumulation/redistribution Tracer metabolism Tracer/metabolites secretion and/or washout (active or passive) energy window-anywhere 0 or before between 3-15% 0-30 min |
| Brain-perfusion-perfusion mapping | Perfusion described by quantitative parameters(ml/min/gr) Cerebral flow reserve (in stress protocols using pharmacological stress agents); parametric quantitation; disease signature (Alzheimer's, depression, schizophrenia, etc....) | Tc-99m | Teboroxine | up to 20mCi for Tc-99m labeled up to 5mCi | Study: Fluid flow Tracer rate of uptake (passive or archive) Tracer accumulation/redistribution Tracer metabolism Tracer/metabolites secretion and/or washout (active or passive) energy window-anywhere 0 or before between 3-15% 0-30 min |
| Hepatobiliary-Tc99m sulfur colloid | routinely is done to lok a liver structure (hemangiomas, abcesses, liver enlargement, | | | immediate up to 5mCi acquision | first 5 minutes should be a real dynamic study and then every 5 minutes for up to an hour; if no activity s seen in intensive a pharmacologic agent is used for all bledder contraction |
| Liver function study | | Tc-99m | Disido (disulfenine Choletec IIIDA (nil bind to bilirubin sites) | up to 10 mCi 0 min or less | Study: Fluid flow Tracer rate of uptake (passive or archive) Tracer accumulation/redistribution Tracer metabolism Tracer/metabolites secretion and/or washout (active or passive) |

Fig. 148T

Dr. Shankar, Nov 6th 2005

Table #

Radiotracers for Molecular Imaging Studies

| Radiotracer | FDA status NDA | FDA status IND | Dose mCi | Target | Clinical Application |
|---|---|---|---|---|---|
| [18F]Fluorodeoxyglucose (FDG) | X | | 5-15 | Substrate for hexokinase in glucose metabolism | Glucose metabolism of tumor, heart and brain and many other cells |
| [18F]-Fluoromisonidazole | | X | | Hypoxia and oxidative metabolism | Radiotherapy treatment planning |
| [18F]3'-Fluoro-3'-deoxythymidine (FLT) | | X | 5-10 | DNA synthesis | |
| [18F]Fluoromethyl choline (FCH) | | X | 10 | Choline precursor for cell membrane synthesis | Choline metabolism of tumors |
| [18F]4-Fluoro-m-tyrosine (FMT) | | X | 10 | Precursor for Dopamine synthesis Substrate for AAAD | Imaging brain tumors |
| [18F]6-Fluoro-L-DOPA | | X | 10 | Precursor for dopamine synthesis. It is a precursor for aromatic amino acid decarboxylase (AAAD). | Imaging and grading Parkinson's disease Imaging neuroendocrine tumors |
| [18F]FP-βCIT | | X | 10 | Binds to dopamine transporter in dopaminergic axons | Same as above |
| [18F]Pencyclovir (FHBG) | | X | 10 | Thymidine kinase | Imaging reporter gene expression |
| [18F]Fluoroestradiol (FES) | | x | 10 | Estrogen receptors | Breast tumor imaging |
| [11C]Methionine | | X | 10 | Amino acid synthesis | Imaging brain tumors |
| 111In-Pentetreotide, (Octreoscan®) | X | | 5-6 | Somatostatin receptors | Neuroendocrine tumors |
| 99mTc-P829, Neotec® | X | | 10-20 | Somatostatin receptors | Neuroendocrine tumors |
| 99mTc-P280, Acutect® | X | | 10-20 | GP IIb/IIIa receptors on platelets | Thrombus detection; DVT and intraarterial thrombus in coronary |

Fig. 148U

Dr. Shenkar, Nov 6th 2005

| | | | | | |
|---|---|---|---|---|---|
| [125I]-VIP (vasoactive intestinal peptide) | | X | 5-10 | VIP receptors | and carotid arteries. Gastrointestinal tumors |
| [125I]-MIBG (meta-iodo benzyl guanidine) | X | | 1-5 | Adrenergic tissue uptake Presynaptic adrenergic receptors | Tumor imaging (Pheochromocytoma) Myocardial failure |
| [131I]-NP-59 | | | 1-3 | LDL receptor, cholesterol metabolism | Adrenal carcinoma, adenoma Cushing's syndrome |
| [11C]Raclopride | | X | 10-20 | Dopamine D2 receptors | Schizophrenia - Brain imaging of Dopamine D2 receptors and assessment of dose for neuroleptics | Bmax, BP |
| [123I]-IBZM | | X | 5-10 | Dopamine D2 receptors | Same as above | Bmax, BP |
| [11C]Carfentanil | | X | 10-15 | Mu opioid receptors in brain | Imaging drug addiction | Bmax, BP |
| [11C]α-methyl-L-tryptophan | | X | 10-15 | Precursor for α-methyl serotonin synthesis. Substrate for AAAD enzyme | Imaging depression | |
| [11C]5-Hydroxytryptophan | | X | 10-15 | Precursor for serotonin synthesis | Imaging neuroendocrine tumors | |
| [18F]MPPF | | X | 10-15 | Binds to 5-HT1A serotonin receptors | Imaging depression, epilepsy | Bmax, BP |
| [18F]Altanserin | | X | 10-15 | Binds to 5-HT2A serotonin receptors | Same as above | Bmax, BP |
| [11C]Acetate | | X | 15-30 | Tricarboxylic acid cycle activity Oxidative metabolism | Myocardial oxygen metabolism | Kinetic parameters |
| [11C]Palmitate | | X | 10-20 | Precursor for Fatty acid metabolism | Myocardial metabolism | Kinetic parameters |
| [18F]Fluorodopamine | | X | 10-15 | Presynaptic adrenergic receptors | | |

Dr. Shankar, Nov 6th 2005

Beta emitting radionuclides which may be used for diagnostic studies at <u>One mCi dose levels</u> using the high sensitivity of Spectrum Dynamics camera

| Nuclide | Half-life (Days) | Decay Mode | Energy (MeV) Max. | Energy (MeV) Average | γ photon (KeV) | Abundance (%) |
|---|---|---|---|---|---|---|
| $^{153}$Sm | 1.95 | β⁻ | 0.81 | 0.225 | 103 | 29 |
| $^{131}$I | 8.04 | β⁻ | 0.61 | 0.20 | 364 | 81 |
| $^{67}$Cu | 2.58 | β⁻ | 0.57 | - | 92, 185 | 11 and 49 |
| $^{177}$Lu | 6.7 | β⁻ | 0.497 | 0.1 | 208 | 11 |
| $^{117m}$Sn | 13.6 | β⁻ | 0.16 | - | 159 | 87 |

These 2 nuclides may have potential value for imaging in the future.

| $^{52}$Fe | 8.3 hr | EC, β⁺ | | | 0.165 | 100 |
| $^{113m}$In | 100 min | IT | | | 392 | 64 |

Fig. 148V

RADIOIMAGING USING LOW DOSE ISOTOPE

RELATED APPLICATIONS

This application is a continuation of U.S. patent application Ser. No. 11/798,017 filed on May 9, 2007, which is a continuation-in-part of PCT Patent Application No. PCT/IL2005/001173 filed on Nov. 9, 2005, which is a continuation-in-part of PCT Patent Application Nos. PCT/IL2005/000572 and PCT/IL2005/000575 filed on Jun. 1, 2005.

PCT Patent Application Nos. PCT/IL2005/000572 and PCT/IL2005/000575 claim the benefit of U.S. Provisional Patent Application Nos. 60/648,690 filed on Feb. 2, 2005; 60/648,385 filed on Feb. 1, 2005; 60/640,215 filed on Jan. 3, 2005; 60/636,088 filed on Dec. 16, 2004; 60/635,630 filed on Dec. 14, 2004; 60/632,515 filed on Dec. 3, 2004; 60/632,236 filed on Dec. 2, 2004; 60/630,561 filed on Nov. 26, 2004 and 60/625,971 filed on Nov. 9, 2004.

PCT Patent Application No. PCT/IL2005/001173 also claims the benefit of Israel Patent Application No. 171346 filed on Oct. 10, 2005 and U.S. Provisional Patent Application Nos. 60/720,541 and 60/720,652 filed on Sep. 27, 2005; 60/720,034 filed on Sep. 26, 2005; 60/702,979 filed on Jul. 28, 2005; 60/700,753 filed on Jul. 20, 2005; 60/700,752 filed on Jul. 20, 2005; 60/700,318 filed on Jul. 19, 2005; 60/700,317 filed on Jul. 19, 2005; 60/700,299 filed on Jul. 19, 2005; 60/691,780 filed on Jun. 20, 2005; 60/675,892 filed on Apr. 29, 2005; and U.S. Provisional Patent Application No. 60/628,105 filed on Nov. 17, 2004.

PCT Patent Application No. PCT/IL2005/001173 is also a continuation-in-part of PCT Patent Application No. PCT/IL2005/000048 filed on Jan. 13, 2005.

U.S. patent application Ser. No. 11/798,017 also claims the benefit of U.S. Provisional Patent Application No. 60/800,845 filed on May 17, 2006.

U.S. patent application Ser. No. 11/798,017 is related to PCT Patent Application No. PCT/IL2006/000834 filed on Jul. 19, 2006, which claims the benefit of U.S. Provisional Patent Application No. 60/741,440 filed on Dec. 2, 2005.

The contents of the above Applications are incorporated herein by reference.

FIELD AND BACKGROUND OF THE INVENTION

The present invention relates to nuclear imaging, and more particularly, to systems, methods, and cameras for radioactive-emission detection and measurements, without coincidence, with sensitivity which meets, and even outperforms that of PET, in terms of speed and spatial resolution, and with a high spectral resolution not available in PET.

Radionuclide imaging aims at obtaining an image of a radioactively labeled substance, that is, a radiopharmaceutical, within the body, following administration, generally, by injection. The substance is chosen so as to be picked up by active pathologies to a different extent from the amount picked up by the surrounding, healthy tissue; in consequence, the pathologies are operative as radioactive-emission sources and may be detected by radioactive-emission imaging. A pathology may appear as a concentrated source of high radiation, that is, a hot region, as may be associated with a tumor, or as a region of low-level radiation, which is nonetheless above the background level, as may be associated with carcinoma.

A reversed situation is similarly possible. Dead tissue has practically no pick up of radiopharmaceuticals, and is thus operative as a cold region.

The mechanism of localization of a radiopharmaceutical in a particular organ of interest depends on various processes in the organ of interest such as antigen-antibody reactions, physical trapping of particles, receptor site binding, removal of intentionally damaged cells from circulation, and transport of a chemical species across a cell membrane and into the cell by a normally operative metabolic process. A summary of the mechanisms of localization by radiopharmaceuticals is found in http://www.lunis.luc.edu/nucmed/tutorial/radpharm/i.htm.

The particular choice of a radionuclide for labeling antibodies depends upon the chemistry of the labeling procedure and the isotope nuclear properties, such as the number of gamma rays emitted, their respective energies, the emission of other particles such as beta or positrons, the isotope half-life, and the decay scheme.

In PET imaging, positron emitting radio-isotopes are used for labeling, and the imaging camera detects coincidence photons, the gamma pair of 0.511 Mev, traveling in opposite directions. Each coincident detection defines a line of sight, along which annihilation takes place. As such, PET imaging collects emission events, which occurred in an imaginary tubular section enclosed by the PET detectors. A gold standard for PET imaging is PET $NH_3$ rest myocardial perfusion imaging with N-13-ammonia ($NH_3$), at a dose level of 740 MBq, with attenuation correction. Yet, since the annihilation gamma is of 0.511 Mev, regardless of the radio-isotope, PET imaging does not provide spectral information, and does not differentiate between radio-isotopes.

In SPECT imaging, primarily gamma emitting radio-isotopes are used for labeling, and the imaging camera is designed to detect the actual gamma emission, generally, in an energy range of approximately 11-511 KeV. Generally, each detecting unit, which represents a single image pixel, has a collimator that defines the solid angle from which radioactive emission events may be detected.

Because PET imaging collects emission events, in the imaginary tubular section enclosed by the PET detectors, while SPECT imaging is limited to the solid collection angles defined by the collimators, generally, PET imaging has a higher sensitivity and spatial resolution than does SPECT. Therefore, the gold standard for spatial and time resolutions in nuclear imaging are defined for PET.

Radiopharmaceuticals are a powerful labeling tool, yet the radiation dose to the patients needs to be taken into account.

In the International System of units (SI), the becquerel (Bq) is the unit of radioactivity. One Bq is 1 disintegration per second (dps). The curie (Ci) is the old standard unit for measuring radioactivity of a given radioactive sample and is equivalent to the activity of 1 gram of radium, originally defined as the amount of material that produces $3.7 \times 10^{10}$ dps. Regarding dose levels applicable to radiopharmaceuticals, 1 GBq=27 millicuries.

The rad is a unit of absorbed radiation dose in terms of the energy deposited in a living tissue, and is equal to an absorbed dose of 0.01 joules of energy per kilogram of tissue.

The biologically effective dose in rems is the dose in rads multiplied by a "quality factor" which is an assessment of the effectiveness of that particular type and energy of radiation. Yet, for gamma and beta rays, the quality factor is 1, and rad and rem are equal. For alpha particles, the relative biological effectiveness (rem) may be as high as 20, so that one rad is equivalent to 20 rems.

The recommended maximum doses of radiopharmaceuticals are 5 rems for a whole body dose and 15 rads per organ, while the allowable dose for children is one tenth of the adult level. The per-organ criterion protects organs where accumulation takes place. For example, radiopharmaceuticals for which removal is primarily by the liver should be administered at a lower dose than those for which removal is partly by the liver and partly by the kidney, because in the former, a single organ is involved with the removal, and in the latter, there is sharing of the removal.

In order to minimize exposure to the tissue, radiopharmaceuticals, which have a long half life, and radiopharmaceuticals, which have radioactive daughters, are generally avoided.

SUMMARY OF THE INVENTION

The present invention relates to radioimaging cameras characterized by unprecedented high sensitivity allowing for high resolution image acquisition for use in diagnostics; algorithms and systems operable in conjunction with the camera, the algorithms and systems include, but are not limited to, predetermined view selection algorithm and system, active vision (on flight view selection) algorithm and system, closed loop administration of a radiopharmaceutical algorithm and system, expert system diagnostic algorithm and system, automatic dose preparation algorithm and kinetic parameter extraction algorithm and system; low dose radiopharmaceuticals; combinations of radiopharmaceuticals either as compositions (cocktails) and/or kits; an administering device of radiopharmaceuticals, which may include syringes, pumps and IV lines; mixers for mixing different radiopharmaceuticals; and an ERP system for controlling and monitoring each one or more of the above.

The present invention emerges from the development of a radioimaging camera characterized by unprecedented sensitivity. The sensitivity of the camera is attributed, as is further detailed hereinbelow, to at least the following constructual features: (a) a plurality of detecting units; (b) movability of the detecting units one with respect to the other; (c) thus allowing concentrated focus on a region-of-interest by the individual detecting units; and (d) wiring diagram with minimal multiplexing, thereby preventing saturation thereof.

As a result of this sensitivity, it is now possible using the camera of the present invention to (a) detect low dose radiopharmaceuticals; (b) perform fast kinetic studies; (c) extract kinetic parameters for the distribution of a radiopharmaceutical under different diagnostic setups, thereby allowing (i) formulating radiopharmaceuticals based on the newly achieved knowledge of the kinetic parameters; (ii) diagnostics based on the kinetic parameters; (iii) formulating new therapeutic drugs based on the kinetic parameters; and (iv) using the kinetic parameters as an input to the expert system for diagnostics; (d) provide images of co-administered radiopharmaceuticals; and (e) allow diagnostically meaningful imaging at a far faster rate as compared to conventional prior art radioimaging cameras.

In order to minimize the exposure of a testee to radioactive substances and in order to maximize the diagnostic capabilities using radioimaging, the inventors of the present invention developed low dose preparations of radiopharmaceuticals and compositions and kits comprising two or more radiopharmaceuticals adapted for use in conjunction with the camera and all other aspects of the invention.

In another exemplary embodiment of the current invention, the
probe system includes multiple blocks of detectors positioned in a structure encircling the imaged area, each is able to rotate about a longitudinal axis substantially parallel to the main axis of the subject.

In a further example case of 10 such blocks of detectors, each covering a 40×160 mm section covering about 180-200 deg of the circle around the imaged area, with 10 blocks of collimators each covering 1024 pixels arranged in a 16×64 pixel matrix, with square collimator opening of 2.46×2.46 mm, and a length of 20 mm], the system demonstrated ability to detect about one out of 1500 of the emitted photons from a 2.7 mCi $Co^{57}$ point source that was moved about in a 40×30×15 cm volume facing the probe.

When located in the center of the imaged area (about 150 mm from the detectors), while the energy window for acquisition was about 5%, and the detectors were sweeping a wide angular range.

In a further exemplary embodiment, substantially all detectors are able to simultaneously image the region of interest containing the point source and thus obtaining one out of every 500 of the emitted photons.

It is known to the skilled in the art that further opening the energy window of the detector to about 15%, enables acquisition of about one out of 250 photons of the photons emission in an experimental setting similar to the previous example.

In a further example, each such detector having multiple pixels is of about 5 cm wide or more, thus producing a region of interest of at least 5 cm in diameter, from which said sensitivity and said resolution is being obtained even without the need to move any of the detectors.

In a further possible embodiment of the present invention the width of each detector is about 10 cm wide, thus enabling regions of interest of even bigger diameters at said resolution and sensitivity with a smaller detector motion such that bigger objects are continuously viewed by the detector with only small angular detector motion.

In a further possible embodiment of the present invention the detectors array may encircle the imaged subject to the extent of 360 deg, for example by having two hemi circles from both sides of the subject. The sensitivity in such case is estimated be about 1 in 125.

In a further exemplary embodiment additional detectors may be positioned to obtain views not perpendicular to the subject's main longitudinal axis, for example by upper view (e.g. from the shoulders) and abdominal view of the target region (in the case of cardiac mapping). It is estimated that such addition may increase the sensitivity but a factor of about ×2.

As a result, an example embodiment is estimated to be able to image a volume of about 5 cm diameter located about 150 mm from the detectors, with energy window of 15%, producing spatial resolution of about 5 mm in approximately 100 sec, with a total sensitivity of about 1 photons being detected out of 65 emitted.

It will be recognized by a person skilled in the art that a system built around the principles as described by the examples and embodiments of the present invention can thus reach the sensitivity necessary to detect substantially more than one photon from every 100 emitted. This result for an imaging system provides more than 100 time better sensitivity than commercially available cameras that have a sensitivity ranging from substantially from 170 counts/microCurie/minute (or 1 photon in 8500 photons emitted for a Low resolution low energy collimator to about 1 photon in every 15000 emitted for a high resolution medium energy collimator), while maintaining similar energy windows, and potentially similar or better resolution.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1B schematically illustrate detecting units and blocks for radioactive emission detection;

FIG. 2 schematically illustrates the basic component of a system, comprising a radioactive-emission camera and a position-tracking device, both in communication with a data-processing system;

FIGS. 3A-3B schematically illustrate the manner of operating the radioactive-emission camera with the position-tracking device;

FIGS. 4A-4C schematically illustrate extracorporeal and intracorporal radioactive-emission camera operative with position-tracking devices;

FIGS. 5A-5F present the principles of modeling, for obtaining an optimal set of views, in accordance with embodiments of the present invention;

FIGS. 6A and 6B pictorially illustrate a view and viewing parameters associated with it, in accordance with definitions of the present invention;

FIGS. 7A-7C schematically illustrate anatomical constraints, which are to be modeled, in accordance with embodiments of the present invention;

FIGS. 9A-9F schematically illustrate possible models and collections of views, for a body structure, in accordance with embodiments of the present invention;

FIGS. 13A-13E schematically illustrate possible camera designs, and the process of obtaining views based on a model and a camera design, in accordance with embodiments of the present invention;

FIG. 14 illustrates, in flowchart form, a method of selecting a camera design optimized with respect to information gained about a body stricture, in accordance with embodiments of the present invention;

FIG. 15 illustrates, in flowchart form, a method of selecting a camera design, based on the rate of data collection and other design considerations, in accordance with embodiments of the present invention;

FIGS. 16A-16L schematically illustrate viewing of an elliptical modeled volume, by the radioactive-emission camera, in accordance with embodiments of the present invention;

FIGS. 17A-17N schematically illustrate various detecting units and blocks, which may be incorporated in camera designs, in accordance with embodiments of the present invention;

FIGS. 20A-20H schematically illustrate possible motions of a radioactive-emission camera, having a plurality of pairs of radioactive-emission blocks;

FIGS. 21A-21D schematically illustrate other possible motions of a radioactive-emission camera, having a plurality of pairs of radioactive-emission blocks;

FIGS. 22A-22X schematically illustrate a radioactive-emission camera system, comprising a plurality of assemblies, motions of individual blocks, and characteristics of an optimal camera, in accordance with embodiments of the present invention;

FIG. 22Y-22AA schematically illustrate a center of viewing, for a given camera design, in accordance with embodiments of the present invention;

FIGS. 23A-23D schematically illustrate a radioactive-emission camera system, in accordance with embodiments of the present invention;

FIGS. 24A-24C schematically illustrate the modeling of a prostate as a process of two iterations, for zooming in on a pathology, in accordance with embodiments of the present invention;

FIGS. 25A-25E schematically illustrate the external appearance and the internal structure of the radioactive-emission camera for the prostate, in accordance with an embodiment of the present invention;

FIGS. 37-39 schematically illustrate the modeling of the heart as a process of two iterations, in accordance with embodiments of the present invention;

FIGS. 40-45 schematically illustrate the basic components of a cardiac camera system, in accordance with an embodiment of the present invention;

FIGS. 56A-56B schematically illustrate the internal structure of the radioactive-emission camera for the dual imaging system, in accordance with an embodiment of the present invention;

FIGS. 57A-57B schematically illustrate a cranial model, in accordance with an embodiment of the present invention;

FIGS. 59A-59C schematically illustrate an imaging system for radioactive-emissions of the head, in accordance with an embodiment of the present invention;

FIGS. 60A-60K schematically illustrate the internal structure of the radioactive-emission camera for the head, in accordance with an embodiment of the present invention;

FIGS. 62A-62C schematically illustrate an imaging system for radioactive-emissions of the breast, in accordance with an embodiment of the present invention;

FIGS. 63A-63E schematically illustrate an imaging camera for radioactive-emissions of the breast, in accordance with an embodiment of the present invention;

FIGS. 64L-64M illustrates, in flowchart form, a method of examining a breast, in accordance with embodiments of the present invention;

FIGS. 67A-67B schematically illustrate effect of distance on detection efficiency of a radiation detector;

FIGS. 68A-68D schematically illustrate effect of distance on resolution of a radiation detector;

FIG. 71 schematically illustrates a non-wasteful radiation detector array, in accordance with an embodiment of the present invention;

FIGS. 76A-80D schematically illustrate experimental data with the camera of the present invention.

FIG. 108 illustrates dynamic behavior of a parameter;

FIG. 109A-D illustrate different behaviors over time of different kinetic parameters.

FIGS. 113A-113C are of cardiac and respiratory gating in accordance with a first embodiment, in accordance with embodiments of the present invention;

FIG. 129 is a simplified diagram showing a single detector detecting from a target region;

FIG. 130 is a simplified diagram showing two detector positions (not necessarily simultaneously) allowing three-dimensional information to be obtained from a target region;

FIGS. 131A-131D show a series of four time absorption characteristics for different radiopharmaceuticals within different tissues;

FIG. 132 is a simplified schematic diagram showing a device for driving an imaging head and allowing control of the imaging head by the image analyzer device;

FIG. 133 is a simplified flow chart illustrating the image analysis process carried out by the analyzer in FIG. 132 in the case of a single marker;

FIGS. 134A-134D illustrate two sets of successive images of the same target area taken using two different markers respectively, according to a preferred embodiment of the present invention;

FIG. 135A is a simplified flow chart illustrating a procedure according to a preferred embodiment of the present invention using two or more markers for firstly identifying an organ and secondly determining the presence or otherwise of a pathology within that organ;

FIG. 135B is a simplified flow chart showing a generalization of FIG. 135A for the general case of two specific patterns;

FIG. 136 is a simplified flow chart illustrating a procedure according to a preferred embodiment of the present invention using two or more markers for identifying a region of low emissivity within a target area and using that identification to control imaging resources to better image the identified region;

FIGS. 137A-137D illustrate two sets of successive images of the same target area taken using two different markers, in a similar way to that shown in FIG. 134, except that this time the regions of interest are one inside the other; and FIG. 138 illustrates differential diagnosis using simultaneous imaging of two different radiopharmaceuticals.

FIGS. 139A-B is a table illustrating various radiopharmaceutical combinations and their uses in nuclear imaging.

Figure 140:
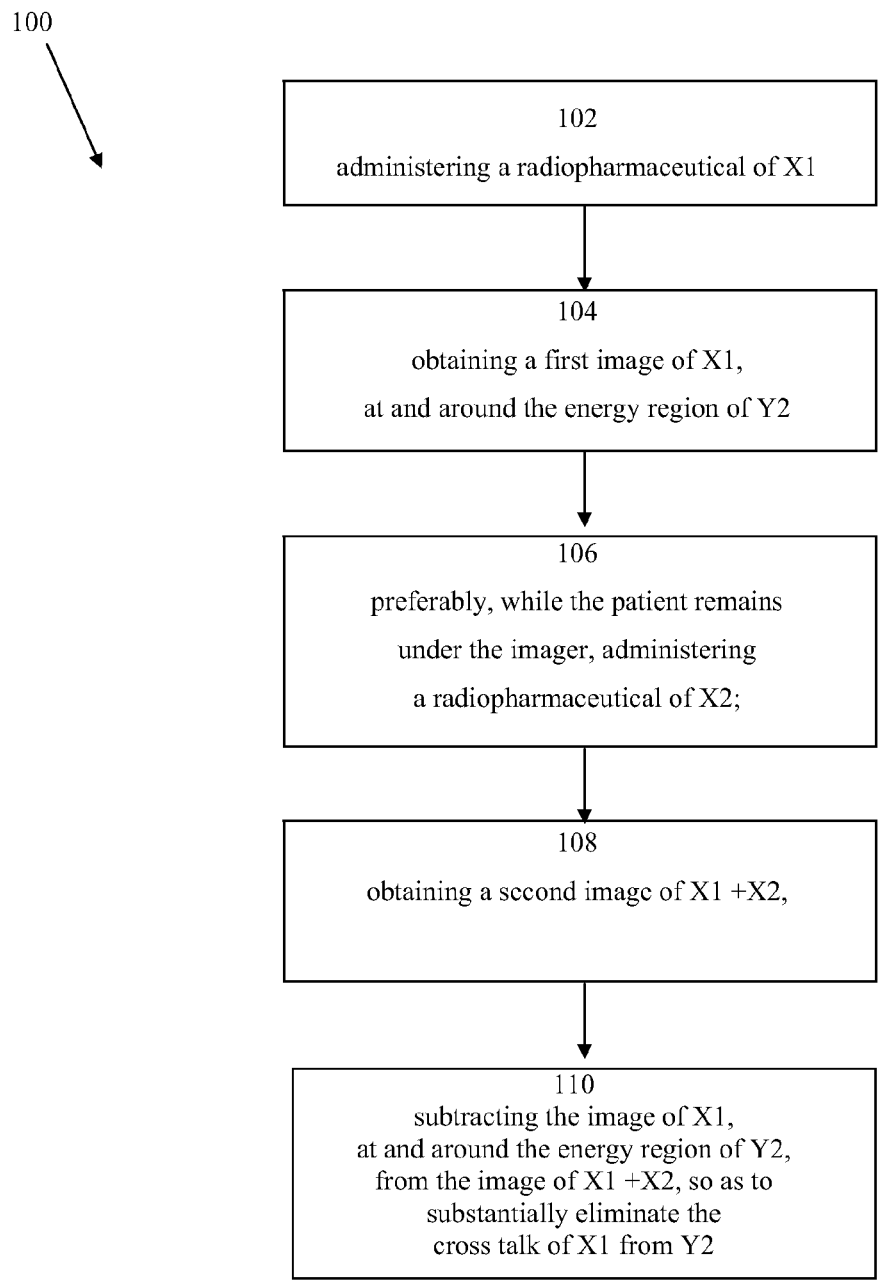
Figure 141:
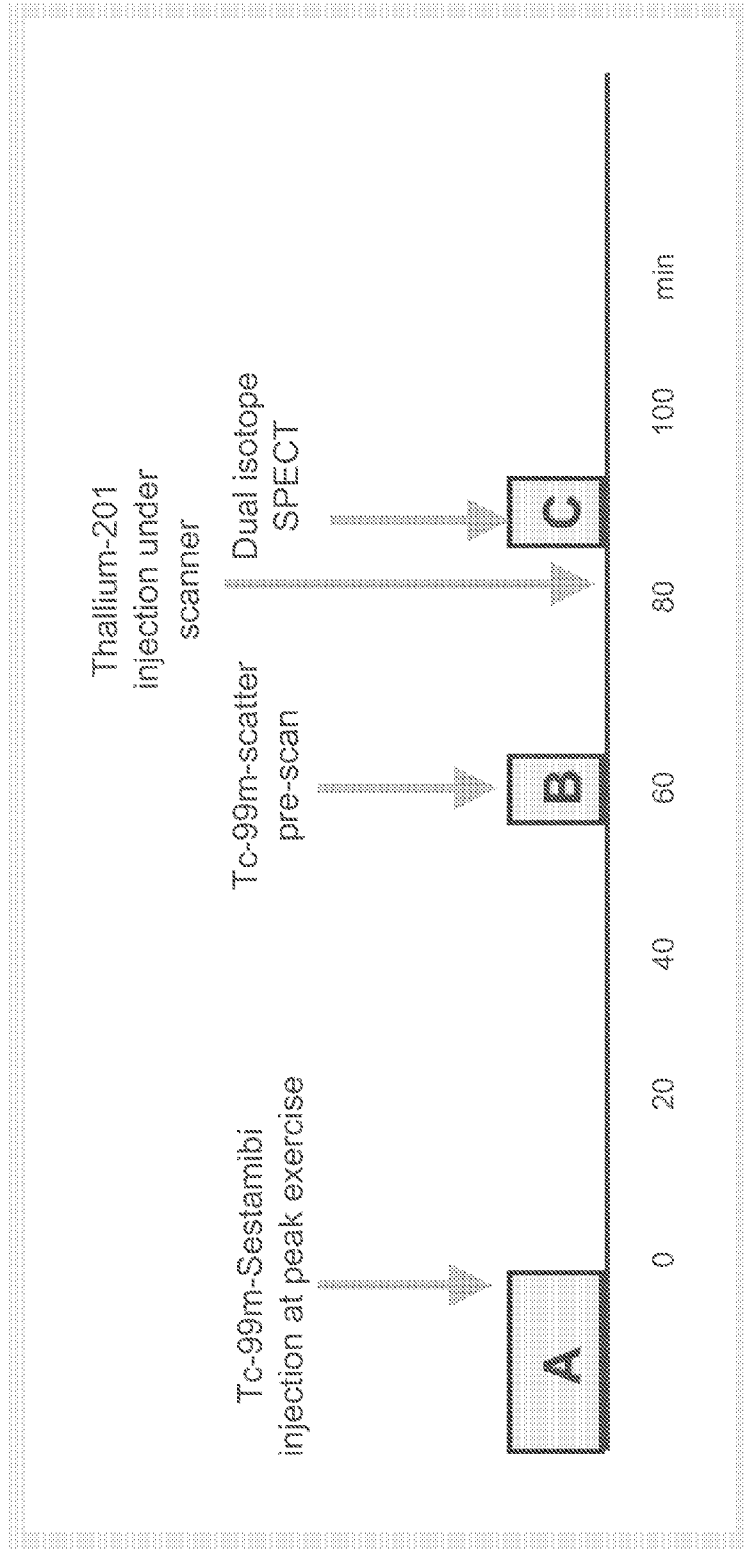

FIG. 140 is a flowchart for imaging two isotopes that provide inappropriate cross talk, in accordance with embodiments of the present invention;

FIG. 141 schematically represents a time line for myocardial perfusion, in accordance with embodiments of the present invention; and FIGS. 142a-142C schematically illustrate photopeaks of $Tc^{99m}$, $Tl^{201}$, and cross talk of $Tc^{99m}$ at the $Tl^{201}$ energy window.

Figure 143:
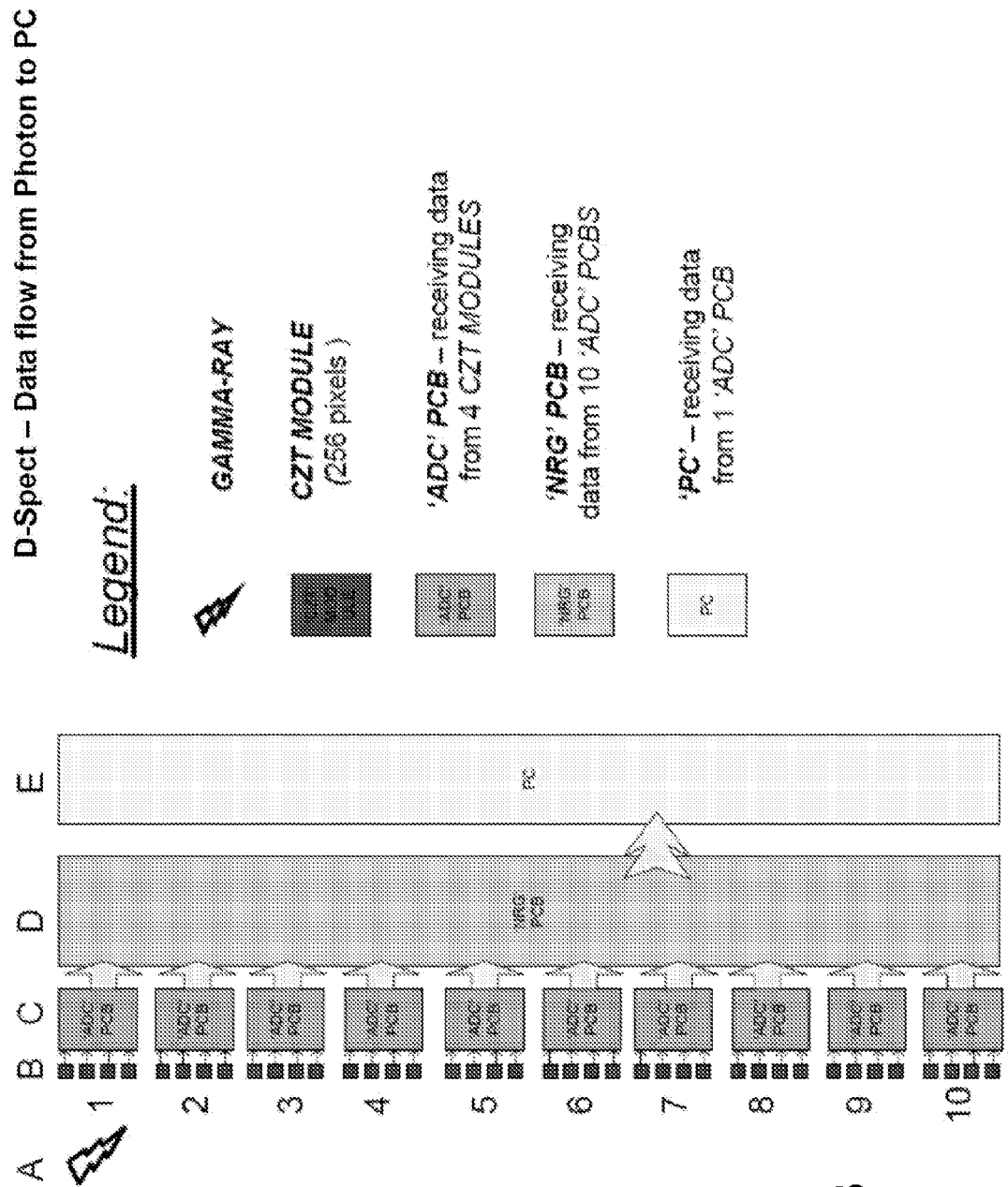

FIG. 143 is a camera electrical diagram showing an electronic block diagram indicating the high limits of the system. In this case, basically, the monolithic crystal of camera is divided to 40×2 blocks each of which is not affecting the others. In the conventional camera-every photon paralyzes the camera until cleared.

Figure 144:
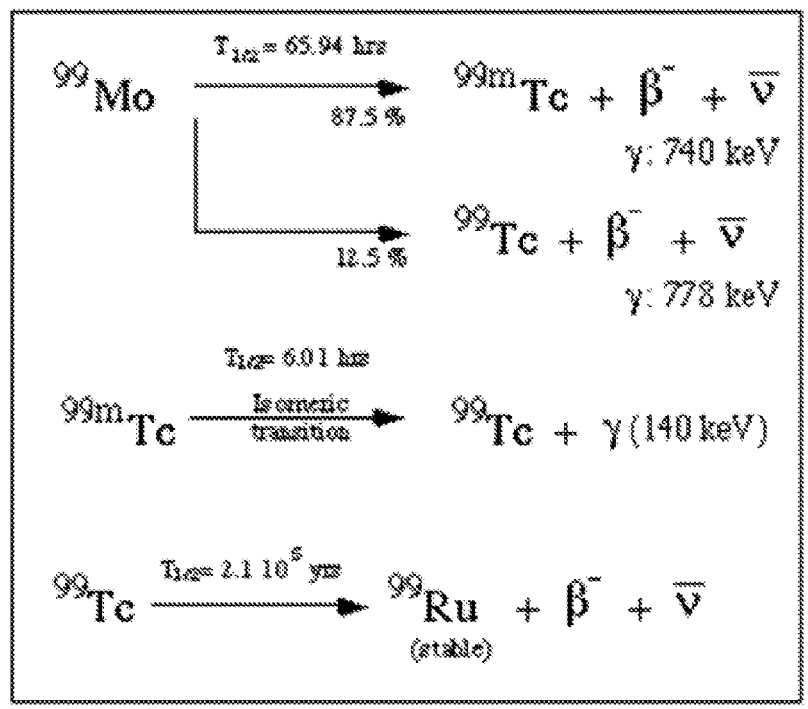
Figure 145:
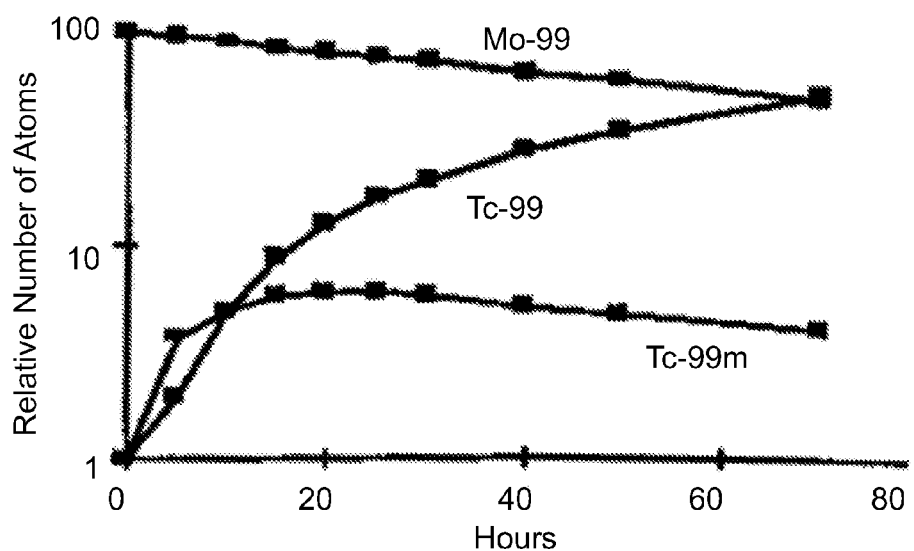

FIG. 144 describes a decay curve of Mo-99 to Tc-99m and to Tc-99;

FIG. 145 describes the build up of Tc-99m and Tc-99 with the decay of Mo-99.

Figure 146:
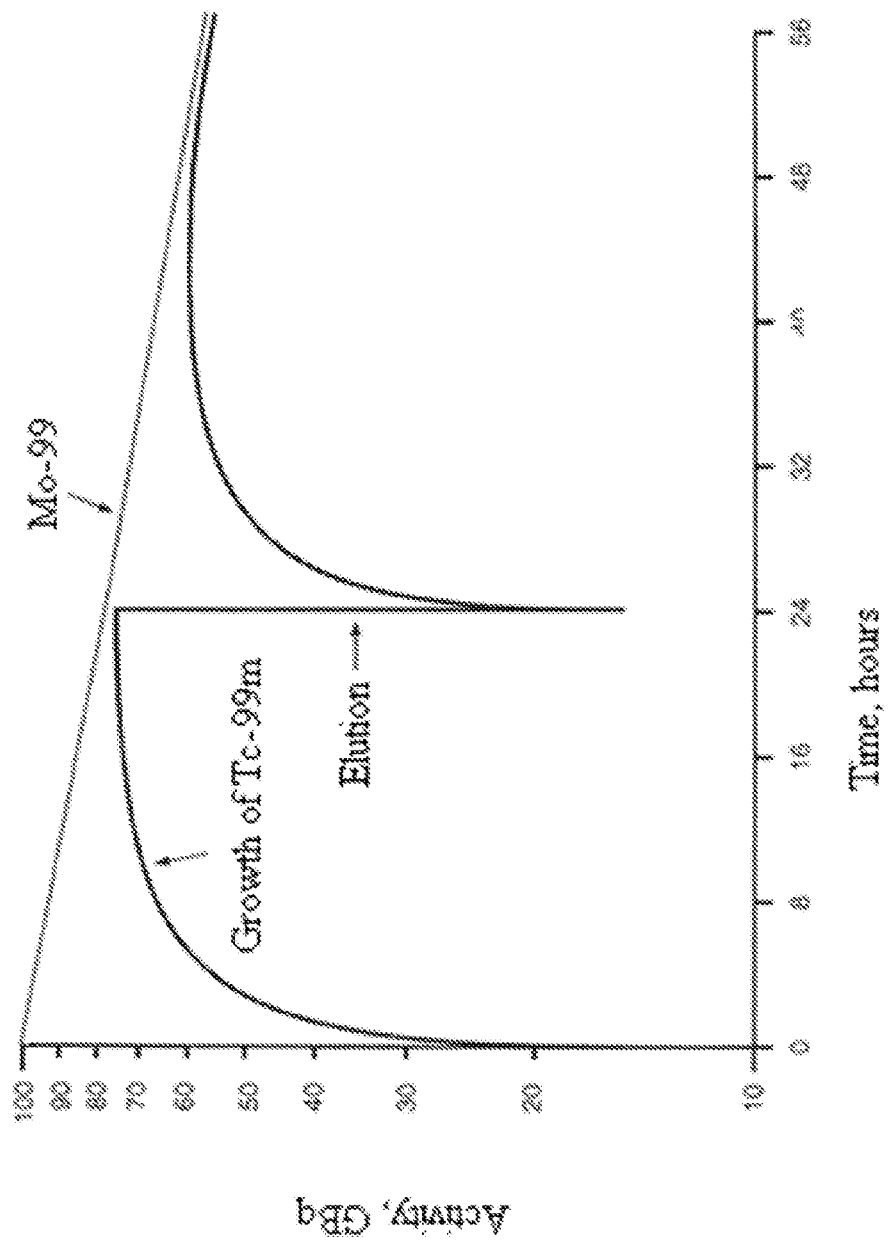
Figure 147:
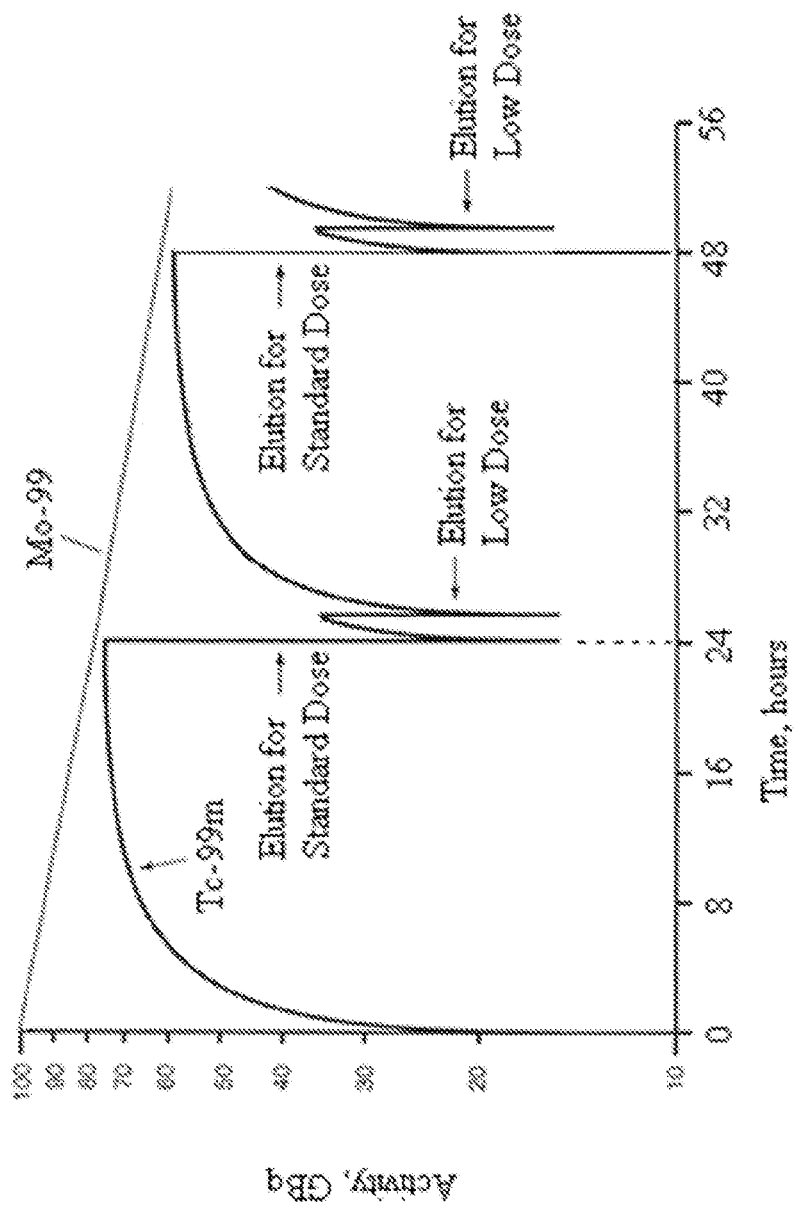

FIG. 146 describes a standard elution curve;

FIG. 147 describes a recommended low-dose elution curve.

FIGS. 148A-V are tables describing protocols according to embodiments of the present invention.

DESCRIPTION OF THE PREFERRED EMBODIMENTS

The present invention relates to radioimaging cameras characterized by unprecedented high sensitivity allowing for high resolution image acquisition for use in diagnostics; algorithms and systems operable in conjunction with the camera, the algorithms and systems include, but are not limited to, predetermined view selection algorithm and system, active vision (on the fly view selection) algorithm and system, closed loop) administration of a radiopharmaceutical algorithm and system, expert system diagnostic algorithm and system, automatic dose preparation algorithm and kinetic parameter extraction algorithm and system; low dose radiopharmaceuticals; combinations of radiopharmaceuticals either as compositions (cocktails) and/or kits; an administering device of radiopharmaceuticals, which may include syringes, pumps and IV lines; mixers for mixing different radiopharmaceuticals; and an ERP system for controlling and monitoring each one or more of the above.

The present invention emerges from the development of a radioimaging camera characterized by unprecedented sensitivity. The sensitivity of the camera is attributed, as is further detailed hereinbelow, to at least the following constructual features: (a) a plurality of detecting units; (b) movability of the detecting units one with respect to the other; (c) thus allowing concentrated focus on a region-of-interest by the individual detecting units; and (d) wiring diagram with minimal multiplexing, thereby preventing saturation thereof.

As a result of this sensitivity, it is now possible using the camera of the present invention to (a) detect low dose radiopharmaceuticals; (b) perform fast kinetic studies; (c) extract kinetic parameters for the distribution of a radiopharmaceutical under different diagnostic setups, thereby allowing (i) formulating radiopharmaceuticals based on the newly achieved knowledge of the kinetic parameters; (ii) diagnostics based on the kinetic parameter's; (iii) formulating new therapeutic drugs based on the kinetic parameters; and (iv) using the kinetic parameters as an input to the expert system for diagnostics; (d) provide images of co-administered radiopharmaceuticals; and (e) allow diagnostically meaningful imaging at a far faster rate as compared to conventional prior art radioimaging cameras.

In order to minimize the exposure of a subject to radioactive substances and in order to maximize the diagnostic capabilities using radioimaging, the inventors of the present invention developed low dose preparations of radiopharmaceuticals and compositions and kits comprising two or more radiopharmaceuticals adapted for use in conjunction with the camera rind all other aspects of the invention.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Basic Imaging Concept

FIGS. 1A and 1B schematically illustrate a detecting unit 12 and a block 90 of detecting units 12, respectively.

As seen in FIG. 1A, the detecting unit 12 is formed of a single-pixel detector 91, having a thickness $\tau_d$ and a diameter D or, in the case of a non-circular detector, a diameter equivalent. Alternatively, several pixels may be summed up so as to operate, in effect, as a single pixel. Both the detector diameter D and the detector thickness $\tau_d$ affect the detecting efficiency. The detector diameter D determines the surface area on which radioactive emission impinges; the greater the surface area, the greater the efficiency. The detector thickness $\tau_d$ affects the stopping power of the detector. High-energy gamma rays may go through a thin detector; the probability of their detection increases with an increase in the detector thickness $\tau_d$.

FIG. 1A illustrates a single-pixel detector 91, which by itself cannot generate an image; rather, all counts are distributed over the surface area of the detector 91.

As seen in FIG. 1B, the block 90 includes a plurality of the detecting unit 12, formed by dividing the detector 91 into a plurality of electrically insulated pixels 106, each associated with a collimator 96. The collimators 96 are of the diameter or diameter equivalent D, a length L, and a septum thickness $\tau$. The collimators 96 may be, for example, of lead, tungsten or another material which substantially blocks gamma and beta rays. The collimators 96 may be shaped as tubes, rectangular grids, or grids of any other polygon. Wide-angle or narrow-angle collimators are also possible.

The collimator's geometry and specifically, the ratio of D/L, provides the detecting unit 12 with a collection solid angle $\delta$ analogous to the viewing solid angle of an optical camera. The collection solid angle $\delta$ limits the radioactive-emission detection to substantially only that radioactive emission which impinges on the detector 91 after passing through a "corridor" of the collimator 96 (although in practice, some high-energy gamma rays may penetrate the collimator's walls). With no collimator, the collection angle $\delta$, is essentially a solid angle of $4\pi$ steradians.

Thus, the collimator's geometry affects both the detection efficiency and the image resolution, which are defined as follows:

i. The detection efficiency is the ratio of measured radiation to emitted radiation; and ii. The image resolution is the capability of making distinguishable closely adjacent manifestations of a pathology, or the capability to accurately determine the size and shape of individual manifestations of a pathology.

While it is naturally desired to optimize both the detection efficiency and the image resolution, they are inversely related to each other. The detection efficiency increases with an increase in the collimator collection angle, and the image resolution decreases with an increase in the collimator collection angle.

In other words, while a wide-aperture, single-pixel detecting unit, such as that of FIG. 1A provides high efficiency, it does not lend itself to the generation of a two-dimensional image, and the wide aperture blurs the information regarding the direction from which the radiation is emitted. Yet as the resolution is increased, for example, in the detecting unit 12 of FIG. 1B, the detection efficiency decreases.

Commonly owned US Applications 20040015075 and 20040054248 and commonly owned PCT publication WO2004/042546, all of whose disclosures are incorporated herein by reference, describe systems and methods for scanning a radioactive-emission source with a radioactive-emission camera of a wide-aperture collimator and, at the same time, monitoring the position of the radioactive-emission camera, at very fine time intervals, to obtain the equivalence of fine-aperture collimation. In consequence, high-efficiency, high-resolution images of a radioactivity emitting source are obtained. This is discussed below with regard to FIGS. 2-3B.

FIG. 2 schematically illustrates the basic component of a system 120 comprising a radioactive-emission camera 122, operative as a detection system, and a position-tracking device 124, both in communication with a data-processing system 126. The radioactive-emission camera 122 is associated with a first coordinate system 128, and the position-tracking device 124 is associated with a second coordinate system 128', wherein the position-tracking device 124 monitors the position of the radioactive-emission camera 122 as a function of time. The data-processing system 126 processes the measurements of both the radioactive-emission camera 122 and the position-tracking device 124 and combines them to form the image.

FIG. 3A schematically illustrates a manner of operating the radioactive-emission camera 122 with the position-tracking device 124 of the system 120. The radioactive-emission camera 122 moves about an area of radioactive emission 110, for example, in the direction of an arrow 118, so as to measure a radioactive emission distribution 112, as a function of time, while the position-tracking device 124 monitors the position of the camera 122. The radioactive-emission camera 122 may be a single-pixel detector of high efficiency, which is incapable, by itself, of producing images. Nonetheless, a data-processing system 126 processes a radioactive-count-rate input 121 together with a position-tracking input 123, using algorithms 125, to reconstruct an image 110' of the area of radioactive emission 110 for example, on a display unit 129.

Imaging according to this concept is illustrated in FIG. 3B. The area of radioactive emission 110 is located in a two-dimensional coordinate system u;v, and includes two hot points 1115. The camera 122 moves from a position P(1), at a time t(1), to a position P(2), at a time t(2), while measuring the radioactive emission distribution 112 of the area of radioactive emission 110, including the hot points 115.

An example of a suitable position-tracking device 124 for use with system 120 is the miniBird™, which is a magnetic tracking and location system commercially available from Ascension Technology Corporation, P.O. Box 527, Burlington, Vt. 05402 USA (http://www.ascension-tech.com/graphic.htm). The miniBird™ measures the real-time position and orientation (in six degrees of freedom) of one or more miniaturized sensors, so as to accurately track the spatial location of cameras, instruments, and other devices. The dimensions of the miniBird™ are 18 mm×8 mm×8 mm for the Model 800 and 10 mm×5 mm×5 mm the Model 500. Alternatively, other optical tracking systems which may be used are NDI-POLARIS of Northern Digital Inc., Ontario, Canada, which provides passive or active systems, a magnetic tracking device of NDI-AURORA, an infrared tracking device of E-PEN system, or an ultrasonic tracking device of E-PEN system. Additionally or alternatively, the position-tracking device may be an articulated-arm position-tracking device, an accelerometer-based position-tracking device, a potentiometer-based position-tracking device, or a radio-frequency-based position-tracking device.

Commonly owned US application 20040054248 and commonly owned PCT publication WO2004/042546 further disclose various extracorporeal and intracorporal systems 120 wherein the position-tracking devices 124 associated with the radioactive-emission cameras 122 have relatively wide apertures. Examples of extracorporeal and intracorporal radioactive-emission cameras of this type are seen in FIGS. 4A-4C.

FIG. 4A schematically illustrates one embodiment of system 120, including a hand-held, extracorporeal device 170, which includes the camera 122, having a detector 132 and a collimator 134. The system 120 also includes a controller 130 and a position-tracking device 124, wherein the camera 122 and the position-tracking device 124 are associated with the data-processing system 126 discussed above with reference to FIGS. 2-3B.

FIG. 4B schematically illustrates another embodiment of system 120 wherein an intracorporal camera device 180 includes the radioactive-emission camera 122 mounted on a catheter 136. The camera 122 includes the detector 132, the collimator 134, and the position-tracking device 124, wherein the camera 122 and the position tracking device 124 are associated with the data-processing system 126 discussed above with reference to FIGS. 2-3B. The camera 122 is configured so as to penetrate a tissue 135, via a Trocar valve 138. A structural imager 137, such as an ultrasound imager or an MRI camera may further be included.

FIG. 4C schematically illustrates yet another embodiment of system wherein an intracorporal camera device 190 is adapted for rectal insertion. The device 190 includes the radioactive-emission camera 122, which includes a plurality of the detectors 132 and the collimators 134 associated with the position-tracking device 124. The intracorporal 190 device may be further adapted for motion along the x and ω directions. For example, the intracorporal device 190 may include a motor 154 for moving the device 190 in the x and ω directions, such that, once inserted into a rectum, it may be propelled therealong. A suitable motor 154 may be obtained, for example, from B-K Medical A/S, of Gentofte, DK, and may be adapted to transmit information to the data-processing system 126, regarding the exact position and orientation of the intracorporal device 190. In some embodiments, the motor 154 may be used in place of the position-tracking device 124. Alternatively, it may be used in addition thereto. The intracorporal device 190 may further include the structural imager 137, such as an ultrasound imager or an MRI.

Initial View Determination

Predetermined Views, Based on a Model of a Body Structure

Definition of a View

Referring now to the drawings, FIGS. 5A-5F present the principles of modeling, for obtaining an optimal set of views, in accordance with embodiments of the present invention.

FIG. 5A schematically illustrates a body section 230 having a region-of-interest (ROI) 200. The region-of-interest 200 may be associated with a body structure 215 having a specific radioactive-emission-density distribution, possibly suggestive of a pathological feature, this feature termed herein organ target 213. Additionally, there may be certain physical viewing constraints associated with the region-of-interest 200.

In accordance with embodiments of the present invention, FIG. 5C illustrates, in flowchart form, a method 205 for best identifying an optimal and permissible set of views for measuring the radioactive-emissions of the region-of-interest 200, such that a three-dimensional image thereof may be reconstructed. The method 205 includes the following steps:

in a box 206: modeling the region-of-interest 200 as a model 250 of a volume U, wherein U is the region-of-interest volume, and wherein the volume U may include one or several radioactive-emission sources, operative as modeled organ targets HS located within anatomical constraints AC, as seen in FIG. 5B;

in a box 207: obtaining an optimal and permissible set of views for the modeled volume U FIG. 5B; and in a box 208: applying the optimal set of views to the in-vivo region-of-interest 200 and the body structure 215 of FIG. 5A.

It will be appreciated that the model 250 of the region-of-interest 200 may be based on general medical information of the body structure 215 and common pathological features associated with it. Additionally, the model may be based on information related to a specific patient, such as age, sex, weight, and body type. Furthermore, in order to facilitate generation of the model 250, a structural image, such as by ultrasound or MRI, may be used for providing information about the size and location of the body structure 215 in relation to the body section 230.

FIGS. 5D-5F schematically illustrate three types of the modeled organ targets HS, as follows:

i. a region of concentrated radiation, or a hot region, for example, as may be associated with a malignant tumor and as seen in FIG. 5D;

ii. a region of low-level radiation, which is nonetheless above background level, for example, as may be associated with carcinoma and as seen in FIG. 5E; and iii. a region of little radiation, or a cold region, below the background level, for example, as may be associated with dead tissue and as seen in FIG. 5F.

Referring further to the drawings, FIGS. 6A and 6B pictorially illustrate a view and viewing parameters associated therewith, in accordance with embodiments of the present invention.

FIG. 6A illustrates the volume U, subdivided into voxels u. The volume U is defined in a six-degree coordinate system x;y;z;ω;θ;σ having a point of origin P0(x0; y0; z0; ω0; θ0; σ0). A detecting unit 102 is positioned at a location and orientation P1(x1; y1; z1; ω1; θ1; σ1). The detecting unit 102 has a detector 104, formed of a specific detector material having a thickness $\tau_d$, and a collimator 108, having a diameter D and a length L and defining a collection angle δ.

FIG. 6B schematically illustrates the emission rate of the volume U, as a function of time, given that a radioactive material of a specific half-life has been administered at a time T0.

A view may thus be defined as a group of nonzero probabilities of detecting a radioactive emission associated with all the voxels that form a sector S (FIG. 6A). A view is sometimes referred to as a projection, and the two terms are synonymous. Furthermore, a view defined over a sector S can be naturally extended to be defined over the set of all voxels, by simply associating a zero probability with every voxel outside the sector S. This makes possible the application of mathematical operations over the entire volume U.

A view is dependent on the following viewing parameters:

Location and Orientation Parameters:

The location and orientation of the detecting unit 12 in a six-dimensional space, P1(x1; y1; z1; ω1; θ1; σ1), with respect to the origin P0(x0; y0; z0; ψ0; θ0; σ0) of the volume U.

Detecting-Unit Parameters:

The collection angle δ which, together with the location and orientation parameters P1(x1; y1; z1; ω1; θ1; σ1) with respect to the origin P0(x0; y0; z0; ω0; θ0; σ0), define the sector S;

The detector material, which affects the detector efficiency;

The detector thickness $\tau_d$, which affects the detector's stopping power, hence, its efficiency; and The diameter of the detecting unit, or the effective diameter, calculated so as to produce a circle of the same area, when the geometry is not a circle.

Attenuation Parameters:

Attenuation properties of all the voxels within the sector S, as they affect the probabilities that radioactive emissions from a specific voxel will reach the detector, wherein different voxels within the sector S may have different attenuation properties, since several types of tissue may be involved.

Radiopharmaceutical Parameters:

The hall life $t_{1/2}$ of the radiopharmaceutical, the types of radioactive emission, whether gamma or beta, and the energies of the radioactive emissions, which affect the probability of detection.

As used herein the phrase "kinetic profile" means a collection of one or more parameters describing the rate of distributing due to flow, uptake, bioclerance, diffusion, active transport, metabolism and the like.

A kinetic profile is either definable in general or per patient, per organ, per tissue and under various conditions, such as pathologies and stimulations.

Time Parameters:

T0 is the time of administrating the radiopharmaceutical, T1 is the time since administration, and the duration of the measurement is $\Delta T1$, which affects the number of emissions that occur during the radioactive-emission measurement.

Some of these viewing parameters are fixed for a particular situation. Specifically, the tissue attenuation parameters are given. Additionally, the time T1 since administration of the radiopharmaceutical is generally governed by the blood pool radioactivity, since it is generally necessary to wait until the blood pool radioactivity dies out for low-level detection to be possible. For the remaining viewing parameters, optimization may be carried out.

The remaining viewing parameters may be divided into two categories:

i. viewing parameters in the design of a radioactive-emission camera;

ii. viewing parameters for an optimal set of views, for a given camera.

Viewing Parameters for an Optimal Set of Views, for a Given Camera

Referring further to the drawings, FIGS. 7A-7C schematically illustrate anatomical constraints, which may hinder measurements.

FIG. 7A schematically illustrates the region-of-interest 200, for which a three-dimensional radioactive-emission image is desired. The region-of-interest 200 is in free space, with no constraints to limit accessibility to it. Thus, a radioactive-emission camera 210 may travel, for example, along tracks 202 and 204, and any other track, unhindered.

In FIG. 7B, the region-of-interest 200 is associated with the body structure 215, such as a prostrate, in vivo. For obtaining a radioactive-emission image, the radioactive-emission camera 210 may be inserted transrectally, so as to travel in a rectum 206, for example, in the direction of an arrow 208. Its ability to image the prostrate is limited by anatomical constraints.

In FIG. 7C, the region-of-interest 200 is associated with the body stricture 215, such as a heart, a breast, or another organ, in vivo, and the radioactive-emission camera 210 may be an extracorporeal camera, which may perform radioactive-emission measurements from outside the body, on an extracorporeal surface 214, for example when moving along a track 212.

In each of these cases, it is desired that a reconstructed three-dimensional radioactive-emission image of the region-of-interest 200 be obtained at a predetermined quality. This is achieved by predefining an optimal set of radioactive-emission measurement views, tailored to the specific body structure 215 and optimized with respect to the information gained regarding the body structure 215.

Figure 8:
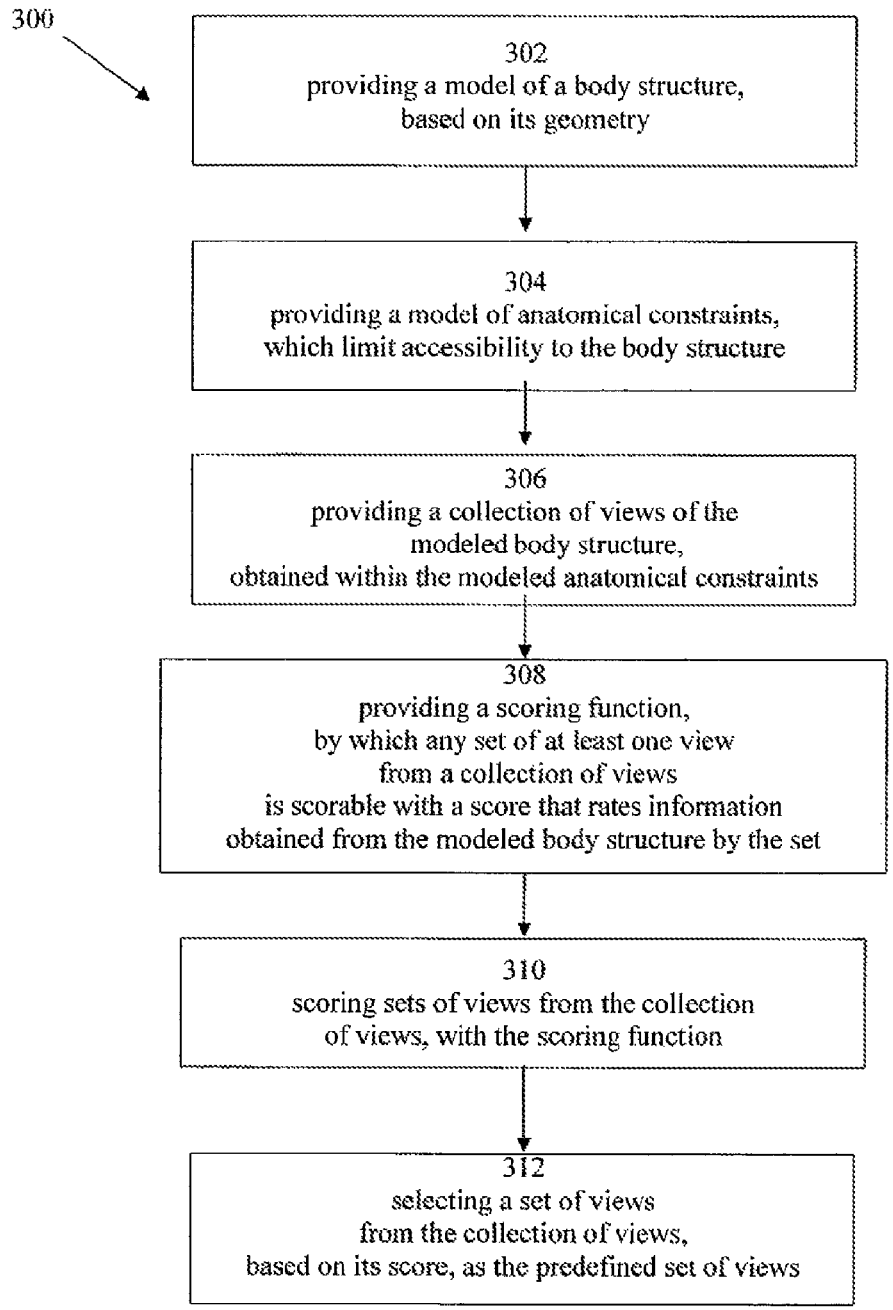
FIG. 8 illustrates, in flowchart form, a method of predefining a set of views for functional imaging, tailored for imaging a specific body structure, and optimized with respect to the functional information gained about the body structure, in accordance with embodiments of the present invention.

Referring further to the drawings, FIG. 8 illustrates, in flowchart form, a method 300 of predefining a set of views for functional imaging, tailored for imaging a specific body structure, and optimized with respect to the functional information gained about the body structure, in accordance with embodiments of the present invention. In effect, FIG. 8 is an expansion of FIG. 5C. The method 300 comprises:

in a box 302: providing a model of the body structure 215, based on its geometry;

in a box 304: providing a model of anatomical constraints, which limit accessibility to the body structure;

in a box 306: providing a collection of views of the modeled body structure obtained within the modeled anatomical constraints;

in a box 308: providing a scoring function, by which any set of at least one view, from a collection of views, is scorable with a score that rates information obtained from the modeled body structure by the set;

in a box 310: forming sets of views from the collection of views and scoring them with the scoring function; and in a box 312: selecting a set of views, from the collection of views, based on their scores, as the predefined set of views.

The model of the body structure is based on anatomical knowledge regarding its size, shape, and weight. In fact, different models may be provided, for example, for different ages, sexes, weights, and body types, such as heavy-built, medium-built, or small-built. In accordance with a first embodiment, the body stricture is modeled assuming that there is no radioactive emission throughout its volume. In accordance with other embodiments, the body structure may be modeled with one or more modeled organ targets, simulating different pathological features. Specifically, the modeled organ targets may be hot regions, of a radioactive-emission intensity higher than the background level, regions of low-level radioactive-emission intensity, which is nonetheless above the background level, and cold regions, of a radioactive-emission intensity lower than the background level. These may be distributed in accordance with medical records, which teach of sites within the body structure that may be more susceptible to certain pathologies.

Similarly, the model of anatomical constraints which limit accessibility to the body structure is based on anatomical knowledge, and different models may be provided, for example, for different ages, sexes, weights, and body types.

The collection of views may be obtained by several methods. It may be calculated analytically for the modeled body, based on the view parameters. Additionally or alternatively computer simulations of the modeled body and the view parameters may provide the collection of views. Additionally or alternatively, measurements may be performed using a point source and a detecting unit of appropriate parameters, at different locations and orientations of the detecting unit, so as to simulate the desired geometries.

It will be appreciated that a combination of these may be used. For example, the measurements may be performed in air, but corrected analytically or by computer simulations, for tissue attenuation.

Referring further to the drawings, FIGS. 9A-9F schematically illustrate possible models and collections of views for a body structure, in accordance with embodiments of the present invention.

Figures 9A, 9B:
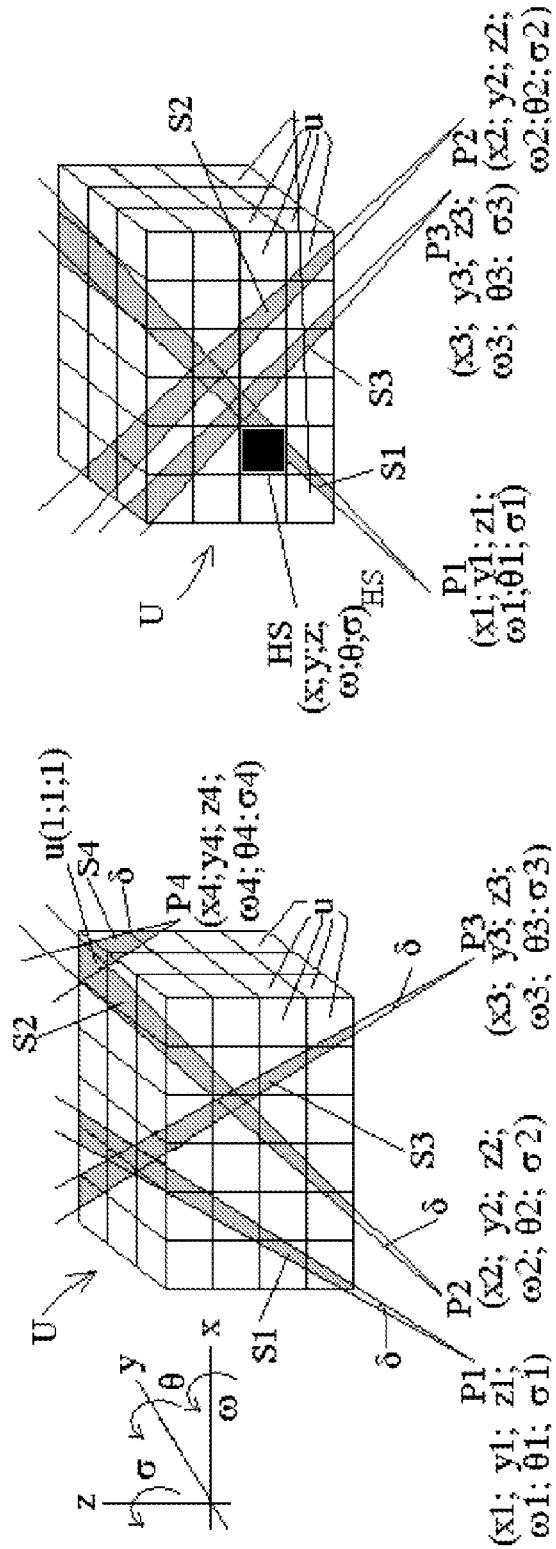

FIG. 9A schematically illustrates four views, formed by sectors S1, S2, S3, and S4 through the volume U, which has an even distribution of radioactive emission.

FIG. 9B schematically illustrates three views, formed by sectors S1, S2, and S3, through the volume U, which includes a modeled pathological feature, which is the modeled organ target, HS.

FIG. 9C schematically illustrates three views, formed by sectors S1, S2, and S3 through the volume U, which includes a modeled organ target, HS', of the same type as that of the modeled organ target HS, (that is, either a hot region or a cold region) but somewhat displaced along the x;y;z coordinate system. Additionally, the modeled organ target HS of FIG. 9B is superimposed in FIG. 9C, for illustrative purposes, in order to show the displacement, delta1, of modeled organ target HS' from modeled organ target HS.

FIG. 9D schematically illustrates three views, formed by sectors S1, S2, and S3 through the volume U, which includes a modeled organ target, HS", of the same type as that of the modeled organ targets HS and HS', but somewhat displaced along the x;y;z coordinate system from them. Additionally, the modeled organ targets HS of FIG. 9B and HS' of FIG. 9C are superimposed in FIG. 9D, for illustrative purposes, in order to show the displacements delta2 and delta3, vis a vis HS" of FIG. 9D.

FIG. 9E schematically illustrates three views, formed by sectors S1, S2, and S3 through the volume U, which includes two modeled organ targets, HS1 and HS2.

Figure 9F:
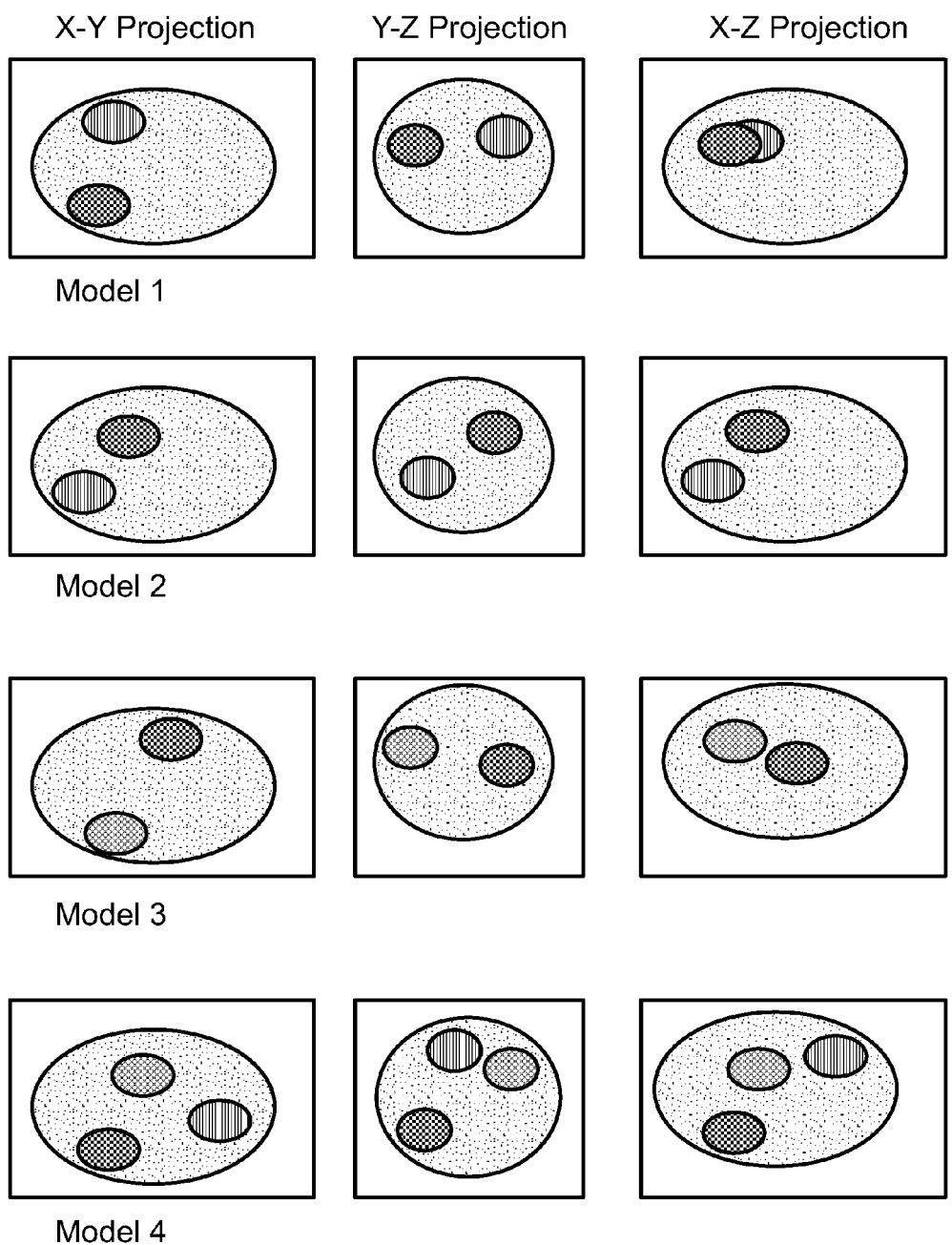

FIG. 9F schematically illustrates four possible models of organs, shown as elliptical volumes, each with a slightly different distribution of modeled organ targets.

The modeled organ targets may be termed emittance models. In general, an emittance model is based on a particular radiopharmaceutical, which fixes both the rate of emission and the change in the rate of emission with time, determining the difference between the modeled organ target and the background level, as a function of time. To study the effect of different radiopharmaceuticals on the views, one may provide different emittance models, based on different radiopharmaceuticals and different elapsed times relative to their administration.

The choice of an optimal set of views from among a collection of views, such as any of those illustrated in FIGS. 9A-9E, is based on a scoring function, which rates different sets of views in terms of their information regarding the volume U. The scoring function is based on information theoretic measures that rate the quality of the data which each set of views provides.

Information Theoretic Measures

A brief description of the information theoretic measures, upon which the scoring function may be based, is as follows:

Uniformity:

The information theoretic measure of uniformity requires that the probability of detecting a radioactive emission from each voxel, by one of the views, be substantially equal, i.e., substantially uniform for all the voxels.

This is illustrated with reference to FIG. 9A. Basically, in one view, a voxel may have a high influence on the counts that are measured while, in another view, the same voxel may have a low influence on the counts that are measured. For example, consider a voxel u(1; 1; 1), in relation to the views associated with the sectors S2 and S4. The voxel u(1; 1; 1) has a high influence on the counts that are measured by the view associated with the sector S4, but a low influence on the counts that are measured by the view associated with the sector S2. The aim of uniformity is to identify a set of views that will balance the influence of each voxel for the entire set of views.

Separability:

The information theoretic measure of separability rates resolution, or the ability to distinguish between a pair of close models of the body structure, each having substantially identical dimensions, so as to define substantially identical volumes U having slightly different distributions of modeled organ targets.

For example, a pair of models of substantially identical volumes are illustrated in FIGS. 9B and 9C, wherein the respective modeled organ targets are HS, whose center is at a location $(x;y;z)_{HS}$ and HS', whose center is at a location $(x;y;z)_{HS'}$. As noted above, the displacement along the x axis is delta1, which may be measured, for example, in mm.

An optimal set of views, from the standpoint of separability, is that which will best distinguish between HS of FIG. 9B and HS' FIG. 9C. Thus, a score, in terms of separability, is given for the pair of models, the score relating to a resolution as defined by the difference between the location of the two models. In the present example, the difference is delta1, so the score given by the information theoretic measure of separability will relate specifically to a resolution as defined by delta1 along the x-axis, relative to the locations of HS and HS'. Other portions of the volume U and other displacements may have different resolutions.

Additionally, as discussed above with regard to the model of FIG. 9D, volume U includes the modeled organ target HS", whose center is at a location $(x;y;z)_{HS''}$. HS" is displaced from HS of FIG. 9B, along the z-axis, the displacement denoted delta2, and is also displaced from HS' of FIG. 9C, along the x- and z-axes, the displacement denoted delta3.

Scores, in terms of separability, may be given to all the pairing combinations, i.e., to the models of FIGS. 9B-9C, with regard to delta1; to the models of FIGS. 9B-9D, with regard to delta2; and to the models of FIGS. 9C-9D, with regard to delta3. An optimal set of views may be selected based on the average scores for all the pairing combinations; for example, the optimal set may be that whose average score for all the pairing combinations is the highest. Alternatively, a weighted average may be applied.

It will be appreciated that more than one modeled organ target may be included in the volume U. It will be further appreciated that a set of views may be selected so as to provide high resolution for portions of the volume U known to be susceptible to pathologies, and so as to provide low resolution for portions of the volume U known to be generally free of pathological features.

With regard to FIG. 9F, any pair of models of organs having different distributions of modeled organ targets, may be utilized for identifying an optimal set of views in terms of separability.

Reliability:

The information theoretic measure of reliability rates repeatability in measurement, so that repeated reconstructions are not substantially different. Reliability may be scored with respect to a single model of a body structure, having a specific distribution of modeled organ targets, for example, any one of the models of FIGS. 9B-9E. Yet, preferably, several models of substantially identical volumes are provided, such as, for example, the four models of FIGS. 9B-9E. Substantially identical sets of views may be applied to all the models and may be scored with respect to reliability. The optimal set is selected based on its average score for the plurality of the models. For example, the optimal set may be that whose average score for the plurality of the models is the highest.

The four models of organs of FIG. 9F, each of which has a slightly different distribution of modeled organ targets, may also be used for identifying an optimal set of views in terms of reliability.

Weighted Combination:

A weighted combination of several information theoretic measures may also be used. For example, a plurality of models may be provided, all having substantially identical dimensions and volumes, as follows:

i. a first model of the volume U, free of modeled organ targets, as seen in FIG. 9A, for scoring sets of views in terms of uniformity;

ii. at least one pair of models of the volume U, with slightly different distributions of modeled organ targets, as seen in any pair of FIGS. 9B-9C, 9B-9D, and (or) 9C-9D, for scoring sets of views in terms of separability;

iii. at least one model of the volume U, with a given distribution of modeled organ targets, as seen in any one of FIGS. 9B, 9C, 9D, and (or) 9E, for scoring sets of views in terms of reliability.

Identical sets of views may be applied to all the models of the volume U, and each view may be scored in terms of uniformity, separability, and reliability. An optimal set of views may be selected based on a summation of the three scores, or based on a weighted average of the three scores.

The Greedy Construction

Some approaches for selecting an optimal set are based on determining a required quality of reconstruction, and finding a set of views that meets that requirement. Others are based on fixing the size for the set (i.e., the number of views in the set) and maximize the quality of the reconstruction for the given set size. Still other approaches define both a desired size for the set and a desired quality of reconstruction and search for a set of the desired size, which meets the desired quality of reconstruction.

However, given a desired size for a set of views and a desired quality of reconstruction, while it may be possible to search through all possible sets of the desired size, scoring, each, in order to identify the set that meets the desired quality, the task may be monumental. For example, where the collection of views includes several thousand views, and a set size of 100 is desired, rating each combination of 100 views would be computationally impractical.

An alternative approach is the Greedy Construction. When applying the Greedy Constriction, an information theoretic measure is chosen, for example, separability, and an initial set of a minimal number of views is defined. The set is gradually built up, so that with every addition, a view is picked so as to maximize the chosen information theoretic measure of the set.

This may be illustrated with reference to FIG. 9E. Given that separability is the chosen information theoretic measure, and an initial set of view S1 is defined, the additions of views S2 and S3 may then be compared in order to determine with which of them separability is maximized. Intuitively, for the present example, the addition of S3 will maximize the chosen information theoretic measure of the set.

It will be appreciated that other scoring functions, as known, may similarly be used.

Performing Measurements

The advantage of the method of the present invention, of predefining a set of views based on a model of a body structure, using an information theoretic measure, so as to optimize the functional information from the views of the corresponding body structure, in vivo, becomes apparent when compared with the prior art alternatives. The prior alt relies on obtaining random views, in vivo, or views dictated by anatomical constraints, with no rigorous approach to the manner by which they are chosen.

The method of the present invention, of predefining a set of views, based on a model of a body structure, using an information theoretic measure, so as to optimize the functional information from the views of the corresponding body structure, in vivo, is further illustrated hereinbelow, with reference to FIG. 10.

Figure 10:
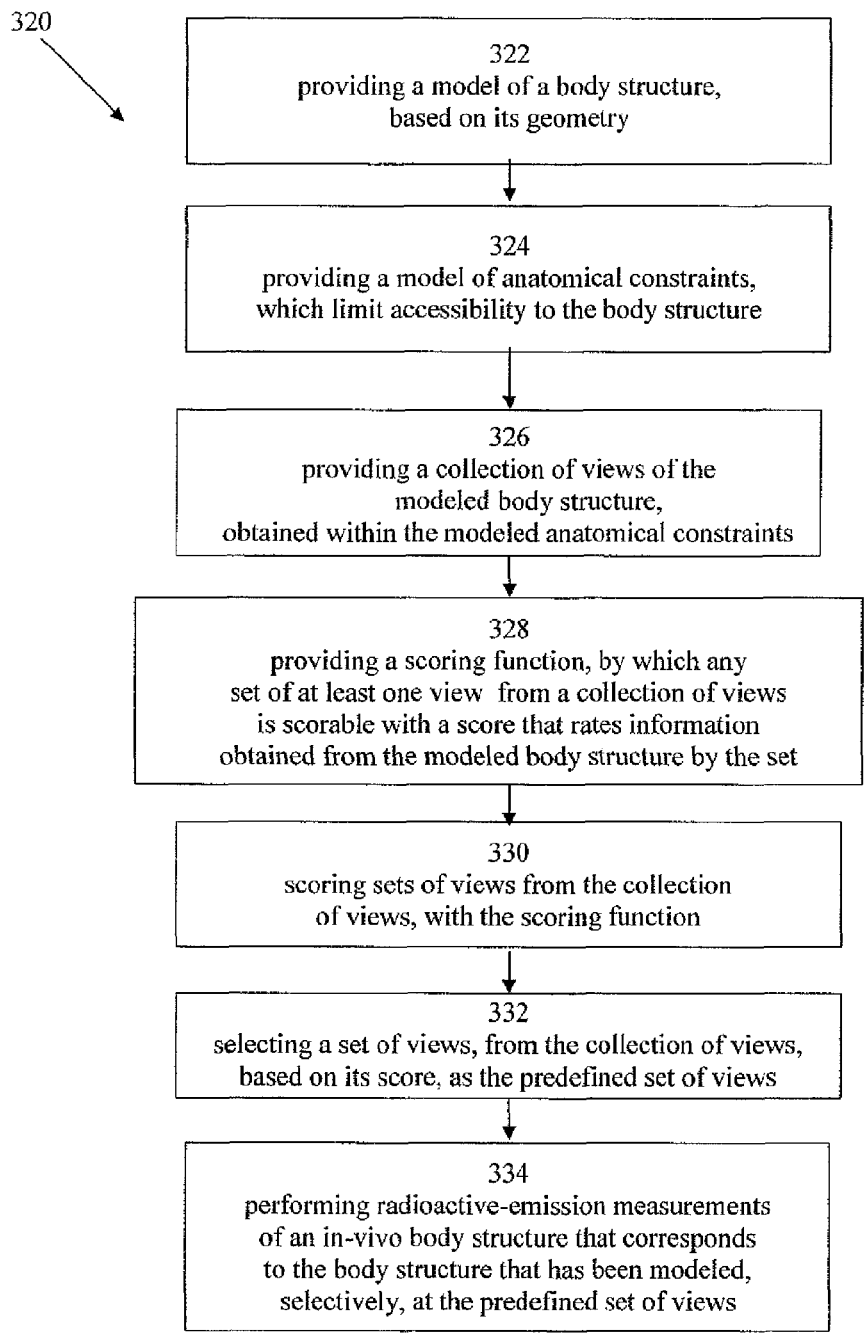
FIG. 10 illustrates, in flowchart form, a method of functional imaging, tailored for imaging from esophagus, and optimized with respect to the functional information gained about the body structure, in accordance with embodiments of the present invention.

FIG. 10 illustrates, in flowchart form, a method 320 of functional imaging, tailored for imaging a body structure optimized with respect to the functional information gained about the body structure, by using the predefined optimal set of views, in accordance with embodiments of the present invention. The method 320 comprises:

in a box 322: providing a model of a body structure, based on its geometry;

in a box 324: providing a model of anatomical constraints, which limit accessibility to the body structure;

in a box 326: providing a collection of views of the modeled body structure, obtained within the modeled anatomical constraints;

in a box 328: providing a scoring function, by which any set of at least one view, from a collection of views is scorable with a score that rates information, obtained from the modeled body structure by the set;

in a box 330: forming sets of views from the collection of views and scoring them, with the scoring function;

in a box 332: selecting a set of views from the collection of views of the modeled body structure, based on its score, as the predefined set of views; and in a box 334: performing radioactive-emission measurements of an in-vivo body structure that corresponds to the body structure that has been modeled, selectively at the predefined set of views.

It will be appreciated that the region-of-interest 200 may include an organ, such as a heart or a pancreas, a gland, such as a thyroid gland or a lymph gland, blood vessels, for example, the coronary artery or the pulmonary artery, a portion of an organ, such as a left atrium of a heart, a bone, a ligament, a joint, a section of the body, such as a chest or an abdomen, or a whole body.

A still more powerful approach may be achieved by taking the method of the present invention through second and third iterations, so as to zoom in on suspected pathological features that are identified. Specifically, when a suspected pathological feature is identified, a second, inner region-of-interest, limited to the region of the pathological feature and its surrounding anatomical structure, can be identified and modeled. An optimal pathology set of views, specifically for the second, inner region-of-interest, may be predefined, based on information theoretic measures, as before. This is illustrated hereinbelow, with reference to FIGS. 11 and 12.

Figure 11:
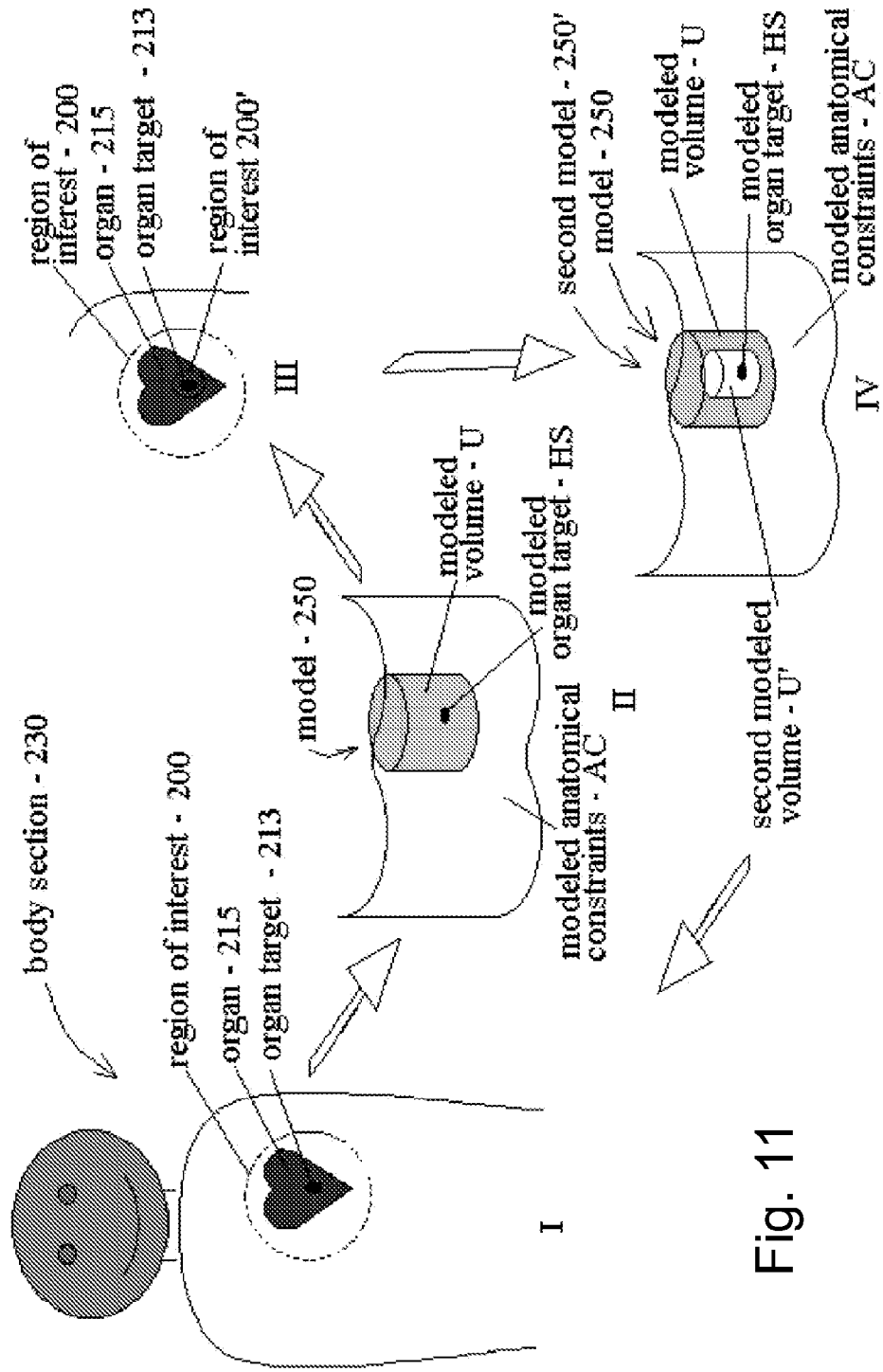
FIG. 11 schematically illustrates the process of modeling in two iterations, for zooming in on a pathological feature, in accordance with embodiments of the present invention.

Referring further to the drawings, FIG. 11 pictorially illustrates a method 340 for zooming in on a suspected pathological feature, as a process of two or more iterations, in accordance with embodiments of the present invention, as follows:

In I: The region-of-interest 200, associated with the body structure 215, is defined for the body section 230.

In II: The model 250 of the volume U is provided for the region-of-interest 200, possibly with one or several of the modeled organ targets HS, and within the anatomical constraints AC, for obtaining the optimal set of views for the region-of-interest 200. The optimal set of views is then applied to the body section 230.

In III: When a suspected organ target 213 is identified, in vivo, by radioactive-emission measurements at the optimal set of views, a second, inner region-of-interest 200' is defined, including the suspected pathological feature.

In IV: A model 250' of a volume U' is provided for the second, inner region-of-interest 200', preferably, with at least one modeled organ target HS, simulating the suspected organ target 213, for obtaining an optimal pathology set of views for the region-of-interest 200'. The second, pathology set of views is then applied to the body section 230.

Figure 12:
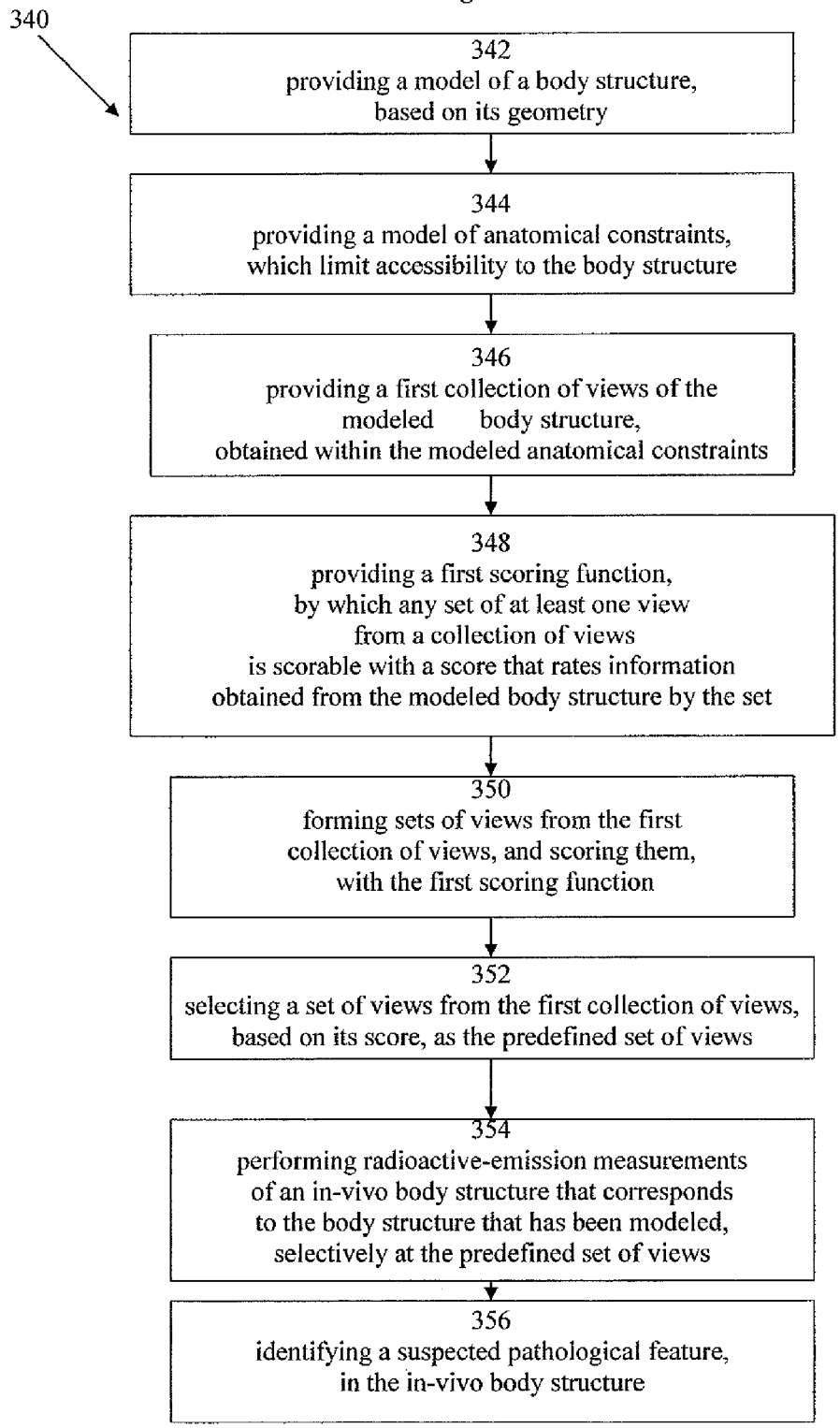
FIG. 12 illustrates, in flowchart form, a method of several iterations for zooming in on a pathological feature, when performing in vivo measurements, in accordance with embodiments of the present invention.

Referring further to the drawings, FIG. 12 illustrates, in flowchart form, the method 340, for zooming in on a suspected pathological feature of the body structure, as a process of two iterations, in accordance with embodiments of the present invention. The method 340 comprises:

in a box 342: providing a model of a body structure, based on its geometry;

in a box 344: providing a model of anatomical constraints, which limit accessibility to the body structure:

in a box 346: providing a first collection of views of the modeled body structure, obtained within the modeled anatomical constraints;

in a box 348: providing a first scoring function, by which any set of at least one view, from a collection of views, is scorable with a score that rates information, obtained from the modeled body structure by the set;

in a box 350: forming sets or views from the first collection of views, and scoring them, with the first scoring function;

in a box 352: selecting a set of views from the first collection of views of the modeled body structure, based on its score, as the predefined set of views;

in a box 354: performing radioactive-emission measurements of an in-vivo body structure that corresponds to the body stricture that has been modeled, selectively at the predefined set of views;

in a box 356: identifying a suspected pathological feature, in the in-vivo body structure;

in a box 358: providing a model of the suspected pathological feature, based on its location in the body structure and general medical knowledge;

in a box 360: providing a model of the anatomical constraints, which limit accessibility to the suspected pathological feature;

in a box 362: providing a second collection of views of the modeled suspected pathological feature, obtained within the modeled pathology's anatomical constraints;

in a box 364: providing a second scoring function;

in a box 365: forming sets of views from the second collection of views, and scoring them, with the second scoring function;

in a box 366: selecting a set of pathology views from the second collection of views, based on its score, as the predefined pathology set of views; and in a box 368: performing radioactive-emission measurements of the suspected pathological feature, selectively at the predefined pathology set of views.

It will be appreciated that the model of the suspected pathological feature may be provided responsive to a patient's complaint, a physician's examination, or based on input from another imaging system, for example, x-rays, CT, MRI, ultrasound, and gamma scanning, for example, with a hand-held gamma camera, rather then based on the findings of the first set of measurements, of the step 356, hereinabove.

Design of the Radioactive-Emission Camera

While the embodiments described with reference to FIGS. 5A-12 relate to predefining a set of optimal views for a given radioactive-emission camera and a body structure, another side of the same coin relates to an optimal design of the radioactive-emission camera and camera system for the body structure, optimized with respect to functional information gained.

Thus, the embodiments described hereinbelow, with reference to FIGS. 13A-15 illustrate methods of designing cameras and camera systems, optimized with respect to information gained about a body structure.

Referring further to the drawings, FIGS. 13A-13E schematically illustrate possible designs of the radioactive-emission camera 10, and the process of obtaining views for a given camera design, in accordance with embodiments of the present invention.

FIGS. 13A-13C schematically illustrate the radioactive-emission camera 10 as a radioactive-emission camera 226 arranged for measuring the radioactive-emission-density distribution of three bodies, U1, U2 and U3. The volume U1 of FIG. 13A has been modeled with no modeled organ targets, in order to score the radioactive-emission camera 226 in terms of uniformity. The volume U2 of FIG. 13B includes two modeled organ targets, HS1 and HS2, and may be used for scoring the radioactive-emission camera 226 in terms of reliability. The volume U3 of FIG. 13C includes two modeled organ targets, HS1 and HS2', so as to form a pair with the volume U2 of FIG. 13B, and the pair may be used for scoring the radioactive-emission camera 226 in terms of separability. Additionally, the volume U3 may be used to obtain a second score in terms of reliability, and the two reliability scores may be averaged. It will be appreciated that additional bodies, of different radioactive emission density distributions may be used, for obtaining additional scores in terms of reliability, and for forming additional pairs, for additional scores in terms of separability, wherein the scores in terms of each scoring function may be averaged. Additionally, the scores of the three functions may be combined, for example, as a sum, or as a weighted average. It will be appreciated that only one of the scoring functions, or only two of the scoring functions may be used. Additionally or alternatively, another scoring function or other scoring functions may be used.

According to the present example, the camera 226 has two detecting units 222A and 222B whose collimators are arranged in parallel. The two detecting units 222A and 222B are adapted for motion in the directions of ±x, within the camera 226, as shown by arrows 224 and 228, so as to provide coverage of a plane within the bodies U1, U2 and U3, in parallel sectors. Upon reaching the end of the travel in the +x direction, as shown by the arrow 224, the two detecting units 222A and 222B may be rotated in the direction of ω, as shown by an arrow 217, and return in the −x direction of the arrow 228. In this manner, complete coverage of the whole body is provided. A representative collection of views of the camera 226 may be defined as a set of views of the bodies U1, U2, and U3, taken at predetermined increments of Δx and Δω.

Intuitively, a set formed of parallel sectors may score poorly in terms of uniformity since radioactive emissions from voxels closer to the detecting unit have higher probabilities of being detected than radioactive emissions from voxels far from the detecting unit. Additionally, a set formed of parallel sectors may score poorly in terms of separability, since it cannot distinguish between two models, which only differ in the depth of a pathological feature, along the z-axis.

Figure 13D:
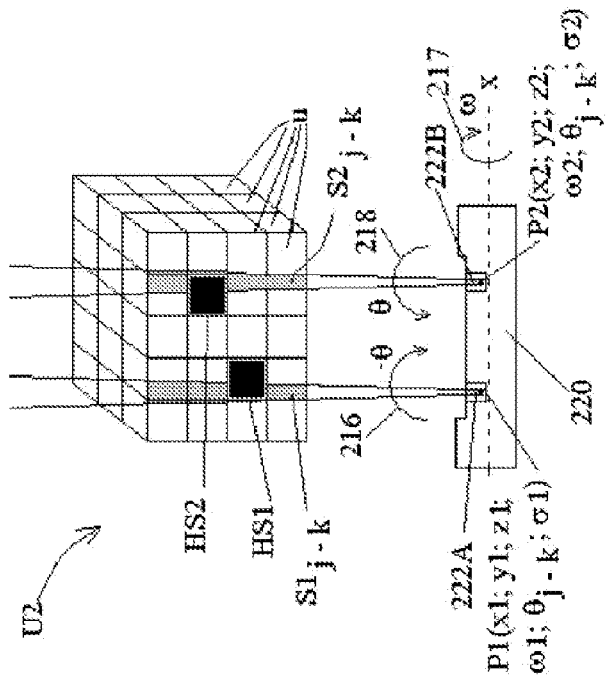

FIG. 13D schematically illustrate the radioactive-emission camera 10 as a radioactive-emission camera 220, arranged for measuring the radioactive-emission-density distribution of the volume U2, which may be used for scoring the radioactive-emission camera 220 in terms of reliability.

The camera 220 has the two detecting units 222A and 222B, arranged to sweep a plane within the volume U2, in a windshield-wiper-like manner, along ±θ, as illustrated by arrows 216 and 218. When sweeping along ±θ is completed, the detecting units 222A and 222B rotate a few degrees along ω, as illustrated by the arrow 217, and sweeping along ±θ is repeated in the new orientation. In this manner, coverage of the whole volume U2 is performed, from two locations and a large plurality of orientations. A representative collection of views of the camera 220 may be defined as a set of views of the volume U2, taken at predetermined increments of Δθ and Δω.

The significance of the present embodiment, is as follows:
i. The different detecting units 222A and 222B provide views from different orientations; and
ii. The different detecting units 222A and 222B may change their view orientations.

A score may be applied to this set, based on the information theoretic measure of reliability.

It will be appreciated that similarly, the camera 220 may be arranged for measuring the radioactive-emission-density distribution of the volume U1 (FIG. 13A) and of the volume U3 (FIG. 13C), and possibly also of other bodies, in order to score the radioactive-emission camera 220 also in terms of uniformity and separability. The scores of the three functions may be combined, for example, as a sum, or as a weighted average. It will be appreciated that only one of the scoring functions, or only two of the scoring functions may be used. Additionally or alternatively, another scoring function or other scoring functions may be used.

Intuitively, the set of representative collection of views of the present example is likely to score more highly in terms of separability than that of the camera 226 of FIG. 13A, as it provides views from different locations and orientations.

Figure 13E:
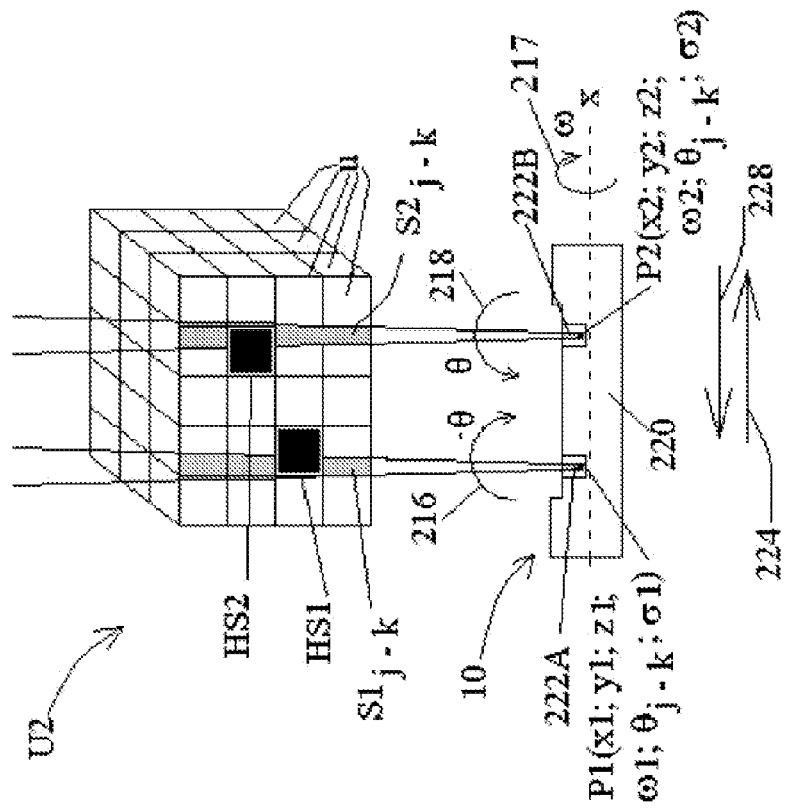
Figure 16L:
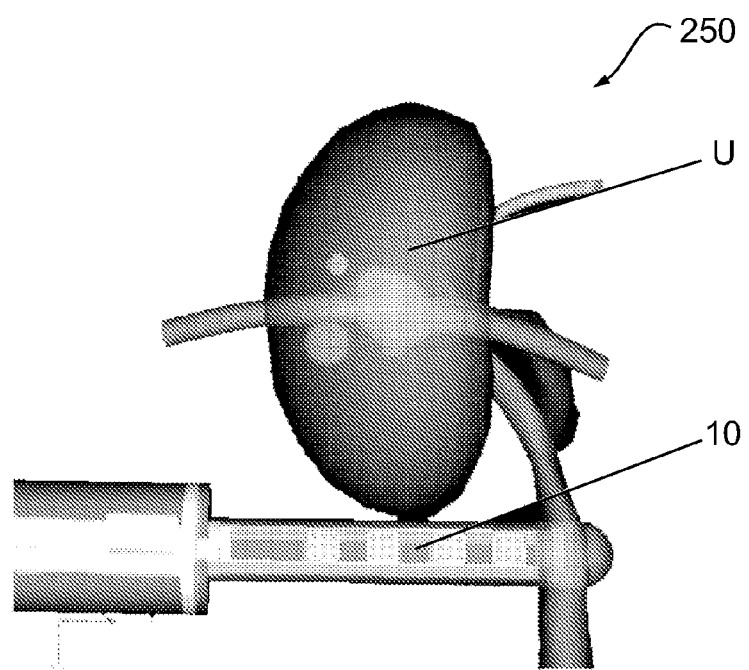

In FIG. 13E the detecting units 222A and 222B of the camera 220 are further adapted for motion in the directions of ±x, within the camera 220, as shown by the arrows 224 and 228.

Intuitively, the set of representative collection of views of the present example is likely to score more highly in terms of all three information theoretic measures, than those of the camera of FIGS. 13A-13C and of the camera of FIG. 13D, as the present example provides views from a large plurality of locations and orientations.

In this manner, the information theoretic measures may be used for scoring representative collections of views of suggested camera designs, and an optimal camera design may be chosen based on this score, as described hereinbelow, with reference to FIG. 14, hereinbelow.

FIG. 14 illustrates, in flowchart form, a method 370 for identifying a camera optimized with respect to information gained about the body structure. The method 370 comprises:

in a box 372: providing a model of a body structure, based on its geometry;

in a box 374: providing a model of anatomical constraints, which limit accessibility to the body structure;

in a box 375: providing representative collections of views of the modeled body structure, within the modeled anatomical constraints, for different camera designs;

in a box 376: providing a scoring function, by which each representative collection of views, associated with a specific camera design, is scorable with a score that rates information, obtained from the body structure;

in a box 377: scoring the representative collections of views, with the scoring function; and in a box 378: selecting a camera design, based on the score of its representative collection of views.

In this manner, a comparison of the quality of the data that may be produced by each camera design can be made. This analysis is important at the camera-design stage, in order to eliminate situations where views which are anatomically possible and which are desired from the standpoint of information theoretic measures, are unattainable because of camera design limitations. For example, the camera 190 of FIG. 4C, hereinabove, cannot be used for the windshield-wiper-like motion, shown in FIG. 13D, by the arrows 216 and 218; however, this type of coverage has proved very valuable. The method 370 may, however, be suitable for another camera design.

Additionally, when selecting a camera design, it is generally desired to consider secondary issues, such as the rate of data collection, the cost of the camera, the complexity of the design, for example, in terms of the number of motors, motion-transfer systems, and the like.

The rate of data collection is important both because it may be associated with patient discomfort and because it affects the number of patients that may be examined in a period of time. Where data collection with one camera design may take an hour and with another camera design may take 10 minutes, the design of the faster camera is highly advantageous. Complexity and cost are important because they affect the accessibility of the camera to the general public.

Thus, a design scoring function may be provided, for rating each camera design with a design score, based on any one or a combination of the secondary issues. The design scoring function may be used for selecting a camera design from several that have been found acceptable in terms of the quality of the data, by the method 370 of FIG. 14.

Referring further to the drawings, FIG. 15 illustrates, in flowchart form, a method 380 of selecting a camera design, optimized with respect to information gained about a body structure and secondary issues, in accordance with embodiments of the present invention. The method 380 comprises:

in a box 382: providing a model of a body structure, based on its geometry;

in a box 384: providing a model of anatomical constraints, which limit accessibility to the body structure;

in a box 385: providing representative collections of views of the modeled body structure, within the modeled anatomical constraints, for different camera designs;

in a box 386: providing a scoring function, by which each representative collection of views, associated with a specific camera design, is scorable with a score that rates information, obtained from the body structure;

in a box 387: scoring the representative collections of views, with the scoring function;

in a box 388: identifying several camera designs as acceptable, based on the scores of their representative collections of view;

in a box 390: providing a design scoring function, by which each camera design is scorable, based on the secondary issues;

in a box 392: scoring the acceptable camera designs with a design score;

in a box 394: selecting a camera design, based on its design score.

It will be appreciated other manners of combining the scoring function, which rates information, and the design scoring function, which rates secondary issues, are possible. For example, a combined scoring function, which takes all these factors into account, may be used.

As will be shown, hereinbelow, with reference to FIGS. 18A-22X, many different camera designs may provide substantially the same information, but are different in terms of their secondary considerations, that is, at different rates of data collection, different costs and different complexity of their designs, for example, in terms of the number of motors and motion-transfer systems. Thus these may score similarly in terms of functional information, and a design scoring function may be used to choose from amongst them.

Referring further to the drawings, FIGS. 16A-16L schematically illustrate viewing the elliptical model 250 of the volume U, with the camera 10, as illustrated specifically in FIGS. 20A-20H, hereinbelow.

FIGS. 16A-16K show the spanning of the elliptical model 250 of the volume U, along an x-z plane, by the sweeping views. FIG. 16L is a pictorial representation of the camera 10 of FIGS. 20A-20H and the elliptical model 250 of the volume U, in accordance with embodiments of the present invention.

The views, obtained in FIGS. 16A-16K may be used both for:

i. a collection of views for the volume U, from which an optimal set of views may be chosen, specific to a body structure, in accordance with the teachings of FIGS. 8, 10, and 12, hereinabove, and ii. a representative collection of views of the camera 10, for optimizing a camera design, in accordance with the teachings of FIGS. 14 and 15, hereinabove.

Imaging Schemes—Stop-Go, Interlacing and Continuous Acquisition

According to embodiments of the present invention there may be several imaging schemes connected with the motion of the detecting units, blocks and/or assemblies as follows:

In a first embodiment the detecting units, blocks and/or assemblies are moved to a position and collect photon emission data while stationary (herein referred to as the Stop-Go imaging scheme).

In a second embodiment, a version of the Stop-Go imaging scheme, a motion of each detecting unit or block or assembly is at a predetermined angle per move (after each move data is collected while the detecting unit or block or assembly is stationary) and characterized by half the angle phase shift when scanning in opposite directions, so as to scan the scanned region every half angle (herein referred to as the Interlacing imaging scheme).

In a third embodiment a motion of each detecting unit or block or assembly is without pause between minimum and maximum sweeping angles (herein referred to as the Sweeping Imaging Scheme).

Prescanning

Oftentimes it is desirable to perform a fast prescan of a subject undergoing diagnosis, find a region-of-interest, thereafter collect higher quality data from the region-of-interest. A prescan according to embodiments of the present invention can be performed by any imaging device, including, but not limited to, ultrasound and MRI or by a physical inspection of the subject undergoing diagnosis. Alternatively, a prescan can be performed by the camera of the present invention preferably using the interlacing imaging scheme as is further described above or by broad view selection as is further described below.

EXAMPLES OF CAMERA SYSTEMS

Reference is now made to the following examples of radioactive-emission cameras and camera systems, for a comparative study taught with reference to FIGS. 14 and 15.

Example 1

Figure 18A:
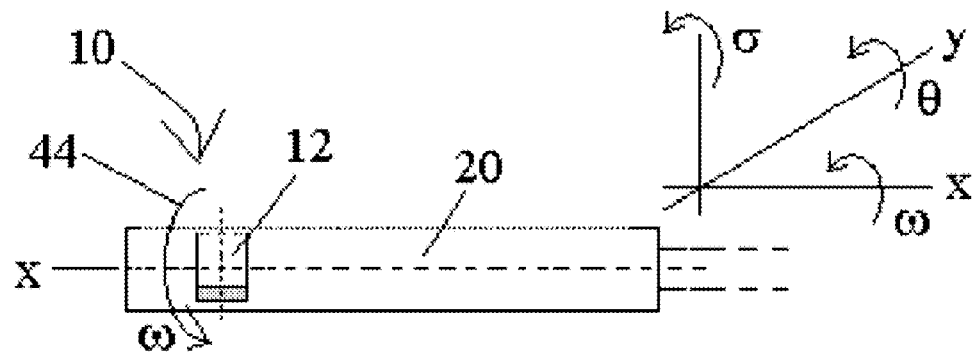
FIGS. 18A-18D schematically illustrate possible motions of a radioactive-emission camera, for a single detecting unit and a single block, in accordance with embodiments of the present invention.
Figure 18B:
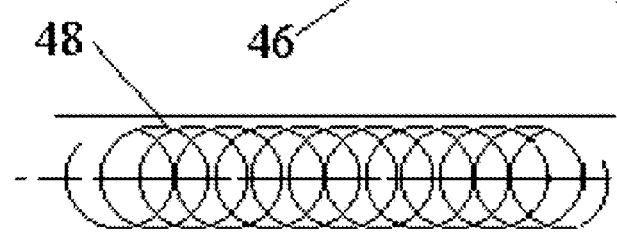

Referring further to the drawings, FIGS. 18A and 18B schematically illustrate the radioactive-emission camera 10, of the single detecting unit 12 (see FIGS. 1A and 17A). The single detecting unit 12 has a motion with respect to the overall structure 20, which is a combination of a rotational motion around the x-axis, in the direction of ω, denoted by an arrow 44, and a translational motion along the x-axis, denoted by an arrow 46.

As a consequence, a spiral trace 48 is formed, for example, on an inner surface of a body lumen 232, as seen in FIG. 18B.

Preferably, the motions of the detecting unit 12 are contained within the overall structure 20, so that the external surface of the camera 10 remains stationary. The external surface of the camera may be formed of a carbon fiber, a plastic, or another material, which is substantially transparent to nuclear radiation.

Example 2

Figure 18C:
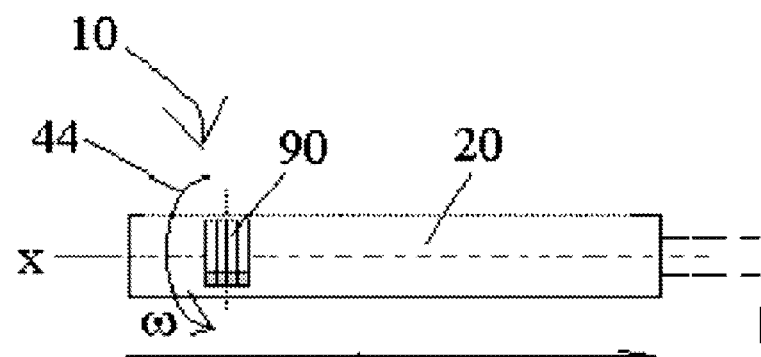
Figure 18D:
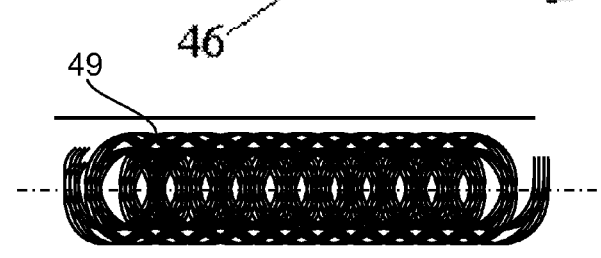

Referring further to the drawings, FIGS. 18C and 18D schematically illustrate the radioactive-emission camera 10, of the single block 90 (FIGS. 1B and 17E). Note that all the detecting units 12 of the single block 90 move as a single body. The single block 90 has a motion with respect to the overall structure 20, which is a combination of the rotational motion around the x-axis, in the direction of ω, denoted by the arrow 44, and the translational motion along the x-axis, denoted by the arrow 46.

As a consequence, a plurality of spiral traces 49 is formed, for example, on an inner surface of a body lumen, as seen in FIG. 18D.

Preferably, the motions of the block 90 are contained within the overall structure 20, so that the external surface of the camera 10 remains stationary, wherein the external surface of the camera is substantially transparent to nuclear radiation.

Example 3

Referring further to the drawings, FIGS. 19A-19E schematically illustrate the radioactive-emission camera 10, of the single block 90 of a plurality of the detecting units 12.

For understanding the motion of the camera 10 of the present example, it is desirable to define a cylindrical coordinate system of a longitudinal axis, x, and a radius r, wherein the motion around the longitudinal axis, x, is denoted by ω, while the motion around the radius r is denoted by φ.

The single block 90 has a motion with respect to the overall stricture 20, which is performed in steps, as follows:

i. the windshield-wiper like oscillatory motion, around the radius r, in the direction of ±φ, as denoted by the arrow 50;

ii. the translational motion along the x-axis, by an amount Δx, to a new measuring position, as denoted by the arrow 46;

iii. after traversing the length of the camera, a rotational motion around the x-axis, in the direction of ω, by an amount Δω, as denoted by the arrow 44, in order to perform the same measurements at a new measuring position of ω.

Figure 19A:
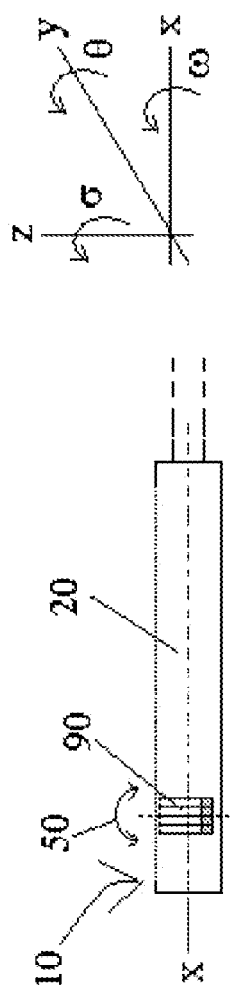
FIGS. 19A-19E schematically illustrate other possible motions of a radioactive-emission camera, for a single block, in accordance with embodiments of the present invention.
Figure 19B:
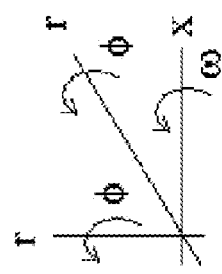
Figure 19C:
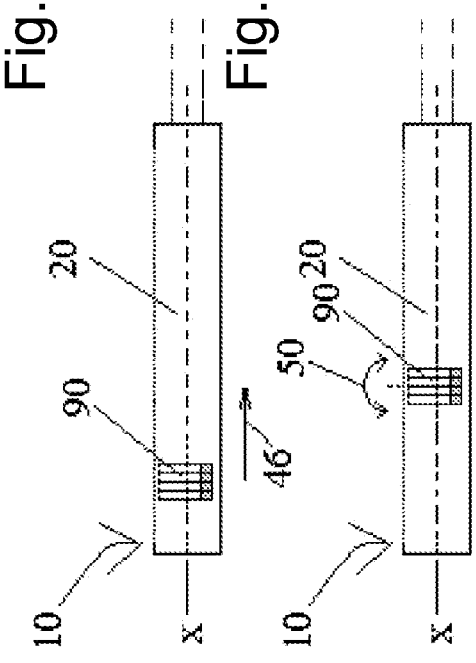
Figure 19D:
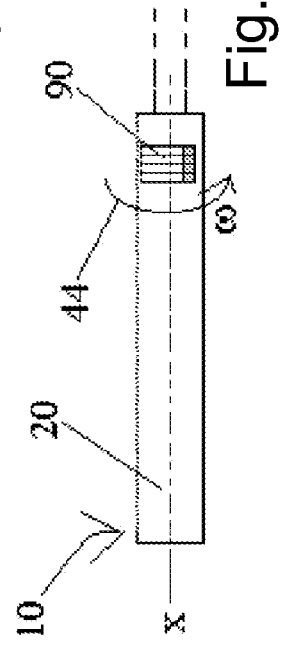
Figure 19E:
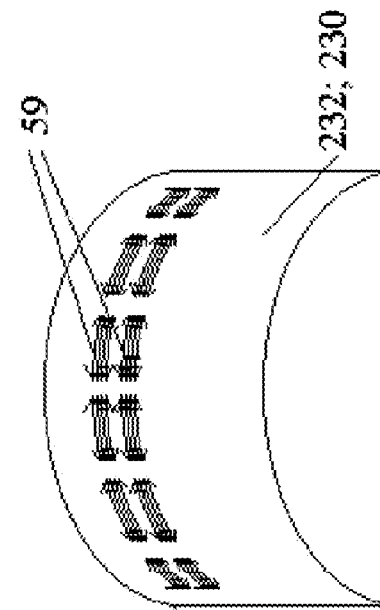

As a consequence, a plurality of broken line traces 59 is formed, as seen in FIG. 19E.

Preferably, the motions of the block 90 are contained within the overall structure 20, so that the external surface of the camera 10 remains stationary, wherein the external surface of the camera is substantially transparent to nuclear radiation.

Example 4

Referring further to the drawings, FIGS. 20A-20H schematically illustrate the radioactive-emission camera 10, having at least one pair, or a plurality of pairs of blocks 90, adapted for the windshield-wiper like oscillatory motion, around the radius r, as denoted by the arrows 50. The oscillatory motions may be synchronized in an antipodal manner, so as to be diametrically opposed to each other, as shown in FIGS. 20B and 20E, by the arrows 54, and as shown in FIGS. 20C and 21F by the arrows 56. It will be appreciated that the oscillatory motions need not be synchronized in an antipodal manner. Rather, all the blocks 90 may move in synchronized motion, or each block 90 may move independently. It will be appreciated that an odd number of blocks 90 is also possible.

Additionally, a rotational motion of the overall structure 20, around the x-axis in the direction of ω, an amount Δω, to a new measuring position along ω, is provided, after each step of the oscillatory motion, as shown in FIG. 20D, by an arrow 52.

The resultant traces are the plurality of broken line traces 59, as seen in FIG. 20G.

In essence, the camera 10 of FIGS. 20A-20F and 20H provides views which are essentially the same as those of FIGS. 19A-19E, but in a more efficient way, since a plurality of blocks is involved.

In accordance with the present example, i. The different blocks 90 provide views from different orientations; and ii. The different blocks 90 may change their view orientations.

Preferably, the motions of the blocks 90 are contained within the overall structure 20, so that the external surface of the camera 10 remains stationary, wherein the external surface of the camera is substantially transparent to nuclear radiation.

In particular, as seen in FIG. 20H, an internal structure 21 may contain all the blocks 90, configured to move together, as a rigid structure, while the overall structure 20 and the external surface of the camera 10 remain stationary.

The operational manner of the camera 10 of FIGS. 20A-20H is described with reference to FIG. 23C, hereinbelow.

It will be appreciated that the single detecting units 12 may be used in place of the single blocks 90.

Example 5

Referring further to the drawings, FIGS. 21A-21D schematically illustrate the radioactive-emission camera 10, having at least one pair, or a plurality of pairs of blocks 90, adapted for the windshield-wiper like oscillatory motion, around the radius r, as denoted by the arrow 50. The oscillatory motions are preferably synchronized in an antipodal manner, so as to be diametrically opposed to each other, as in, for example, FIG. 20B. It will be appreciated that the oscillatory motions need not be synchronized in an antipodal manner. Rather, all the blocks 90 may move in synchronized motion, or each block 90 may move independently. It will be appreciated that an odd number of blocks 90 is also possible.

Additionally, a rotational motion of each of the blocks 90 around the x-axis, in the direction of ω, an amount Δω, to a new measuring position along ω, is provided, after each step of the oscillatory motion, as shown in FIG. 21B, by the arrows 44. This is unlike FIG. 20D, wherein the internal structure 21 moved as a rigid unit, as shown in FIGS. 20D and 20H.

The resultant traces are the plurality of broken line traces 59, as seen in FIG. 21D. In essence, the camera 10 of FIGS. 21A-21C provides views which are essentially the same as those of FIG. 19E, and of FIG. 20G, but in a different manner.

In accordance with the present example, i. The different blocks 90 provide views from different orientations; and ii. The different blocks 90 may change their view orientations Preferably, the motions of the blocks 90 are contained within the overall structure 20, so that the external surface of the camera 10 remains stationary, wherein the external surface of the camera is substantially transparent to nuclear radiation.

It will be appreciated that the detecting units 12 may be used in place of the blocks 90.

Example 6

Referring further to the drawings, FIGS. 22A-22C and 22E-22G schematically illustrate the radioactive-emission camera 95, comprising the plurality of assemblies 92, each assembly 92 being similar in construction to the structure 21 of FIG. 20H, in accordance with embodiments of the present invention.

The plurality of assemblies 92 are preferably arranged in parallel, and their rotational motions, around the x-axis, may be synchronized in an antipodal manner, so as to be diametrically opposed to each other, as shown in FIG. 22C, by arrows 62, and in FIG. 22G, by arrows 64. It will be appreciated that the rotational motion around the x-axis need not be synchronized in an antipodal manner, and may be performed in parallel, or independently.

Thus, the resultant traces are a large plurality of the broken line traces 66 and 68, as seen in FIGS. 22D and 22H.

In essence, the camera 95 provides views which are essentially the same as those of FIGS. 19E, 20G, and 21D, but far more efficiently, since a plurality of assemblies is involved.

In accordance with the present example, i. The different blocks 90 provide views from different orientations;

ii. The different blocks 90 may change their view orientations;

iii. The different assemblies 92 provide views from different orientations; and iv. The different assemblies 92 may change their view orientations.

The operational manner of the camera 95 is described with reference to FIG. 23D, hereinbelow, for the at least two assemblies 92A and 92B.

Preferably, the motions of the blocks 90 and of the assemblies 92 are contained within the overall structure 20, so that the external surface of the camera 95 remains stationary, wherein the external surface of the camera 95 is substantially transparent to nuclear radiation.

It will be appreciated that camera 95 may include a plurality of assemblies 92, which are not parallel to each other. For example, the assemblies 92 may be at right angles to each other, or at some other angle.

It will be appreciated that the assemblies 92 may include the detecting units 12 rather then the blocks 90.

Figures 22I, 22J:
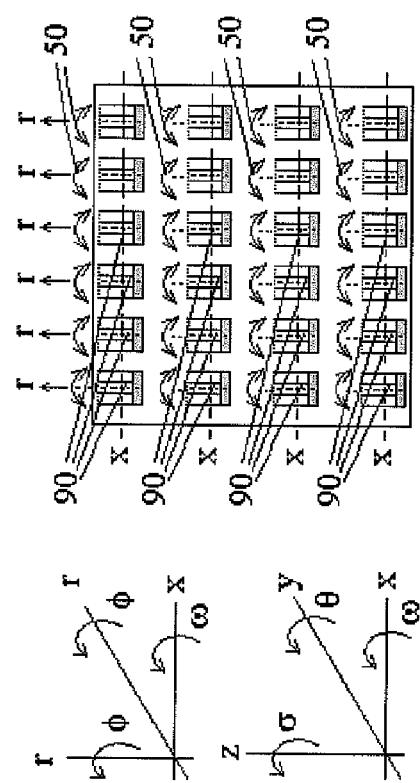

Referring further to the drawings, FIGS. 22I-22X schematically illustrate possible individual motions for blocks 90, in accordance with embodiments of the present invention.

In essence, in the present example, the blocks 90 are not arranged in assemblies 92, and each moves independently of the other blocks 90.

In accordance with a first embodiment, of FIGS. 22I-22M, each of the blocks 90 may be in communication with two motion providers, for providing the oscillatory motion about the r-axis, as seen by the arrows 50, and for providing the rotational motion around the x-axis, as seen by the arrows 44.

A first set of measurements is performed as the blocks 90 oscillate about the r-axis, as seen in FIG. 22J.

Figures 22K, 22L, 22M:
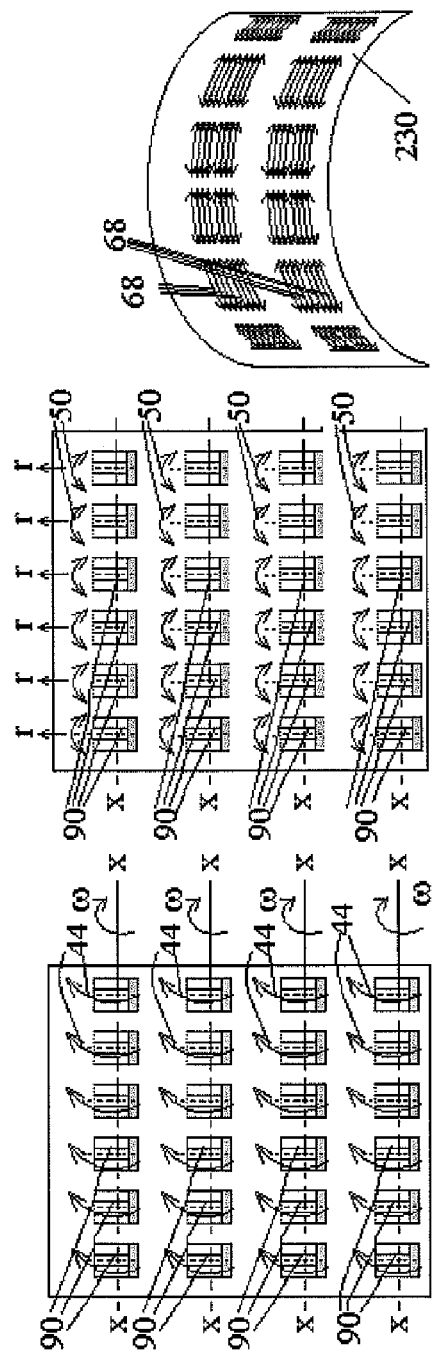

The blocks 90 then rotate around the x-axis, to a new measuring position, as seen in FIG. 22K.

A second set of measurements is performed at the new position, as the blocks 90 oscillate about the r-axis, as seen in FIG. 22M.

The blocks then rotate around the x-axis, to a new measuring position, as shown in FIG. 22K, and so on.

The resultant traces are a large plurality of the broken line traces 66 and 68, as seen in FIGS. 22J and 22M, and are substantially the same as those of FIGS. 22D and 22H.

In accordance with a second embodiment, each of the blocks 90 (FIG. 22N) may be in communication with two motion providers, for providing an oscillatory motion about the x-axis as seen by an arrow 61, and a rotational motion around the x-axis, as seen by an arrows 63. The resultant trace is star shaped, as seen by the lines 65 of FIG. 22O.

Additionally, a tertiary motion provider may be included, for providing a cluster 67 of overlapping lines, for a substantially complete coverage of a region, for example, as seen in FIG. 22P by a cluster 67 of the overlapping star-shaped lines 65.

It will be appreciated that many other forms of motion may be provided, and may include one, two, three or more motion providers.

FIGS. 22Q and 22R illustrate another set of dual motions and corresponding measurements for an individual one of the blocks 90, while FIGS. 22S and 22T illustrate those of a set of a tertiary motion, by three motion providers.

Similarly, FIGS. 22U and 22V illustrate still another set of two rotational motions and corresponding measurements, provided for each block individually, and FIGS. 22W and 22X illustrate still another set of a rotational motion, provided for each block individually, and coupled with a linear motion.

It will be appreciated that each block 90, or detecting unit 12 may be provided with at least one, and preferably, two, three, or possibly as many as six degrees of motion, for example, rotational motion around the x, y, and z, axis, or oscillatory motion about these axes, and possibly also translational motion, along the x, and (or) y, and (or) the z-axis. In this manner, each block 90 may be preprogrammed to view each portion of the body section 230, in accordance with some predetermined schedule, dedicated to the specific block 90. For example, one of the blocks 90 may perform oscillatory motion, while an adjacent one of the blocks 90 may perform rotational motion.

Referring further to the drawings, FIGS. 22Y and 22AA schematically illustrate a center of viewing 200A, for a given camera design, in accordance with embodiments of the present invention.

As the detecting units 12, or blocks 90, or assemblies 92 move or sweep across the region-of-interest volume U, for example, as illustrated by the arrows 203, different portions of the volume U are viewed at different frequencies and duration. The region which is viewed most heavily may be defined as the center of viewing 200A. It is surrounded by regions, which are viewed somewhat less. In essence, a shell-like viewing structure may be formed, with decreasing viewing intensities, as the distance from the center of viewing 200A increases. This is illustrated, for example, by the center of viewing 200A and surrounding shells 201, 209, and 211.

It will be appreciated that the center of viewing 200A may be a region of uniform viewing, rather than a mere point. For example, the region 201 may be a region of uniform viewing, which forms the center of viewing 200A.

Example 7

Having designed a radioactive-emission camera capable of obtaining a collection of views, and having predefined a set of views, which is optimal for a body structure, based on its model, the task of performing measurements, selectively at the predefined set of views, would be quite impossible if it were to be performed manually. Generally, between several hundred and several thousand views are taken, and manually tuning each to a predetermined location, orientation, and possibly also duration would be impractical. Therefore, the camera and method of the present invention are operative with an overall system, in which computer controlled motion providers govern the motions of the detecting units or of the overall camera. The computer may be any one of a personal computer, a laptop, a palmtop, or another computer, adapted for communication with the camera, or a microcomputer, built into the camera. Additionally, a combination of a microcomputer, built into the camera, and an external computer such as a personal computer, a laptop, a palmtop, or the like, may be used.

Preferably, before measurements are performed, personal details are fed into the computer, and the models of the body structure and anatomical constraints are adapted to these details. The personal details may include age, sex, weight, body type, and the like.

Referring further to the drawings, FIGS. 23A-23D schematically illustrate a radioactive-emission camera system 400 in accordance with embodiments of the present invention.

Figure 23A:
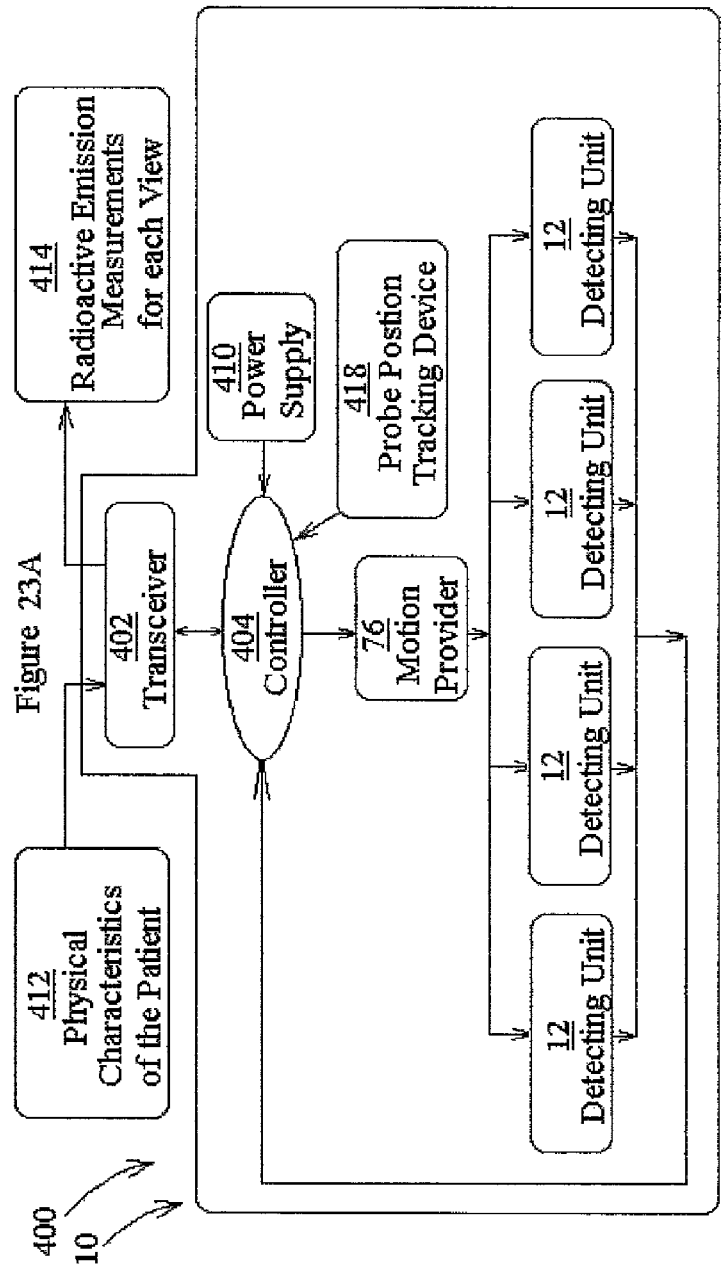

As seen in FIG. 23A, the camera system 400 includes the camera 10, having a controller 404, in communication with one or several motion providers 76, for sending signals of the locations and orientations of views to the one or several motion providers 76. The one or several motion providers 76, in turn, govern the motions of one or several of the detecting units 12. The one or several of the detecting units 12 collect the measurements at the predefined locations and orientations and communicate the data to the controller 404. Signals of new locations and orientations are then communicated by the controller 404 to the one or several motion providers 76. Each of the motion providers 76 may control the motion of one of the detecting units 12 or of a plurality of the detecting units 12.

Preferably, the controller 404 registers the location and orientation of each of the detecting unit 12 as it moves. Additionally or alternatively, a position-tracking device may be associated with each of the detecting units 12.

Preferably, a position-tracking device 418 is associated with the camera 10 as a whole, for registering its position with respect to, for example, the body structure 215 (FIG. 5A).

A power supply 410 powers the camera 10. Alternatively, power may be supplied from the grid.

Preferably, a transceiver or transmitter 402, reports the measurements to an external computer (not shown). Alternatively, a cable (not shown) may be used. Alternatively, the controller 404 includes a microcomputer, or the like, and performs the data analysis.

Additionally, the transceiver 402 may be adapted to receive input data relating to the personal details of the patient, such as the age, sex, weight, body type, and the like, in order to adjust the model of the body structure, hence the locations and orientations of the predefined, optimal set of views, to the particular patient.

Furthermore, the transceiver 402 may be adapted to receive input data from an ultrasound imager, for providing information such as location, size of the body structure and the like, by ultrasound imaging, in order to adjust the model of the body structure, hence the locations and orientations of the predefined, optimal set of views, to the particular patient.

Preferably, the motion of the one or several motion providers 76 relates to motion of the detecting units 12, with respect to the camera overall structure 20 (FIG. 20H), for example, by the motion of detecting units 222A and 222B (FIG. 13E), with respect to the overall structure 220, as shown by the arrows 216 and 218.

Alternatively or additionally, the motion of the one or several motion providers 76 may relate to motion of the overall structure 20 or 220 as a whole, for example, as taught with reference to FIG. 13E, by the motion the camera 220, as shown by the arrows 224 and 228.

It will be appreciated that the controller 404, while being part of the system 400, need not part of the actual camera 10. Rather it may be an external computer, communicating with the camera 10 either by cables or via a transceiver.

As seen in FIG. 23B, the camera 10 includes the blocks 90, each comprising a plurality of the detecting units 12, each block 90 moving as a single body.

Figure 23C:
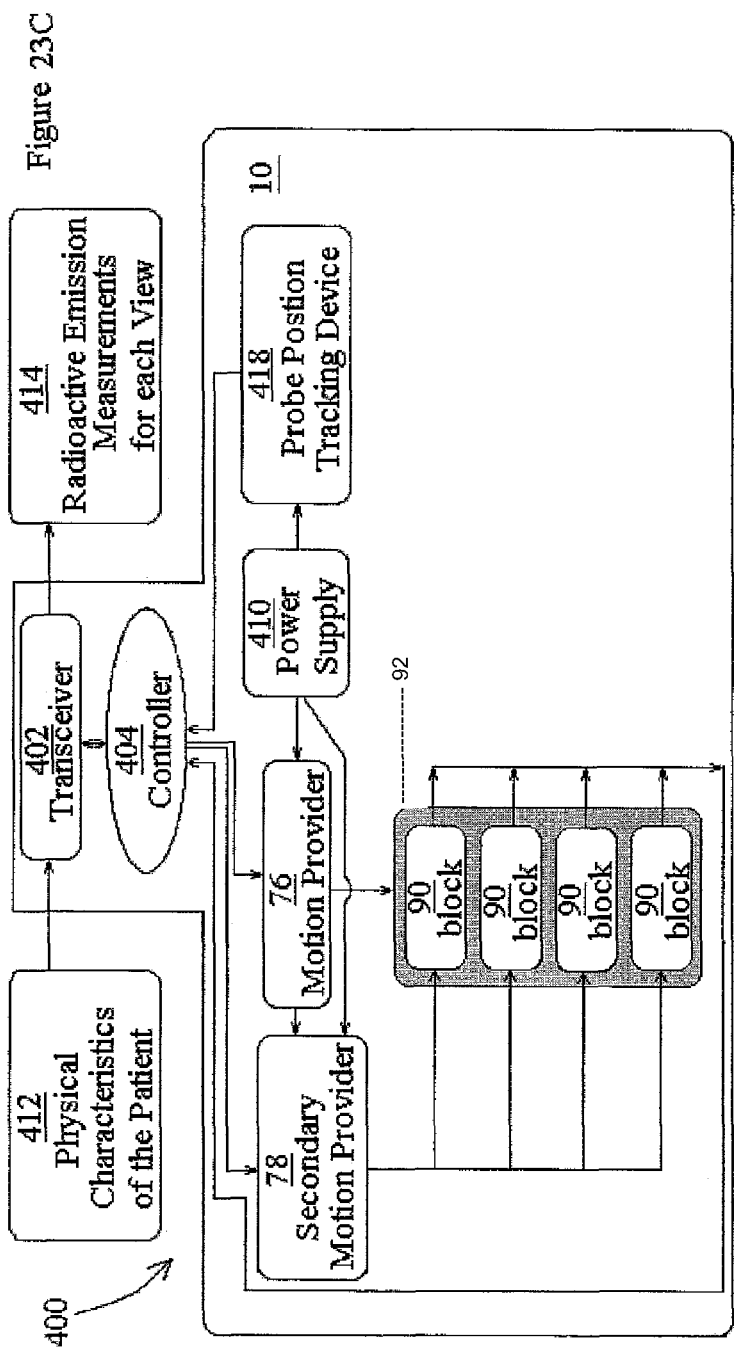

As seen in FIG. 23C, the individual motion of the blocks 90 is governed by a secondary motion provider 78. Additionally, all of the blocks 90 form an assembly 92, which moves by the motion provider 76, for example, within an internal structure 21, as illustrated hereinbelow with reference to FIG. 20H. For example, the secondary motion provider 78 may provide the motion described by the arrows 50 of FIGS. 20B and 20C or 20F and 20F, hereinbelow while the motion provider 76 may provide the motion described by the arrow 52 of FIG. 20H, hereinabove.

It will be appreciated that the multiple motions may be provided to the detecting units 12, rather then to the blocks 90.

It will be appreciated that a tertiary motion provider may also be used and that many arrangements for providing the motions are possible, and known.

Figure 23D:
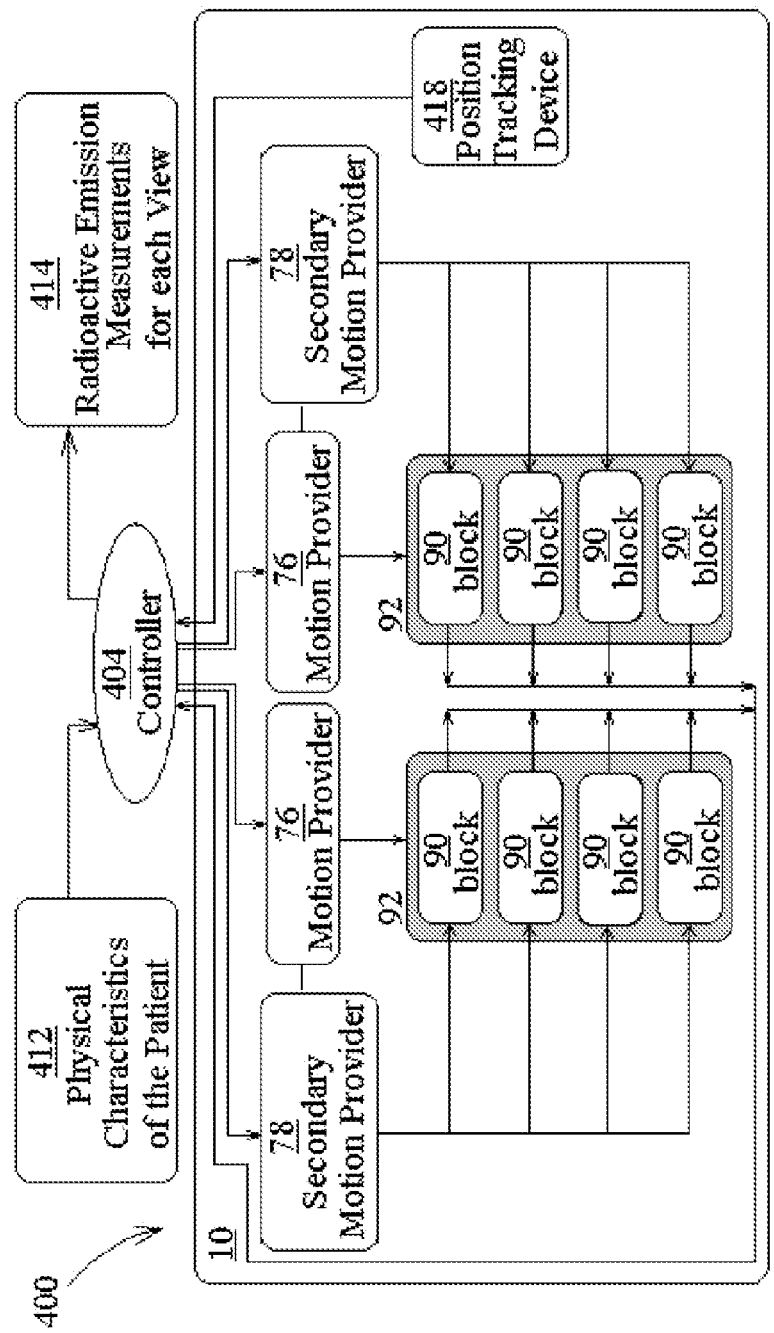

As seen in FIG. 23D, at least two assemblies 92 may be provided, each with a dedicated motion provider 76 and a dedicated secondary motion provider 78. It will be appreciated that the multiple motions may be provided to the detecting units 12, rather then to the blocks 90. It will be appreciated that tertiary motion providers may also be used and that many arrangements for providing the motions are possible, and known.

In the example of FIG. 23D, the controller 404, while being part of the system 400, may not be part of the actual camera 10. For example, it may be an external computer, communicating with the camera 10 either by cables or via a transceiver.

EXAMPLES OF CAMERA SYSTEMS FOR SPECIFIC APPLICATIONS

Reference is now made to the following examples of radioactive-emission cameras and camera systems, for specific applications.

Example 8

Referring further to the drawings, FIGS. 24A-32 schematically illustrate the radioactive-emission camera 10, for the prostate, in accordance with an embodiment of the present invention.

Figure 24C:
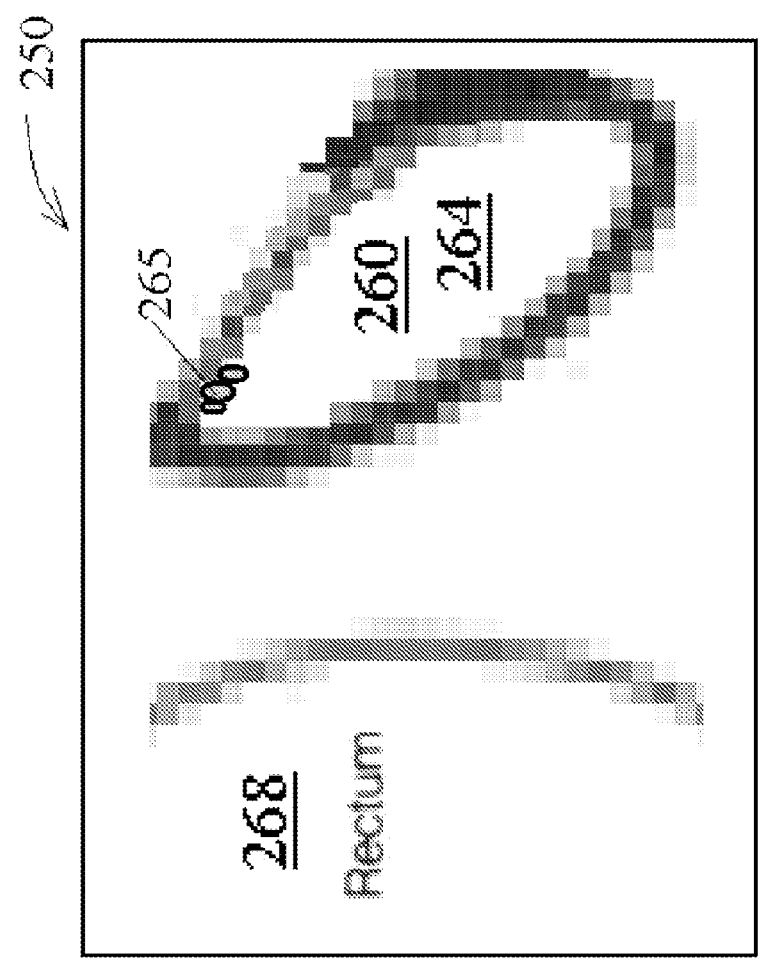

FIGS. 24A-24C schematically illustrate the modeling of a prostate and a location of pathology, as a process of two iterations, for zooming in on the pathology, in accordance with embodiments of the present invention.

FIG. 24A schematically illustrates a body section 230, which includes a prostate 260, which has sections 262, 264 and 266, and a pathology 265 in section 264. Additionally, the body section 230 includes a rectum 268, from which the prostate 260 may be viewed.

FIG. 24B schematically illustrates the model 200 of the body section 230, including the prostate 260, of sections 262, 264 and 266, and the rectum 268. An optimal set of views is predefined based on the model 200 and a first scoring function. The first scoring function may be based on regions of interest similar to the pathology 265, as known, from medical records of common pathologies. Measurements of radioactive emission are then taken at the predefined views, in vivo, for the prostate 260.

As seen in FIG. 24C, upon discovering the pathology 265, by the in-vivo measurements, a second model 250 of the section 264 is made, for zooming in on the pathology 265, and a second optimal set of views is predefined, based on the second model 250 of the section 264 and a second scoring function, for zooming in on the pathology 265. Measurements of radioactive emission are then taken at the predefined second set of views, in vivo, for the section 264 and the pathology 265.

It will be appreciated that the first and second scoring functions may be based on any one of or a combination of the information theoretic measures of uniformity, separability, and reliability. It will be further appreciated that the first and second scoring functions need not be the same.

FIGS. 25A-25E illustrate an external appearance and an internal structure, of the camera 10. The radioactive-emission camera 10 for the prostate has an extracorporeal portion 80 and an intracorporal portion 82, which is adapted for insertion into a rectum. The overall structure 20 of the intracorporal portion 82 is preferably shaped generally as a cylinder and defines a longitudinal axis along the x-axis, and a radius, perpendicular to the longitudinal axis. The intracorporal portion 82 preferably includes two pairs of assemblies 90, arranged in the overall Structure 20. It will be appreciated that another number of assemblies, for example, a single pair, or three pairs, is similarly possible. An odd number of assemblies is similarly possible. In essence, the camera 10 of the present example is analogous to the camera 10 of FIG. 23C and FIGS. 20A-20F and 20H, and particularly, to FIG. 20H. The rotational motion, in the direction of the arrow 52 of FIG. 20H, is provided by a motor 88 (FIG. 25C) and a main shaft 85. The motor 88 may be an electric motor, for example, a servo motor. The motor 88 and main shaft 85, together, form a motion provider 76 for the rotational motion in the direction of the arrow 52 of FIG. 20H. The oscillatory motion, in the direction of the arrows 50 of FIG. 20B, is provided by a secondary motor 86, a secondary shaft 84 and a motion transfer link 74. The secondary motor 86 may also be an electric motor, for example, a servo motor. The secondary motor 86, secondary shaft 84 and the motion transfer link 74, together, form the secondary motion provider 78, in the direction of the arrows 224 and 228 of FIG. 13E.

The significance of the present embodiment, is as follows:
i. The different assemblies 90 provide views from different orientations; and
ii. The different assemblies 90 may change their view orientations independent of each other.

It is important to point out that during the operation of the camera 10, the external surface of the intracorporal portion 82 (FIG. 25A) remains stationary, while the internal structure 21 (FIG. 25C) rotates around the x-axis. The external surface of the intracorporal portion 82 may be formed of a carbon fiber, a plastic, or another material, which is substantially transparent to nuclear radiation.

Figure 25B:
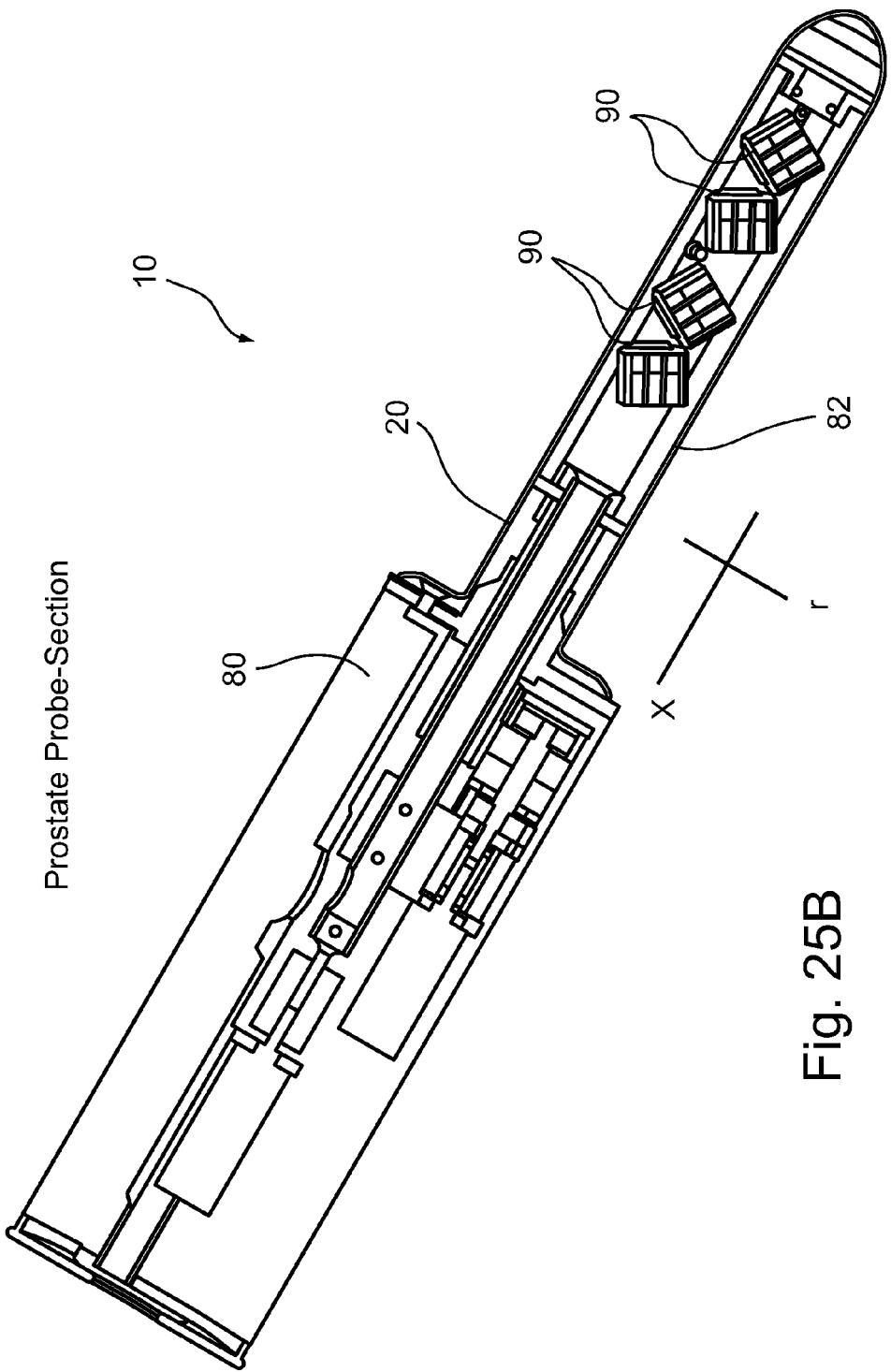
Figure 25C:
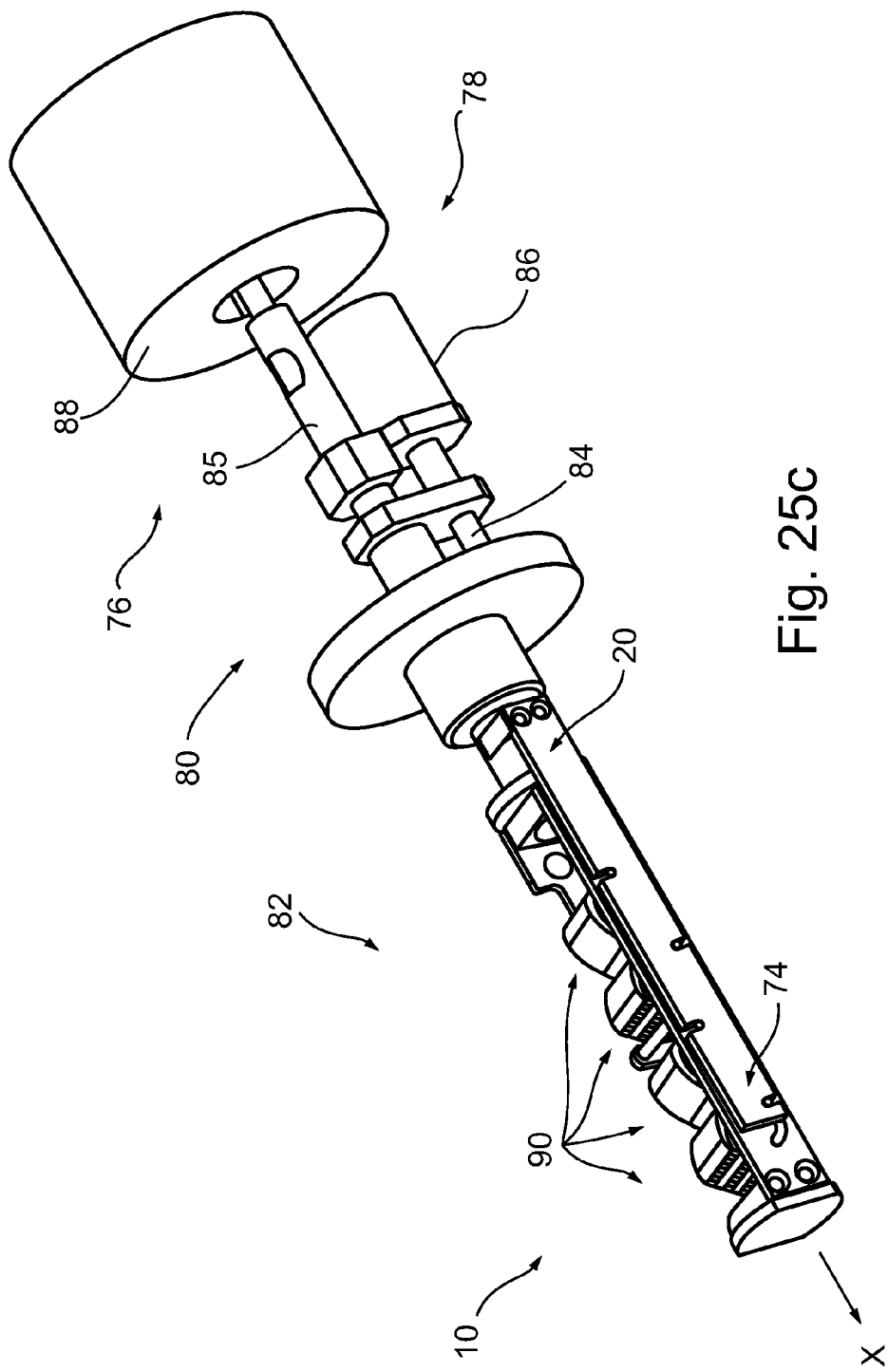
Figure 25D:
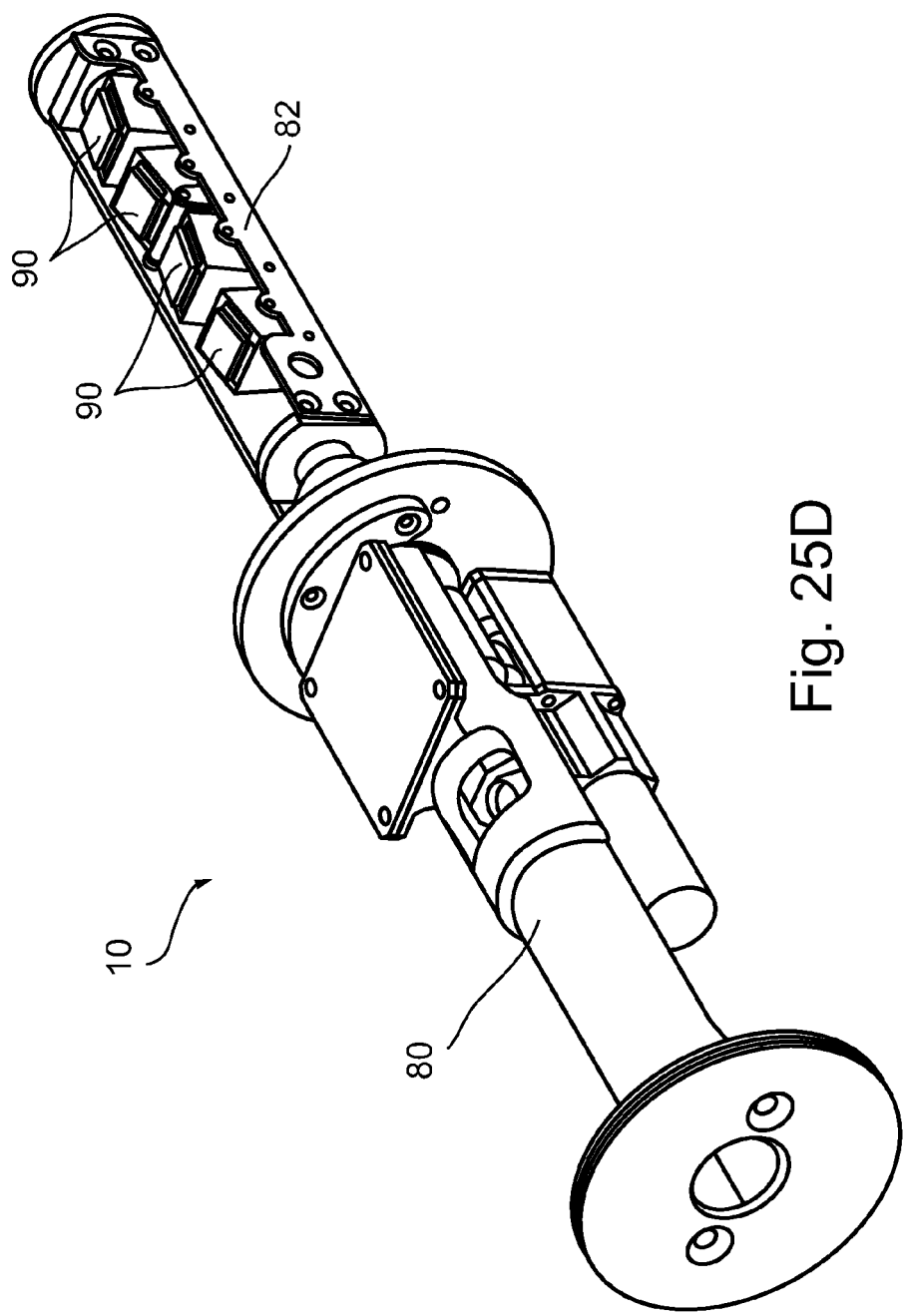
Figure 25E:
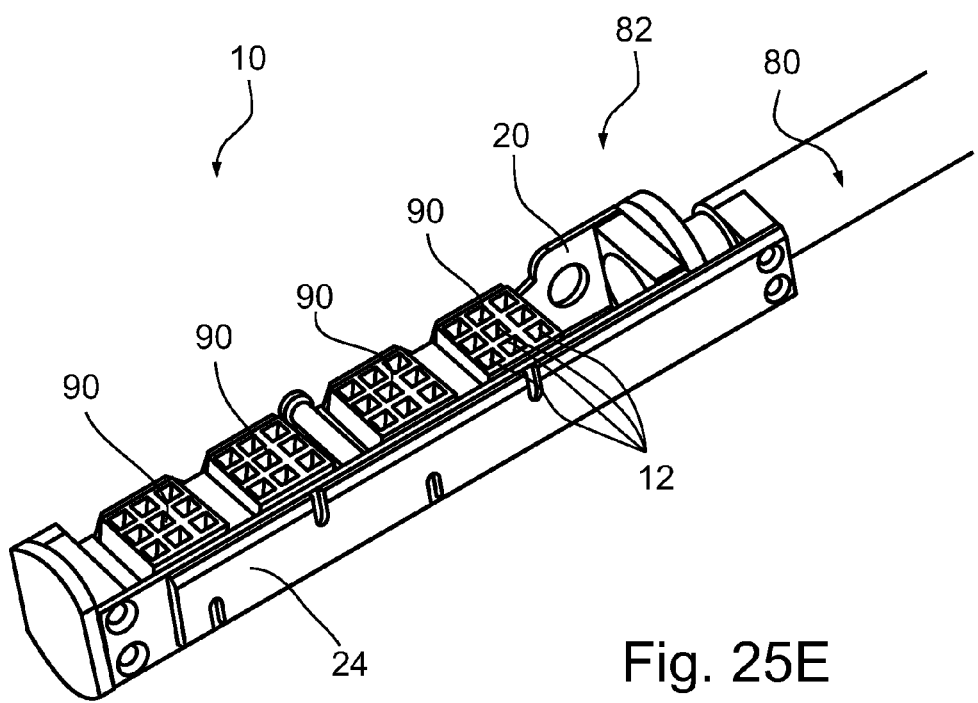

FIG. 25E illustrates further the internal structure of the radioactive-emission camera for the prostate, in accordance with an embodiment of the present invention, showing the assemblies 90 within the overall structure 20. Each assembly may be a single detecting unit 12, or a plurality of the detecting units 12, for example, 36 of the detecting units 12, for example, as an array of 6×6, or 99 of the detecting units 12, for example, as an array of 11×9, or another number of the detecting units 12, arranged as an array or arranged in another geometry.

Figure 26:
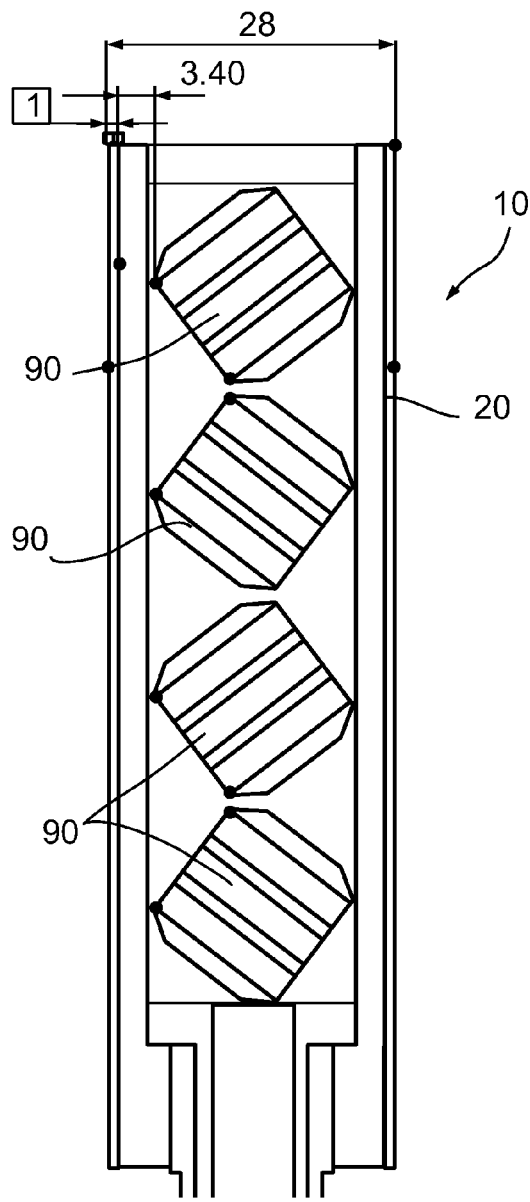
FIG. 26 illustrates further the internal structure of the radioactive-emission camera for the prostate, in accordance with an embodiment of the present invention.

Referring further to the drawings, FIG. 26 illustrates further the internal structure of the radioactive-emission camera for the prostate, in accordance with an embodiment of the present invention, showing the oscillatory motion (in the direction of the arrows 50 of FIGS. 20A, and 20C) of the assemblies 90 within the overall structure 20.

Figure 27:
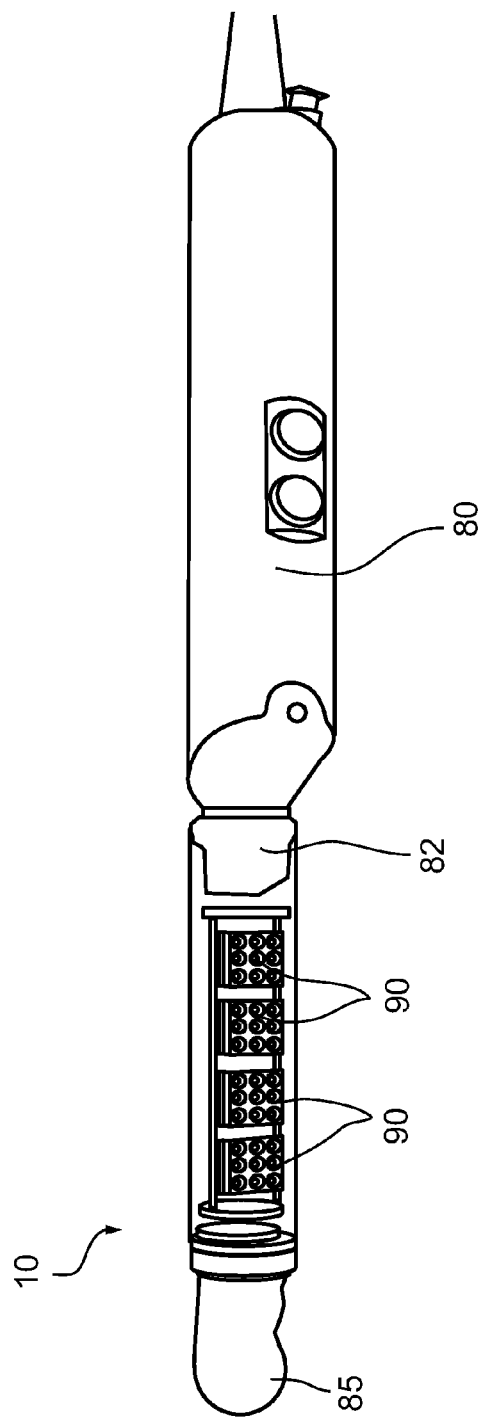
FIG. 27 schematically illustrates the radioactive-emission camera for the prostate, integrated with an ultrasound camera, in accordance with another embodiment of the present invention.
Figure 28:
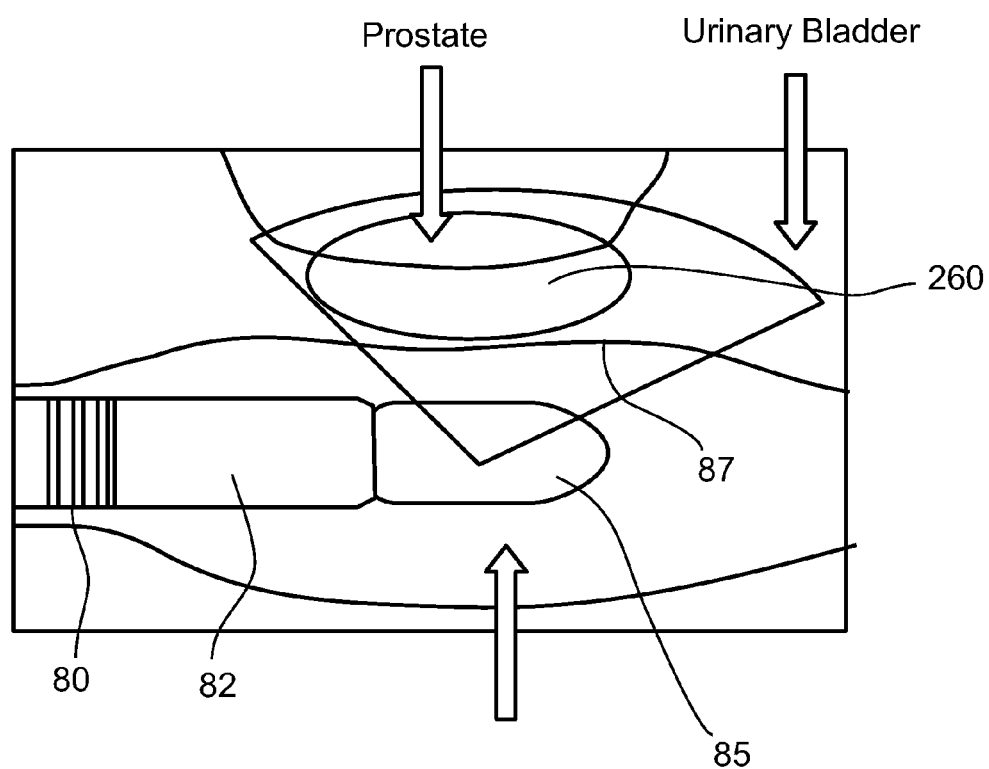
FIG. 28 schematically illustrates an ultrasound wave impinging on a prostate, in accordance with embodiments of the present invention.

FIGS. 27-28 schematically illustrate the radioactive-emission camera 10, for the prostate, in accordance with another embodiment of the present invention. In accordance with the present embodiment, the camera 10 further includes an ultrasound transducer 85, arranged, for example, at the tip of the intracorporal portion 82.

FIG. 27 illustrates the external appearance of the camera 10 with the ultrasound transducer 85 at its tip.

FIG. 28 illustrates the ultrasound wave 87, impinging on the prostate 260.

Figure 29A:
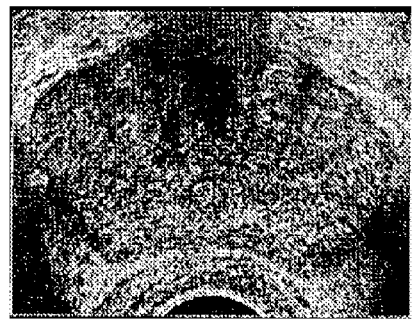
FIGS. 29A-29C illustrate the co-registering of a radioactive-emission image and an ultrasound image, in accordance with embodiments of the present invention.
Figure 29B:
Figure 29C:

FIGS. 29A-29C illustrate the co-registering of a radioactive-emission image and an ultrasound image, to illustrate the functional information of the radioactive-emission image with the structural information of the ultrasound image. The ultrasound image is seen in FIG. 29A, the radioactive-emission image is seen in FIG. 29B, and the co-registering of the two is seen in FIG. 29C.

Figure 30:
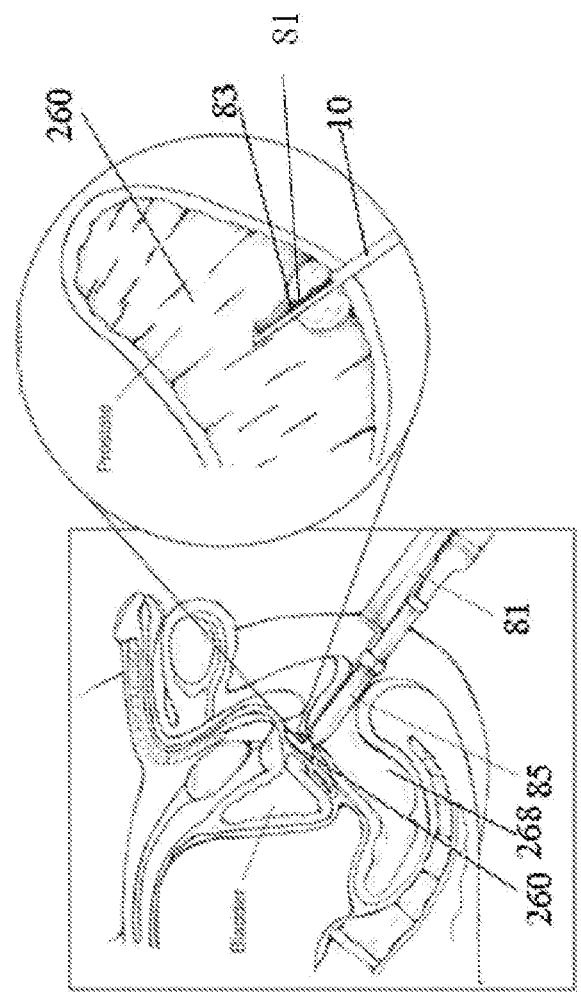
FIG. 30 schematically illustrates the radioactive-emission camera for the prostate, integrated with a surgical needle, in accordance with another embodiment of the present invention.

FIG. 30 schematically illustrates the radioactive-emission camera 10, for the prostate, in accordance with another embodiment of the present invention. In accordance with the present embodiment, the camera 10 further includes an ultrasound transducer 85, and a surgical needle 83, in a needle guide 81, arranged alongside the camera 10, for obtaining a biopsy or for other minimally invasive procedures. FIG. 30 schematically illustrates the surgical needle 83 as it penetrates the prostate 260 from the rectum 268.

Figure 31:
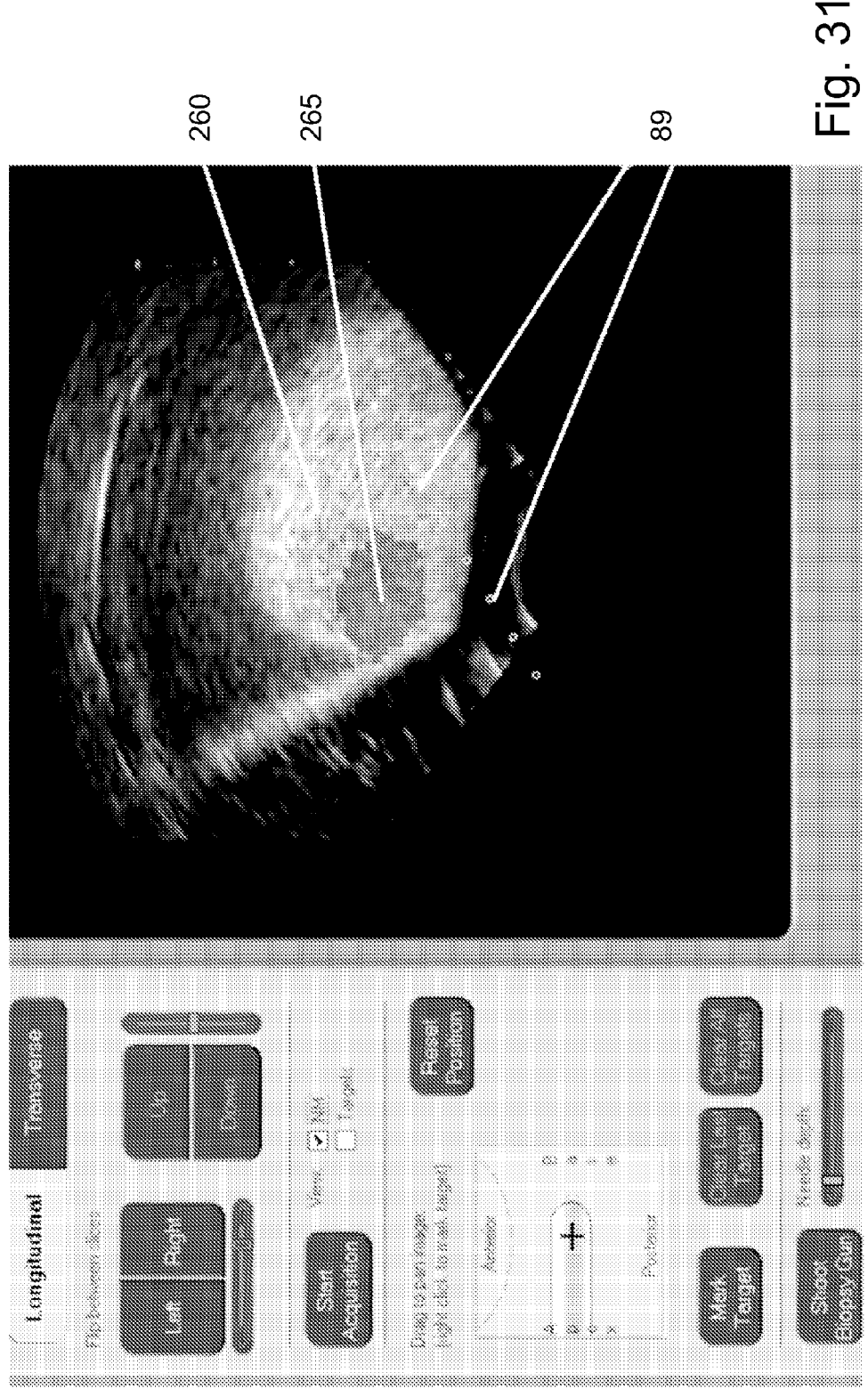
FIGS. 31 and 32 schematically illustrates the operation of the surgical needle of FIG. 30.
Figure 32:
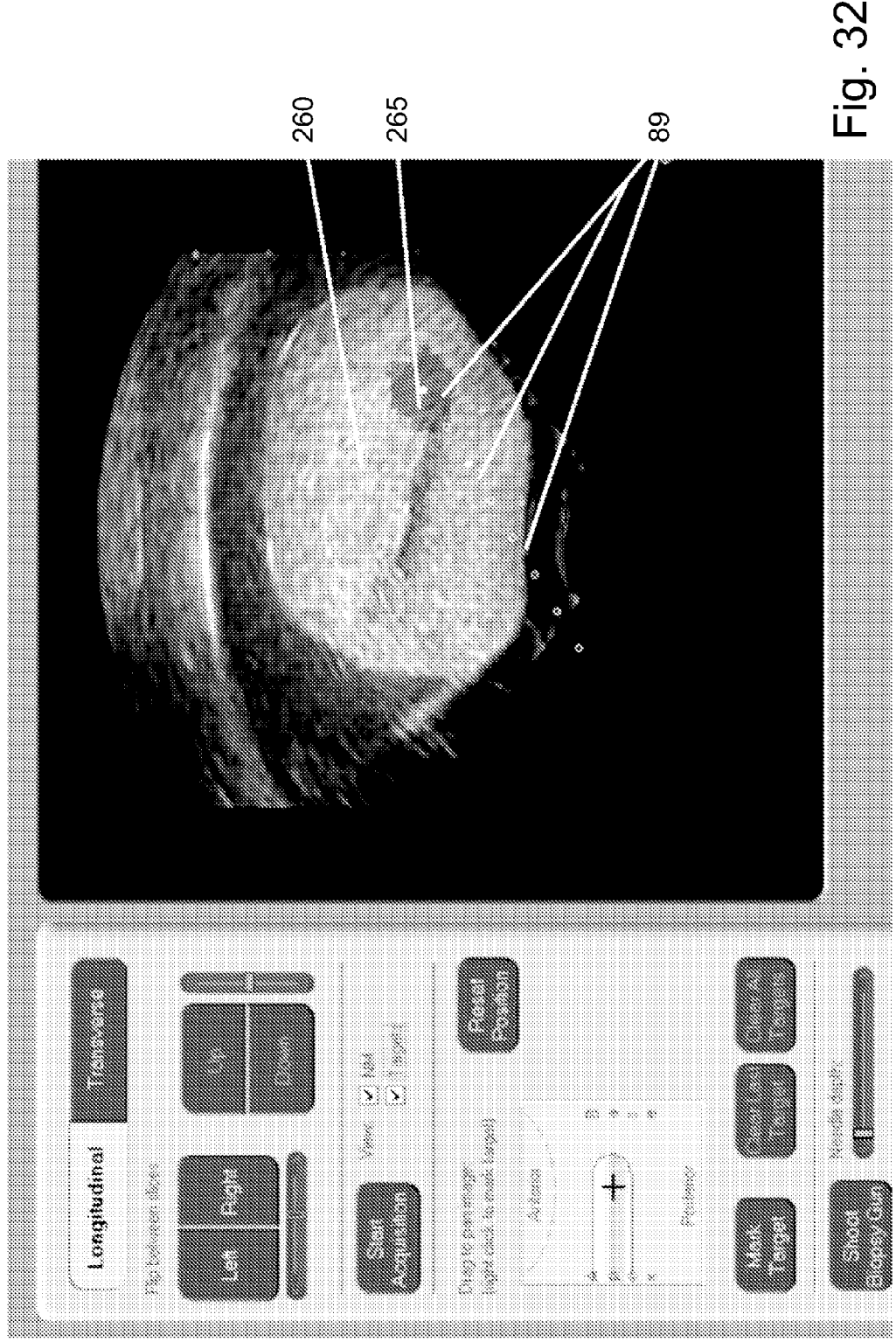

FIGS. 31 and 32 schematically illustrate the manner of guiding the needle 83. A track 89 shows the surgeon the direction of the needle, while the camera 10 produces the functional image of the pathology 265 in the prostate 260. By moving the camera 10, manually, the surgeon can align the track 89 with the pathology 265, as shown in FIG. 32. Once aligned, he can insert the needle 83, as shown in FIG. 30.

Example 9

Figure 33:
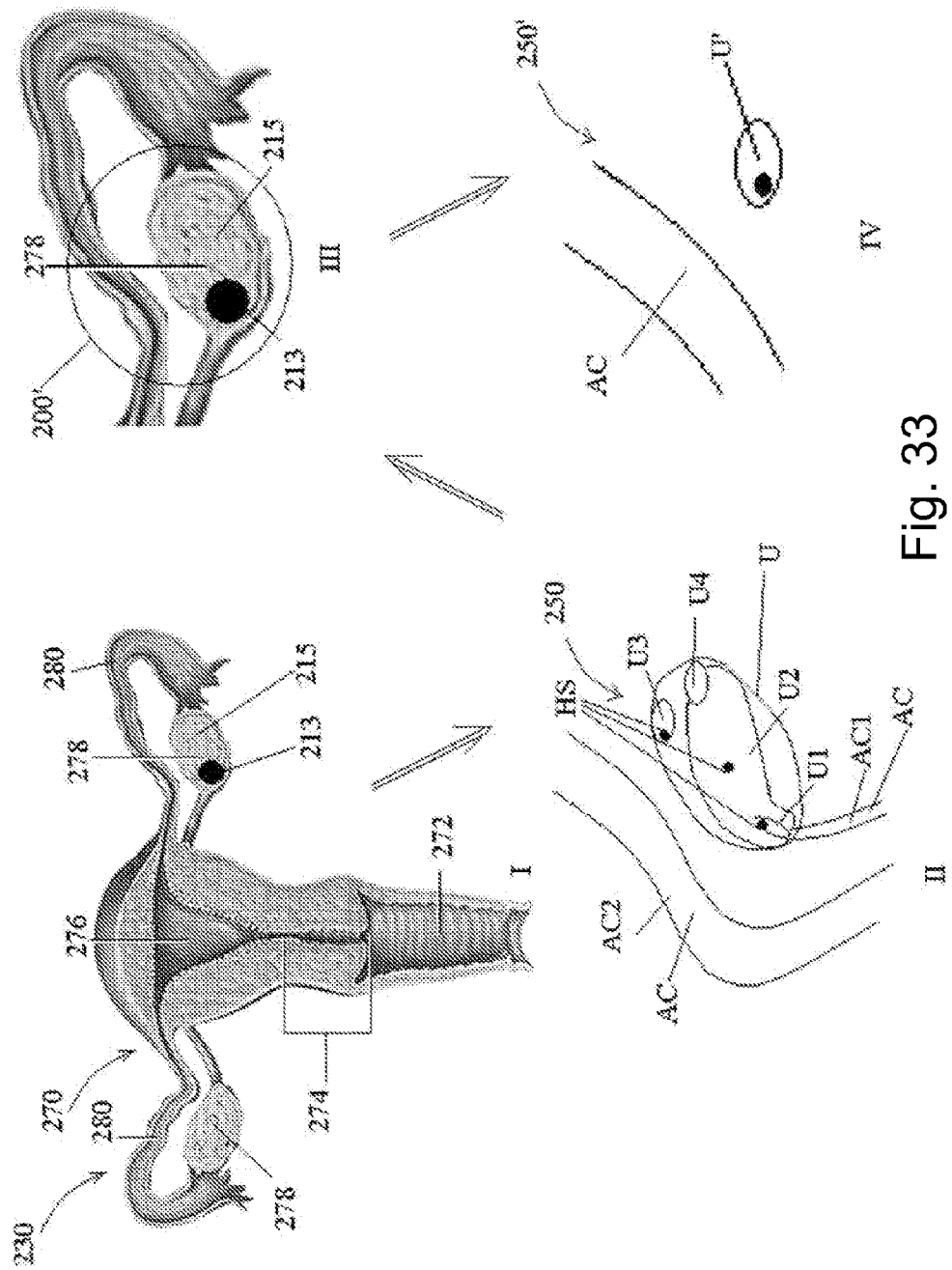
FIG. 33 schematically illustrates the modeling of the female reproductive system as a process of two iterations, for zooming in on a pathology, in accordance with embodiments of the present invention.

Referring further to the drawings, FIG. 33 pictorially illustrates the method 340 for zooming in on a suspected pathological feature in a woman's reproductive system, as a process of two or more iterations, in accordance with embodiments of the present invention, as follows:

As seen in FIG. 33, the method 340 may be described, pictorially, as follows:

In I: The region-of-interest 200, associated with a woman's reproductive system 270, is defined for the body section 230 having the body structure 215.

In II: The model 250 of the volume U, is provided for the region-of-interest 200, possibly with one or several of the modeled organ targets HS, and within the anatomical constraints AC, for obtaining the optimal set of views for the region-of-interest 200. The optimal set of views is then applied to the body section 230.

In III: When a suspected organ target 213 is identified, in vivo, by radioactive-emission measurements at the optimal set of views, a second, inner region-of-interest 200' is defined, encircling the suspected pathological feature.

In IV: A model 250' of a volume U' is provided for the second, inner region-of-interest 200', preferably, with at least one modeled organ target HS, simulating the suspected organ target 213, for obtaining an optimal pathology set of views for the region-of-interest 200'. The second, pathology set of views is then applied to the body section 230.

Figure 34A:
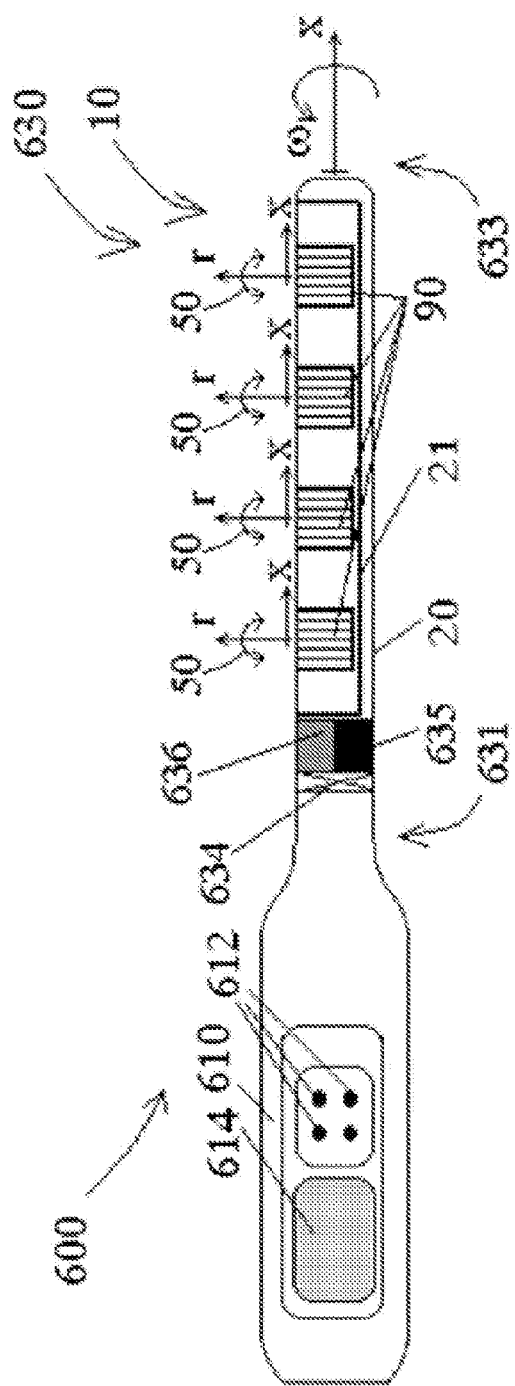
FIGS. 34A-34R schematically illustrate the external appearance and the internal structure of the radioactive-emission camera for the female reproduction tract, in accordance with an embodiment of the present invention.
Figure 34F:
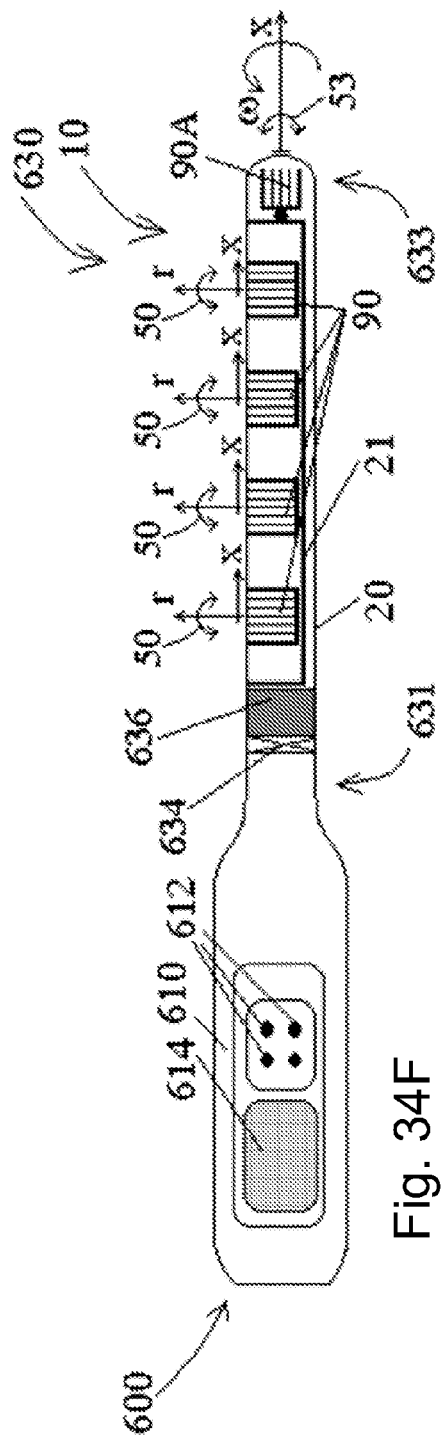
Figure 34I:
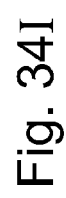
Figure 34H:
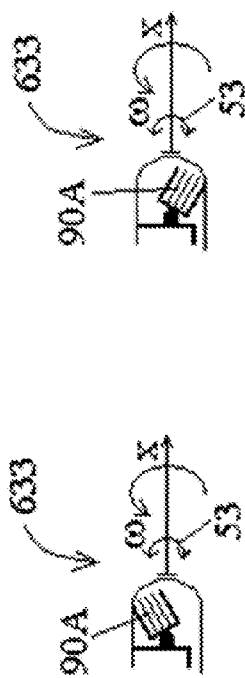
Figure 34G:
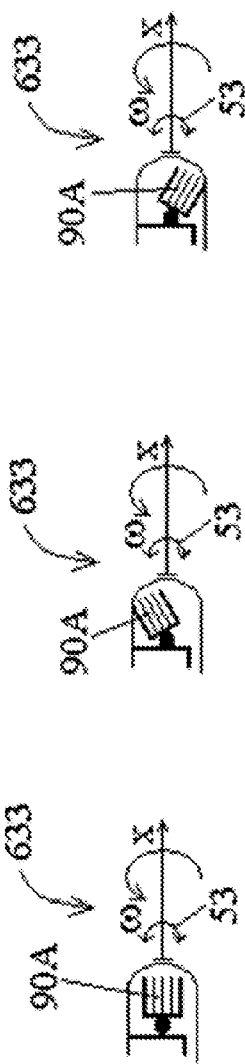
Figure 34K:
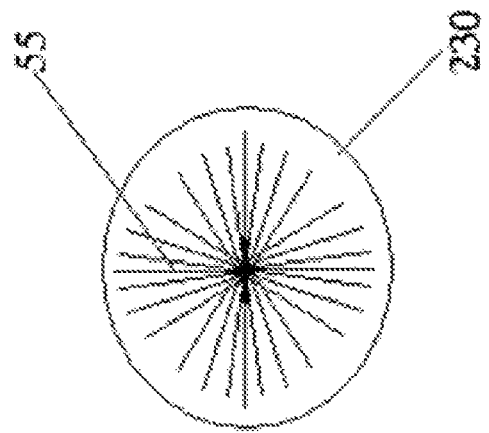
Figure 34J:
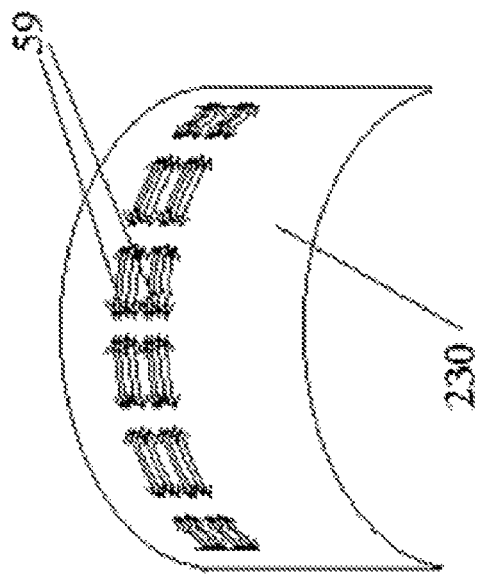
Figure 34R:
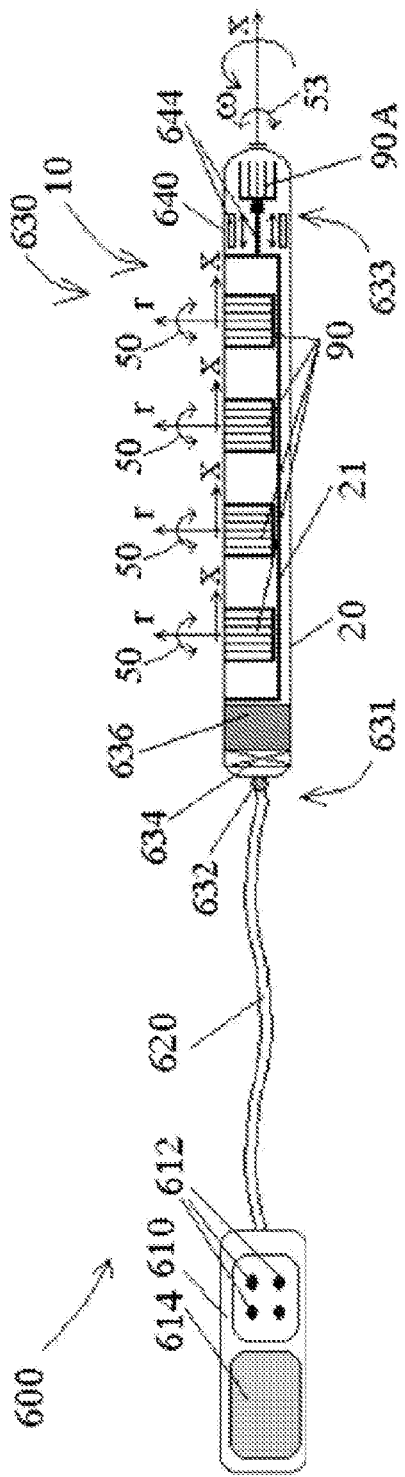

Referring further to the drawings, FIGS. 34A-34R schematically illustrate radioactive-emission measuring cameras 600, tailored for imaging the woman's reproductive system 270 and optimized with respect to the functional information gained, regarding the body structures of the woman's reproductive system, Such as the cervix 274, the uterus 276, the ovaries 278, and the fallopian tubes 280 (FIG. 33), in accordance with preferred embodiments of the present invention.

FIG. 34A schematically illustrates the basic radioactive-emission measuring camera 600, for a body lumen, for example, the vagina 272, the cervix 274, the uterus 276, the rectum (not shown), or the sigmoid colon (not shown). The camera 600 includes an extracorporeal portion 610, which preferably comprises a control unit, and an intracorporal portion 630, having proximal and distal ends 631 and 633, with respect to an operator (not shown).

The control unit of the extracorporeal portion 610 may include control buttons 612 and possibly a display screen 614, and may provide connections with a computer station. It may receive power from a grid or be battery operated. The control unit of the extracorporeal portion 610 may further include a computer or a microcomputer. It will be appreciated that the control unit may be incorporated with the intracorporal section 630, and operated remotely.

The intracorporal portion 630 defines a cylindrical coordinate system of x;r, wherein x is the longitudinal axis. The plurality of blocks 90 along the length of the intracorporal portion 630 is housed in an internal structure 21 (FIG. 20H).

Each of the blocks 90 is adapted for the windshield-wiper like oscillatory motion, around the radius r, as denoted by the arrows 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Additionally, the internal structure 21 is adapted for rotational motion around the x-axis, in the direction of ω, wherein after each step of oscillatory motion at a certain orientation of ω, the internal structure rotates by a step to a new orientation of ω, and the oscillatory motion is repeated.

As a consequence, a plurality of broken line traces 59 are formed, in the body section 230, as seen in FIG. 34J.

Preferably, the controller or the computer registers the locations and orientations of each detecting unit or block and correlates the measurements with the corresponding positions and orientations.

A position-tracking device 635 may also be used, for providing information regarding the position of the camera 600 relative to a known reference. For example, if a structural scan, or another scan by another imager has been made, the position-tracking device 635 may be used to register that scan with the measurements of the camera 600.

It will be appreciated that the camera 600 may include detecting units 12 rather then blocks 90.

Preferably, the overall structure 20 remains stationary and is substantially transparent to nuclear radiation, formed, for example, of a hydrocarbon material.

The intracorporal portion 630 may further include dedicated electronics 634 and motion providers 636, such as miniature motors and motion transfer systems, as known.

FIGS. 34B and 34C schematically illustrate side and distal views, respectively, of the radioactive-emission measuring camera 600, having an ultrasound imager 640 at its distal tip 633. The ultrasound imager 640 may provide a structural image which may be correlated with the functional image. Additionally, it may be used for providing the size and location of the body structure for modeling. Furthermore, it may be used for providing attenuation correction to the radioactive emission measurements.

FIGS. 34D and 34E schematically illustrate side and distal views, respectively, of the radioactive-emission measuring camera 600, having an MRI imager 642 at its distal tip 633. The MRI imager 642 may provide a structural image which may be correlated with the functional image. Additionally, it may be used for providing the size and location of the body structure for modeling. Furthermore, it may be used for providing attenuation correction to the radioactive emission measurements.

FIGS. 34F-34I schematically illustrate the radioactive-emission measuring camera 600, having a distal block 90A at its distal tip 633. The distal block 90A at the distal tip is also adapted for oscillatory motion, but about the x-axis, as seen by an arrow 53. When combined with the rotational motion around the x-axis, it produces traces 55 in the shape of a star, in the body section 230, as seen in FIG. 34K.

It will be appreciated that a single distal detecting unit may be employed in place of the distal block 90A.

FIGS. 34L-34Q schematically illustrates the radioactive-emission measuring camera 600, for a body lumen, having the distal block 90A at its distal tip 633, adapted for a deployed and a retracted position, and for oscillatory motion about the x-axis, when deployed. The camera 600 further has the ultrasound imager 640 at its distal tip 633, as a ring, similarly having a deployed and a retracted position.

FIGS. 34N-34P illustrate the distal block 90A deployed, and the ultrasound imager 640 retracted. In this manner, the ultrasound imager 640 does not obstruct the oscillatory motion of the distal block 90A at the distal tip 633.

FIG. 34Q illustrates the distal block 90A retracted and the ultrasound imager deployed so the distal block 90A does not obstruct the view of the ultrasound imager. It will be appreciated that the ultrasound image is to be taken once, from the distal tip 633, while the radioactive-emission measurements are to be taken at a plurality of orientations, from the distal tip 633.

FIG. 34R illustrates the camera 600 with a cable 620 connecting the intracorporal portion 630 and the extracorporeal portion 610, for example, for imaging the ovaries and the fallopian tubes from the sigmoid colon.

It will be appreciated that the cameras 600 of the present invention may also be moved manually, both linearly, into the body lumen and rotationally, around its longitudinal axis, preferably while the position-tracking device 635 (FIG. 34A) registers its position.

It will be appreciated that a camera with a single block or a single detecting unit may also be used.

Example 10

Figure 35A:
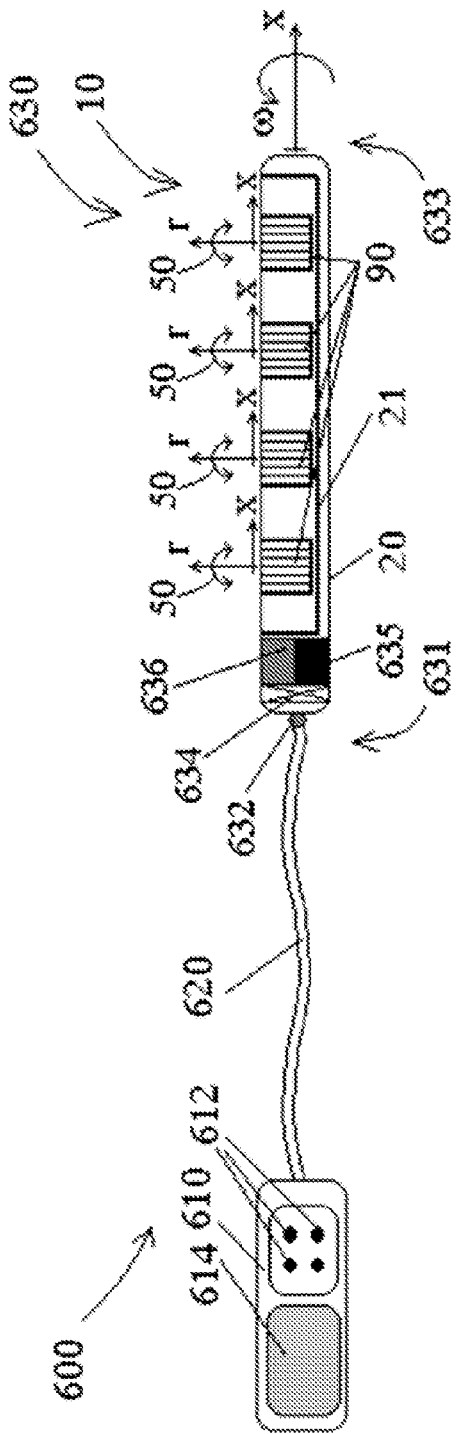
FIGS. 35A-35Q schematically illustrate the external appearance and the internal structure of the radioactive-emission camera for the esophagus, in accordance with an embodiment of the present invention.

Referring further to the drawings, FIGS. 35A-35Q schematically illustrate radioactive-emission measuring cameras 600, adapted for the esophagus, in accordance with preferred embodiments of the present invention.

FIG. 35A schematically illustrates the basic radioactive-emission measuring camera 600, for the esophagus. The camera 600 includes an extracorporeal portion 610, which comprises a control unit, and an intracorporal portion 630, having proximal and distal ends 631 and 633, with respect to an operator (not shown). A flexible cable 620 connects between them.

The control unit 610 may include control buttons 612 and possibly a display screen 614, and may provide connections with a computer station. It may receive power from a grid or be battery operated. The control unit 610 may further include a computer or a microcomputer.

The intracorporal portion 630 is constructed essentially as the camera 10 of FIG. 23C and FIGS. 20A-20H, and specifically, FIG. 20H.

Thus, the intracorporal section 630 defines a cylindrical coordinate system of x;r, wherein x is the longitudinal axis. The plurality of blocks 90 along the intracorporal portion 630 is housed in an internal structure 21.

Each of the blocks 90 is adapted for the windshield-wiper like oscillatory motion, around the radius r, as denoted by the arrows 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Additionally, the internal structure 21 is adapted for rotational motion around the x-axis, in the direction of ω, wherein after each step of oscillatory motion at a certain orientation of ω, the internal structure 21 rotates by a step to a new orientation of ω, and the oscillatory motion is repeated.

Figure 35K:
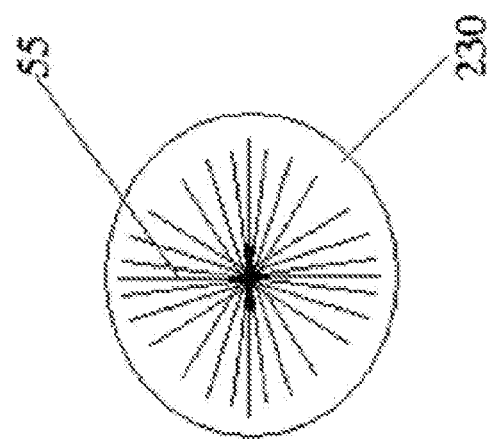
Figure 35J:
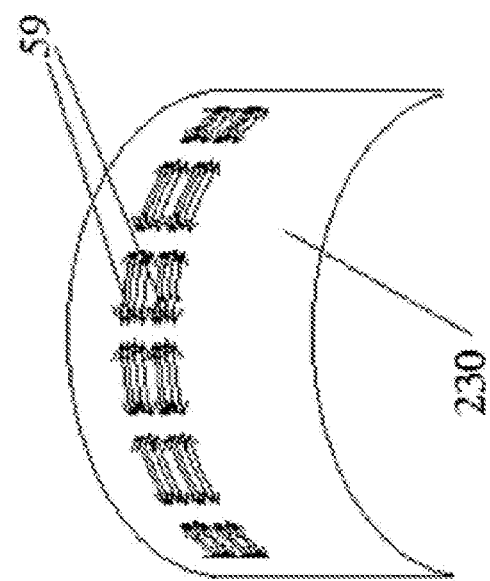

As a consequence, a plurality of broken line traces 59 are formed, in the body section 230, as seen in FIG. 35J.

Preferably, the controller or the computer registers the locations and orientations of each detecting unit or block and correlates the measurements with the corresponding positions and orientations.

A position-tracking device 635 may also be used, for providing information regarding the position of the camera relative to a known reference.

It will be appreciated that the camera 600 may include detecting units 12 rather then blocks 90.

Preferably, the overall structure 20 remains stationary, and has an external surface, which is substantially transparent to nuclear radiation.

A ball bearing 632 may be used at the connecting point with the cable 620, to enable the rotational motion.

The intracorporal section 630 may further include dedicated electronics 634 and motion providers 636, such as miniature motors and motion transfer systems, as known. Alternatively, the motion may be transferred via the cable 620.

FIGS. 35B and 35C schematically illustrate side and distal views, respectively, of the radioactive-emission measuring camera 600, for the esophagus, having an ultrasound imager 640 at its distal tip 633. The ultrasound imager 640 may provide a structural image which may be correlated with the functional image. Additionally, it may be used for providing the size and location of the relevant organ for modeling. Furthermore, it may be used for providing attenuation correction to the radioactive emission measurements.

FIGS. 35D and 35E schematically illustrate side and distal views, respectively, of the radioactive-emission measuring camera 600, for the esophagus, having an MRI imager 642 at its distal tip 633. The MRI imager 642 may provide a structural image which may be correlated with the functional image. Additionally, it may be used for providing the size and location of the relevant organ for modeling. Furthermore, it may be used for providing attenuation correction to the radioactive emission measurements.

FIGS. 35F-35I schematically illustrate the radioactive-emission measuring camera 600, for the esophagus, having a block 90 at its distal tip 633. The block 90 at the distal tip is also adapted for oscillatory motion, but about the x-axis, as seen by an arrow 53. When combined with the rotational motion around the x-axis, it produces traces 55 in the shape of a star, in the body section 230, as seen in FIG. 35K.

FIGS. 35L-35Q schematically illustrates the radioactive-emission measuring camera 600, for the esophagus, having a block 90 at its distal tip 633, adapted for a deployed and a retracted position, and for oscillatory motion about the x-axis, when deployed. The camera 600 further has the ultrasound imager 640 at its distal tip 633, as a ring, similarly having a deployed and a retracted position.

FIGS. 35N-35P illustrate the block 90 deployed, and the ultrasound imager 640 retracted. In this manner, the ultrasound imager 640 does not obstruct the oscillatory motion of the block 90 at the distal tip 633.

FIG. 35Q illustrates the block 90 retracted and the ultrasound imager deployed so the block 90 does not obstruct the view of the ultrasound imager. It will be appreciated that the ultrasound image is to be taken once, from the distal tip 633, while the radioactive-emission measurements are to be taken at a plurality of orientations, from the distal tip 633.

Figure 36A:
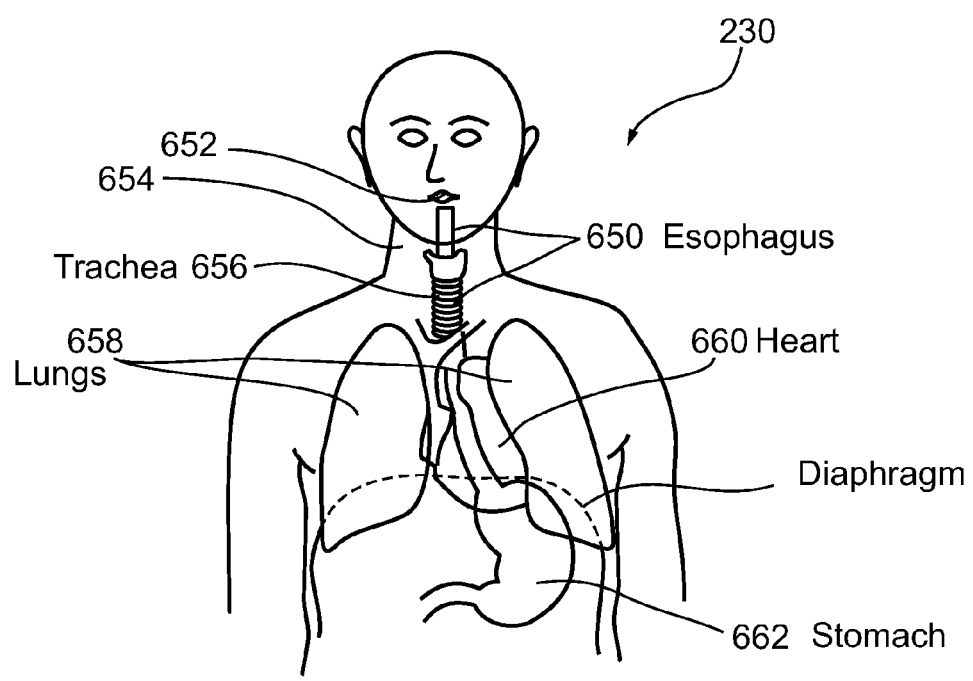
FIGS. 36A and 36B schematically illustrate body organs, including an esophagus.
Figure 36B:
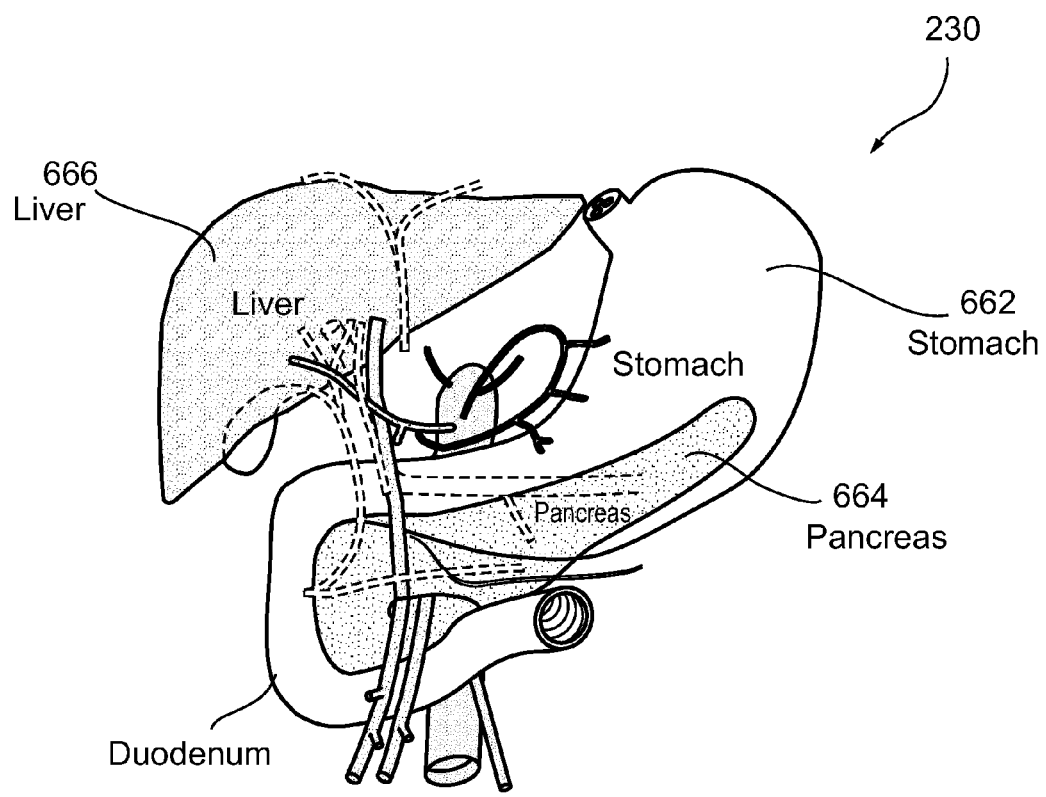

FIGS. 36A and 36B schematically illustrates the body section 230, showing an esophagus 650. The radioactive-emission measuring camera 600 for the esophagus (FIGS. 35A-35Q), is adapted for oral insertion, through a mouth 652, and is further designed for identifying pathological features in a neck area 654, for example, as relating to the vocal cords, the thyroid gland, the submandibular glands. Additionally, it is designed for identifying pathological features in the trachea 656, the lungs 658, the heart 660, the breasts, the stomach 662, the pancreas 664, and the liver 666, as well as other relevant organs and glands, for example, the lymph glands.

The camera system of the present invention allows imaging of internal organs from a close proximity. Additionally, it is particularly advantageous for overweight people and for women with large breasts, for whom extracorporeal imaging, for example, extracorporeal cardiac imaging by nuclear emission measurements, is ineffective, because of losses in the tissue.

For cardiac imaging, the radiopharmaceuticals associated with the camera of FIGS. 35A-35Q may be Myoview™ (technetium Tc-99m tetrofosmin), a cardiac imaging agent, of GE Healthcare, GE Medical Systems, http://www.ge-healthcare.com/contact/contact_details.html#diothiers. Alternatively, it may be Cardiolite (Sestamibi radiolabeled with Tc-99m), of DuPont, http://www1.dupont.com/NA-SApp/dupontglobal/corp/index.jsp?page=/content/US/en_US/contactus.hltml. It will be appreciated that other agents may be used, as known, for other relevant organs, for example, for the detection of cancerous tissue or other pathologies.

In accordance with the preferred embodiment of the present invention, cardiac imaging is performed with Teboroxime, for example, for myocardial perfusion imaging.

It will be appreciated that the radioactive-emission measuring camera 600, for the esophagus of the present invention may also be used in parallel with the cardiac camera system 500 of Example 12, described hereinbelow.

Example 11

Referring further to the drawings, FIGS. 37-39 schematically illustrate the body section 230, as a heart, which includes the region-of-interest 200, associated with the organ 215, being the heart, which includes an aorta 242, a left atrium 244 and a right atrium 246.

FIG. 38 schematically illustrates a second, inner region-of-interest 200', associated with the aorta 242.

Similarly, FIG. 39 schematically illustrates a second, inner region-of-interest 200', associated with the left atrium 244.

Referring further to the drawings, FIGS. 40-52E schematically illustrate a cardiac camera system 500, in accordance with a preferred embodiment of the present invention.

FIGS. 40-45 schematically illustrate the basic components of the cardiac camera system 500, in accordance with embodiments of the present invention. These include an operator computer station 510, a chair 520, and a radioactive-emission camera assembly 530.

Figure 43:
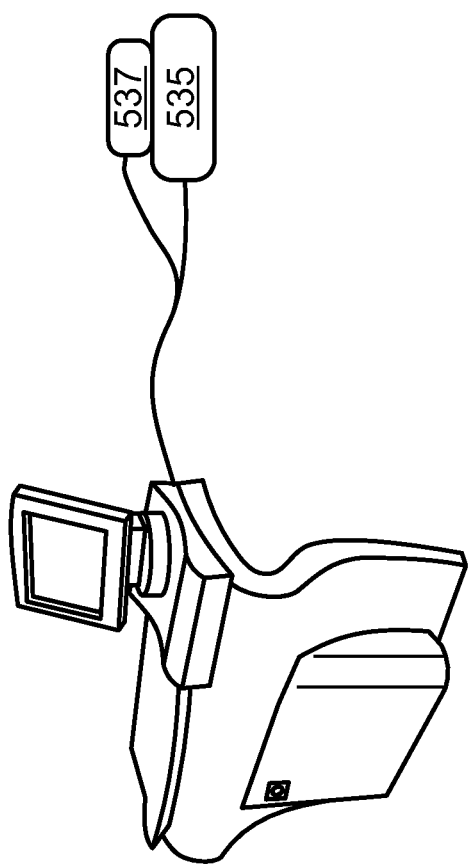

As seen in FIG. 43, computer station 510 may be further adapted for input of an ultrasound imager 535, for example, a handheld ultrasound imager 535, possibly with a position-tracking device 537, or a 3-D ultrasound imager. The data provided by the ultrasound imager 535 may be used in the modeling of the heart. Preferably, the data of the ultrasound imager may be co-registered with the radioactive emission measurements, on the same frame of reference, for providing co-registration of structural and functional images. It will be appreciated that the imager 535 may be an MRI imager.

A problem in cylindrical volumes, when viewed along the periphery of the cylinder is that the innermost information is blocked by the concentric information around it. Thus, it is often advisable to obtain views from the bases of the cylinder.

Figure 44:
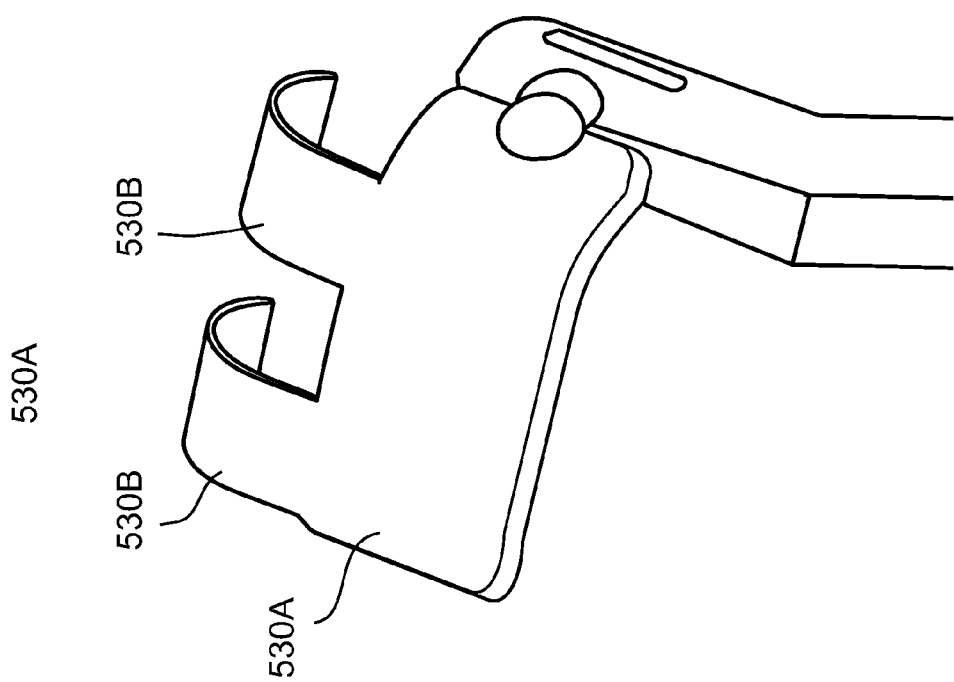

FIG. 44 schematically illustrate a camera 530A, which includes shoulder sections 530B, for viewing the heart essentially from a base of the cylindrical volume, in accordance with embodiments of the present invention.

Figure 45:
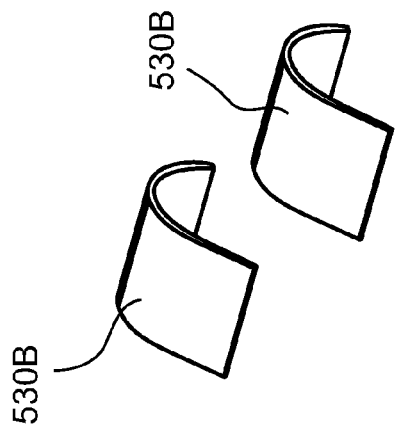

FIG. 45 schematically illustrate cameras 530B, formed as shoulder sections for viewing the heart essentially from a base of the cylindrical volume, in accordance with an alternative embodiment of the present invention.

Views from the shoulders, either as in FIG. 44 or 45 provides information not blocked or hidden by the chest.

It will be appreciated that the design of cameras 530B is possible because of the small size of the blocks 90 relative to the contour or of the body section 230.

Figure 46:
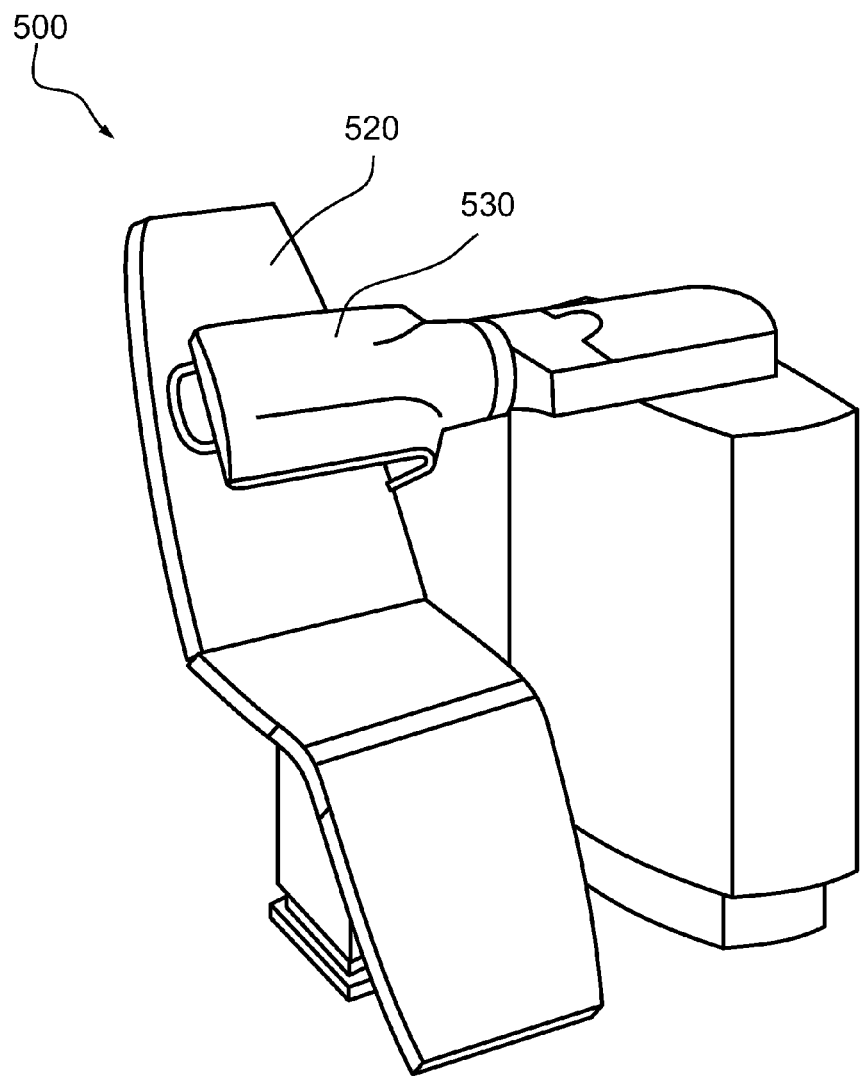
FIG. 46 schematically illustrates the external appearance of a radioactive-emission-camera system for the heart, in accordance with an embodiment of the present invention.

FIG. 46 schematically illustrates the chair 520 and the camera assembly 530, arranged for operation, in accordance with a preferred embodiment of the present invention. Preferably, the chair 520 is in a partial reclining position, and the camera assembly 530 is designed to face it, opposite the chest of a person sitting on the chair 520. Preferably, the camera assembly 530 includes a housing, operative as the overall structure, which is substantially transparent to radioactive emission. Alternatively, a skeleton, which is open on the side facing a patient, may be used as the overall structure.

It will be appreciated that another chair or a bed may be used rather than the chair 520. Alternatively, the patient may be standing.

Figure 47:
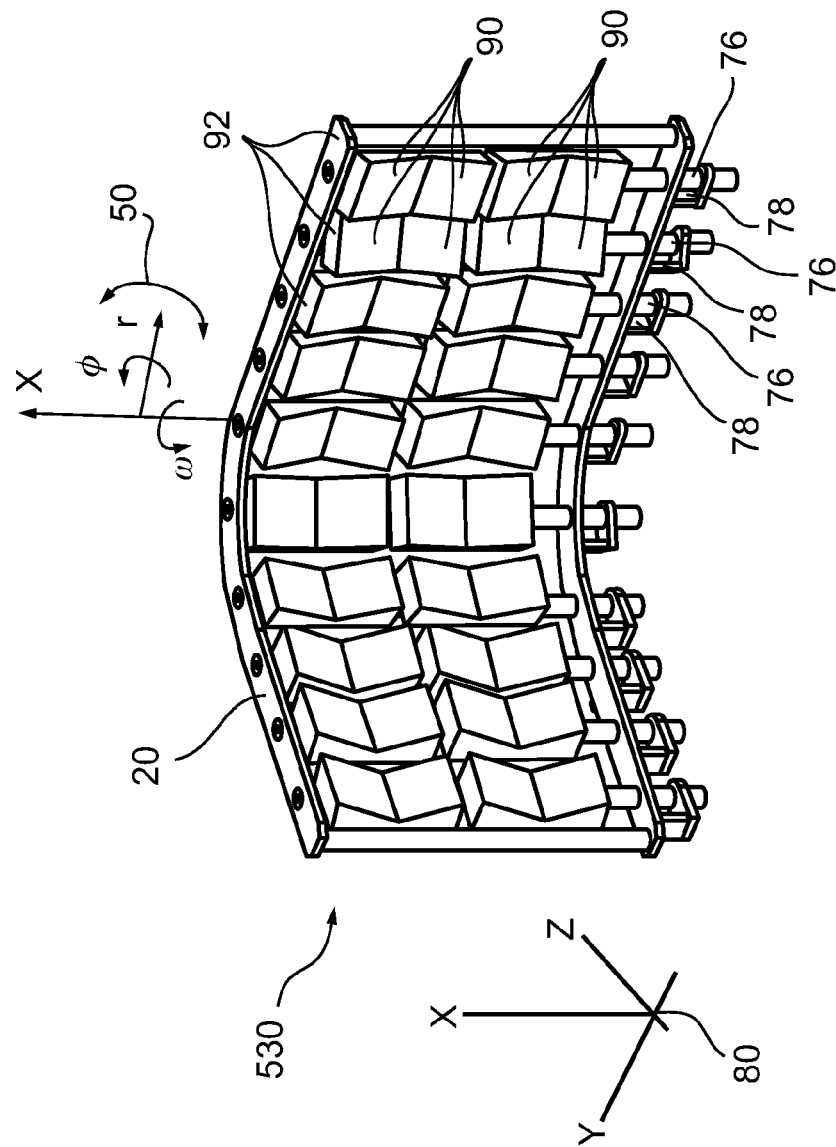
FIGS. 47 and 48 schematically illustrate the internal structure of the radioactive-emission camera for the heart, in accordance with an embodiment of the present invention.
Figure 48:
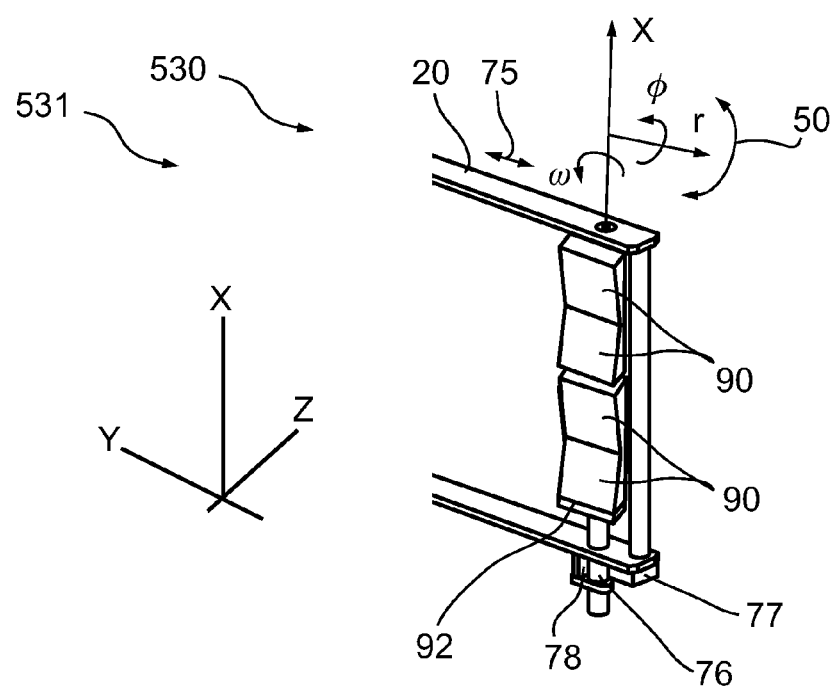

FIGS. 47-48 schematically illustrate possible inner structures of the camera assembly, in accordance with preferred embodiments of the present invention.

FIG. 47 schematically illustrates the inner structure of the camera assembly 530, showing the overall structure 20, the parallel lines of assemblies 92, possibly of an even number, each with a dedicated motion provider 76 and a dedicated secondary motion provider 78, and the rows of blocks 90, possibly arranged in pairs, along the assemblies 92.

The camera assembly 530 defines an internal frame of reference 80, while each assembly 92 has a reference cylindrical coordinate system of x;r, with rotation around x denoted by ω and rotation around r denoted by φ, wherein the oscillatory motion about r is denoted by the arrow 50.

Preferably, the motion of the camera assembly 530 corresponds to that described hereinabove, with reference to FIGS. 20A-20H and 22A-22H, as follows:

The plurality of blocks 90 is adapted for the windshield-wiper like oscillatory motion, around the radius r, as denoted by the arrow 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Furthermore, the plurality of assemblies 92 are preferably arranged in parallel, and their rotational motions, around the x-axis, in the direction of ω, may also be synchronized in an antipodal manner, so as to be diametrically opposed to each other, as shown hereinabove, in FIG. 22C, by arrows 62, and as shown hereinabove in FIG. 22G, by arrows 64. However, other motions are also possible. For example, the assemblies 92 may move together, or independently. It will be appreciated that an odd number of assemblies 92 is also possible.

Thus, the resultant traces are a large plurality of the broken line traces 59, as seen hereinabove, with reference to FIGS. 22D and 22H, on the chest of the patient.

In accordance with the present example,
i. The different blocks 90 provide views from different orientations;
ii. The different blocks 90 may change their view orientations;
iii. The different assemblies 92 provide views from different orientations; and
iv. The different assemblies 92 may change their view orientations.

The operational manner of the camera 530 is described hereinbelow with reference to FIG. 23D, for the at least two assemblies 92.

Preferably, the motions of the blocks 90 and of the assemblies 92 are contained within the overall structure 20, so that the external surface of the camera assembly 530 remains stationary, wherein the external surface of the camera assembly 530 is substantially transparent to nuclear radiation. Alternatively, the overall structure may be a skeleton, open on the side facing the patient.

It will be appreciated that the oscillatory motions need not be synchronized in an antipodal manner. Rather, the blocks 90 may move together, or independently. It will be appreciated that an odd number of blocks 90 is also possible.

It will be appreciated that camera 530 may include a plurality of assemblies 92, which are not parallel to each other.

For example, the assemblies 92 may be at right angles to each other, or at some other angle. It will be appreciated that the assemblies 92 may include detecting units 12 rather then blocks 90, for example, as in the camera 10 of FIGS. 20A-20G.

FIG. 48 schematically illustrates a section 531 of the camera assembly 530, showing the inner structure thereof, in accordance with another embodiment of the present invention. Accordingly, the camera assembly 530 may include the overall structure 20, and a single one of the assemblies 92, within the overall structure 20, having the dedicated motion provider 76, the dedicated secondary motion provider 78, and the rows of blocks 90. Additionally, in accordance with the present embodiment, the camera assembly 530 includes a tertiary motion provider 77, for sliding the assembly 90 laterally, in the directions of the arrow 75, along the chest of the patient (not shown). In this manner, imaging of the chest may be performed with the single assembly 92.

Figures 49A, 49B:
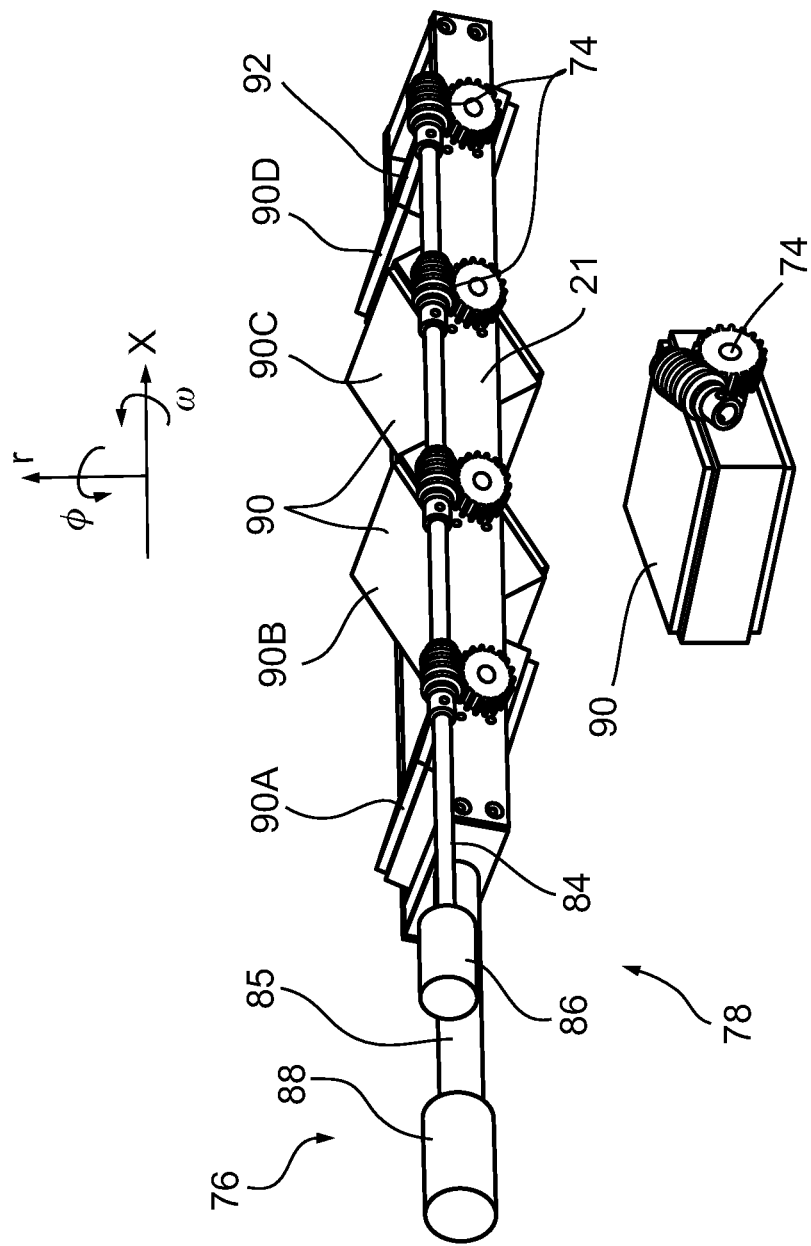
FIGS. 49A and 49B schematically illustrate the internal structure of the radioactive-emission camera for the heart, in accordance with an embodiment of the present invention.

FIGS. 49A and 49B schematically illustrate the assembly 92 and the block 90, in accordance with a preferred embodiment of the present invention. In essence, the assembly 92 is constructed in a manner similar to the camera 10 of FIGS. 20A-20H, and specifically FIG. 20H, and according to FIG. 23D, hereinabove.

Thus the assembly 92 includes a row of at least two blocks 90, each adapted for oscillatory motion about r. The blocks 90 are arranged within the internal structure 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provide 78 to the blocks 90. The motion transfer systems 74, for example, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

Figure 50:
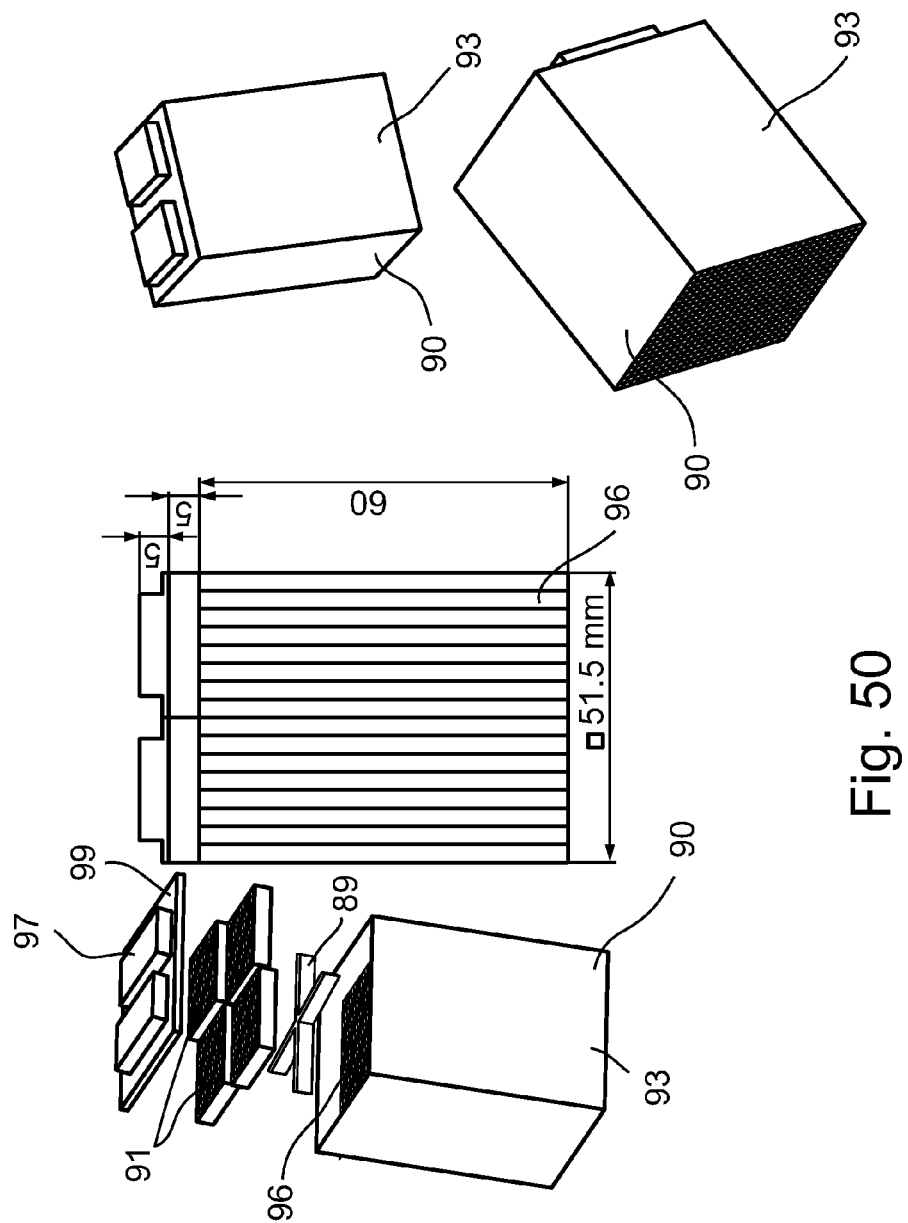
FIG. 50 schematically illustrates the construction of radiation detection blocks, in accordance with an embodiment of the present invention.

FIG. 50 schematically illustrates the block 90, in accordance with a preferred embodiment of the present invention. The block 90 includes a frame 93, which houses the detector material 91, which is preferably pixelated, and the collimators 96. Additionally, the frame 93 houses dedicated electronics 97, preferably on a PCB board 99. Furthermore, where several modules of the detector material 91 need to be used, a structural element 89 may be provided to hold the different modules of the detector material 91 together. It will be appreciated that a single pixel detector may be used. Alternatively, a single module of a pixelated detector may be used. Alternatively, the block 90 may be constructed as any of the examples taught with reference to FIGS. 17A-17N, or as another block, as known.

The dimensions, which are provided in FIG. 50, are in mm. It will be appreciated that other dimensions, which may be larger or smaller, may similarly be used.

Figure 51:
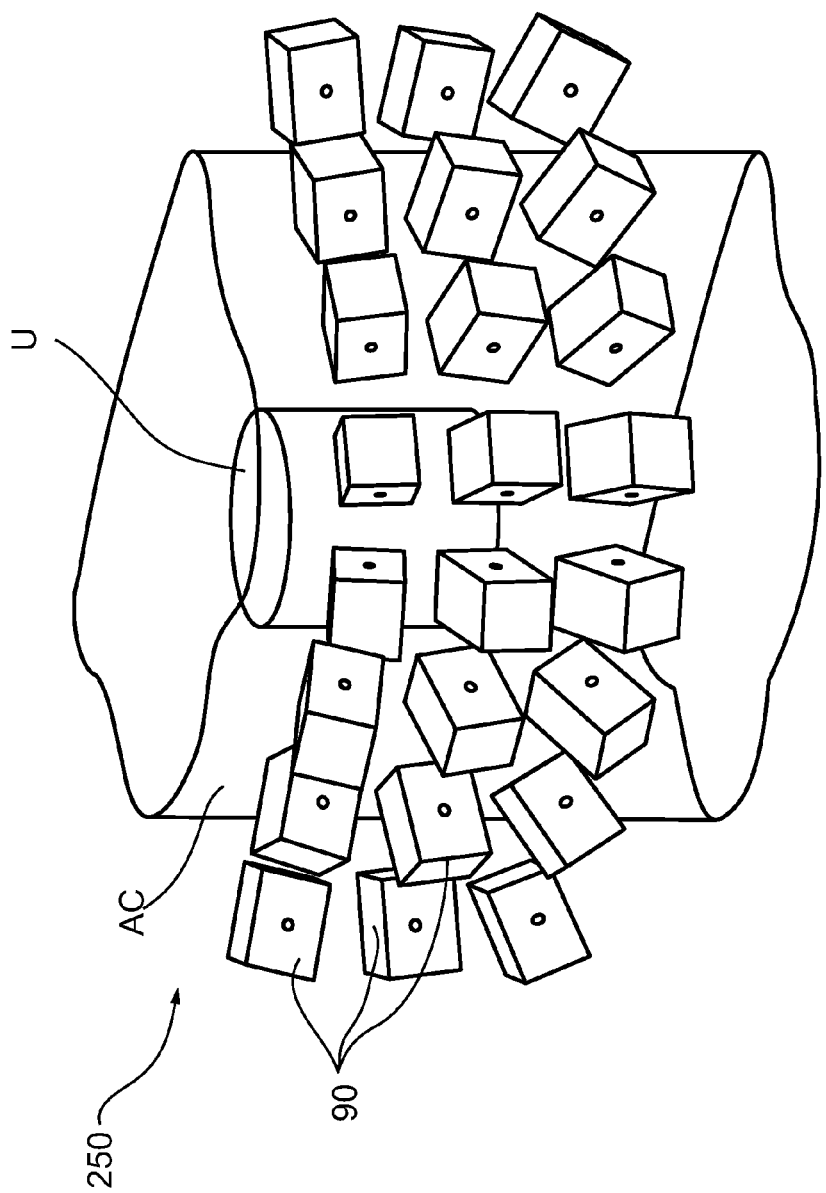
FIG. 51 schematically illustrates a cardiac model, in accordance with an embodiment of the present invention.
Figure 52:
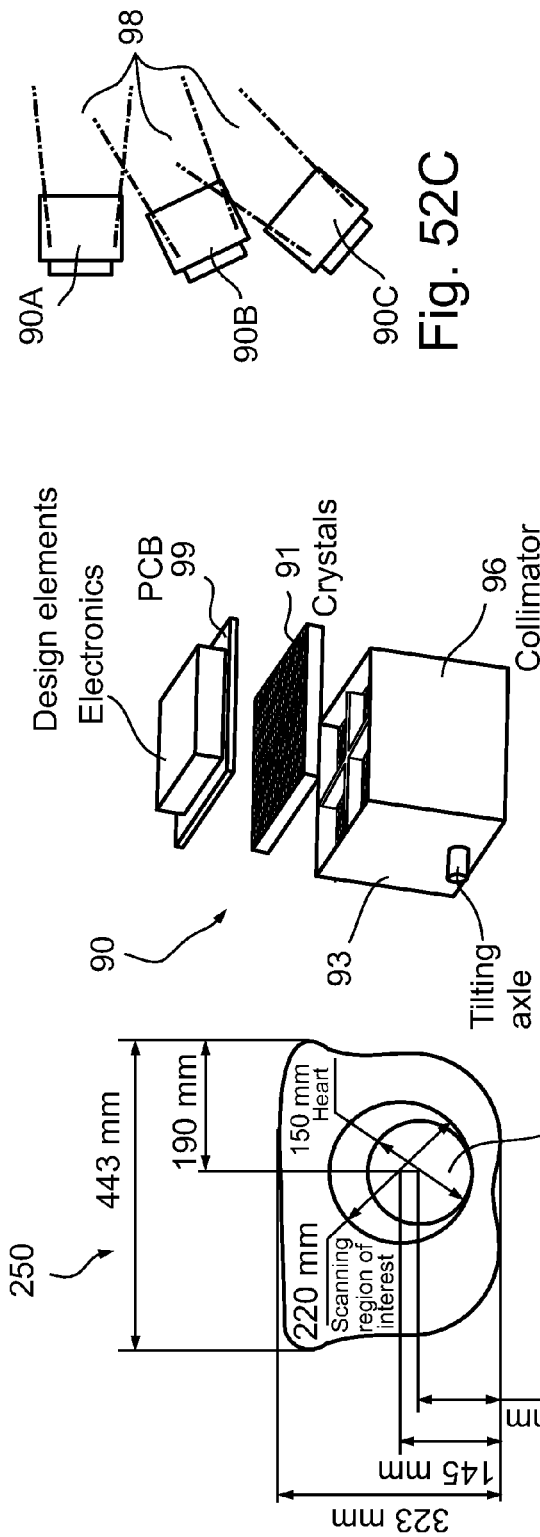
FIGS. 52A-52E schematically illustrate radiation detection blocks arranged for viewing a cardiac model, in accordance with an embodiment of the present invention.

FIG. 51 schematically illustrates the cardiac model 250, in accordance with a preferred embodiment of the present invention. The cardiac model 250 includes the volume U, for example, as a cylinder, and the anatomical constraints AC. The rows of blocks 90 are arranged around the volume U, as permissible by the anatomical constraints AC.

FIGS. 52A-52E schematically illustrate the blocks 90, arranged for viewing the cardiac model 250, in accordance with a preferred embodiment of the present invention.

In FIG. 52A, the block 90 is shown with the frame 93, which houses the detector material 91, which is preferably pixelated, and the collimators 96. Additionally, the frame 93 houses the dedicated electronics 97, on the PCB board 99.

In FIG. 52B, fields of view 98 of the blocks 90 are seen for a situation wherein adjacent blocks 90A and 90B move in an antipodal manner, while adjacent blocks 90B and 90C move in a nearly parallel manner. The figure illustrates that when moving in an antipodal manner, the blocks 90 do not obstruct each other's field of view 98. Yet, when moving in a parallel manner, or a near parallel manner, obstruction may occur.

A similar observation is made by FIG. 52C, wherein the adjacent blocks 90B and 90C move in an antipodal manner, while the adjacent blocks 90A and 90B move in a near parallel manner.

Again, it will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

FIG. 52D illustrates possible dimensions for the cardiac model 250. The dimensions are in mm. It will be appreciated that other dimensions are similarly possible. Furthermore, it will be appreciated that the model 250 may be based on general medical information of the organ 215 and common pathological features associated with it. Additionally, the model may be based on information related to a specific patient, such as age, sex, weight, and body type. Furthermore, a structural image, such as by ultrasound or MRI, may be used for providing information about the size and location of the heart 215 in relation to the body section 230 (FIG. 5A), for generating the model 250.

FIG. 52E schematically illustrates a possible arrangement of the blocks 90 for viewing the volume U of the model 250, within the anatomical constrains AC. The significance of the present invention, as illustrated by Figures and 52E is that all the blocks maintain a close proximity to the modeled volume U, and to the region-of-interest, in vivo, even as they move. This is in sharp contrast to the prior art, for example, as taught by U.S. Pat. No. 6,597,940, to Bishop, et al, and U.S. Pat. No. 6,671,541, to Bishop, in which the blocks are fixed within a rigid overall structure, so that as some of the blocks are placed in close proximity to the body, others are forced away from the body, and their counting efficiency deteriorates.

Preferably, the radiopharmaceuticals associated with the camera of FIGS. 40-52E may be Myoview™ (technetium Tc-99m tetrofosmin), a cardiac imaging agent, of GE Healthcare, GE Medical Systems, http://www.gehealtlhcare.com/contact/contact_details.html#diothers. Alternatively, it may be Cardiolite (Sestamibi radilabeled with Tc-99m), of DuPont, http://www1.dupont.com/NASApp/dupontgloba/corp/index.jsp?page=/content/US/en_US/contactus.html. It will be appreciated that other agents may be used.

In accordance with the preferred embodiment of the present invention, esophagus imaging is performed with Teboroxime as the radiopharmaceutical.

It will be appreciated that cardiac imaging, in accordance with embodiments of the present invention relates to the imaging of the whole heart, or to a portion of the heart, or to blood vessels near the heart, for example, the coronary artery.

Example 12

Figure 53:
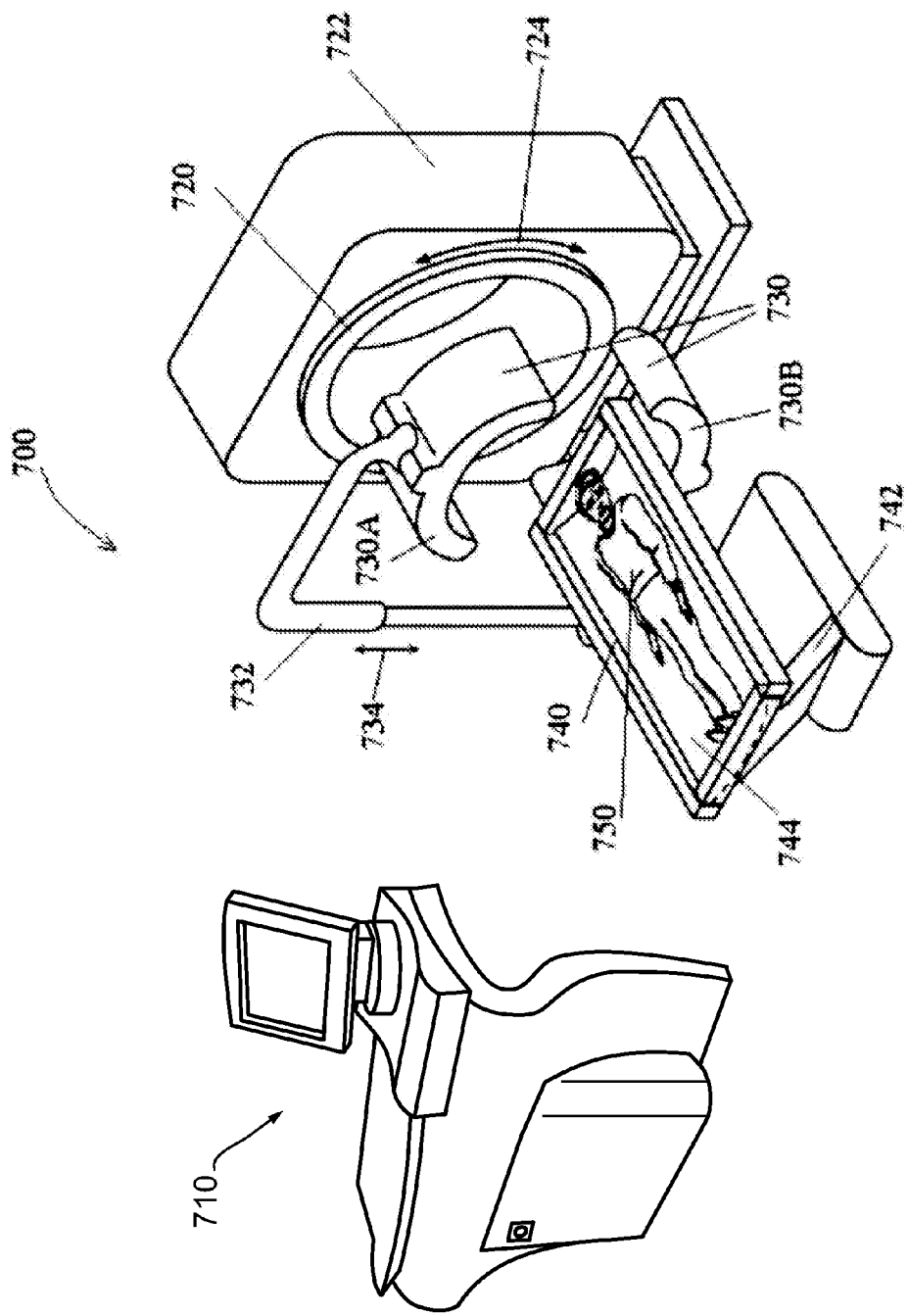
FIG. 53 schematically illustrates a dual imaging system for radioactive-emissions in tandem with a three-dimensional structural imager, in accordance with an embodiment of the present invention.

Referring further to the drawings, FIG. 53 schematically illustrates a dual imaging system 700 for radioactive-emissions in tandem with a three-dimensional structural imager, in accordance with a preferred embodiment of the present invention.

The dual imaging system 700 includes a three-dimensional structural imager 720, preferably, on a structural-imager gantry 722, and a radioactive-emission measuring camera 730, preferably, on a camera gantry 732. A patient 750 may lie on a bed 740, which is adapted for motion into the radioactive-emission measuring camera 730 and the three-dimensional structural imager 720, on a bed gantry 742.

A control unit 710 controls the operation of the dual system 700, including the three-dimensional structural imager 720, the radioactive-emission measuring camera 730, and the bed 740. The control unit 710 may also analyze the data.

Alternatively, two control units may be used, one for controlling the three-dimensional structural imager 720 and another for controlling the radioactive-emission measuring camera 730. It will be appreciated that the control system of the radioactive-emission measuring camera 730 generally controls the order of the operation of the dual system 700, wherein the radioactive-emission measuring may be performed before or after the structural imaging.

It will be further appreciated that the radioactive-emission measuring camera 730 may be configured as an add-on system, adapted for operating with an existing structural imager. It may be supplied with a dedicated software, for example, in a CD format, or with its own control unit, which is preferably adapted for communication with the structural imager control unit.

The three-dimensional structural imager 720 may be, for example, a CT or an MRI, which defines a frame of reference, wherein the radioactive-emission measuring camera 730 is co-registered to the frame of reference.

In this manner, co-registration of functional and structural images is possible. Additionally, the structural image may be used for providing tissue information for attenuation correction of the functional image, resulting in a more accurate functional image.

The radioactive-emission measuring camera 730 may be constructed as one arc 730A, preferably adapted for viewing a full width of a body from a single position of the camera 730. Alternatively, the radioactive-emission measuring camera 730 may be constructed as two arcs 730A and 730B, which are adapted for viewing a full circumference of a body, from a single position of the camera 730. It will be appreciated that the camera 730 may have other geometries, for example, a circle, an ellipse, a polygon, a plurality of arcs forming a circle, or a plurality of sections, forming a polygon, or other shapes.

Preferably, where the camera 730 is adapted for viewing a full circumference of a patient, from a single position, the bed 740 is formed as a stretcher, with a sheet 744, which is substantially transparent to radioactive emission, for example, of a hydrocarbon material.

Figure 54:
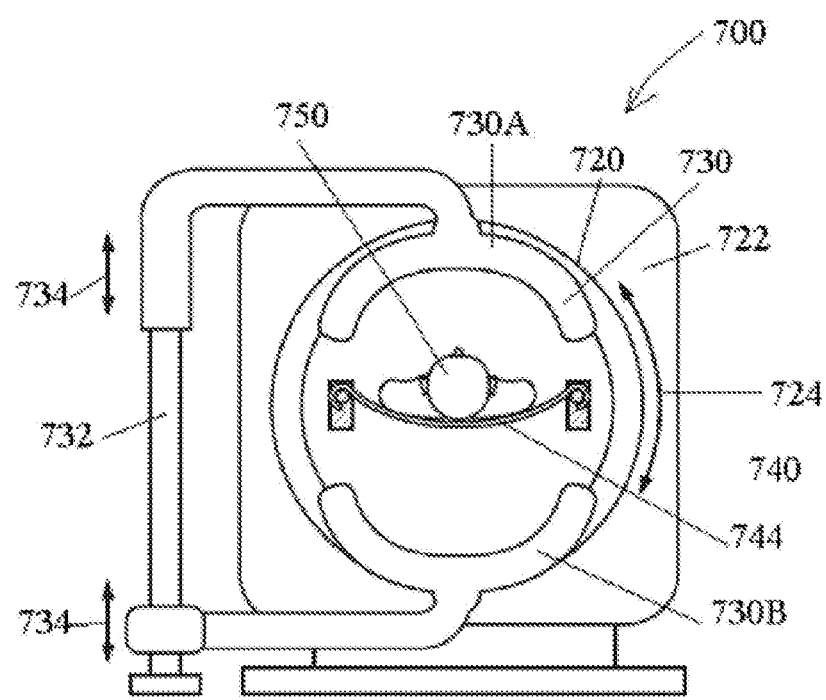
FIG. 54 schematically illustrates a dual imaging system for radioactive-emissions in tandem with a three-dimensional structural imager, in accordance with an embodiment of the present invention.

FIG. 54 schematically illustrates a cross-sectional view of dual imaging system 700 for radioactive-emissions in tandem with a three-dimensional structural imager, in accordance with a preferred embodiment of the present invention.

Preferably, the gantry 732 of the camera 730 is adapted for vertical motion, as described by the arrows 734, so as to bring the camera 730 closer to the patient 750.

Additionally, the gantry 722 of the three-dimensional structural imager 720 may be adapted for rotation, as described by an arrow 724.

The bed 740 is preferably adapted for motion into and out of the camera 730 and the three-dimensional structural imager 720.

Preferably, the rate of imaging by the three-dimensional structural imager 720 and by the radioactive-emission measuring camera is substantially the same, so the bed moves into the two imagers at a constant speed.

In accordance with embodiments of the present invention, the camera 730, formed of portions 730A and 730B, as illustrated in FIGS. 53 and 54 may also be a radioactive-emission measuring PET camera. Additionally, while the patient 750 appears lying, the patient may be sitting standing, lying on the back or lying on the stomach.

It will be appreciated that the body structure that may be imaged may be an organ, such as a heart or a pancreas, a gland, such as a thyroid gland or a lymph gland, blood vessels, for example, the coronary artery or the pulmonary artery, a portion of an organ, such as an aorta or a left atrium of a heart, a bone, a ligament, a joint, a section of the body, such as a chest or an abdomen, or a whole body.

Preferably, the radiopharmaceuticals associated with the camera of the present invention be any one of the following:

1. anti-CEA, a monoclonal antibody fragment, which targets CEA—produced and shed by colorectal carcinoma cells—and may be labeled by Tc-99m or by other radioisotopes, for example, iodine isotopes (Jessup J M, 1998, Tumor markers—prognostic and therapeutic implications for colorectal carcinoma, Surgical Oncology; 7: 139-151);

2. In-111-Satumomab Pendetide (Oncoscint®), designed to target TAG-72, a mucin-like glycoprotein, expressed in human colorectal, gastric, ovarian, breast and lung cancels, but rarely in healthy human adult tissues [Molinolo A; Simpson J F; et al., 1990, Enhanced tumor binding using immunohistochemical analyses by second generation anti-tumor-associated glycoprotein 72 monoclonal antibodies versus monoclonal antibody B72.3 in human tissue, Cancer Res., 50(4): 1291-8];

3. Lipid-Associated Sialic Acid (LASA), a tumor antigen, used for colorectal carcinoma, with a similar sensitivity as anti-CEA monoclonal antibody fragment but a greater specificity for differentiating between benign and malignant lesions (Ebril K M, Jones J D, Klee G G, 1985, Use and limitations of serum total and lipid-bound sialic acid concentrations as markers for colorectal cancer, Cancer; 55:404-409);

4. Matrix Metaloproteinase-7 (MMP-7), a proteins enzyme, believed to be involved in tumor invasion and metastasis (Mori M, Barnard G F et al., 1995, Overexpression of matrix metalloproteinase-7 mRNA in human colon carcinoma, Cancer; 75: 1516-1519);

5. Ga-67 citrate, used for detection of chronic inflammation (Mettler F A, and Guiberteau M J, Eds., 1998, Inflammation and infection imaging, Essentials of nuclear medicine, Fourth edition, Pgs: 387-403);

6. Nonspecific-polyclonal immunoglobulin G (IgG), which may be labeled with both In-111 or Tc-99m, and which has a potential to localize nonbacterial infections (Mettler F A, and Guiberteau M J, ibid);

7. Radio-labeled leukocytes, such as such as In-111 oxine leukocytes and Tc-99m HMPAO leukocytes, which are attracted to sites of inflammation, where they are activated by local chemotactic factors and pass through the endothelium into the soft tissue [Mettler F A, and Guiberteau M J, ibid; Corstens F H; van der Meer J W, 1999, Nuclear medicinie's role in infection and inflammation, Lancet; 354 (9180): 765-70]; and 8. Tc-99m bound to Sodium Pertechnetate, which is picked up by red blood cells, and may be used for identifying blood vessels and vital organs, such as the liver and the kidneys, in order to guide a surgical instrument without their penetration.

Additionally, certain organic materials can replace normal atoms in organic molecules with radioactive atoms, and thus can be used to label metabolism. In general, these are used for PET imaging. However, they can be used for other nuclear imaging as well. The radionuclides may be, for example:

1. F-18 fluoro-deoxyglucose (FDG)
2. F-18 Sodium Fluoride
2. C-11 methionine
3. Other less common C-11 amino acid tracers, such as:
   C-11 thymidine,
   C-11 tyrosine,
   C-11 leucine
4. N-13 ammonia
5. O-15 water
6. Rb-82 Rubidium Rb-82
7. Cu-62 copper
8. Ga-68 gallium In accordance with the preferred embodiment of the present invention, the dual imaging and any whole body imaging may be performed with Teboroxime as the radiopharmaceutical.

It will be appreciated that other agents may be used.

Figure 55A:
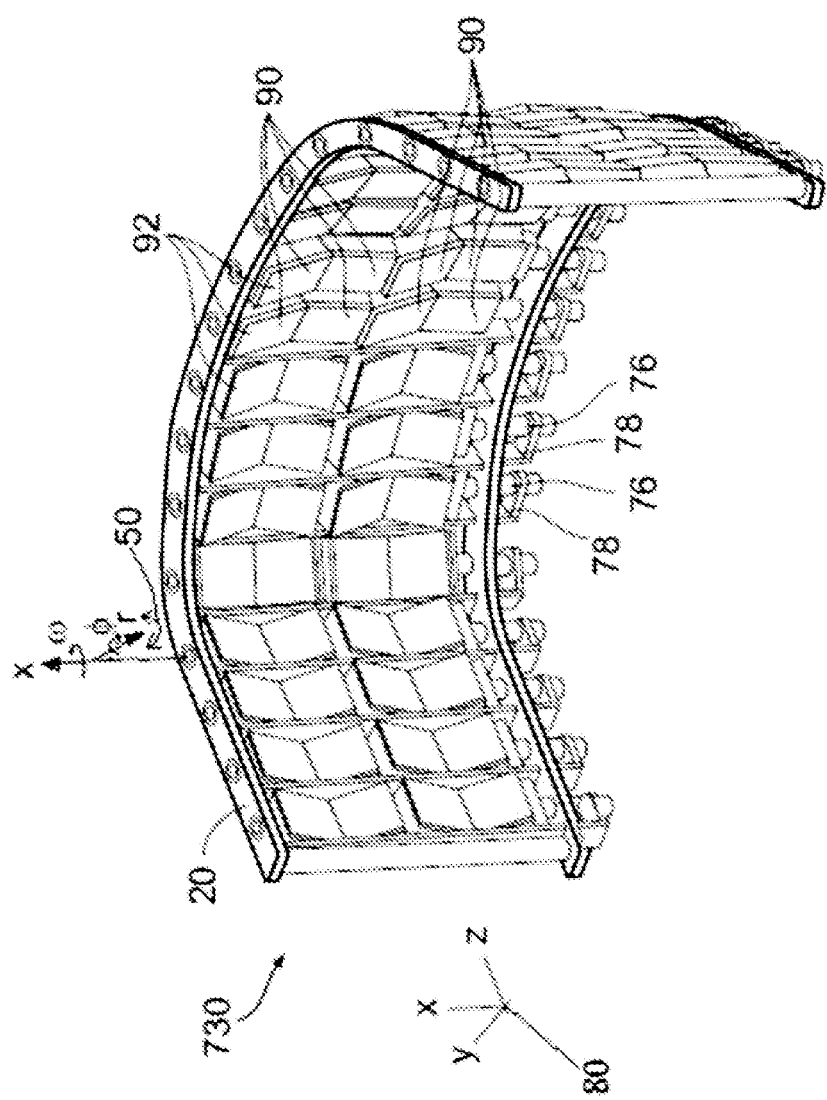
FIGS. 55A-55C schematically illustrate the internal structure of the radioactive-emission camera for the dual imaging system, in accordance with an embodiment of the present invention.
Figure 55B:
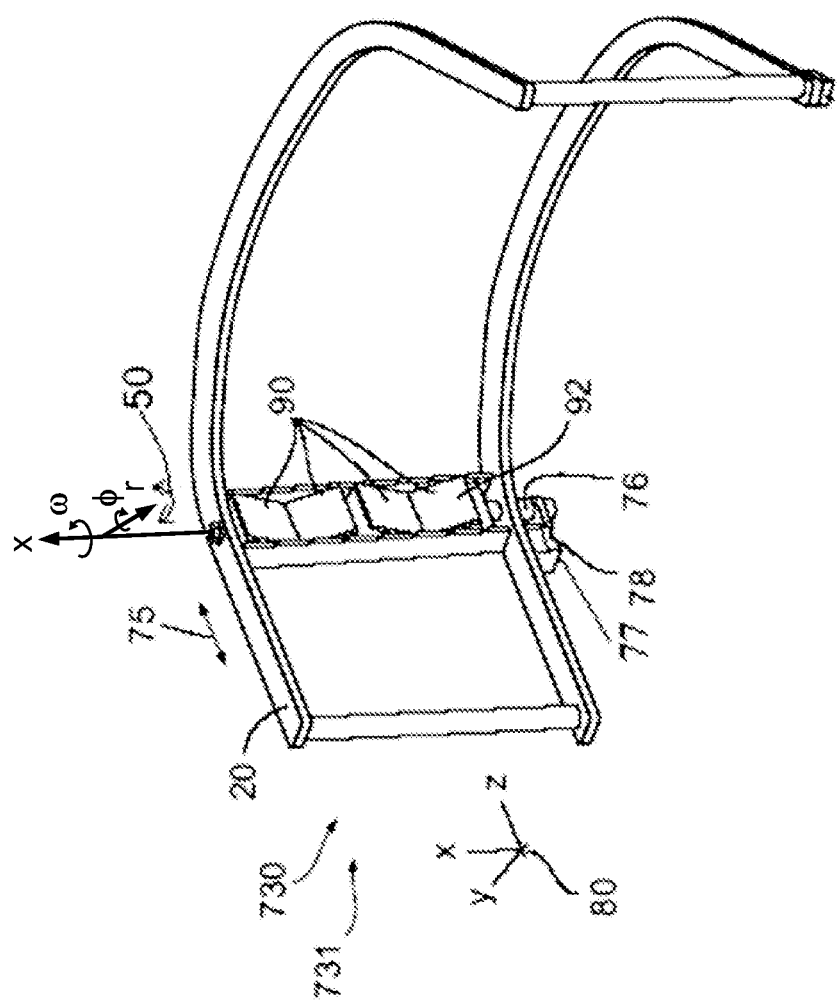
Figure 55C:
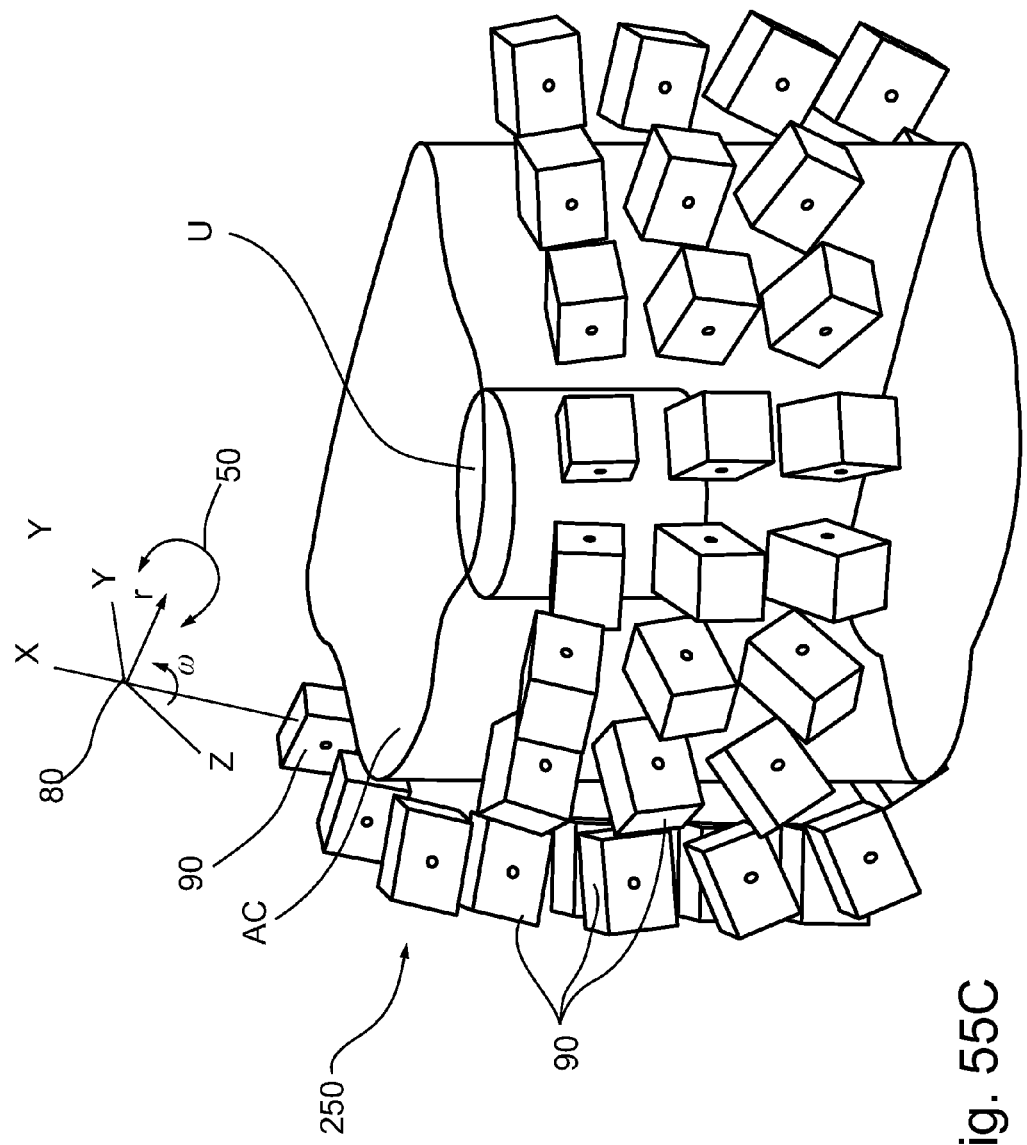

FIGS. 55A-55C schematically illustrate possible inner structures of the camera 730, in accordance with preferred embodiments of the present invention.

FIG. 55A schematically illustrates the inner structure of the camera 730, showing the overall structure 20 and the parallel lines of the assemblies 92, possibly of an even number, each with the row of blocks 90, possibly arranged in pairs. Each of the assemblies 92 preferably includes the dedicated motion provider 76, for providing the rotational motion around x, and the dedicated secondary motion provider 78, for providing the oscillatory motion about r in the direction of the arrow 50.

The camera 730 defines an internal frame of reference 80, while each assembly 92 has a reference cylindrical coordinate system of x;r, with rotation around x denoted by $\omega$ and rotation around r denoted by $\phi$, wherein the oscillatory motion about r is denoted by the arrow 50.

Preferably, the motions of the assemblies 92 and the blocks 90 correspond to those described hereinabove, with reference to FIGS. 20A-20H and 22A-22H, as follows:

The plurality of blocks 90 is adapted for the windshield-wiper like oscillatory motion, around the radius r, as denoted by the arrow 50. The oscillatory motions may be synchronized in an antipodal manner, so as to be diametrically opposed to each other, as shown hereinabove in FIGS. 20B and 20E, by the arrows 54, and as shown hereinabove in FIGS. 20C and 20F by the arrows 56. However, other motions are also possible. For example, the blocks 90 may move together, or independently. It will be appreciated that an odd number of blocks 90 is also possible.

Furthermore, the plurality of assemblies 92 are preferably arranged in parallel, and their rotational motions, around the x-axis, in the direction of ω, may also be synchronized in an antipodal manner, so as to be diametrically opposed to each other, as shown hereinabove, in FIG. 22C, by arrows 62, and as shown hereinabove in FIG. 22G, by arrows 64. However, other motions are also possible. For example, the assemblies 92 may move together, or independently. It will be appreciated that an odd number of assemblies 92 is also possible.

Thus, the resultant traces are a large plurality of the broken line traces 59, as seen hereinabove, with reference to FIGS. 22D and 22H, on the skin of the patient.

In accordance with the present example, i. The different blocks 90 provide views from different orientations;

ii. The different blocks 90 change their view orientations;

iii. The different assemblies 92 provide views from different orientations; and iv. The different assemblies 92 change their view orientations.

The operational manner of the camera 730 is described hereinbelow with reference to FIG. 23D, for the at least two assemblies 92.

Preferably, the motions of the blocks 90 and of the assemblies 92 are contained within the overall structure 20, so that the overall structure 20 of the camera 730 remains stationary, wherein the external surface of the camera 730 is substantially transparent to nuclear radiation. Alternatively, the overall structure may be a skeleton, open on the side facing the patient.

It will be appreciated that the oscillatory motions need not be synchronized in an antipodal manner. Rather, the blocks 90 may move together, or independently. It will be appreciated that an odd number of blocks 90 is also possible.

It will be appreciated that the camera 730 may include a plurality of assemblies 92, which are not parallel to each other. For example, the assemblies 92 may be at right angles to each other, or at some other angle. It will be appreciated that the assemblies 92 may include detecting units 12 rather then blocks 90, for example, as in the camera 10 of FIGS. 20A-20G.

FIG. 55B schematically illustrates a section 731 of the camera 730, showing the inner structure thereof, in accordance with another embodiment of the present invention. Accordingly, the camera 730 may include the overall structure 20, and a single one of the assemblies 92, within the overall structure 20, having the dedicated motion provider 76, the dedicated secondary motion provider 78, and the rows of blocks 90. Additionally, in accordance with the present embodiment, the camera 730 includes a tertiary motion provider 77, for sliding the assembly 90 laterally, in the directions of an arrow 75.

FIG. 55C schematically illustrates an alternative arrangement of the blocks 90 around the volume U of the model 250, wherein each of the blocks 90 is provided with motion around the x-axis, in the direction of ω, and with the oscillatory motion about r, preferably in the y-z plane, as illustrated by the arrow 50. Accordingly, the assemblies 92 need not be used. Rather, each of the blocks 90 may communicate with two motion providers which provide it with the two types of motion.

FIGS. 56A and 56B schematically illustrate the assembly 92 and the block 90, in accordance with a preferred embodiment of the present invention. In essence, the assembly 92 is constructed in a manner similar to the camera 10 of FIG. 20H, and according to FIG. 23D, hereinabove.

Thus the assembly 92 includes a row of at least two blocks 90, each adapted for oscillatory motion about r. The blocks 90 are arranged within the internal structure 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

It will be appreciated that many other cameras and camera systems may be considered and the examples here are provided merely to illustrate the many types of combinations that may be examined, in choosing and scoring a camera design, both in terms of information and in terms of secondary considerations, such as rate of data collection, cost, and complexity of the design.

Example 13

Brain cancer is the leading cause of cancer-related death in patients younger than age 35, and in the United States, the annual incidence of brain cancer generally is 15-20 cases per 100,000 people.

There are two types of brain tumors: primary brain tumors that originate in the brain and metastatic (secondary) brain tumors that originate from cancer cells that have migrated from other parts of the body.

Approximately 17,000 people in the United States are diagnosed with primary cancer each year; nearly 13,000 die of the disease. Amongst children, the annual incidence of primary brain cancer is about 3 per 100,000.

Primary Brain Tumors are generally named according to the type of cells or the part of the brain in which they begin. The most common are gliomas, which begin in glial cells, and of which there are several types, as follows:

Astrocytoma, a tumor which arises from star-shaped glial cells called astrocytes, which most often arises in the cerebrum in adults, whereas, in children, it occurs in the brain stem, the cerebrum, and the cerebellum;

Brain stem glioma, a tumor that occurs in the lowest part of the brain and is diagnosed in young children as well as in middle-aged adults;

Ependymoma, a tumor most common in middle-aged adults, which arises from cells that line the ventricles or the central canal of the spinal cord, and also occurs in children and young adults; and Oligodendroglioma, a rare tumor, which arises from cells that make the fatty substance that covers and protects nerves and usually occurs in the cerebrum, grows slowly and generally does not spread into surrounding brain tissue.

Some types of brain tumors do not begin in glial cells. The most common of these are:

Medulloblastoma, also called a primitive neuroectodermal tumor, a tumor which usually arises in the cerebellum and is the most common brain tumor in children;

Meninigioma, which arises in the meninges and usually grows slowly;

Schwannoma, also called an acoustic neuroma, and occurring most often in adults, it is a tumor that arises from a Schwann cell, of the cells that line the nerve that controls balance and hearing, in the inner ear;

Craniopharyngioma, a tumor which grows at the base of the brain, near the pituitary gland, and most often occurs in children;

Germ cell tumor of the brain, a tumor which arises from a germ cell, generally, in people younger than 30, the most common type of which is a germinoma; and Pineal region tumor, a rare brain tumor, which arises in or near the pineal gland, located between the cerebrum and the cerebellum.

Certain inherited diseases are associated with brain tumors, for example, Multiple endocrine neoplasia type 1 (pituitary adenoma), Neurofibromatosis type 2 (brain and spinal cord tumors), Retinoblastoma (malignant retinal glioma), Tuberous sclerosis (primary brain tumors), and Von Hippel-Lindau disease (retinal tumor, CNS tumors). Furthermore, genetic mutations and deletions of tumor suppressor genes (i.e., genes that suppress the development of malignant cells) increase the risk for some types of brain cancer.

Additionally, exposure to vinyl chloride is an environmental risk factor for brain cancer. Vinyl chloride is a carcinogen, used in the manufacturing of plastic products such as pipes, wire coatings, furniture, car parts, and house wares, and is present in tobacco smoke. Manufacturing and chemical plants may release vinyl chloride into the air or water, and it may leak into the environment as a result of improper disposal. People who work in these plants or live in close proximity to them have an increased risk for brain cancer.

Secondary brain cancer occurs in 20-30% of patients with metastatic disease and its incidence increases with age. In the United States, about 100,000 cases of secondary brain cancer are diagnosed each year. Patients with a history of melanoma, lung, breast, colon, or kidney cancer are at risk for secondary brain cancer.

Brain tumors can obstruct the flow of cerebrospinal fluid (CSF), which results in the accumulation of CSF (hydrocephalus) and increased intracranial pressure (IICP). Nausea, vomiting, and headaches are common symptoms. They can damage vital neurological pathways and invade and compress brain tissue. Symptoms usually develop over time and their characteristics depend on the location and size of the tumor.

The first step in diagnosing brain cancer involves evaluating symptoms and taking a medical history. If there is any indication that there may be a brain tumor, various tests are done to confirm the diagnosis, including a complete neurological examination, imaging tests, and biopsy.

Referring now to the drawings, FIGS. 57A-57F present the principles of modeling, for obtaining an optimal set of views, for a body organ 215, in accordance with embodiments of the present invention.

FIG. 57A schematically illustrates a body section 230, illustrating the organ 215, being the brain 215. The brain 215 is enclosed within a skull 830 and includes:

a cerebellum 802, the part of the brain below the back of the cerebrum, which regulates balance, posture, movement, and muscle coordination;

a corpus callosum 804, which is a large bundle of nerve fibers that connect the left and right cerebral hemispheres;

a frontal lobe of the cerebrum 806, which is the top, front regions of each of the cerebral hemispheres, and is used for reasoning, emotions, judgment, and voluntary movement;

a medulla oblongata 808, which is the lowest section of the brainstem (at the top end of the spinal cord) and controls automatic functions including heartbeat, breathing, and the like;

a occipital lobe of the cerebrum 810, which is the region at the back of each cerebral hemisphere, at the back of the head, and contains the centers of vision and reading ability;

a parietal lobe of the cerebrum 812, which is the middle lobe of each cerebral hemisphere between the frontal and occipital lobes, located at the upper rear of the head, and which contains important sensory centers;

a pituitary gland 814, which is a gland attached to the base of the brain that secretes hormones, and is located between the pons and the corpus callosum;

pons 816, which is the part of the brainstem that joins the hemispheres of the cerebellum and connects the cerebrum with the cerebellum, located just above the medulla oblongata;

a spinal cord 818, which is a thick bundle of nerve fibers that runs from the base of the brain to the hip area, through the spine (vertebrae);

a temporal lobe of the cerebrum 820, which is the region at the lower side of each cerebral hemisphere, located at the sides of the head and containing centers of hearing and memory.

The brain 215 may include a pathological feature 213, termed herein an organ target 213. A region-of-interest (ROI) 200 may be defined so as to encompass the brain 215 and the pathological feature 213.

As seen in FIG. 57B, the region-of-interest 200 of FIG. 57A is modeled as a model 250 of a volume U, and the organ target 213 is modeled as a modeled organ targets 213. Additionally, there are certain physical viewing constraints, associated with the region-of-interest 200, which are modeled as anatomical constraints AC. In the present case, the skull 830 creates viewing constraints, and generally, imaging the brain is performed extracorporeally.

Figure 58:
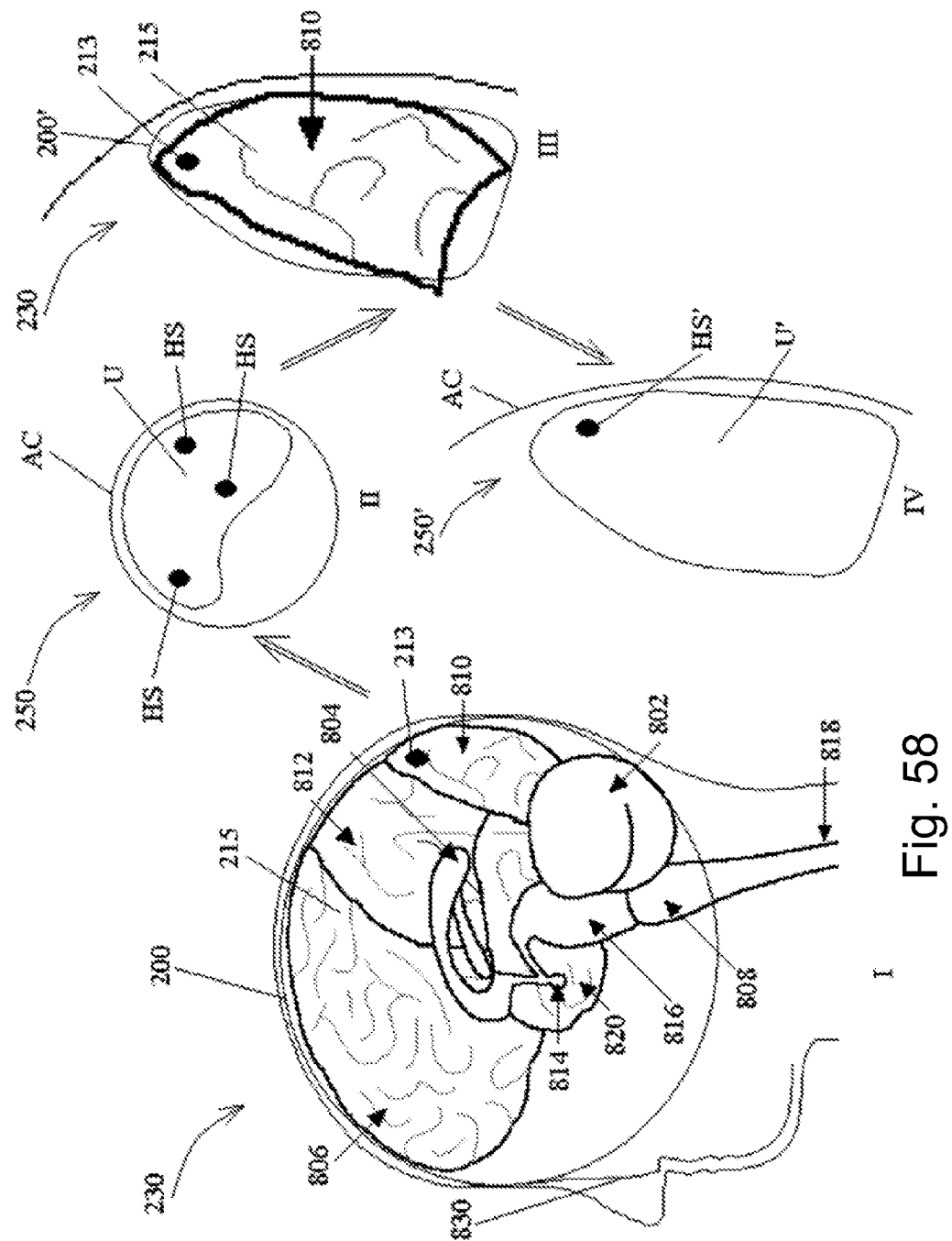
FIG. 58 schematically illustrates a cranial model, in accordance with an embodiment of the present invention.

Referring further to the drawings, FIG. 58 pictorially illustrates a method 340 for zooming in on a suspected pathological feature, as a process of two or more iterations, in accordance with embodiments of the present invention, as follows:

As seen in FIG. 58, the method 340 may be described, pictorially, as follows:

In I: The region-of-interest 200, associated with the organ 215, such as the brain 215, is defined for the body section 230.

In II: The model 250 of the volume U is provided for the region-of-interest 200, possibly with one or several of the modeled organ targets HS, and within the anatomical constraints AC, for obtaining the optimal set of views for the region-of-interest 200. The optimal set of views is then applied to the region-of-interest 200, encompassing the brain 215 of the body section 230.

In III: When the suspected organ target 213 is identified, in vivo, in the brain 215, by radioactive-emission measurements at the optimal set of views, a second, inner region-of-interest 200' is defined, encircling the suspected pathological feature. For example, if a suspected pathology 213 is identified in the occipital lobe 810 of the cerebrum, that is, the region at the back of each cerebral hemisphere at the back of the head, the second region-of-interest 200' is defined so as to encircle the occipital lobe 810 of the cerebrum.

In IV: A model 250' of a volume U' is provided for the second, inner region-of-interest 200', preferably, with at least one modeled organ target HS, simulating the suspected organ target 213, for obtaining an optimal pathology set of views for the region-of-interest 200'. The second, pathology set of views is then applied to the second, inner region-of-interest 200' of the body section 230. In the present example, the second, pathology set of views is then applied to the occipital lobe 810 of the cerebrum, in vivo.

Referring further to the drawings, FIGS. 59A-60J schematically illustrate a camera system 850 for the brain, in accordance with a preferred embodiment of the present invention.

FIGS. 59A-59C schematically illustrate the radioactive-emission camera for the brain, in accordance with embodiments of the present invention;

Preferably, radioactive-emission camera 850 for the brain is shaped as a helmet 860, adapted for wearing on a head 862. The helmet 860 is preferably mounted on a gantry 870, which may be adjustable in the directions of arrows 872, 874 and 876, for adapting to individual heights and comfort requirements.

Alternatively, no gantry is used, and the helmet 860 may be worn directly on the head 862, for example, like a motorcycle helmet.

A chair 880 may be provided for the comfort of the patient.

Preferably, the radioactive-emission camera 850 for the brain is operable with a control unit 890, which may be a desktop computer, a laptop, or the like. The control unit 890 is preferably used both for controlling the motions of the detecting units 12, blocks 90 and assemblies 92 of the radioactive-emission camera 850 for the brain and for analyzing the data.

It will be appreciated that the radioactive-emission camera 850 for the brain may be supplied merely as the camera helmet 860 and a data storage device, such as a CD 892, a disk 892, or the like, containing the appropriate software, for operation with an existing computer, at the site.

It will be appreciated that the present camera system for the brain may also be used as a PET system, for coincident counting.

It will be appreciated that the radioactive-emission camera 850 for the brain may be operable with a structural imager, as taught by commonly owned PCT publication WO2004/042546, whose disclosure is incorporated herein by reference. The structural imager may be a handheld ultrasound imager, possibly with a position-tracking device, a 3-D imager such as an ultrasound imager, a CT imager, or an MRI imager, as known. The data provided by the structural imager may be used for any one or a combination of the following:

i. obtaining accurate dimensional data for modeling the brain 215, as taught with reference to FIGS. 57A-58 and 11-12;

ii. providing attenuation correction for the radioactive-emissions, based on the structural data, as taught by commonly owned PCT publication WO2004/042546; and iii. co-registering the functional and structural images, as taught, for example, by commonly owned PCT publication WO2004/042546.

Referring further to the drawings FIGS. 60A-60K schematically illustrate inner structures of the camera 850 in accordance with several embodiments of the present invention.

FIG. 60A schematically illustrates the assembly 92, comprising, for example foul of the blocks 90, adapted for oscillatory motion about the r-axis, as illustrated by the arrows 50, and adapted for rotational motion about the x-axis, as illustrated by the arrow 62, as taught, for example, with reference to FIGS. 22A-22H. It will be appreciated that detecting units 12 may be used in place of blocks 90.

FIG. 60B schematically illustrates a possible cross sectional view of the camera 850 (FIG. 59C), showing an arrangement of the assemblies 92, laterally around the head 862.

FIG. 60C schematically illustrates a top view of the camera 850, showing an arrangement of the assemblies 92, laterally around the head 862. It will be appreciated that the number of the blocks 90 may vary around the head 862.

FIGS. 60D and 60E schematically illustrate other possible cross sectional views of the camera 850, showing arrangements of the assemblies 92, vertically around the head 862.

FIG. 60F schematically illustrates the camera 850 formed as the helmet 860, with the assemblies 92, arranged as illustrated by the cross sectional view of FIG. 60E. It will be appreciated that other arrangements are similarly possible. Preferably, the camera helmet 860 includes an overall structure 864. Preferably, the motions of the blocks 90 and of the assemblies 92 are contained within the overall structure 864.

Preferably, the proximal side of the overall structure 864 with respect to the head 862 (FIG. 59C) is transparent to nuclear radiation. Alternatively, the proximal side with respect to the head 862 is open.

FIG. 60G schematically illustrates another arrangement of the blocks 90 around the head 862, wherein the blocks 90 are not arranged in assemblies 92; rather each block 90 moves as an individual body. It will be appreciated that the detecting units 12 may be used in place of the blocks 90.

FIGS. 60H-60K schematically illustrate possible rotational motions of the blocks 90, each of the blocks 90 moving as an individual body for obtaining views of different orientations. As seen in FIG. 60H, the block 90 rotates around x as seen by an arrow 852 and at each position around x, oscillates about x, as seen by an arrow 851. The resultant traces are seen in FIG. 60I as a star of line traces 854.

Alternatively, as seen in FIG. 60J, the block 90 rotates around y as seen by an arrow 853 and at each position around y, oscillates about x, as seen by the arrow 851. The resultant traces are seen in FIG. 60K, as line traces 855.

The assembly 92 and the block 90, in accordance with a preferred embodiment of the present invention are described in FIGS. 49A and 49B, hereinabove.

Thus the assembly 92 includes a row of at least two blocks 90, each adapted for oscillatory motion about r. The blocks 90 are arranged within the internal structure 21.

A motor 88 and a shaft 85 form the motion provider 76, while a secondary motor 86 and a secondary shaft 84 form the secondary motion provider 78, for the oscillatory motion about r. A plurality of motion transfer systems 74, for example gear systems, equal in number to the number of blocks 90, transfer the motion of the secondary motion provider 78 to the blocks 90. The motion transfer systems 74, of gears, make it possible to provide the row of blocks 90 with any one of parallel oscillatory motion, antipodal oscillatory motion, or independent motion, depending on the gear systems associated with each block 90. It will be appreciated that other motion transfer systems, as known, may be used.

It will be appreciated that detecting units 12 may be used in place of blocks 90.

In accordance with the present example, adjacent blocks 90A and 90B may move in an antipodal manner and adjacent blocks 90C and 90D may move in an antipodal manner, while adjacent blocks 90B and 90C may move in parallel. It will be appreciated that many other arrangements are similarly possible. For example, all the pairing combinations of the blocks 90 may move in an antipodal manner, all the blocks 90 may move in parallel, or the blocks 90 may move independently. It will be appreciated that an odd number of blocks 90 may be used in the assembly 92.

It will be appreciated that imaging, in accordance with embodiments of the present invention relates to the imaging of the whole brain, or to a portion of the brain, or to blood vessels near the brain, for example, the coronary artery.

Preferably, the radiopharmaceuticals associated with the camera of the present invention may be Tc99m-d, 1-hexamethyl propylene amine oxime (1-HMPAO) commercially known as Ceretec by GE-Amersham, or Tc-99m-ECD, commercially known as Neurolite, and made by Bristol Myers Squibb.

The present invention applies to the two types of brain tumors: primary brain tumors, which originate in the brain and metastatic (secondary) brain tumors that originate from cancel cells that have migrated from other parts of the body.

Additionally, the primary brain tumors may be gliomas, which begin in glial cells, and of which there are several types, as follows:

Astrocytoma, a tumor which arises from star-shaped glial cells called astrocytes, and which in adults, most often arises in the cerebrum, whereas in children, it occurs in the brain stem, the cerebrum, and the cerebellum.

Brain stem glioma, a tumor that occurs in the lowest part of the brain, and is diagnosed in young children as well as in middle-aged adults.

Ependymoma, a tumor, most common in middle-aged adults, which arises from cells that line the ventricles or the central canal of the spinal cord and which occurs in children and young adults.

Oligodendroglioma, a rare tumor, which arises from cells that make the fatty substance that covers and protects nerves and usually occurs in the cerebrum, grows slowly and generally does not spread into surrounding brain tissue.

Additionally or alternatively, the present invention applies to other types of brain tumors, which do not begin in glial cells. The most common of these are:

Medulloblastoma, also called a primitive neuroectodermal tumor, a tumor which usually arises in the cerebellum and is the most common brain tumor in children.

Meningioma, which arises in the meninges and usually grows slowly.

Schwannoma, also called an acoustic neuroma, and occurring most often in adults, it is a tumor or that arises from a Schwann cell, of the cells that line the nerve that controls balance and hearing, in the inner ear.

Craniopharyngioma, a tumor which grows at the base of the brain, near the pituitary gland, and most often occurs in children.

Germ cell tumor of the brain, a tumor which arises from a germ cell, generally, in people younger than 30, the most common type of which is a germinoma.

Pineal region tumor, a rare brain tumor, which arises in or near the pineal gland, located between the cerebrum and the cerebellum.

Additionally or alternatively, the present invention applies to tumors associated with certain inherited diseases, for example, Multiple endocrine neoplasia type 1 (pituitary adenoma), Neurofibromatosis type 2 (brain and spinal cord tumors), Retinoblastoma (malignant retinal glioma), Tuberous sclerosis (primary brain tumors), and Von Hippel-Lindau disease (retinal tumor, CNS tumors), and genetic mutations and deletions of tumor suppressor genes (i.e., genes that suppress the development of malignant cells), which increase the risk for some types of brain cancer.

Additionally or alternatively, the present invention applies to tumors associated with exposure to vinyl chloride.

Additionally or alternatively, the present invention applies to secondary brain cancer, for example, originating from the lungs, the breasts, or other parts of the body.

It will be appreciated that the present invention further applies to other types brain tumors, which may be malignant or benign, blood clots in the brain, and other brain pathologies. It will be appreciated that many other cameras and camera systems may be considered and the examples here are provided merely to illustrate the many types of combinations that may be examined, in choosing and scoring a camera design, both in terms of information and in terms of secondary considerations, such as rate of data collection, cost, and complexity of the design.

Example 14

Figure 61A:
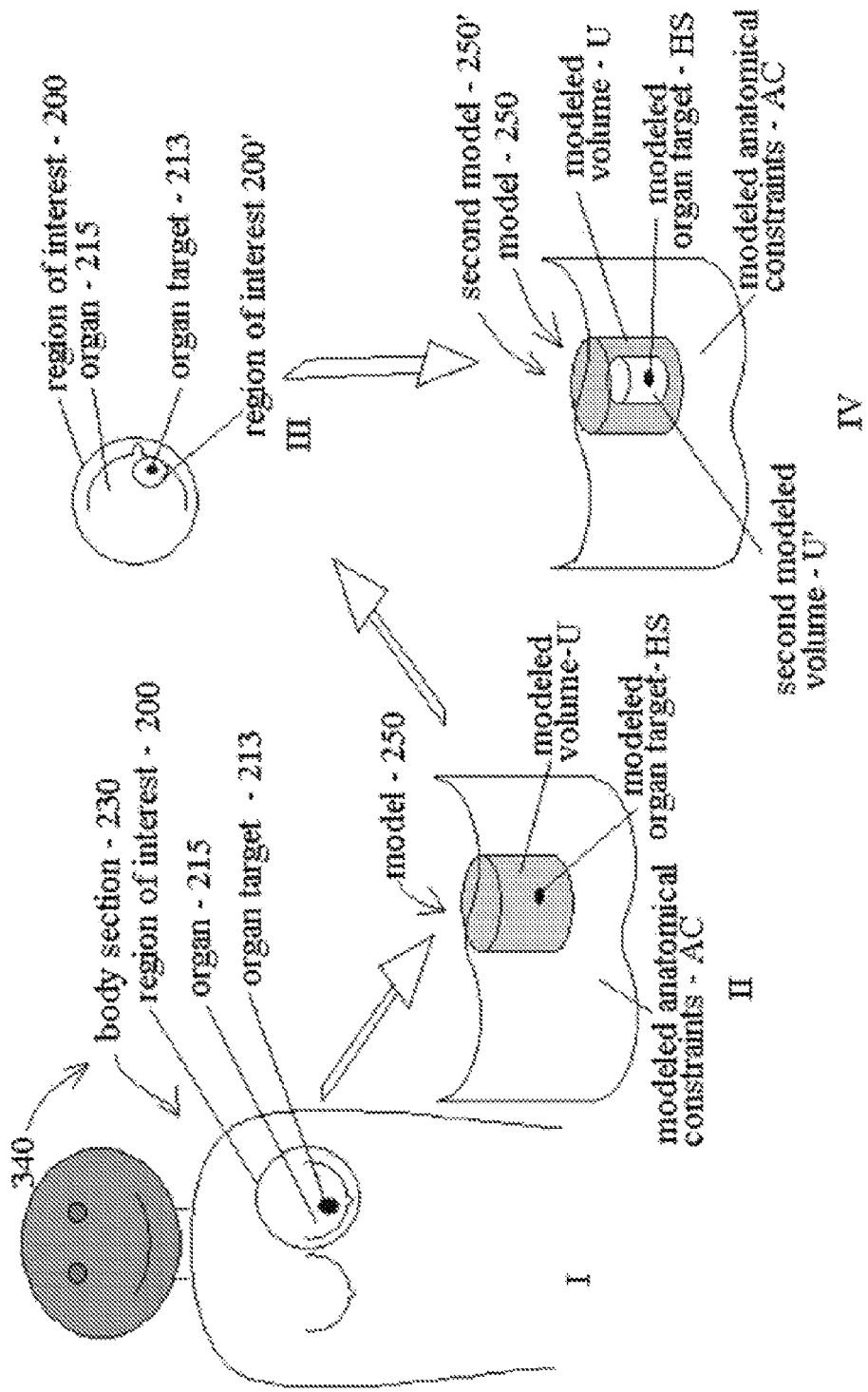
FIGS. 61A and 61B schematically illustrate a breast model, in accordance with an embodiment of the present invention.

Referring further to the drawings, FIG. 61A pictorially illustrates a method 340 for zooming in on a suspected pathological feature in a breast, as a process of two or more iterations, in accordance with embodiments of the present invention.

As seen in FIG. 61A, the method 340 may be described, pictorially, as follows:

In I: The region-of-interest 200, associated with the organ 215, such as the breast 215, is defined for the body section 230.

In II: The model 250 of the volume U is provided for the region-of-interest 200, possibly with one or several of the modeled organ targets HS, and within the anatomical constraints AC, for obtaining the optimal set of views for the region-of-interest 200. The optimal set of views is then applied to the region-of-interest 200, encompassing the breast 215 of the body section 230.

In III: When the suspected organ target 213 is identified, in vivo, in the breast 215, by radioactive-emission measurements at the optimal set of views, a second, inner region-of-interest 200' is defined, encircling the suspected pathological feature.

In IV: A second model 250' of a second volume U' is provided for the second, inner region-of-interest 200', preferably, with at least one modeled organ target HS, simulating the suspected organ target 213, for obtaining an optimal pathology set of views for the second region-of-interest 200'. The second, pathology set of views is then applied to the second, inner region-of-interest 200' of the body section 230.

Figure 61B:
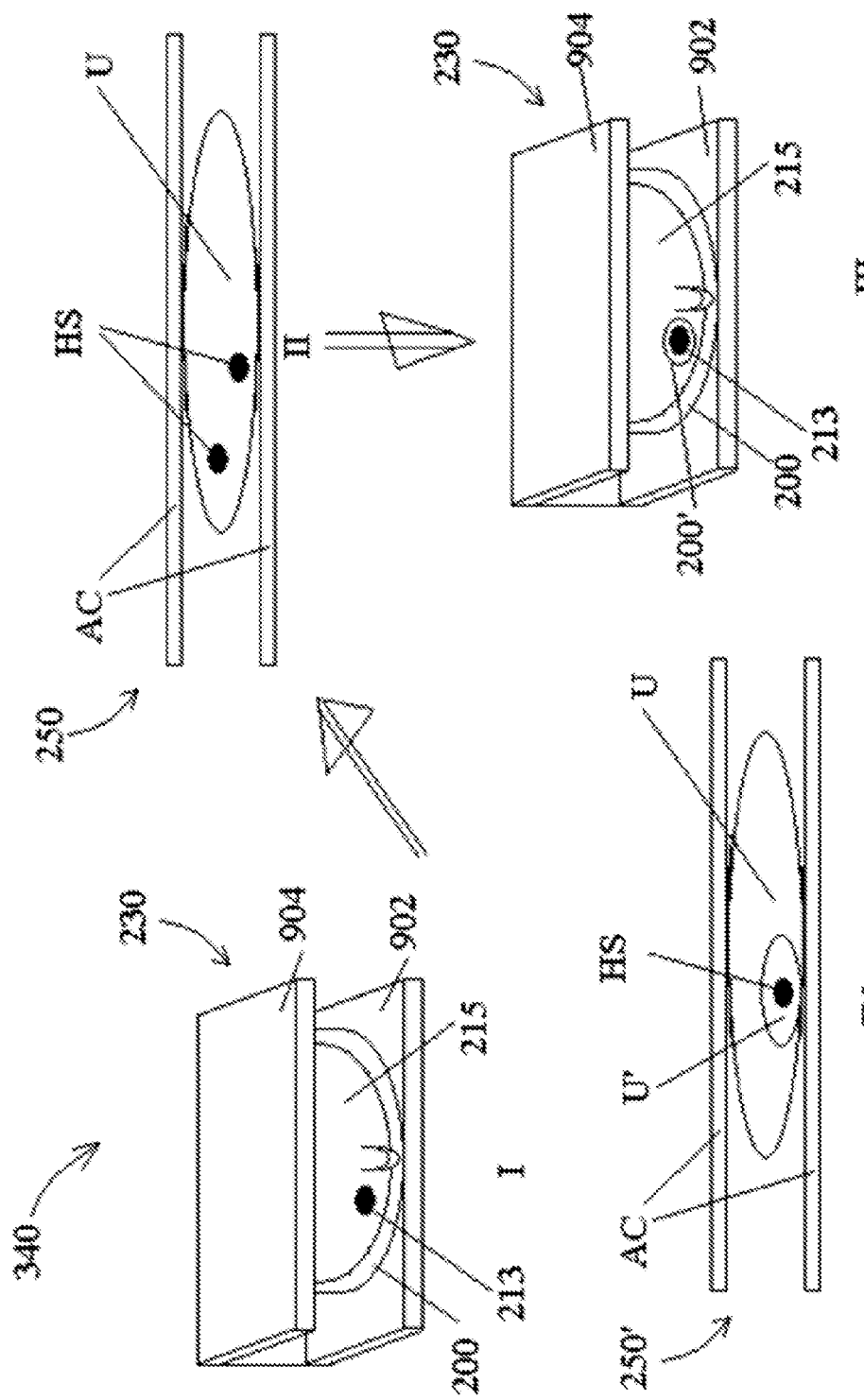

Alternatively, as seen in FIG. 61B, the method 340 may be described, pictorially, as follows:

In I: The region-of-interest 200, associated with the organ 215, such as the breast 215, is defined for the body section 230, when compressed between two plates 902 and 904, for example, mammograph plates.

In II: The model 250 of the volume U is provided for the region-of-interest 200, possibly with one or several of the modeled organ targets HS, and within the anatomical constraints AC, representing the mammograph plates, for obtaining the optimal set of views for the region-of-interest 200. The optimal set of views is then applied to the region-of-interest 200, encompassing the organ 215 of the body section 230.

In III: When the suspected organ target 213 is identified, in vivo, in the organ 215, by radioactive-emission measurements at the optimal set of views, a second, inner region-of-interest 200' is defined, encircling the suspected organ target 213.

In IV: A second model 250' of a second volume U' is provided for the second, inner region-of-interest 200', preferably, with at least one modeled organ target HS, simulating the suspected organ target 213, for obtaining an optimal pathology set of views for the second region-of-interest 200'. The second, pathology set of views is then applied to the second, inner region-of-interest 200' of the body section 230.

It will be appreciated that this camera system may also be used as a PET.

FIGS. 61A-61B schematically illustrate the modeling of a breast in accordance with embodiments of the present invention. However, generally the breast is tested when compressed, as described hereinbelow.

Mammography is currently the most effective method of screening for breast cancer, for the detection of early non-palpable tumors. In essence, it involves compressing the breast between two plates, a support plate and a compression plate, and passing x-rays through the compressed breast. The compression is desirous both in order to spread the breast fatty tissue thin, to reduce its attenuation, and in order to fix the breast tissue, with respect to a frame of reference, so that the x-ray image may be correlated with a surgical tool frame of reference, such as a biopsy needle frame of reference, for guiding the surgical tool to a suspected location on the x-ray image, without the breast tissue moving between the taking of the x-ray image and the guiding of the surgical tool.

Often stereotactic mammography is applied, meaning that the x-ray head is rotated with respect to the plates, so as to provide at least two views of the fixed breast, compressed between the plates, from at least two angles, for stereo imaging.

In general, each breast is imaged separately, generally, both in a vertical direction and from the side (laterally), preferably, stereotactically. In other words, generally, at least four views of each breast are taken, two vertically and two laterally.

A surgical instrument, for example, a biopsy needle, or an ablation device, such as a cryosurgery device, an ultrasound ablation device, a knife, or a laser ablation device, may be built onto the mammograph, its frame of reference correlated with that of the x-ray image.

FIG. 62A schematically illustrates the basic mammograph 900, showing a structural support 929, which defines a frame of reference 80, and which includes a support plate 902 and a compression plate 904, the compression plate 904 being adapted for motion along an arrow 906, so as to compress a breast 909 on the support plate 902.

An x-ray tube 905 is preferably arranged so as to move within a track 907, for obtaining x-ray images of the compressed breast 909 from at least two views, so as to obtain stereotactic viewing, for depth evaluation. A film 901 is preferably arranged under the breast 909, for example, under the support plate 902, for registering the x-ray image.

Additionally, the mammograph 900 is preferably adapted for rotation, as illustrated by an arrow 908, for compressing a breast from at least two orientations, for example vertically and laterally.

A surgical tool 903, for example, a biopsy needle 903 or an ablation device 903, such as by cryosurgery or laser, or a knife 903, may be built onto the mammograph 900, its frame of reference correlated with the frame of reference 80, using position tracking devices or a linkage system, as known.

FIGS. 62B and 62C schematically illustrate a system 925 of an ultrasound imager 915, operative with the two plates 902 and 904, in accordance with embodiments of the present invention. The importance of performing ultrasound between two plates, as in the case of x-rays, is that the two plates fix the breast with respect to the frame of reference 80, and in fact, convert the breast to a rigid-like tissue, so that any suspicious findings can be located by the surgical tool 903.

In FIG. 62B, the ultrasound imager 915 is arranged to slide along tracks 917, for example, on the compression plate 904, while a layer of gel 913 or hydrogel 913, between the compression plate 904 and the breast 909 ensures good contact for ultrasound imaging. In this manner, an ultrasound image, correlated to the frame of reference 80, when the breast is under compression, may be obtained.

Alternatively, as seen in FIG. 62C the ultrasound imager 915 may be built onto the structural support 929, its frame of reference correlated with the frame of reference 80, using position tracking devices or a linkage system, as known.

Referring further to the drawings, FIGS. 63A-63E schematically illustrate a radioactive-emission camera 1000 for the breast, for operation with the mammograph 900 of FIG. 62A, or for operation with another system, wherein a breast is compressed between two plates, in accordance with embodiments of the present invention.

FIG. 63A schematically illustrates an external appearance of the radioactive-emission camera 1000, for the breast. The camera 1000 has a driving portion 990 and an imaging portion 980, enclosed in a sheath 985. The imaging portion 980 defines cylindrical coordinates 987 of a longitudinal axis along the x-axis, and an r-axis, perpendicular to the longitudinal axis.

Figure 63B:
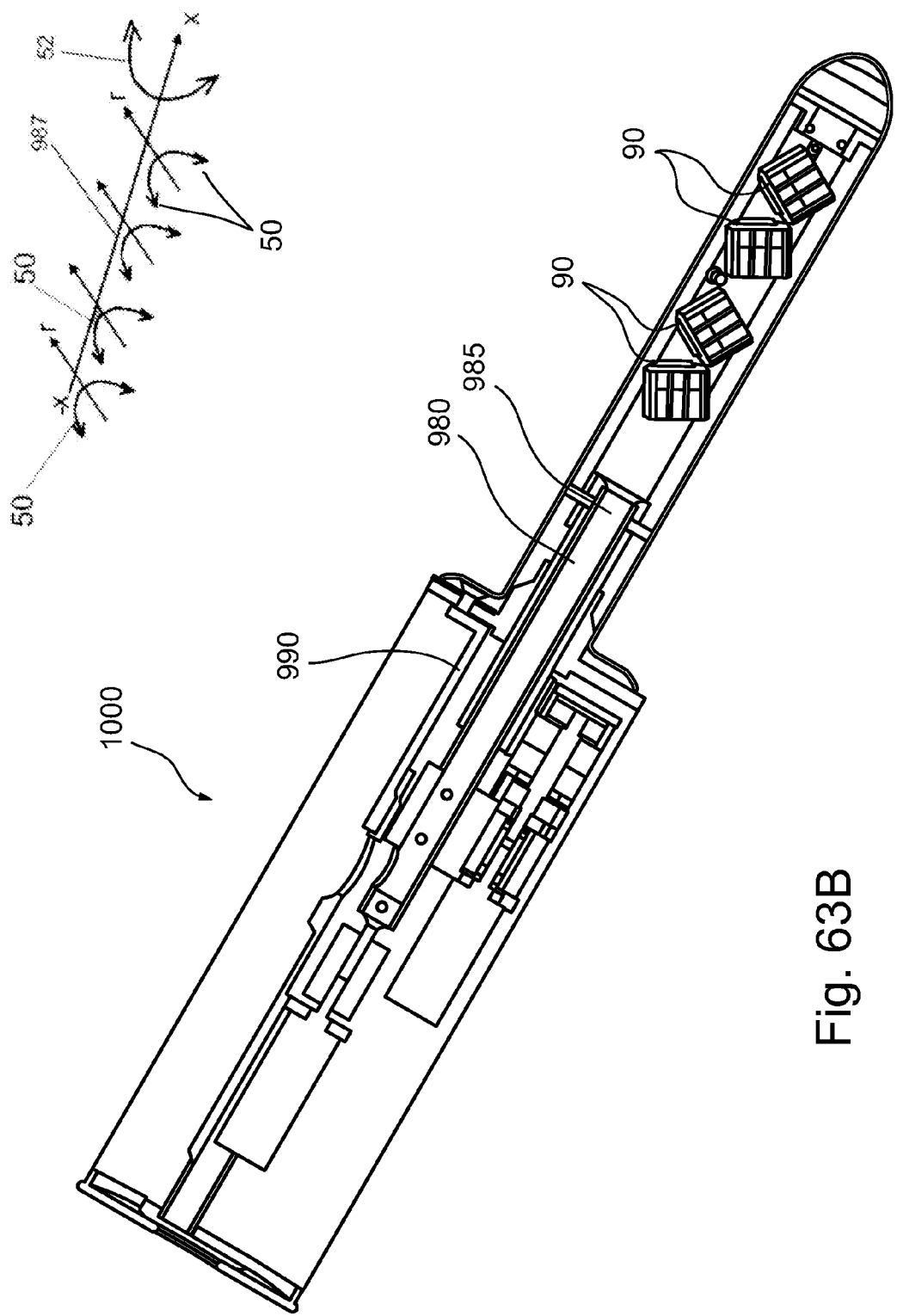
Figure 63C:
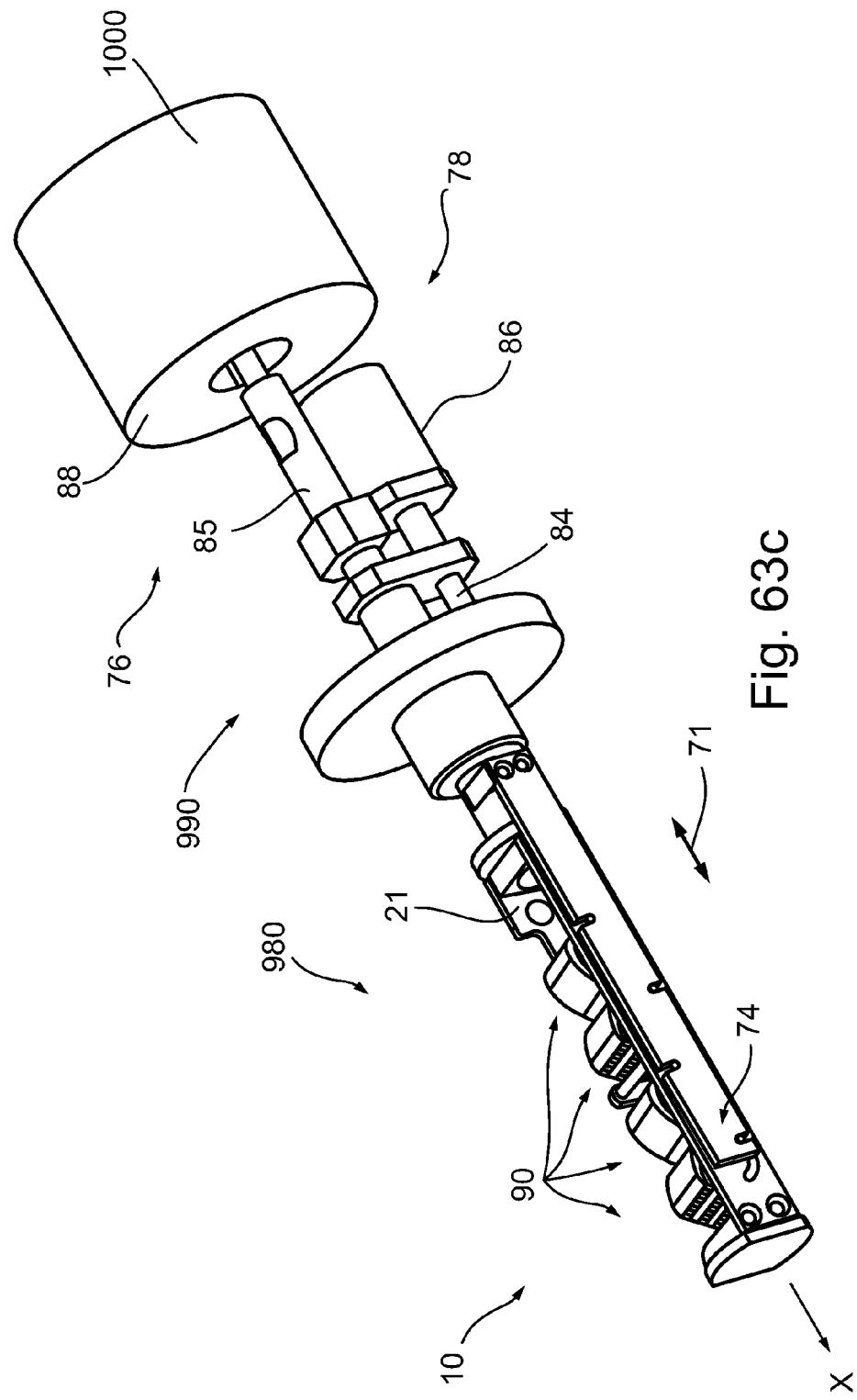

FIGS. 63B-63C schematically illustrate an internal structure of the radioactive-emission camera 1000, for the breast. The imaging portion 980 includes several of the blocks 90, for example, between two and six of the blocks 90, arranged within the sheath 985. It will be appreciated that another number, which may be larger or smaller, and which may be odd or even, may be employed.

In FIG. 63B, the motions experienced by the blocks 90 are illustrated with respect to the cylindrical coordinates 987 of x;r.

A first motion is a rotational motion of all the blocks 90, moving as a single body, with the shaft 85 and the internal structure 21, around the x-axis, in the direction between $+\omega$ and $-\omega$, as illustrated by the arrow 52. The first motion is powered by the motor 88.

A second motion is an oscillatory motion of the individual blocks 90, powered by the secondary motor 86, the secondary shaft 84, and the motion transfer link 74, the motion transfer link 74 moving in a linear, sliding motion, as shown by the arrow 71.

At each orientation of the internal structure 21 with respect to $\omega$, around x, the second, oscillatory motion about r takes place, individually by each of the block 90, the oscillatory motion about r being between $-\phi$ and $+\phi$, as illustrated by the arrow 50, and as taught hereinabove, with reference to FIGS. 20A-20H.

Thus, the overall motion is as illustrated hereinabove, with reference to FIG. 23C and FIG. 20H.

Further as seen in FIG. 63C, the rotational motion in the direction of the arrow 52 is provided by a motor 88 and the shaft 85, which together form the motion provider 76. The motor 88 may be an electric motor, for example, a servo motor. The oscillatory motion in the direction of the arrow 50 is provided by a secondary motor 86, a secondary shaft 84 and a motion transfer link 74. The secondary motor 86 may also be an electric motor, for example, a servo motor. The secondary motor 86, secondary shaft 84 and the motion transfer link 74, together, form the secondary motion provider 78, for the oscillatory motion, in the direction of the arrow 50.

Thus, for the radioactive-emission camera 1000, for the breast:

i. The different blocks 90 provide views from different orientations; and ii. The different blocks 90 may change their view orientations independent of each other.

It is important to point out that during the operation of the camera 1000, the sheath 985 of the imaging portion 980 (FIGS. 63A and 63B) remains stationary, while the internal structure 21 (FIG. 63C) rotates around the x-axis. The sheath 985 may be formed of a carbon fiber, a plastic, or another material, which is substantially transparent to nuclear radiation.

FIGS. 63D and 63E illustrate further the oscillatory motion of the blocks 90, within the sheath 985, as described by the arrows 50, by showing the blocks 90 at different positions, along their oscillatory travel. FIGS. 63D and 63E further illustrate a viewing side 986 and a back side 988 for the camera 1000.

Referring further to the drawings, FIGS. 64A-64M schematically illustrate systems 910, which include the radioactive-emission cameras 1000 for the breast, operating with systems, in which a breast is compressed between two plates, for example, as in the mammograph 900, in accordance with embodiments of the present invention.

Figures 64A, 64B:
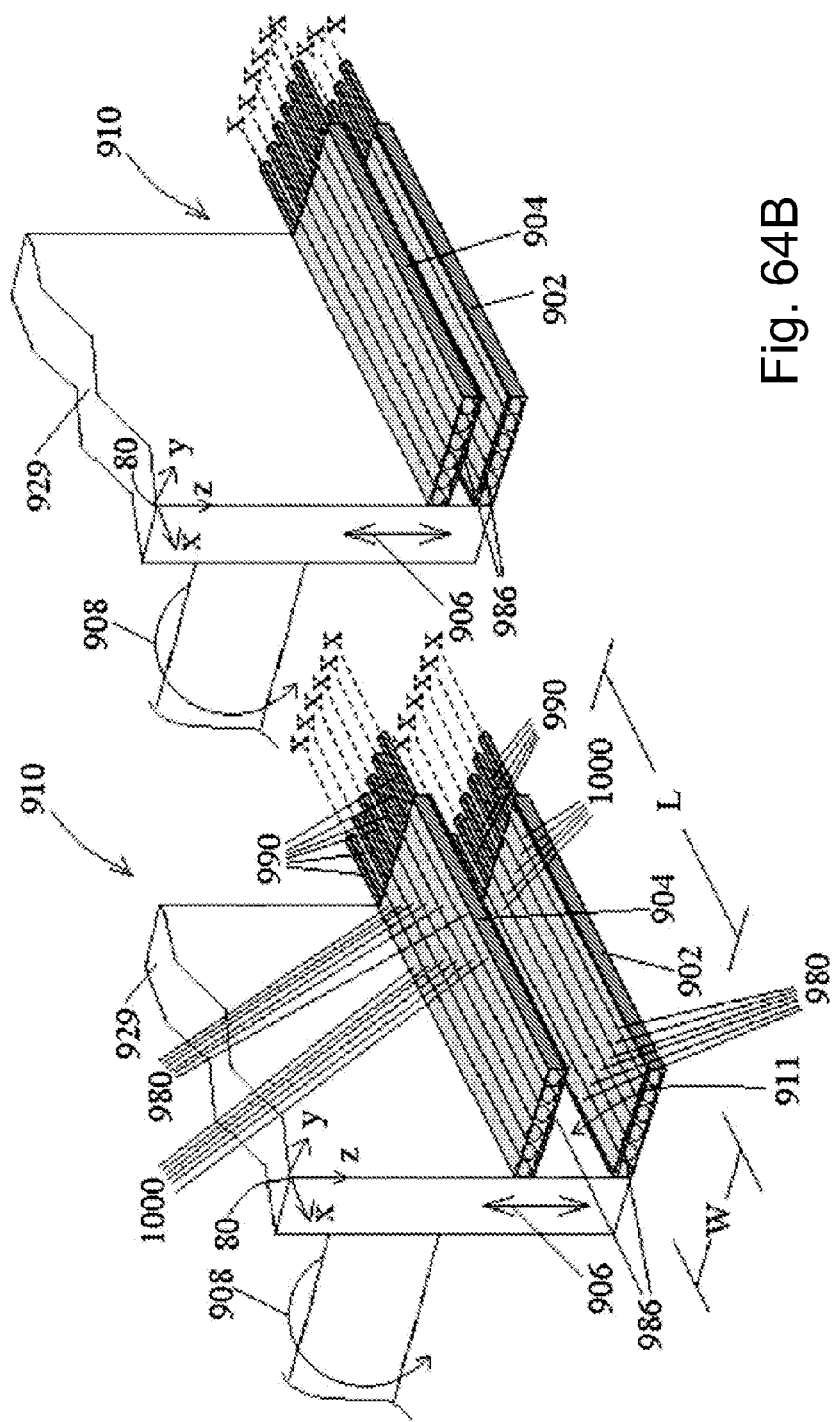
FIGS. 64A-64K schematically illustrate an imaging system for radioactive-emissions of the breast, in accordance with an embodiment of the present invention.

Preferably, as seen in FIGS. 64A and 64B, the cameras 1000 are mounted onto the two plates, the compression plate 904, and the support plate 902, such that their viewing sides 986 face each other. Preferably, the cameras 1000 are aligned with the x-axis, as seen. Alternatively, the cameras 1000 may be aligned with the y-axis. It will be appreciated that the cameras 1000 may be mounted only on one plate, the compression plate 904 or the Support plate 902.

Figure 64C:
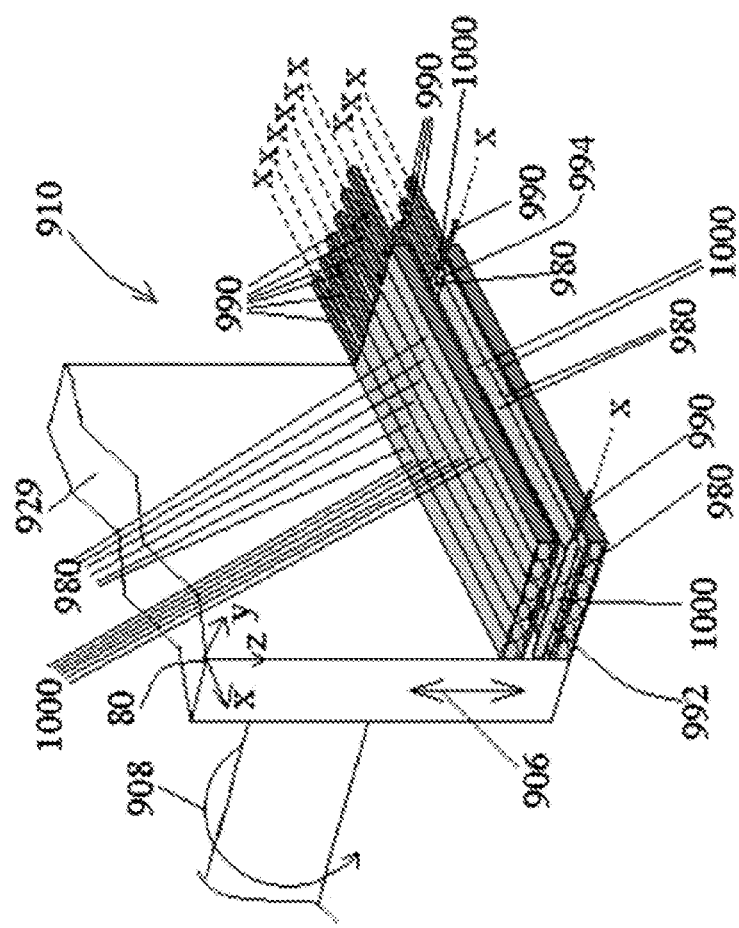

Additionally, as seen in FIG. 64C, one or several of the cameras 1000 may be mounted as edge cameras, for positioning at edges 992 and 994, supplementing the cameras 1000 mounted on the plates, for obtaining views from the sides of the compressed breast.

Figure 64E:
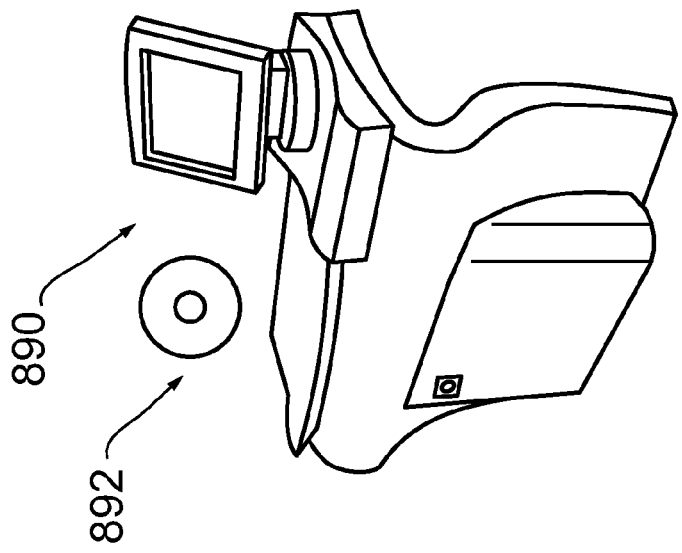
Figure 64D:
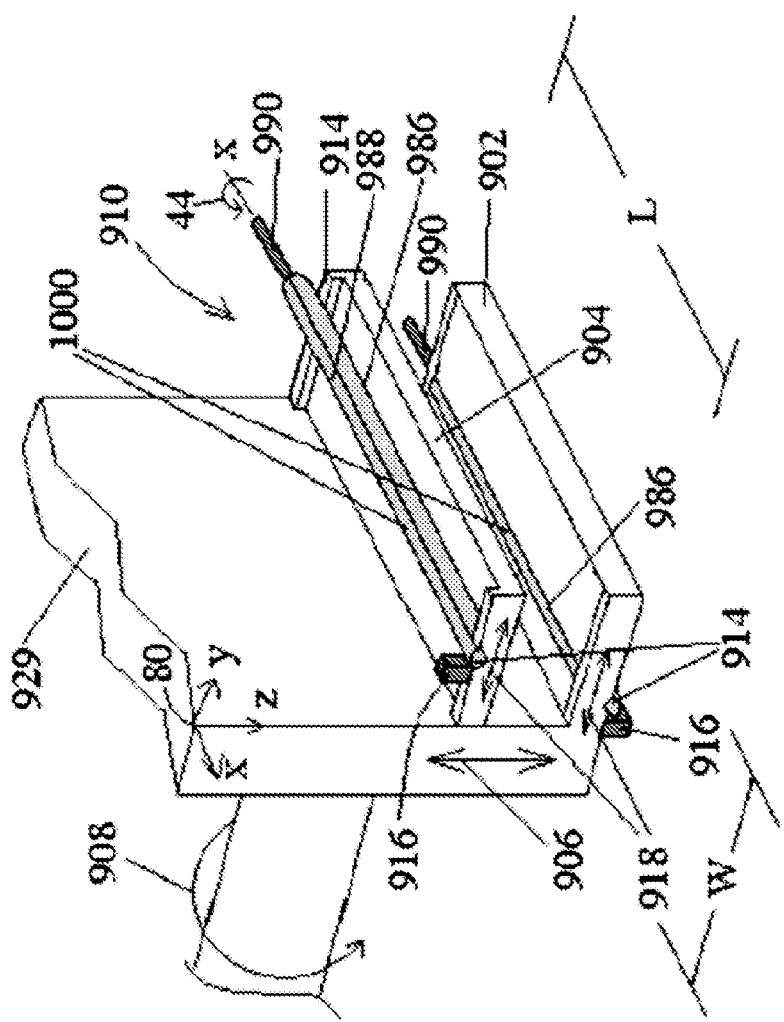

An alternative embodiment is illustrated in FIG. 64D, wherein a single one of the cameras 1000 may be mounted on each of the plates 902 and 904, the camera 1000 being adapted for travel along a track 914, in a direction of an arrow 918, by a dedicated motion provider 916, thus providing the views that a plurality of the cameras 1000 would have provided, as illustrated in FIGS. 64A-64B.

It will be appreciated that edge cameras 1000, may be added to the embodiment of FIG. 64D, in a manner similar to that of FIG. 64C.

FIG. 64E schematically illustrates a control unit 890, for controlling the motions of the blocks 90 (or the detecting units 12, when not arranged in blocks) of the cameras 1000 and for analyzing the measurements and constructing the images. Preferably, a single control unit is used both for the x-ray imager, or the ultrasound imager 915, on the one hand, and the radioactive-emission cameras 1000, on the other. Alternatively, individual control units may be used, one for each modality. Alternatively, the system 910 for the breast is provided with a storage device 892, such as a CD or a disk, which contains the software for operating the system 910 for the breast with an existing computer on the site. It will be appreciated that the control unit 890 may be a PC, a laptop, a palmtop, a computer station operating with a network, or any other computer as known.

In accordance with embodiments of the present invention, frames may be provided for mounting the radioactive-emission cameras 1000 on the plates 902 and 904.

Figures 64H, 64I:
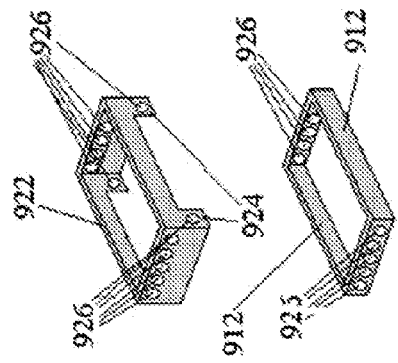
Figures 64F, 64G:
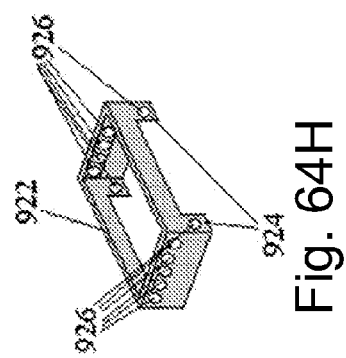

As seen in FIG. 64F, a frame 912 may be provided for either the support plate 902 or the compression plate 904, designed for accepting the cameras 1000 lengthwise, by inserting the cameras 1000 in holes 926.

Alternatively, as seen in FIG. 64G, the frame 912 may be designed for accepting the cameras 1000 widthwise.

Additionally, as seen in FIG. 64H, a frame 922 is designed for accepting the cameras 1000 widthwise or lengthwise, wherein the frame 922 further includes an edge section 924, for supporting the edge cameras of FIG. 64C.

Furthermore, as seen in FIG. 64I, two complementary frames may be provided, one designed as the flame 922, for accepting the cameras 1000 lengthwise (or widthwise) along the plate and for accepting the edge cameras, as illustrated in FIG. 64H, and the other, designed as the frame 912, for accepting the cameras 1000 lengthwise (or widthwise) along the plate.

Figure 64K:
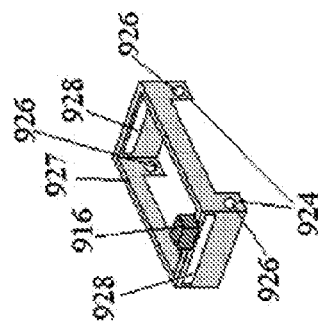
Figure 64J:
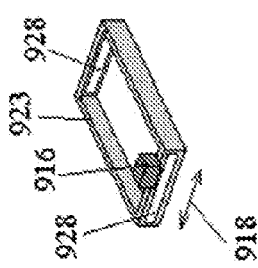

As seen in FIG. 64J, a frame 923 may be designed for accepting a single one of the cameras 1000, lengthwise, adapted for sliding widthwise along the plate, in a channel 928, by the dedicated motion provider 916. Alternatively, the frame 923 may be designed for accepting the camera 1000 widthwise, adapted for sliding lengthwise.

As seen in FIG. 64K, a frame 927 may be designed for accepting a single one of the cameras 1000, for example, lengthwise, adapted for sliding widthwise along the plate, in a channel 928, by the dedicated motion provider 916, wherein the frame 927 further includes the edge section 924, for supporting the edge camera 1000 of FIG. 64C.

In accordance with embodiments of the present invention, nuclear imaging by radioactive-emissions, co-registered with x-ray mammography, may be obtained by a method 1010, illustrated in FIG. 64L, in flowchart form, as follows:

in a box 1012: the breast is compressed between the plates;

in a box 1014: an x-ray mammography is performed, as seen in FIG. 62A, preferably from at least two orientations of the x-ray tube 905;

in a box 1016: the cameras 1000 are mounted on the plates, and radioactive-emission measurements are performed;

in a box 1018: where necessary, the surgical tool 903 may be employed, while the breast is still compressed between the two plates.

It will be appreciated that the order of the steps of boxes 1014 and 1016 may be reversed.

Preferably, the images of the x-ray mammography and the nuclear imaging are co-registered and analyzed together.

However, it will be appreciated that only nuclear imaging by radioactive-emission measurements may be performed, without x-ray imaging.

Where ultrasound imaging co-registered with nuclear imaging by radioactive-emissions is desired, a method 1020, illustrated in FIG. 64M, in flowchart form, applies, as follows:

in a box 1022: a hydrogel layer is placed between one of the plates, for example, the compression plate 904 and the breast, or a gel is spread over the breast, so as to serve as an ultrasound interface between the plate and the breast;

in a box 1024: the breast is compressed between the plates;

in a box 1026: the cameras 1000 are mounted on the plates, and radioactive-emission measurements are performed;

in a box 1028: the cameras 1000 are replaced by an ultrasound imager, for example as illustrated in FIG. 62B or 62C, and ultrasound imaging is performed;

in a box 1030: where necessary, the surgical tool 903 may be employed, while the breast is still compressed between the two plates.

It will be appreciated that the order of the steps 1026 and 1028 may be reversed.

Preferably, the images of the x-ray mammography and the nuclear imaging are co-registered and analyzed together.

Figure 65A:
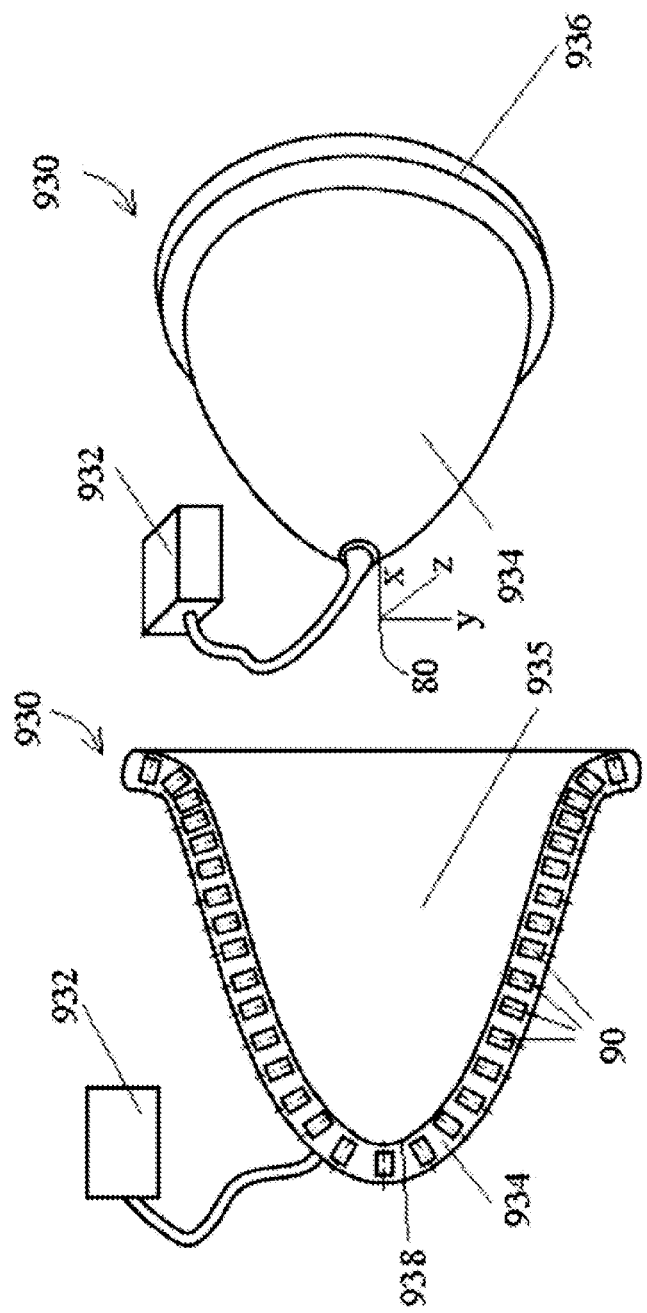
FIGS. 65A-65C schematically illustrate an imaging camera for radioactive-emissions of the breast, in accordance with an embodiment of the present invention.
Figure 65B:
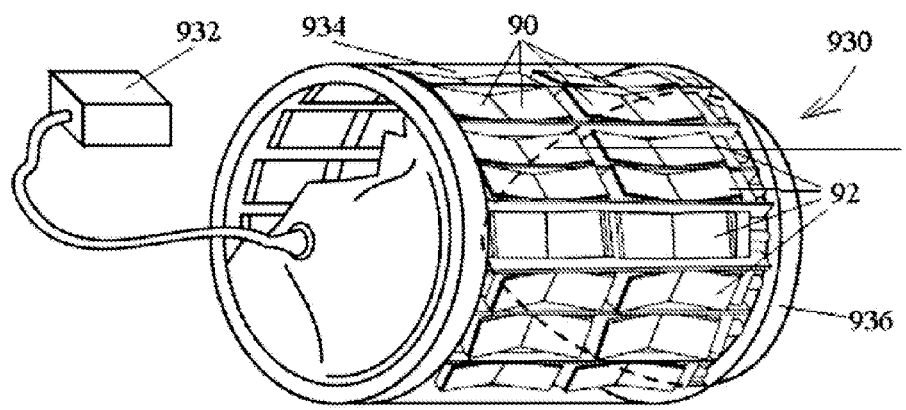
Figure 65C:
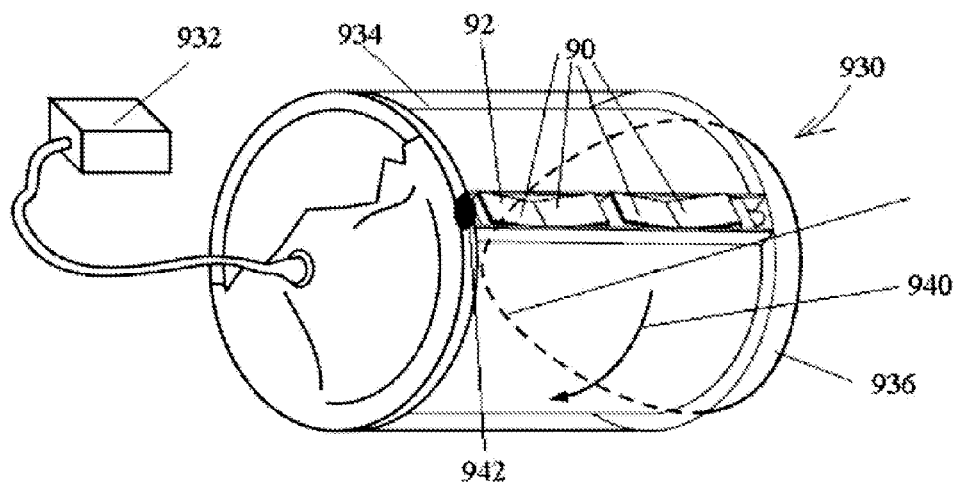

Referring further to the drawings, FIGS. 65A-65C schematically illustrate a radioactive-emission camera 930, for imaging a breast under vacuum, in accordance with another preferred embodiment of the present invention.

As seen in FIG. 65A, the camera 930 includes a vacuum cup 934, shaped as a cone and connected to a vacuum system 932, for creating a vacuum in a cavity 935 within. The vacuum in the cavity is used both to stretch the breast so as to spread the fatty tissue thin and to fix the breast tissue with respect to a frame of reference, so a surgical device may be employed, where needed, while the breast tissue remains fixed in place.

A vacuum ring 936, for example of natural or synthetic rubber, helps maintain the vacuum in the cup 934.

The vacuum cup 934 defines the frame of reference 80 and a plurality of the blocks 90 are arranged along the walls 938 of the suction cup 934, each adapted for at least one, and preferably two rotational motions, for example, as illustrated with reference to FIGS. 22I-22M and FIGS. 22Q-22R, or FIGS. 22N-22P, for imaging a breast in the cavity 935. Alternatively, the blocks 90 may be arranged in the assemblies 92, as illustrated with reference to FIGS. 22A-22H.

A surgical tool may be attached to the camera 930, and correlated to its frame of reference, for example as taught with reference to FIG. 62B.

The motions of the blocks 90 are preferably automatic, controlled by the control unit 890 (FIG. 64C).

Preferably, the inner walls 938 of the cup 934 are substantially transparent to radioactive emission.

FIG. 65B schematically illustrates an embodiment wherein a vacuum cylinder 934 is used in place of a conical cup, and the blocks 90 are arranged in assemblies 92, for example, as illustrated with reference to FIGS. 16E and 24A-24H.

FIG. 65C schematically illustrates an embodiment wherein the vacuum cylinder 934 is used, and a single one of the assemblies 92 is arranged for traveling around the cylinder 934, in the direction of an arrow 940, by a motion provider 942.

Referring further to the drawings, FIGS. 66A-66F schematically illustrate a radioactive-emission camera 950, for imaging the breasts in the natural state, in accordance with another preferred embodiment of the present invention.

Figure 66C:
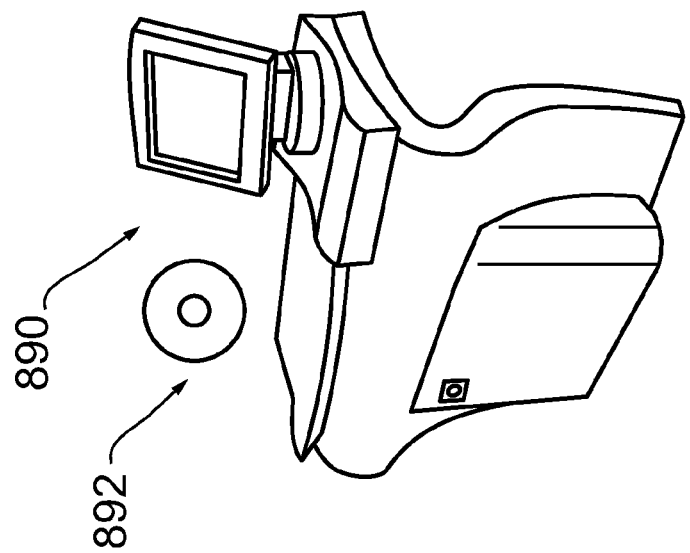
FIGS. 66A-66G schematically illustrate an imaging system for radioactive-emissions of the breast, in accordance with an embodiment of the present invention.
Figure 66A:
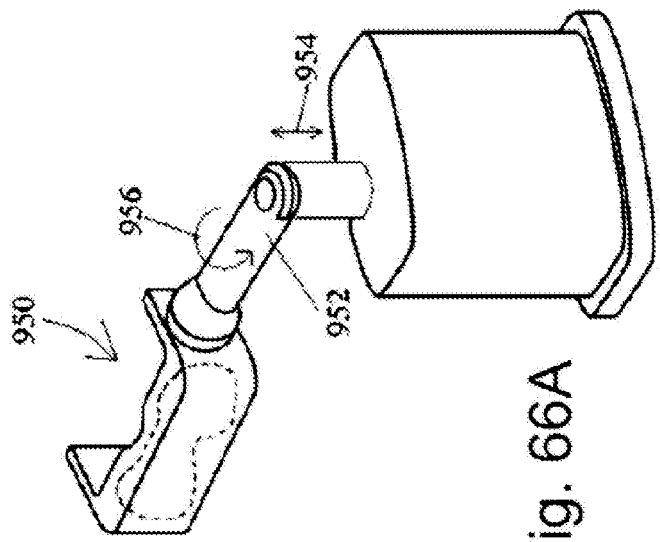

As seen in FIG. 66A, the radioactive-emission camera 950, for imaging the breasts in a natural state, is designed as an extracorporeal unit which may be positioned against the breasts, operating as taught with reference to any one of FIGS. 20A-22R. Preferably, the radioactive-emission camera 950, for imaging the breasts is attached to a gantry 952, which may provide adjustments as seen by arrows 954 and 956.

Figure 66B:
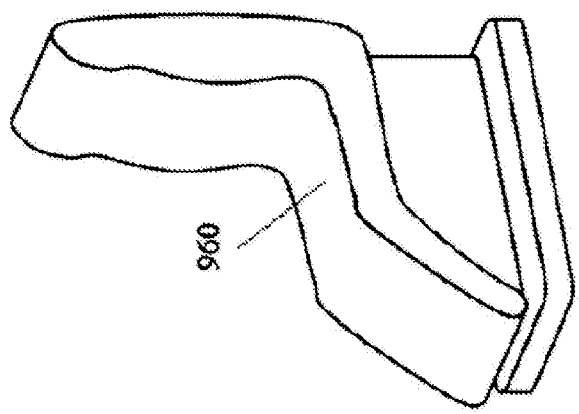

Additionally, the patient may be positioned on a chair 960, as seen in FIG. 66B.

The control unit 890 may be used for controlling the motions of the blocks 90 (FIGS. 22A-22H or 22I-22R) or the detecting units 12, when not arranged in blocks, and for analyzing the measurements and constructing the images. Alternatively, the radioactive-emission camera 910 for the breast is supplied with a storage device 892, which contains the software for operating the radioactive-emission camera 910 for the breast with an existing computer on the site. It will be appreciated that the control unit 890 may be a PC, a laptop, a palmtop, a computer station operating with a network, or any other computer as known.

Figure 66E:
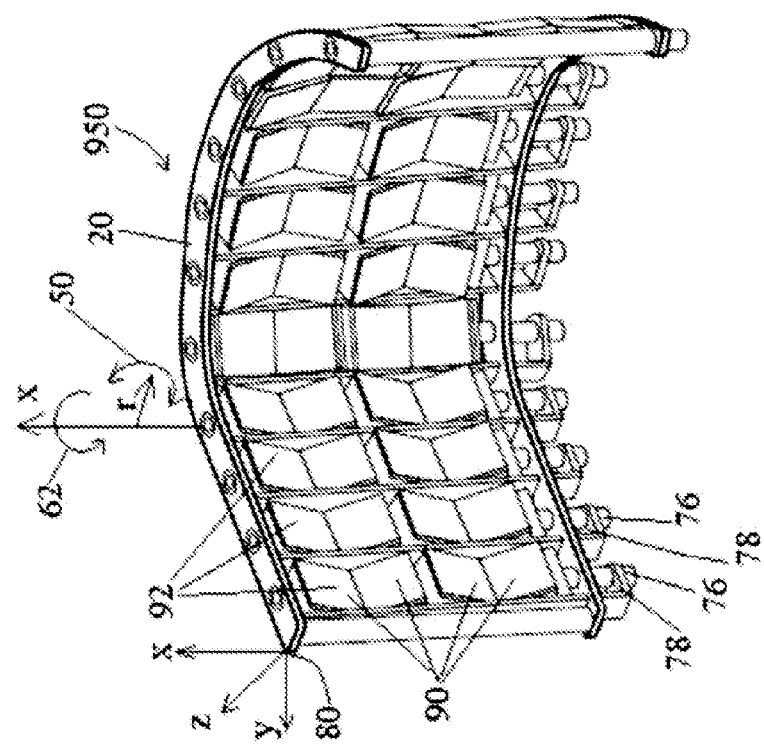
Figure 66D:
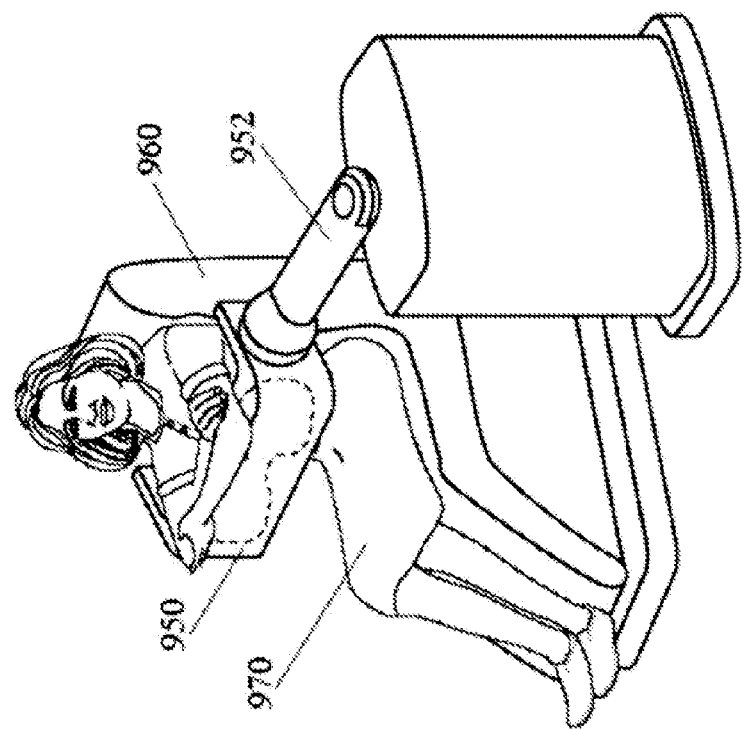

FIG. 66D schematically illustrates a woman 970 being examined by the radioactive-emission camera 950, when seated on the chair 960. It will be appreciated that the examination may also be conducted when the woman 970 is standing or lying on a bed.

FIG. 66E schematically illustrates the inner structure radioactive-emission camera 950 in accordance with a preferred embodiment of the present invention. FIG. 66E shows the overall structure 20, the parallel lines of assemblies 92, possibly of an even number, each with a dedicated motion provider 76 and a dedicated secondary motion provider 78, and the rows of blocks 90, possibly arranged in pairs, along the assemblies 92.

The camera 950 defines the frame of reference 80, while each assembly 92 has a reference cylindrical coordinate system of x;r, with rotation around x denoted by the arrow 62 and oscillatory motion about r, denoted by the arrow 50.

Figure 66F:
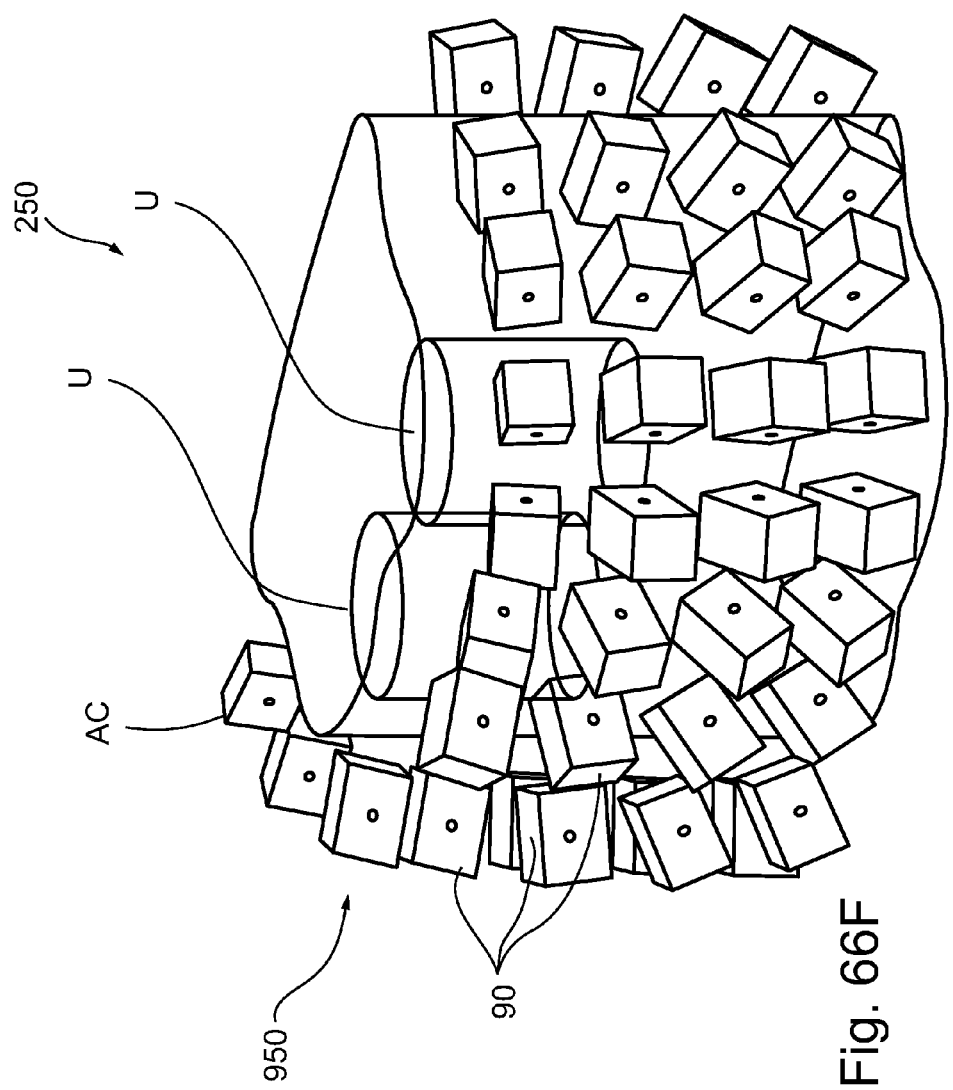

FIG. 66F schematically illustrates the model 250 of the two breasts, modeled as the volumes U, and the anatomical constraints associated with them, for determining an optimal set of views for radioactive-emission measurements.

It will be appreciated that imaging, in accordance with embodiments of the present invention relates to the imaging of the whole breast, or to a portion of the breast, the armpits near the breasts, (and) or the two breasts.

Preferably, the radiopharmaceuticals associated with the radioactive-emission camera for the breast may be Tc-99m bound to Sestamibi, a small protein molecule, made for example, by Bristol Myers Squibb, and marketed as Miraluma, used widely for breast cancer detection.

Figure 66G:
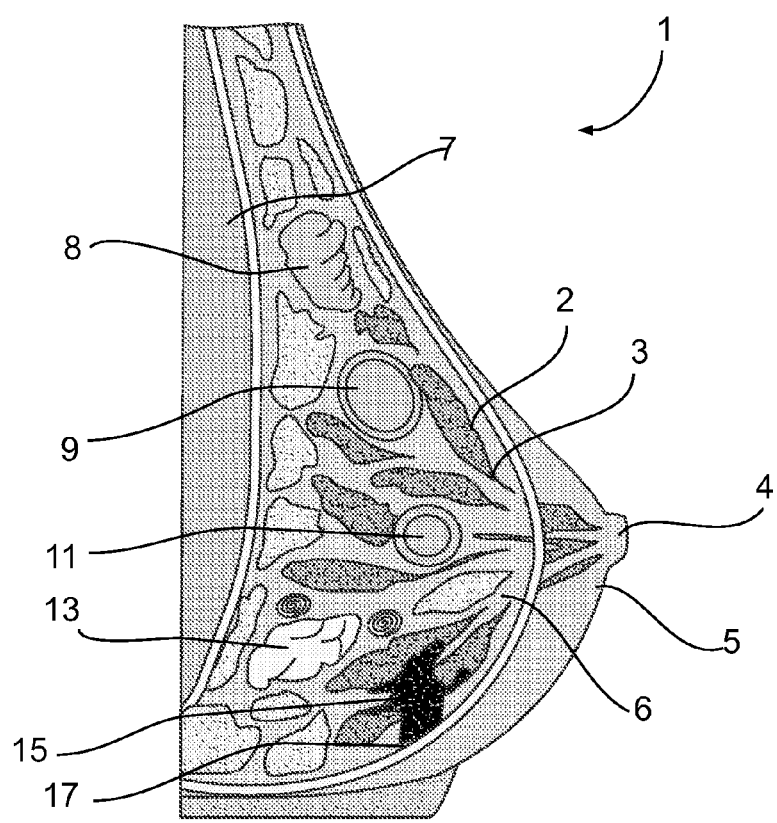

The present invention applies to detecting and differentiating between various types of breast disorders, for example as illustrated in FIG. 66G, hereinabove, as follows:

i. fibroadenomas 8, which are fibrous, benign growths in breast tissue.

ii. cysts 9, which are fluid-filled sacs and may disappear sometimes by themselves, or a doctor may draw out the fluid with a needle.

iii. a breast abscess 11, which is a collection of pus, resulting from an infection.

iv. fibrocystic breast disease 13, which is a common condition characterized by an increase in the fibrous and glandular tissues in the breasts, resulting in small, nodular cysts, noncancerous lumpiness, and tenderness, wherein treatment of the cysts may be all that is needed.

v. a tumor 15, which may be precancerous or cancerous, and which usually shows up as a white area on a mammogram even before it can be felt. In cases where the tumor 15 is cancerous, it may appear as a white area with radiating arms. A cancerous tumor 15 may have no symptoms or may cause swelling, tenderness, discharge from the nipple 4, indentation of the nipple 4, or a dimpled appearance 17 in the skin over the tumor.

Additionally, the present invention applies to detecting various types of breast cancers, such as:

i. ductal cancer, which affects the cells of the ducts;

ii. lobular cancer, which begins in the lobes or lobules of the breast; and iii. inflammatory breast cancer, which is an uncommon type of breast cancer and causes the breast to be warm, red, and swollen.

It will be appreciated that the present invention further applies to other types breast disorders, which may be cancerous, precancerous, or benign.

Additionally or alternatively, the present invention applies to secondary breast cancer, for example, originating from the lungs, or other parts of the body.

Furthermore, the radioactive-emission camera for the breast may be designed for and used on a single breast or designed for and used simultaneously on the two breasts.

It will be appreciated that although breast cancer in men and children is rare, the present invention may be used for the detection of breast cancer in men and children as well.

Overall Camera Performance

The following section reviews the overall camera performance for different camera designs and illustrates configurations which conform to body contours, so as to be as close as possible to the anatomical constraints (FIG. 5B). Additionally, the importance of distance between the organ target 213 and the detecting block 90 is explained. The camera performance is considered with respect to the following:
  i. detecting efficiency;
  ii. acquisition time;
  iii. spatial resolution;
  iv. wasteful viewing, in regard to ordinary gamma cameras;
  v. adjustable design;
  vi. independent viewing by each block or detecting unit;
  vii. criteria for camera design;
  viii. experimental results.
  i. Detecting Efficiency Referring further to the drawings, FIGS. 67A and 67B schematically illustrate the solid angle by which the radiation emission source 213 "sees" the detecting block 90. At a distance of R1, the solid angle is $\beta 1$ and at the distance of R2, the solid angle is $\beta 2$, wherein an inverse relation exists between R1 and R2 and $\beta 1$ and $\beta 2$, such that when R2>R1 then $\beta 1 > \beta 2$.

Furthermore, for the detecting block 90 of an area $\pi r^2$, at a distance R from a point source, the detecting efficiency is a function of the ratio of the detecting area $\pi r^2$ to the area of the sphere $4\pi R^2$, so as to behave as a function of $r^2/R^2$. Thus, for the detecting block 90 of a fixed detecting area, as the distance R from the source 213 increases, the detecting efficiency decreases, proportionally to $R^2$.

It will be appreciated that a similar analysis is valid for the detecting unit 12, on a pixel basis, as well.

ii. Acquisition Time

A related issue is the acquisition time, for statistically meaningful results Radioactive emission may be described by the Poisson distribution, for which the counting error for N counts is described by $N^{1/2}$. For example, when 10,000 Counts have been detected, the counting error is $10,000^{1/2}$, or 100, which is 1% of N. Where it is desired to obtain data at a predetermined level of accuracy, a minimal level of Counts must be obtained. Thus, for an accuracy level of 1%, 10,000 Counts must be obtained; for an accuracy level of 0.1%, 1,000,000 counts must be obtained, and so on.

Yet, when the distance R between the source 213 and the detecting block 90 is increased, the counting efficiency falls proportionally to $R^2$ and the number of Counts per minutes falls proportionally to $R^2$, and so the acquisition time required to reach a predetermined number of counts, for a predetermined accuracy level, increases proportionally to $R^2$ iii. Spatial Resolution Referring further to the drawings, FIGS. 68A-68B schematically illustrate the effect of the distance R on the spatial resolution.

As seen in FIG. 68A, the organ target 213 has a radius q, which may be, for example, of the order of magnitude of the radius r of the detecting block 90, so that q~r. The organ target 213 may have a distribution of activity, for example, a high-level portion 213A, a medium-level radiation portion 213B, and a relatively low-level radiation portion 213C.

As seen in FIG. 68B, given, for example, a 3×3 pixel arrangement and a collection angle $\beta$, when the block 90 is very close to the organ target 213, such that R1 is substantially zero, and given that q~r, the organ target 213 is viewed by practically all the 3×3 pixels, resulting in a high-resolution image.

As seen in FIG. 68C, at a distance R2, the organ target 213 is barely viewed by more than one pixel, resulting in a low-resolution image.

As seen in FIG. 68D, at a distance R3, the organ target 213 is viewed by less than one pixel, resulting in a very low-resolution image.

Thus, the number of pixels in the block 90 provides for a spatial resolution capability. In order for this resolution capability to be realized, however, the distance between the detecting block 90 and the organ target 213 should be as small as possible.

iv. Wasteful Viewing, in Regard to Ordinary Gamma Cameras

Referring further to the drawings, FIGS. 69A-69D schematically illustrate different view arrangements.

Figure 69A:
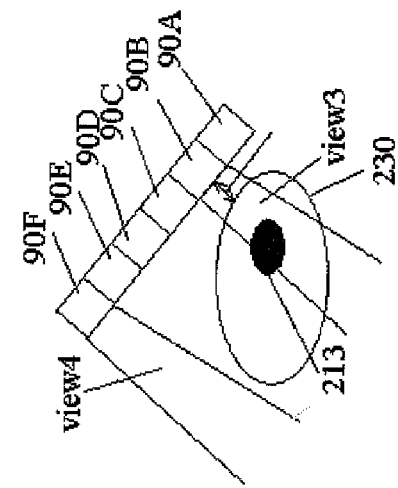
FIGS. 69A-69D schematically illustrate "wasteful viewing" by an array of radiation detectors.

FIG. 69A illustrates four blocks 90A, 90B, 90C, and 90D for viewing the organ target 213, the blocks arranged around the body section 230. The block 90A, at the distance R1 from the organ target 213, is as close as possible to the external surface of the body section 230, such that it is substantially touching it. Therefore, the block 90A is at an optimal viewing position for the organ target 213. The block 90B is at a distance R2 from the organ target 213, where R2>R1, but it is still in position to view the target 213, from that distance. Therefore, the block 90B is at a suboptimal position for viewing the organ target 213. The block 90C does not view the organ target 213, yet it does view the body section 230, so it may also be considered at a suboptimal position. The block 90D does not view the body section 230, so the view of the block 90D is wasteful, in that it does not provide any information regarding the body section 230.

As FIG. 69A illustrates, blocks which substantially touch the surface of the body section 230 will always provide some information about it. Yet blocks 90 that are distant from the body section 230 may view areas altogether outside the body section 230, so their contribution is wasteful.

Figure 69B:
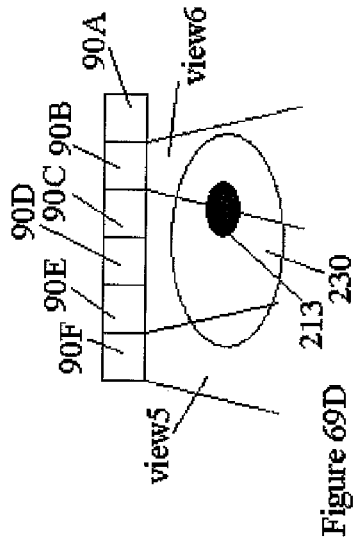
Figure 69C:
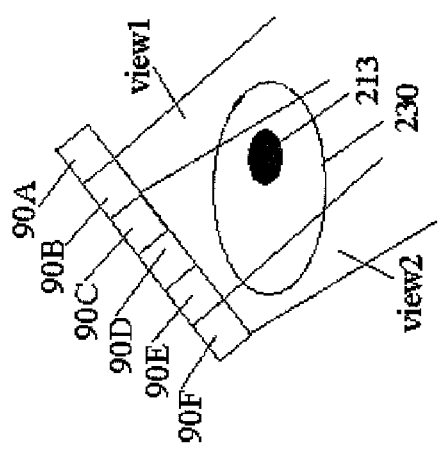
Figure 69D:
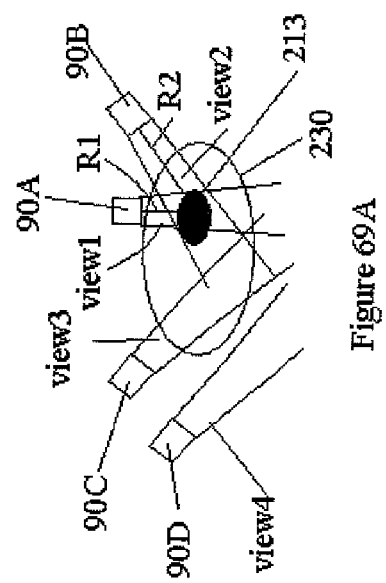

This point is further illustrated in FIGS. 69B-69D, which illustrate the use of a rigid camera of the prior art, for example, as taught by U.S. Pat. Nos. 6,597,940 and 6,671,541, both to Bishop et al. As may be understood from FIG. 69B-C, as the blocks 90A and 90B are brought into close proximity with the body section 230, blocks 90C, 90D, 90E and 90F are moved away from it, and their views become suboptimal or even wasteful. Conversely, as the blocks 90F and 90E are brought into close proximity with the body section 230, blocks 90D, 90C, 90B and 90A are moved away from it, and their views become suboptimal or even wasteful Similarly, as the blocks 90B, 90C, and 90D are brought into close proximity with the body section 230, the views of blocks 90F and 90A become suboptimal or even wasteful v. Adjustable Designs Referring further to the drawings, FIG. 71 schematically illustrates an adjustable PET camera 1150, in accordance with embodiments of the present invention. The PET camera 11150 is formed of a plurality of the blocks 90, placed substantially on the body section 230. Such a camera, when completely surrounding the body section 230, essentially sees all coincident emissions coming out of the body, and greatly increases the counting efficiency for PET.

Referring further to the drawings, FIGS. 72A-72E schematically illustrate adjustable cameras 1160 and 1170A-B mounted on adjustable overall structures, for conforming to contours of the body section 230, in accordance with embodiments of the present invention.

Figure 72A:
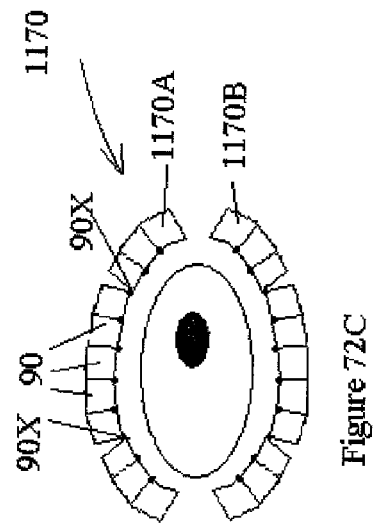
FIGS. 72A-72E schematically illustrate non-wasteful radiation detector arrays, in accordance with an embodiment of the present invention.
Figure 72B:
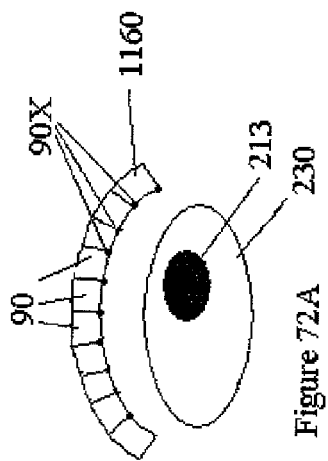
Figure 72C:
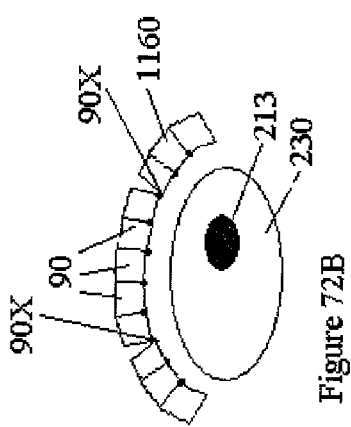

As seen in FIGS. 72A-72B, the cameras 1160 and 1170A-B include hinges 90X between the blocks 90, such that the positions of the blocks may be adjusted. Alternatively, as seen in FIG. 72C, several blocks 90 may be arranged in a row to form an assembly 92 and the camera may include hinges 90X between the assemblies 92, such that assemblies 92 may be adjusted. FIG. 72A illustrates the camera 1160 prior to the adjustment, and FIG. 72B illustrates the camera 1160 after adjustment. FIG. 72C illustrates the camera 1170, as may be used for coincident imaging or another whole body imaging.

Figure 72D:
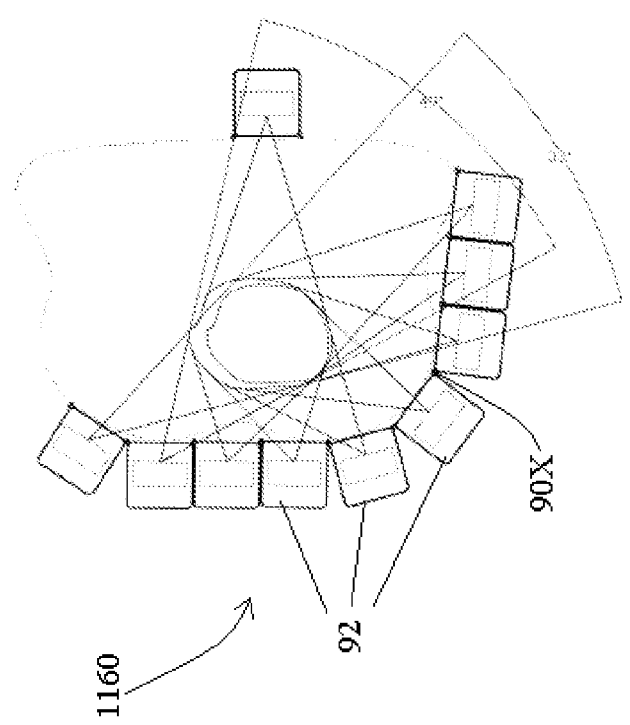

FIG. 72D schematically illustrates the viewing range of the camera 1160, in accordance with the present embodiment.

Figure 72E:
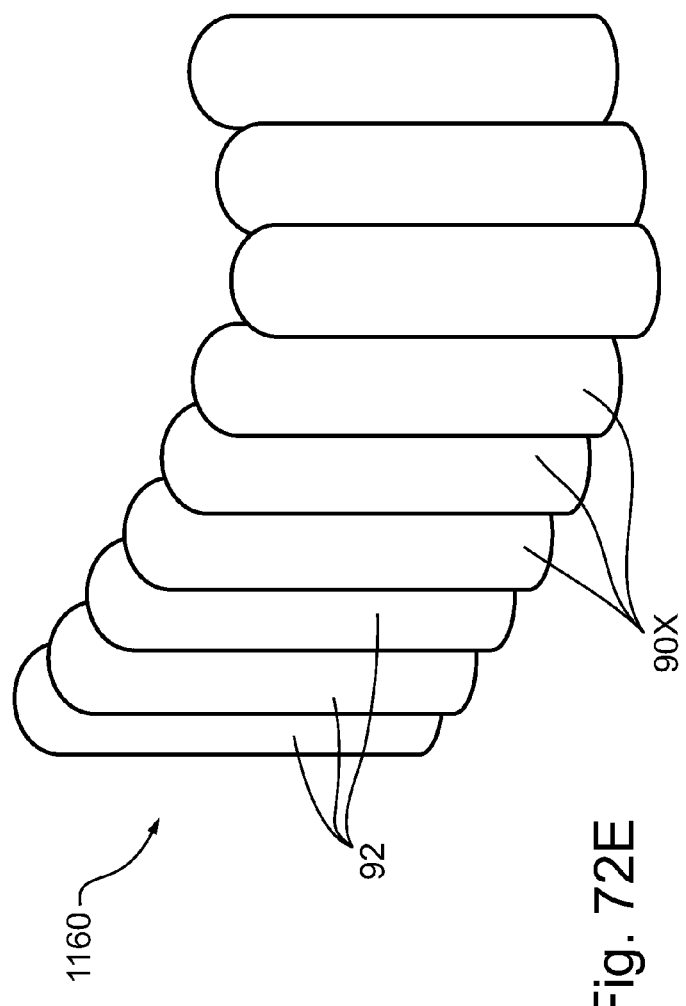

FIG. 72E schematically illustrates a pictorial view of the camera 1160, of the present embodiment.

Figure 73:
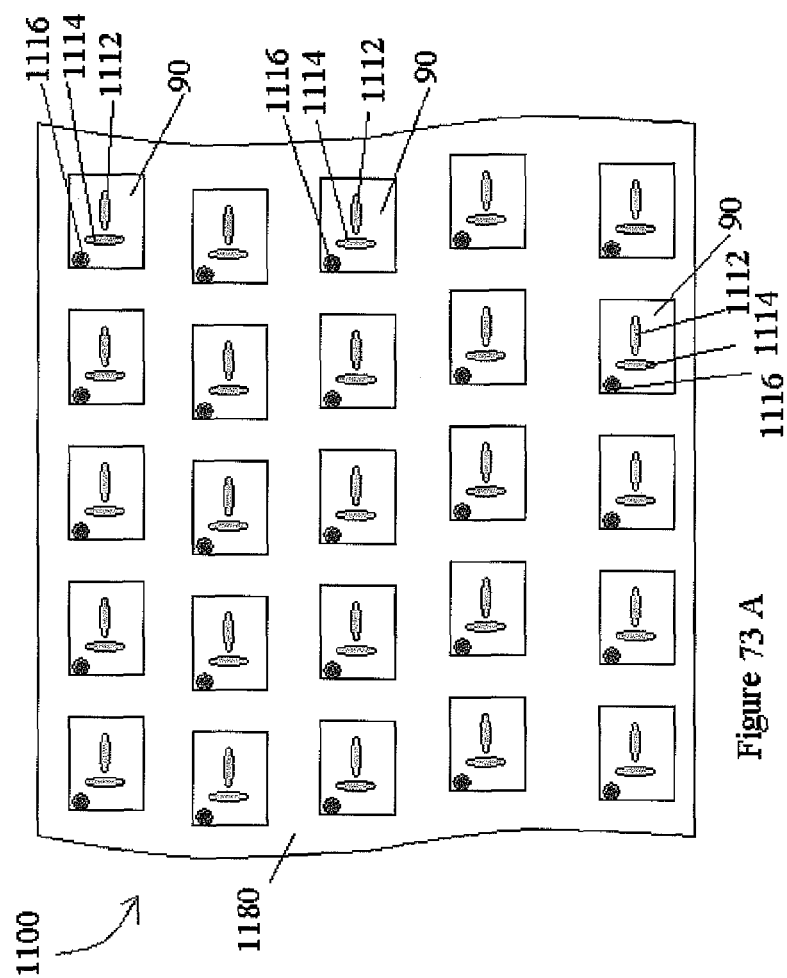
FIGS. 73A and 73B schematically illustrate non-wasteful radiation detector arrays, in accordance with an embodiment of the present invention.
Figure 73B:
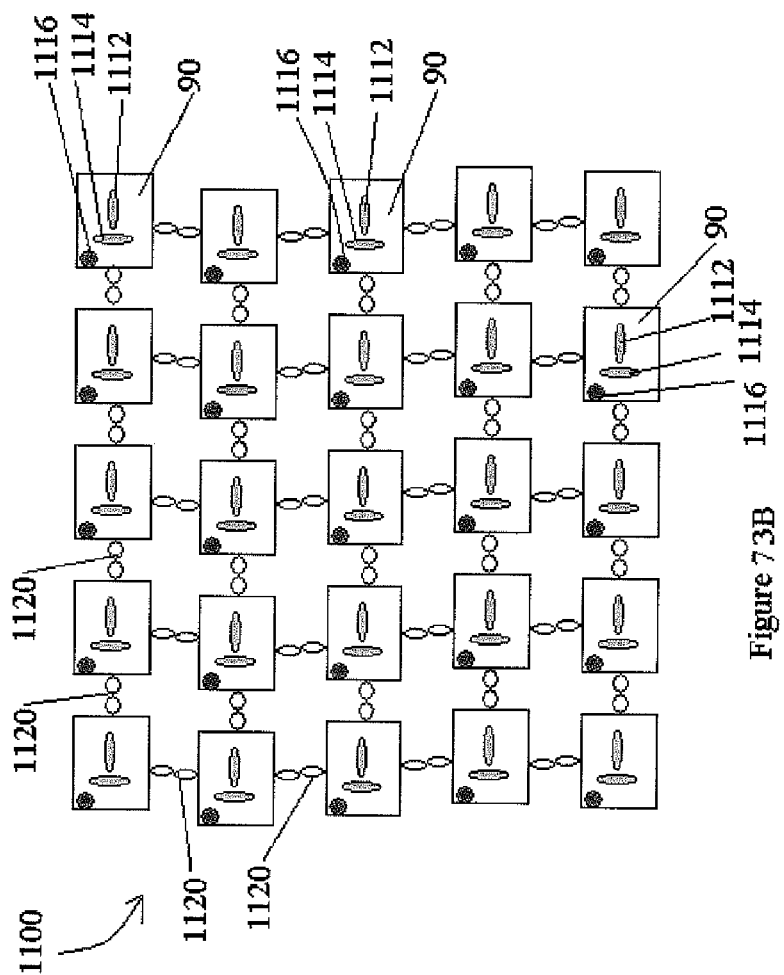

Referring further to the drawings, FIGS. 73A-73B schematically illustrate adjustable cameras 1100, in accordance with another embodiment of the present invention.

FIG. 73A illustrates the blocks 90 mounted on a flexible structure 1180 such as cloth, vinyl or the like. Each assembly 90 preferably includes a position tracking device 1116 and at least one but preferably two or more motion providers, such as motion providers 1114 and 1112, to provide the assembly 90 with at least one, but preferably two, three, or possibly up to six degrees of motion.

FIG. 73B illustrates the blocks 90 linked by chains 1120, to provide the adjustable character.

It will be appreciated that the position tracking device may be magnetic, electromagnetic, optical, or another device, as known. For example, each block 90 may include a Minibird™. Alternatively, two cameras may track the position of each block 90. Alternatively, other tracking methods may be used.

Figures 74A, 74B:
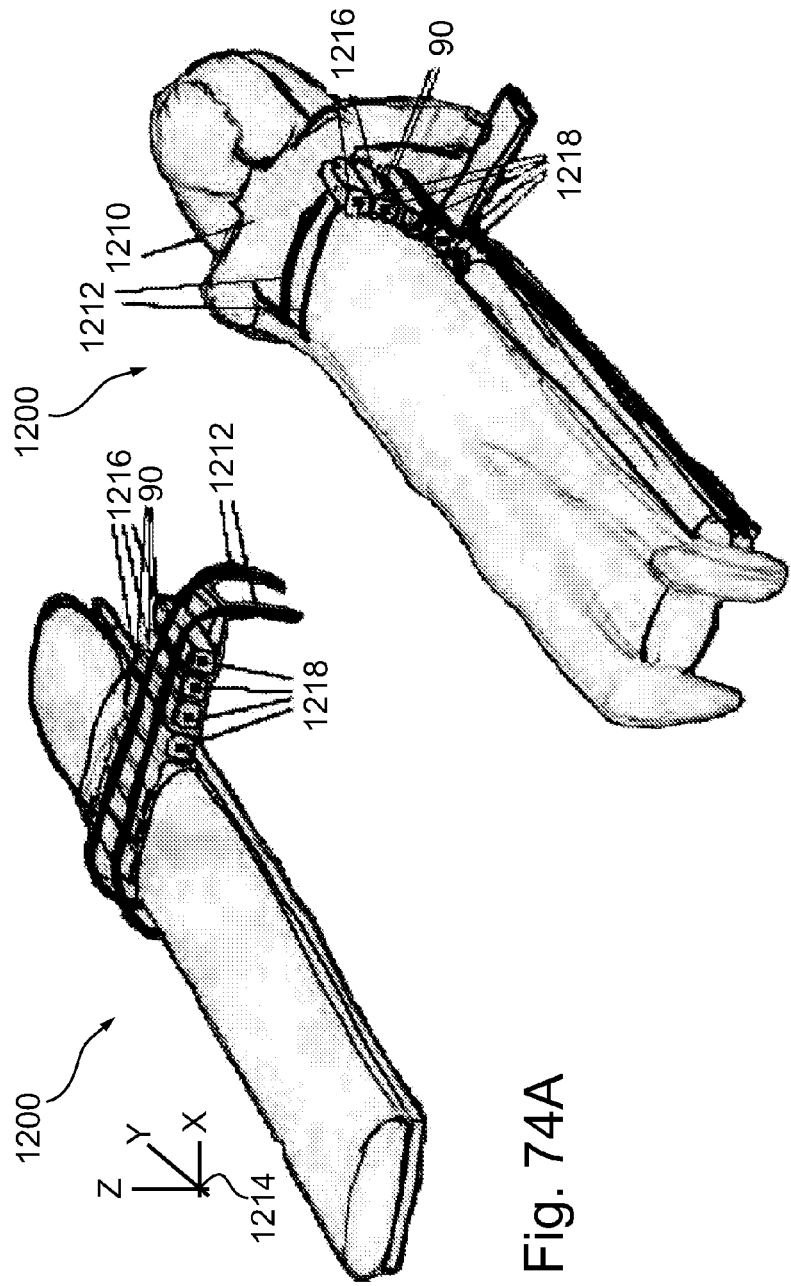
FIGS. 74A and 74B schematically illustrate the use of a non-wasteful radiation detector array, in accordance with an embodiment of the present invention.

Referring further to the drawings, FIGS. 74A-74B schematically illustrate adjustable cameras 1200, in accordance with still another embodiment of the present invention. The cameras 1200 are constructed as detecting modules 1216, which contain blocks 90 or detecting units 12, the detecting modules 1216 being arranged on tracks 1212 which are associated with a coordinate system 1214. Each of the detecting modules 1216 includes an encoder 1218, operative as the position tracking device 124 (FIGS. 2 and 3A), as known. The modules move along the tracks 1212 by means of a motion provider (not shown) while sending information regarding their coordinates together with measurements taken to the data-processing system 126 (FIGS. 2 and 3A).

vi. Independent Viewing by Each Block or Detecting Unit

In accordance with embodiments of the present invention, each block 90 of the adjustable camera construction (FIGS. 71-73B) or each detecting unit 12, where single-pixel detecting units 12 are used, may be provided with at least one, and preferably, two, three, or as many as six degrees of motion such as, for example, rotational motion around the x, y, and z, axis, oscillatory motion about these axes, or translational motion along these axes. In this manner, each block 90 may be preprogrammed to view each portion of the body section 230, in accordance with some predetermined schedule. For example, one of the blocks 90 may perform oscillatory motion, while an adjacent one of the blocks 90 may perform rotational motion. Thus, areas that are known to pose little susceptibility to abnormalities may be viewed differently from areas that are more susceptible to abnormalities. Additionally, active vision may take place. For example, where something suspicious is viewed, a decision to view it for a longer period of time and to thus obtain better data may be made by the data-processing system 126 (FIG. 2), so that the associated blocks 90 may be instructed to view an area longer. Alternatively, where not enough data has been acquired for the desired level of accuracy, more data may be collected, i.e., the number of Counts may be increased so as to reduce the margin or error to 1%. In other words, when using multiple, independent blocks 90 or detecting units 12, each may spend more time in one region than in another, and each may spend the time needed to reach a desired level of accuracy. Thus, one block or detector may spend a long time (within a predetermined limit) in one region, while another may spend less time and move on to another angle and position so as to provide a new view. Similarly, one block 90 or detecting unit 12 may use large steps, while another may use fine steps.

The present invention relates to situations that are unlike current systems, where the detecting units or blocks are fixed, with respect to each other, so individual optimization by block or by detecting unit is not possible.

The reverse is also possible, and a decision to obtain data for less than originally intended may be made. Also, cursory imaging may be performed and, where necessary, a decision may be made to acquire more data. It will be noted that the blocks along the camera may be designed differently and may include different collimators, for the different portions of the body section 230, such as those taught with reference to FIGS. 17C-17F. For example, the blocks 90 at the edge may have wide-angle collimators and those that are in the central portion of the blocks 90 may have narrow collimators.

vii. Criteria for Camera Design

An overall camera design may be based on the following criteria:

i. a distance from the surface of the body section 230 to the detecting unit 12 or the block 90 which is no greater than 5 cm and, preferably, no greater than 3 cm, and, more preferably, no greater than 2 cm.

ii. wasteful viewing for less than 50% of the viewing of each detecting unit 12 or block 90 and, preferably, less than 30% of the viewing time and, more preferably, less than 20% of the viewing time.

iii. Substantially no detecting unit 12 or block 90 is positioned so as not to view the body structure at all.

iv. a collimator solid collection angle of at least 0.0005 steradians, or at least 0.001 steradians, or at least 0.003 steradians, or at least 0.005 steradians, or at least 0.01 steradians, or at least 0.03 steradians, or at least 0.05 steradians, or at least 0.08 steradians.

v. alternatively, a collimator collection solid angle which is configured to view substantially a whole organ, such as a heart, or substantially a large portion of the organ.

vi. a block size along the rotational axis, for the block 90, of less than 10 cm and, preferably, of less than 6 cm and, more preferably, of less than 2 mm.

vii. independent motion control for each of the blocks 90, along at least one rotational axis, preferably along at least two rotational axes and, more preferably, along the three rotational axes and the three translational axes.

Wherein a portion of these or all of these may be incorporated into the camera design.

viii. Experimental Results

Figure 75A:
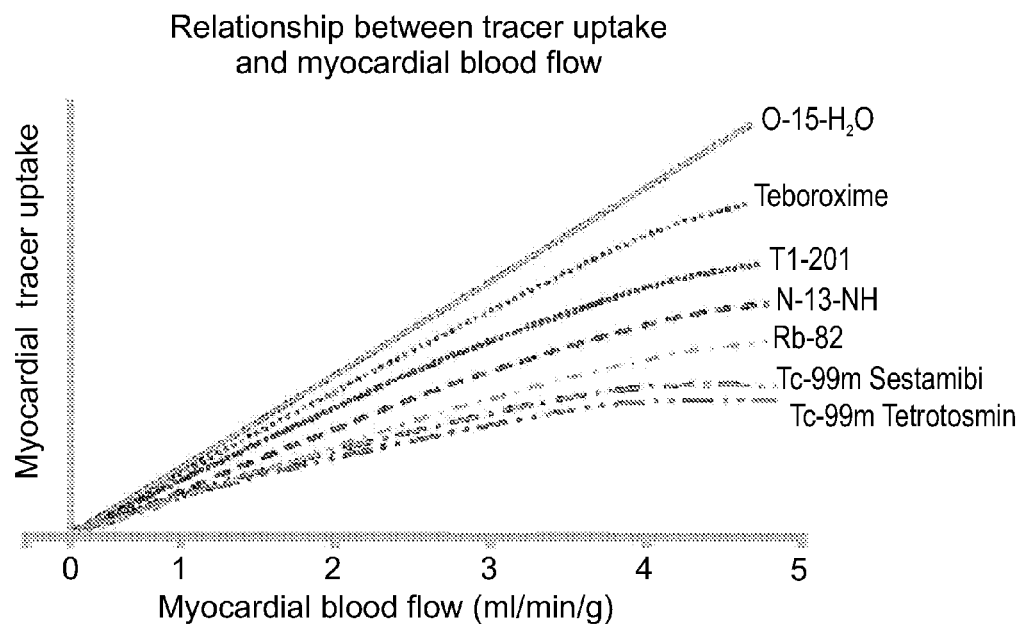
FIGS. 75A and 75B illustrate Teboroxime physiological behavior, according to Garcia et al. (Am. J. Cardiol. $51^{st}$ Annual Scientific Session, 2002).
Figure 75B:
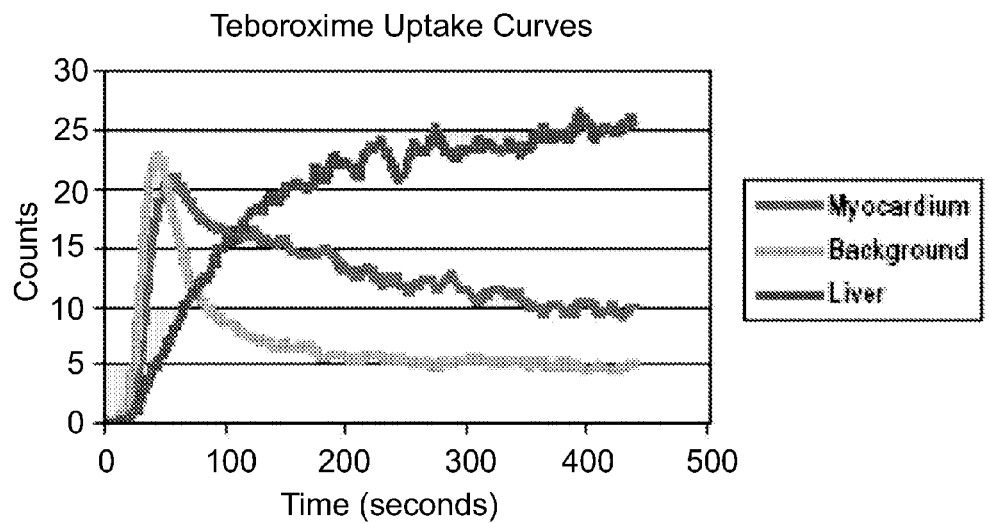

Referring to the drawings FIGS. 75A and 75B illustrate Teboroxime physiological behavior, according to Garcia et al. (Am. J. Cardiol. 51$^{st}$ Annual Scientific Session, 2002).

Referring further to the drawings, FIGS. 76A-80D illustrate experimental results of the camera of the present invention and results of a conventional gamma camera, in terms of resolution, speed, and contrast. In all the experiments, the detectors used were 16×16 pixilated (2.54×2.54 mm in size) CZT arrays made by Imarad, Rehovot, Israel and driven by the XA controller system made by IDEAS asa., Norway.

Test No 1: Speed and Resolution

Performances of the camera of the present invention and of the conventional gamma camera were compared by equivalent setups, as follows:

For the camera of the present invention, a center of viewing was at a distance of 150 mm from the collimators' distal end with respect to an operator. A 5 mili Curie Cobalt 57 line source was placed at a distance of 1 cm from the center of viewing, so as to be off center for the viewing. A total of 13.5 million photon counts were taken. Acquisition time was 49 seconds.

For the conventional gamma camera, a center of rotation was at a distance of 150 mm from the collimators' distal end with respect to an operator. A 5 mili Curie Cobalt 57 line source was placed at a distance of 1 cm from the center of rotation, so as to be off center for the rotation, and the same number of counts, 13.5 million photon counts, was taken. Acquisition time was 600 seconds.

Thus, the camera of the present invention was about 12 times more sensitive than the conventional gamma camera.

The image of the source was reconstructed using dedicated reconstruction algorithms based on the EM method and developed by the inventors. The reconstruction algorithms used on the conventional unit were OSEM/MLEM based.

FIG. 76A represents results with the camera of the present invention.

FIG. 76B represents results of the conventional gamma camera.

The measured FWHM (Full Width at Half Maximum) resolutions are shown in Table 1, as follows:

TABLE 1

| System/Reconstruction | Resolution FWHM (NEMA) [mm] |
|---|---|
| camera of the present invention | 5.5 |
| conventional gamma camera | 10.4 |

Test No. 2: Resolution as a Function of Scattering Distance

A standard NEMA cylindrical phantom was filled with water, and a 5 mili Curie Cobalt 57 line source of 190 mm in length and 1 mm in diameter was placed at its center, as illustrated in FIG. 76C. The cylindrical phantom was placed at a distance R from the distal end of the cameras' collimators. Reconstruction images from two 40-second acquisitions were performed and analyzed, wherein the first acquisition was based on equal angle span for all views (Fixed Angle Spans), and the second acquisition was based on adjusted angle viewing, for viewing equal sectors of the region-of-interest (Fixed ROI).

Figure 76D:
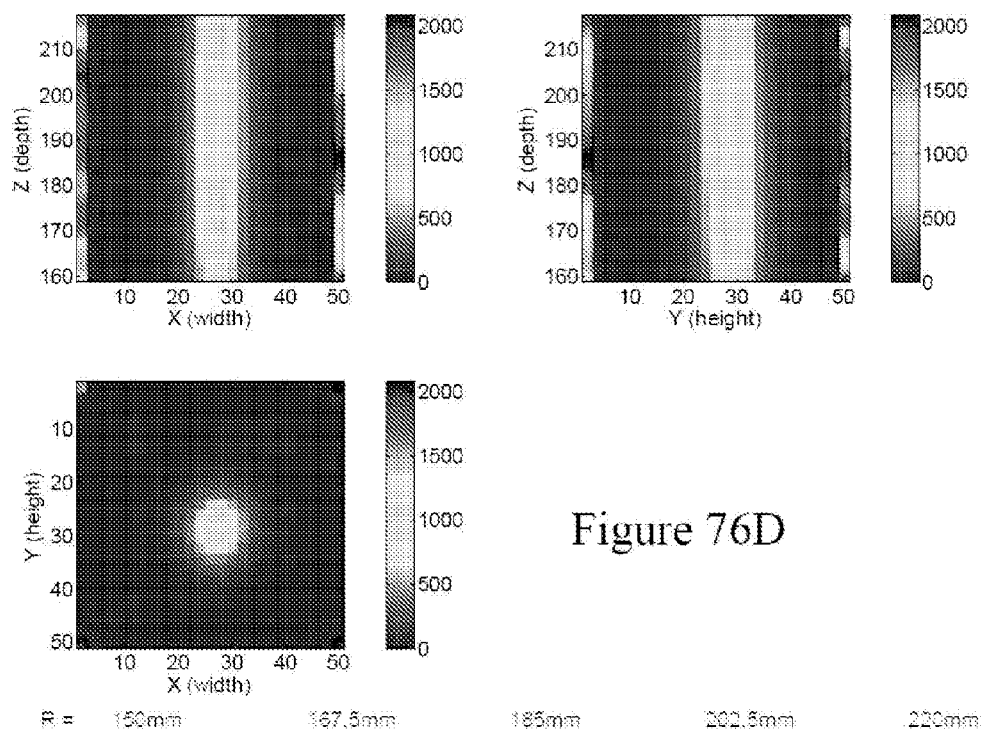

For image reconstruction, a maximal intensity projection (MIP) of the reconstruction without attenuation correction is given in FIG. 76D, based on the combined total of the two acquisitions. The x-z and the y-z planes each show the line source as a line, and the x-y plane provides a cross-sectional view of the line.

Figure 76E:
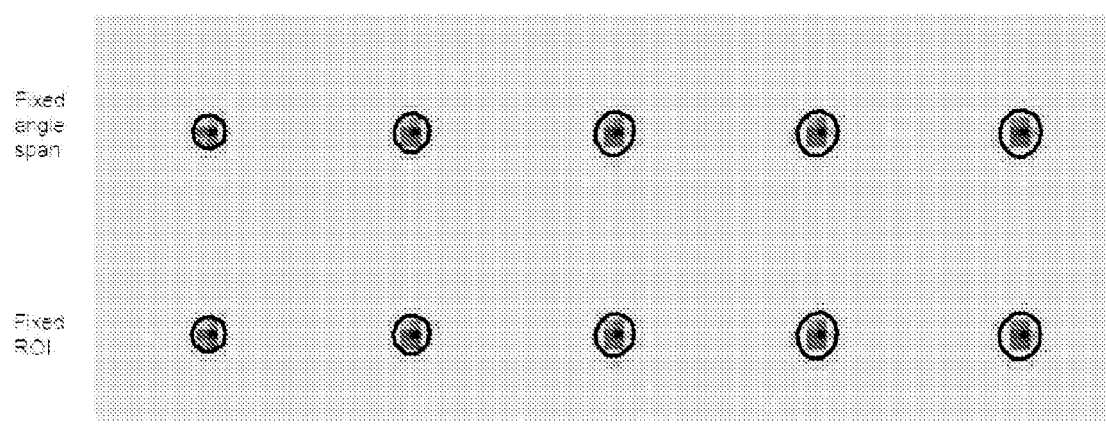

FIG. 76E illustrates the reconstructed cross-sectional intensity of the line source for the fixed scan angle and Fixed ROI cases, respectively, and for varying distances R from the camera. As expected, the FWHM increases with increasing R.

Figure 76F:
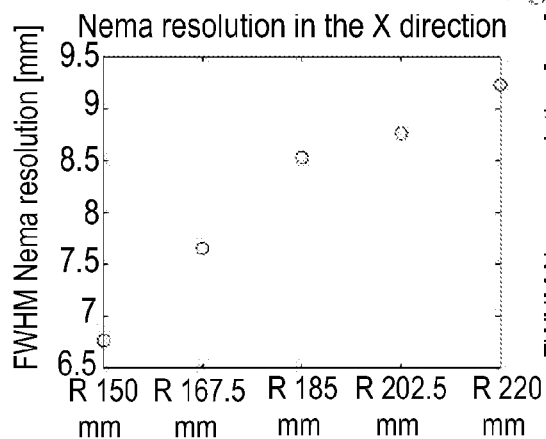
Figure 76G:
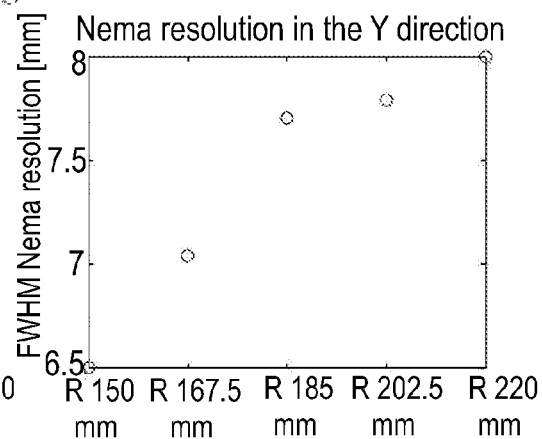
Figure 76I:
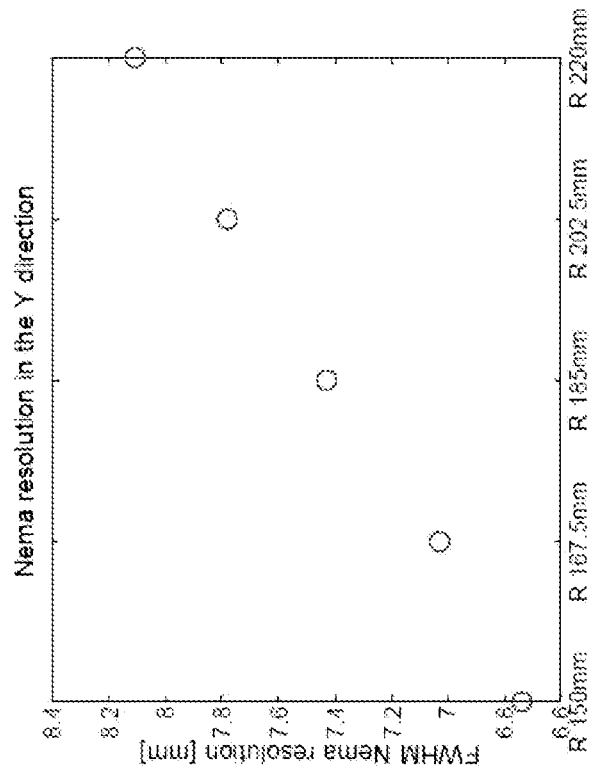
Figure 76H:
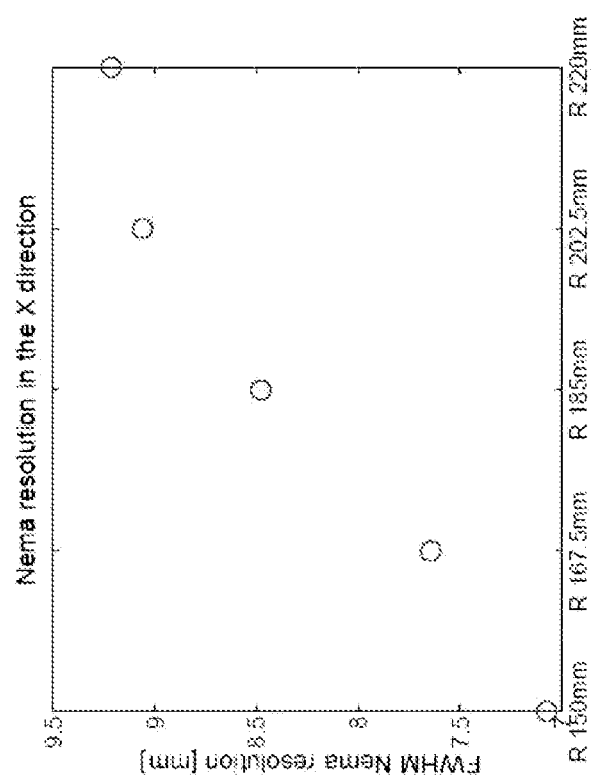

FIGS. 76F and 76G schematically show NEMA resolutions in the x and y directions, respectively, for the fixed-angle span acquisition, while FIGS. 76H and 76I schematically show NEMA resolutions in the x and y directions, respectively, for the fixed-ROI acquisition.

Test No. 3: NEMA Three Line Source Acquisition

Three Cobalt 57 line sources were placed inside a standard NEMA phantom, as seen in FIG. 77A.

Viewing coverage was 200 degrees, wherein the distance from the distal end of the collimators to the center of viewing was 150 mm. The total net acquisition time was 60 seconds. The images shown in FIGS. 77B-77D are based on raw reconstruction, without attenuation correction or smoothing.

After application of a simplistic, model-based attenuation correction, which is acceptable in the case of water as the scattering and absorbing medium and circular symmetry of an object, the results are shown in FIGS. 77E-77G.

Table 1 below provides resolution numbers for the pre- and post-attenuation correction results, as follows:

TABLE 1

| | NEMA resolution FWHM [mm] | | |
|---|---|---|---|
| | Point #1 | Point #2 (Center) | Point #3 |
| Without Attenuation Correction | | | |
| X-Direction | 5.6 | 7.7 | 4.4 |
| Y-Direction | 5.4 | 7 | 4.4 |
| With Attenuation Correction | | | |
| X-Direction | 6.1 | 7.6 | 3.9 |
| Y-Direction | 6.3 | 7.6 | 4 |

Test No. 4: Resolution, Acquisition Time, and Contrast

As shown in FIGS. 78A-78C, two sources, A and B, were placed in a cylindrical Perspex phantom, designed to allow the insertion of sources of different sizes and intensities.

A comparison of radioactive-emission imaging of the camera of the present invention and of a conventional gamma camera was made, and this included image evaluation, sensitivities, and contrast differences.

The cylindrical Perspex phantom was placed with its center at the center of viewing of the camera. The distance from the distal end of the collimators to the center of the phantom cylinder was 100 cm.

The total radiation coming from the cylinder, including radiation from background, insert A, and insert B, was 930 μCi of Tc-99m. The ratio of the amount of radiation from insert A to background radiation was 2:1, while that of radiation from insert B to background radiation was 3:1. Acquisition time was 40 seconds and 1.4 million counts were acquired. The reconstructed images are seen in FIGS. 79A-79C. Both the 2:1 and 3:1 Target to Background ratio targets are visible.

The resulting measured contrasts are 2.6:1 and 1.6:1 for the 3:1 and 2:1 input contrasts, respectively, in the case of the camera of the present invention.

Figure 79D:
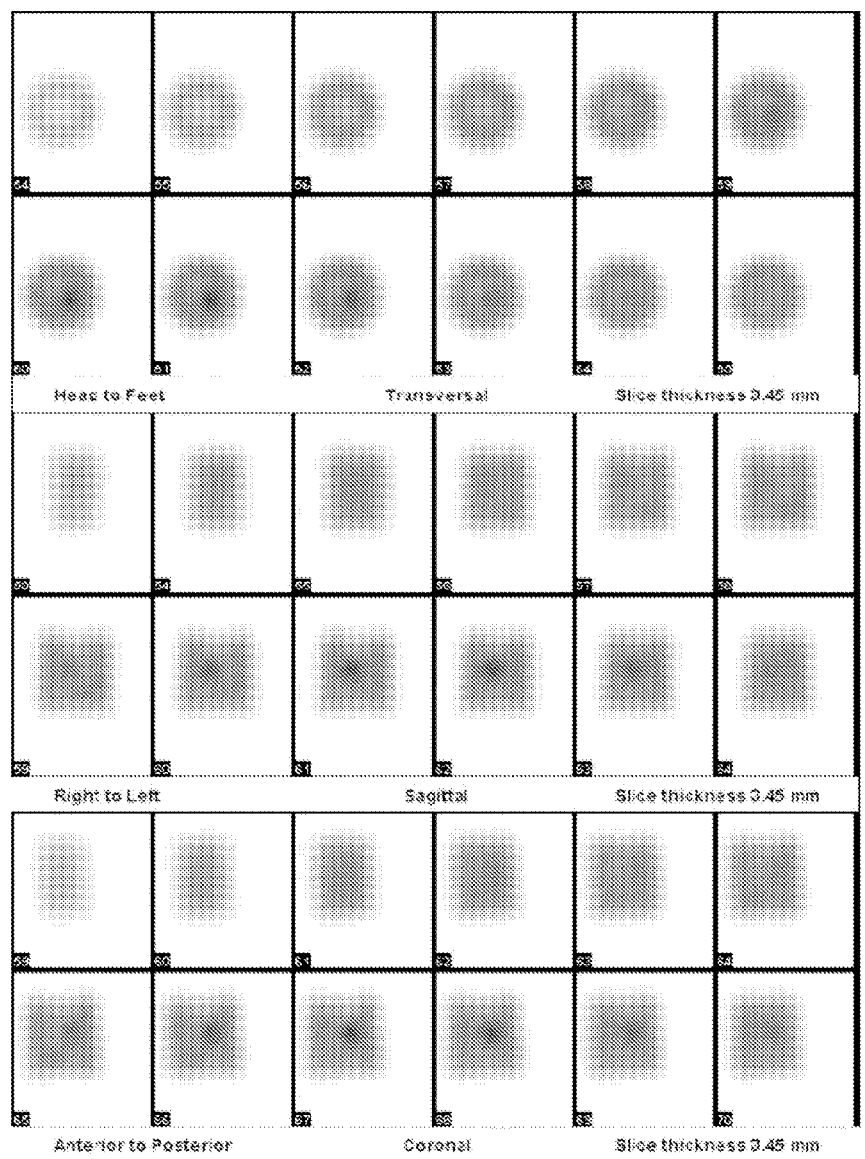

FIG. 79D represents the reconstructed results using the conventional camera, for which the acquisition time to reach the 1.4 million counts was 20 minutes. The 3:1 target was reconstructed as a 1.3:1 ratio while the 2:1 target was indistinguishable from the background radiation. The main reason for this loss of contrast is the poor spatial resolution of the conventional camera when compared to that of the camera of the present invention.

Test No. 5: Reconstruction of Complex Objects—Torso Phantom Acquisition

A standard torso phantom of Anthropomorphic Torso Phantom Model ECT/TOR/P, produced by Data Spectrum Corporation, USA, was provided, as seen in FIG. 80A.

The radioisotope Tc-99m was used as the tracer. The activity of the various organs was: Cardio—0.5 mCi, Background—2 mCi (0.19 mCi/liter) and Liver—0.23 mCi (0.19 mCi/liter).

An acquisition time of 1.25 minutes was used for the camera of the present invention, and an acquisition time of 12.5 minutes was used for the conventional camera. In both cases, 2.5 M counts were obtained.

FIG. 80B illustrates the results using the camera of the present invention, and FIG. 80C illustrates the results using the conventional gamma camera.

The sensitivity ratio was thus 10:1. The reconstruction is visibly better in the case of the camera of the current invention.

Figure 80D:
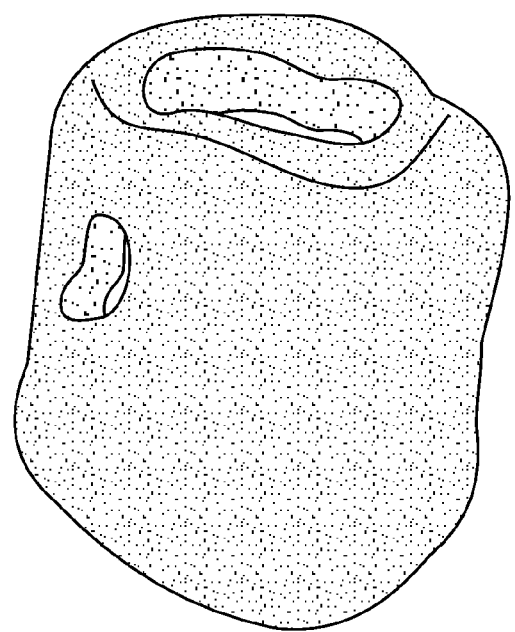

FIG. 80D illustrates a reconstructed three-dimensional image of the heart, from the phantom, using the camera of the present invention.

A cold area of 1 cm×1 cm×0.5 cm at a left side of the heart is clearly seen. Other cold areas are similarly visible.

Test No. 6: Sensitivity Studies

In another exemplary embodiment of the current invention, the probe system includes multiple blocks of detectors positioned in a structure encircling the imaged area, each is able to rotate about a longitudinal axis substantially parallel to the main axis of the subject.

In a further example case of 10 such blocks of detectors, each covering a 40×160 mm section covering about 180-200 deg of the circle around the imaged area, with 10 blocks of collimators each covering 1024 pixels arranged in a 16×64 pixel matrix, with square collimator opening of 2.46×2.46 mm, and a length of 20 mm], the system demonstrated ability to detect about one out of 1500 of the emitted photons from a 2.7 mCi $Co^{57}$ point source that was moved about in a 40×30× 15 cm volume facing the probe.

When located in the center of the imaged area (about 150 mm from the detectors), while the energy window for acquisition was about 5%, and the detectors were sweeping a wide angular range.

In a further exemplary embodiment, substantially all detectors are able to simultaneously image the region of interest containing the point source and thus obtaining one out of every 500 of the emitted photons.

It is known to the skilled in the art that further opening the energy window of the detector to about 15%, enables acquisition of about one out of 250 photons of the photons emission in an experimental setting similar to the previous example.

In a further example, each such detector having multiple pixels is of about 5 cm wide or more, thus producing a region of interest of at least 5 cm in diameter, from which said sensitivity and said resolution is being obtained even without the need to move any of the detectors.

In a further possible embodiment of the present invention the width of each detector is about 10 cm wide, thus enabling regions of interest of even bigger diameters at said resolution and sensitivity with a smaller detector motion such that bigger objects are continuously viewed by the detector with only small angular detector motion.

In a further possible embodiment of the present invention the detectors array may encircle the imaged subject to the extent of 360 deg, for example by having two hemi circles from both sides of the subject. The sensitivity in such case is estimated be about 1 in 125.

In a further exemplary embodiment additional detectors may be positioned to obtain views not perpendicular to the subject's main longitudinal axis, for example by upper view (e.g. from the shoulders) and abdominal view of the target region (in the case of cardiac mapping). It is estimated that such addition may increase the sensitivity but a factor of about ×2.

As a result, an example embodiment of the present invention is estimated to be able to image a volume of about 5 cm diameter located about 150 mm from the detectors, with energy window of 15%, producing spatial resolution of about 5 mm in approximately 100 sec, with a total sensitivity of about 1 photons being detected Out of 65 emitted.

It will be recognized by a person skilled in the alt that a system built around the principles of this invention can thus reach the sensitivity necessary to detect substantially more than one photon from every 100 emitted. This result for an imaging system provides more than 100 time better sensitivity than commercially available cameras that have a sensitivity ranging from substantially from 170 counts/microCurie/minute (or 1 photon in 8500 photons emitted for a Low resolution low energy collimator to about 1 photon in every 15000 emitted for a high resolution medium energy collimator), while maintaining similar energy windows, and potentially similar or better resolution.

Test No. 7: Sensitivity Studies—Grid Point Source

Figure 70:
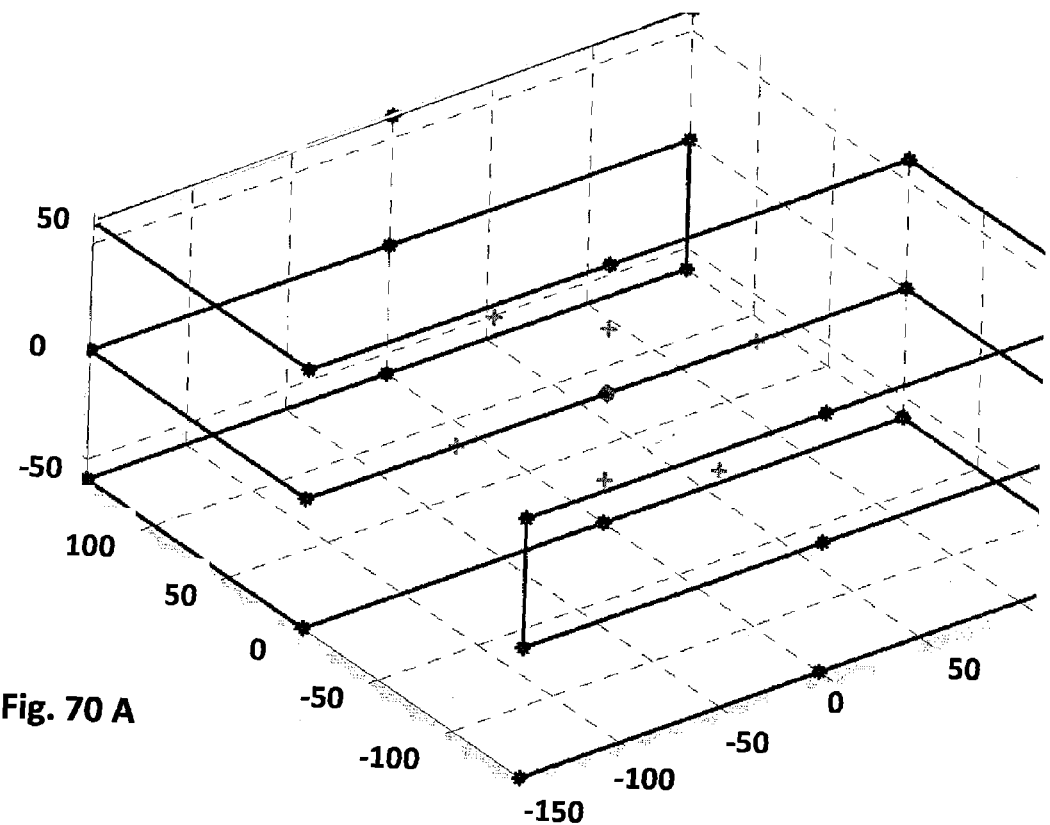
FIGS. 70A-70C describe experimental results with grid point sources.
Figure 70B:
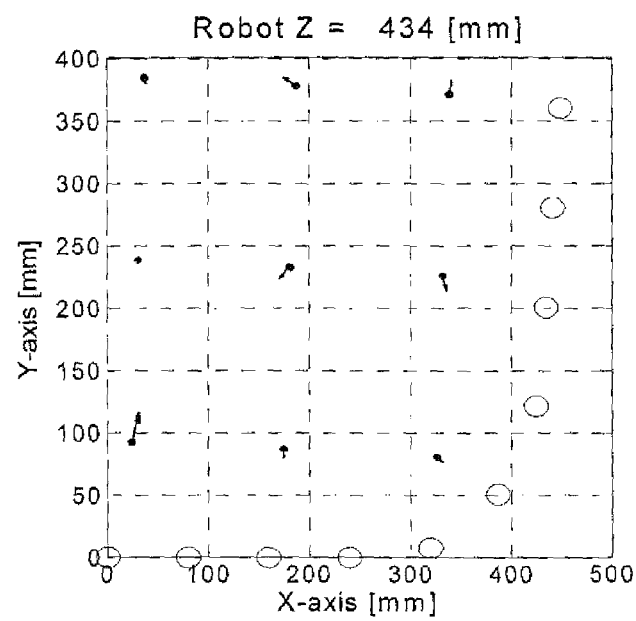
Figure 70C:
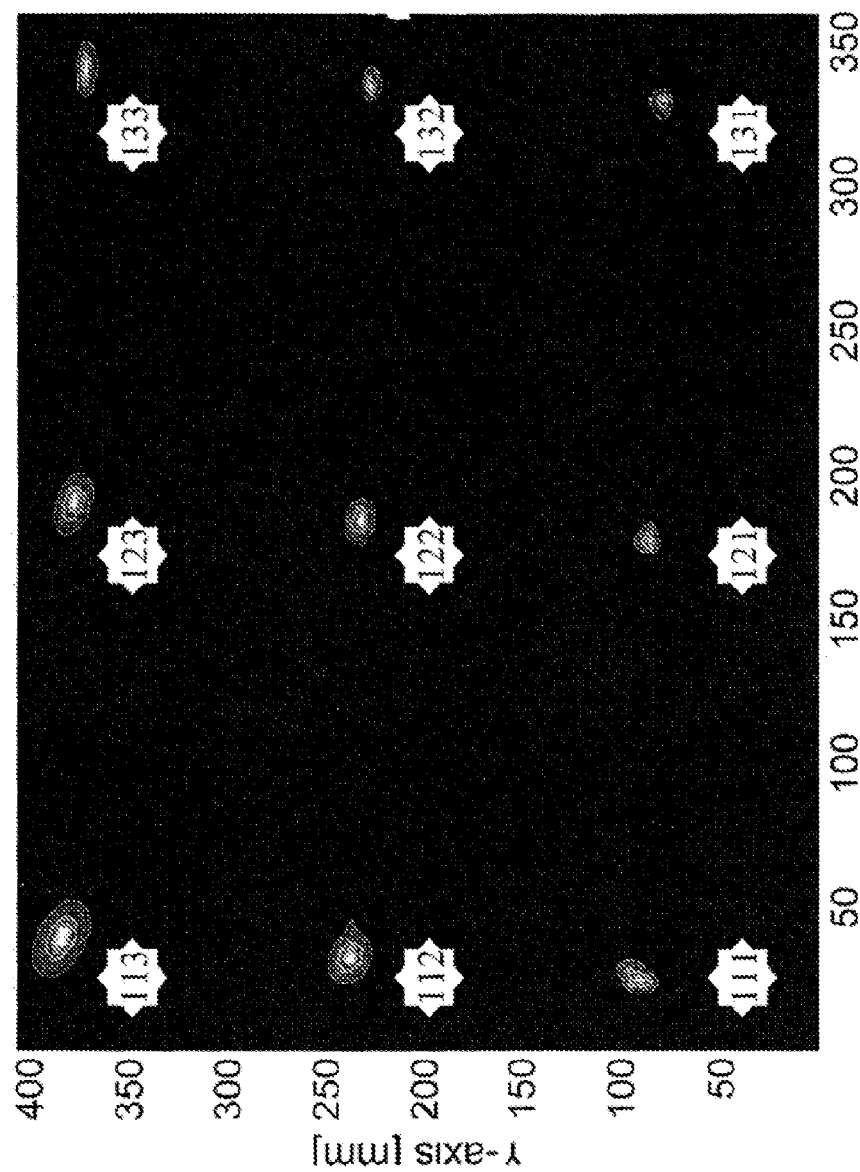

In a further experiment a $Co^{57}$ point source of 2.7 mCi activity was used in order to measure the sensitivity, resolution and geometric accuracy of the probe. A probe composed out of 10 detector columns, each containing detector pixels in a 16×64 pixel arrangement, where each pixel element had a dimension of 2.46×2.46 mm and being covered by a Tungsten collimator matrix with 0.2 mm septal thickness and 20 mm septal length was used to image the point source. The energy window was set at 5% FWHM (6 KeV total). A robotic arm was used to move the point source within a 40×30×15 cm rectangular volume at positions shown in FIG. 70A. FIG. 70B is a diagram showing the error of the reconstructed position relative to the nominal position as placed by the robot. It is evident that the deviation in position is less than 1 mm for most points and less than 2.5 mm for all points. FIG. 70C shows the FWHM diameter and the FWHM (Full Width Tenth Maximum) diameter for all points in the volume. It is noted that the resolutions measured according to the NEMA standards are substantially under 10 mm throughout the volume and do not exceed 15 mm for all points, a performance equal to or superior to existing nuclear cameras for similar fields of View. The total net acquisition time for each point was 120 seconds and the typical count rate for most points (with the exception of positions that could not be viewed by all columns due to mechanical limitations), and the collected number of photons was substantially 7-8 million counts for most positions fully viewed, yielding a sensitivity of 1 photon out of 1500 emitted in the energy window of 5%.

Electrical Scheme

FIG. 143 describes an example of a system that includes multiple detection, amplificationa and signal processing paths, thereby avoiding saturation due to single hot source in space. Gamma-Ray photon (A) is hitting a pixelized CZT crystal. A hit is named 'Event'. The crystal is part of a 'CZT MODULE' (B) containing the CZT crystal divided into 256 pixels and 2 ASICS each receiving events from 128 pixels. The ASIC is OMS 'XAIM3.4' made by Orbotech Medical Systems, Rehovot, Israel, together with the CZT crystal. The 2 ASICs share a common output and transmit the data to 'ADC PCB' (C) that handles in parallel 4 'CZT MODULES'. Thus, a total of 1024 pixels are presently channeled through one ADC board. The system is capable of further increasing the accepted event rate by channeling every 2 ASICS through a single ADC. The 'ADC PCB' transmits the data to the 'NRG PCB' (D) that handles in parallel 10 'ADC PCBS', but could be further replicated should one want to further decrease "dead time". The 'NRG PCB' transmits the data to the 'PC' (E) where it is stored.

All in all, in the present embodiment, 40 'CZT MODULE' containing a total of 10240 pixels are transmitting in parallel to the PC.

The bottle neck, and hence the only constraint, of the system data flow is the ASICS in the 'CZT MODULE' and it's connection to the 'ADC PCB':

1. An ASIC (128 pixels) can process only one photon hit within 3.5 uSec, or 285,000 events/sec over 128 pixels, i.e. over 2200 events/px/sec-an exceedingly high rate.

2. 2 ASICS share the same output, and hence coincident event output of the 2 ASICS in a 'CZT MODULE' will cause a collision and information loss. The duration of an event output from the ASIC is 1 uSec.

General Designs of Detecting Units, Blocks, Assemblies and Cameras

Referring further to the drawings, FIGS. 17A-17H schematically illustrate detecting units 12 and blocks 90 that may be considered for possible camera designs.

FIGS. 17A and 17B schematically illustrate side and top views, respectively, of the basic detecting unit 12 (see also FIG. 1A), having a detector 91 and a collimator 96, formed as a tube, of a collection angle $\delta 1$.

FIGS. 17C and 17D schematically illustrate side and top views, respectively, of the detecting unit 12, with the collimator 96 formed as a wide angle collimator, of a collection angle $\delta 2$.

FIGS. 17E and 17F schematically illustrate side and top views, respectively, of the block 90 (see also FIG. 1B) of the detecting units 12, with the collimator 96 formed as a grid, and each of the detecting unit 12 having a collection angle $\delta 3$. As few as two or four, and as many as a hundred or several hundred of the detecting units 12 may be included in the block 90.

FIGS. 17G and 17H schematically illustrate side and top views, respectively, of the block 90 of the detecting units 12, with the collimator 96 formed as a grid, with two sizes of the detecting units 12, as follows: small detecting units 94A, of collection angles $\delta 4$, at the center of the grid, and large detecting units 94B, of collection angles $\delta 5$, at the periphery. It will be appreciated that other arrangements of detecting units of different sizes may be used.

It will be appreciated that a combination of these may be used. For example, the block 90 may include wide-angle collimators (FIG. 17C) at the periphery and normal collimators of 90-degrees (FIG. 17A) at the center.

It will be appreciated that the camera 10 may contain blocks 90 and (or) detecting units 12 of different collection angles.

Referring further to the drawings, FIGS. 17I and 17J schematically illustrate a detecting unit 12A with an adjustable collimator 96Z, for adjusting the collection angle, in accordance with embodiments of the present invention. Preferably, the detecting unit 12A includes the detector 91 and an adjustor 91A at the bottom of the collimator 96Z. Additionally, the collimator 96Z is formed of a plurality of petal collimators 96A, 96B, 96C, and so on, wherein the collimator 96Z may be partially open, as shown in FIG. 17I, or fully open, as shown in FIG. 17J, by the action of the adjustor 91A, which may be, for example, a rotating knob, controlled by the data-processing system 126 (FIGS. 2, 3A). Preferably, the extent of opening of the collimator 96Z is adjustable, so it may be essentially closed, with the petal collimators 96A, 96B, 96C and so on substantially vertical with the detector 91, partially open, or fully open, much like a flower.

FIGS. 17K-17N schematically illustrate the block 90, wherein the detector 91 is a single-pixel scintillation detector, such as NaI(Tl), LSO, GSO, CsI, CaF, or the like, operative with photomultipliers 103.

As seen in FIG. 17K, the block 90, having proximal and distal ends 109 and 111, respectively, vis a vis an operator (not shown), is formed of the scintillation detector 91, of a single pixel, and the collimators 96, to create the detecting units 12. A plurality of photomultipliers 103 is associated with the single pixel scintillation detector 91, and with dedicated algorithms, as known, their output can provide a two dimensional image of the scintillations in the single pixel scintillation detector 91. In essence, this is an Anger camera, as known.

The distal view 111 of the collimator grid is seen in FIG. 17L.

Two optional proximal views 109 of the photomultipliers 103 are seen in FIGS. 17M and 17N, as a square grid arrangement, and as an arrangement of tubes.

The detector may be a room temperature, solid-state CdZnTe (CZT) detector, configured as a single-pixel or a multi-pixel detector, obtained, for example, from eV Products, a division of II-VI Corporation, Saxonburg Pa., 16056, or from IMARAD IMAGING SYSTEMS LTD., of Rehovot, ISRAEL, 76124, www.imarad.com, or from another source. A detector thickness $\tau_d$ may range from about 0.5 mm to about 100 mill, depending on the energy of the radioactive emission and typically about 2 mm to about 50 mm, and in some cases about 5 mm to about 30 mm.

Alternatively, another solid-state detector such as CdTe, HgI, Si, Ge, or the like, or a scintillation detector (such as NaI(Tl), LSO, GSO, CsI, CaF, or the like, or a combination of a scintillation detector and a photomultiplier, to form an Anger camera, or another detector as known, may be used. Additionally, a combination of scintillation materials and photodiode arrays may be used.

It will be appreciated that the methods of the present invention apply to pathological features that may be modeled as regions of concentrated radiations, or hot regions, regions of low-level radiation, which is nonetheless above background level, and regions of little radiation, or cold regions, below the background level. However, in general, for identifying a pathological feature of the heart, they relate to cold regions.

It will be appreciated that the methods of the present inventions may be operable by computer systems and stored as computer programs on computer-readable storage media.

It will be appreciated that the body may be an animal body or a human body.

It will be appreciated that the radioactive-emission-camera systems, cameras and methods of the present invention may be used with commonly owned US Applications 20040015075 and 20040054248 and commonly owned PCT publication WO2004/042546, all of whose disclosures are incorporated herein by reference. These describe systems and methods for scanning a radioactive-emission source with a radioactive-emission camera of a wide-aperture collimator, and at the same time, monitoring the position of the radioactive-emission camera, at very fine time intervals, to obtain the equivalence of fine-aperture collimation. In consequence, high-efficiency, high-resolution, images of a radioactive-emission source are obtained.

Commonly owned US application 20040054248 and commonly owned PCT publication WO2004/042546 further disclose various extracorporeal and intracorporal systems, of radioactive-emission cameras, of relatively wide apertures, associated with position-tracking devices.

It will be appreciated that the radioactive-emission-camera systems, cameras and methods of the present invention may be used with commonly owned U.S. Pat. No. 6,173,201 to Front, whose disclosure is incorporated herein by reference, as well as by M. W. Vannier and D. E. Gayou, "Automated registration of multimodality images", Radiology, vol. 169 pp. 860-861 (1988); J. A. Correia, "Registration of nuclear medicine images, J. Nucl. Med., vol. 31 pp. 1227-1229 (1990); J-C Liehn, A. Loboguerrero, C. Perault and L. Demange, "Superposition of computed tomography and single photon emission tomography immunoscinigraphic images in the pelvis: validation in patients with colorectal or ovarian carcinoma recurrence", Eur. J. Nucl. Med., vol. 19 pp. 186-194 (1992); F. Thomas et al., "Description of a prototype emission transmission computed tomography imaging system", J. Nucl. Med., vol. 33 pp. 1881-1887 (1992); D. A. Weber and M. Ivanovic, "Correlative image registration", Sem. Nucl. Med., vol. 24 pp. 311-323 (1994); and Hasegawa et al., U.S. Pat. No. 5,376,795.

These relate to the acquisition of both a functional image of the body, such as a radioactive-emission image, and a structural image, such as an ultrasound, an x-ray, or an MRI image, and their co-registration on a single frame of reference.

In essence, several images may be acquired and co-registered to the same frame of reference, as follows:

i. a first functional image scan, based for example, on anti-CEA monoclonal antibody fragment, labeled by iodine isotopes, may be acquired for targeting CEA—produced and shed by colorectal carcinoma cells for detecting a pathological feature, such as colorectal carcinoma;

ii. a second functional image, based for example, on non-specific-polyclonal immunoglobulin G (IgG), which may be labeled with $Tc^{99m}$, may be acquired for locating blood vessels and vital structures, such as the heart, or the stomach, co-registered with the first functional image and the pathological feature detected on it, in order to locate the pathological feature in reference to blood vessels and vital organs; and iii. a structural image, such as an ultrasound image, may be used for general structural anatomy, co-registered with the first and second functional images, in order to locate the pathological feature in reference to bones and the general anatomic structure.

Thus, a physician may locate the pathological feature in reference to the blood vessels, vital organs, and the bones, and guide a minimally invasive surgical instrument to the pathological feature, while avoiding the blood vessels, vital organs, and bones. The minimally invasive surgical instrument may be a biopsy needle, a wire, for hot resection, a knife for cold resection, an instrument of focused energy, to produce ablation, for example, by ultrasound, or by laser, an instrument for cryosurgery, an instrument for cryotherapy, or an instrument for brachytherapy, wherein seeds of a radioactive metal are planted close to a tumor, for operating as a radioactive source near the tumor.

Commonly owned PCT publication WO2004/042546 further discloses that the surgical instrument may be visible on at least one of the images, for example, on the structural image, to enable the physician to see the instrument, the pathological feature, and the surrounding anatomy on the display 129 (FIG. 3A). Additionally, the surgical instrument may be radioactively labeled, to be visible also on the functional image. PCT publication WO2004/042546 further disclose various extracorporeal and intracorporal systems, of radioactive-emission cameras, and structural imagers such as an ultrasound camera or an MRI camera.

Commonly owned U.S. Pat. No. 6,173,201, to Front further discloses a method of stereotactic therapy, wherein a frame, which includes at least three markers, visible on a structural image, is rigidly secured to a patient. The structural image of a region inside the patient's body, which includes a pathological feature and the markers, is acquired. A functional image of the pathological feature is then acquired and co-registered with the structural image, to correlate the images to the same frame of reference. A stereotactic guide is rigidly attached to the frame and is used to guide a surgical instrument, such as a biopsy needle or a brachytherapy needle, to the pathological feature, with reference to the co-registered images.

Thus the radioactive-emission-camera systems, cameras and methods of the present invention may be used together with position tracking devices, for enhanced image acquisition, they may be used together with structural imager and structural imaging for correlating functional and structural images, and they may be used for guiding minimally invasive surgical instruments, such as a biopsy needle, a wire, for hot resection, a knife for cold resection, an instrument of focused energy, to produce ablation, for example, by ultrasound, or by laser, an instrument for cryosurgery, an instrument for cryotherapy, or an instrument for brachytherapy.

It will be appreciated that a structural image, such as by ultrasound may further be used and in order to provide information about the size and location of the body structure 215 for the purpose of creating the model 250 (FIG. 5A).

It will be appreciated that a structural image, such as by ultrasound may further be used and in order to provide information about tissue attenuation, for example, as taught in conjunction by commonly owned PCT publication WO2004/042546, whose disclosure is incorporated herein by reference. The information may then be used to correct the radioactive-emission measurements.

Active Vision

At present, radioactive-emission imaging of a body structure is a three-stage process. First the radiopharmaceutical is administered. Then measurements are taken at a set of predetermined views, that is at predetermined locations, orientations, and durations. Finally, the data is analyzed to reconstruct the emission distribution of the volume and an image of the body structure is formed. The imaging process is sequential, and there is no assessment of the quality of the reconstructed image until after the measurement process is completed. Where a poor quality image is obtained, the measurements must be repeated, resulting in inconvenience to the patient and inefficiency in the imaging process.

According to this embodiment, the present invention teaches using radioactive-emission measurements to define views for further radioactive-emission measurements of a body structure, to be performed during the current measurement process. Specifically, the methods teach analyzing the previously obtained measurement results to determine which further views are expected to provide a high quality of information. The analysis may be based directly on the photon counts obtained for the current or recent measurements and/or on a reconstruction of the body structure performed upon the completion of a set of measurements.

The present embodiments address the problem of ensuring that the quality of data gathered during the measurement process is adequate to provide a high quality image. The collected data and/or the image reconstructed from the collected data is analyzed the while the measurement process is taking place. Based on the analysis, further views are defined.

Since each view is associated with known values of the viewing parameter(s), selecting a view effectively specifies known viewing parameter values. The defined further views thus define a set of viewing parameter values, which are used during the current measurement process in order to collect data which yields a high-quality reconstruction of the body structure.

The following embodiments are of a method for determining further views for the imaging of a body structure, and are not confined to a specific reconstruction algorithm. Further views are preferably defined based on one or more of the following:

1) Detector photon count
2) Geometric properties of the reconstructed body structure
3) Information theoretic measures that quantify the quality of the data fed to the reconstruction algorithm Each of these criteria is discussed in detail below.

Figure 81:
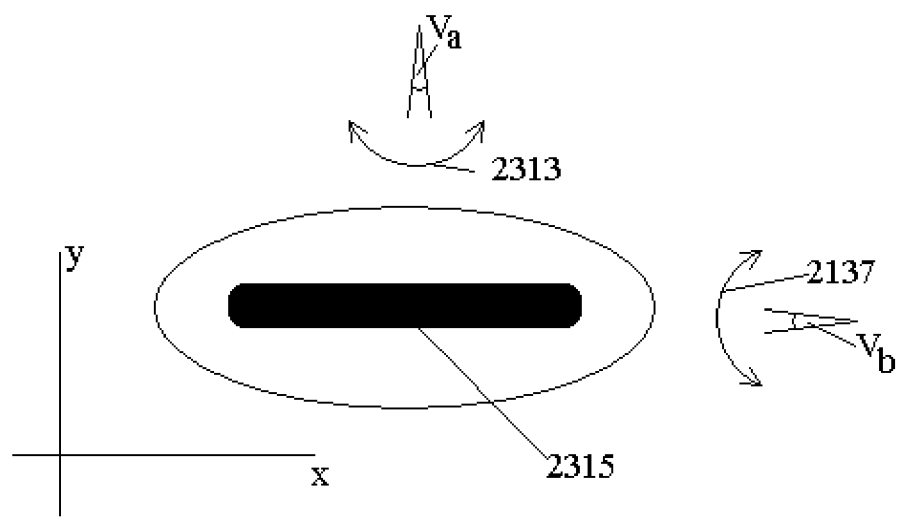
FIG. 81 is a description of advantageous and disadvantageous viewing positions according to embodiments of the present invention.

Reference is now made to FIG. 81 which is a self explanatory description of advantageous and disadvantageous viewing positions according to embodiments of the present invention.

Figure 82:
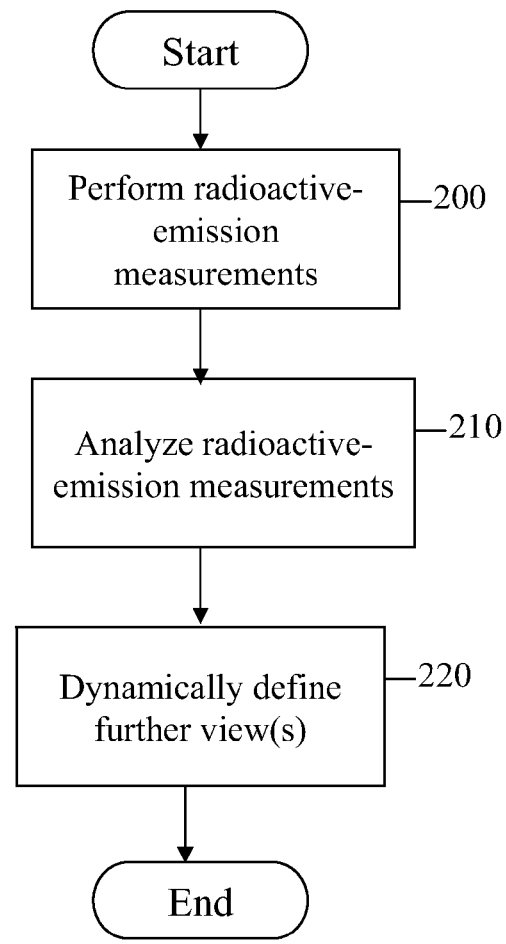
FIG. 82 is a simplified flowchart of a method of performing radioactive-emission measurements of a body structure, according to a preferred embodiment of the present invention.

Reference is now made to FIG. 82, which is a simplified flowchart of a method of performing radioactive-emission measurements of a body structure, according to a preferred embodiment of the present invention. In step 200, radioactive-emission measurements of the body structure are performed at predetermined views, preferably in vivo. Preferably the measurements are performed for diagnostic purposes. These predetermined views are selected prior to the measurement process, based on a model of the body structure being imaged. In the model more and less informative viewing directions have been identified. The predetermined views of step 200 preferably include those views expected to be informative, based on an analysis of the model.

Preferably the body structure is all or a portion of: a prostate, a heart, a brain, a breast, a uterus, an ovary, a liver, a kidney, a stomach, a colon, a small intestine, an oral cavity, a throat, a gland, a lymph node, the skin, another body organ, a limb, a bone, another part of the body, and a whole body.

In step 210 the radioactive-emission measurements are analyzed. Preferably the analysis includes one or more of:

1) Analyzing detector photon count(s)
2) Analyzing detector photon count rate(s) and rate changes from one view to another
3) Identifying detector saturation
4) Reconstructing a body structure image from emission measurements
5) Identifying geometric properties of the reconstructed image
6) Applying information-theoretic measures to the reconstructed image In step 220, further views for measurements are dynamically defined, based on the analysis performed in step 210. Preferably, each of the views is associated with viewing parameters selected from the group consisting of: detector unit location, detector unit orientation, collection angle, and measurement duration. Defining a view consists of providing a value for each of the parameters associated with the given view. The analysis (step 210) and/or dynamic view definition (step 220) may take into account external parameters including: measurement duration, time elapsed from the administration of the pharmaceutical to the measurement, radiopharmaceutical half life, radioactive emission type, and radioactive emission energy.

Each of these analysis techniques, and their application to view definition, is now discussed in turn. While each of the analysis/view determination techniques is discussed as a separate embodiment, multiple techniques may be used together to obtain the desired image quality.

In a first preferred embodiment, a photon count analysis ensures that the photon count at a given view yields an acceptable measurement error. As discussed above, the radiative emissions of the body structure being imaged is a Poisson process. In a Poisson process the Poisson noise grows inversely to the square root of the number of photons detected. In other words, if N photons are collected from a given view, the resulting signal to noise ratio (SNR) equals:

$$\text{SNR} = N/\sqrt{N} = \sqrt{N} \tag{12}$$

The unprocessed detector photon count at a given view thus provides significant information regarding the quality of the information obtained at a given view. If the photon Count is too low, it may be desired to continue to collect photons at the current location/orientation in order to obtain a satisfactory SNR. Alternatively, it may be determined that enough photons have already been collected, and to terminate the current view and move on to the next view.

The analysis is preferably performed by defining a global or local required measurement error, and comparing the square root of the obtained photon count to the required measurement error. Photon count analysis can be applied to the current and/or previous views. When a photon Count of a current view is found to be too low, the duration of the current view is preferably extended in order to obtain the required error value. When a photon count of a past view is found to be too low, an emission measurement at substantially the same location and orientation but having a longer-duration than previously is preferably performed. Alternately or additionally, the collection angle at the given location/orientation is preferably increased.

In an additional preferred embodiment, a detector photon count is analyzed to identify detector saturation at a given view. Preferably, when a detector is determined to have saturated, a new view or views are selected to reinforce those views that have saturated. In an alternate preferred embodiment, further views are defined to avoid highly-radiating portions of the body structure.

In a second preferred embodiment, a photon collection rate at a given view is analyzed to determine if it is within a specified range. In the preferred embodiment, the photon Count rate is used to identify regions of high or low interest. In prostate imaging, for example, a region of high interest may be identified by a high photon rate, indicative of a tumor. In a second example, a region of high interest may be identified in heart imaging by a low photon rate, indicative of non-functional tissues. After one or more areas of high and/or low interest are found, further views are preferably defined by selecting views to concentrate on regions of high interest and/or to avoid regions of low interest. It is thus possible to zoom in on a suspected pathology without repeating the emission measurement process.

In a further preferred embodiment, the analyzing of step 210 includes reconstructing a radioactive-emission density distribution of the body structure. Reconstruction may be performed according to any applicable technique known ii the art. The reconstruction is then used as the basis for further analysis.

Reconstruction based on the data collected from the predetermined views provides information regarding the quality of information obtained from the preceding measurements, and which further views are likely to be most informative.

Selecting new views based on reconstruction is intended to bring us into viewing from the more informative views or combinations of views.

Figure 83:
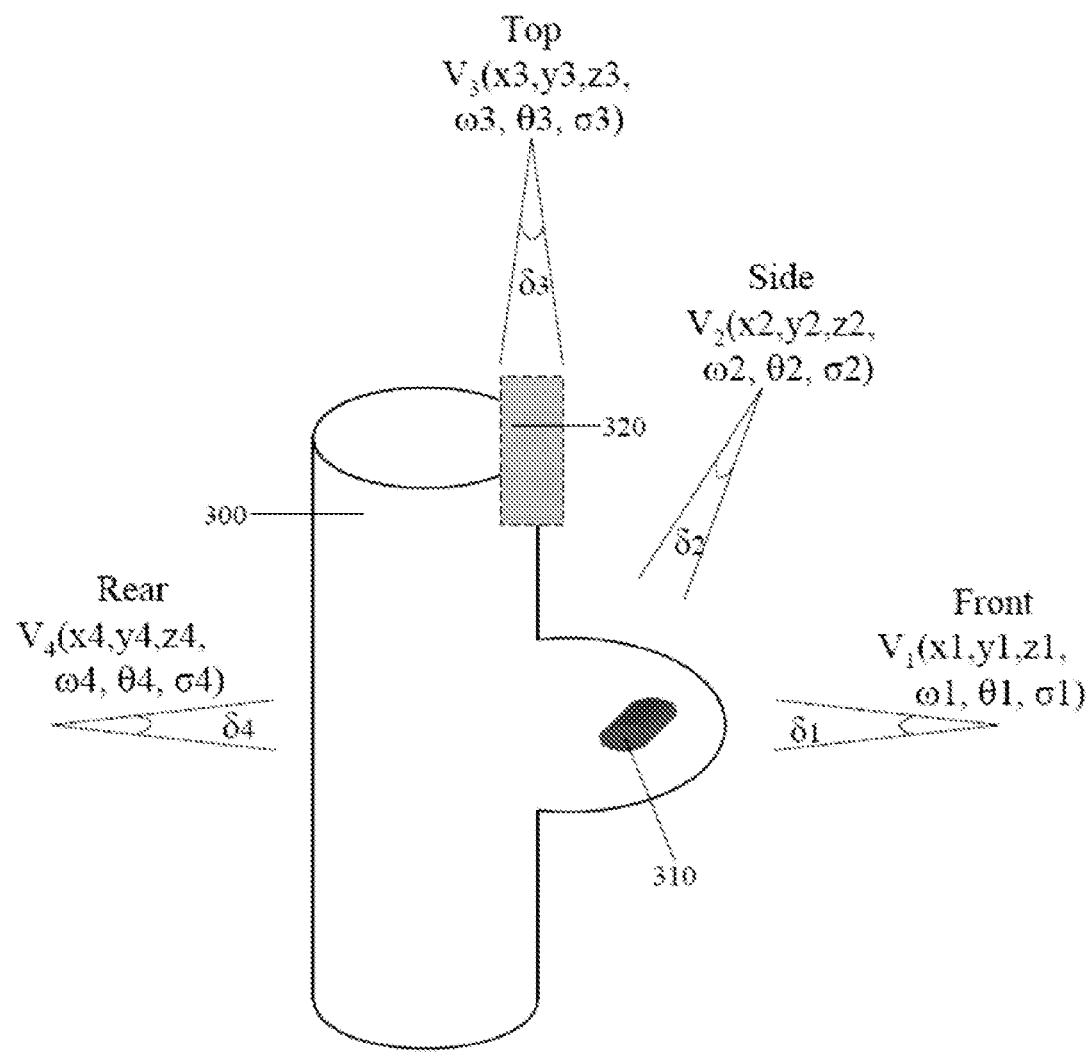
FIG. 83 shows an object shaped as a cylinder with a front protrusion, and having a high-remittance portion (hotspot).
Figure 84A:
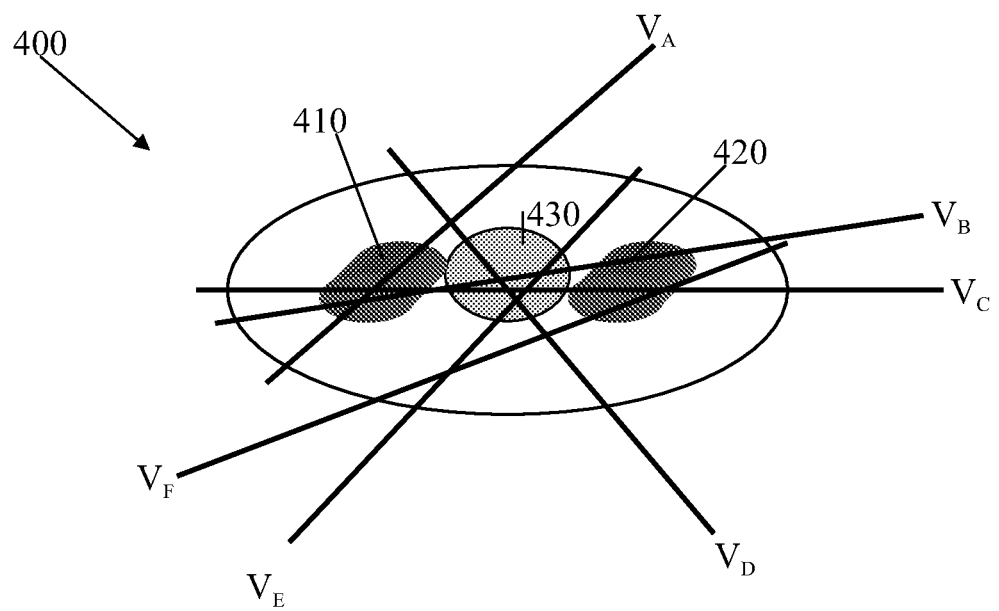
FIG. 84a illustrates an object having two high-emission regions of interest.
Figure 84B:
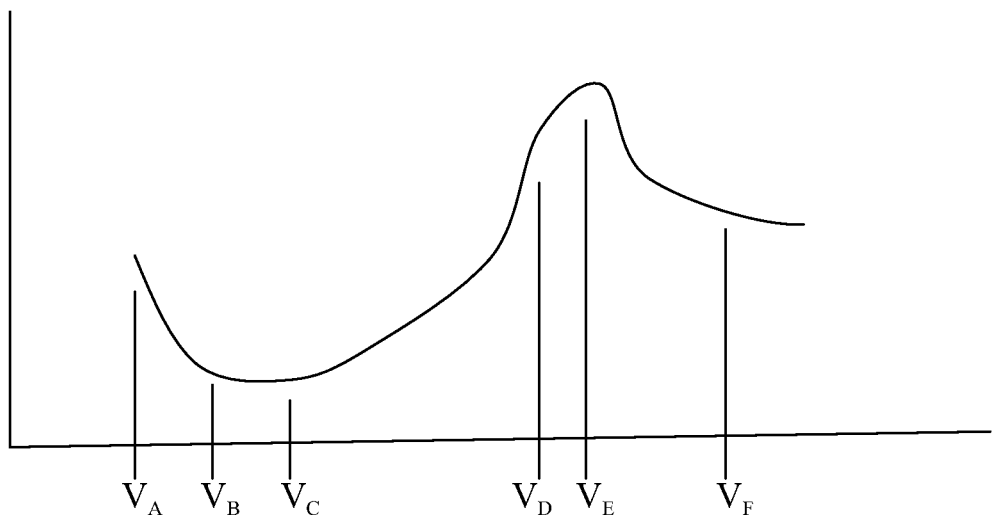
FIG. 84b illustrates the added information provided by each of views $V_A$ to $V_F$.

Reference is now made to FIGS. 83 and 84a-84b, which pictorially illustrate how different views provide differing types and quality of information. FIG. 3 shows an object 300 shaped as a cylinder with a front protrusion, and having a high-emittance portion (hotspot) 310. Foul views of object 300 are shown, which can be seen to provide different levels of information. Front views, such as $V_1$, provide little information regarding the shape of object 300 and have relatively little attenuation between the detector and hotspot 310. Side views, such as $V_2$, provide edge information regarding the object shape or profile, and when correlated with front views help locate hotspot 310 spatially within object 300. Top views, such as $V_3$, provide information regarding the cylinder edge region 320. Finally, rear views, such as $V_4$, are uninformative about the shape of object 300 and have high attenuation relative to hot region 310.

FIGS. 84a and 84b demonstrate how the proper selection of views may improve the quality of information obtained for the body structure, for example in distinguishing between two regions of interest within a given volume.

FIG. 84a illustrates an object 400 having two high-emission regions of interest (ROI), 410 and 420. For clarity the views $V_A$ to $V_F$ are shown as lines in FIG. 84a, however in practice they will each have a finite collection angle δ. The position of ROIs 410 and 420 are assumed to have been estimated based on a model of object 400 and/or a previously performed prescan. A goal of an aspect of the present invention is to select an additional new view or views which increase the information we have regarding the separation of ROIs 410 and 420 within object 400.

In simple terms, consider the object as having three regions: ROI 410 with intensity $I_1$, ROI 420 with intensity $I_2$, and a low-emission region 430 between the two ROIs with intensity $I_3$. The detected intensity at a given detector is proportional to $I_n/r_{ni}^2$, where $I_n$ is the emission intensity of region n and $r_i$ is the distance of region n from detector $V_i$.

FIG. 84b illustrates the added information provided by each of the shown views, $V_A$ to $V_F$. Views $V_B$ and $V_C$ collect emissions from all three regions, and are therefore least informative. Views $V_D$ and $V_E$ collect emissions from only low emittance region 430, and therefore provide most information regarding the location of each ROI within the volume and the separation between ROIs 410 and 420. Views $V_A$ and $V_F$ pass only through a single ROI, and therefore provide an intermediate level of information. It is a goal of the present invention to determine, while the emission measurements of the body structure are taking place, that views in the Vicinity of $V_D$ and $V_E$ are highly informative, and to add these further views to the measurement process.

A body structure reconstruction can be utilized in several ways to define further views. A first way is to identify interesting portions of the contour and structure of the reconstruction. For example, it is seen in FIG. 83 that top views are informative about edge region 320. Further top view measurements will therefore be informative the edge region 320, and may enable defining the edge more accurately.

In a preferred embodiment, the reconstruction is analyzed to identify textual edges within the reconstruction, and view definition preferably includes selecting views at an angle to the textural edges. In the preferred embodiment, the angle is a substantially sharp angle in order to provide information regarding the edge.

In another preferred embodiment, the reconstruction is analyzed to identify volumetric boundaries within the reconstruction, and view definition preferably includes selecting views at an angle to the volumetric boundaries. It is expected that the defined views will provide information regarding the boundary and differences in surrounding tissues on either side of the boundary. In the preferred embodiment, the angle is a substantially sharp angle.

Another way to utilize the reconstruction to define further views is to identify suspected organ targets within the reconstruction, and to select further view(s) in close proximity to the suspected organ targets. A suspected organ target is typically detected by identifying portions of the reconstruction whose emission intensity distribution and spatial characteristics are typical of a suspect region.

In a first preferred embodiment, a suspected organ target is defined as a high-emittance portion of the reconstruction. In a second preferred embodiment, a suspected organ target is defined as a low-emittance portion of the reconstruction.

In the preferred embodiment the further views are used immediately for radioactive-emission measurements. The results of the new measurements are then used in another analysis to define new further views for additional measurements. The radioactive-emission measurements may then be said to be performed iteratively.

Figure 85A:
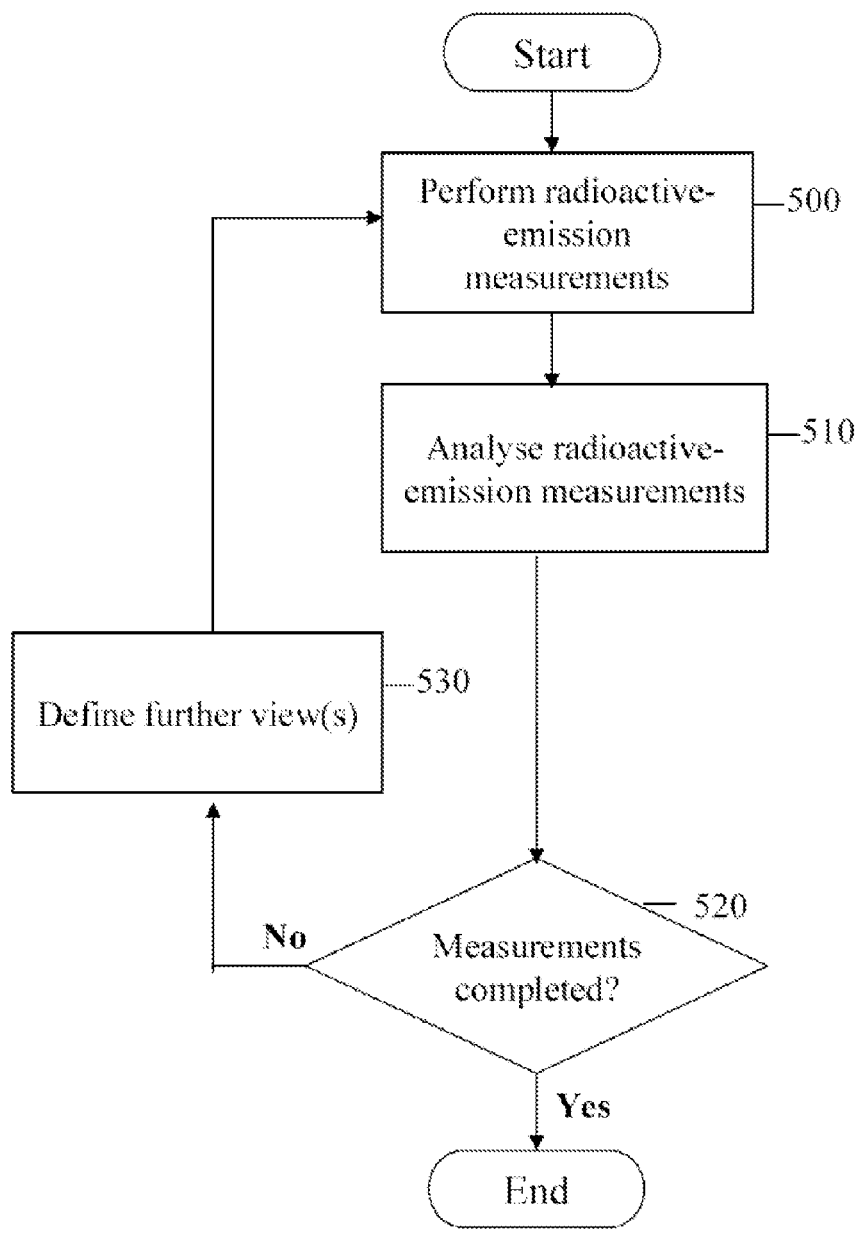
FIGS. 85a and 85b are simplified flowcharts of iterative methods of performing radioactive-emission measurements of a body structure, according to a first and a second preferred embodiment of the present invention.

Reference is now made to FIG. 85a, which is a simplified flowchart of an iterative method of performing radioactive-emission measurements of a body structure, according to a first preferred embodiment of the present invention. In step 500, radioactive-emission measurements of the body structure are performed at predetermined views. In step 510, an analysis is performed of the previously performed emission measurements. In step 520 a decision is made whether to continue with further measurements. If yes, in step 530 further views are defined based on the analysis. Subsequent iterations continue until the decision to end the emission measurement process. After the first iteration, the analysis performed at a given stage may include consideration of all or on part of the measurements performed during one or more previous iterations, in addition to the new measurements.

Figure 85B:
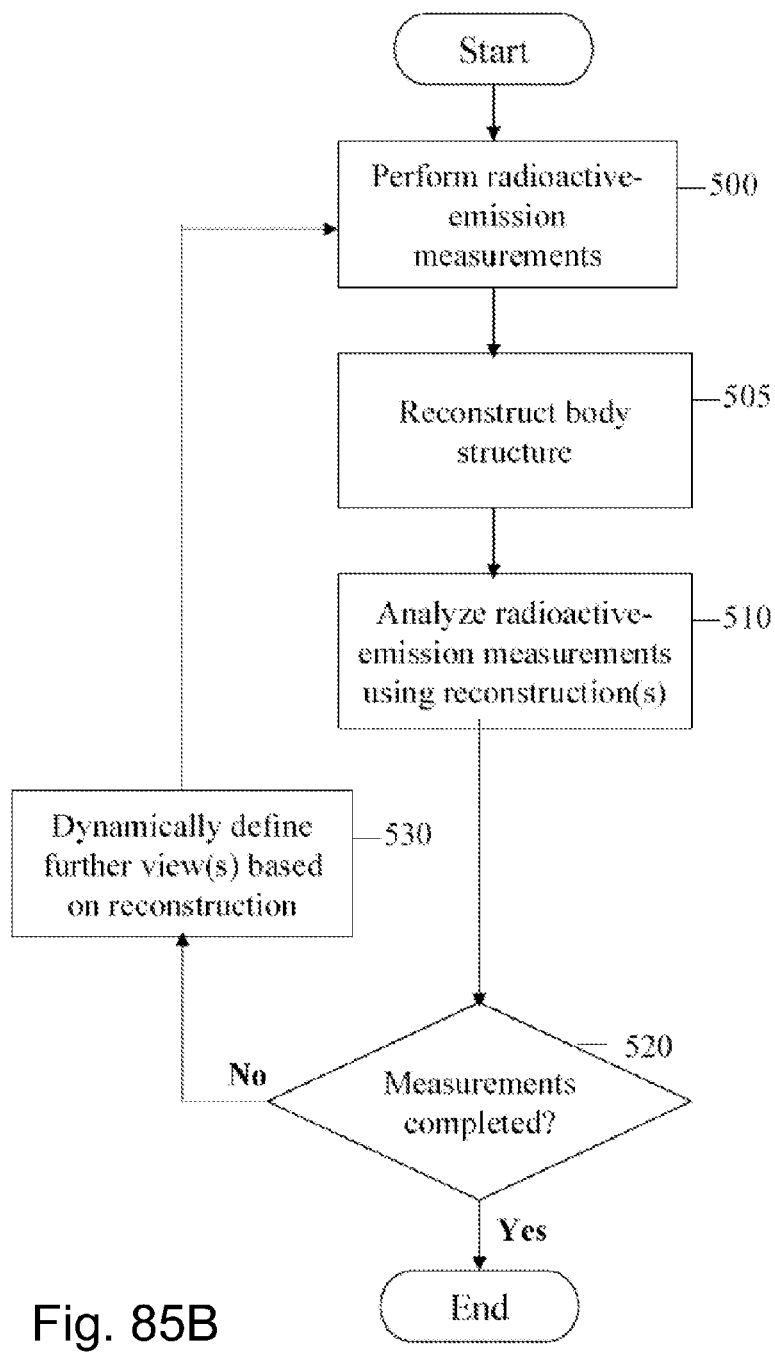

Reference is now made to FIG. 85b, which is a simplified flowchart of an iterative method of performing radioactive-emission measurements of a body structure, according to a second preferred embodiment of the present invention. In the present preferred embodiment, a reconstruction of the body structure is formed in step 505. The analysis step 510 is then performed utilizing data provided by the reconstruction(s).

Referring again to FIG. 82, preferably, analysis step 210 includes determining an accuracy of the reconstruction. Accuracy is preferably determined by analyzing the variance of the reconstructions formed over multiple iterations. Preferably, further views are defined in step 220 to concentrate on the region for which higher accuracy is required. Regions of the reconstruction having low variance provide a high degree of confidence regarding the accuracy of the reconstruction in the given region (where a portion may include the entirely of the body structure being imaged). Further views may be added to the current measurements until the variance is reduced to a required level.

Preferably, analysis step 210 includes determining a resolution of the reconstruction. Resolution is preferably determined by analyzing the full width at half maximum (FWHM) of peak values of the reconstruction. The FWHM is given by the distance between points at which the reconstructions reaches half of a peak value. Preferably, further views are defined in step 220 to concentrate on the region for which higher resolution is required.

An additional way to define future views using the reconstruction is on an information-theoretic basis. A quality function expressing an information theoretic measure is defined. The quality function rates the information that is obtainable from the body structure when one or more permissible views are added to current measurement process. Several examples of quality functions based on information-theoretic measures are discussed in detail below. The quality function is used to rate potential further views. The measurement process may then continue at those further views whose addition to the previous views yields a high rating.

Figure 86A:
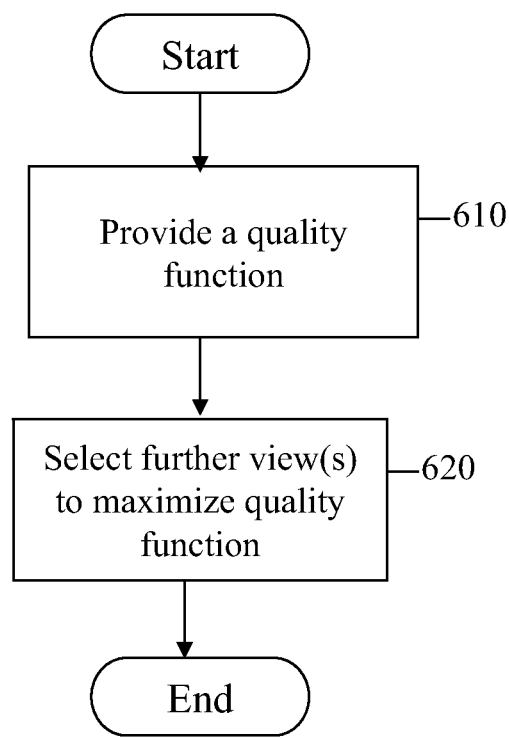
FIGS. 86a and 86b are simplified flowcharts of methods for dynamically defining further views, according to a first and a second preferred embodiment of the present invention.

Reference is now made to FIG. 86a, which is a simplified flowchart of a method for dynamically defining further views, according to a first preferred embodiment of the present invention. In step 610 a quality function is provided. The quality function expresses an information-theoretic measure which rates the quality of information obtainable from potential further views. In step 620 a set of further views is selected to maximize the quality function. Preferably the selected further views fulfill certain constraints; for example the further views may be selected from a predefined set or may be located in the vicinity of a region of interest within the body structure.

In the abovedescribed reconstruction-based analyses, the quality function is evaluated independently for a single reconstruction of the emission intensity of the body structure. However, quality functions may be defined which calculate the score for a given set in relation to one or more reconstructions and/or emittance models. As is further discussed herein, given an object or class of objects, emittance models may be devised to reflect expected or typical emission patterns for the given object.

For simplicity, the following discussion describes the evaluation of information-theoretic quality functions based on emittance models only. It is to be understood that at least one of the emittance models is a reconstruction of the body structure based on past measurements. Any remaining emittance models are provided externally, and may be based on general medical knowledge or on information gathered during a previous round of emission measurements of the body structure.

Figure 86B:
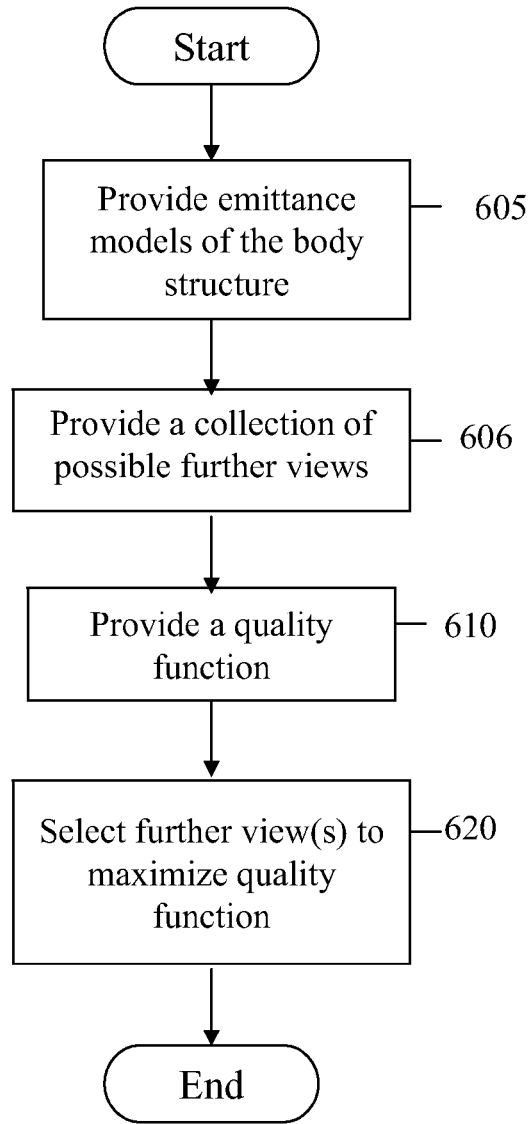

Reference is now made to FIG. 86b, which is a simplified flowchart of a method for dynamically defining further views, according to a second preferred embodiment of the present invention. The current method differs from the method of FIG. 86a by the addition of steps 605-606. In step 605 a set of one or more emittance models is provided (where the set includes one or more reconstructions of the body structure). An emittance model specifies the radiative intensity of each voxel in the body structure. As discussed above, some of the viewing parameters affect the radiative intensity of the voxels in the volume, for example the type of radiopharmaceutical and the time since administration of the radiopharmaceutical. Therefore, the emittance models provided in step 605 preferably correspond to the relevant viewing parameters. In step 606 a collection of possible further views of the body structure is provided. The collection of views includes possible further views for future measurements, preferably based on anatomical and other constraints. Furthermore, the quality function provided in step 610 may utilize multiple emission models.

In the preferred embodiment, one or more of the emittance models contains at least one high-emittance portion (i.e. hot region). A prostate containing a tumor, for example, may be modeled as an ellipsoid volume with one or more high-emittance portions.

In the preferred embodiment, one or more of the emittance models contains at least one low-emittance portion. A diseased heart may therefore be modeled as a heart-shaped volume with low-emittance portions.

Note that an emittance model need not contain high- or low-emittance portions, but may have a uniform intensity or a slowly varying intensity.

In a first preferred embodiment the quality function implements a separability criterion. The implementation and evaluation of the separability criterion for active view determination is performed substantially as is further described herein.

In a second preferred embodiment, the quality function implements a reliability criterion. The implementation and evaluation of the reliability criterion for active view determination is performed substantially as described herein.

Maximization of the quality function may be performed utilizing any method known in the art such as simulated annealing and gradient ascent. In the simulated annealing (SA) method, each point of the search space is compared to a state of some physical system. The quality function to be maximized is interpreted as the internal energy of the system in that state. Therefore the goal is to bring the system from an arbitrary initial state to a state with the minimum possible energy.

The neighbors of each state and the probabilities of making a transition from each step to its neighboring states are specified. At each step, the SA heuristic probabilistically decides between moving the system to a neighboring state s' or staying put in states. The probabilities are chosen so that the system ultimately tends to move to states of lower energy. Typically this step is repeated until the system reaches and acceptable energy level.

Gradient ascent, on the other hand, is based on the observation that if a real-valued function F(x), such as the quality function of the present embodiments, is defined and differentiable in a neighborhood of a point a, then F(x) increases fastest if one goes from a in the direction of the gradient of F at a, $\nabla F(a)$. It follows that if:

$$b = a + \gamma \nabla F(a) \quad (19)$$

for $\gamma > 0$ a small enough number, then $F(a) \leq F(b)$. Gradient ascent starts with a guess $x_0$ for a local maximum of F, and considers the sequence $x_0, x_1, x_2, \ldots$ such that:

$$x_{n+1} = x_n + \gamma \nabla F(x_n), n \geq 0. \quad (20)$$

Since $F(x_0) \leq F(x_1) \leq F(x_2) \leq \ldots$, the sequence $(x_n)$ is expected converges to a local maximum.

Preferably, the set of views selected with the quality function is increased by at least one randomly selected view. The randomly selected view(s) increase the probability that the quality of information obtained with the further views is maximized globally rather than locally.

As discussed above, selecting the best set of size N from amongst a large set of candidate projections is computationally complex. Since the size of the collection of views and of the required set may be large, a brute force scheme might not be computationally feasible.

In an additional preferred embodiment, a so-called "greedy algorithm" is used to incrementally construct larger and larger sets, until the required number of further views is defined. When multiple further views are required, it is computationally complex to maximize the quality function over all possible combinations of further views. The greedy algorithm reduces the computational burden by selecting the further views one at a time. The algorithm starts with a current set of views, and for each iteration determines a single view that yields the maximum improvement of the set score (hence the name "greedy").

In theoretical terms, assume ρ(•) is the quality measure we are using for the view selection, and assume without loss of generality that we are trying to maximize this measure. We gradually build a set W of projections as follows. We start with an empty set W=Ø, and at every stage choose the projection that maximizes the quality measure when added to the current set:

$$W \leftarrow \arg\max_{W'}\{\rho(W') | W'=W\cup\{\phi\}, \phi \in \Phi\} \quad (21)$$

In other words, during a given iteration, a respective score is calculated for a combination of the previous set with each of the views which is not a member of the current set. The current set is then expanded by adding the view which yielded the highest respective score, and the expanded current set serves as the input to the following iteration. Thus the number of times the scoring function is calculated per iteration drops from iteration to iteration. For a large collection of possible views, the greedy algorithm reduces the total number of computations required for set selection.

Figure 87:
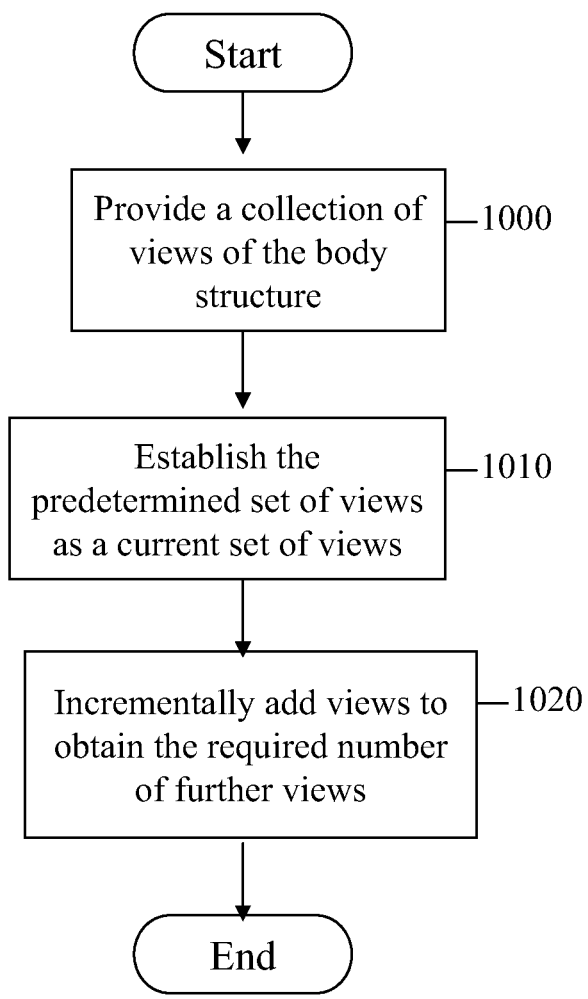
FIG. 87 is a simplified flowchart of an iterative method for selecting further views, according to a preferred embodiment of the present invention.

Reference is now made to FIG. 87, which is a simplified flowchart of an iterative "greedy" method for defining further views, according to a preferred embodiment of the present invention. The greedy algorithm is implemented substantially as described herein. In step 1000 a collection of views of the body structure is provided. The collection of views includes possible further views for future measurements, preferably based on anatomical and other constraints. In step 1010, the set of views used for the previous emission measurements is established as a current set of views. In step 1020 the view set is incrementally increased by a single further view during each iteration, until the required number of further views has been selected.

Figure 88:
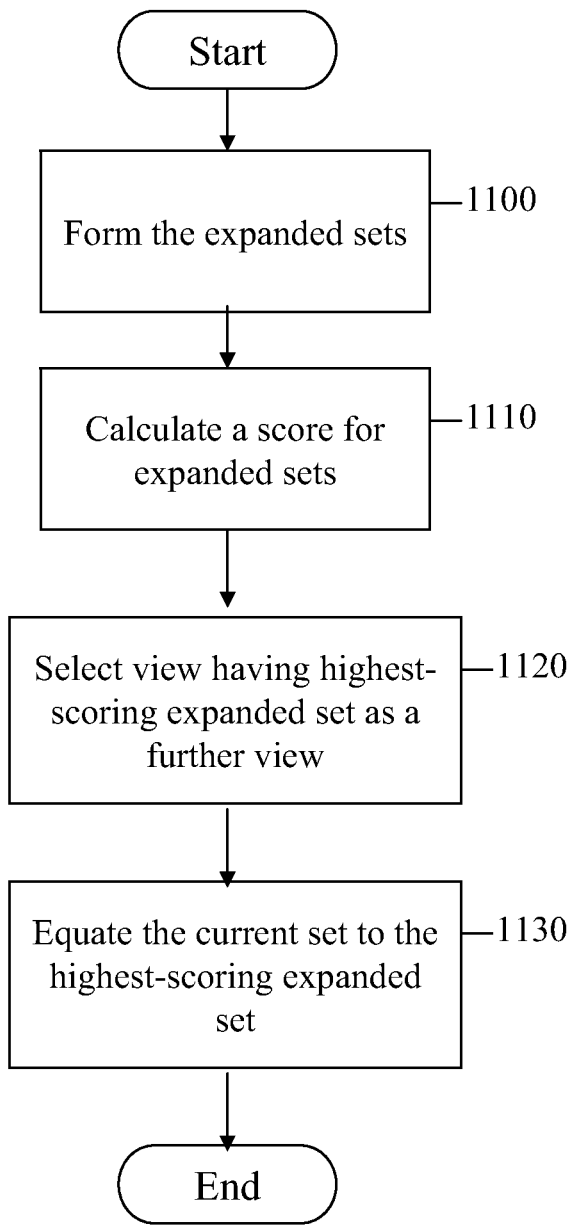
FIG. 88 is a simplified flowchart of a single iteration of a view selection method, according to a preferred embodiment of the present invention.

Reference is now made to FIG. 88, which is a simplified flowchart of a single iteration of the view selection method of FIG. 87, according to a preferred embodiment of the present invention. The method of FIG. 88 expands the current set of views by a single view. The method begins with a current set of views, which is the predetermined set (step 1010 above) for the first iteration of the greedy algorithm, or the set formed at the end of the previous iteration (step 1120 below) for all subsequent iterations. In step 1100, a respective expanded set is formed for each view not yet in the current set of views. A given view's expanded set contains all the views of the current set of views as well as the given view. In step 1110, a respective score is calculated for each of the expanded sets using the quality function. In step 1120, the view which yielded the highest-scoring expanded set is selected as a further view, to be used for further radioactive emission measurements. Finally, in step 1130, the current set is equated to the highest-scoring expanded set by adding the selected view to the current set. The newly formed current set serves as an input to the subsequent iteration, until the desired number of views is attained.

Figure 89:
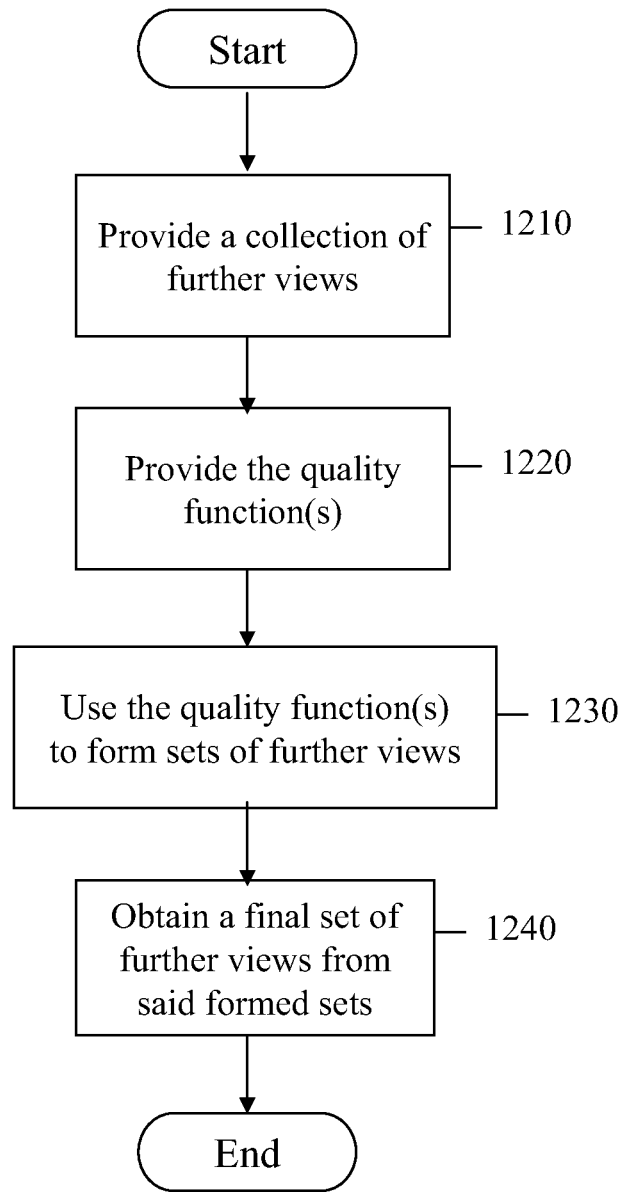
FIG. 89 is a simplified flowchart of a method for dynamically defining further views, according to a third preferred embodiment of the present invention.

Reference is now made to FIG. 89, which is a simplified flowchart of a method for dynamically defining further views, according to a third preferred embodiment of the present invention. In step 1210, a collection of possible further views for performing radioactive-emission measurements of the body structure are provided. Each of the views is associated with at least one viewing parameter. Preferably the viewing parameters consist of at least one the following: detector unit location, detector unit orientation, collection angle, and measurement duration.

In step 1220 at least one quality function is provided. Each quality function is for evaluating sets of views, essentially as described above. A single quality function may be used to select several sets of views, where each set of views contains a different number of views.

In step 1230, multiple sets of further views (where a set may include a single further view) are formed from the collection of views, using the quality function(s) provided in step 1220. In a first preferred embodiment, each of the sets is formed using a different one of the quality functions. In an alternate preferred embodiment, one or more of the quality functions are used to form more than one set of views, where sets formed with the same quality function have differing numbers of views.

In step 1240, a selected set of views is obtained from the sets formed in step 1230.

In a first preferred embodiment, the final set of views is obtained by choosing one of the sets formed in step 1230 using a set selection criterion. For example, a respective set is formed in step 1230 for the separability and reliability criteria independently. A set selection criterion which calculates an overall performance rating for a given set taking both criteria into account is defined, and the formed set with the highest overall rating is selected as the final set.

In another preferred embodiment, the selected set of views is obtained by merging the sets formed in step 1230 according to the relative importance of the respective quality function used to form each set.

In the preferred embodiment, the method further consists of providing at least one emittance model and/or reconstruction representing the radioactive-emission density distribution of the volume, and of evaluating with at least one of the quality functions of step 1220 is performed in r elation to the emittance models.

As discussed above, since each view is associated with one or more parameters, the selected set yields a group of parameter values for performing effective detection of the intensity distribution of the body stricture. For example, if each view is associated with a view location parameter the selected set defines a set of locations for collecting emission data from an object, in order to provide a high-quality reconstruction of the intensity distribution of the body structure.

Figure 90:
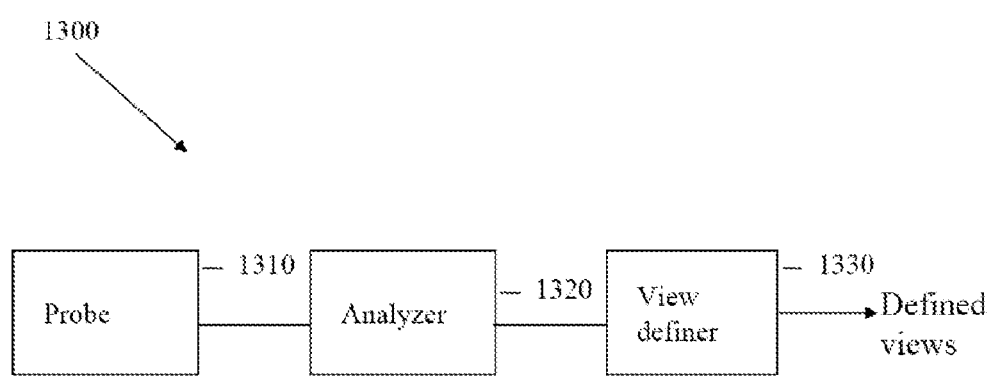
FIG. 90 is a simplified block diagram of measurement unit for performing radioactive-emission measurements of a body structure, according to a preferred embodiment of the present invention.

Reference is now made to FIG. 90, which is a simplified block diagram of measurement unit for performing radioactive-emission measurements of a body structure, according to a preferred embodiment of the present invention. Measurement unit 1300 includes probe 1310, analyzer 1320 and view definer 1330. Probe 1310 performs the radioactive-emission measurements of the body structure. Radioactive-emission-measuring probe 1310 preferably comprises several detecting units, which may be of different geometries and different collection angles δ, within a housing. Preferably, the orientation and/or collection angle of the individual collimators is controllable. Analyzer 1320 analyzes the radioactive-emission measurements obtained from probe 1310. View definer 1330 dynamically defines further views for measurements, based on the analysis provided by analysis unit 1320. The analysis and view definition are performed substantially as described above.

The abovedescribed methods for radioactive-emission measurements of a body structure begin by performing measurements at a predetermined set of views. The results of the initial measurements are then analyzed and further views are defined.

The initial set of views is preferably selected based on information theoretic measures that quantify the quality of the data fed to the reconstruction algorithm, in order to obtain the best data for reconstructing a three-dimensional image of the body structure, as described herein. The following section concentrates on the second step of the process, namely, obtaining the optimal and permissible set of initial views for performing the radioactive-emission measurements of the body structure. The initial predetermined set of views is denoted herein the optimal set of views.

The initial predetermined set of views is preferably selected in accordance with the method of the view selection as described herein. Preferably the initial predetermined set of views is selected on the basis of one or a combination of the separability, reliability, and uniformity criteria.

The abovedescribed methods may each be embodied as a computer program stored on a computer-readable storage medium. In the preferred embodiment, computer-readable storage medium contains a set of instructions for defining views for radioactive-emission measurements of the body structure. An analysis routine analyzes the radioactive-emission measurements obtained from a radioactive-emission-measuring probe, and a view definition routine dynamically defines further views for measurements, based on the analyzing.

By enabling high-quality reconstruction based on data collected from a limited collection of views, the abovedescribed view set selection techniques present a way to resolve the current conflict between the relatively large-pixel detectors needed for measurement speed and data processing considerations, with the small-pixel detectors needed until now to obtain a high-resolution reconstruction. The data obtained using the selected set of views enables a high-resolution reconstruction from a smaller number of measurements. Additionally, reconstructing the intensity distribution from a smaller quantity of collected data simplifies the computational process. The abovedescribed embodiments are particularly suitable for medical imaging purposes, where a high-resolution image is needed and it is desired to minimize the difficulties of the patient undergoing the diagnostic testing or treatment.

Voxel Dynamic Modeling

Dynamic modeling is a technique in which the parameters of a dynamic system are represented in mathematical language. Dynamic systems are generally represented with difference equations or differential equations. Measurements obtained from the modeled system can then be used to evaluate the values of parameters of interest that cannot be measured directly.

In the present case, the system being modeled is the body structure (or portion thereof) being imaged. During imaging, the emittance from a given voxel is affected by the chemical properties of the radiopharmaceuticals well as by the half-life of the tracer, as well as by the nature of the body structure being imaged. For example, the chemical properties of the antibody to which the tracer is attached govern factors such as binding to the tissue, accumulation, and clearance rate.

The goal of the presented models is to recover the kinetics per voxel of one or more parameters of interest. Each of the models reflects a different mechanism for the diffusion of the radiopharmaceutical into and out of the voxel, as well as the possibility of accumulation within the voxel. For a given measurement process the dynamic model should be selected to match the known properties of the radiopharmaceutical being used.

Figure 91:
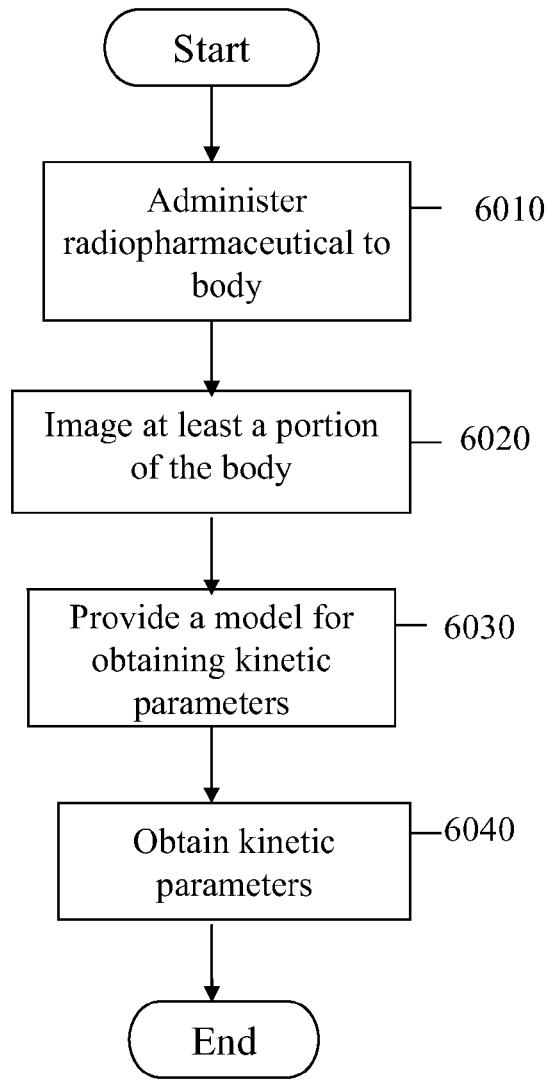
FIG. 91 is a simplified flowchart of a method for measuring kinetic parameters of a radiopharmaceutical in a body, according to a preferred embodiment of the present invention.

Reference is now made to FIG. 91, which is a simplified flowchart of a method for measuring kinetic parameters of a radiopharmaceutical in a body, according to a preferred embodiment of the present invention. In step 6010, the radiopharmaceutical is administered to the body. In step 6020, the body or a portion of the body are imaged. In step 6030, a model is provided for obtaining kinetic parameters from the imaging is provided. Several preferred embodiments of dynamic models are presented below. Finally, in step 6040, the kinetic parameters are obtained by applying the measurements to the provided model in order to extract the value of the required parameter(s). The kinetic parameters may provide information on factors such as actual uptake, rate of uptake, accumulation, and clearance of the radiopharmaceutical, which in turn provide information about the health of tissue in the voxel. The obtained parameter values can thus be analyzed to evaluate the health of the imaged body structure and of other portions of the body (for example renal functioning). (See description of expert system) The parameter values can also be analyzed and used to control future administration of the radiopharmaceutical (See description of closed loop injection system). The parameters obtained in step 6040 preferably include at least one of: local (in-voxel) representation of blood pool, blood flow, and diffusion to and/or from the local tissue as representative of function (e.g. viability).

Three preferred embodiments of dynamic models for provision in step 6030 are now presented. The following rationale and assumptions are common to all of the presented embodiments.

The analysis is of one voxel versus the rest of the body, not of the entire organ.

The dynamic model relates the per pixel emission levels to factors such as the blood in voxel, the tissue in voxel (and uptake from blood), and blood re-fill (perfusion/flow).

An additional assumption is that the amount of the tracer in the voxel is insignificant compared with the rest of the body and with the global blood pool. Therefore, the voxel in the region of interest (ROI) is affected by the global blood pool, but does not affect it. As a result, the concentration of tracer in the global blood pool can be recovered separately by one or more of: modeling the known kinetics given the exact injected dose, measuring the concentration at a pre-identified blood region using the imaging equipment, or by taking blood samples over time.

It is also assumed that the concentration of the tracer in the global blood may be controlled in a complex fashion by various injection profiles, such as:

1) Bolus injection
2) Constant drip
3) Smart injection—in which the radiopharmaceutical is injected in a controlled manner over time. The smart injection profile may be predetermined, or responsive to external events and/or feedback from the imaging equipment (see closed loop description). For example, rather than injecting a single bolus dose of radiopharmaceutical, one can inject a tenth of the dose for each of a series of ten injections. Examples of smart injection profiles are described below.

It is assumed that in ischemic conditions, not enough blood flow reaches the voxel, thus the concentration of the tracer in the blood of that voxel is different than in global blood pool. For example, if oxygen is the tracer, then ischemic region has lower oxygen concentration in the capillaries than in global blood pool due to poor refill.

An additional assumption is that the processes affecting the tracer concentration are slower than fractions a second, so that the volume and flow values (as defined below) relate to an average over the heart cycle. Thus gating will not separate the uptake into the tissue for different time slices in the heartbeat. Gated analysis (which is synchronized with the heart cycle) may be developed for fast processes which do not involve slow accumulation in the muscle tissue, or, alternatively, model the accumulation, both of which requires motion compensation.

A final assumption is that each voxel is large enough so that variables may be defined to relate to the voxel structure in global terms. The dynamic models described below are for voxels having a millimetric size, which are therefore significantly larger than the blood vessels (unlike during imaging of blood vessels). The models therefore include parameters for both blood and tissue parameters. In cases where a very high-resolution reconstruction (i.e. sub-millimetric) is required, a different model should be applied to handle voxels which are pure blood (e.g. voxels inside coronaries).

The following parameters are defined for all of the dynamic model embodiments presented below:

1) Vt—Volume of tissue in voxel.
2) Vb—Volume of blood within the capillaries in the given voxel. Vb is normally constant for a given tissue type, but may vary for different tissue types such as blood vessel, connective tissue, or tumor before or after angiogeniesis
3) V—Voxel volume. The voxel volume is the slum of the tissue volume and blood volume within the voxel:

$$V = Vt + Vb \quad (1)$$

V is a fixed value dictated by the imaging equipment (i.e. camera) performing the radioactive-emission measurements.

4) Rb—Density of blood within the voxel. Rb is the ratio of the volume of the blood in the voxel to the total voxel volume:

$$Rb = Vb/V \quad (2)$$

For example, in cross section, the diameter of a capillary is about 10-15 um. To allow diffusion to cells the capillaries are spaced about 50-150 um apart. Therefore, it is reasonable to assume that healthy tissue has Rb~1-5%

5) F—Blood flow to voxel. It is assumed that blood flow is not affected by neighboring voxels (i.e. blood flow is of "fresh" blood from the arteries).

6) Cb—Tracer concentration in blood within the voxel (reflects the capillaries in the voxel).

7) Ct—Tracer concentration in tissue within the voxel.

8) C—Tracer concentration in voxel, as measured by the imaging equipment.

9) Cg—Tracer concentration in global blood. The concentration in the global blood supply is assumed to be given. C may be determined with a separate model, or by measuring the global blood concentration directly. A fill model of Cg should reflect many of the patient's conditions, including cardiac output, prior diseases (such as metabolic disorders or diabetes), hyper/hypo-fluid volume, hyper/hypo-blood pressure, liver and/or kidney function, drugs (diuretics), and so forth.

Note that all of the above parameters other than Cg are defined per voxel.

Figure 92:
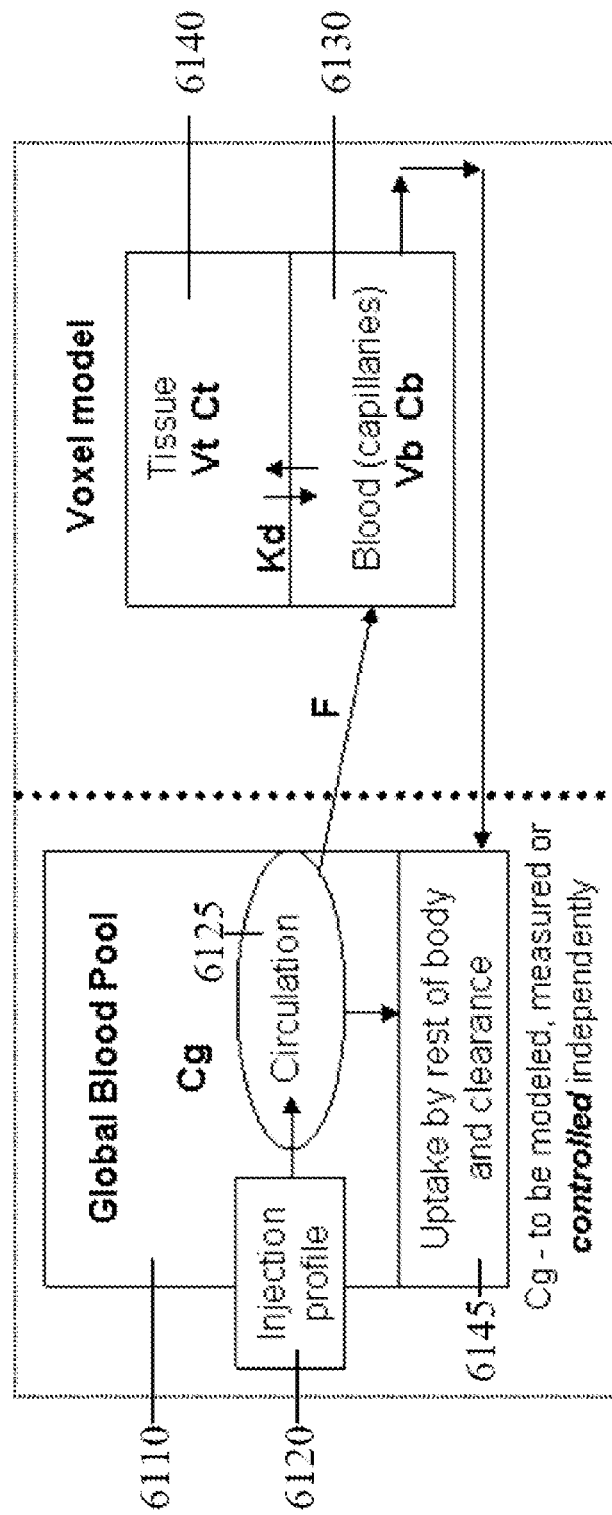
FIG. 92 is a schematic representation of a dynamic model of a voxel, according to a first preferred embodiment of the present invention.

Reference is now made to FIG. 92, which is a schematic representation of a dynamic model of a voxel, according to a first preferred embodiment of the present invention. The present embodiment (denoted herein model 1) assumes symmetric diffusion (i.e. the tracer diffusion coefficients into and out of the voxel are equal), and that there is no accumulation of the tracer within the voxel. FIG. 92 illustrates the role of each of the parameters described above.

The radioactive pharmaceutical is introduced into the global blood pool 6110 by injection according to an injection profile 6120. The radiopharmaceutical is conveyed to the voxel via the circulatory system 6125. The radiopharmaceutical flows through the voxel via the capillaries 6130 running through the voxel at flow rate F. Diffusion from the capillaries 6130 to the voxel tissue 6140 (uptake) and from the voxel tissue 6140 to the capillaries 6130 (release) occurs with a common diffusion coefficient Kd. Kd is an effective coefficient which takes into account both the uptake and outtake diffusion coefficients, and the Surface area to volume ratio of the capillaries 6130. The remainder of the pharmaceutical is dispersed to the rest of the body for uptake and clearance 6145.

Similar or identical components are indicated with the same reference numbers throughout the figures.

Model 1 assumes tracer delivery to the voxel by diffusion to and from the local tissue, rather than by accumulation and dissolution. Therefore, model 1 can serve for applications with materials like Thallium and CardioTech, but not with Mibi which accumulates due to different diffusion rates in and out of the tissue. Models 2 and 3, which are presented below, allow for accumulation, and are therefore more suitable for radiopharmaceuticals such as Mibi.

Equations 3-5 present the relationship between the kinetic parameters for model 1:

$$C = \frac{Ct \cdot Vt + Cb \cdot Vb}{V} \quad (3)$$
$$= Cb \cdot Rb + Ct \cdot (1 - Rb)$$

$$\frac{dCt}{dt} = Kd(Cb - Ct) \quad (4)$$

$$\frac{dCb}{dt} = \frac{F}{Vb}(Cg - Cb) - Kd(Cb - Ct) \quad (5)$$

Initial condition: $Ct = 0, Cb = 0$

C is measured dynamically by the imaging equipment and Cg is determined separately by measurement or independent modeling from the art.

Figure 93:
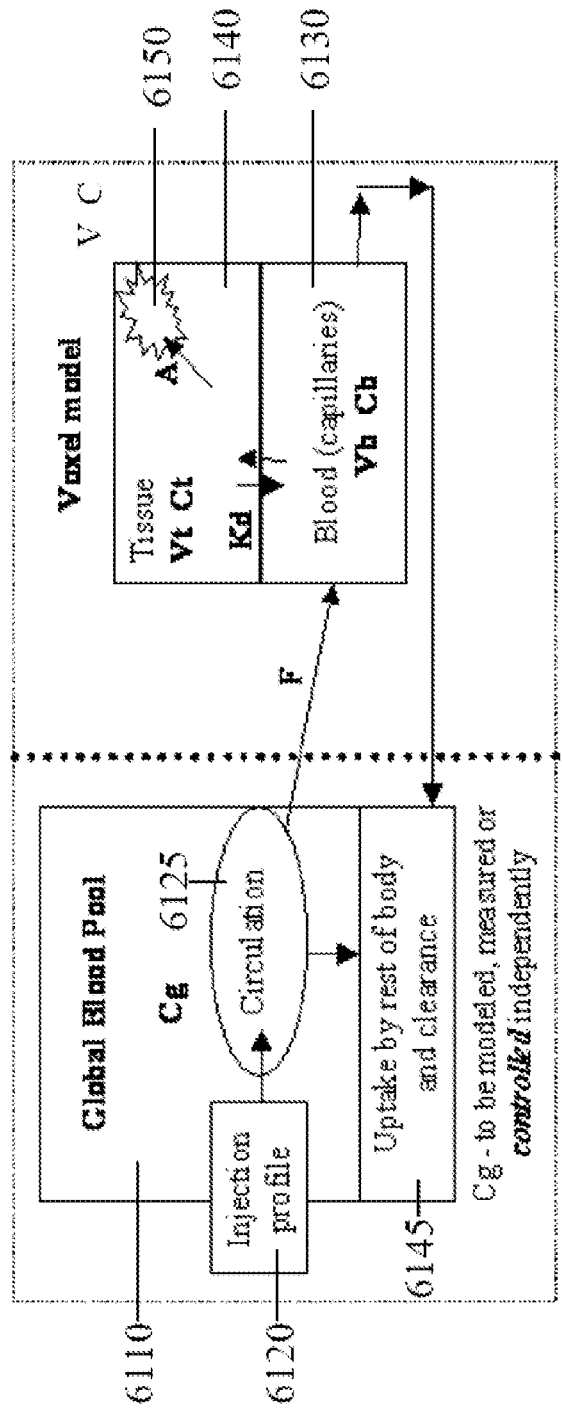
FIG. 93 is a schematic representation of a dynamic model of a voxel, according to a second preferred embodiment of the present invention.

Reference is now made to FIG. 93, which is a schematic representation of a dynamic model of a voxel, according to a second preferred embodiment of the present invention. The present embodiment (denoted herein model 2) assumes symmetric diffusion, with a diffusion coefficient of Kd. As in model 1, Kd is an effective coefficient which takes into account both the uptake and outtake diffusion coefficients, and the surface area to volume ratio of the capillaries 6130. However, in contrast with model 1, model 2 assumes that a fraction 6150 of the tracer concentration within the tissue is accumulated and is not diffused back to blood (for example by metabolism). The tracer accumulation within the voxel occurs at a rate of A.

Equations 6-9 present the relationship between the kinetic parameters for model 2:

$$C = \frac{Ct \cdot Vt + Cb \cdot Vb}{V} + Accum \quad (6)$$
$$= Cb \cdot Rb + Ct \cdot (1 - Rb) + Accum$$

$$\frac{dCt}{dt} = Kd(Cb - Ct) - A \cdot Ct \quad (7)$$

$$\frac{dCb}{dt} = \frac{F}{Vb}(Cg - Cb) - Kd(Cb - Ct) \quad (8)$$

$$Accum = \int_0^t A \cdot Ct \, dt \quad (9)$$

Initial conditions $Ct = 0, Cb = 0, Accum = 0$

Figure 94:
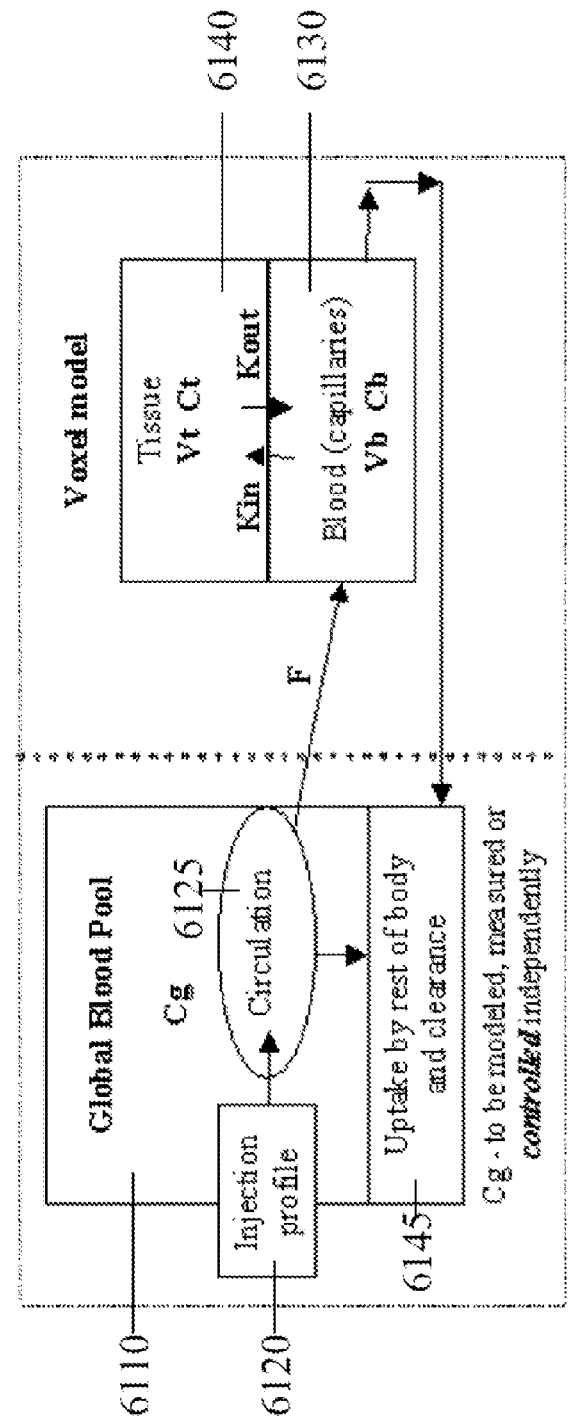
FIG. 94 is a schematic representation of a dynamic model of a voxel, according to a third preferred embodiment of the present invention.

Reference is now made to FIG. 94, which is a schematic representation of a dynamic model of a voxel, according to a third preferred embodiment of the present invention. The present embodiment (denoted herein model 3) assumes asymmetric diffusion, with uptake and release occurring according to the blood concentration (vs. zero) for uptake, and to the tissue concentration (vs. zero) for release, not according to the difference in concentrations (blood vs. tissue) as in model 1. Transport to the tissue is modeled by a diffusion coefficient of Kin, depending only on the outside concentration of capillary blood. Outgoing transport is modeled by a diffusion coefficient of Kout for outgoing transport, depending only on the internal (tissue) concentration. This way, accumulation is described by a high Kin and a low Kout. Kin and Kout are effective coefficients, which account for the surface area to volume ratio of capillaries.

Equations 10-12 present the relationship between the kinetic parameters for model 3:

$$C = \frac{Ct \cdot Vt + Cb \cdot Vb}{V} \quad (10)$$
$$= Cb \cdot Rb + Ct \cdot (1 - Rb)$$

$$\frac{dCt}{dt} = Kin \cdot Cb - Kout \cdot Ct \quad (11)$$

$$\frac{dCb}{dt} = \frac{F}{Vb}(Cg - Cb) - Kin \cdot Cb + Kout \cdot Ct \quad (12)$$

Initial conditions $Ct = 0, Cb = 0$

Models 2 and 3 are suitable for use with tracers like Thallium and Mibi, since they do not assume symmetric diffusion to/from the local tissue, but rather allow accumulation.

Regarding the parameters of the abovedescribed dynamic models, it may be possible to attribute the physiological meaning as follows:

1) F may correspond to perfusion

2) Kd+A may correspond to viability and metabolism (Model 2)

3) Kin may correspond to viability (Model 3)

Referring again to FIG. 92, in step 6040 the kinetic parameters for the voxel are obtained by applying the measured values to the provided model and extracting the value of the required parameters. Parameter extraction may be performed utilizing any technique known in the art, such as numerical analysis. Repeated measurements may be made of the given voxel, and the parameters calculated with increasing accuracy.

In a preferred embodiment, parameter extraction the dynamic system is provided in step 6030 as an analogous RLC electronic circuit. An RLC circuit is an electrical circuit consisting of resistors (R), inductors (L), and capacitors (C), connected in series and/or in parallel. Any voltage or current in an RLC circuit can be described by a second-order differential equation. Since all of the abovedescribed models present the voxel kinetic parameters as a second order system, the dynamic model provided in step 6030 may be described as an arrangement of resistors, capacitors, and inductors.

Voltage analysis of an RLC circuit is based on expressing the voltage over each of the circuit elements as a function of the circuit current as follows:

$$\text{Resistor:} V_R(t) = R \cdot i(t) \quad (13)$$

$$\text{Capacitor:} V_C(t) = \frac{1}{C} \int_{-\infty}^{t} i(\tau) d\tau \quad (14)$$

$$\text{Inductor:} V_L(t) = L \frac{di}{dt} \quad (15)$$

Figure 95:
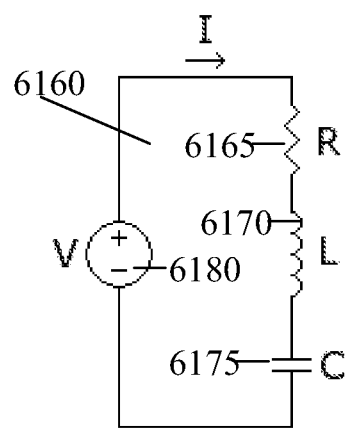
FIG. 95 is a circuit diagram of a series RLC electronic circuit.

As an example of RLC circuit analysis, consider the series RLC circuit 6160 shown in FIG. 95. RLC circuit 6160 consists of resistor 6165, inductor 6170, and capacitor 6175 connected in series, with an input voltage provided by voltage source 6180. In a series RLC circuit, the total voltage drop over the circuit is the sum of the voltage drop over each of the circuit elements, so that:

$$V(t) = R \cdot i(t) + L \frac{di}{dt} + \frac{1}{C} \int_{-\infty}^{t} i(\tau) d\tau \quad (16)$$

and:

$$\frac{dV}{dt} = L \frac{d^2 I}{dt^2} + R \frac{di}{dt} + \frac{1}{C} i(t) \quad (17)$$

Presenting the dynamic model as an RLC circuit enables using well-known circuit analysis techniques to derive the values of the desired parameters based on the measurements, and to analyze the behavior of the dynamic system. In terms of the abovedescribed dynamic modeling, the voltage, V, represents the administered radiopharmaceutical, and dV/dt represents the rate of change of the administered radiopharmaceutical, that is the administration protocol. The circuit function (e.g. the right hand side of equation 17) is analogous to the obtained image. Since the obtained image is dependent on Ø, the probability that a photon emitted by the given voxel is detected by the imaging equipment, the circuit function is a functional of Ø. The RLC analogy can thus be used in order to determine the radiopharmaceutical input function, dV/dt, which optimizes Ø.

Possible forms for dV/dt include bolus injection (V(t) is a single pulse at t=0), constant drip (V(t) is a constant), and smart injection profile. Following are non-limiting examples of smart injection profiles:

1) Randomly (e.g. in the range of about every 1 to 200 sec)

2) Periodically every T seconds

3) Synchronized to the camera acquisition cycle. For example, if the camera produces a full volume scan every 5 seconds the injections are synchronized with each repetition of the scan. Synchronizing with camera acquisition allows better spatio-temporal coverage, as the injection and the scanning plans may be optimized together.

4) Synchronized to motion-related events. Motion-related events may include one or more of expiration, inspiration, cardiac movement, stomach contraction, gastro-intestinal movement, joint movement, organ movement, and so forth. For example, motion-synchronized injection may be used to inject and/or acquire during a relatively stable time period or a relatively motion-intensive time period.

5) Synchronized to physiological events (which may be acquired by another system). Physiological events may include a change in the activity of an organ or tissue (such as $O_2/CO_2$ concentration), glucose concentration, changes in perfusion, electrical activity (ECG, EMG, EEG, etc. . . . ), neuronal activity, muscular activity, gland activity, and so forth.

6) Synchronized to an external event, for example to an external stimulation (e.g. by motion, sound, or light) or drug administration. Synchronizing with a drug administration may be useful for procedures such as imaging of cerebral perfusion events (like in functional MRI), so that a small bolus may be injected per stimulus and the region that uptakes the radiopharmaceutical will be more likely to be related to the stimulus.

7) Responsive to the radiopharmaceutical concentration in the blood. By monitoring the level of the radiopharmaceutical in the blood (either by drawing blood samples or by determining the level with the camera or other measurement system) it is possible to control the pattern in the blood, for example to keep a desired level, a desired slope, cycles, and so forth. In particular, when the frequency domain is used for the final analysis it may be beneficial to have the injection profile in one or more fixed periods (frequencies) selected to fit the expected kinetic profile, and to keep the concentration in the blood controlled so as to produce a desired spectral performance of the blood concentration, for example an approximately sinusoidal, saw-tooth, other harmonic form. When the level in the blood is provided by the camera, a closed loop system is obtained (see closed loop description).

By synchronized to an event it is meant that the injection timing is substantially linked to the timing of the event; for example the injection is performed at the time of the event, at a predetermined delay after it, or at a predicted time before the event. Such synchronization may allow summing and/or averaging the collected data in a synchronized fashion, similar to gating. Such summing/averaging enables the analysis and amplification of information related to the desired event, while all events which are not synchronized become "blurred", and have less influence on the final result. For example, an injection profile of once every two seconds allows data accumulated for a dynamic event synchronized to a two second period to be collected and averaged. External interferences, such as breathing, heart motion, and sudden patient motion, become less influential as they are not synchronized with the two second cycle. Therefore the signal to noise ratio and errors in the reconstructed kinetic parameters are reduced.

Figure 96:
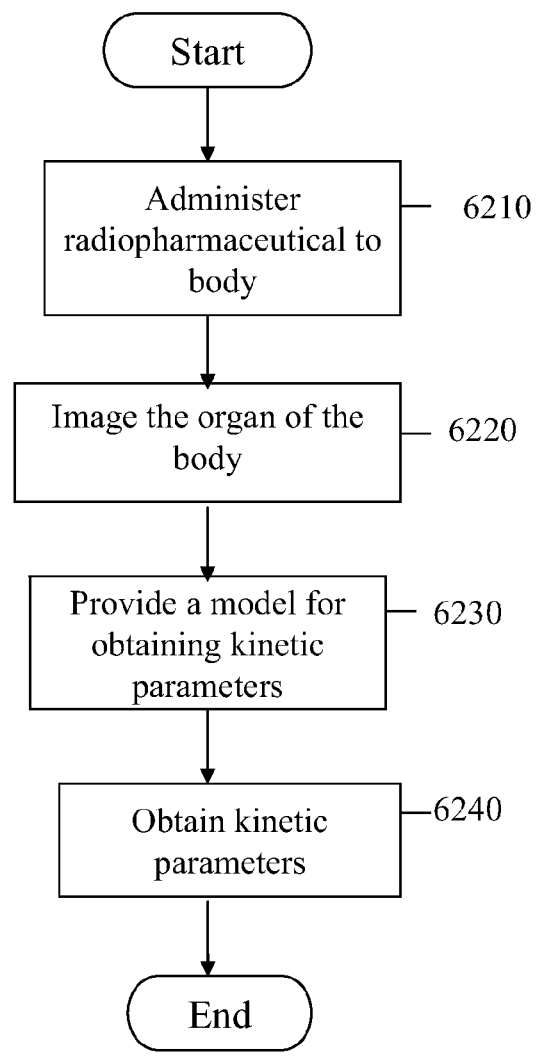
FIG. 96 is a simplified flowchart of a method for measuring kinetic parameters of a radiopharmaceutical in an organ of a body, according to a preferred embodiment of the present invention.

Reference is now made to FIG. 96, which is a simplified flowchart of a method for measuring kinetic parameters of a radiopharmaceutical in an organ of a body, according to a preferred embodiment of the present invention. The present method differs from the method of FIG. 91 in that it images a specific organ of the body. In step 6210, the radiopharmaceutical is administered to the body. In step 6220, the organ is imaged. In step 6230, a model is provided for obtaining kinetic parameters from the imaging is provided. Finally, in step 6240, the kinetic parameters are obtained by applying the measurements to the provided model and extracting the value of the required parameter(s).

Figure 97:
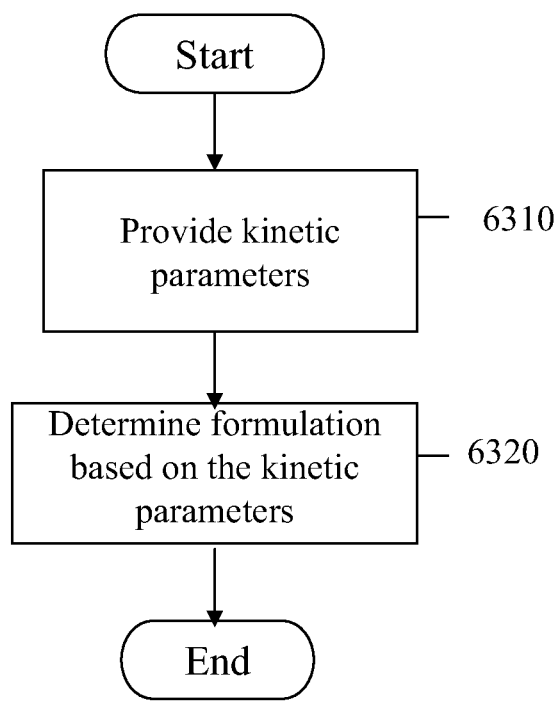
FIG. 97 is a simplified flowchart of a process for obtaining the drug formulation, according to a preferred embodiment of the present invention.

A further preferred embodiment of the present invention is a drug formulation for a radiopharmaceutical. Reference is now made to FIG. 97, which is a simplified flowchart of a process for obtaining the drug formulation, according to a preferred embodiment of the present invention. In step 6310, kinetic parameters for the radiopharmaceutical are provided. In step 6320, the formulation is determined, based on the provided kinetic parameters. The values of the kinetic parameters are preferably obtained by the method of FIG. 91 described above.

In the abovedescribed models C is modeled as a concentration. Alternatively, C may be modeled as a count rate. For each radiopharmaceutical there is a conversion ratio from concentration to count rate which depends on several factors. Factors influencing the conversion may include: mg of matter to number of molecules, the radiopharmaceutical half-life (which determines the average time for a photon to be emitted per molecule), and the rate of isotope decay. If the half-life is short, there is a reduction in available isotopes over the time of acquisition. Modeling the count rate may therefore be easier, and allow later conversion to concentrations.

Commonly, the time for a compound to become widespread in the body is in the time scale of about one minute. Thus the sharp slope in concentration observed immediately following injection lasts only a few seconds before various organs begin uptaking the compound. It is therefore preferable to allow scanning and reconstruction of volumes of interest in a time resolution of about 5-10 seconds. Since the model equations include relatively few parameters, it is assumed that with acquisition of a few minutes long (1, 2, 5, 10 minutes) the number of time points obtained per voxel is in the range of 10-20 (preferably 50 or more), which is expected to enable stable estimation of the kinetic parameters. With radiopharmaceuticals having slower uptake and release activity it may be preferred to have longer acquisition times, such as 20, 30, or 60 minutes.

The analysis and determination of parameter values may be performed in the time domain, the frequency domain, or in any other transform domain. In the time domain, analysis is performed by solving the differential equation, either analytically or numerically, in order to reach a model which best fits the acquired data. Various numerical tools are known to fit equations of this complexity to a given data set. An example of frequency domain analysis is presented below.

The analytical solution may include integration over the input $Cg$, which may not be available with sufficient accuracy. In such cases, numerical methods for fitting the differential equations may prove more stable and accurate.

It is expected that frequency domain analysis will be particularly effective when the data is acquired in a frequency representation. It is expected that time domain analysis will be particularly effective when the data is obtained over time. Alternative approaches may be tested by converting the data from one form to the other, and the more stable approach may be selected.

In some cases, the model above may further include interstitial volume, so that substances move from capillaries to the interstitial domain and from there to the cells, and vice versa. Transfer to and from the interstitial domain may be added to the equations. In many cases the difference in concentration between the interstitial volume and the capillaries is insignificant, thus they may be modeled as one domain.

It should be noted that the general blood concentration, $Cg$, may differ from one location to another, for example between veins and arteries. Therefore, it may be preferable to measure the blood concentration by a sample from the arteries or by measuring the concentration inside the left chambers of the heart.

Similarly, in the case of cardiac imaging there might be poor blood flow along one or more of the coronary arteries, and thus uptake of substance by cells in one voxel might reduce the remaining concentration in the artery available for voxels further along the given artery. Thus the value of $Cg$ may actually be lower for the more distal voxels. Changes in the value of $Cg$ may be handled by iterating the parameter estimation while correcting the $Cg$ value once the uptake in the more proximal voxels has been estimated.

Note that if the radiopharmaceutical administration is based on a periodic injection protocol, the concentration in the general blood pool (either arterial or venous) may respond in a periodic pulsatile profile, which has a harmonic spectrum.

Following is a discussion of the application of frequency domain analysis to the abovedescribed voxel dynamic modeling. Frequency domain analysis allows the use of techniques for measuring the frequency response to a periodic injection protocol, similarly to the way frequency response is evaluated in passive electrical circuitries. For example, the frequency response may be measured by injecting the radiopharmaceutical to several frequencies, and then determining the amplitude of the response at a given frequency, the phase response, or the comparative amplitudes at several frequencies. The results are then compared with the model of the frequency response and parameters of interest are extracted (e.g. resistors and capacitor values in electrical circuitry, or diffusion coefficients and blood flow, F, in the voxel dynamic model).

Taking model 3 as an example, the Fourier transform equivalents of Equations 10-12 are:

$$C = (Ct*Vt + Cb*Vb)/V = Cb*Rb + Ct*(1-Rb) \qquad (18)$$

$$jwCt = Kin \cdot Cb - Kout \cdot Ct \qquad (19)$$

$$jwCb = \frac{F}{Vb}(Cg - Cb) - Kin \cdot Cb + Kout \cdot Ct \qquad (20)$$

where C, Cb, Ct, Cg are in the frequency domain, w is the angular frequency, and j is the imaginary unit, $\sqrt{-1}$)

Equations 18-20 result in Equation 21, which relates the concentration in the voxel of interest (C) to the concentration in the arterial blood (Cg) in the frequency domain:

$$C = \frac{\frac{F \cdot Cg}{V}\left[\frac{Vt}{Vb} + \frac{jw + Kout}{Kin}\right]}{\left(jw + \frac{F}{Vb} + Kin\right) \cdot \left(\frac{jw + Kout}{Kin}\right) - Kout} \qquad (21)$$

The relationship between C and Cg can be measured in several frequencies, enabling the extraction of F, Kin, and Kout.

Equation 21 is useful for analyzing the value of the kinetic parameters. Consider the case of w<<Kout, that is the case in which rate of clearance is much faster than the rates of changes in the blood flow. In practice, it is difficult to obtain w<<Kout for some radiopharmaceuticals, requiring slow and controlled changes in the blood concentration.

For w<<Kout, Equation 21 becomes:

$$\frac{C}{Cg} = \frac{\frac{F}{V}\left[\frac{Vt}{Vb} + \frac{Kout}{Kin}\right]}{\left(jw + \frac{F}{Vb}\right) \cdot \left(\frac{Kout}{Kin}\right)} = \frac{F}{V} \cdot \frac{\frac{Vt \cdot Kin}{Kout} + Vb}{jwVb + F} \qquad (22)$$

Equation 22 provides a highly important relationship, as the ratio between two measurements, each with two different low frequencies w1 and w2 (i.e. two slow derivatives of concentration changes), provide a direct measure of flow rate:

$$\frac{(C/Cg)_2}{(C/Cg)_1} = \frac{jw_1 \cdot Vb + F}{jw_2 \cdot Vb + F} \qquad (23)$$

The ability to isolate parameters, so that the values of different parameters do not affect each other, is of high importance. Parameter isolation combined with the high sensitivity and the ability to produce multiple repetitions in different frequencies or slopes may enable extracting some parameters in a quantitative and efficient manner.

Quantification in the case of w<<Kout depends on the prior estimation of the partial volume in each voxel containing the blood compartment. Once F is known, the ratio of Kin/Kout is obtainable from the Equation 22 above.

In a more typical scenario, w>>Kout, and equation 21 becomes:

$$\frac{C}{Cg} \cong \frac{F}{V} \cdot \frac{Kin \cdot Vt + jw \cdot Vb}{jw(jw \cdot Vb + Kin \cdot Vb + F)} \qquad (24)$$

For w>>Kout, measuring the ratio of C/Cg in multiple frequencies allows the recovery of the flow F and the wash-in rate Kin (which is associated with the well being of the cells) in a quantitative manner.

It is possible to perform all analyses in terms of the absolute amplitudes of C and Cg by converting the modeling equations (which include complex numbers) to absolute numbers. Alternatively, phase analysis may be used. An additional alternative is to transform time-domain signals into the frequency domain with the Fourier transform, and to perform the remaining analysis in the frequency domain.

Closed Loop Injection

The ability to perform analysis of the image while imaging takes place provides many avenues for dynamically controlling the measurement process, so as to optimize the imaging. The present embodiments address the analysis of radioactive-emission measurements obtained during a current measurement process in order to control the administration of the radiopharmaceutical in real-time.

Controlling the administration of the radiopharmaceutical in real-time (denoted herein closed loop administration) enables the development of protocols for continuous administration of the radiopharmaceutical, or of repeated administrations while imaging is taking place. Continuing the administration of the radiopharmaceutical during testing allows the use of radiopharmaceuticals with a high clearance rate such as teboroxine, whose rapid clearance from the body has made its use for imaging impractical until now.

Figure 98:
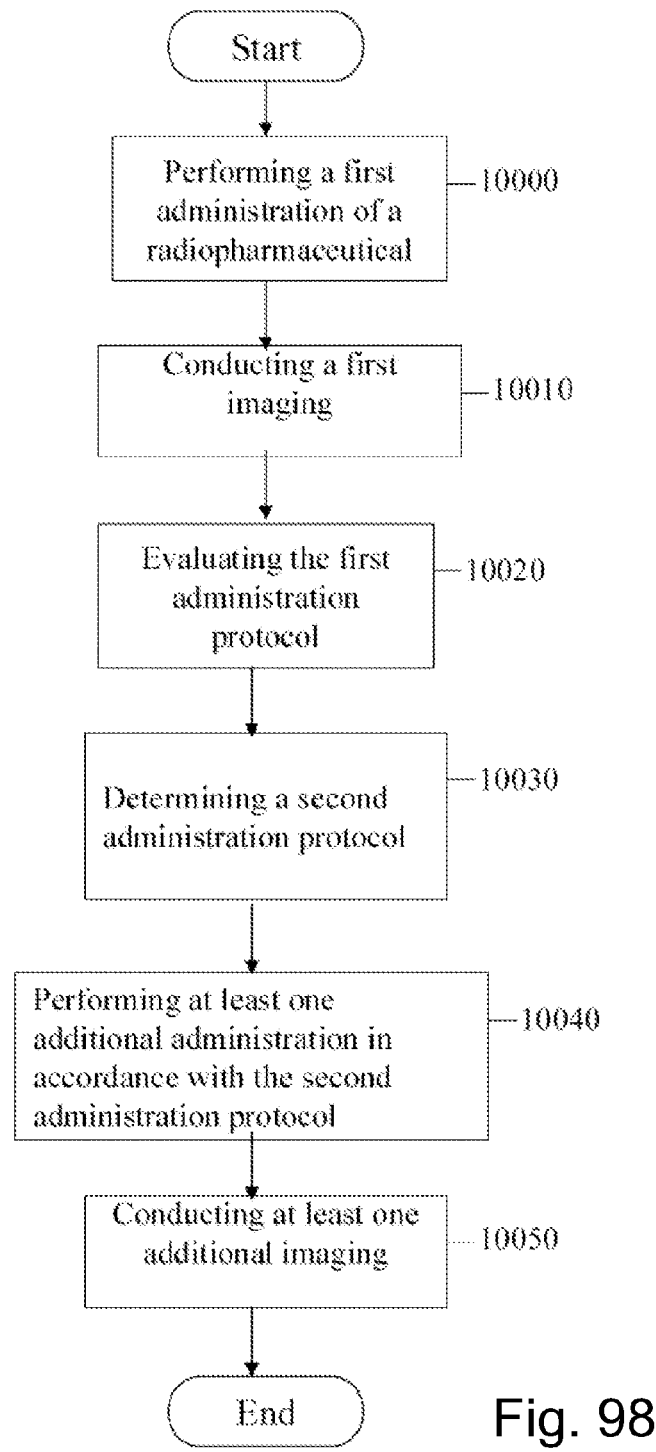
FIG. 98 is a simplified flowchart of a method of radiopharmaceutical administration and imaging, according to a first preferred embodiment of the present invention.

Reference is now made to FIG. 98, which is a simplified flowchart of a method of radiopharmaceutical administration and imaging, according to a first preferred embodiment of the present invention. The present method (denoted herein the stepwise method) is of a stepwise imaging process, which performs a repetitive process of administration followed by imagining and analysis. In step 10000 a first administration of a radiopharmaceutical to a body is performed, in accordance with a first administration protocol. The first administration protocol may require a single injection of a specified quantity of the radiopharmaceutical. In step 10010 a first imaging of at least a portion of the body is performed. In step 10020, the first administration protocol is evaluated, based on the first imaging. The evaluation is preferably based on the detector photon counts and/or on a reconstruction of the body structure as described below. In step 10030, a second administration protocol is determined, based on the evaluating. If the evaluation indicates that the first administration protocol is correct, the second administration protocol may be identical to the first administration protocol. In step 10040, at least one additional administration of the radiopharmaceutical to the body is performed, in accordance with the second administration protocol. In step 10050, at least one additional imaging is conducted.

Figure 99:
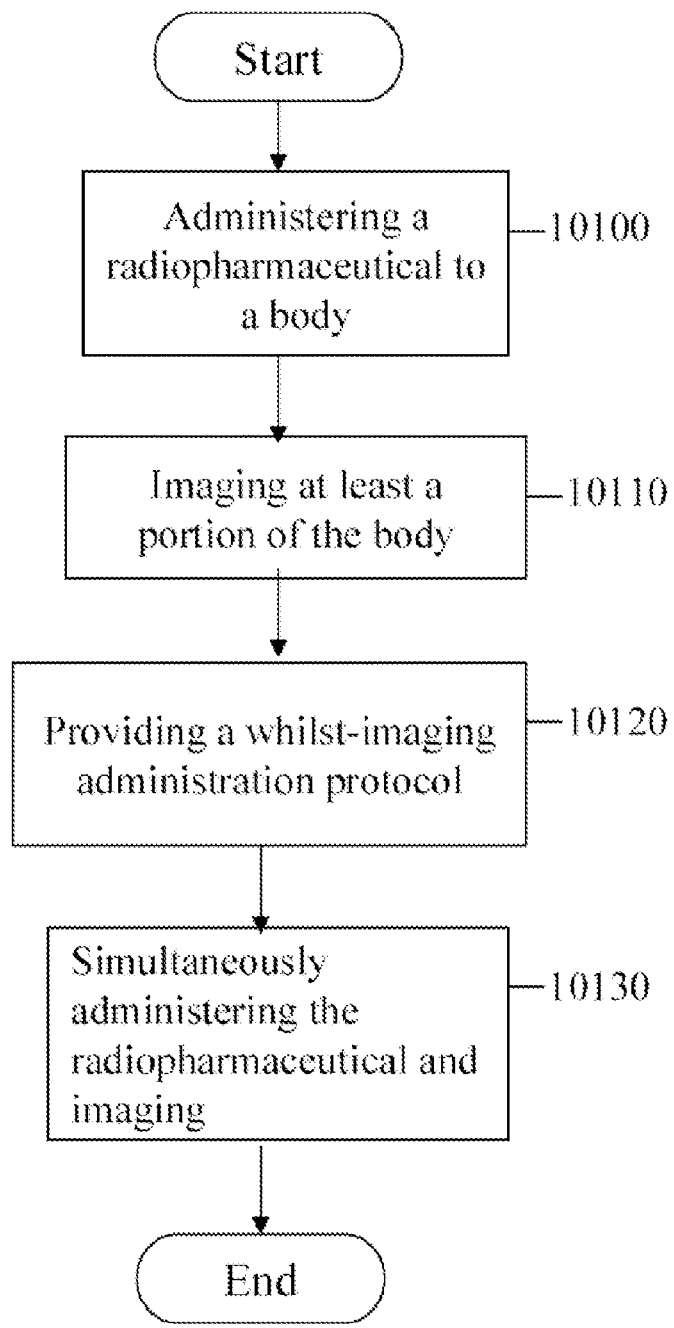
FIG. 99 is a simplified flowchart of a method of radiopharmaceutical administration and imaging, according to a second preferred embodiment of the present invention.

Reference is now made to FIG. 99, which is a simplified flowchart of a method of radiopharmaceutical administration and imaging, according to a second preferred embodiment of the present invention. The present method (denoted herein the dynamic method) evaluates the measurement data while the radioactive-emission measurements are being made, so that the administration of the radiopharmaceutical is controlled simultaneously with the imaging. In step 10110 a radiopharmaceutical is administered to a body, in accordance with an initial administration protocol. In step 10120, at least a portion of the body is imaged. In step 10130, a whilst-imaging administration protocol is provided, based on the imaging. The whilst-imaging protocol indicates the manner in which the radiopharmaceutical is to be administered while the imaging is taking place. The imaging process need not be interrupted in order to administer additional quantities of the radiopharmaceutical. In step 10140, imaging is performed simultaneously with the administration of the radiopharmaceutical, in accordance with the whilst-imaging administration protocol.

In essence, the second administration protocol and the whilst-imaging protocol form a feedback signal which controls radiopharmaceutical administration. In the preferred embodiment, the injection system is a controllable system, and the second administration protocol or whilst-imaging protocol (denoted herein the new protocol) is provided by an evaluation and control unit as a control signal for the injection system. For example, the control signal for the stepwise method may consist of a series of pulses, with the imaging being performed between the pulses. An example of a control signal for the dynamic method is a linear input, where the dosage is steadily increased until it is determined that a desired level has been reached. The injection system, imaging equipment, and evaluation and control unit effectively form a closed loop system, with the control signal providing feedback to the injection system. See the dynamic modeling description for additional examples of administration protocols.

The determination of the new protocol is preferably based on detector photon counts and/or reconstructed images obtained from previous measurements, similarly to active view determination see active vision description.

In the preferred embodiment, determination of the new protocol is based all or in part on the unprocessed detector photon counts. For example, during evaluation (step 10020 of FIG. 98) it may be determined that the detector has saturated. The new protocol would then be to allow the radiopharmaceutical to clear and then to apply a smaller dose.

In the preferred embodiment, determination of the new protocol is based all or in part on the analysis of one or more reconstructions. For example, it may be desired to maintain a steady state. A series of reconstructions is analyzed dynamically, in order to determine when steady state is reached. The analysis is preferably based on dynamic modeling—see dynamic modeling description. Reaching steady state may be determined from the dynamic model by evaluating Ct, the tracer concentration in tissue within the voxel, and adjusting the radiopharmaceutical administration in order to maintain Ct at a desired level.

Closed loop administration opens up many new possibilities for radioactive-emission imaging studies. It is anticipated that techniques for controlling closed loop administration will be optimized based on future studies of responses to different administration protocols.

ERP System and Smart Syringe

The present invention relates to the management of radiopharmaceutical substances used for body structure imaging. More particularly, the present invention relates to a system and method for managing the radiopharmaceutical handling processes and the actual imaging processes in a unified manner, so that the managed processes work together in a coordinated manner.

In the business environment, Enterprise Resource Planning (ERP) systems are information management systems that integrate and automate many of the business practices associated with the operations or production aspects of a company into a single system. ERP systems are customarily used by large organizations to provide a single system that can manage the manufacturing, logistics, distribution, inventory, and other business processes across departments in the enterprise. ERP systems generally have a modular structure, with each module handling a different aspect of the business processes. The modules are designed to work together, generally using a common database, so as to coordinate all the business processes to work seamlessly together.

The preferred embodiments described below extend the ERP concept by providing a management system which not only supervises the processes involved in ensuring that the radiopharmaceutical is available for the imaging process, but also actively supervises the imaging procedure in order to ensure that the proper substance is administered to the correct individual and in the correct quantity.

Figure 100:
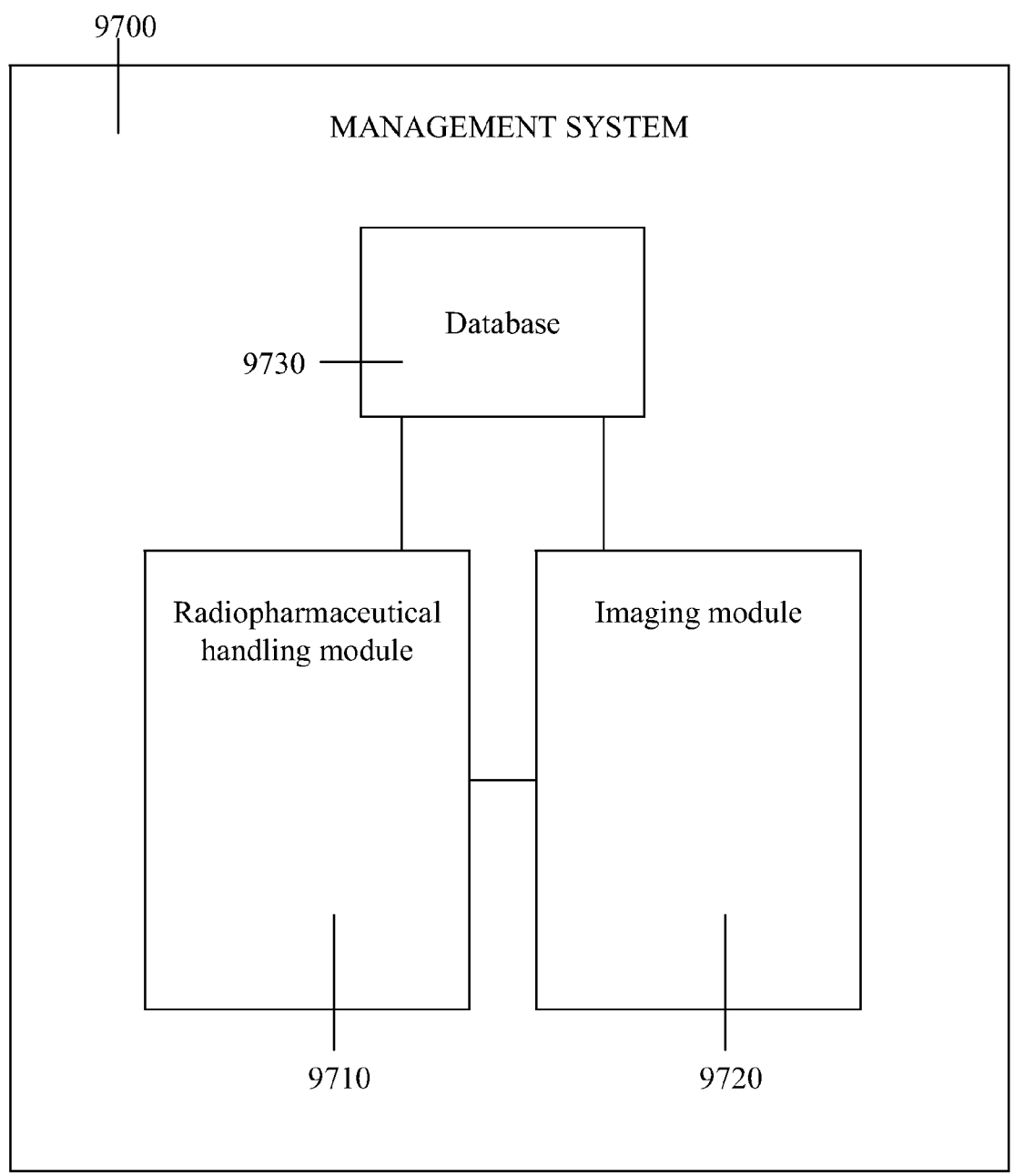
FIG. 100 is a simplified block diagram of a radiopharmaceutical management system, according to a preferred embodiment of the present invention.

Reference is now made to FIG. 100, which is a simplified block diagram of a radiopharmaceutical management system, according to a preferred embodiment of the present invention. Management system 9700 includes radiopharmaceutical handling module 9710 and imaging module 9720, both of which preferably utilize a common database 9730. Radiopharmaceutical handling module 9730 coordinates all processes which relate to radiopharmaceutical handling prior to the imaging process, preferably including one or more of: procurement (from outside supplier or by generating in-house), inventory (storage), dose preparation, disposal, reporting, and any additional processes required to ensure that a required radiopharmaceutical is available for the imaging procedure. Some processes may be specific to a particular radiopharmaceutical. Imaging module 9720 coordinates all processes relating to the actual imaging process, preferably including one or more of: patient admission, radiopharmaceutical administration, communication with camera and/or administration device, and any additional processes required for performing the imaging. In a further preferred embodiment, described below, the radiopharmaceutical is administered by a remotely-controllable administration device with communication capabilities, as described below. Proper design of management system 9700 will ensure that adequate safety procedures are in place at all times.

Figure 101:
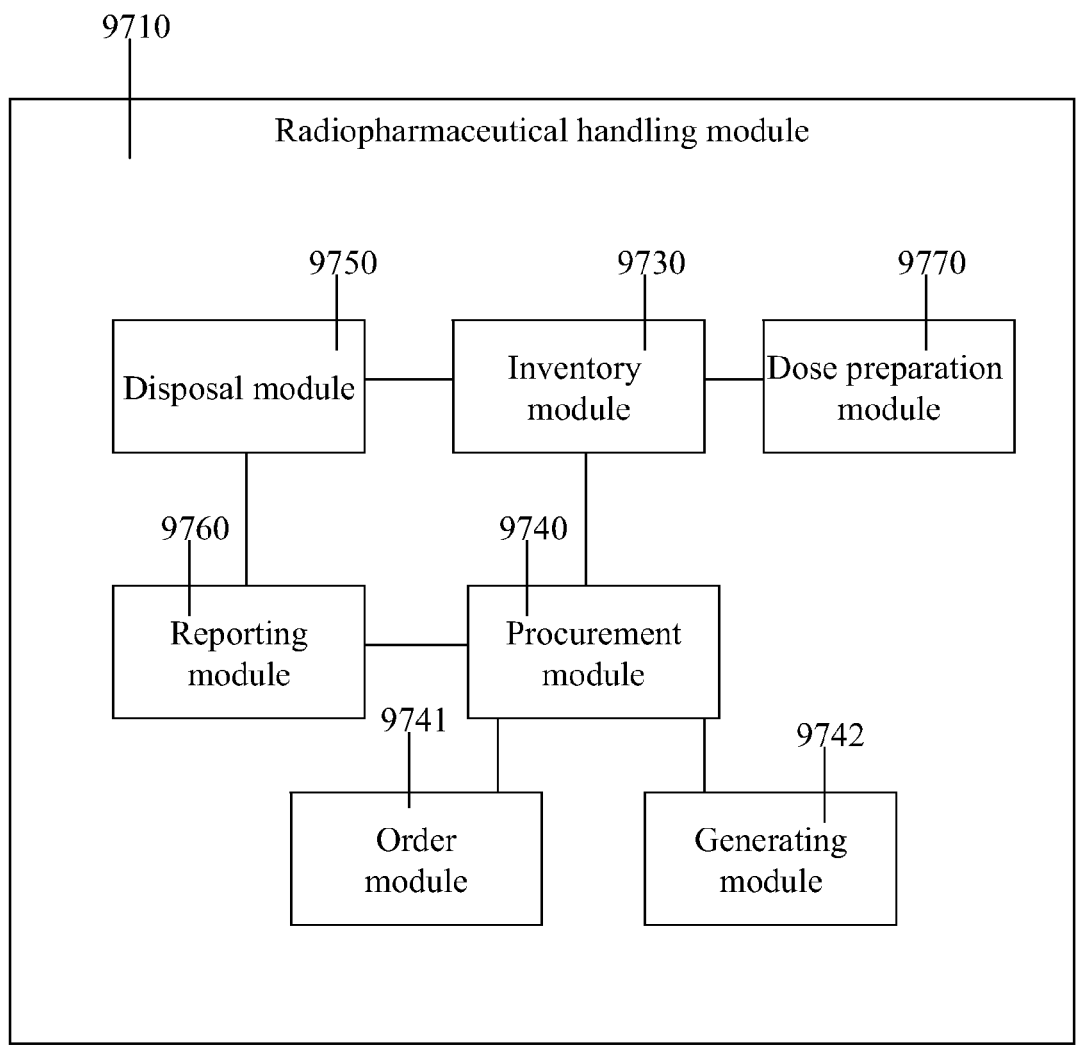
FIG. 101 is a simplified block diagram of an exemplary embodiment of a radiopharmaceutical handling module.

Reference is now made to FIG. 101, which is a simplified block diagram of an exemplary embodiment of a radiopharmaceutical handling module. Radiopharmaceutical handling module 9710 has a modular structure. A central component of radiopharmaceutical handling module 9710 is inventory module 9730. Inventory module 9730 tracks the types and quantities of the radiopharmaceuticals currently in storage.

Inventory module 9730 is responsible for ensuring that all necessary radiopharmaceuticals are available. When inventory module 9730 identifies that stocks of a given radiopharmaceutical are lower than needed, inventory module 9730 notifies procurement module 9740 that additional quantities should be procured. Procurement module 9740 obtains the necessary radiopharmaceutical, via order module 9741 and/or via generating module 9742. Order module 9741 places orders with external suppliers and tracks delivery. Generating module 9742 manages the generation of those radiopharmaceuticals which can be generated in house (such as Technicium 99m).

When it is necessary to dispose of radiopharmaceuticals, inventory module 9730 coordinates with disposal module 9750, which manages the disposal process.

Both procurement module 9740 and disposal module 9750 operate in accordance with the per country requirements for radiopharmaceutical use. Reporting module 9760 reports to the nuclear regulatory commission as required, based on information obtained from procurement, disposal, and other modules.

Dose preparation module 9770 manages all tasks related to the preparation of the radiopharmaceutical doses as required. For a given imaging procedure, dose preparation module 9770 preferably provides instructions to a dose preparation system (see FIG. 106) for preparing the necessary dose, preferably including calculating the required dosage to be dispensed based on factors such as the type of imaging procedure, time of dose preparation, scheduled imaging time, and patient related factors such as age, weight, medical condition and so forth. Dose preparation module 9770 tracks the number of patient doses drawn from the inventory (e.g. mother vial) and updates inventory module 9730 accordingly. Additionally, dose preparation module 9770 issues a machine-readable radiopharmaceutical label to be attached to the dose, identifying the radiopharmaceutical type, isotope type, preparation date and time, time dose should be administered, intended patient, and the intended imaging procedure. The radiopharmaceutical label may consist of any means of attaching the required information to a given dose, such as a printed label or bar code. In the preferred embodiment described below, the radiopharmaceutical label includes a memory and wireless communication device (in such case the radiopharmaceutical label is denoted herein a smart label or RFID), to enable direct communication and information transfer between dose preparation module 9770 and the management system. By dose it is intended to include both a single radiopharmaceutical and a cocktail of radiopharmaceuticals, as required by the imaging procedure.

Figure 102:
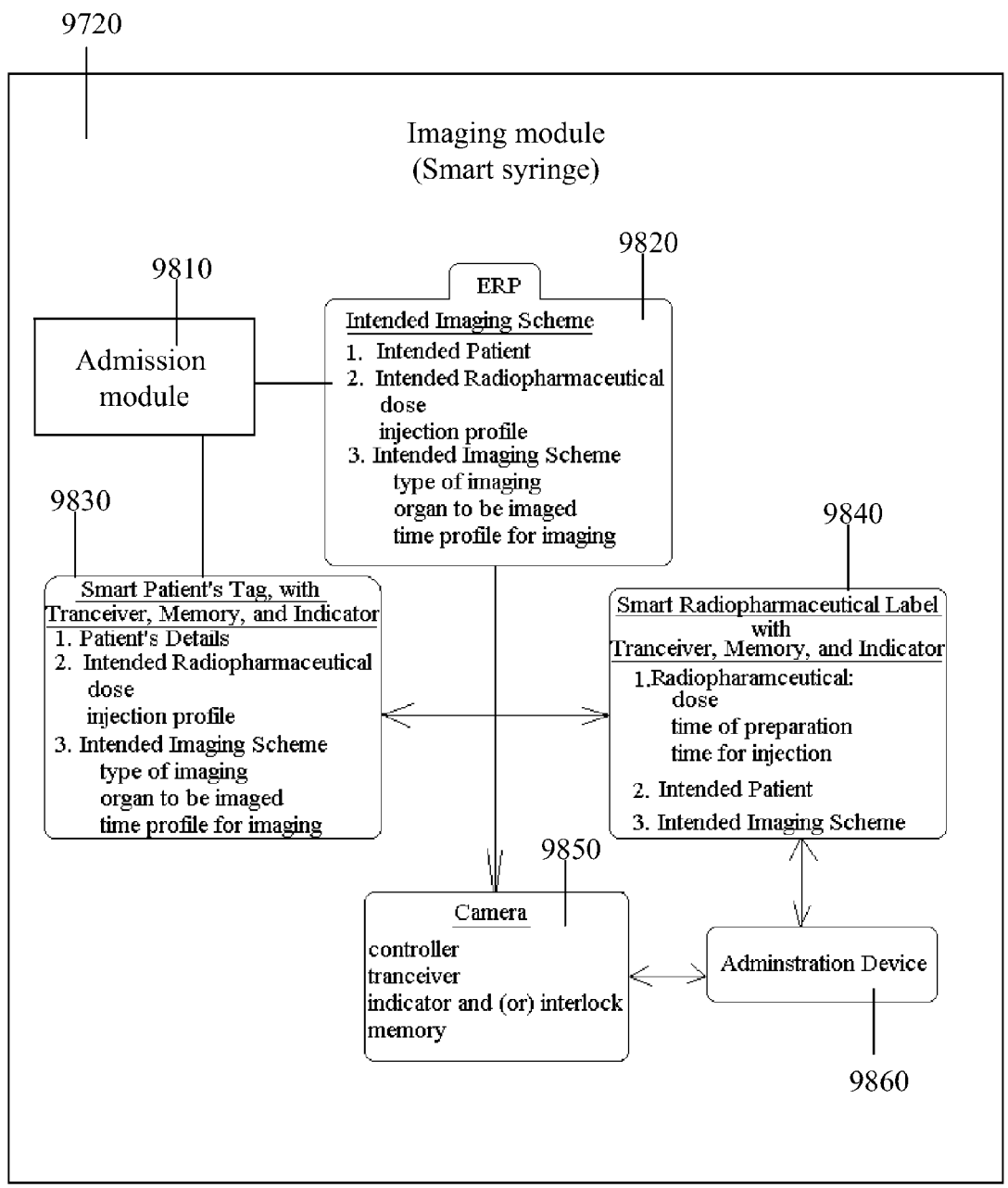
FIG. 102 is a block diagram of an exemplary embodiment of an imaging module.

Reference is now made to FIG. 102, which is a block diagram of an exemplary embodiment of an imaging module. Admission module 9810 supervises patient admission. At the time of patient arrival, patient details such as name, ID number, purpose of visit (type of study), and medical history are entered, and a patient file is created. Admission module 9810 then generates the patient tag, which is a machine-readable tag to be worn or carried by the patient, and which contains relevant patient details such as the patient details, intended radiopharmaceutical dose, and intended imaging scheme. In the preferred embodiment the patient tag is a smart tag 9830 which includes a transceiver, memory, and optionally indicator as described below. The patient tag may be in the form of a bracelet or necklace, and Additionally or alternately, the details may be recorded as text or a bar code. Admission module 9810 also notifies ERP module 9820 that the patient has been admitted, and provides the patient file, including details of the intended study, to ERP module 9820.

ERP module 9820 manages all aspects of the imaging process, by coordinating between admission module 9820, patient tag, smart label 9840, camera 9850, and administration device 9860, in concert with radiopharmaceutical handling module 9710. ERP module 9820 orders and obtains the required radiopharmaceutical dose from dose preparation module 9770. The dose is supplied with a smart label 9840. ERP module 9820 determines when imaging can begin by comparing data obtained from smart tag 9830 (dose), smart label 9840 (patient), and camera 9850, During imaging, ERP module 9820 activates camera 9850 and controls dose administration by administration device 9860. Preferably communication between the various modules is wireless, according to wireless protocols such as Bluetooth, WiFi, W-LAN, and IEEE 802.11.

Camera 9850 includes a controller, communication element (such as a transceiver) for communicating with ERP module 9820, a memory, and an indicator controller, and optionally locking mechanism. Camera 9850 is preferably activated by ERP module 9820, when ERP module 9820 determines that the imaging process may be initiated. The interlock prevents camera activation, if the imaging study has not been verified by ERP module 9820. ERP module 9820 then controls the camera 9850 in accordance with the requirements of the current imaging study. For example, ERP module 9820 may instruct the camera 9850 to sequentially perform emission measurements at a specified set of views. When imaging is initiated, a light or beep may be provided by the indicator, to notify imaging personnel that imaging is about to begin.

Administration device 9860 includes a memory and communication element (such as a transceiver) for communicating with ERP module 9820, and possibly other system components. Administration device 9860 may be any device used to administer a radiopharmaceutical, including a manual syringe, a controllable-syringe, an IV drip, a pump, or a closed-loop administration system (see closed loop description). Controllable embodiments of administration device 9860, such as those of FIGS. 103-105, include components (such as a motor) for automatically administering and regulating the dose to the patient according to instructions provided by ERP module 9820. Administration device 9860 may be preprogrammed with the required administration profile or may be under online control. In a preferred embodiment, administration device 9860 is responsive to responsive to external events and/or feedback from the imaging equipment such as those of the smart injection profile (see dynamic modeling description). Administration device 9860 may also include an indicator, similar to that of camera 9850. Administration device 9860 may be a bedside unit or a portable unit which can be carried by the patient.

Following are exemplary embodiments of the control of the imaging procedure by ERP module 9820. Prior to administration, ERP module 9820 obtains the required dose with a smart label 9840, and sends the dose to the injection point. In a first preferred embodiment, the radiopharmaceutical is administered by injection prior to imaging, for example a day early. At the time of administration, ERP module 9820 prepares or updates the patient's tag, with the details of the type and dose of radiopharmaceutical that was administered, and preferably the patient file opened at admission. The following day, at the scheduled time, the patient arrives at the injection point with the smart tag 9830. At the injection point, ERP module 9820 performs a recognition test. If there is correlation between the smart label 9840 on the supplied dose and the patient smart tag 9830, ERP module 9820 determines that imaging may commence. Alternately or additionally, ERP module 9820 may require manual authorization to begin the imaging process, possibly by requiring that a personnel member press "START" button on a computerized camera control screen. ERP module 9820 may additionally review medical test results, such as an ECG, for the given patient, to ensure that the test results permit performing the imaging. Administration is performable only after ERP module 9820 has unlocked any interlock mechanism or controllable valve on the administration device 9860. Additionally, an indication may be provided by indicators on the smart tag 9830, administration device 9860 and/or camera 9850. The recognition test ensures that the correct dose is administered to the patient. Any mismatch between the patient, the radiopharmaceutical, and the intended imaging study prevents radiopharmaceutical from being administered.

When dynamic studies are performed it is highly important to image the time period immediately following administration, when the recently administered radiopharmaceutical causes a rising concentration of the radiopharmaceutical in the blood and in the tissue. Therefore, after recognition ERP module 9820 first activates the camera 9850, and authorizes radiopharmaceutical administration only after the camera 9850 is ready. Administration may be performed manually, by preprogramming, or under the control of ERP module 9820 when a controllable syringe (or other administration device) is used. Upon injection a report is sent to ERP module 9820, and at least the patient tag, or both the patient's tag and the ERP, are updated that injection took place.

In a second preferred embodiment, the radiopharmaceutical is administered at the time of the imaging study. When the patient arrives, ERP module 9820 first performs recognition, to ensure a match between the scheduled study, imaging protocol, patient's smart tag 9830, and syringe smart label 9840. Next ERP module 9820 activates the camera 9850. When the camera 9850 has begun imaging, ERP module 9820 initiates administration by the administration device 9860, according to either a predetermined administration protocol or to a protocol provided dynamically during the imaging process, possibly via feedback from the camera (i.e. closed loop).

Figure 103:
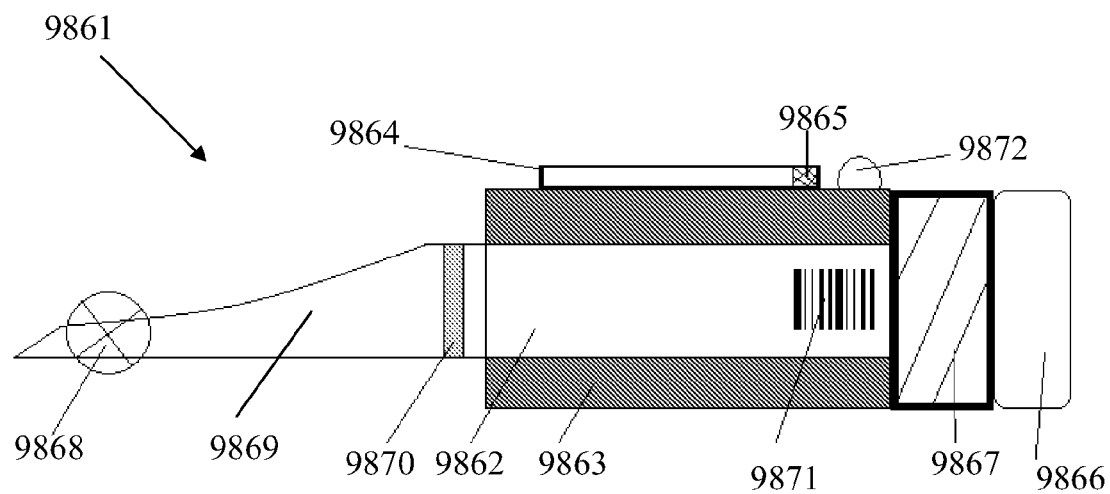
FIG. 103 is a simplified illustrative diagram of a single-reservoir controllable syringe.
Figure 104:
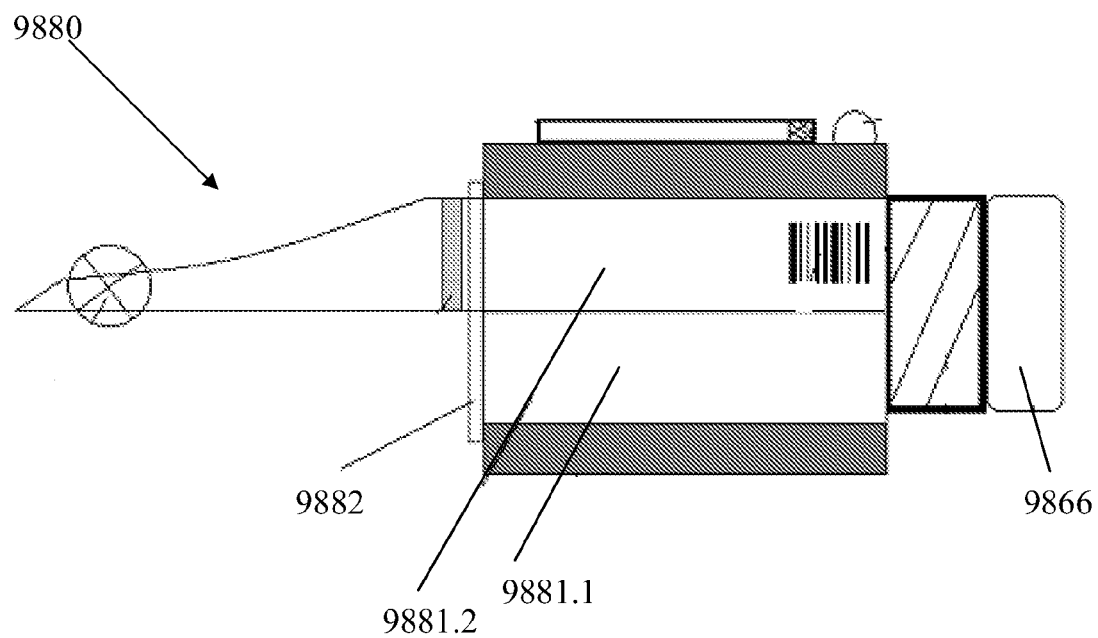
FIG. 104 is a simplified illustrative diagram of a multiple-reservoir controllable syringe.

Reference is now made to FIGS. 103 and 104, which are simplified illustrative diagrams of controllable radiopharmaceutical administration devices, according to a first and second preferred embodiment of the present invention. In the first preferred embodiment, shown in FIG. 103, the administration device is a single-reservoir controllable syringe 9861. Controllable syringe 9861 consists of a reservoir 9862, with an injection volume between about 0.5 to 30 milliliters, surrounded by protective shielding 9863. Smart label 9864 is attached to the shielding, and is communication with transceiver 9865. Transceiver 9865 additionally communicates with the ERP module, for example during recognition and while obtaining administration protocol instructions. Transceiver 9865 conveys the administration protocol instructions to controller 9866. Controller 9866 controls motor 9867 in order to inject the pharmaceutical and unlocks controllable valve 9868 (also denoted the interlock) on needle 9869. Flow rate gate 9870 monitors the dose as it is administered, and provides information about the actual administered dose to one or more of the smart label, smart tag, camera, ERP module and controller 9866. Controllable syringe is preferably able to administer various injection profiles, such as bolus, pulsatile, sinusoidal, or closed loop. Labeling information is optionally additionally provided on the syringe as a barcode 9871 or printed label. Controllable syringe 9861 optionally further includes indicator 9872, for providing a visual or audible indication that the radiopharmaceutical is being administered.

In a second preferred embodiment, shown in FIG. 104, the administration device is a multiple-reservoir controllable syringe 9880. Multiple-reservoir controllable syringe 9880 contains multiple reservoirs 9881.1-9881.n for the separate storage of different radiopharmaceuticals. (FIG. 104 shows a non-limiting example where n=2.) Multiple-reservoir controllable syringe 9880 further contains a mechanism for separately controlling administration by each of reservoirs 9881.1-9881.n. The control mechanism shown in FIG. 104 is a slide 9882 under the control of controller 9866, which prevents administration from all reservoirs other than the one called for by the administration protocol.

In the preferred embodiment, a trigger signal is provided by the syringe to the ERP module, indicating that the injection has started and marking the time point in the patient file. Preferably a trigger is additionally provided to mark the end of injection, thereby indicating the duration of administration. In the case of multiple injections, a trigger may be provided to indicate the start and/or finish of each of the administrations. The trigger indicating that administration has started may be obtained by noting when communication is interrupted between the ERP module and a transmitter placed on the plunger portion of the syringe, as the transmitter signal is blocked by the shielding around the reservoir.

Figure 105:
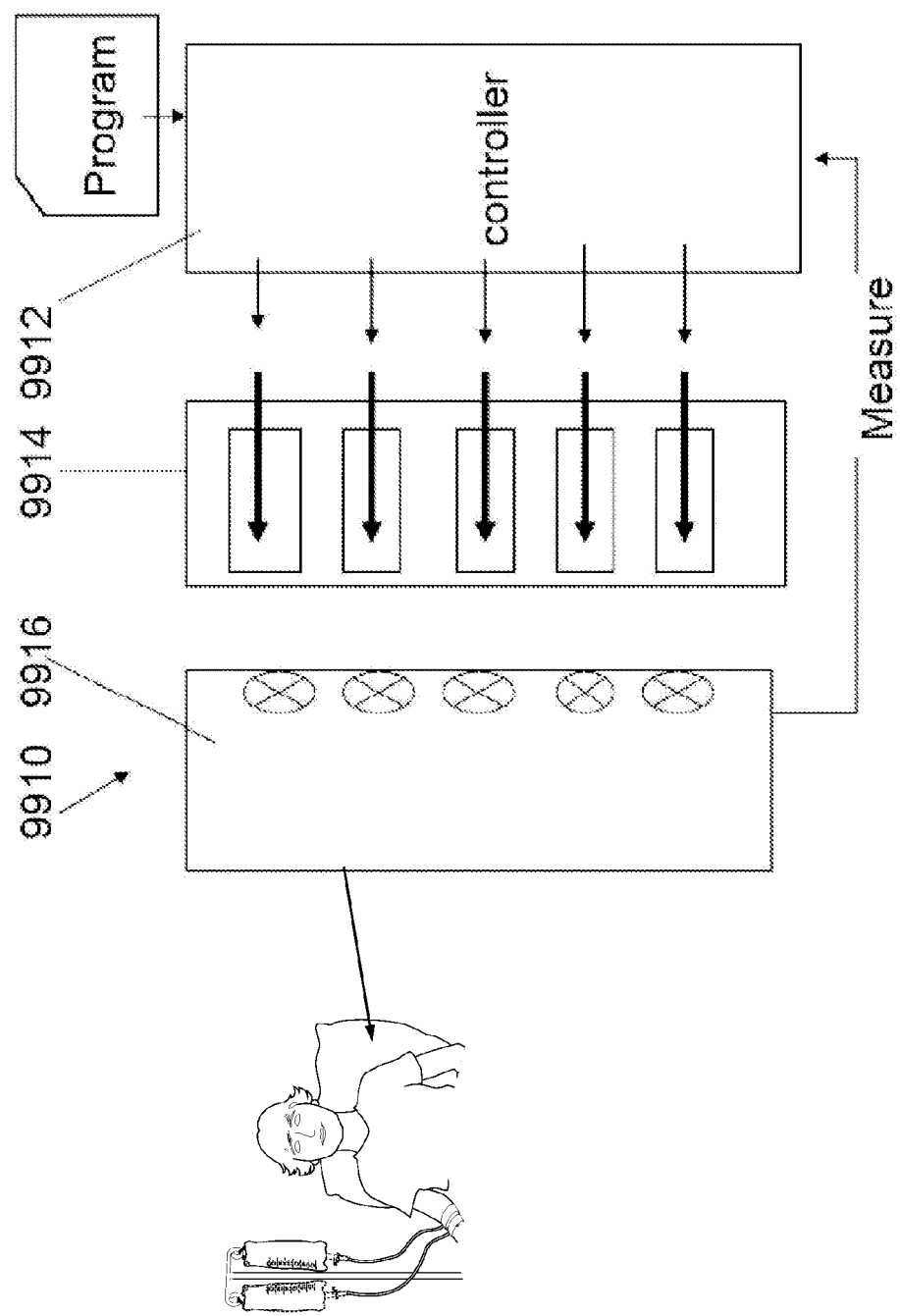
FIG. 105 is a simplified illustrative diagram of an administration device for controlled injection of multiple substances into a patient under the supervision of an imaging module, according to a preferred embodiment of the present invention.

Reference is now made to FIG. 105, which illustrates an administration device for controlled injection of multiple substances into a patient under the supervision of an imaging module, according to a preferred embodiment of the present invention. The administration device 9910 comprises a controller 9912 which receives data from a program and uses the data to operate a series of syringes 9914 each provided with a different tracer or cocktail of tracers. Each syringe contains a substance which needs to be injected at a certain dose at a certain time. A valve unit 9916 comprises one or more controllable or one-directional valves which can be used to regulate the amount of substance that reaches the patient or prevent mixing. One valve is provided per syringe. In essence, administration device 9910 is similar to a parallel battery of single-reservoir syringes all controlled by a central controller.

The dosage can be controlled by controlling the valves. Control can be provided based on measuring of the uptake of the radiopharmaceuticals by the body and/or based on data from flow meters situated respectively on each one of the valves. Measurement and control can also be carried out via the syringes themselves, by controlling the plunger.

Uptake and clearance of the radiopharmaceuticals may be monitored by measurements of physiological reference points such as blood, saliva, and secretion systems, such as urine, breath, fecal, sweat. These measurements can serve to estimate pharmacokinetics of the radiopharmaceuticals in the body organs, and to predict optimal imaging timing. This can be achieved by commonly used devices and kits, or by imaging. Imaging can tell if enough of the substance has for example reached the liver. Imaging preferably uses a controllable camera under the control of a management system, however it can use a standard camera or other stand-alone imaging device.

Based on these estimates, it is also possible to determine expected level of uptake of the radiopharmaceuticals in the target organ, and thus determine pathologies based on absolute uptake levels in the target organs.

Dynamic measurements are important in PET. Materials involved in PET, which produce photons, have relatively short lifetimes and the general trend is to use extra large doses just to overcome the difficulty of the short lifetime.

Use of administration device 9910 allows for injection during the time of imaging, thereby permitting dynamic evaluations, for example imaging and measurement of blood flow, and imaging of blood vessels, including both major blood vessels and ranging down to the smallest capillaries. Furthermore the system may permit synchronized imaging of different systems, thus imaging of a kind that shows up blood flow which is synchronized with a different imaging operation for bone, so that the two can be matched up.

The administration device of FIG. 105 may be shielded to prevent radioactive contamination of the environment.

Figure 106:
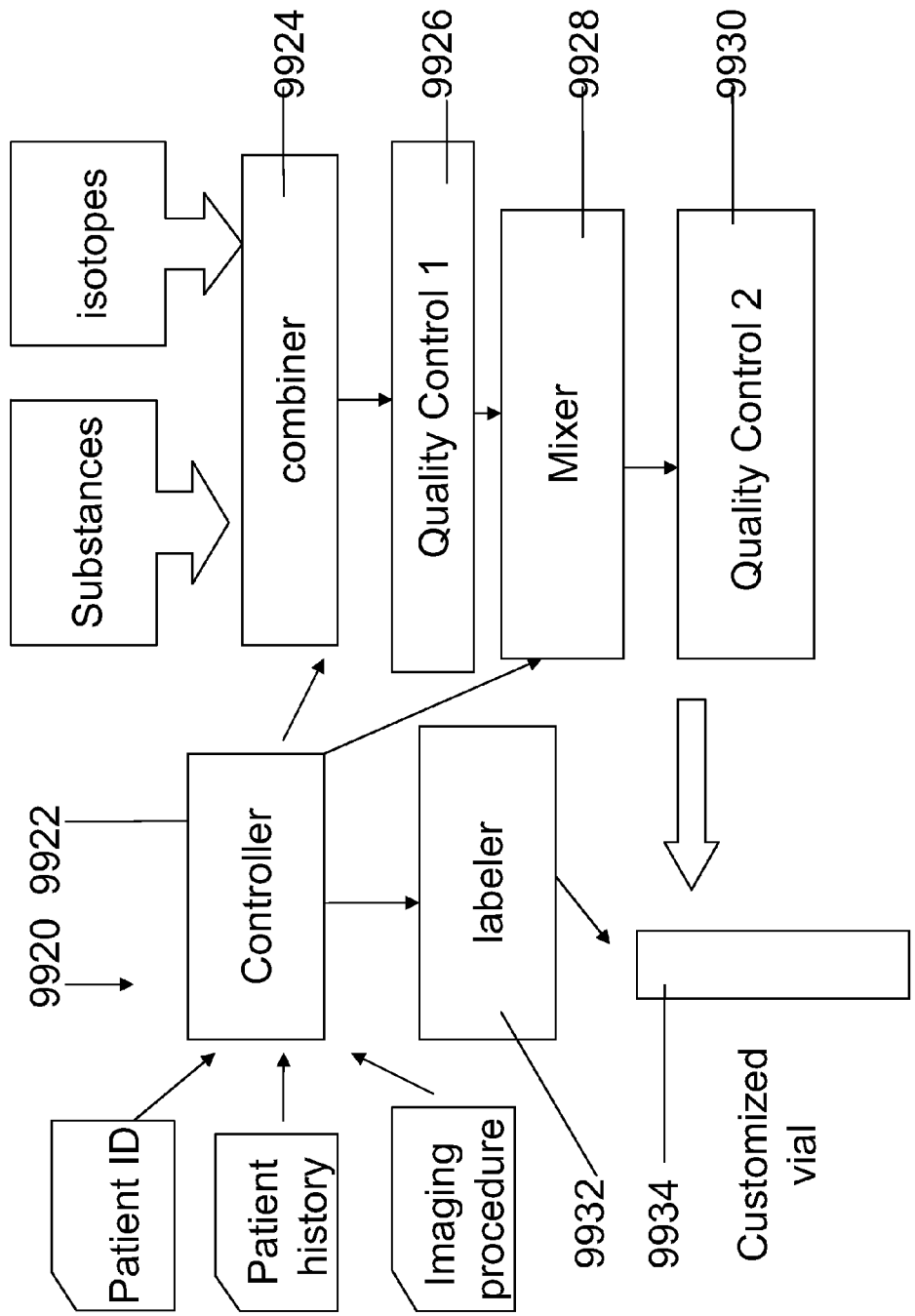
FIG. 106 is a simplified block diagram of a dose preparation system, according to a preferred embodiment of the present invention.

Reference is now made to FIG. 106, which is a simplified block diagram of a dose preparation system 9920, according to a preferred embodiment of the present invention. Dose preparation system 9920 is preferably controlled by dose preparation module 9770 of the management system. Dose preparation system 9920 comprises a controller 9922 which receives as input the identity of the patient for whom the present preparation is being made, the patient history, especially pertinent information such as age, weight, sensitivities, morbidity etc, and the imaging procedure that the doctor desires to carry out. The imaging procedure may be a detailed procedure or simply indicate the imaging that it is desired to carry out. The controller 9922 designs a cocktail of substances or a series of substances to carry out the desired imaging, and uses constraints from the physical properties of the substances, from the patient history and from other sources such as safety and efficacy requirements. The controller 9922 is able to determine what constitutes an appropriate dose for a patient of the given weight and age, and is able to determine at what times different substances should be administered to the patient in order to achieve optimal imaging. Thus certain of the isotopes may be administered together and need to be combined in a single preparation. In other cases certain isotopes may need to be taken at different times and thus need to be prepared and packaged separately.

The controller 9922 may be connected to a combiner 9924 which mixes a single carrier substance with a single isotope, possibly drawn from a mother vial. The controller 9922 preferably informs the inventory module of the quantities of substances which have been used to prepare the dose. The mixture is passed to first quality control unit 9926 where it is checked for safety and efficacy.

The checked substance is then passed to mixer 9928. In mixer 9928 it waits for the next carrier isotope combination. All required carrier isotope combinations are collected and mixed in mixer 9928 into a single preparation, which is then passed through second quality control unit 9930 where it is tested for safety and efficacy.

A labeler unit 9932 produces a label indicating the patient ID, the imaging program, timing information, and other information as described above, and the label and mixture are combined into vial 9934. The label may be a smart label or a radio frequency identifier (RFID) or a barcode or a printed label as convenient. The RFID may also be usable for identifying the patient.

The same patient may be provided with a series of vials, each for injection at a different time. Each vial may contain one or more isotopes as appropriate. The vials are inserted into the syringes of FIG. 104.

In more detail FIG. 106 shows a dose preparation system for providing a mixture of carrier substances, tracers and isotopes in a manner suitable to fit a prescribed diagnosis, customized per patient. The system and processes include the evaluation, verification, customization, and combination of the radiopharmaceuticals used in nuclear imaging. In an exemplary embodiment of the invention, the system produces a cocktail of different radiopharmaceuticals, at various dosages, that is customized to one or more specific patient injections.

In a first preferred embodiment, control functions are provided by the dose preparation module of the management system. In as second preferred embodiment, controller 9922 of dose preparation system 9920 controls dose preparation, and updates the dose preparation module. In the second embodiment, controller 9922 receives data concerning a specific patient undergoing an imaging procedure. Data includes:

Patient ID
Prescription from the physician (which imaging procedure is required, of what organ, what are the suspected pathologies)
Patient parameters such as age, weight, BMI and gender
Preferred administration (IV, oral, ventilation,)
Patient sensitivity to one or more chemical compounds
History of recent radiopharmaceuticals administrations to the patient (antibodies, isotopes residuals, etc)
Physiological tests, e.g. blood, saliva, and secretion systems, such as urine, breath, fecal, sweat
Information concerning patient morbidities such as metabolic disorders (i.e. diabetes), GI complications and heart disease, claustrophobia, and other mental disorders
Physiological information concerning functioning and/or complications in liver, spleen, intestines and kidneys Controller 9922 processes the information and customizes the radiopharmaceutical cocktail according to patient specifications. The time for radiopharmaceutical pick up and removal, as well as optimal timing for injection-to-measurement delta, is all customized. This information is provided for multiple injections in series or in parallel as well.

The system includes a verification unit that performs quality control checks on the raw materials such as the tracer and isotope kits. For example, the unit verifies that a specific tracer isotope meets manufacturer purity standards, required activity levels and identification requirements.

The system may include combiner 9924 that combines an individual carrier substance or tracer to a specific radioisotope.

The system may include mixing unit 9928 that combines and stores multiple radiopharmaceuticals that have already undergone an initial verification process in first quality control unit 9926.

The system preferably has a radiopharmaceutical cocktail verification and identification unit, or labeling unit 9932 that, in combination with second quality control unit 9930, verifies the presence of the correct substances, at the correct dosages. The labeling unit 9932 provides a bar code or chip for the patient and the vial 9934 and contains information concerning the prescription, dose preparation, timing, injection(s), gamma camera calibration, and analysis of results. All this information is linked to the patient smart tag.

The data stored on the smart tag can be read or retrieved in various locations:

In an exemplary embodiment of the invention the smart tag (RFID/chip/barcode) is read by the administration device and camera, which is in communication with and under the control of the MRP module.

Low Dose Radiopharmaceuticals

The present invention relates to diagnostic nuclear medicine and, more particularly, to packaged dose units of diagnostic radiopharmaceuticals kits and to methods of using same in nuclear imaging.

Diagnostic nuclear medicine began more than 50 years ago and has evolved into a major medical branch. Its practitioners use low activity levels of radioactive materials in a safe way to gain information about health and disease by administering small amounts of radioactive materials, known as diagnostic radiopharmaceuticals, into the body by injection, swallowing, or inhalation. Following uptake of the radioactive Source, a radiation-emission collecting probe, which may be configured for extracorporeal or intracorporal use, is employed for locating the position of the active area.

Nuclear imaging is one of the most important tools of diagnostic medicine wherein an estimated 12-14 million nuclear medicine procedures are performed each year in the United States alone. Diagnostic nuclear imaging is therefore crucial for studies which determine the cause of a medical problem based on organ function, in contrast to radiographic studies, which determine the presence of disease based on static structural appearance.

Diagnostic radiopharmaceuticals and radiotracers are often designed or selected capable of selective binding to specific receptors by means of a binding moiety, such as an antibody, a specific inhibitor or other target-specific ligand. These targeted markers can therefore concentrate more rapidly in areas of interest, such as inflamed tissues, tumors, malfunctioning organs or an organ undergoing heightened expression of certain proteins. Thus, a blood circulating radiopharmaceutical is picked up by a specific organ or pathological tissue to a different extent than by other or non-pathological tissue. For example, a highly vascularized tissue (e.g., of a growing tumor) may concentrate more of a radiopharmaceutical while an ischemic tissue may concentrate less of the radiopharmaceutical than the surrounding tissues. Nuclear imaging relies on these general phenomena of varied distribution of radiopharmaceutical according to different tissue as well as different pathologies. As a result, specific tissue types (e.g., tumor tissues) may be distinguished from other tissues in radioactive-emission imaging.

Radiopharmaceuticals, which may be used in the process of differential diagnosis of pathologies may be conjugated to targeting (recognition binding) moieties and include a wide range of radioisotopes as mentioned below. Such radiopharmaceuticals therefore include recognition moieties such as, for example, monoclonal antibodies (which bind to a highly specific pre-determined target), fibrinogen (which is converted into fibrin during blood clotting), glucose and other chemical moieties and agents. Commonly used diagnostic conjugated radiopharmaceuticals include, for example, 2-[$^{18}$F]fluoro-2-deoxy-D-glucose ($^{18}$FDG), $^{111}$In-Pentetreotide ([$^{111}$In-DTPA-D-Phe$^1$]-octreotide), L-3-[$^{123}$I]-Iodo-α-methyl-tyrosine (IMT), O-(2-[$^{18}$F]fluoroethyl)-L-tyrosine (L-[$^{18}$F]FET), $^{111}$In-Capromab Pendetide (CYT-356, Prostascint) and $^{111}$In-Satumomab Pendetide (Oncoscint).

Two basic techniques are widely used for nuclear imaging: positron emission tomography (PET) and single photon emission computed tomography (SPECT). PET detects photons generated through positron-electron annihilation of positrons from a diagnostic radiopharmaceutical tracer placed in the subject, e.g., patient, to be imaged, and analyzes the photon energy and trajectory to generate tomographic images of the patient. SPECT generates images by computer analysis of photon emission events from a diagnostic radiopharmaceutical tracer having gamma emitting isotopes. Both PET and SPECT require the detection and analysis of single photon events, which are characterized by low signal to noise ratio and scarcity relative to the background radiation. Other constraints on the PET and SPECT image qualities include the sensitivity, temporal and spatial resolution, dynamic range, response time and Counting rate characteristics of the data acquisition probe devices, e.g., photomultipliers and the like.

Radioisotopes that emit both high energy gamma and/or low energy gamma, beta and/or position radiation and which can be used per se or as a part of a compound as radiopharmaceuticals, include, without limitation, technetium-99m ($^{99m}$Tc), gallium-67 ($^{67}$Ga), thallium-201 ($^{201}$Tl), indium-111 ($^{111}$In), iodine-123 ($^{123}$I), iodine-125 ($^{125}$I), iodine-131 ($^{131}$I), xenon-133 ($^{133}$Xe), and fluorine-18 ($^{18}$F). All these isotopes, except $^{99m}$Tc, $^{131}$I and $^{133}$Xe, are produced in particle accelerators.

The main limitation associated with diagnostic nuclear imaging is the risk associated with humans coming in contact with radioactive materials. In 1901, five years after discovering radioactivity, Henri Becquerel recognized the risks involved in exposure to radioactive isotopes. A short time after he had carried a sample of uranium in his pocket, he observed that the underlying skin developed first erythema (reddening of the skin) and then tissue necrosis, which he attributed to the radioactive properties of the specimen.

Ionizing radiation sources can produce pathological damage by direct cell damage or by producing free radicals which are formed through ionization or excitation reactions and which destruct the chemical integrity of biological molecules such as DNA and proteins, leading to cell death and cancer. Radiation damage to DNA is due primarily to indirect action of radicals, which leads to the lethal and mutagenic effects attributed to ionizing radiation. On the other hand, the same effect is harnessed therapeutically as more rapidly dividing cells are more sensitive to ionizing radiation.

Other than being a source of ionizing radiation, most radioisotopes and radiopharmaceuticals such as heavy metals, and some targeting (recognition binding) moieties of radiotracers are chemically and/or metabolically toxic, and can disrupt enzymatic reactions and other metabolic processes in the body.

The current conservative hypothesis assumes that some risk is associated with even the smallest doses of radiation. Furthermore, it is long known that while there are safety guidelines for exposure to ionizing radiation such as radioactivity, any dose is harmful because radiative damage is cumulative over the life span. Today, after more than a century of careful review of the evidence for radiation effects from the radiation doses associated with diagnostic nuclear medicine, there appears to be little reason for apprehension about either genetic or somatic effects (including thyroid cancel) if exposure is controlled, monitored and utterly minimized. Most practitioners and regulation agencies base their dosage regimes on the Nuclear Regulation Committee (NRC) guidelines and follow NRC regulations.

In order to reduce the harmful effects of radiopharmaceuticals and radiotracers, medical use of these chemicals is closely monitored and controlled by the NRC which has issued strict guidelines for the manufacture, storage and administered doses of such substances (Siegel, J. A., *Guide for Diagnostic Nuclear Medicine*, 2002, U.S. Nuclear Regulatory Commission).

Diagnostic dose guidelines are set according to the effect of the radiopharmaceutical on body tissue. One parameter which is useful in setting dose limits of diagnostic radiopharmaceuticals is the effective dose equivalence (EDE) which can be expressed as Roentgen Equivalent Man (rein, the amount of ionizing radiation required to produce the same biological effect as one rad of high-penetration x-rays) or Sievert (Sv) units, as this unit is defined hereinbelow, wherein 1 rem equals 0.01 Sv.

Following are the acceptable definitions of the units serving to measure radiation doses and effective dose equivalents (EDE, described supra).

The Sievert (symbol Sv) or millisievert (mSv) is an SI (International Standards and Units Organization) derived unit of equivalent dose or effective dose of radiation, and so is dependent upon the biological effects of radiation as opposed to the physical aspects, which are characterized by the absorbed dose, measured in grays (see, definition below). The millisievert (mSv) is commonly used to measure the effective dose in diagnostic medical procedures, e.g., X-rays, nuclear medicine, positron emission tomography (PET) and computed tomography (CT). For example, the natural background effective dose rate varies considerably from place to place, but typically is around 3.5 mSv/year. For a full body equivalent dose, 1 Sv causes slight blood changes, 2-5 Sv causes nausea, hair loss and hemorrhage, and will cause death in many cases. More than 3-6 Sv will lead to death in less than two months in more than 80% of cases.

The Becquerel (symbol Bq) is the SI derived unit of radioactivity, defined as the activity of a quantity of radioactive material in which one nucleus decays per second. It is therefore equivalent to second$^{-1}$. The older unit of radioactivity was the curie (Ci), defined as $3.7 \times 10^{10}$ becquerels or 37 GBq. It was named after Henri Becquerel, who shared a Nobel Prize with Marie Curie for their work in discovering radioactivity. In a fixed mass of radioactive material, the number of becquerels changes with time. In some circumstances, amounts of radioactive material are given after adjustment for some period of time. For example, one might quote a ten-day adjusted figure, that is, the amount of radioactivity that will still be present after ten days. This deemphasizes short-lived isotopes.

The curie (symbol Ci) or millicurie (mCi) is a former unit of radioactivity, defined as $3.7 \times 10^{10}$ decays per second. This is roughly the activity of 1 gram of the radium isotope $^{226}$Ra, a substance studied by the pioneers of radiology, Marie and Pierre Curie. The Ci has been replaced by Bq. One $Bq = 2.7027 \times 10^{-11}$ Ci The gray (symbol Gy) or milligray (mGy) is the SI unit of energy for the absorbed dose of radiation. One gray is the absorption of one joule of radiation energy by one kilogram of matter. The gray replaced the rad, which was not coherent with the SI system. One Gy equals 100 rads.

Rem (symbol rem) is the amount of ionizing radiation required to produce the same biological effect as one rad of high-penetration x-rays.

Radiation absorbed dose (symbol rad) is a unit of radiation dose or the amount of radiation absorbed per unit mass of material. Rad was superseded in the SI by the Gy. The United States is the only country to still use the rad. Rads are often converted to units of rein by multiplication with quality factors to account for biological damage produced by different forms of radiation. The quality factor for X-rays is 1, so rads and reins are equivalent.

EDE (effective dose equivalence) takes into account the type of radiation, half life and distribution of an isotope to derive a number which represents the effect on human tissues for milliCurie (mCi, as this unit is defined hereinbelow) of the isotope administered.

For example, brain perfusion SPECT imaging performed by administration of a 20 mCi dose of $^{99m}$Tc is equivalent to 0.7 rem. This EDE value is similar to that received during a radionuclide bone scan, is 1.5 times that received from a CT of the abdomen and the pelvis, and is 43% of the annual average background radiation in the United States.

When administered to a 70 kg adult male, the average EDE of such doses falls within a range of 0.5 to 1.5 rem. Table 2 below presents typical doses from several commonly practiced nuclear medicine exams and scans based on a 70 kg individual, and provide information on prior art diagnostic radiopharmaceutical doses utilized to carry out these scans.

TABLE 2

| Nuclear Medical Scan | Radiopharmaceutical | Activity mCi (mBq) | Effective Dose mrem (mSv) |
|---|---|---|---|
| Brain | $^{99m+}$Tc DTPA | 20 (740) | 650 (6.5) |
| Brain | $^{15}$O water | 50 (1,850) | 170 (1.7) |
| Brain | $^{99m}$Tc HMPAO | 20 (740) | 690 (6.9) |
| Hepatobiliary | $^{99m}$Tc SCO | 5 (185) | 370 (3.7) |
| Bone | $^{99m}$Tc MDP | 20 (740) | 440 (4.4) |
| Lung Perfusion/Ventilation | $^{99m}$Tc MAA & $^{133}$Xe | 5 & 10 (185 & 370) | 150 (1.5) |
| Kidney | $^{99m}$Tc DTPA | 20 (740) | 310 (3.1) |
| Kidney | $^{99m}$Tc MAG3 | 20 (740) | 520 (5.2) |
| Tumor | $^{67}$Ga | 3 (110) | 1,220 (12.2) |
| Heart | $^{99m}$Tc sestimibi | 30 (1,100) | 890 (8.9) |
|  | $^{99m}$Tc pertechnetate | 30 (1,100) | 1,440 (14.4) |
| Heart | $^{201}$Tl chloride | 2 (74) | 1,700 (17) |
|  | $^{99m}$Tc tetrofosmi | 30 (1,100) | 845 (8.45) |
| Various | $^{18}$F FDG | 10 (370) | 700 (7.0) |

The regulations for use of radiopharmaceuticals changes in cases of patients with lower mass, such as fetuses, infants and children. If a pregnant patient undergoes a diagnostic nuclear medicine procedure, the embryo/fetus will be exposed to radiation. Typical embryo/fetus radiation doses for more than 80 radiopharmaceuticals have been determined by Russell et al. (*Health Phys.*, 1997, 73: 756-769). For the most common diagnostic procedures in nuclear medicine, the doses range from $0.5 \times 10^{-4}$ to 3.8 rad, the highest doses being for $^{67}$Ga. Most procedures result in a dose that is a factor of 10 or more lower than the 3.8 rad dose.

In situations involving the administration of radiopharmaceuticals to women who are lactating, the breastfeeding infant or child will be exposed to radiation through intake of radioactivity in the milk, as well as external exposure from close proximity to the mother. Radiation doses from the activity ingested by the infant have been estimated for the most common radiopharmaceuticals used in diagnostic nuclear medicine by Stabin and Breitz (*J. Nucl. Med.*, 2000, 41:862-873). In most cases, no interruption in breast feeding is needed to maintain a radiation dose to the infant well below 100 mrem (1 mSv). Only brief interruption (hours to days) of breast feeding was advised for $^{99}$mTc-macroaggregated albumin, $^{99m}$Tc-pertechnetate, $^{99m}$Tc-red blood cells, $^{99mTc}$-white blood cells, $^{123}$I-metaiodobenzylguanidine, and $^{201}$Tl. Complete cessation was suggested for $^{67}$Ga-citrate, $^{123}$I-sodium iodide, and $^{131}$I-sodium iodide. The recommendation for $^{123}$I was based on a 2.5% contamination with $^{125}$I, which is no longer applicable.

Representative data of radiation dose estimates for a number of radiopharmaceuticals commonly used in nuclear medicine; each listed in a table for all major source organs, several other organs typically of interest, and the effect of an administered dose (per mCi) of a specific radiopharmaceutical on target organs expressed in rem per mCi, is presented in Appendix 1 hereinbelow. Data was collected from "Radiation Dose Estimates for Radiopharmaceuticals" by Michael G. Stabin, James B. Stubbs and Richard E. Toohey of the Radiation Internal Dose Information Center, Oak Ridge Institute for Science and Education, mail stop 51, P.O. Box 1117, Oak Ridge, Tenn. 37831-0117.

Although the presently administered doses of radiopharmaceuticals are considered safe, there is a great need to substantially reduce the radiation and toxic effects attributed to use of such substances. Due to the finite sensitivity exhibited by today's imaging probes, currently established doses of radiopharmaceuticals are at the upper limits of those allowed by the NRC.

One inherent limitation of radioactive-emission imaging stems from the weighing of risks and benefits, namely the conflict between the requirement to limit the use of potentially harmful radioactive isotopes on one hand, and the need to generate sufficient photons from the diagnosed subject in order to produce a meaningful image on a camera or detector of limited sensitivity, on the other. Although low amounts of such radioisotopes are typically administered so as to not exceed recommended doses, currently available detectors require substantial and potentially hazardous amounts of radioisotopes in order to efficiently detect emission. This problem is intensified in cases where a patient is required to undergo several diagnostic procedures over the time of disease treatment, and more so in cases where the patient is a pregnant woman, an infant or a child.

Another limitation of the currently used techniques is the relatively short time periods which are available to the practitioner to collect diagnostic nuclear images due to decay of the radioisotopes (most diagnostic radiopharmaceuticals are characterized by short half-life), and rapid clearance of the diagnostic radiopharmaceuticals from the body by natural bio-processes. Moreover, the rapid decay and clearance of the radiopharmaceuticals prevents sufficient diagnosis of a dynamic system such as the body, wherein a series of images must be taken, so as to characterize a constantly changing environment. In these cases, a static image will not suffice but rather a series of images, much like in a movie. Again, this limitation could have been partially lessened if high dosage could be administered or images could be collected by more sensitive devices.

Thus, although the presently administered doses of diagnostic radiopharmaceuticals are considered safe there is still a widely recognized need for, and it would be highly advantageous to have radiopharmaceutical kits and methods in which the radiation and toxic effects of the radiopharmaceuticals are substantially reduced, whereby the diagnosis quality is at least maintained and desirably improved.

The present inventors have recently devised and constructed single and multi-collector emission detection probes which have vastly improved emission collection capabilities which enable highly sensitive and/or short-termed image capture. These novel emission detection/collection systems are at least ten-fold more efficient than presently utilized systems (the ratio of measured radiation to emitted radiation is at least 10 to 100-fold higher than prior art systems). This is primarily due to the use of either very sensitive radioactivity emission detectors coupled to high resolution position sensing detectors or to the use of multiple scannable detectors, and further to the use of dedicated algorithms as is disclosed, for example, in the following international applications: PCT/IL2005/000394, PCT/IL2005/000572, PCT/IL2005/000575, PCT/IL2005/000048, WO20040054248 and WO200216965, the contents of which are hereby incorporated by reference. These novel systems employ emission probes which are highly efficient in collecting emissions and thus enable, in combination with dedicated processing algorithms, more sensitive and accurate emission mapping.

The present inventors have now envisioned that the exceptional performance of the abovementioned device, can be efficiently utilized in diagnostic nuclear medicine and imaging, by opening a path to the desired minimization of exposure to ionizing radiation of patients and staff members and/or to the desired high resolution imaging.

The present invention relates to diagnostic radiopharmaceutical dose units and methods of using same in diagnostic nuclear imaging. Specifically, the present invention can be used to image specific tissue such as pathological tissue and acquire dynamic imagery while minimizing the harmful effects of radiation caused by use of ionizing radiation sources in diagnostic radiopharmaceuticals. The present invention can further be used to image tissues while utilizing otherwise inefficient radiopharmaceuticals (e.g., having inherent low emission rate) and/or to perform dynamic imagery during short time periods and/or in high resolution.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The use of radioactive substances which produce ionizing radiation is necessary for advanced methods of pathologic diagnosis and for planning an optimal treatment regime of a growing number of medical conditions. Use of radioactive substances allows the practice of minimally invasive surgical techniques, which save the patients most of the trauma, pain, suffering, hospitalization, recovery and adverse complications associated with conventional "open surgical" procedures. Yet, the use of diagnostic radiopharmaceuticals in diagnostic nuclear medicine is associated with some risk since it exposes the probed subject as well as the medical and technical staff to harmful radiation, and further posses the obligation of expensive and complicated disposal of to radioactive materials.

In view of the above, there is a constant need to minimize the exposure of any subject, to ionizing radiation. This can be achieved by minimizing the amount/concentration of the radioactive substance and/or the duration of the exposure to the radioactive substance.

A patient undergoing a nuclear medicine procedure will receive a radiation dose. Under present international guidelines it is assumed that any radiation dose, however small, presents a risk.

An effective dose of a nuclear medicine investigation is typically expressed by units of millisieverts (mSv). The effective dose resulting from an investigation is influenced by the amount of radioactivity administered in megabecquerels (MBq), the physical properties of the diagnostic radiopharmaceutical used (e.g., the type of ionizing radiation, the rate of emission and decay), its distribution in the body (e.g., the accumulation of the emitting agent per tissue) and its rate of clearance from the body. For example, effective doses can range from 0.006 mSv for a 3 MBq for $^{51}$Cr-EDTA measurement of glomerular filtration rate (measurement of the kidneys' waste filtration and removal) to 37 mSv for a 150 MBq $^{201}$Tl non-specific tumor imaging procedure. The common bone scan with 600 MBq of $^{99m}$Tc-MDP has an effective dose of 3 mSv.

As mentioned above, the present inventors have developed a system which employs emission probes that are highly efficient in collecting emissions and thus enable, in combination with dedicated processing algorithms, more sensitive and accurate emission mapping.

These novel systems have encouraged the present inventors to conceive novel diagnostic kits and diagnosis methods which enable (i) substantially lower diagnostic radiopharmaceutical doses (as compared with the presently used doses); (ii) shorter time of exposure (i.e., collecting the imaging data is a shorter time); (iii) use of radioisotopes that have short half-life and which are typically impractical when the presently known imaging devices are utilized; and (iv) mapping of organs in which rapid substance clearance is observed, and any combination of the foregoing.

Furthermore, the present inventors hypothesized that the heightened sensitivity and overall higher efficiency of the data acquisition device, which allows for the shorter exposure time for diagnostic nuclear imaging, will open the possibility of invasive, minimally invasive and noninvasive time-resolved imagery, or dynamic imagery of biological systems in a living organism.

Thus, the present inventors have now uncovered that the use of such probes facilitates the use of substantially lower amounts of diagnostic radiopharmaceuticals than those presently utilized and thus enables packaging and diagnostic use of novel radiopharmaceutical dose units of substantially lower radioactivity. As is illustrated above, the probe and imaging systems described in previous disclosures of the present inventors enable, for the first time, use of substantially lower doses of various diagnostic radiopharmaceuticals in nuclear imaging.

Thus, according to one aspect of the present invention, there is provided a diagnostic pharmaceutical kit which can be utilized in nuclear imaging techniques. The kit contains a packaged dose unit of a diagnostic radiopharmaceutical having an effective dose equivalence (EDE) of 2.5 millirem (mrem) or less per kg body weight of a subject. This packaged dose is considerably lower than the packaged dose of the prior art, and is in line with the general motivation to reduce to a minimum the exposure of the subject to substances which emit ionizing radiation. Preferably, the EDE of the packaged dose unit in accordance with an aspect of the present invention is 0.01-2 millirem per kg body weight of a subject, and more preferably it is 0.01-1 millirem per kg body weight of a subject.

Similarly, the diagnostic pharmaceutical kit of the present invention contains a packaged dose unit of a diagnostic radiopharmaceutical having an effective dose equivalence (EDE) of 150 millirem (mrem) or less, which is a typical whole-body dose for a 70 kg person. Preferably, the EDE of the packaged whole-body dose unit of in accordance with an aspect of the present invention is 15-100 millirem per 70 kg subject, more preferably 15-50 millirem per 70 kg subject.

Compared to a typical whole-body dose of $^{99m+}$Tc DTPA of 650 mrem for a brain scan according to prior art, a whole-body dose of the present invention can be as low as 65 mrem and less; compared to a typical whole-body dose of $^{99m}$Tc-Sestimibi of 890 mrem for a heart scan according to prior art, a whole-body dose of the present invention can be as low as 89 mrem and less; and compared to a typical whole-body dose of $^{18}$F FDG of 700 mrem for a general somatic scan according to prior art, a whole-body dose of the present invention can be as low as 70 mrem and less.

Alternatively, the dose unit can include an amount of a diagnostic radiopharmaceutical which will result in an amount of detected counts sufficient for imaging when using the abovementioned imaging device having a heightened sensitivity. In nuclear medicine, the dose in mCi of a diagnostic radiopharmaceutical can also be determined according to the sensitivity of the detector utilized, the total time of scan, and the total counts needed for imaging (typically about $2-4 \times 10^6$ for a scanned region and about $10^5$ for a target organ such as the heart). These parameters can be utilized to determine the collection efficiency of prior art emission detection systems. For example, in a $^{99m}$Tc heart scan a typical administered dose is 20-30 mCi of which about 1.2-1.5% to 1.5-4% are uptaken by the heart (namely 0.3 mCi-1.2 mCi, typically 0.5-1.0 mCi) and a typical scan is conducted for approximately 10 minutes (600 seconds). Since a single mCi accounts for $3.7 \times 10^7$ counts per second, the efficiency of a typical detection system calculates to approximately 1.8 photons captured for every 10,000 photons emitted from the organ. Since the present system is at least 10 fold more efficient at photon capturing (e.g., capable of capturing at least 1 photon Out of every 1000 photons emitted) a tenth of a diagnostic radiopharmaceutical dose can be utilized for scanning. Thus, for the above described example, a packaged dose unit of 2.5 mCi $^{99m}$Tc or less can be utilized for imaging a heart over a period of 10 minutes.

Since the dose reaching the target organ (e.g., the heart) is a fraction of the dose administered, for example, and as stated above, in the case of mapping the cardiac muscle, about 1.5-4% of the dose injected intravenously (20-30 mCi) reaches the heart (0.3 mCi in the heart), mapping a directly injected dose unit of 0.03 mCi or less is possible using the systems developed by the present inventors.

As used herein the phrase "packaged dose unit" refers to a dosage unit (or unit dose) which is packaged in one or more containers such as vials, ampoules or a delivery syringe. Preferably, the dose unit is manufactured and packaged for inhalation or injection (intravenous or subcutaneous) according to FDA regulatory guidelines for human use [Rules and Regulations, *Federal Register* (1999), Vol. 64, No. 94, pp 26657-70].

The dose unit may be ready for administration or may require premixing prior to administration. The latter case is exemplified by a radiotracer preparation which includes an isotope attached to a recognition binding moiety such as an antibody, as is detailed hereinbelow.

Adapting to the definition by the FDA [Code of Federal Regulations (2005), Title 21, Vol. 7, CITE: 21CFR601.31], the phrase "diagnostic radiopharmaceutical" refers to (a) an article that is intended for use in the diagnosis or monitoring of a disease or a manifestation of a disease in humans and that exhibits spontaneous disintegration of unstable nuclei with the emission of nuclear particles or photons; or (b) any non-radioactive reagent kit or nuclide generator that is intended to be used in the preparation of such article as defined in (a) hereinabove.

Radiopharmaceuticals are therefore compounds that include one or more radioisotopes having such an unstable nuclei.

The term "radioisotope", refers to a radioactive atom that has a specific radioactivity above that of the background level for the same atom. It is well known, in this respect, that naturally occurring elements are present in the form of varying isotopes, some of which are radioactive isotopes. The radioactivity of the naturally occurring elements is a result of the natural distribution of these isotopes, and is commonly referred to as a background radioactive level. However, there are known methods of enriching a certain element with isotopes that are radioactive. The result of such enrichment is a population of atoms characterized by higher radioactivity then a natural population of that atom, and thus the specific radioactivity thereof is above the background level.

A diagnostic radiopharmaceutical can be a compound containing one or more radioisotopes per se, or, a radiotracer, in which the compound is bound to a recognition moiety, as follows.

In cases where the organ, tissue or cells to be imaged can be characterized by a known specific and localized (fixed) biochemical moieties, such as a peptide, a protein, a receptor, a membrane, a glycan, a nucleic acid (i.e., RNA and/or DNA) or any combination thereof, the radiopharmaceutical can be designed so as to specifically bind to one or more of these biochemical moieties by way of molecular recognition. This binding is afforded by virtue of one or more recognition moieties which form a part of the radiopharmaceutical. These recognition binding moieties are selected so as to have a high affinity to the specific biochemical moieties characterizing the target organ, tissue or cells to be imaged. This affinity allows for the radiopharmaceutical to concentrate at the target organ, tissue or cells at higher rates than the surrounding organs, tissues or cells, thereby affording an image wherein the target organ, tissue or cells are highlighted by the contrast of radioactive emission.

Radiopharmaceuticals having such binding moieties which act as a vehicle for transporting and delivering the radioactive isotope to a specific target are referred to herein as radiotracers. Therefore, the term "radiotracer", as used herein, refers to a radiopharmaceutical having one or more recognition binding (targeting) moieties attached thereto.

As used herein, the phrase "recognition binding moiety" or "targeting moiety" refers to a moiety that interacts (binds) with a target recognition site by means of molecular recognition, and include, without limitation, a ligand, an inhibitor, a co-factor, an antibody, a monoclonal antibody, an antibody fragment, an antigen, a hapten, a receptor, a receptor affine peptide, a peptide, a protein, a membrane, a nucleotide and a nucleic acid.

Molecular recognition, also known as "host-guest chemistry", is a phenomenon in which molecules are distinguished accurately from other molecules. Chemically, it indicates that certain molecules abnormally bond with certain molecules and are relatively inert with respect to other molecules found in the same environment. This phenomenon involves the three-dimensional positioning of various sub-molecular functionalities which can form interactions via reciprocal actions such as hydrogen bonds, hydrophobic interactions, ionic interactions, aromatic interactions and/or other non-covalent bond interactions and combination thereof. General examples of molecular recognition include ligand-receptor interactions, enzyme-substrate interactions, antibody-antigen interactions, biotin-avidin affinity interactions and the like.

Non-limiting examples of commonly used radiotracers include $^{99m}$Tc-Arcitumomab (CEA-Scan™) which is a monoclonal antibody for imaging colorectal tissues afflicted with colorectal cancer, $^{99m}$Tc-sestamibi (Cardiolite™) and $^{99m}$Tc-tetrofosmin (Myoview™) for imaging the heart of a subject for myocardial perfusion, $^{111}$In-Capromab pendetide (ProstaScint™) which is a monoclonal antibody for imaging prostate tissues afflicted with prostate cancer, $^{99m}$Tc-Fanolesomab (NeutroSpec™) which is a monoclonal antibody for imaging inflamed and infectious tissues and $^{90}$Y/$^{111}$In-Zevalin (Ibritumomab Tiuxetan) which is a monoclonal antibody directed against the CD20 antigen, whereby this antigen is found on the surface of normal and malignant B lymphocytes.

Any diagnostic radiopharmaceutical can be utilized in the kit of the present embodiments. In general, the kit of the present embodiments may contain a reduced radiation dose emitted from each radiopharmaceutical, which ranges from 0.1 of the dose of the prior art to 0.01 of the dose of the prior art.

Exemplary radiopharmaceuticals that can be utilized in this context of the present invention include, without limitation, $^3$H-water, $^3$H-insulin, $^{11}$C-carbonmonoxide, $^{13}$N-ammonia, $^{14}$C-insulin, $^{15}$O—H$_2$O, $^{15}$O—O$_2$, $^{18}$F-fluorodeoxyglucose, $^{18}$F-sodium fluoride, $^{51}$Cr-erythrocytes (RBC), $^{57}$Co-vitamin B$_{12}$ (cyanocobalamin) $^{58}$Co-vitamin B$_{12}$ (cyanocobalamin), $^{59}$Fe-citrate, $^{60}$Co-vitamin B$_{12}$ (cyanocobalamin), $^{67}$Ga-citrate, $^{68}$Ga-citrate, $^{75}$Se-selenomethionine, $^{81m}$Kr-krypton for inhalation, oral administration or injections, $^{82}$Rb, $^{85}$Sr-nitrate, $^{90}$Y/$^{111}$In-ibritumomab tiuxetan ($^{90}$Y/$^{111}$In-Zevalin), $^{99m}$Tc-albumin microspheres, $^{99m}$Tc-disofenin, lidofenin and mebrofenin, $^{99m}$Tc-DMSA, $^{99m}$Tc-DTPA (injection), $^{99m}$Tc-DTPA (aerosol), $^{99m}$Tc-ECD (ethylene cystate dimer), $^{99m}$Tc-exametazime (HMPAO), $^{99m}$Tc-glucoheptonate, $^{99m}$Tc-HEDP, $^{99m}$Tc-HMDP, $^{99m}$Tc-HSA, $^{99m}$Tc-MAA, $^{99m}$Tc-MAG$_3$, $^{99m}$Tc-MDP, $^{99m}$Tc-tetrofosmin (Myoview), $^{99m}$Tc-sestamibi (Cardiolite), $^{99m}$Tc-oral administrations, $^{99m}$Tc-pertechnetate, $^{99m}$Tc-pyrophosphate, $^{99m}$Tc-RBC in vitro and in vivo labeling, $^{99m}$Tc-sulfur colloid, $^{99m}$Tc-teboroxime, $^{99m}$Tc-white blood cells, $^{111}$In-ibritumomab tiuxetan ($^{111}$In-Zevalin), $^{111}$In-DTPA, $^{111}$In-platelets, $^{111}$In-RBC, $^{111}$In-white blood cells, $^{123}$I-hippuran, $^{131}$I-IMP, $^{123}$I-mIBG, $^{123}$I-sodium iodide, $^{124}$I-sodium iodide, $^{125}$I-fibrinogen, $^{125}$I-IMP, $^{125}$I-mIBG, $^{125}$I-sodium iodide, $^{126}$I-sodium iodide, $^{130}$I-sodium iodide, $^{131}$-hippuran, $^{131}$I-HSA $^{131}$I-MAA, $^{131}$I-mIBG, $^{131}$I-Rose Bengal, $^{131}$I-sodium iodide, $^{127}$Xe-inhalation and injection, $^{133}$Xe-inhalation and injection, $^{197}$Hg-chlormerodrin, $^{198}$Au-colloid and $^{201}$Tl-chloride.

Following are several non-limiting examples of the radioactive dose of exemplary radiopharmaceuticals utilized in accordance with this aspect of the present invention. Since an administered dose is typically measured in mCi activity of the radioisotope, the following lists the radioactivity of a packaged dose unit in the kit of the present embodiments, compared to the radioactivity of the presently used doses.

Radioactive ammonia typically comprises a $^{13}$N isotope having a half-life of 9.96 minutes. A radioactive dose of $^{13}$N-ammonia is typically 20 mCi. According to a preferred embodiment of the present invention, a radiopharmaceutical kit comprises a radioactive dose of $^{13}$N-ammonia that ranges from 5 mCi to 0.01 mCi, more preferably from 2 mCi to 0.02 mCi and thus can be, for example, 5, 2, 1, 0.5, 0.2, 0.1, 0.05, 0.02 or 0.01 mCi.

Radioactive fluorodeoxyglucose (FDG) typically comprises an $^{18}$F isotope having a half-life of 110 minutes. A radioactive dose of $^{18}$F-FDG is typically 10 mCi. According to a preferred embodiment of the present invention, a radiopharmaceutical kit comprises a radioactive dose of $^{18}$F-FDG that ranges from 3 mCi to 0.1 mCi, more preferably from 1 mCi to 0.1 mCi and thus can be, for example, 3, 1 or 0.1 mCi.

Radioactive capromab pendetide (ProstaScint), typically comprises an $^{111}$In isotope having a half-life of 72 hours. A radioactive dose of $^{111}$In-capromab pendetide is typically 5 mCi. According to a preferred embodiment of the present invention, a radiopharmaceutical kit comprises a radioactive dose of $^{111}$In-capromab pendetide that ranges from 2 mCi to 0.01 mCi, more preferably from 0.5 mCi to 0.01 mCi and thus can be, for example, 2, 1, 0.5, 0.1, 0.05 or 0.01 mCi.

Radioactive WBCs (non-protein peptide), typically comprises an $^{111}$In isotope. A radioactive dose of $^{111}$In-WBCs is typically 0.5 mCi. According to a preferred embodiment of the present invention, a radiopharmaceutical kit comprises a radioactive dose of $^{111}$In-WBCs that ranges from 0.2 mCi to 0.001 mCi, more preferably from 0.05 mCi to 0.001 mCi and thus can be, for example, 0.2, 0.1, 0.05, 0.01, 0.005 or 0.001 mCi.

Radioactive Satumomab Pendetide (OncoScint), typically comprises an $^{111}$In isotope. A radioactive dose of $^{111}$In-Satumomab Pendetide is typically 5 mCi. According to a preferred embodiment of the present invention, a radiopharmaceutical kit comprises a radioactive dose of $^{111}$In-Satumomab Pendetide that ranges from 2 mCi to 0.01 mCi, more preferably from 0.2 mCi to 0.01 mCi and thus can be, for example, 2, 1, 0.5, 0.1, 0.05 or 0.01 mCi.

Radioactive Pentetreotide typically comprises an $^{111}$In isotope. A radioactive dose of $^{111}$In-Pentetreotide is typically 6 mCi. According to a preferred embodiment of the present invention, a radiopharmaceutical kit comprises a radioactive dose of $^{111}$In-Pentetreotide that ranges from 1 mCi to 0.005 mCi, more preferably from 0.5 mCi to 0.005 mCi and thus can be, for example, 1, 0.5, 0.2, 0.1, 0.05, 0.01 or 0.005 mCi.

Radioactive Arcitulimomab typically comprises a $^{99m}$Tc isotope having a half-life of 6 hours. A radioactive dose of $^{99m}$Tc-Arcitumomab typically ranges from 20 mCi to 30 mCi. According to a preferred embodiment of the present invention, a radiopharmaceutical kit comprises a radioactive dose of $^{99m}$Tc-Arcitumomab that ranges from 5 mCi to 0.05 mCi, more preferably from 3 mCi to 0.05 mCi and thus can be, for example, 5, 2, 1, 0.5, 0.1 or 0.05 mCi.

Radioactive Sodium pertechnetate typically comprises a $^{99m}$Tc isotope. A radioactive dose of $^{99m}$Tc-Sodium pertechnetate typically ranges from 10 mCi for a whole-body scan to 0.1 mCi, whereby the packaged dose unit is typically formulated as a drop for an eye scan. According to a preferred embodiment of the present invention, a radiopharmaceutical kit comprises a radioactive dose of $^{99m}$Tc-Sodium pertechnetate that ranges from 5 mCi to 0.01 mCi, more preferably from 1 mCi to 0.01 mCi and thus can be, for example, 5, 2, 1, 0.5, 0.2, 0.1, 0.05, 0.02 or 0.01 mCi.

A radioactive dose of Erythrocytes (RBC) comprising a $^{99m}$Tc isotope typically ranges from 10 mCi to 25 mCi. According to a preferred embodiment of the present invention, a radiopharmaceutical kit comprises a radioactive dose of $^{99m}$TC-RBC that ranges from 5 mCi to 0.05 mCi, more preferably from 1 mCi to 0.05 mCi and thus can be, for example, 5, 2, 1, 0.5, 0.1, 0.05, 0.02 or 0.01 mCi.

Radioactive Depreotide (NeoTect), apcitide (AcuTect), pyrophosphate, medroniate (MDP), exametazime (HMPAO) and bicisate (ECD, Neurolite) all comprise a $^{99m}$Tc isotope. A radioactive does of these radiopharmaceuticals is typically 20 mCi. According to a preferred embodiment of the present invention, radiopharmaceutical kits comprise a radioactive dose of such a $^{99m}$Tc-radiopharmaceuticals that ranges from 5 mCi to 0.05 mCi, more preferably from 1 mCi to 0.05 mCi and thus can be, for example, 5, 2, 1, 0.5, 0.2, 0.1, 0.05 mCi.

A radioactive dose of $^{99m}$Tc-Sestamibi typically ranges from 10 mCi (for stress) to 30 mCi (for rest). According to a preferred embodiment of the present invention, a radiopharmaceutical kit comprises a radioactive dose of such a $^{99m}$Tc-radiopharmaceutical that ranges from 5 mCi to 0.01 mCi, more preferably from 1 mCi to 0.01 mCi and thus can be, for example, 5, 2, 1, 0.5, 0.2, 0.1, 0.05, 0.02 or, 0.01 mCi.

Radioactive Cyanocobalamin typically comprises an $^{57}$Co isotope having a half-life of 271.8 days. A radioactive dose of $^{57}$Co-Cyanocobalamin is typically 0.001 mCi. According to a preferred embodiment of the present invention, a radiopharmaceutical kit comprises a radioactive dose of $^{57}$Co-Cyanocobalamin that ranges from 0.0003 mCi to 0.00001 mCi, more preferably from 0.0001 mCi to 0.00001 mCi and thus can be, for example, 0.0003, 0.0001, 0.00005 or 0.00001 mCi.

Radioactive Gallium Citrate, typically comprises a $^{67}$Ga isotope having a half-life of 271.8 days. A radioactive dose of $^{67}$Ga-Gallium citrate is typically 5 mCi for PET imaging and 10 mCi for SPEC imaging. According to a preferred embodiment of the present invention, a radiopharmaceutical kit comprises a radioactive dose of $^{67}$Ga-Gallium citrate that ranges from 1 mCi to 0.01 mCi, more preferably from 0.5 mCi to 0.01 mCi and thus can be, for example, 1, 0.5, 0.2, 0.1, 0.05 or 0.01 mCi.

$^{81}$Kr isotope, having a half-life of 210,000 years, is presently used as a gas for dynamic imaging. A radioactive dose of $^{81}$Kr is typically 10 mCi. According to a preferred embodiment of the present invention, a radiopharmaceutical kit comprises a radioactive dose of $^{81}$Kr that ranges from 2 mCi to 0.05 mCi, more preferably from 1 mCi to 0.05 mCi and thus can be, for example, 2, 1, 0.5, 0.1 or 0.05 mCi.

Radioactive sodium iodide typically comprises an $^{123}$I isotope having a half-life of 13.2 hours. A radioactive dose of $^{123}$I-sodium iodide typically ranges from 0.1 mCi to 0.4 mCi, and the radiopharmaceutical dose unit is often provided in capsules. According to a preferred embodiment of the present invention, a radiopharmaceutical kit comprises a radioactive dose of $^{123}$I-sodium iodide that ranges from 0.05 mCi to 0.001 mCi, more preferably from 0.01 mCi to 0.001 mCi and thus can be, for example, 0.1, 0.05, 0.02, 0.01, 0.005 or 0.001 mCi, whereby the $^{123}$I-sodium iodide can be packaged as capsules.

Radioactive Sodium iodide can alternatively comprise an $^{131}$I isotope having a half-life of 8 days. A radioactive does of $^{131}$I-sodium iodide typically ranges from 0.01 mCi to 0.004 mCi. According to a preferred embodiment of the present invention, a radiopharmaceutical kit comprises a radioactive dose of $^{131}$I-sodium iodide that ranges from 0.001 mCi to 0.00005 mCi, and thus can be, for example, 0.001, 0.0005, 0.0002, 0.0001 or 0.00005 mCi, whereby the $^{131}$I-sodium iodide can be packaged as capsules.

Radioactive albumin typically comprises an $^{125}$I isotope having a half-life of 59.4 days. A radioactive does of $^{125}$I-albumin is typically 0.02 mCi. According to a preferred embodiment of the present invention, a radiopharmaceutical kit comprises a radioactive dose of $^{125}$I-albumin that ranges from 0.005 mCi to 0.0001 mCi, more preferably from 0.001 mCi to 0.0001 mCi and thus can be, for example, 0.005, 0.002, 0.001, 0.0005 or 0.0001 mCi.

Radioactive sodium chromate typically comprises a $^{51}$Cr isotope having a half-life of 27.7 days. A radioactive dose of $^{51}$Cr-sodium chromate typically ranges from 0.15 mCi to 0.3 mCi. According to a preferred embodiment of the present invention, a radiopharmaceutical kit comprises a radioactive dose of $^{51}$Ci-sodium chromate that ranges from 0.05 mCi to 0.001 mCi, more preferably from 0.01 mCi to 0.001 mCi and thus can be, for example, 0.05, 0.02, 0.01, 0.005 or 0.001 mCi.

As is provided in the list above, the mCi dose range of the present dose unit of each listed exemplary diagnostic radiopharmaceutical is substantially lower than that of prior art dose units.

The kit of the present embodiments can be used with any suitable nuclear imaging technique, examples of which are provided in Appendix 1 hereinafter.

The radiopharmaceutical of the diagnostic kit of the present embodiments can be prepared using any suitable prior art approach. Such approaches are well known to the ordinary skilled artisan and as such no further description of specific synthesis approaches of diagnostic radiopharmaceuticals and in particular radiotracers are provided herein.

However, in cases where the radiopharmaceutical is a radiotracer, it is sometimes preferred that the isotope be provided separate from the recognition binding moiety especially in cases of isotopes exhibiting a short half life, since a specific activity of such a radiotracer preparation will substantially decrease over a short time period.

As mentioned hereinabove, an effective dose of any given radiopharmaceutical is influenced, among other factors, by the amount of the radioisotope and the state of decay of the radioisotope, namely the radioactivity which is currently measured at any given time. In essence, an isotope which already decayed no longer contributes to the activity of the administered sample, and therefore is considered an impurity. In addition, radiopharmaceuticals which contain chelators or recognition moieties attached thereto may decompose, both in vivo and in vitro, so as to produce, for example, the radioisotope, the chelating moiety and/or the recognition moiety. The free chelators and recognition moieties are also considered impurities.

Radioisotopes utilized for synthesis are therefore typically >60% pure, and preferably are >90% pure; during radiotracer synthesis, a recognition binding moiety is mixed with a radioisotope and quality is checked to maintain approximately a 95% pure composition of the radiotracer. The remaining 5% is composed of non-radioactive isotopes, chelators, recognition moieties and the like.

Following mixing and prior to injection, isotope decay and chemical decomposition may reduce the specific activity of the diagnostic radiopharmaceutical in proportion to isotope decay time and the instability of the radiopharmaceutical.

Few diagnostic radiopharmaceuticals depend on "specific activity" or purity, since they "compete" for receptors with their decomposition products or their decomposition products produce adverse effects (e.g. to lungs).

The kit of the present invention can further include instructions for use in carrying out a nuclear scan as well as instructions for handling and additional packaging materials (e.g. pig) as required by federal regulations. Radioisotopes must be carefully handled, therefore vials or syringes containing such substances are delivered inside containers offering some degree of radiation shielding. Furthermore, government regulations require syringes to be disposed of in a disposal container that shields others from the risk of injury posed by their sharp, biologically-contaminated hypodermic needles. Such a container generally referred to herein as a "sharps" container, typically has an inner cavity or chamber that can hold one or more syringes.

One type of conventional delivery container currently used for the delivery of syringes containing radioactive drugs is known as a radiopharmaceutical pig. The radiopharmaceutical pig has a shielded inner chamber suitable for enclosing a syringe that is itself held inside of a sharps container. In particular, the chamber is lined with elemental lead to shield individuals from the radioactive drug in the syringe. The exterior of the radiopharmaceutical pig is a plastic polystyrene shell. The sharps container has an insert and a cap that can be engaged by two snaps that fit into two aligned slots formed on the insert.

Prior to administration, the syringe is loaded with the required dose of a radioactive drug and is placed in the insert, which is nested in the chamber of the radiopharmaceutical pig. The radiopharmaceutical pig is then closed and delivered to the hospital, whereupon the pig is disassembled and the syringe is used to inject the dose into the patient. The spent syringe may then be placed back into the sharps insert and the cap may then be placed on the housing to hold the spent syringe within the sharps container. The radiopharmaceutical pig is reassembled and taken to a disposal area, which may or may not be at the pharmacy.

While exposure to ionizing radiation presents a major, widely recognized limit to the presently known nuclear imaging techniques, these techniques are oftentimes limited by other factors. These include, for example, rapid decay of the radioisotope (i.e., short half-life), rapid clearance of the radiopharmaceutical from the targeted organ, and low energy and/or rate of disintegration of the radiopharmaceutical.

These characteristics determine the amount and energy of detectable photons which reach the detector per time unit. When used with the presently known emission detectors, low amount and/or energy of the detectable photons results in a weak or no signal and hence fail to provide a meaningful image. Thus, for example, radioisotopes that rapidly decay or are rapidly cleared from the target organ, fail to produce a sufficient amount of detectable photons at the time of data collection.

According to embodiments of the present invention, the highly sensitive emission detector designed by the present inventors can be used to detect Sufficient photons from such radioisotopes due to its higher efficiency and wider dynamic range, even for radioisotope characterized by a short half-life, low rate and low energy of disintegration, which may or may not be combined with a low rate of accumulation in the organ of interest and a rapid clearance from the body by metabolic and chemical processes.

The present inventors have now uncovered that the high sensitivity of the novel imaging probes described above can be used, due to higher efficiency and wider dynamic range, to collect sufficient imaging data even in cases of radiopharmaceuticals that are characterized by low amount and/or energy of the emitted photons within a time frame of a nuclear investigation. Thus, these highly sensitive probes enable to perform efficient imagery even with such radiopharmaceuticals that are incompatible or at least inefficient when utilized with the presently known techniques. These radiopharmaceuticals are collectively referred to herein as having an inherent low emission rate, as this phrase is defined hereinbelow.

Thus, according to another aspect of the present invention there is provided a radiopharmaceutical kit which comprises a packaged dose unit of a radiopharmaceutical that have an inherent low emission rate.

The phrase "inherent low emission rate", as used herein, defines radiopharmaceuticals that emit such levels of radiation which are too low for producing a useful image under presently used nuclear imaging techniques due to physical, chemical and biological characteristics which render them incompatible or impractical for use with presently available emission detectors.

The characteristics accounting for inherent low emission rate of radiopharmaceuticals include, for example, a rapid decay (i.e. short half-life), low disintegration rate, low energy of disintegration of the radioisotope, rapid clearance from the body, and any combination of the foregoing.

Thus, in one embodiment of this aspect of the present invention, the inherent low emission rate of the radiopharmaceutical stems from rapid clearance of the radiopharmaceutical from the body.

The phrase "rapid clearance", as used herein, encompasses any chemical or biological process involved in reducing the amount of the radiopharmaceutical in both the targeted organ and the body. This phrase is therefore used herein to describe the bioavailability of the radiopharmaceutical in terms of the rate of its accumulation in a target organ, the rate of its clearance from the target organ, the rate of its decomposition in the body and the rate of its excretion from the system.

The bioavailability of a given radiopharmaceutical therefore determines the time required for the radiopharmaceutical to reach and accumulate in the organ of interest, the affinity of the radiopharmaceutical to its target (in cases where the radiopharmaceutical is a radiotracer) and the rate of clearance of the radiopharmaceutical from the body.

Slow accumulation in the tissue of interest and rapid clearance from the body are adverse effects for any beneficial pharmaceutical, drug and in the present invention, of any radiopharmaceutical, as the body rids itself from the foreign substance by means of metabolic processes, natural toxic waste disposal as in the kidneys, and other secretion mechanisms. In radiopharmacology, this problem becomes even more detrimental as the requirement to have a sufficient amount of the substance in its radioactive fort in the body for a sufficient duration for data collection, is opposed by the combination of rapid clearance and chemical decomposition.

According to this embodiment of the present invention, the kit comprises a radiopharmaceutical that has a clearance rate that ranges from several minutes to several days.

According to another embodiment of this aspect of the present invention, the inherent low emission rate of the radiopharmaceutical stems from rapid decay of the radiopharmaceutical.

As discussed hereinabove, the half-life time of some diagnostic radiopharmaceuticals is very short, in the order of seconds to minutes and the scanning time of such radiopharmaceuticals is therefore always limited. Following a short scanning time-window, no further imaging benefits are derived from additional scanning since rapid decay results in a small fraction of emitting isotopes.

A rapid decay of a radiopharmaceutical typically results from an inherent short half-life of the radioisotope included in the radiopharmaceutical.

Exemplary radioisotopes which have relatively short half-life which renders them impractical for use with currently available emission detectors, and which can be efficiently utilized according to embodiments of the present invention include, without limitation, $^{39}Cl$ having a half-life of 55.6 minutes; $^{69}Zn$ having a half-life of 56 minutes; $^{38}S$ having a half-life of 2.84 hours; $^{56}Mn$ having a half-life of 2.579 hours; $^{49}Cr$ having a half-life of 42.3 minutes; and $^{83}Br$ having a half-life of 2.40 hours.

According to another embodiment of this aspect of the present invention, the inherent low emission rate of the radiopharmaceutical stems from low energy of disintegration of the radiopharmaceutical.

According to another embodiment of this aspect of the present invention, the inherent low emission rate of the radiopharmaceutical stems from low rate of disintegration of the radiopharmaceutical.

Each of the radiopharmaceutical kits described herein can be efficiently utilized for obtaining nuclear images of tissue and organs of interest, by employing non- or minimally invasive techniques in vivo.

Thus, according to an additional the present invention there is provided a method of imaging a tissue of a subject. The method is effected by administering to the subject, either systemically or locally, a dose unit of a diagnostic radiopharmaceutical having a dose equivalent of 2.5 mrem or less per kg body weight, as detailed hereinabove; collecting the emission produced by the diagnostic radiopharmaceutical, as detailed hereinbelow; and translating the emission data collected into a two-dimensional or three-dimensional image data.

Typically, the radiopharmaceutical is administered systematically in order to achieve two main goals, a) reach the target organ which is typically out of reach when using non-invasive or minimally invasive techniques, and b) in order to create the appropriate background for the organ to be imaged and obtain the contrast between the areas of interest (those serving as targets for the radiopharmaceutical) and their surrounding. Systematic administration can be effected, for example, by intravenous injection, by inhalation or orally.

As the use of the abovementioned high sensitivity emission detector becomes available, the limitations associated with low signal are alleviated considerably. Thus, imaging of tissues or organs using radiopharmaceuticals that have low emission rate and hence presently lead to collection of insufficient data during a scan, is facilitated.

Thus, according to another aspect of the present invention, there is provided another method of imaging a tissue of a subject. The method, according to this aspect of the present invention is affected by administering to the subject, either systemically or locally, a dose unit of a radiopharmaceutical which is characterized by an inherent low emission rate, as detailed hereinabove; collecting the emission produced by the diagnostic radiopharmaceutical; and translating the emission data collected into a two-dimensional or three-dimensional image data.

The method, according to this aspect of the present invention, therefore allows to use radiopharmaceuticals and to image organs and/or tissues that are otherwise impractical.

The high sensitivity of the emission detector taught by the present inventors further enables to collect sufficient image data in a short time period. This feature is exceptionally advantageous since it allows to minimize the time during which a subject is exposed to radiation. Hence, using any diagnostic radiopharmaceuticals, including the radiopharmaceuticals described herein, nuclear imaging can be performed during a shorter time period, compared to the presently known imaging methods.

Thus, according to a further aspect of the present invention there is provided a method of imaging a tissue, which is effected by administering to the subject a dose unit of a diagnostic radiopharmaceutical; collecting emission of the diagnostic radiopharmaceutical during a time period that does not exceed, e.g., 1-30 minutes; and translating the emission collected into image data.

The method according to this aspect of the present invention is particularly advantageous in PET and SPECT imaging techniques.

Positron Emission Tomography (PET), is a nuclear medicine imagine technology which requires the administration to a subject of a molecule labeled with a positron-emitting nuclide. Single Photon Emission Computed Tomography (SPECT) is a form of chemical imaging in which emissions from radioactive compounds, labeled with gamma-emitting radionuclides, are used to create cross-sectional images of radioactivity distribution in vivo.

These techniques require relatively high emission levels for obtaining a meaningful image. In addition, radiopharmaceuticals that are suitable for use in these techniques are often characterized by relatively short half-lives. Thus, for example, $^{15}O$, $^{13}N$, $^{11}C$ and $^{18}F$, which are often used in PET, have half-lives of 2, 10, 20, and 110 minutes, respectively. Due to the high emission level required and the short half-lives of the radiopharmaceuticals, relatively high radiation doses of the radiopharmaceutical are administered to the subject.

Performing such nuclear imaging procedures in relatively short time periods is therefore exceptionally beneficial since it reduces the time the subject is exposed to high radiation level.

The ability to obtain all the required data during a short time period, which is not possible with other currently used detectors, further allows the investigator to collect several consecutive images during that time scan in which the emission rate is still sufficient for significant data collection.

These consecutive images can be used to provide time-resolved data of the tissue or organ of interest, showing the development in time of imaged system.

Thus, according to preferred embodiments of the present invention, for any of the methods described herein, a time-resolved data can be obtained by performing consecutive images of the investigated tissue.

Nuclear imaging techniques stiffer from other limitations which are related to a weak signal or a low signal-to-noise ratio. Such limitations stem from the fact that any detector has a limited sensitivity, and at any dose of the radiopharmaceutical, only a fraction of the emitted radiation can be picked-up by the detector and/or be distinguished from the background noise.

Using the improved emission detector taught by the present invention can further enable and facilitate the provision of a high-resolution image of a tissue, which so far was impossible, difficult or required exceptionally high doses of the radiopharmaceutical and/or prolonged exposure of the subject to the radiopharmaceutical t.

Thus, according to an aspect of the present invention, there is provided a method of obtaining a high-resolution image of a tissue of a subject.

Any suitable extracorporeal or intracorporal imaging technique employing any suitable probe types can be used to image the administered diagnostic radiopharmaceutical in the methods described herein. Preferably an imaging system employing a probe having a wide angle or a wide view of collection is employed.

Further preferably, the emission data is collected by one or mole radioactive-emission probes which are characterized by a collection efficiency of 1%, each of which is separately adjustable within its housing.

Further preferably, the radioactive-emission probes, or emission detectors are scintillation probes which have a collection angle that enables a collection target area of 15 mm$^2$ when placed 15 cm away from the target area.

Extra and intra-corporeal probe types which are highly suitable for use with the kit of the present invention are described in detail in the PCT applications referenced hereinabove.

A non-limiting example of a widely used radiopharmaceutical, $^{99m}$Tc-sastamibi, is used herein to demonstrate the various novel features of the present invention. $^{99m}$Tc is characterized by a half-life ($t_{1/2}$) of 6.02 hours. Table 3 below presents the physical decay of $^{99m}$Tc, wherein the calibration time is set to 0 arbitrarily and the activity is defined as 100%. The remaining fraction of radioactivity is recorded every hour from that time point. This decay chart is used by the medical staff when preparing the sample for injection into a patient undergoing diagnostic imaging. The absolute activity of the product is measured at the manufacturer site on the day of shipment, and the complete assay data is provided on the tag attached to the vial.

TABLE 3

| Hours | Fraction remaining |
|---|---|
| 0 | 1.000 (100%) |
| 1 | 0.891 (89.1%) |
| 2 | 0.794 (79.4%) |
| 3 | 0.708 (70.8%) |
| 4 | 0.631 (63.1%) |
| 5 | 0.562 (56.2%) |
| 6 | 0.501 (50.1%) |
| 7 | 0.447 (44.7%) |
| 8 | 0.398 (39.8%) |
| 9 | 0.355 (35.5%) |
| 10 | 0.316 (31.6%) |
| 11 | 0.282 (28.2%) |
| 12 | 0.251 (25.1%) |

Apart for radioactivity decay, the product is cleared from the body by natural processes. Myocardial uptake which is coronary flow dependent is 1.2% of the injected dose at rest and 1.5% of the injected dose at exercise. Table 4 below illustrates the biological clearance as well as effective clearance which include biological clearance and radionuclide decay of $^{99m}$Tc-Sestamibi from the heart and liver.

TABLE 4

| Time | Rest | | | | Stress | | | |
| | Heart | | Liver | | Heart | | Liver | |
| (minutes) | Biological | Effective | Biological | Effective | Biological | Effective | Biological | Effective |
| 5 | 1.2 | 1.2 | 19.6 | 19.4 | 1.5 | 1.5 | 5.9 | 5.8 |
| 30 | 1.1 | 1.0 | 12.2 | 11.5 | 1.4 | 1.3 | 4.5 | 4.2 |
| 60 | 1.0 | 0.9 | 5.6 | 5.0 | 1.4 | 1.2 | 2.4 | 2.1 |
| 120 | 1.0 | 0.8 | 2.2 | 1.7 | 1.2 | 1.0 | 0.9 | 0.7 |
| 240 | 0.8 | 0.5 | 0.7 | 0.4 | 1.0 | 0.6 | 0.3 | 0.2 |

The agent is excreted without any evidence of metabolism. The major pathway for clearance of $^{99m}$Tc-Sestamibi is the hepatobiliary system. Activity from the gall bladder appears in the intestines within one hour of injection. Twenty-several percent of the injected dose is excreted in the urine, and approximately thirty-three percent of the injected dose is cleared through the feces in 48 hours.

A typical published preparation procedure of $^{99m}$Tc-Sestamibi [CARDIOLITE®, *Kit for the Preparation of Technetium Tc99m Sestamibi for Injection*, Document No. 513121-0300, March 2000, DuPont Pharmaceuticals Company, Billerica, Mass., USA] includes transferring a known volume of a solution containing the radioactive isotope sodium salt into a vial containing the rest of the ingredients, including the MIBI (2-methoxy isobutyl isonitrile) component. This amount should correspond to 925-5550 MBq (25-150 mCi) in approximately 1 to 3 ml. After heating the reaction mixture, the reaction vial sample is assayed using a suitable radioactivity calibration system, and the results of the assay determine the amount which will be injected into the patient. According to this prior art procedure, the prepared product should be stored at 15-25° C. before and after reconstitution and used within 6 hours after preparation. The patient dose and radiochemical purity (see the above-mentioned Document No. 513121-0300 for procedures) should be measured by a suitable radioactivity calibration system immediately prior to patient administration.

As can be deduced from the above description, there are two major physical attributes which determine the time regime for the nuclear imaging process which are crucial for its effectiveness: the rate of decay and the rate of clearance.

According to aspects of the present invention, the above procedure can be altered in two principle ways; one addresses the decay chronology and the other addresses the quantity required for effective imaging of the relevant organ in the patient. Since the sensitivity of the emission detector associated with aspects of the present invention is 10-100 folds higher than the currently used detectors, a kit according to these aspects of the present invention may contain a smaller amount of the radioactive isotope to be used, or may allow a longer time for data collection after administration, as compared to the presently known kits. The latter allows for data collection of dynamic processes which take place in the patient, i.e., following in-vivo changes in the organs which are monitored by the nuclear imaging technique, hence allowing for time-resolved analysis of the medical condition of interest.

Other examples for the preparation procedure of any commercially available radiopharmaceutical and radiotracer can be in the instruction documents provided in presently available kits, such as the kit for the preparation of $^{111}$Indium Capromab Pendetide. $^{111}$Indium Capromab Pendetide is a radiotracer containing a murine monoclonal antibody, 7E11-05.3 (the site-specific delivery vehicle), which is covalently conjugated to the linker-chelator, glycyl-tyrosyl-(N,-diethylenetriaminepentaacetic acid)-lysine hydrochloride (GYK-DTPA-HCl). The 7E11-05.3 antibody is of the IgG1, kappa subclass (IgG1K). This antibody is directed against a glycoprotein expressed by prostate epithelium known as prostate specific membrane antigen (PSMA). The PSMA epitope recognized by monoclonal antibody (MAb) 7E11-05.3 is located in the cytoplasmic domain. The radioisotope $^{111}$In is brought in contact with the antibody-linker-chelator conjugate upon preparation of the sample prior to administration, and the indium is therefore incorporated into the site-specific delivery vehicle. Detailed quantities, characteristics and procedures for the preparation of this radiotracer for administration can be found in http://www.cytogen.com/professional/prostascint/pi.php.

As in the example of $^{99m}$Tc-sestamibi, $^{111}$Indium capromab pendetide (ProstaScint®) is provided as a two-vials kit which contain all of the non-radioactive ingredients necessary to produce a single unit dose of $^{111}$In ProstaScint®, an immunoscintigraphic agent for administration by intravenous injection only. The ProstaScint® vial contains 0.5 mg of capromab pendetide in 1 ml of sodium phosphate buffered saline solution adjusted to pH 6; a sterile, pyrogen-free, clear, colorless solution. The vial of sodium acetate buffer contains 82 mg of sodium acetate in 2 ml of water for injection adjusted to pH 5-7 with glacial acetic acid; it is a sterile, pyrogen-free, clear, and colorless solution. The sodium acetate solution must be added to the sterile, non-pyrogenic high purity $^{111}$InCl solution to buffer it prior to radiolabeling ProstaScint®. The immunoscintigraphic agent $^{111}$In capromab pendetide is formed after radiolabeling with $^{111}$In.

Expert System

The following describes a method, based on imaging a patient using multiple kinetic parameters and measuring the distance between respective kinetic parameters, to relate the patient or individual voxels or groups of voxels to existing groups or populations, which are available in a database, thereby arriving at a decision, regarding the patient or individual voxels or groups of voxels. The existing populations in the database may be populations of generally healthy individuals, or are previous measurements of the same patient.

A platform is provided, which carries out a two-fold function in terms of three-dimensional images. First of all the platform sets up databases of parameter behavior from populations or from individuals and secondly it uses those databases to make inferences about a current image in light of knowledge from the databases. That is to say the platform decides which group in the database the current measurements most closely belong to. The body image obtains voxels and the voxels store multiple dimensional data therein. For example, a single voxel may store values of multiple parameters for a given location in the body and furthermore, for individual parameters, the voxel may store the time varying behavior of that parameter over the duration of the image.

The platform may then use the multiple dimensional data in the voxels to identify behavior, and decide on grouping, and an extension of the platform may make inferences or decisions as will be described in greater detail below. The grouping may identify pathology or tissue type or other group parameters as will be explained below and then the expert system may use rules to make decisions say about further treatment of the individual. Grouping may be of individual voxels to tissue types, or about groups of voxels as belonging to a particular tissues and/or pathology and/or organ, or about a pathology shown in the image as a whole.

In general, the different parameters in the voxel are not independent, since they all relate to the same tissue in the same person. Rather, certain parameters tend to correlate with one another. Thus if a certain parameter changes in a certain way we may expect, with a certain level of probability, that one of the other parameters will also behave in a certain way. Thus a healthy membrane regulates flow of any fluid, and an unhealthy membrane provides little regulation, so that a certain pathology would affect numerous flow parameters.

A scoring system can be used to decide if a pattern that emerges, for example, from the behavior of one or more parameters, indicates healthy tissue or fits a particular pathology. Alternatively, the scoring system can be used to decide what tissue type is being viewed.

More particularly, it is possible, given a matrix of voxels with multi-dimensional kinetic parameters representing a three-dimensional image scan over time, and similar-matrices from a database, to define a covariance matrix between the two. The covariance matrix can be used to measure a statistical distance between the two matrices. The distance may be computed to numerous matrices in the database and the current scan can be assigned a parameter represented by the matrix to which it is closest. Thus, given a vector X of test K taken under condition L, the set may be found to be closest to a database set which represents subjects suffering from early symptoms of heart disease. It may therefore be assumed that the present patient is suffering from heart disease and the expert system may recommend a treatment regime. Alternatively the comparison may be with tissue types and particular voxels can be for tissue type, for example, heart tissue.

Certain tissues may, for example, be hard to distinguish. For example tumor-tissue may look like muscular tissue under certain tests. In the event of such an ambiguity, a deciding test could be applied.

Figure 107:
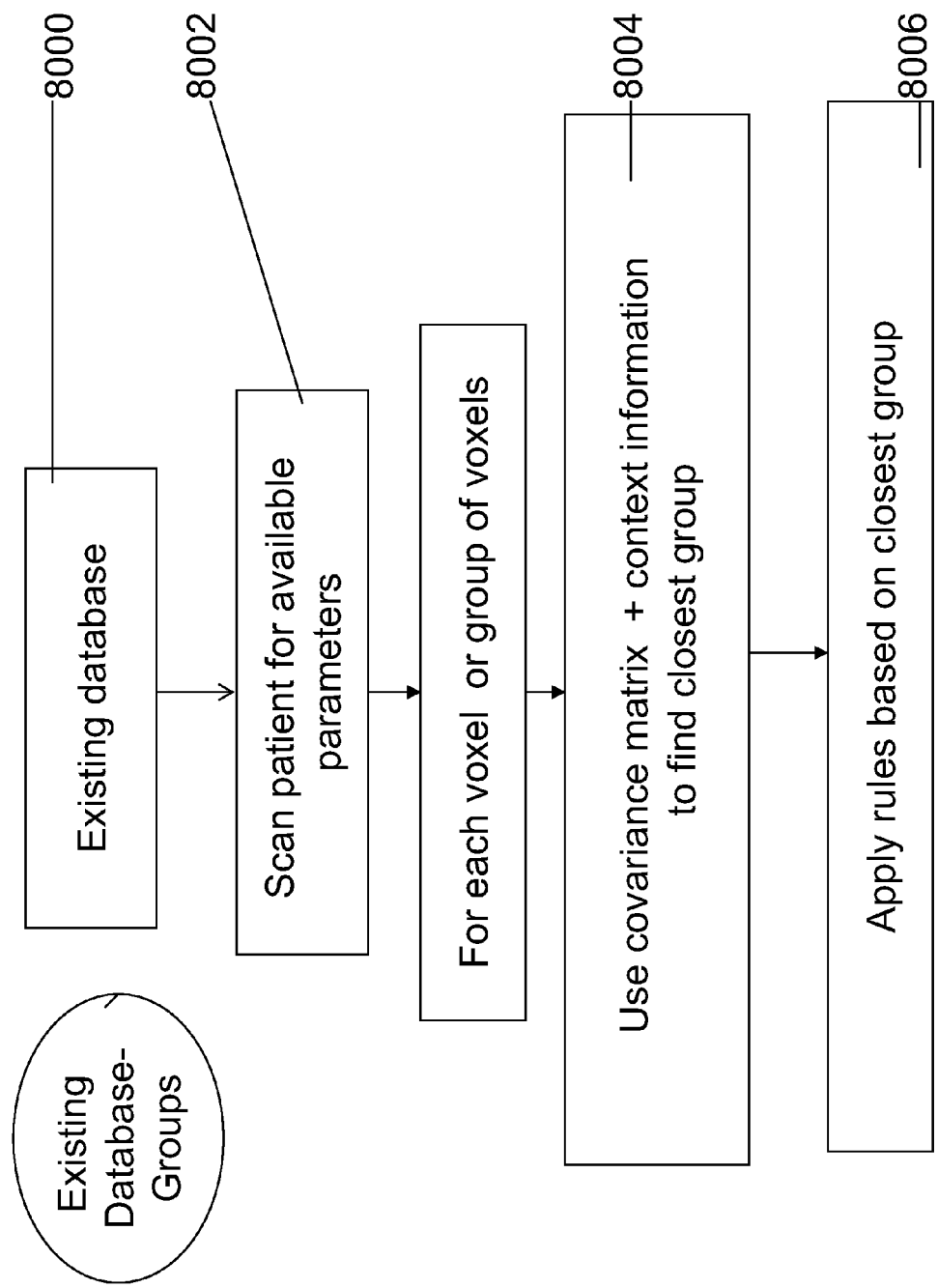
FIG. 107 is a simplified flow chart, illustrating a process for imaging a patient using multiple kinetic parameters and measuring the distance between respective kinetic parameters, to relate the patient or individual voxels or groups of voxels to existing groups, thereby to arrive at a decision, regarding the patient or individual voxels or groups of voxels, according to embodiments of the present invention.

Reference is now made to FIG. 107, which illustrates a procedure for using a covariance matrix in the kind of platform described above in order to make inferences. As explained, a database is set up in stage 8000 to show existing data. The database is built up over time over different populations of patients or volunteers or for specific populations or even for the patient himself. The data sets are preferably normalized to give a standard presentation of the data so that they can be compared. Thus a reference average brightness value may be used or a reference orientation or a reference set of co-ordinates may be used, for example.

The database can be constructed using any combination of healthy volunteers and patients, who may be tested under different environmental situations, for example, physical stress, sensory stress, etc. Alternatively the database may comprise tests carried out on the patient himself using data taken at an earlier time, if such data is available.

The database may comprise matrices containing average results for identified groups, thus all persons under 25 undergoing environmental stress. Alternatively the separate results for individuals may be retained, each matrix being labeled with a group to which it is known to belong.

The database may be constructed on the basis of any one of numerous models to represent dynamic behavior as required. A standard interface allows all models to be used together. The dynamic model being used may be varied and, with it, the meanings of given parameters or the identities of the actual parameters being used may be varied. The different models may change the meanings of the different parameters in terms of the meanings of correlation of kinetic values to organ or tissue type, or to pathology or to test condition or to patient group.

The individual is imaged in stage 8002. The image is three-dimensional and typically extends for a finite amount of time. The results are stored in an array of voxels $X^{\wedge}$. Each voxel stores a range of parameters that the image was able to measure directly and the parameters may include the behavior of a variable of interest over a period of time, for example, the kinetic or K parameter for passage of a certain radiopharmaceutical (tracer) through a membrane. The imaging process essentially creates a map of tracer uptake and also of dynamic uptake parameters such as flow of the tracer across given boundaries.

The K parameter may vary, for example, depending on what kind of tissue is being examined, or the pathology present, and so may other parameters, so that from the behavior of a group of parameters it is possible to identify the tissue or pathology, provided that one has the mathematical tools to compare groups of multi-dimensional dynamic parameters. Referring now to FIG. 108, within a first tissue and/or a first pathology, two dynamic variables K1 and K2 may covary with a mean over time defined by line 8010 and a standard deviation defined by circle 8012. Similarly, the same pair of variables may have statistical behavior defined by mean 8014 and standard deviation 8016 when located within a second tissue or a second pathology.

It will be noted that there is a region of overlap between the two regions, so that unless the behavior of the variable is followed over time it may not be possible to determine clearly to which tissue type or pathology the current voxel or group of voxels belong. Only by following the dynamic behavior do the two cases resolve themselves as belonging to separate groups.

Returning now to FIG. 107, in stage 8004 a covariance matrix is calculated and used to provide a measure of the distance between a voxel or a group of voxels or the image results as a whole, and various groups existing in the prior data. As well as distance measurement, context information may be used. Thus the system may be constrained not to identify tissue types that are not relevant to the part of the body currently being imaged. For example an image of the abdominal cavity should not find brain tissue. An image of bone tissue may be expected to find the bone itself, as well as gristle, marrow and blood vessels. An image of muscle tissue may be expected to find blood vessels, nerves and ligaments, etc.

Context information may also include information from other types of imaging, such as CT images, MRI images, ultrasound images, and the like.

Context information may further include known data about the specific patient such as age, gender, etc. Thus the scan from a patient aged 65 or over need only be measured against groups relevant for that patient, and the scans for a pregnant female patient need only be compared against other pregnant female patients.

An image of heart tissue may determine flow parameters and the like and then the covariance matrix may be used to identify ischemic regions or regions of dead tissue. Dead tissue would probably show up as regions in which fluid flow through the membranes is not being regulated at all.

It is noted that the grouping system can be open or closed. In a closed group system the existing groups are regarded as the only available groups and the patient is assigned to the closest existing group no matter how unrelated it might be. In an open group system the patient is assigned to the closest group if he is within a certain distance therefrom but, if he is not within that distance, say further than two standard deviations from the group, then the patient is regarded as belonging in a group of his own.

Finally, in stage 8006, an expert system may use decision-making rules, based on the parameters found, in order to advise on a course of treatment, to make a diagnosis for the patient, or the like. Thus, for example, a rule may set thresholds of percentages of ischemic or dead tissue within the heart for different treatment regimes.

The expert system may accept data sheets for the tracers (radiopharmaceuticals) or may accept algorithms for scoring and rules for analysis, thus, as mentioned above, providing a way of measuring a probability that a particular set of readings fits a particular tissue, a particular disease, etc. The system may be constrained to check within a limited list of suspected diseases only or within anatomical constraints, that is, to take into account the region of the body being imaged or the known or expected shape or location of organs and the like. The data compared can be matched with the existing databases over various suspected pathologies or conditions. The data may include a kinetics value (K), as explained, and the rules may require matching of high level or derived criteria. The platform may match the measured behavior to the nearest scenario in the database. Alternatively it may do something beyond matching the nearest scenario in the database. For example, it may check ratios between values, ratios between different locations in the body, or ratios between takeup, it may check accumulation of different radiopharmaceuticals, among multi-time points, or among different tests, such as tests carried out under stress, rest, etc.

In the following description, a series of suitable parameters will be discussed, as will a series of environmental variables under which measurements may be made.

Parameters that are directly measurable from the image include kinetic flow rates through membranes, hereinafter K values. Also accumulation levels of a particular tracer in a region may be measured. It will be appreciated that the voxels are of the size range of millimeters whereas individual cells are much smaller, so the voxel is in any event showing only macro-behavior in the region. Actual behavior on the cellular level, say takeup of sugar in mitochondria, has to be inferred from the measured parameters.

These values can be measured for one or more different tracers or pharmaceuticals and tend to have a behavior over time. FIGS. 109A . . . 109D show behavior of K values for four different radiopharmaceuticals over time for a given tissue having a given pathology.

Figure 110B:
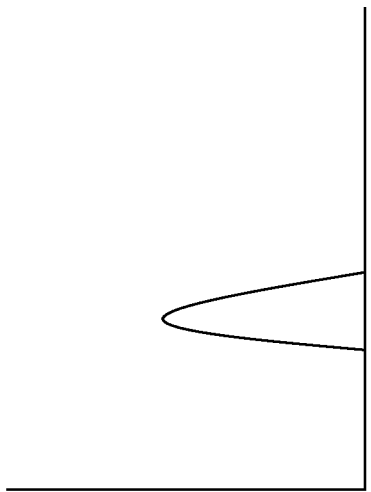
FIG. 110A illustrates dynamic behavior of an absorption parameter with a dead or diseased membrane, and, FIG. 110B illustrates the dynamic behavior of the same parameter with a healthy membrane.
Figure 110A:
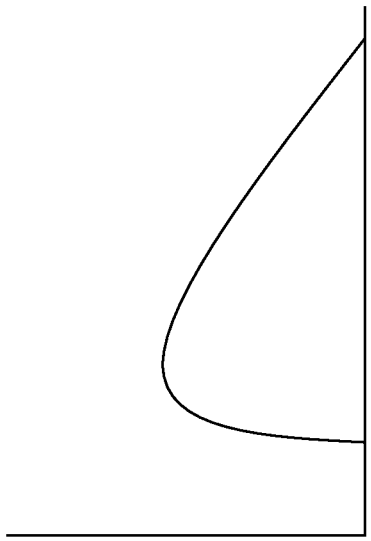

FIG. 110A illustrates accumulation of a tracer substance in a scarred tissue, where the membrane is not carrying out regulation. The substance simply enters and then leaves fairly rapidly and in an unregulated fashion. FIG. 110B by contrast illustrates accumulation of the tracer substance in a healthy tissue with an active membrane.

Another parameter that can be considered is glomerular filtration rate.

The parameters can be measured over time and under different conditions. Thus a person being imaged may be placed under physical stress, sensory stress, or the like, or may be exposed to a sensory event over the course of the image. Any given test is made under a single condition and the conditions are added as a label to the test, hereinafter L. Hence new graphs may be drawn of the behavior of a given parameter over the course of a particular event or whilst the patient is under a particular stress.

In the following, $\hat{X}$ represents a matrix resulting from an individual scan. A database $\tilde{X}$ is built of multiple scans taken under different conditions L, different pathologies j and for different tissues. The aim is that given a scan where one knows two of I, j, and L, one can use distance measurements against the database to determine the third.

The database $\tilde{X}$ preferably contains groups for all combinations of I, j and L that are of interest.

The initial scan is carried out on the patient in such a way that two of I, j and L are known, to obtain say $\hat{X}$ I,L.

Now each parameter in the measured scan has a kinetic behavior, including a mean and a standard deviation. Likewise any pair of parameters can have a covariance that has its own mean and standard deviation. Any individual measurement can be said to have a distance from this behavior measured in standard deviations from the mean. A series of measurements over time can be said to have a distance from behavior which is a summation of distances of the individual points.

This for a single parameter X, the distance may be given by $$\sigma^1(X-\hat{X})$$

For the entire database, we measure distances $$\hat{\sigma}_{ikL}(\bar{X}_{i,l}-\tilde{X}_{i,k,l})$$

Then we find the closest group in the database to the current measurements and assign the missing label.

At this point reference is again made to the point above about open and closed groups. With a closed group system a definite allocation is made to the closest group. With an open group system an allocation is only made if the new scan is found to be within a predetermined threshold distance from an existing group from the database, say two standard deviations or one and a half standard deviations. Otherwise the new scan is assumed to be an independent group.

If the missing parameter is an organ or a tissue then the above procedure can identify which organ or tissue the voxel or group of voxels belongs to. If on the other hand the missing parameter is a pathology, then the entire scan or the group of voxels can be assigned a pathology.

Gatting

Introduction

In myocardial perfusion imaging (MPI), an intravenously administered radiopharmaceutical is utilized to depict the distribution of nutritional blood flow in the myocardium. Perfusion imaging identifies areas in the heart of reduced myocardial blood flow, are associated with ischemia or scar. The relative regional distribution of perfusion may be assessed at different levels of activity, such as rest, cardiovascular stress, or both. Imaging can also be performed during acute events, such as chest pain of unknown etiology, for example, in the coronary care unit or emergency department. Radiopharmaceuticals, which may be used for MPI and are approved by the Food and Drug Administration (FDA), include thallium Tl-201, and technetium Tc-99m-labeled radiopharmaceuticals such as sestamibi, tetrofosmin, and Teboroxime, for SPECT imaging and ribidium Rb-82 for PET imaging.

Patients having significant coronary artery narrowing, for example, as a result of coronary artery disease (CAD), or abnormal coronary flow reserve, will have a zone in the heart muscle of diminished radiopharmaceutical concentration in the area of decreased perfusion.

While some body organs, such as the kidney, the prostate, or the liver, are relatively static, so as to enable imaging of a period of time that allows acquiring a statistically significant number of counts, the heart moves relatively rapidly, at about 80-100 beats per minute, on the average, while an average image acquisition may take between 10 and 20 minutes. Thus, some manner of correcting for the heart motion is required.

Current techniques record data with SPECT and electrocardiogram (ECG), and perform some gating to the data, to incorporate the global and regional atrial and ventricular function and assessment of the relationship of perfusion to regional function.

Figure 111B:
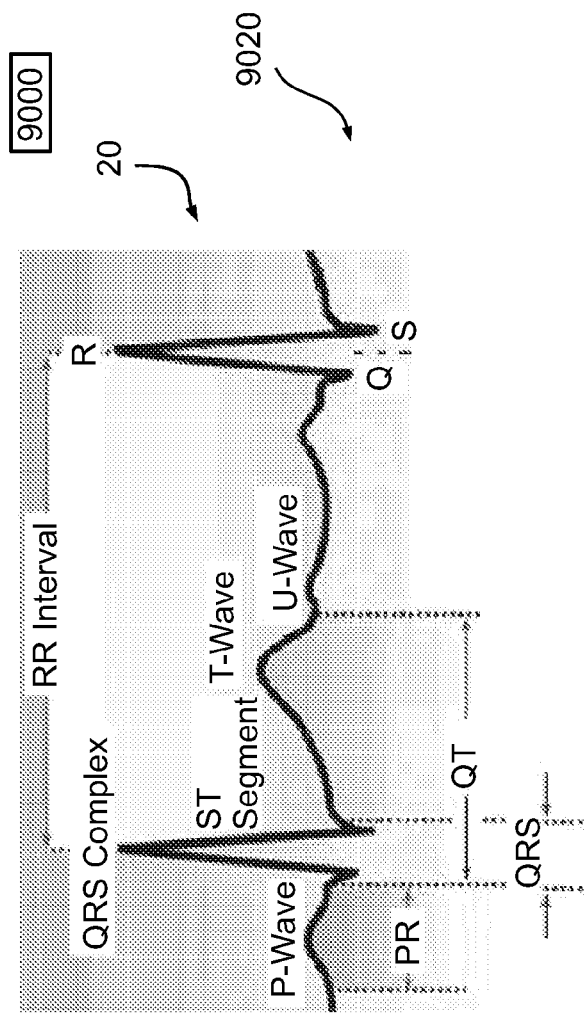
FIGS. 111A and 111B are of cardiac electrical cycles.
Figure 111A:
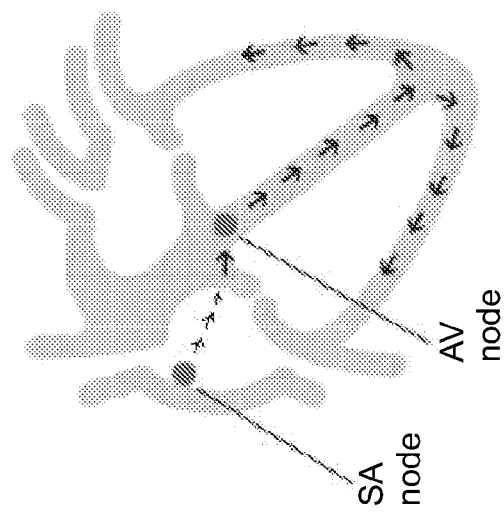

The Cardiac Electric Cycle:

FIGS. 111A and 111B schematically illustrate a cardiac electrical cycle 9020, with appropriate notations, where:

P wave—the depolarization of the right and left atria;

QRS complex—right and left ventricular depolarization, which are normally activated simultaneously;

ST Segment and T wave—ventricular repolarization;

U wave—probably, "after depolarizations" in the ventricles;

PR interval—time interval from the onset of atrial depolarization (the P wave) to the onset of ventricular depolarization (the QRS complex);

QRS duration—the duration of ventricular muscle depolarization;

QT interval—the duration of ventricular depolarization and repolarization;

RR interval—the duration of ventricular cardiac cycle, which is an indicator of ventricular rate; and PP interval—the duration of atrial cycle, which is an indicator of the atrial rate.

Phase 1: Atrial Contraction.

The first phase of the cardiac cycle because it is initiated by the P-wave of the electrocardiogram (ECG), described in greater detail below, and represents electrical depolarization of the atria. Atrial depolarization then causes contraction of the atrial musculature. As the atria contract, the pressure within the atrial chambers increases so that a pressure gradient is generated across the open atrio-ventricular (AV) valves, thereby causing a rapid flow of blood into the ventricles. Retrograde atrial flow back into the vena cava is impeded by venous return (inertial effect) and by the wave of contraction ("milking effect") throughout the atria. However, atrial contraction does produce a small increase in venous pressure.

Atrial contraction only accounts for about 10% of left ventricular filling when a person is at rest because most of the ventricular filling occurs before the atria contract and therefore is passive. However, if heart rate is very high (e.g., during exercise), the atrial contraction may account for up to 40% of ventricular filling. This is sometimes referred to as the "atrial kick". Atrial contribution to ventricular filling varies inversely with duration of ventricular diastole and directly with atrial contractility.

After atrial contraction is complete, the atrial pressure begins to fall causing a pressure gradient reversal across the AV valves. This causes the valves to float upward (pre-position) before closure. At this time, the ventricular volumes are maximal, which is termed the end-diastolic volume (EDV). The left ventricular EDV (LVEDV), which is typically about 120 ml, comprises the ventricular preload, defined as the initial stretching of the cardiac myocytes prior to contraction. LVEDV is associated with end-diastolic pressures of 8-12 mm Hg and 3-6 mm Hg in the left and right ventricles, respectively.

A heart sound is sometimes noted during atrial contraction. This sound is caused by vibration of the ventricular wall during atrial contraction. Generally, it is noted when the ventricle compliance is reduced ("stiff" ventricle) as occurs in ventricular hypertrophy (i.e., increased ventricular mass).

Phase 2: Isovolumetric Contraction:

This phase of the cardiac cycle is initiated by the QRS complex of the ECG waveform that represents ventricular depolarization. As the ventricles depolarize, excitation-contraction coupling (a process by which an action potential triggers a myocyte to contract), leads to myocyte contraction and the development of ventricular wall tension and a rapid increase in intraventricular pressure. Early in this phase, the rate of pressure development becomes maximal.

The abrupt rise in pressure causes the A-V valves to close as intraventricular pressure exceeds atrial pressure. Contraction of the papillary muscles with attached chordae tendineae prevents the A-V valve leaflets from bulging back into the atria and becoming incompetent (i.e., "leaky"). Closure of the A-V valves results in the First Heart Sound. This sound is normally split (~0.04 sec) because mitral valve closure precedes tricuspid closure.

During the time period between the closure of the AV valves and the opening of the semilunar valves, ventricular pressure rises rapidly without a change in ventricular volume (i.e., no ejection Occurs). Contraction, therefore, is said to be "isovolumic" or "isovolumetric." Individual myocyte contraction, however, is not necessarily isometric. Individual fibers contract isotonically (i.e., concentric, shortening contraction), while others contract isometrically (i.e., no change in length) or eccentrically (i.e., lengthening contraction). Therefore, ventricular chamber geometry changes considerably and the heart becomes more spheroid in shape; circumference increases and atrial base-to-apex length decreases.

Phase 3: Rapid Ejection.

When the intraventricular pressures exceed the pressures within the aorta and pulmonary artery, the aortic and pulmonic valves open and blood is ejected out of the ventricles. Blood is ejected because the total energy of the blood within the ventricle exceeds the total energy of blood within the aorta. In other words, there is an energy gradient to propel blood into the aorta and pulmonary artery. During this phase, ventricular pressure normally exceeds outflow tract pressure by only a few mm Hg. Although blood flow across the valves is very high, the relatively large valve opening (i.e., low resistance) requires only on few mm Hg of a pressure gradient to propel flow across the valve. Maximal outflow velocity is reached early in the ejection phase, and maximal (systolic) aortic and pulmonary artery pressures are achieved.

No heart sounds are ordinarily noted during ejection; the opening of healthy valves being silent. The presence of sounds during ejection (i.e. ejection murmurs) indicates valve disease (valve stenosis and/or valve insufficiency) or intra-cardiac shunts.

Atrial pressure initially decreases as the atrial base is pulled downward, expanding the atrial chamber. Blood continues to flow into the atria from their respective venous inflow tracts.

Phase 4: Reduce Ejection.

Approximately 150-200 msec after the QRS, ventricular repolarization occurs (WKG Waveform T-wave). This causes ventricular active tension to decrease and the rate of ejection (ventricular emptying) to fall. Ventricular pressure falls slightly below outflow tract pressure; however, outward flow still occurs due to kinetic (or inertial) energy of the blood.

Phase 5: Isovolumetric Relaxation.

As the ventricles continue to relax and intraventricular pressure falls, a point is reached when the total energy of blood within the ventricles is less than the energy of blood in the outflow tracts. When this occurs, the pressure reversal causes the aortic and pulmonic valves to abruptly close (aortic precedes pulmonic) causing the Second Heart Sound. Valve closure is associated with a small backflow of blood into the ventricles and a characteristic notch (incisura or dicrotic notch) in the aortic and pulmonary artery pressure tracings. The decline in aortic and pulmonary artery pressures is not as abrupt as in the ventricles because of potential energy stored in outflow vessel walls.

Ventricular pressures decrease, but volumes remain constant because all valves are closed. The volume of blood that remains in a ventricle is called the end-systolic volume and is ~50 ml in the left ventricle. The difference between the end-diastolic volume and the end-systolic volume is ~70 ml and represents the stroke volume. Atrial pressures continue to rise due to venous return.

Phase 6: Rapid Filling.

When the ventricular pressures fall below atrial pressures, the AV valves open and ventricular filling begins. The ventricles continue to relax despite the inflow, which causes intraventricular pressure to continue to fall by a few additional mm Hg.

The opening of the AV valves causes a rapid fall in atrial pressures and a fall in the jugular pulse. The peak of the jugular pulse just before the valve opens is the v-wave.

If the AV valves are healthy, no prominent sounds is heard during filling. When a Third Heart Sound is audible, it may represent tensing of chordae tendineae and AV ring during ventricular relaxation and filling. This heart sound is normal in children, but is often pathological in adults.

Phase 7: Reduced Filling.

As the ventricles continue to fill with blood and expand, they become less compliant and the intra-ventricular pressure rises. This reduces the pressure gradient across the AV valves so that the rate of filling falls.

Aortic pressure (and pulmonary arterial pressure) continues to fall during this period.

Electrocardiogram (ECG or EKG)

As the heart undergoes de-polarization and re-polarization, the electrical currents that are generated spread not only within the heart, but also throughout the body. This electrical activity generated by the heart can be measured by an array of electrodes placed on the body surface. The recorded tracing is called an electrocardiogram (ECG).

As noted, FIG. 111B illustrates a typical ECG waveform. The different waves that comprise the ECG waveform represent the sequence of depolarization and repolarization of the atria and ventricles.

The "P wave" represents the wave of depolarization that spreads from the SA node throughout the atria, and is usually 0.08 to 0.1 seconds (80-100 ms) in duration. The brief iso-electric (zero voltage) period after the P wave represents the time in which the impulse is traveling within the AV node where the conduction velocity is greatly retarded.

The period of time from the onset of the P wave to the beginning of the QRS complex is termed the "P-R interval", which normally ranges from 0.12 to 0.20 seconds in duration. This interval represents the time between the onset of atrial depolarization and the onset of ventricular depolarization. If the P-R interval is less than 0.2 sec, a conduction defect (usually within the AV node) is present (first-degree heart block).

The "QRS complex" represents ventricular depolarization and the duration of the QRS complex is normally 0.06 to 0.1 seconds. This relatively short duration indicates that ventricular depolarization normally occurs very rapidly. If the QRS complex is prolonged (longer than 0.1 sec), conduction is impaired within the ventricles. This can occur with bundle branch blocks or whenever a ventricular foci (abnormal pacemaker site) abnormally become the pacemaker driving the ventricle. Such an ectopic foci nearly always results in impulses being conducted over slower pathways within the heart, thereby increasing the time for depolarization and the duration of the QRS complex.

During the isoelectric period "ST segment" following the QRS, the entire ventricle is depolarized and roughly corresponds to the plateau phase of the ventricular action potential. The ST segment is important in the diagnosis of ventricular ischemia or hypoxia because under those conditions, the ST segment can become either depressed or elevated.

The "T wave" represents ventricular re-polarization and is longer in duration than depolarization (i.e., conduction of the re-polarization wave is slower than the wave of de-polarization).

The "Q-T interval" represents the time for both ventricular depolarization and re-polarization to occur and therefore roughly estimates the duration of an average ventricular action potential. This interval can range from 0.2 to 0.4 seconds, depending upon heart rate. At high heart rates, ventricular action potentials shorten in duration, which decreases the Q-T interval. Because prolonged Q-T intervals can be diagnostic for susceptibility to certain types of tachyarrhythmias, it is important to determine if a given Q-T interval is excessively long. In practice, the Q-T interval is expressed as a "corrected Q-T (Q-Tc)" by taking the Q-T interval and dividing it by the square root of the R-R interval (interval between ventricular depolarizations). This allows an assessment of the Q-T interval that is independent of heart rate. Normal corrected Q-Tc intervals are less than 0.44 seconds.

There is no distinctly visible wave representing atrial repolarization in the ECG because it Occurs during ventricular depolarization. Because the wave of atrial repolarization is relatively small in amplitude (i.e., has low voltage), it is masked by the much larger ventricular-generated QRS complex.

Cardiac Volume and Pressure Changes

Figure 114A:
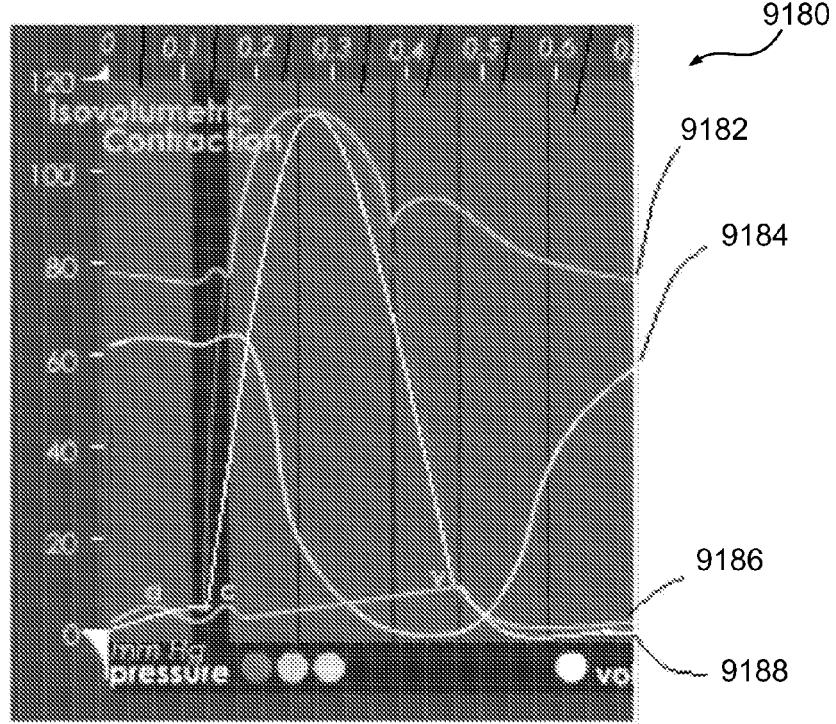
FIGS. 114A, 114B and 114C are of typical cardiac volumes and pressures, superimposed against the ECG tracing of FIG. 1B and the time scale 10 of FIG. 3A, in accordance with embodiments of the present invention.
Figure 114B:
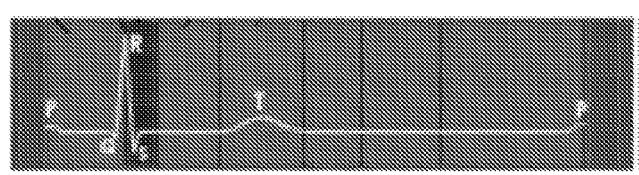
Figure 114C:
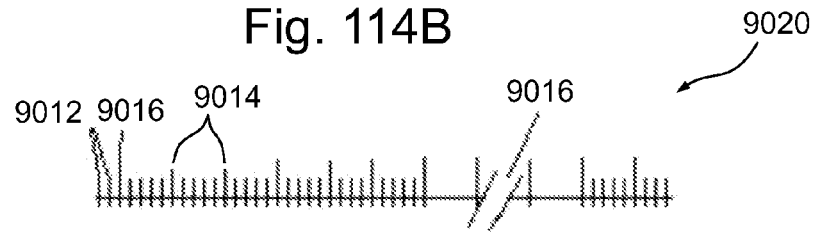
Figure 115:
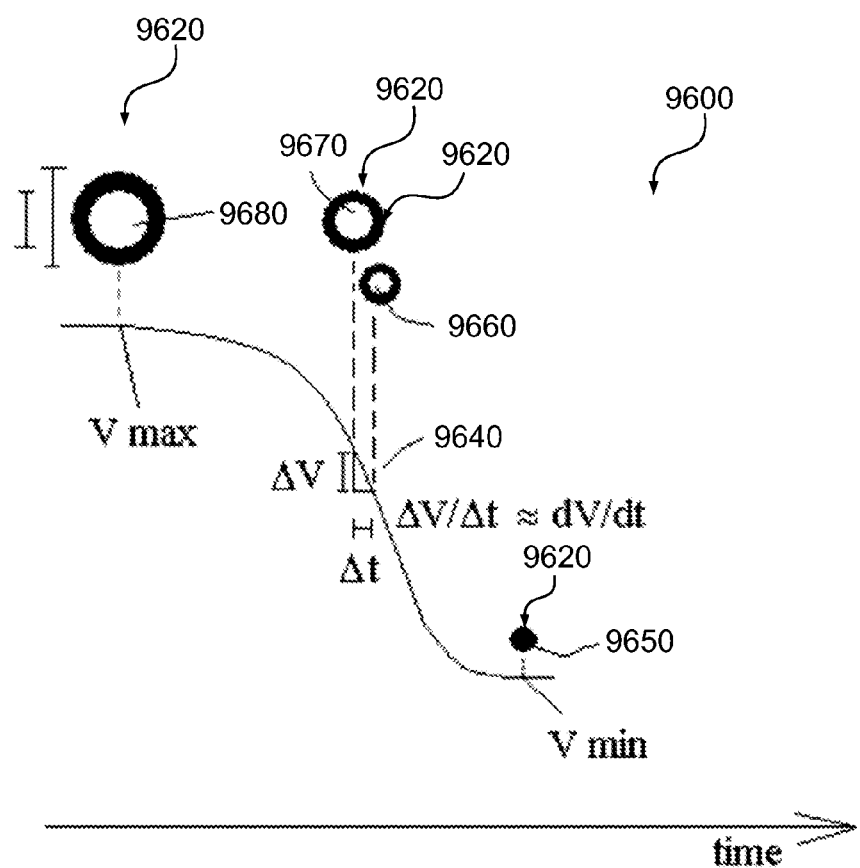
FIG. 115 is a graph of cardiac volume versus pressure over time and exemplary volumetric images, in accordance with embodiments of the present invention.

FIGS. 114A, 114B and 114C show the cardiac electrical cycle 9020 and the graduation time scale 9010, superimposed against a typical cardiac volume and pressure graph 9180 including an aorta pressure tracing 9182, a ventricular volume tracing 9184, an atrial pressure tracing 9186 and a ventricular pressure tracing 9188.

As the cycle 9020 passes through the P wave, atrial pressure volume 9184 increases.

In the QRS complex, ventricular depolarization occurs and ventricular pressure 9188 increases. Following the T wave, ventricular pressure 9188 drops while ventricular volume 9184 increases. The atrial pressure 9186 increases briefly at "v" as the blood hits the closed AV valve, following which atrial pressure 9186 rises slowly.

Gated Imaging

Figure 112A:
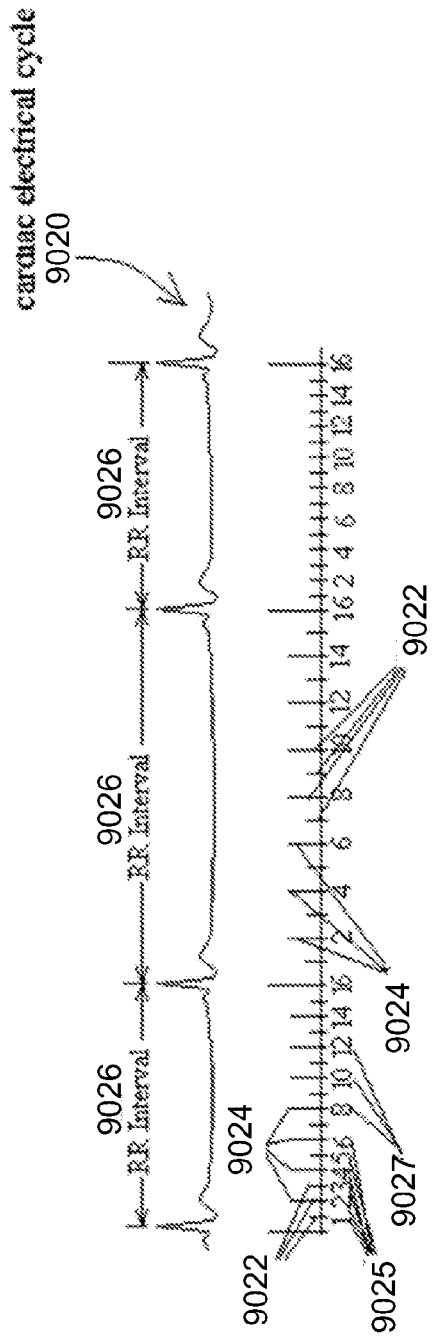
FIGS. 112A and 112B are of cardiac and respiratory gating in accordance with a first embodiment, in accordance with embodiments of the present invention.

Reference in now made to FIG. 112A, which schematically illustrates a method of radioactive-emission imaging of a heart, in accordance with embodiments of the present invention, comprising:

imaging the heart of a body, for an imaging period greater than at least 2 cardiac electrical cycles 9020;

post processing for identifying an average RR interval, based on actual RR intervals 9026, for the body;

post processing for evaluating each specific cardiac electrical cycle, vis-à-vis the average RR interval, and identifying each of the specific cardiac electrical cycles 9020, either as "good," which is to be included in the imaging, or as "bad," which is to be discarded;

dividing each of the "good" cardiac electrical cycles to time graduations 9022;

indexing each graduation 9022 with cardiac-cycle indices 9025; and adding tip photon counts that occurred within the graduations of the same cardiac-cycle index 9025.

Additionally, the method may include performing ECG concurrent with the imaging.

Furthermore, the method may include using the ECG input for identifying durations of the RR intervals 9026.

Additionally, cardiac electrical cycles deemed associated with arrhythmias are identified as "bad", during the post processing.

Additionally, the graduations 9022 may be fine graduations, and the method further includes:

amalgamating the fine graduations 9022 to coarse graduations 9024, wherein each of the coarse graduation 9024 includes at least two fine graduations 9022;

indexing each coarse graduation of each of the dedicated graduation time scales with cardiac-cycle indices 9027; and adding up photon counts that occurred within the coarse graduations 9024 of the same cardiac-cycle index 9027. This is preferably done for a portion of the cardiac cycle, which may be of lesser interest, for example, the portion between the U-wave and the P-wave.

Figure 112B:
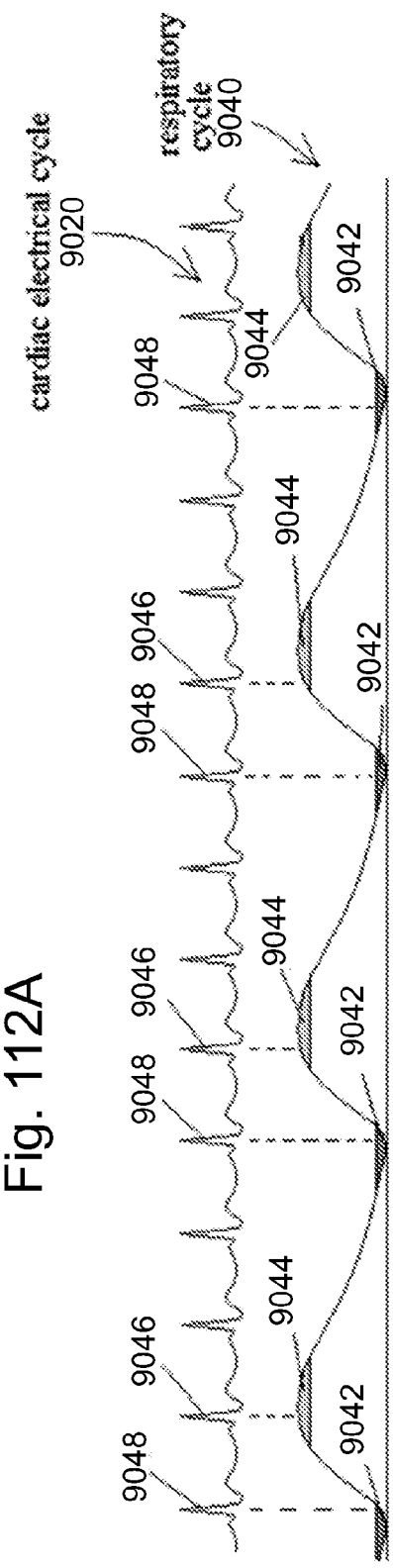

Reference in now made to FIG. 112B, which schematically illustrates respiratory gating, in accordance with embodiments of the present invention, comprising:

extending the imaging period to cover at least two respiratory cycles 9040;

dividing each of the respiratory cycles 9040 to respiratory-cycle stages and assigning each of the respiratory-cycle stages a respiratory-cycle index, such as indices 9042 or 9044;

adding up photon counts that occurred within the graduations of common cardiac-cycle and respiratory-cycle indices, such as cardiac-cycle index 9048 and respiratory index 9042, or cardiac-cycle index 9046 and respiratory index 9044; thereby eliminating respiratory effects.

Figure 116:
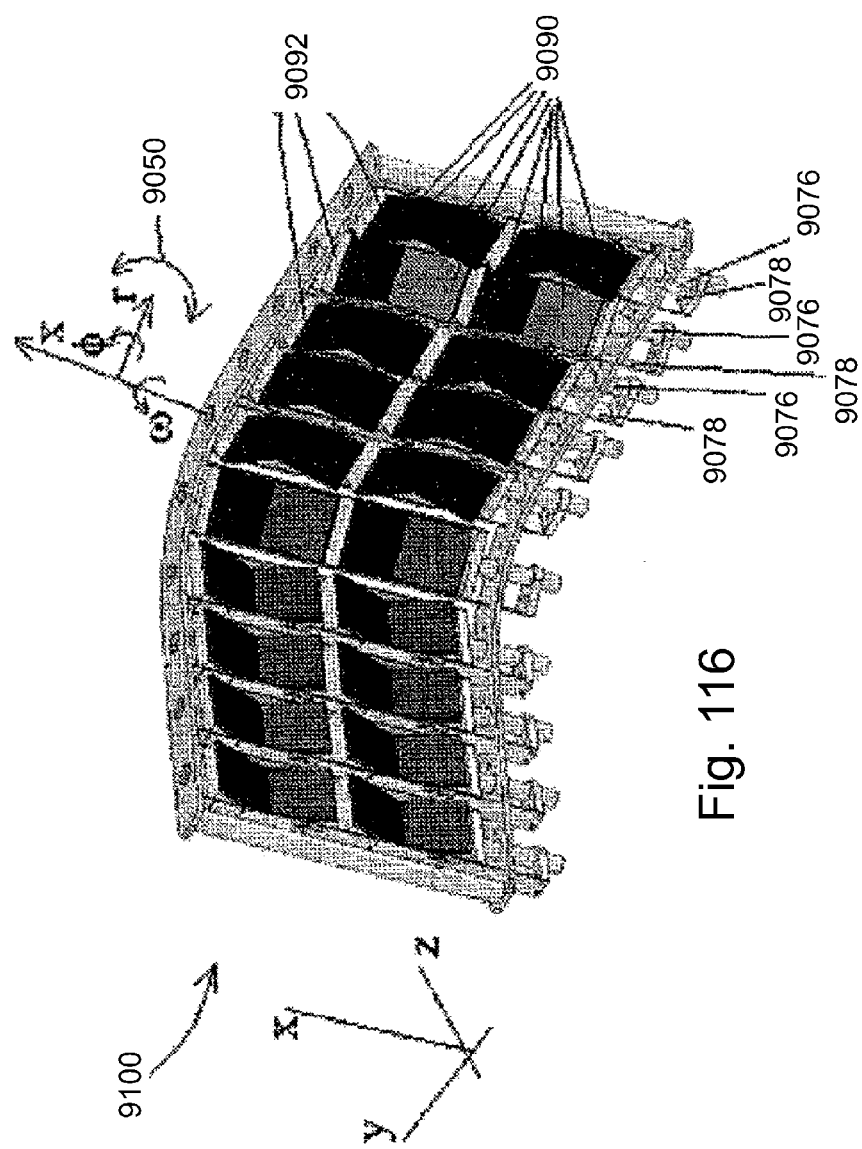
FIG. 116 is of a cardiac probe, in accordance with embodiments of the present invention.

Additionally, in accordance with an embodiment of the present invention, illustrated in FIG. 116, the method includes:

providing a probe 9100, which comprises a plurality of detecting units 9090, or assemblies 9092, each preferably formed as a line of detecting units 9090, and each having motion providers 9076 and 9078, for providing motion in a coordinate system 9050, having at least one, and preferably two degrees of freedom;

wherein for each of the detecting units 9090, time, position and viewing angle are substantially known for every detected photon, and wherein the imaging the heart further includes imaging by the plurality of detecting units 9090, to provide a 3 dimensional image of the heart.

Additionally, the plurality of detecting units 9090 may image the heart in sweeping motions.

Furthermore, the sweeping motions are without pause between minimum and maximum sweeping angles.

Alternatively, the plurality of detecting units 9090 image the heart in stepped motions.

Furthermore, the detecting units 9090 are moved to new viewing positions at a predetermined stage of the cardiac electrical cycle.

In accordance with embodiments of the present invention, photon counts of each voxel are added, wherein the photon counts occurred within the graduation of the same cardiac index for all of the detecting units.

Additionally or alternatively, photon counts of each voxel of common cardiac-cycle and respiratory-cycle indices of a reconstructed image are added, wherein the photon Counts occurred within the graduation of the same cardiac index for all of the detecting units 9090.

In accordance with embodiments of the present invention, the detecting units 9090 may sweep in an interlacing manner.

Figure 113A:
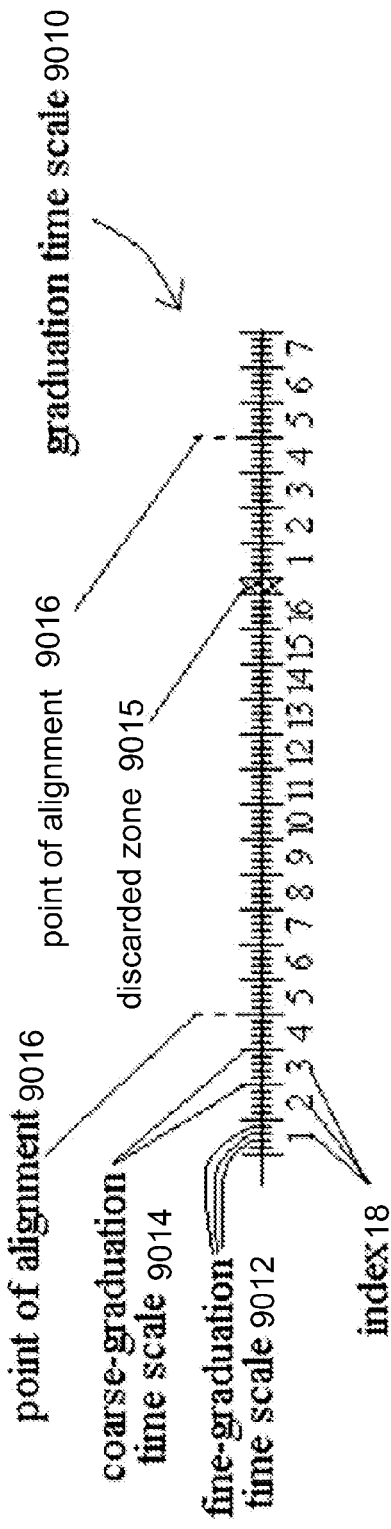

Reference is now made to FIGS. 113A and 113B, which schematically illustrate an alternative method of radioactive-emission imaging of a heart, in accordance with embodiments of the present invention, comprising:

imaging the heart for an imaging period greater than at least 2 cardiac electrical cycles 9020;

providing a graduation time scale 9010, with graduations 9012 and at least one graduation mark 9016, operative as a point of alignment;

aligning the point of alignment with a specific stage of each of the cardiac electrical cycles, such as "Q," or "R," thus, in effect assigning each one of the cardiac electrical cycles 9020 a dedicated one of the graduation time scales 9010; and allowing for a discard zone 9015, between adjacent ones of the dedicated graduation time scales 9010, where necessary.

Additionally, the method includes performing ECG concurrent with the imaging.

Furthermore, the method includes using the ECG input for the aligning of the point of alignment 9016 with the specific stage of each of the cardiac electrical cycles, such as "Q," or "R."

Additionally, the method includes indexing each graduation 9012 of each of the dedicated graduation time scales 9010, with cardiac-cycle indices; and adding up photon counts that occurred within the graduations of the same cardiac-cycle index.

Furthermore, the method includes rejecting photon counts of cardiac electrical cycles associated with Arrhythmias.

Additionally, as seen in FIG. 113C, the method includes respiratory gating, by:

extending the imaging period to cover at least two respiratory cycles 9040;

dividing each of the respiratory cycles to respiratory-cycle stages and assigning each of the respiratory-cycle stages a respiratory-cycle index, such as the index 9044 or 9042; and adding up photon counts that occurred within the graduations of common cardiac-cycle and respiratory-cycle indices, such as the cardiac-cycle index 9048 and the respiratory cycle index 9042, or the cardiac-cycle index 9046 and the respiratory cycle index 9044.

Furthermore, as seen in FIGS. 113A and 113B, the graduations 9012 may be fine graduations, and the method may includes:

amalgamating the fine graduations 9012 to coarse graduations 9014, wherein each of the coarse graduation 9014 includes at least two fine graduations 9012, for example, in an area between the U-wave and the P-wave, or another area that may be of lesser interest;

indexing each coarse graduation of each of the dedicated graduation time scales 9010 with cardiac-cycle indices 9018; and adding up photon Counts that occurred within the coarse graduations of the same cardiac-cycle index 9018.

Additionally, the method includes rejecting photon counts of cardiac electrical cycles associated with Arrhythmias.

In accordance with still another embodiment of the present invention, a method of cardiac imaging is provided, which includes:

providing probe 9100, which comprises the plurality of detecting units 9090, for which time, position and viewing angle are substantially known for every detected photon, as seen in FIG. 116;

imaging the heart for an imaging period which is somewhat greater than a single cardiac electrical cycle 9020 but which is less than two cardiac electrical cycles;

dividing the RR interval to graduations 9022 or 9024, as seen in FIG. 112A;

indexing each graduation 9022 or 9024 with the cardiac-cycle index 9025 or 9027, respectively; and for each voxel of a reconstructed image, adding up photon counts that occurred within the graduations of the same cardiac-cycle index, for that voxel, from the different detecting units 9090.

FIG. 114A is a graph 9600 of cardiac volume versus pressure over time and exemplary corresponding volumetric images 9620 in a typical cardiac cycle. Cardiac images 9620 are taken according to graduation time scale 9010 in which rapidly increasing cardiac volume 9684 is imaged during repeated fine graduations 9012 shown in FIG. 114C. During the cardiac cycle, where minimal volumetric changes occur, during a period of slowly increasing cardiac volume, coarse graduations 9014 of FIG. 114C, are optionally used.

Additionally, graph 9600 shows an almost linear change in volume over time along a slope 9640, the slope being represented by the formula $\Delta V/\Delta t \approx dV/dt$. Corresponding to slope 9640, image 9670 shows a moderately decreased cardiac volume 9620 and a greatly decreased cardiac volume 9660.

Calibration

When radiation emitted by radiopharmaceuticals in the body of the subject propagates through the body it can be attenuated due to absorption or scattering effects. Any radiological imaging procedure is therefore preceded by a calibration step for in which data are collected for calculating attenuation corrections to the radiological image. The calibration step involves the transmission of additional radiation through the subject so as to estimate the attenuation caused by various tissues within the target region.

In one technique, a computerize tomography (CT) image of the subject is obtained and the corrections due to attenuation of the radiopharmaceutical radiation are estimated based on the knowledge of the internal structure of the subject. This technique is, however, limited from standpoint of cost and availability. Additionally, the spectral lines of the X-ray radiation employed by the CT system are broader than the spectral lines characterizing radiopharmaceutical. Such spectra mismatch introduces inaccuracies hence increases the attenuation uncertainties.

In another technique, a radioactive source such as cesium-137 is positioned in proximity to the subject and allowed to emit radiation therethrough. The radiological imaging system is then used for detecting this radiation. The attenuation corrections are calculated from based on the precise location, emission spectrum and radiation activity of the radioactive source, the operator calibrates of the radiological imaging system according to the radiation readings.

It is recognized, however, that the interaction between radiation and matter such as biological material depends on the spectrum of the radiation. Thus, although the spectral lines of the radioactive source is clearer than the spectral lines of X-ray photons, this technique is still far from being satisfactory because the difference between emission spectra of the external radioactive source and the radiopharmaceutical introduces uncertainties to the calculation of the attenuation corrections.

There is thus a widely recognized need for, and it would be highly advantageous to have, a method and device for calibrating radiological imaging system devoid of the above limitations.

The present embodiments comprise a method and device which can be used for radiological imaging. Specifically, the present embodiments can be used to calibrate a radiological imaging system. Particularly, but not exclusively, the present embodiments can be used in radiological imaging systems which use multi-dimensional data to image non-homogenous target regions having different tissue types or pathologies, as explained in U.S. Patent Application No. 60/535,830, the contents of which are hereby incorporated by reference.

Figure 117:
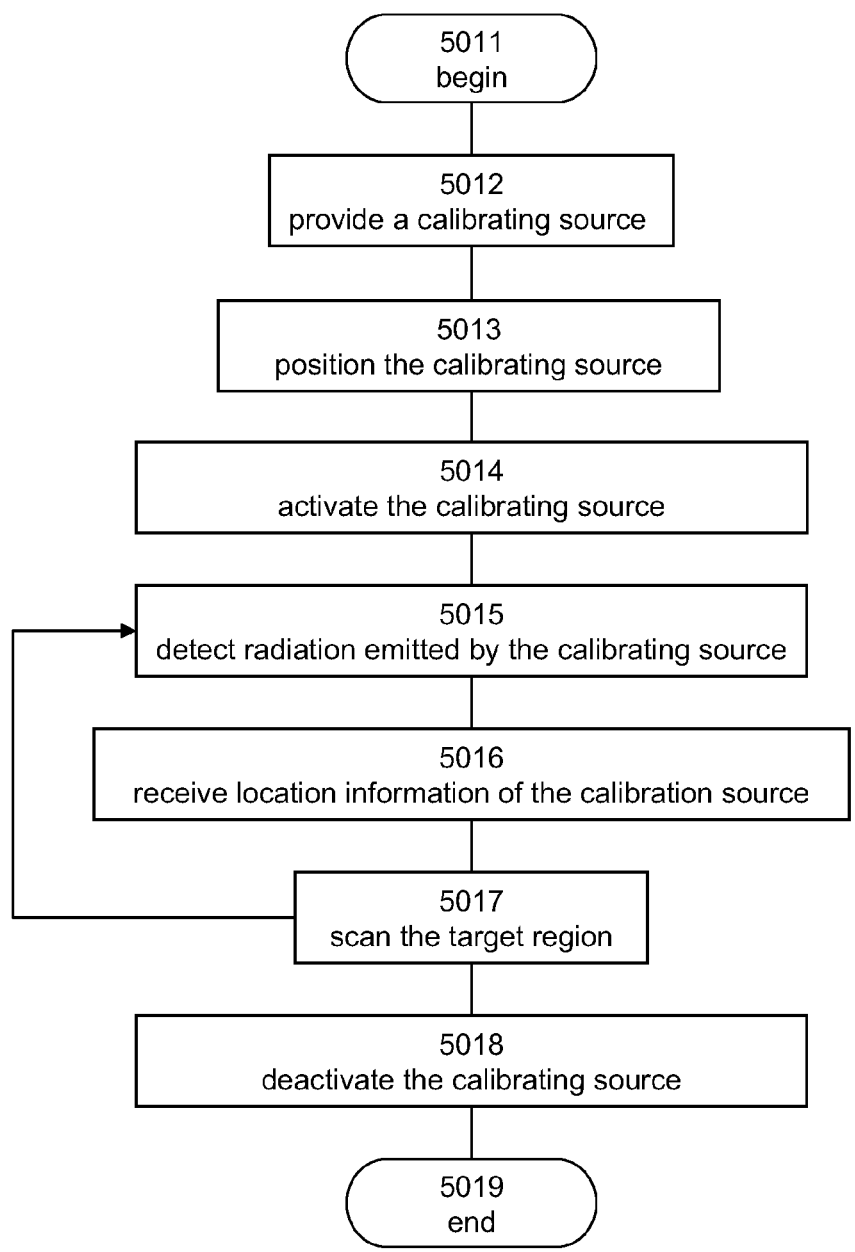
FIG. 117 is a flowchart diagram of a method for calibrating a radiological imaging system by detecting radiation from one or more calibration sources, according to various exemplary embodiments of the invention.

Referring now to the drawings, FIG. 117 is a flowchart diagram of a method 5010 for calibrating a radiological imaging system. The radiological imaging system detects radiation from a target region of a subject having therein at least one radiopharmaceutical characterized by an emission spectrum. Method 5010 begins at step 5011 and continues to step 5012 in which one or more calibration sources are provided.

The calibration source can be, for example, one or more radioisotopes having a relatively short half-life, of the order of a few days, e.g., 10 days, a week or less.

In various exemplary embodiments of the invention the calibration sources are characterized by the same emission spectrum as the emission spectrum of the radiopharmaceutical. In various exemplary embodiments of the invention the calibration source comprises a radioisotope which is identical to the radioisotope of the radiopharmaceutical.

The advantage of using identical radioisotopes (hence also identical emission spectrum) for the radiopharmaceutical and the calibration source is that the identical emission spectrum eliminates spectral mismatch errors which may be introduced during the calculations of the attenuation corrections.

The method continues to step 5013 in which the body of the subject and/or the radiological imaging system is engaged with the calibration source. When the calibration source engages the body, it is preferably positioned in proximity to- and/or within the target region. The calibration source can be extracorporeal or extracorporeal calibration source. In the former case, the calibration source can be provided in a form of a patch containing a single radioisotope or an arrangement of radioisotopes. In this embodiment, the calibration source is preferably attached to an external organ of the subject, being in proximity to the target region. When an intracorporal calibration source is employed, the source can be endoscopically inserted to the subject. This can be done, for example, by mounting the calibration source on a probe such as a transesophageal or transrectal catheter. The calibration source can also be encapsulated in a capsule to be taken orally or rectally by the subject.

When the calibration source engages the radiological imaging system, it is preferably mounted on or within the camera, probe or detector of the system. In this embodiment, the calibration source can be provided within a container which is transparent to the type of radiation emitted by the source. The container is preferably manufactured sizewise and shapewise compatible with the part of the system which receives it. For example, when the calibration source is positioned in the probe of the system, the probe can have an opening through which the container holding the calibration source is inserted into the probe. A device suitable for holding the calibration source in the embodiment in which the source engages the imaging system is described hereinbelow with reference to FIG. 120.

In various exemplary embodiments of the invention the radiation activity (number of disintegrations per unit time) of the calibration source is selected sufficiently high to be detectable by the radiological imaging system and sufficiently low so as not to mask radiation emitted by the radiopharmaceuticals present in the subject.

The radiation activity of the calibration source can also be used for identifying the calibration source. Specifically, the calibration source can be distinguished from the radiopharmaceuticals and/or other calibration sources (if present), according to its radiation activity. Other identification criteria are also contemplated as further detailed hereinbelow.

Preferably, but not obligatorily, the calibration source is a directional source. In other words, the radiation is emitted by the source at one or more predetermined directions, with minimal or no radiation in other directions. This can be done, for example, by providing a calibration source having absorbing or reflecting surface covering a portion of the radioisotope's "field-of-view".

The absorbing or reflecting surface can also be controlled from an external location so as to activate and deactivate the calibration source as desired. In this embodiment, when the source is inactive, the absorbing or reflecting surface is closed to prevent radiation from penetrating the target region.

According to a preferred embodiment of the present invention the method continues to step 5014 in which the calibration source is activated. This can be done by remotely control the absorbing or reflecting surface such that a window is formed in the surface to allow radiation to pass therethrough.

The method continues to step 5015 in which the radiological imaging system is used for detecting radiation emitted by the calibration source, so as to calibrate the radiological imaging system. The calibration can be done by employing an attenuation map, constructed prior to the calibration procedure. The attenuation map includes attenuation information associated with tissue present within target region. The attenuation map can be a general map, or, alternatively, a specific attenuation map can be tailored to each subject or group of subjects having similar body structure within the target region.

The attenuation map is typically based on probability distributions for photons emitted by the calibration source to interact with the tissue in the target region. Broadly speaking, when a photon interacts with the tissue, it can experience one of the following three processes: absorption (also known as the photoelectric effect), elastic scattering (also known as coherent scattering or Thompson scattering), and inelastic scattering (also known as incoherent scattering or Compton scattering).

When the photon is absorbed, all of its energy is transferred to the tissue (resulting in emission of free electron) and the attenuation of the radiation is manifested as a decrement in the number of photons arriving at the imaging system. When the photon experiences elastic scattering, its propagation direction can be deflected but its energy is preserved. In this case, the scattering process is manifested by detection of photons with the original wavelength at a direction which is deflected with respect to the emission direction. When the photon experiences inelastic scattering, a portion of the photon's energy is lost during the interaction with the tissue. In this case, the scattering process is manifested by detection of photons with a wavelength which is longer than the characteristic wavelength of the source.

According to a preferred embodiment of the present invention the method continues to step 5016 in which location information of the calibration source is received. This embodiment is useful when the location of the calibration source varies or not known. The location information can be obtained in more than one way.

Hence, in embodiments in which the source is mounted on a mechanical device, such as a catheter or an arm, the location information can be obtained directly from directly from the mechanical device. Alternatively, the calibration source can communicate (mechanically, electrically or via wireless communication) with a position sensing system to enable the determination of its location, substantially in real time.

Knowing the location, radiation activity and emission spectrum of the calibration source, and given the radiation readings of the radiological imaging system (intensity, direction, wavelength, etc.), the attenuation map can be used for calibrating the imaging system. A mathematical procedure for calculating probability distributions is provided hereinafter.

In various exemplary embodiments of the invention the method comprises an additional step (designated 5017) in which the target region is scanned with the calibration source. The scanning of the region can be done by displacing the calibration source such that at each position of the source the radiation interacts with a different portion of the target region.

The motion of the calibration source can be establish using an external mechanism, e.g., an movable arm which can be controlled manually or automatically. The calibration source can also be a self-propelling source, moving, e.g., in the vasculature either using an internal propulsion mechanism or via blood flow.

Alternatively or additionally to the motion of the source, the scan of the target region can be achieved by controlling the direction at which radiation is emitted from the calibration source. This can be done by rotating the source or by directly controlling the absorbing or reflecting surface of the source to allow the radiation to propagate at the desired location.

Once the imaging system is calibrated, the method, optionally and preferably, continues to step 5018 in which the calibration source is deactivated. This can be done by remotely controlling the absorbing or reflecting surface so as to close the aforementioned window hence to prevent radiation to enter the target region.

The method ends at step 5019.

Figure 118:
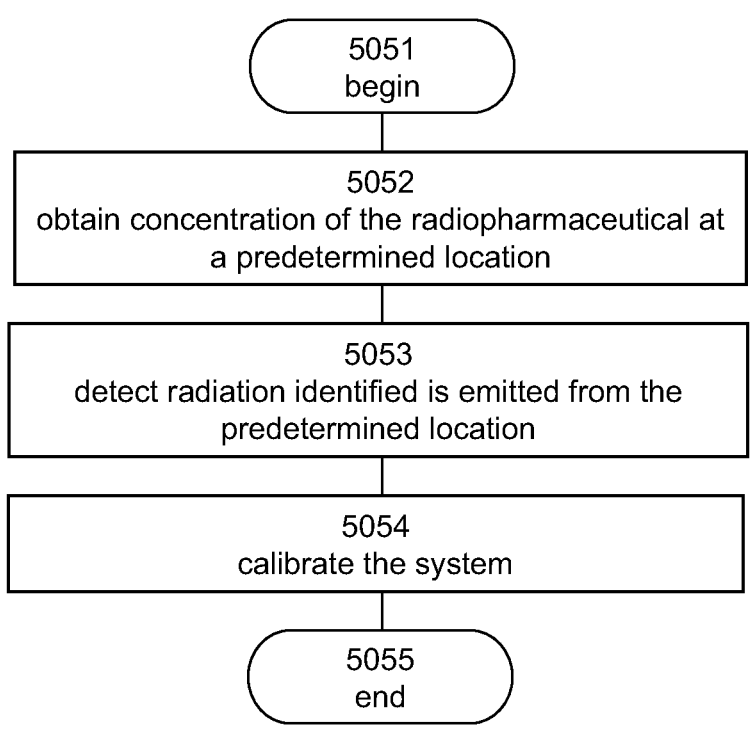
FIG. 118 is a flowchart diagram of a method for calibrating a radiological imaging system by detecting radiation from one or more radiopharmaceuticals, according to various exemplary embodiments of the invention.

Reference is now made to FIG. 118 which is a flowchart diagram of a method 5050 for calibrating the radiological imaging system, according to another aspect of the present invention.

Method 5050 begins at step 5051 and, optionally and preferably, continues to step 5051 in which the concentration of the radiopharmaceutical(s) in a predetermined location or locations of the body of the subject is obtained. The concentration can be obtained either by an appropriate model, which is typically based on the amount of radiopharmaceutical(s) administered to the subject, or by removing a sample of a biological material from the predetermined location(s) and measuring amount of radiation emitted therefrom. Many predetermined locations are contemplated.

One such predetermined location is the vasculature of the subject. In this embodiment, the concentration of radiopharmaceutical in the blood can be obtained by modeling the vasculature as a reservoir in which the concentration of the radiopharmaceutical(s) is uniform. Alternatively, the concentration of the radiopharmaceutical(s) can be obtained using a more complex model which takes into account different concentrations of radiopharmaceutical(s) in the blood in different regions of the vasculature. For example, higher concentrations in regions in which blood flows into a specific organ (e.g., lungs, liver) and lower concentrations in regions in which blood flows out of the specific organ. Still alternatively, the concentration can be obtained by performing an ex-vivo measurement of amount of radiation emitted from a blood sample removed from the subject subsequently to the administration of the radiopharmaceutical(s).

The predetermined location or locations can also comprise other body fluids. In various exemplary embodiments of the invention the predetermined location is the bladder, in which case the concentration of radiopharmaceutical in the urine can be obtained by modeling or by ex-vivo measurement of amount of radiation emitted from a urine sample taken subsequently to the administration of the radiopharmaceutical(s).

Also contemplated are the feces, in which case the predetermined location can be the bowel, and the concentration can be obtained by modeling and/or ex-vivo measurement as detailed above.

The predetermined location can also be an organ other than the vasculature, bladder or bowel, provided that the concentration of radiopharmaceutical(s) in the location is known, e.g., from a model or by ex-vivo measurement, such as, but not limited to, biopsy.

Irrespectively of the source of information from which the predetermined concentration(s) of the radiopharmaceutical(s) is known, method 5050 proceeds to step 5053 in which radiation being identified as emitted from the predetermined location or locations is detected. Method 5050 then proceeds to step 5053 in which the detected radiation is used for calibrating the system. The calibration is based on the location from which the radiation is emitted and the concentration of radiopharmaceutical present in the location. The operator thus detects the radiation and calibrates the radiological system such that the radiation readings (intensity, direction, wavelength) are identified as originated from the predetermined location and predetermined concentration.

It is recognized that the concentration of the radiopharmaceutical(s) varies with time. Thus, in various exemplary embodiments of the invention the detection is performed within a sufficiently small time period. The time period depends on the rate of concentration change. Thus, the time period is preferably shorter than the time scale by which dynamical changes in the concentration occur. For example, when the predetermined location comprises body fluids or feces, the detection of the radiation is preferably performed substantially prior to diffusion of the radiopharmaceutical out of the body fluids or feces. Typical time periods include, without limitation, less than a few minutes, more preferably less than one minute, even more preferably less than 30 seconds from the administration of the radiopharmaceutical.

Such short time periods are particularly useful when the predetermined location from which the radiation is emitted is close to the location to which the radiopharmaceutical(s) is administrated. Thus, for example, when the radiopharmaceutical(s) is administrated intra intravenously, the detection can be done while the vasculature is the only location from which radiation is emitted. In this case any detected radiation is identified as emitted from the predetermined location and the system can be calibrated accordingly.

Method 5050 can be executed either as a "stand alone" method or in combination with the method 5010 above, in which case method 5050 serves for improving the calibration of the system. When method 5050 is combined with method 5010, selected steps of method 5050 can be executed at any stage of method 5010. For example, selected steps of method 5050 (e.g., steps 5052, 5053 and 5054) can be executed prior to steps 5012 or 5013 of method 5010. In this embodiment, method 5050 can be used as a first iteration for the calibration procedure. The operator can thus execute steps 5052-5054 of method 5050 and then continue to selected steps of method 5050 for improving the calibration. Selected steps of method 5050 can also be executed contemporaneously with selected steps of method 5010.

Figure 119:
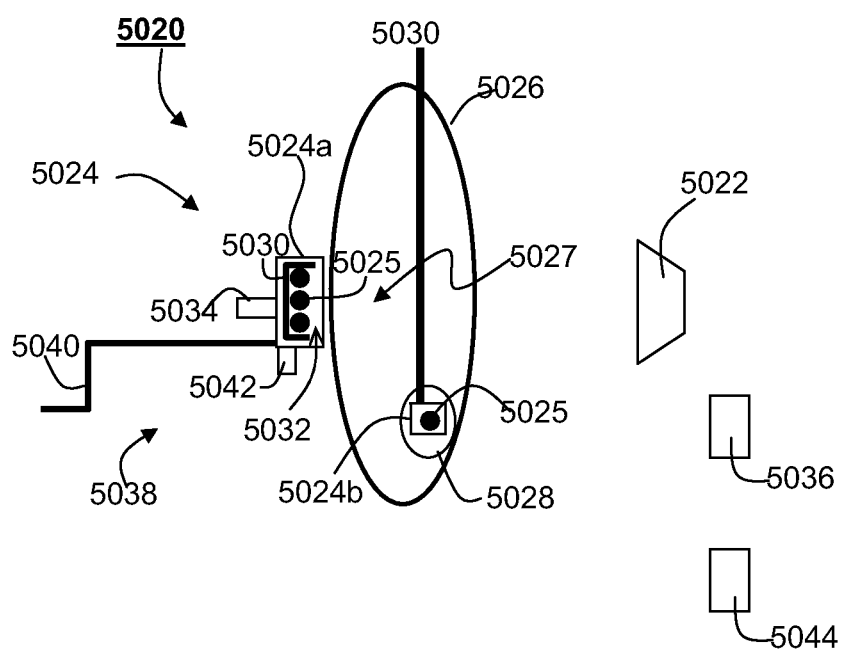
FIG. 119 is a schematic illustration of a device for calibrating a radiological imaging system, according to various exemplary embodiments of the invention.

Reference is now made to FIG. 119 which is a schematic illustration of a device 5020 for calibrating a radiological imaging system 5022, according to a preferred embodiment of the present invention. Device 5020 comprises one or more calibration sources 5024 capable of emitting radiation and being configured to engage the body 5026 of the subject. Calibration source 5024 can include one or more radioisotopes 5025, preferably of short half-life, as further detailed hereinabove. Representative examples of radioisotopes include radioisotopes of a chemical element such as, but not limited to, copper, cobalt, gallium, zinc, germanium, yttrium, strontium, technetium, indium, ytterbium, gadolinium, samarium, thallium and iridium.

Any number of calibration sources can be used. In the exemplified configuration shown in FIG. 119 calibration source 5024 comprises an extracorporeal calibration source 5024a and an intracorporal calibration source 5024b. Intracorporal calibration source 5024b can be encapsulated in a capsule 5028 to be taken orally or rectally by the subject, or in can be mounted on a probe 5030 such as a transesophageal or transrectal catheter.

As already stated hereinabove, source 5024 is preferably characterized by the same emission spectrum as the radiopharmaceutical(s) present in the subject. The number of radioisotopes employed by device 5020, either within a single calibration source or within different calibration sources, preferably equals the number of radiopharmaceuticals present in the subject. Thus, according to the presently preferred embodiment of the invention each radioisotope of device 5020 is preferably characterized by an emission spectrum of a respective radiopharmaceutical.

Additionally, the radiation activity of source 5024 is selected sufficiently high to be detectable by the radiological imaging system and sufficiently low so as not to mask radiation emitted by the radiopharmaceuticals present in the subject.

Source 5024 preferably comprises a communication unit 5034 for allowing source 5024 to communicate with a remote unit 5036 as further detailed hereinbelow. The communication can be wired communication or, more preferably, wireless communication, such as, but not limited to, radiofrequency or infrared communication.

The ability to accurately calibrate system 5022 depends inter alia on the identification of source(s) 5024, including its location such that the radiation detected by system 5022 can be traced back to the emitting source. There are several identification criteria which are contemplated.

Hence, in one embodiment, the radioisotopes of source 5024 are arranged gridwise over a grid, such that each radioisotope is characterized by a different emission spectrum and a different coordinate of grid. The identification in this embodiment is therefore by mapping emission spectrum to a coordinate on the grid.

In another embodiment, different radioisotopes have different radiation activity so as to allow their identification according to the intensity of the radiation arriving at system 5022.

In still another embodiment, each calibration source is characterized by a distinguishable geometrical shape. The geometrical shape can be a shape of the patch containing the radioisotopes. The geometrical shape can also be a barcode formed, for example, by a specific arrangement of the radioisotopes within the patch. Thus, in this embodiment the identification of source 5024 is by the shape of the image generated by system 5022.

In yet another embodiment, the calibration sources are identified by specific identification codes. In this embodiment each source is associated with a unique identification code which can be transmitted by source 5024, e.g., via communication unit 5034.

As stated, a remote activation and deactivated of source 5024 can be obtained using an absorbing or reflecting surface 5030. Surface 5030 can be manufactured with a window 5032 which can be opened and closed by remote activation via communication unit 5034.

Source 5024 is preferably capable of moving to allow source 5024 to scan target region 5027. The motion can be translational motion or rotational motion and can be established manually or automatically as further explained above. According to a preferred embodiment of the present invention source 5024 is associated with a motion mechanism 5038 which can be a movable arm 5040 or a propulsion mechanism 5042. When source 5024 is self-propelled, motion signals can be transmitted thereto via unit 5034.

Unit 5034 can also be used for establishing communication between source 5024 and a position sensing unit 5044 so as to allow the determination of the location of source 5024 as further detailed hereinabove.

Figure 120:
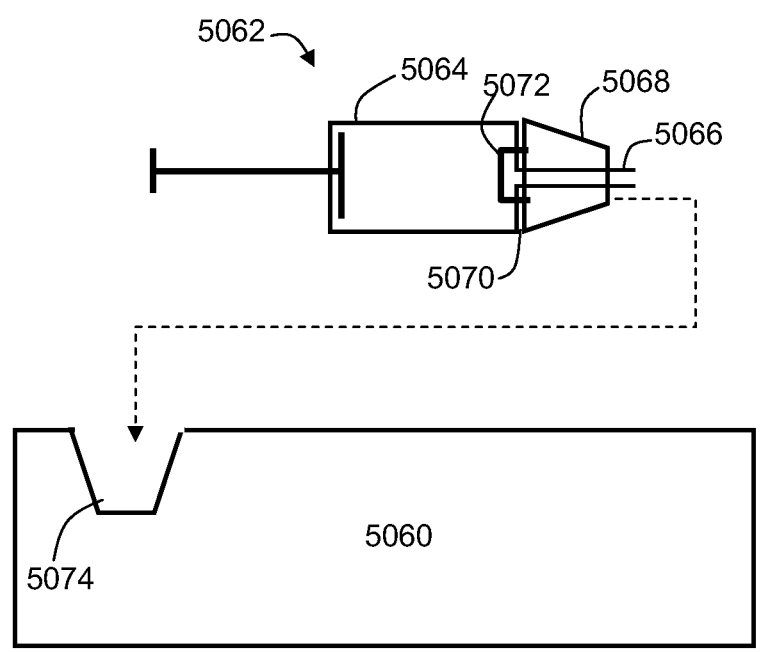
FIG. 120 is a schematic illustration of a device for administering radiopharmaceuticals to a subject, according to various exemplary embodiments of the invention.

Reference is now made to FIG. 120, which is a schematic illustration of a radiological imaging system 5060 and an administration device 5062, according to a preferred embodiment of the present invention. Device 5062 can be used to administer one or more radiopharmaceuticals during or prior to a radiological imaging procedure.

Device 5062 comprises a device body 5064 configured for holding the radiopharmaceutical(s) therein. The device body can be a disposable. In the exemplified embodiment of FIG. 120 device 5062 is manufactured as a syringe, but this need not necessarily be the case, since, for some applications, it may not be necessary for the device to function as a syringe. For example, in various exemplary embodiments of the invention device 5064 may serve as an intravenous bag of an intravenous access kit.

Device body 5064 is in fluid communication with an outlet conduit 5066. During administration, the radiopharmaceutical, which is typically provided in a liquid form, is extruded from body 5064 through conduit 5066. Conduit 5066 can be flexible or rigid as desired. For example, in one embodiment conduit 5066 is a needle which can be introduced into the lumen of a blood vessel of the subject, and in another embodiment conduit 5066 is a flexible tube configured to be connected to an inlet conduit (not shown), such as a hub or a cannula on the subject's body.

Device body 5062 has a detachable part 5068 holding a calibration source which can be any of the aforementioned calibration sources. For example, the calibration source can be identical to the radiopharmaceutical being administered into the subject. Detachable part 5068 can be connected to any location on device body 5064. In the representative example shown in FIG. 120 part 5068 covers outlet conduit 5066. Thus, part 5068 can also serve as a cap to body 5064. Alternatively, part 5068 can be connected to the side of device body 5064 without covering conduit 5066.

In any event, the interface 5070 between body 5064 and detachable part 5068 is designed and constricted to avoid leakage of the radiopharmaceutical or the calibration source while part 5068 is detached from body 5064. This can be achieved by anyway known in the art, include, without limitation, a valve, a double partition and the like.

The detachment of part 5068 from body 5064 can be done in a reversible or non-reversible manner. When the detachment is in a reversible manner, interface 5070 comprises a connector 5072 which can connect and disconnect the two parts. When the detachment is in a non-reversible manner, interface 5070 is designed such that the user breaks interface 5070, e.g., by twisting or bending body 5064, to detach part 5068.

Once detached, part 5068 can be mounted on a mounting location 5074 of system 5060, such that radiation emitted from the calibration source is detected by system 5060. According to a preferred embodiment of the present invention part 5068 is sizewise and shapewise compatible with mounting location 5074, so as to allow system 5060 to receive part 5068. The radiation emitted from the calibration source can then by utilized to calibrate system 5060 as further detailed hereinabove.

Compton Mapping

The present embodiments comprise a radiological imaging system and method for providing a three-dimensional anatomical image.

Studies which produce three-dimensional images are known in the art and include single photon emission computerized tomography (SPECT) and positron emission tomography (PET).

SPECT or PET cameras include one or more two-dimensional detectors which rotate around the biological body and detect radiation emitted from the radiopharmaceuticals as projection data. Data processing means perform reconstruction of multiple-slice images of radiopharmaceutical distribution in the body through the convolution and back-projection of the projection data. The images of the temporal and spatial distributions of the radiopharmaceuticals are reconstructed by using mathematical imagery construction techniques similar to those applied in CT. SPECT and PET provide unique functional information on blood flow and metabolism not easily obtainable by other technologies.

SPECT and PET differ both in the detection hardware and in the radiopharmaceuticals used. The detection hardware for SPECT and PET systems is different in terms of the manner in which the systems detect and record events and is also different because PET systems operate at higher count rates over SPECT systems.

The radiopharmaceuticals differ in terms of half-lives and energy levels. PET involves the detection of gamma rays in the form of annihilation photons from positron emitting radiopharmaceuticals, which typically include radioisotopes having short half-lives of less than a few hours. SPECT, on the other hand, uses longer-lived isotopes with half-lives of several hours to several tens of hours. Examples of radiopharmaceutical suitable for PET cameras include, $^{18}$F (half-life of approximately 110 minutes), $^{11}$C (approximately 20 minutes), $^{13}$N (approximately 10 minutes) and $^{15}$O (approximately 2 minutes). Examples of radiopharmaceutical suitable for SPECT cameras include, $^{99}$Tc (half life of approximately 6 hours) and $^{201}$Tl (approximately 74 hours).

As the radiopharmaceuticals employed by prior art radiological imaging are designed to mark specific sites within the region of interest, prior art radiological imaging techniques are suitable mainly for diagnosing tumors, infection and other disorders which are detected by evaluating the function of organs, such as the kidney, heart, lungs, gallbladder, bowel, thyroid and the like.

Radiological imaging, however, is a less favored technique for constructing three-dimensional anatomical images. Most presently available three-dimensional anatomical imaging techniques are based on magnetic resonance, X-ray or ultrasound.

There is thus a widely recognized need for, and it would be highly advantageous to have a radiological imaging system and method for providing a three-dimensional anatomical image.

The present embodiments can be used to provide anatomical three-dimensional image via with SPECT or PET cameras.

Figure 121A:
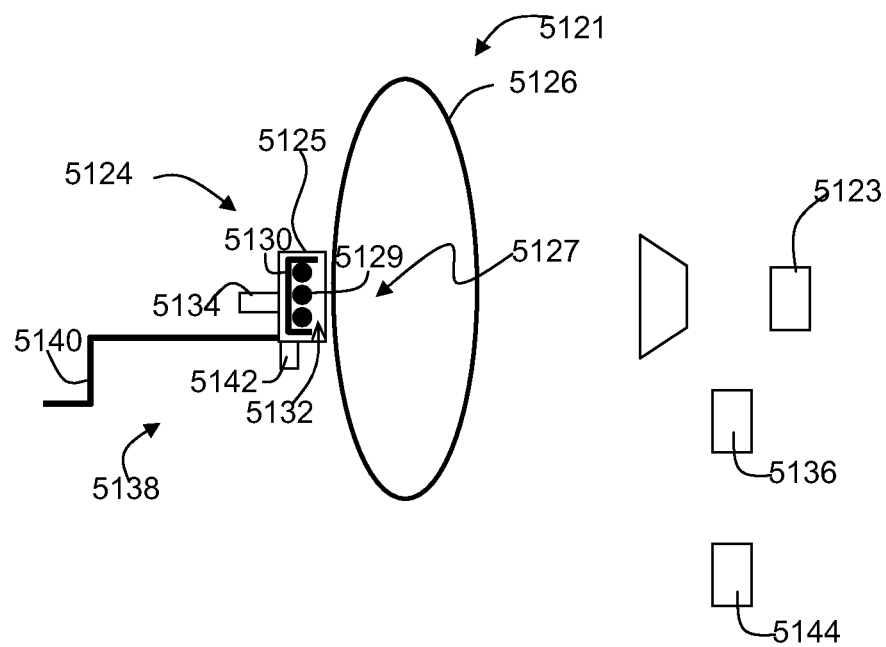
FIGS. 121a-e are schematic illustrations of a system for generating a three-dimensional image of a target region of a subject, according to various exemplary embodiments of the invention.
Figure 121B:
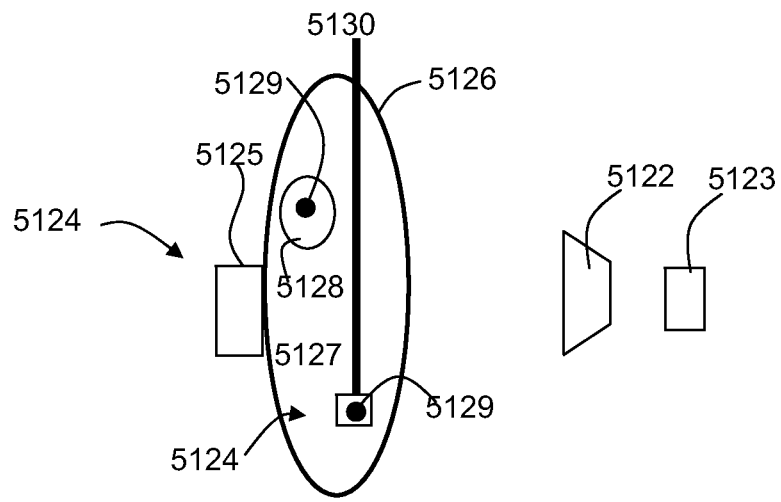
Figure 121C:
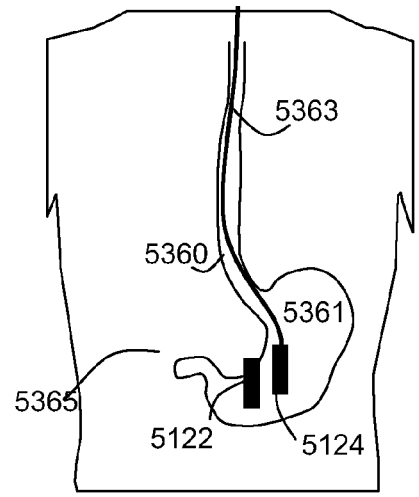
Figure 121D:
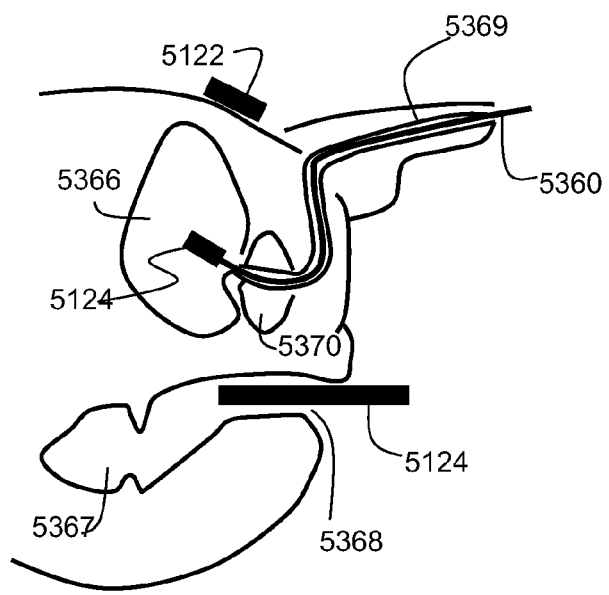
Figure 121E:
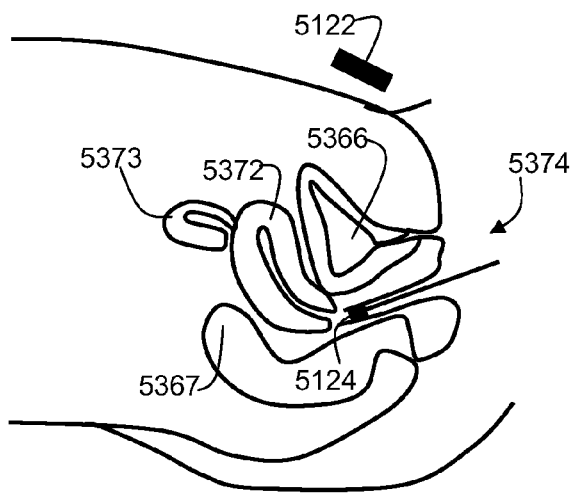

Referring now to the drawings, FIGS. 121*a-e* are schematic illustrations of a system 5120 for generating a three-dimensional image of a target region 5127 of a subject 5121. In its simplest configuration, system 5120 comprises one or more radioactive sources 5124, configured to engage body 5126 of subject 5121. Source 5124 can be an extracorporeal source, as shown in FIG. 121*a*, an intracorporal source, as shown in FIGS. 121*c-e*, or a combination of one or more intracorporal sources and one or more extracorporeal sources, as shown in FIG. 121*b*. One skilled in the art will recognize that several components of system 5120 have been omitted from FIGS. 121*b-c* for clarity of presentation.

Any number of radioactive sources can be used, where each radioactive source can independently comprise one or more radioisotopes 5129 having a relatively short half-life, of the order of a few days, e.g., 10 days, a week or less.

System 5120 further comprises a radiological imaging camera 5122, for detecting from target region 5127 radiation emitted by source 5124 to provide radiation data. Camera 5122 can be any type of radiological imaging camera, including, without limitation, a SPECT camera and a PET camera. System 5120 further comprises an analyzer 5123, for receiving and analyzing the radiation data from camera 5122. Analyzer 5123 uses the radiation data and constructs a three-dimensional image of target region 5127.

Many methods for constructing the image are contemplated.

In one embodiment, analyzer 5123 determines the attenuation properties of the tissue and uses these properties to construct anatomical three-dimensional image of the target region. In another embodiment, the image is constructed by computerized tomography, in which case absorption data are processed using a mathematical procedure, such as Radon transform or exponential projection. In an additional embodiment, the image can be constructed by inverse scattering, in which case scattering data are treated as a mathematical inverse problem which is then solved numerically, for example, using a set of linear integral equations in which time appears only implicitly. The image can also be constructed by a combination of methods, for example, a combination of computerized tomography and inverse scattering, in which case both absorption and scattering data are used.

According to a preferred embodiment of the present invention analyzer 5123 uses the radiation information for constructing an attenuation map, which can includes attenuation information associated with tissue present within target region.

System 5120 can be used either for obtaining a three-dimensional image per se, or in combination with more complex diagnostic procedures, such as, but not limited to, radiological imaging. It is recognized that the knowledge of body contours during radiological imaging allows the physician or operator to accurately position the camera. In conventional radiological imaging, an X-ray CT scan is performed prior to the radiological imaging procedure so as to determine the body contours of the subject. Subsequently, the radiological imaging camera is positioned about an inch above the subject highest point.

However, as the X-ray CT images and radiological images are captured at different times, the correlation between the images is oftentimes erroneous due to subject motions. In particular, although the X-ray CT images can accurately provide information regarding the internal structure of the subject, this information is not useful, e.g., for calculating attenuation corrections to the radiological images, due to the non-overlapping times at which the X-ray CT and radiological images are taken.

In contrast, system 5120 can be used to obtain, substantially simultaneously (e.g., within a few seconds), both a three-dimensional anatomical image and a (preprocessed) radiological image. Being taken substantially simultaneously, the information collected from the three-dimensional anatomical image can be used for the calculation of the attenuation corrections. The preprocessed radiological image can then be processed using the calculated attenuation corrections. The calculation of attenuation corrections from the information collected by system 5120 is particularly useful in situations in which the body contours includes complex morphology such as, for example, non-convex morphology (armpit, breast, etc.). In such situations, the numerical error of the preprocessed radiological image can be considerable, and the attenuation corrections can significantly improve the quality of the image.

According to a preferred embodiment of the present invention the radiation activity (number of disintegrations per unit time) of the radioactive sources is selected sufficiently high to be detectable by the radiological imaging system. In the embodiments in which system 5120 is used in combination with radiological imaging, the radiation activity is selected sufficiently low so as not to mask radiation emitted by the radiopharmaceuticals present in the subject.

The radiation activity of radioactive source 5124 can also be used for identifying source 5124. Specifically, source 5124 can be distinguished from the radiopharmaceuticals and/or other radioactive sources (if present), according to its radiation activity. Other identification criteria are also contemplated as further detailed herein.

In the embodiments in which system 5120 is used in combination with radiological imaging, source 5124 is preferably characterized by the same emission spectrum as the radiopharmaceutical(s) present in the subject. The number of radioisotopes employed by system 5120, either within a single radioactive source or within different radioactive sources, preferably equals the number of radiopharmaceuticals present in the subject. Thus, according to the presently preferred embodiment of the invention each radioisotope is preferably characterized by an emission spectrum of a respective radiopharmaceutical.

Source 5124 preferably comprises a communication unit 5134 for allowing source 5124 to communicate with a remote unit 5136 as further detailed hereinbelow. The communication can be wired communication or, more preferably, wireless communication, such as, but not limited to, radiofrequency or infrared communication.

Preferably, but not obligatorily, source 5124 is a directional source. In other words, the radiation is emitted by the source at one or more predetermined directions, with minimal or no radiation in other directions. This can be done, for example, by providing a radioactive source having absorbing or reflecting surface 5130 covering a portion of the radioisotope's "field-of-view".

Surface 5130 can also be controlled from an external location so as to activate and deactivate the radioactive source as desired. In this embodiment, when the source is inactive, the absorbing or reflecting surface is closed to prevent radiation from penetrating the target region. For example, surface 5130 can be manufactured with a window 5132 which can be opened and closed by remote activation via communication unit 5134.

Source 5124 is preferably capable of moving to allow source 5124 to scan target region 5127. The motion can be translational motion or rotational motion and can be established manually or automatically as further explained above. According to a preferred embodiment of the present invention source 5124 is associated with a motion mechanism 5138 which can be a movable arm 5140 or a propulsion mechanism 5142. When source 5124 is self-propelled, motion signals can be transmitted thereto via unit 5134.

Unit 5134 can also be used for establishing communication between source 5124 and a position sensing unit 5144 so as to allow the determination of the location of source 5124.

The use of a plurality of radioactive sources at known locations for constructing a three-dimensional image has many advantages.

First, in conventional anatomical imaging (e.g., X-ray CT), it is oftentimes required to acquire more than one image at different body positions (and different times) and to combine the image at a later stage. For example, when the imaging is of the cardiac muscle, one set of images is acquired when the subject is in supine position and another set of images is acquired when the subject is in prone position such as to image the cardiac muscle from both sides. This technique, however, requires image registration.

The use of a plurality of radioactive sources at known locations, in accordance with the present embodiments, successfully overcomes this problem. The known locations provide registration capabilities and there is no need to change the body position. Furthermore, the use of source 5124 facilitates the registration of rest versus stress tests.

Second, in conventional anatomical imaging, it is required to perform motion correction, to account for volitional or non-volitional motion (e.g., breathing) of the subject. Traditionally in X-ray CT, the physician visually examines each projection (raw image) to determine whether the projection was taken while the subject was moving or significantly displaced. Such projections are considered corrupted and are either corrected using an image correction algorithm or excluded from the image reconstruction. In severe cases (e.g., when there are many corrupted) the entire imaging process is repeated.

The use of a plurality of radioactive sources at known location, in accordance with the present embodiments, can significantly improve the motion correction because the motions of the subject can be monitored, substantially in real time, by determining changes in the locations of the radioactive sources.

An additional advantage of the present embodiments is that source 5124 can also be used as a calibration source for camera 5122, as further detailed herein.

As stated, source 5124 can be an extracorporeal or an intracorporal source. In the former case, the source can be provided in a form of a patch 5125 containing a single radioisotope or an arrangement of radioisotopes. In this embodiment, the source is preferably attached to an external organ of the subject, being in proximity to the target region. When an intracorporal source is employed, the source can be endoscopically inserted to the subject. This can be done, for example, by mounting the source on a probe 5130 such as a transesophageal or transrectal catheter. The source can also be encapsulated in a capsule 5128 to be taken orally or rectally by the subject.

FIG. 121*c* is a schematic illustration of an embodiment in which the intracorporal source is used for imaging the stomach. Shown in FIG. 121*c* is the esophagus 5360 and the stomach 5361. Also shown are the intracorporal source 24, which is inserted through esophagus 5360 by a catheter 5363 and positioned in stomach 5361. Camera 5122 is positioned externally on the upper abdomen 5365, opposite to source 5124. In operation mode, radiation is transmitted through the stomach to provide an image thereof as further detailed above. This embodiment can be used for imaging benign tumors such as Leomyoma, or malignant tumors such as carcinoma or lymphoma.

The ability to insert the intracorporal radioactive source through the esophagus allows the operator to obtain images of the esophagus itself, thereby to locate pathologies, such as the carcinoma of the esophagus, thereon. In this embodiment, both the source and the camera are positioned such that the radiation is transmitted through the gap between two ribs.

Reference is now made to FIG. 121*d*, which is a schematic illustration of an embodiment in which the intracorporal radioactive source is used for imaging the prostate or bladder. Shown in FIG. 121*d* are the rectum 5367, the bladder 5366, the prostate 5370 and the urethra 5369. In the present embodiments, intracorporal radioactive source 5124 can be inserted through the anus 5368 into the rectum 5367, or through the urethra 5369. When source 5124 is inserted through the urethra it can be used for imaging the prostate, in which case source 5124 is positioned near the prostate, or the bladder, in which case source 5124 is inserted into the bladder as shown in FIG. 121*d*. Camera 5122 can then be positioned on the lower external abdomen, and a three-dimensional image of the prostate or the bladder can be obtained.

Reference is now made to FIG. 121*e*, which is a schematic illustration of an embodiment in which the intracorporal radioactive source is used for imaging the uterus, bladder or ovary. Shown in FIG. 121*e* are the rectum 5367, the bladder 5366, the uterus 5372 and the ovary 5373. In the present embodiments, source 5124 can be inserted through the vagina 5374. Source 5124 can be mounted on a catheter and can be inserted into the uterus. Camera 5122 can then be positioned on the mid external abdomen, and a three-dimensional image of the uterus, bladder or ovary can be obtained. This embodiment can be used for locating or diagnosing polyps in the uterus or bladder. Additionally this embodiment can be used for locating or diagnosing benign tumors in the uterus (e.g., myomas) or any malignant tumors therein. For the ovary, this embodiment can be used for imaging any primary or secondary malignant tumors therein.

Following is a description of imaging methods according to various aspects of the present invention. It is to be understood that, unless otherwise defined, the method steps described hereinbelow can be executed either contemporaneously or sequentially in many combinations or orders of execution. Specifically, the ordering of the flowcharts of FIGS. 122 and 123 below is not to be considered as limiting. For example, two or more method steps, appearing in the following description or in a corresponding flowchart in a particular order, can be executed in a different order (e.g., a reverse order) or substantially contemporaneously.

Figure 122:
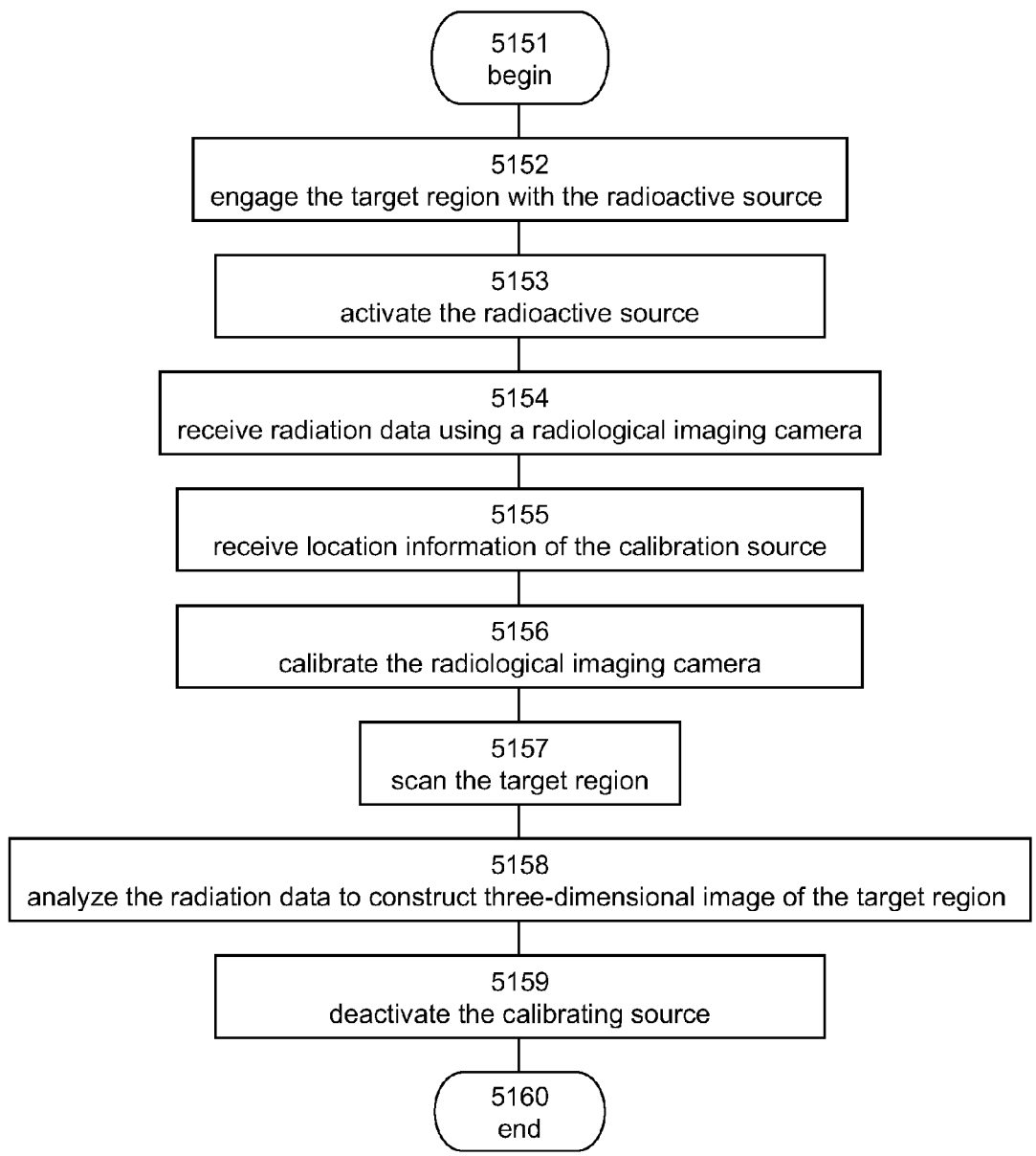
FIG. 122 is a flowchart diagram of a method for constructing a three-dimensional image of a target region of a subject, according to various exemplary embodiments of the invention.

Reference is now made to FIG. 122 which is a flowchart diagram of a method 5150 for constructing a three-dimensional image of a target region of a subject, according to various exemplary embodiments of the present invention.

Method 5150 begins at step 5151 and continues to step 5152 in which the target region is engaged by one or more extracorporeal and/or intracorporal radioactive sources, which can be in a form of a patch, a capsule or it can be mounted on an endoscopic device as further detailed hereinabove. Depending on the type of the source, the engagement of the target region can be done by attaching the source to an external organ of the subject (when the source is an extracorporeal patch), by endoscopically inserting the source to the subject (when the source is mounted on an endoscopic device), or by administering the source to the subject either orally or rectally (when the source is in a form of a capsule).

According to a preferred embodiment of the present invention method 5150 continues to step 5153 in which the source is activated. This can be done by remotely control the absorbing or reflecting surface such that a window is formed in the surface to allow radiation to pass therethrough. The method continues to step 5154 in which radiation data corresponding to radiation emitted by the radioactive source is received from the target region. The radiation data can be received by a radiological imaging camera.

According to a preferred embodiment of the present invention the method continues to step 5155 in which location information of the source is received. This embodiment is useful when the location of the source varies or not known.

The location information can be obtained in more than one way.

Hence, in embodiments in which the source is mounted on a mechanical device, such as a catheter or an arm, the location information can be obtained directly from the mechanical device. Alternatively, the calibration source can communicate (mechanically, electrically or via wireless communication) with a position sensing system to enable the determination of its location, substantially in real time.

According to a preferred embodiment of the present invention method 5150 continues to step 5156 in which the radiological imaging camera is calibrated. The calibration is preferably done using the radioactive source which, in the present embodiments also serves as a calibration source.

The calibration can be done by employing an attenuation map, constructed prior to the calibration procedure. The attenuation map includes attenuation information associated with tissue present within target region. The attenuation map can be a general map, or, alternatively, a specific attenuation map can be tailored to each subject or group of subjects having similar body structure within the target region. Thus, knowing the location, radiation activity and emission spectrum of the calibration source, and given the radiation readings of the radiological imaging camera (intensity, direction, wavelength, etc.), the attenuation map can be used for calibrating the camera. A mathematical procedure for calculating probability distributions is provided hereinafter.

In various exemplary embodiments of the invention the method comprises an additional step (designated 5157) in which the target region is scanned with the source. The scanning of the region can be done by displacing the source such that at each position of the source the radiation interacts with a different portion of the target region. The motion of the source can be establish using an external mechanism, e.g., a movable arm which can be controlled manually or automatically. The source can also be a self-propelling source, moving, e.g., in the vasculature either using an internal propulsion mechanism or via blood flow.

Alternatively or additionally to the motion of the source, the scan of the target region can be achieved by controlling the direction at which radiation is emitted from the source. This can be done by rotating the source or by directly controlling the absorbing or reflecting surface of the source to allow the radiation to propagate at the desired location.

Method 5150 continues to step 5158 in which the radiation data is analyzed so as to construct the three-dimensional image of the target region, as further detailed hereinabove.

Once the three-dimensional image is constructed, the method, optionally and preferably, continues to step 5159 in which the source is deactivated. This can be done by remotely controlling the absorbing or reflecting surface so as to close the aforementioned window hence to prevent radiation to enter the target region.

The method ends at step 5160.

As stated, the three-dimensional image can be constructed as a part of a radiological imaging procedure.

Figure 123:
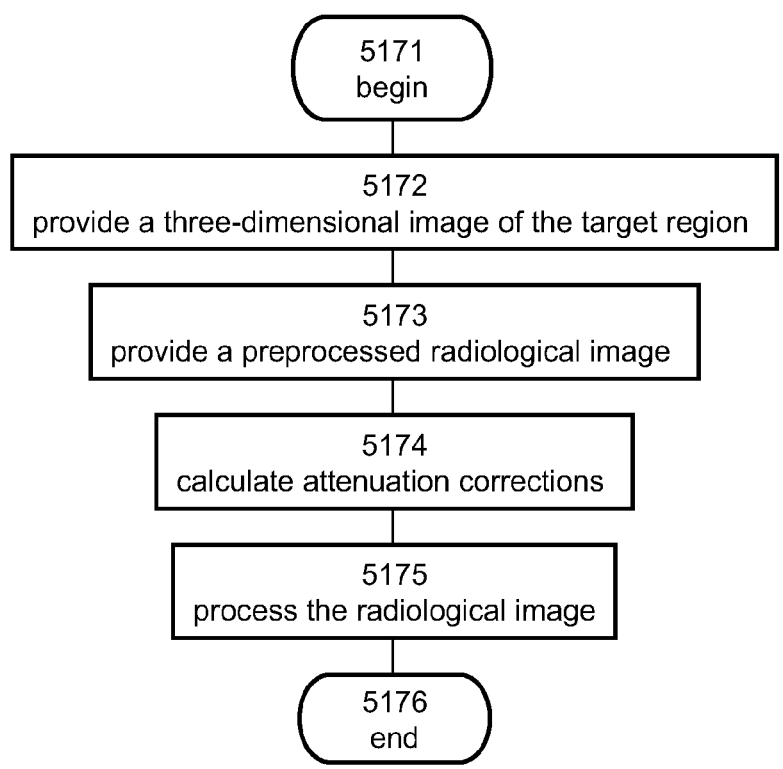
FIG. 123 is a flowchart diagram of a method for constructing a radiological image of a target region of a subject, according to various exemplary embodiments of the invention.

Reference is now made to FIG. 123 which is a flowchart diagram of a method 5170 for constructing a radiological image of a target region, according to various exemplary embodiments of the invention. Method 5170 begins at step 5171 and continues to step 5172 in which a three-dimensional image of the region is provided, for example, by executing selected steps of method 5150. Method 5170 continues to step 5173 in which a preprocessed radiological image of the target region is provided. Step 5173 can be performed by any radiological imaging procedure known in the art. Typically, the procedure includes the administration of radiopharmaceuticals to the subject and the detection of radiation data from the radiopharmaceuticals using a radiological imaging camera. According to a preferred embodiment of the present invention the same radiological imaging camera is used for the three-dimensional image (step 5172) and the preprocessed radiological image (step 5173).

Method 5170 continues to step 5174 in which attenuation corrections to the preprocessed radiological image are calculated. The attenuation corrections are based on the three-dimensional image and preferably include probability distribution for photons to interact (via absorption or scattering) with tissue in the as viewed in the three-dimensional image of the target region. The attenuation corrections can be provided in a form of, e.g., an attenuation map, representing the contribution of different sectors of the target region to the attenuation of radiation. Method 5170 then continues to step 5175 in which the (preprocessed) radiological image is processed. The processing preferably includes the correction of the preprocessed image in accordance with the attenuation corrections (or attenuation map) to thereby provide a radiological image.

The method ends at step 5176.

Figure 124:
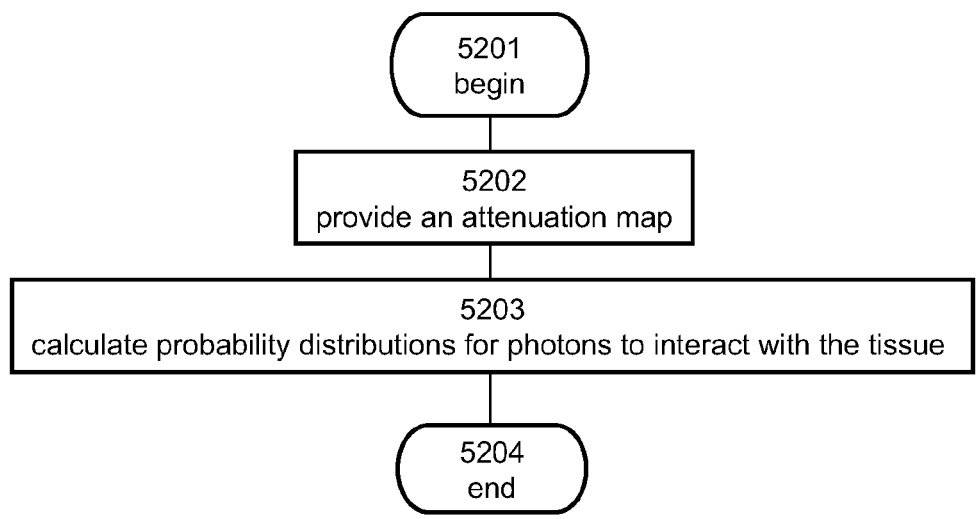
FIG. 124 is a flowchart diagram of a method for calculating intensity attenuation of a radiological image, according to various exemplary embodiments of the invention.

Reference is now made to FIG. 124 which is a flowchart diagram of a method 5200 for calculating intensity attenuation of a radiological image, according to various exemplary embodiments of the present invention.

The method begins at step 5201 and continues to step 5202 in which an attenuation map is provided. The attenuation map can be obtained in any way known in the art. For example, in one embodiment, the attenuation map is obtained using computerized tomography (CT) image or a magnetic resonance image (MRI) of the target region. Given an MRI or CT image, the attenuation map is constructed from the image by extracting information on the types and shape of tissues present in the target region (e.g., bones, lungs) and utilizing this information for calculating the attenuation associated with each tissue type.

In another embodiment, the attenuation map can be obtained by constructing a model of the target region. In the simplest case, the model comprises at least one geometrical shape representing water bulk. Thus, in this embodiment, the body is modeled as a water bulk (of a specific shape), whereby all the attenuations are calculated assuming the photons interact with water. This model can be improved by considering, in addition to the interaction with water, the passage of photons through the air gap between the detector of the radiological imaging system and the body. The distance between the detector(s) and the body can be calculated (e.g., knowing the size of the imaging system and the approximate shape of the body) or measured.

In an additional embodiment, the attenuation map can be obtained using one or more radioisotopes which can be present within the target region, in proximity thereto or outside the body. For example, in various exemplary embodiments of the invention the aforementioned calibration source is used for constructing the attenuation map, as further detailed hereinabove. Alternatively or additionally, one or more non-specific radioisotopes can be administered to the subject, e.g., into the vasculature. Readings of emissions from the administered radioisotope(s) can then be used for constructing attenuation map, as further detailed in the Examples section that follow.

In still another embodiment, the attenuation map can be obtained from the radiological image per se. In this embodiment, a mathematical algorithm determines the contribution for each voxel of the radiological image to the attenuation.

For example, the algorithm can classify the voxels into different groups (water, bone, air, etc.) whereby each group is associated with different attenuation. The classification can be done by correlating intensity levels of the voxels with their type, or by inputting information from other resources.

Two or more of the above embodiments can also be combined so as to improve the quality of the attenuation map.

Once the attenuation map is obtained, the method proceeds to step 5203 in which the attenuation map is utilized for calculating probability distributions for photons emitted by the radiopharmaceutical(s) to interact with the tissue. As stated, the probability distributions can comprise probabilities of photons to be absorbed by or scattered off the tissue. Knowing the interaction probability of the photons at each voxel, the intensity attenuation of the radiological image can be calculated.

The above process can be performed for one or more energy bin. As stated, when the photon is scattered off matter (tissue, water molecule etc.) via Compton scattering some of its energy is lost. Thus, even when the emission spectrum of the radiopharmaceutical is narrow, there is more than one possible energy level at which the emitted photons can be detected. The number of possible energy level is further increased when there is more than one radiopharmaceutical. For a plurality of radiopharmaceuticals and a plurality of energy levels, the method associates to each voxel a local probability which describes (in probabilistic manner) whether photons emitted by each of the radiopharmaceuticals are absorbed, scattered coherently or scattered incoherently. In case of coherent or incoherent scattering, the method can also calculate the propagation direction and energy of the photon after the interaction.

The local probabilities associated with each voxel in the image form an absorption-scattering map of the target region in a sense that for each elementary portion of the voxel, the outgoing photon has a known (again, probabilistically) energy and propagation direction. Thus, when a detector, tuned to a specific energy bin and positioned at a known location with respect to the target region, detects a photon, the method can calculate the location in the target region from which the photon was emitted. A plurality of detectors (or a single detector scanning a plurality of location) can thus be employed at a plurality of predetermined energy bins and the spatial distribution of each radiopharmaceutical can calculated at each energy bin, thereby increasing the amount of information which can be extracted from the target region.

The method ends at step 5204.

The following example relates to the issue of reconstructing intensity distributions.

An intensity distribution I, conventionally defined in terms of radioactive emissions per seconds, is now redefined as a vector of distributions over the volume U, forming the input space. Each dimension of the vector corresponds to a different radioisotope. The universal set U comprises a set of basic elements u (e.g., pixels in two dimensional spaces, voxels in three dimensional spaces), and I(u) is the intensity in a given basic element u∈U. For j radioisotopes this becomes $I(u)^{(j,t)}$. An inverse (or reconstruction) problem arises when one cannot sample directly from I, but can sample from a given set of views Φ. A projection φ∈Φ is defined by the set of probabilities {φ(u): u∈U}, where φ(u) is the probability of detecting a radioactive emission from a voxel u, as defined by viewing parameters, such as the physical and geometrical properties of the detecting unit, as well as the attenuation parameters of the viewed volume U, and the time parameters. A measurement is obtained by choosing a view φ∈Φ, and then sampling according to the viewing parameters.

For j radioisotopes or markers and k detectors, the probability of seeing a particle becomes $\phi_j^k(u)$ In the following analysis, I is the intensity of a radioactive substance, and the viewing parameters include the geometrical properties of a collimated detecting unit and the detecting unit's position and orientation with respect to volume U. The number of radioactive emissions counted by the detecting unit within a time interval is a Poisson distribution, where φ(u) is the detection probability of a photon emitted from voxel u∈U and the mean of the distribution is the weighted sum $\Sigma_{u \in U} \phi(u) I(u)$.

For the case of the kth detector a measurement $Y_k = \Sigma_{u \in U} X_t(u)$, where X(U) is a Poisson distribution.

$$X_{(j,k,t)}(u) = I^{(j,t)}(u) \cdot \phi(u)_j^k(u), \quad (1)$$

where, $$Y_{(j,k,t)} = \Sigma X_{(j,k,t)}(u). \quad (2)$$

Hence:

$$Y_{(j,k,t)} = \text{Poisson}(Y_{(j,k,t)}). \quad (3)$$

The projection set is thus defined by a matrix Φ, whose rows are the projections of the chosen views. I is a vector of densities (specified per each element in U), and ΦI is a vector of respective effective intensity levels for the views in the set. A vector of measurements y is obtained by a random sample from each view (according to the associated Poisson distribution). There are various known reconstruction methods that provide estimators for I given the projections Φ and the measurements y.

Signal Isolation

The intensity density of isotope i in voxel u is denoted by $I^i(u)$. Detector t, detects $y_{tb}$ photons at energy bin b. A detector is referred to a as a composite of a collimator and a radiation sensor such as CZT, placed at some location. In an actual system, a physical detector that takes snap shots from several locations is regarded as different detectors for the purpose of the following derivations. The probability of a photon emitted from isotope i in voxel u, to be detected by detector t at energy bin b, is denoted by $\phi_{tb}^i(u)$. This probability can be determined by the geometrical and physical properties of the detector, its position, orientation, and the reduction of the energy of the photon emitted from isotope I, to the measured energy b. In the following derivations $\phi_{tb}^i(u)$ will be referred to as a functional, which can be calculated analytically, e.g., using geometrical considerations combined with the experimentally measured scattering effects. Alternatively the functional can be calculated only in part with further tuning via experiment.

The change of angle θ of a photon emitted at energy $E_0$, and scattered to energy E is given by:

$$E(E_0, \theta) = E_0 \left[ \frac{m_e c^2}{m_e c^2 + E_0(1 - \cos(\theta))} \right] \Leftrightarrow \cos(\theta) = 1 - \left( \frac{1}{E} - \frac{1}{E_0} \right) m_e c^2, \quad (4)$$

Where $m_e$ represents the rest mass of the electron, and c is the speed of light in a vacuum.

The random count $X_{tb}^i(u)$ of photons that are emitted from voxel u and detected in measurement tb (detector t at energy bin b), is modeled by a Poisson process with mean $\Sigma_i \phi_{tb}^i(u) I^i(u)$. The total count of photons detected in measurement tb is $Y_{tb} = \Sigma_u X_{tb}(u)$, and the problem is to reconstruct the intensities $I^i(u)$ from the measurements $y_{tb}$.

Simultaneous Submission of Multiple Isotopes

The measurements have a Poisson distribution $$Y_{tb} \sim \text{Poiss}(\Sigma_i \Sigma_u \phi_{tb}^i(u) I^i(u)). \quad (5)$$

The log-likelihood is given by:

$$L(y \mid I^1, I^2, \ldots) = \sum_{tb} \ln \text{Poiss}\left(y_{tb} \mid \sum_i \sum_u \phi_{tb}^i(u) I^i(u)\right) = \quad (6)$$

$$= \sum_{tb} \left\{ -\sum_i \sum_u \phi_{tb}^i(u) I^i(u) + y_{tb} \ln\left[\sum_i \sum_u \phi_{tb}^i(u) I^i(u)\right] - \ln(y_{tb}!) \right\}$$

The maximum likelihood is the solution of set of non-linear equations:

$$\sum_{tb} \sum_u \phi_{tb}^i(u) = \sum_{tb} \frac{\phi_{tb}^i y_{tb}}{\hat{y}_{tb}}, \quad (7)$$

for all i, where $$\hat{y}_{tb} = \Sigma_i \Sigma_u \phi_{tb}^i(u) I^i(u). \quad (9)$$

The solution may be solved via the Expectation Maximization (EM) approach:

$$X_{tb}^i(u) \sim \text{Poiss}(\phi_{tb}^i(u) I^i(u)). \quad (9)$$

The likelihood of the complete data:

$$\ln P(x \mid I^1, I^2, \ldots) = \Sigma_{tb} \Sigma_i \Sigma_u \{-\phi_{tb}^i(u) I^i(u) + x_{tb}^i(u) \ln [\phi_{tb}^i(u) I^i(u)] - \ln(x_{tb}^i(u)!)\} \quad (10)$$

The EM based algorithm is an iterative procedure. Since the likelihood depends on the complete data which is only partially observable, at any iteration step the expectation of the likelihood is taken with respect to the space of the unobserved data, given the current set of hypothesized parameters. The result is a function, $Q(I^i \mid I^{i'})$ which assigns likelihood to sets $I^i$ of model parameters, given the current set $I^{i'}$, and given the observed data $y_{tb}$:

$$Q(I^i \mid I^{i'}) = E[\ln P(x \mid I^i) \mid y; I^{i'}] \quad (11)$$

$$= \sum_{tb} \sum_i \sum_u \{-\phi_{tb}^i(u) I^i(u) + E[x_{tb}^i(u) \mid y_{tb}; I^{i'}] \ln[\phi_{tb}^i(u) I^i(u)] + C\}$$

where C is a term which is independent of the intensities I. The function Q, can be maximized by the following estimate for all $u \in U$:

$$I^i(u) = \frac{1}{\sum_{tb} \phi_{tb}^i(u)} \sum_{tb} E[x_{tb}^i(u) \mid y_{tb}; I^{i'}]. \quad (12)$$

Assuming conventional Poisson distributions, the expectation of $I^i$ can be calculated, resulting in the following expression for E:

$$E[x_{tb}^i(u) \mid y_{tb}; I^{i'}] = y_{tb} \frac{\phi_{tb}^i(u) I^{i'}(u)}{\sum_v \phi_{tb}^i(v) I^{i'}(v)}. \quad (13)$$

The EM based algorithm is therefore give by:

$$I^i(u) = \frac{1}{\sum_{tb} \phi_{tb}^i(u)} \sum_{tb} \frac{y_{tb}}{\hat{y}_{tb}} \phi_{tb}^i(u) I^{i'}(u), \quad (14)$$

for all i where $$\hat{y}_{tb} = \Sigma_i \Sigma_u \phi_{tb}^i(u) I^{i'}(u). \quad (15)$$

It is provable that the likelihood is improved at each iteration step. Thus, given a random starting estimator, the EM based algorithm iterates until it converges to a local maximum of the likelihood. Several random starts can increase the chance of finding a globally good estimator.

Separate Submissions

Following are examples for the case of two isotopes being submitted in two separate submissions. The utilization can be performed in a two-step estimation procedure or in a combined estimation procedure.

In the two-step estimation procedure, the first step comprises the submission of the first isotope (i=1) and the estimation of its density distribution, $I^1(u)$, using the EM based algorithm. The second step comprises the submission of the second isotope (i=2), while the first isotope is still distributed in the volume. Given the already estimated $\hat{I}^1(u)$, $\hat{I}^2(u)$ can be estimated by:

$$I^2(u) = \frac{1}{\sum_{tb} \phi_{tb}^2(u)} \sum_{tb} \frac{y_{tb}}{\hat{y}_{tb}} \phi_{tb}^2(u) I^2(u), \quad (16)$$

where $$\hat{y}_{tb} = \Sigma_u \phi_{tb}^2(u) I^2(u) + \Sigma_u \phi_{tb}^1(u) \hat{I}^1(u). \quad (17)$$

Extension to multiple (e.g., 3, 4 or more) submissions is straightforward.

In the combined estimation procedure, a first scan is performed after submitting the first isotope and a second scan is performed when both isotopes are distributed. In other words, the procedure is as follows: submit the first isotope, scan, submit the second isotope and scan again. The measurements of the first and second scans are denoted by $y^{(1)}_{tb}$ and $y^{(2)}_{tb}$, respectively. The functional of the first scan is denoted $\phi_{tb}^{1(1)}$, and the functionals of the second scan are denoted $\phi_{tb}^{1(2)}$, $\phi_{tb}^{2(2)}$.

The measurements have the Poisson distributions:

$$y_{tb}^{(1)} \sim \text{Poiss}(\Sigma_u \phi_{tb}^{1(1)}(u) I^1(u))$$

$$y_{tb}^{(2)} \sim \text{Poiss}(\Sigma_u \phi_{tb}^{1(2)}(u) I^1(u) + \phi_{tb}^{2(2)}(u) I^2(u)) \quad (18)$$

The solution based on the EM approach:

$$I^1(u) = \frac{1}{\sum_{tb} \phi_{tb}^{1(1)}(u) + \phi_{tb}^{1(2)}(u) + \phi_{tb}^{2(2)}(u)} \quad (19)$$

-continued $$I^2(u) = \frac{1}{\sum_{tb}\phi_{tb}^{1(1)}(u) + \phi_{tb}^{1(2)}(u) + \phi_{tb}^{2(2)}(u)} \sum_{tb}\left(\frac{y_{tb}^{(1)}\phi_{tb}^{1(1)}(u)}{\hat{y}_{tb}^{(1)}} + \frac{y_{tb}^{(2)}\phi_{tb}^{1(2)}(u)}{\hat{y}_{tb}^{(2)}}\right)I^1(u)$$

$$\cdot \sum_{tb}\left(\frac{y_{tb}^{(2)}\phi_{tb}^{2(2)}(u)}{\hat{y}_{tb}^{(2)}}\right)I^2(u),$$

where $$\hat{y}_{tb}^{(1)} = \Sigma_u \phi_{tb}^{1(1)}(u)I^1(u)$$

$$\hat{y}_{tb}^{(2)} \Sigma_u \phi_{tb}^{1(2)}(u)I^1(u) + \phi_{tb}^{2(2)}(u)I^2(u). \quad (20)$$

The EM iterative process can also be formulated by maximizing the expected posterior probability (given a proper prior) rather than the expected likelihood.

For conciseness and simplification of the notations, the isotope and energy bin indices (i and b, respectively) have been omitted from the following description. It is to be understood, however, that it is not intended to limit the scope of the present invention to the case of a single isotope or a single energy bin. One of ordinary skill in the art would appreciate that the following description can be extended to the case of more than one isotope and/or more than one energy bin as further detailed hereinabove.

In the embodiment in which the expected posterior probability is maximized, a prior probability $P(I)=\pi_{u,u}P(I(u))$ is assumed on the intensities I. A proper conjugate prior for the Poisson distribution is the Gamma distribution, $$P(I(u)) = \text{Gamma}(I(u) \mid \alpha_u; \beta_u) = \frac{\beta_u^{\alpha_u+1}}{\Gamma(\alpha_n+1)}I(u)^{\alpha_u}e^{-\beta_u I(u)} \quad (21)$$

Now the function Q is defined as:

$$Q(I/I') = E[\ln P(x|I)p(I)|y;I']. \quad (22)$$

Plugging the Gamma prior into Q, and solving for I(u), the following EM iteration for the maximum posterior estimation is obtained:

$$I(u) = \frac{\alpha_u + \sum_t E[x_t(u) \mid y_t; I']}{\beta_u + \sum_t \phi_t(u)}$$

$$= \frac{1}{\beta_u + \sum_t \phi_t(u)}\left[\alpha_u + \sum_t y_t \frac{\phi_t(u)I'(u)}{\sum_v \phi_t(u)I'(v)}\right]. \quad (23)$$

In matrix notation, the EM procedure can be written as follows. Let $\Phi$ be the matrix of the views $[\phi_t(u)]_{t,u}$, and let I, I', y, $\alpha$ and $\beta$ be represented as column vectors. Equation 23 can be written in vector and matrix notations as:

$$I = \frac{\alpha + I' \cdot \left(\Phi^T \frac{y}{\Phi I'}\right)}{\beta + \Phi^T 1} \quad (24)$$

where the explicit multiplication and division denote element-wise operations, and 1 is a vector (of the appropriate length) consisting solely of 1's.

When the computational resources are limited, the iterative process can be divided according to a partition of the view matrix $\Phi$ into a set of sub-matrices ($\Phi_k$. In this case the intensities can be updated gradually (using only one sub-matrix at each step) as follows:

$$I = \frac{\alpha + I' \sum_k \Phi_k^T \frac{y_k}{\Phi_k I'}}{\beta + \sum_k \Phi_k^T 1} \quad (25)$$

where $y_k$ is the vector of observations that are obtained using the views of $\Phi_k$.

The above described algorithm enables identification of the different energy level photons (energy signature) emitted from a radioisotope (produced from directly collected photons as well as photons generated from Compton scattering), or a plurality of radioisotopes (e.g., cocktail) detected by the radiological imaging system. Thus, such an algorithm enables association between various energy level photons and an isotope source. In essence, this algorithm produces for every radioisotope an energy signature which is composed of the various energy photons produced thereby in a body as a function of a voxel imaged by the system.

The following additional example relates to the issue of calculating attenuation correction simultaneously with body emission. Attenuation correction can be important in reducing artifacts (e.g., due to the presence of low density lungs in the proximity of the heart). Attenuation maps can be obtained using modalities such as CT scans, or they can be estimated from transmission data, using external sources coupled with an appropriate collimation. These methods, however, suffer from an increase in complexity and overall scanning time. Additionally, there is a potential crosstalk contamination between the emission and transmission data.

The present embodiments successfully estimate the density and attenuation solely from the emission data or, in special cases, from transmission data. In this example, the isotope and energy bin indices (i and b, respectively) have been omitted from the following description for conciseness and simplification of the notations. One of ordinary skill in the art would appreciate that the following description can be extended to the case of more than one isotope and/or more than one energy bin as further detailed hereinabove.

Let A(u) be the attenuation of voxel u and let $\delta_t(u,v)$ be the average length of the intersection of voxel v with the lines from (the center of) voxel u reaching detector t. If there is no such intersection then $\delta_t(u,v)=0$. Additionally, the quantity $\psi_t(u)$ is defined in terms of A and $\delta$ as follows:

$$\psi_t(u) = e^{-\Sigma_v \delta_t(u,v)A(u)}. \quad (26)$$

The measurement $Y_t$ is now a Poisson random variable with mean $\Sigma_u \xi_t(u) I(U)$, where $\xi_t(u)=\phi_t(u) \psi_t(u)$. When the map A(•) is known, the maximum likelihood estimation algorithm presented above can be used, by replacing $\phi_t(u)$ with $\xi_t(u)$, for every measurement t and every voxel u, thus obtaining the following maximum-likelihood updates:

$$I(u) = \frac{1}{\sum_t \xi_t(u)} \sum_t y_t \frac{\xi_t(u)I'(u)}{\sum_v \xi_t(v)I'(v)} \quad (27)$$

To compute the likelihood of the data, a new (hidden) variable $X_t(u,v)$, is defined. $X_t(u,v)$ is the number of photons emitted from voxel u, directed towards detector t and entered voxel v. Note that $X_t(u,v)$ represents the photon which would have been detected by detector t in the absence of attenuation. Let $X_t(u)$ be the number of photons emitted from u and detected in measurement t (recall that detector t is associated with measurement t). The number of photons leaving v and entering the next voxel, v+1, along the line from the center of u to the center of detector t is denoted $X_t(u,v+1)$.

The likelihood of the completed data can thus be written as:

$$P(X \mid I, A) = \prod_t \left[ \prod_u Poisson(X_t(u, u) \mid \phi_t(u)I(u)) \prod_v Binomial(X_t(u, v+1) \mid e^{-\delta_t(u,v)A(v)} X_t(u, v)) \right], \quad (28)$$

and the log-likelihood is:

$$\ln P(X \mid I, A) = \sum_t \sum_u \left\{ -\phi_t(u)I(u) + X_t(u, u)\ln(\phi_t(u)I(u)) + \sum_{v \in l_1(u)} [-\delta_t(u)A(u)X_t(u, v+1) + \ln(1 - e^{-\delta_t(u)A(u)})(X_t(u, v) - X_t(u, v+1))] + C \right\}, \quad (29)$$

where C represents all the terms that are independent of the parameters I and A. The calculation of the expectation of the log-likelihood, is base on the expectation of $X_t(u,v)$ given $Y_t$, I and A:

$$E[X_t(u, v) \mid Y_t, I, A] = \sum_{x_t(u,v)} X_t(u, v) P(X_t(u, v) \mid Y_t, I, A) \quad (30)$$

$$= \sum_{x_t(u,v)} X_t(u, v) \sum_{x_t(u)} P(X_t(u, v) \mid X_t(u), Y_t, I, A) P(X_t(u) \mid Y_t, I, A)$$

$$= \sum_{x_t(u)=0}^{Y_t} \sum_{x_t(u,v)=X_t(u)}^{\infty} X_t(u, v) P(X_t(u, v) \mid X_t(u), I, A) P((X_t(u) \mid Y_t, I, A)$$

$$= \sum_{x_t(u)=0}^{Y_t} P(X_t(u) \mid Y_t, I, A) E[X_t(u, v) \mid X_t(u), I, A]$$

Let $$\psi_t(u, v) = e^{-\sum_{w<v} \delta_t(u,w)A(w)}, \quad (31)$$

where the notation "w<v" is to be understood as the set of all the voxels preceding v on the line from u to t (recall that $\psi_t(u)$ was defined as $\exp[-\Sigma_w \delta_t(u,w)A(w)]$). To calculate the expectation of $P(X_t(u,v) \mid X_t(u), I, A)$, it is noted that:

$$P(X_t(u, v) \mid X_t(u), I, A) = \frac{P(X_t(u) \mid X_t(u, v), I, A) P(X_t(u, v) \mid I, A)}{P(X_t(u) \mid I, A)} \quad (32)$$

$$= \frac{Poisson(X_t(u, v) \mid \phi_t(u)\psi_t(u, v)I(u)) \; Binomial\left(X_t(u) \mid \frac{\psi_t(u)}{\psi_t(u,v)} X_t(u, v)\right)}{Poisson(X_t(u) \mid \phi_t(u)\psi_t(u)I(u))}$$

$$= Poisson(X_t(u, v) - X_t(u) \mid \phi_t(u)(\psi_t(u, v) - \psi_t(u))I(u))$$

meaning that $$E[X_t(u,v) - X_t(u) \mid X_t(u), I, A] = E[X_t(u,v) \mid I, A] - E[X_t(u) \mid I, A], \quad (33)$$

hence $$E[X_t(u, v) \mid X_t(u), I, A] = X_t(u) + E[X_t(u, v) - X_t(u) \mid I, A] \quad (34)$$

$$= X_t(u) + \phi_t(u)(\psi_t(u, v) - \psi_t(u))I(u).$$

The following expectations (E-Step) are thus obtained:

$$E[X_t(u, v) \mid Y, I, A] = \sum_{x_t(u)=0}^{Y_t} P(X_t(u) \mid Y_t, I, A) \quad (35)$$

$$\{X_t(u) + \phi_t(u)(\psi_t(u, v) - \psi_t(u))I(u)\}$$

$$= E[X_t(u) \mid Y_t, I, A] + \phi_t(u)(\psi_t(u, v) - \psi_t(u))I(u)$$

$$= y_t \frac{\phi_t(u)\psi_t(u)I(u)}{\sum_w \phi_t(w)\psi_t(w)I(w)} + \phi_t(u)[\psi_t(u, v) - \psi_t(u)]I(u)$$

To get the update I of I', the complete-data log-likelihood is maximize with respect to I' (M-step):

$$I(u) = \frac{1}{\sum_t \phi_t(u)} \sum_t E[X_t(u, u) \mid I', A, y] \quad (36)$$

$$= \frac{1}{\sum_t \phi_t(u)} \sum_t \left[ y_t \frac{\phi_t(u)\psi_t(u)I'(u)}{\sum_w \phi_t(w)\psi_t(w)I'(w)} + \phi_t(u)(1 - \psi_t(u))I'(u) \right]$$

The maximization with respect to the attenuations A(u) results in transcendental equations:

$$0 = \sum_t \sum_{u<v} \left[ \frac{E[X_t(u, v) \mid I', A, y] - E[X_t(u, v+1) \mid I', A, y]}{e^{\delta_t(u,v)A(v)} - 1} \delta_t(u, v) - \delta_t(u, v)E[X_t(u, v+1) \mid I', A, y] \right] \quad (37)$$

These equations can be solved using the approximation:

$$(38) \quad 1/(e^{\delta_t(u,v)A(v)} - 1) \approx 1/(\delta_t(u,v)A(v)) - 1/2.$$

With the observation that, typically, the product $\delta_t(u,v)A(v)$ is close to unity, one obtains:

$$A(v) = \frac{\sum_t \sum_u \phi_t(u) I(u) [\bar{x}_t(u, v) - \bar{x}_t(u, v+1)]}{\frac{1}{2} \sum_t \sum_u \phi_t(u) I(u) [\bar{x}_t(u, v) + \bar{x}_t(u, v+1)] \delta_t(u, v) I(u)}, \quad (39)$$

where (interpreting the relation "w<v" as before):

$$\bar{x}_t(u, v) = y_t \frac{\phi_t(u) \psi_t(u) I(u)}{\sum_w \phi_t(w) \psi_t(w) I(w)} + \phi_t(u) I(u) [\psi_t(u, v) - \psi_t(u)] \quad (40)$$

$$\psi_t(u, v) = e^{-\sum_{w<v} \delta_t(u,w) A(w)}.$$

As will be understood by one ordinarily skilled in the art, although the same notation, A, is used for the current value of the attenuation and the updated value thereof, no confusion can occur, as it is a common practice to interpret each of the above formulae as an assignment. Thus, for example, A(v) appearing in the LHS of Formula 39 represents an updated value, while A(w) appearing in the RHS of Formulae 40 represents a current value.

The following is a description of a method for calculating attenuation map using transmission data, in accordance with various exemplary embodiments of the invention.

For a single transmitting source, a transmitting voxel s, for which the intensity I(s) is known (with zero attenuation) is added. For all other voxels u≠s, the intensity I(u) is zero. The only non-zero expectations are therefore:

$$\bar{x}_t(s,u) = E[X_t(s,u)|A,y] = y_t + \phi_t(s)[\psi_t(s,u) - \omega_t(s)] I(s), \quad (41)$$

and the maximum likelihood updates of the attenuations are:

$$A(u) = \frac{\sum_t \phi_t(s) [\bar{x}_t(s, u) - \bar{x}_t(s, u+1)] I(s)}{\frac{1}{2} \sum_t \phi_t(s) [\bar{x}_t(s, u) + \bar{x}_t(s, u+1)] \delta_t(s, u) I(s)}. \quad (42)$$

In the "blank scan" case, where detection is made with no patient in the scanner, there is no attenuation and the function $B_t(s) = I(s) \phi_t(s)$ represents the expected counts measured by detector t. $B_t(s)$ can be measured using a (periodic) blank scan, scaled for the transmission scan, and used in the estimation of the attenuation coefficients, as follows:

$$A(u) = \frac{\sum_t B_t(s) [\bar{x}_t(s, u) - \bar{x}_t(s, u+1)]}{\frac{1}{2} \sum_t B_t(s) [\bar{x}_t(s, u) + \bar{x}_t(s, u+1)] \delta_t(s, u)} \quad (43)$$

where, $$\bar{x}_t(s,u) = y_t + B_t(s) [\omega_t(s,u) - \omega_t(s)] \quad (44)$$

When there is a set S of transmitting sources, a separate calibration scan can be performed for each source s∈S, so as to estimate $B_t(s)$ for every measurement t. The reason for separating the blank scans is that the counts in measurement t can potentially originate from different sources. This is because the transmission beams may overlap. Note also that the existence of different sources implies different intersections with the voxels, for any given measurement. In this case, an iterative procedure can be derived from Formula 39 as follows:

$$A(u) = \frac{\sum_t \sum_s B_t(s) [\bar{x}_t(s, u) - \bar{x}_t(s, u+1)]}{\frac{1}{2} \sum_t \sum_s B_t(s) [\bar{x}_t(s, u) + \bar{x}_t(s, u+1)] \delta_t(s, u)}, \quad (45)$$

where, $$\bar{x}_t(s, u) = y_t \frac{B_t(s) \psi_t(s)}{\sum_r B_t(r) \psi_t(r)} + B_t(s) [\psi_t(s, u) - \psi_t(s)]. \quad (46)$$

Diagnosis in a Multidimensional Space

There is also provided in accordance with an exemplary embodiment of the invention, a method of diagnosis, comprising:

measuring a plurality of patient parameters to determine a patient state; and identifying a disease state by matching the patient state using a plurality of said plurality of parameters. Optionally, said patient state comprises a dynamic patient state.

In an exemplary embodiment of the invention, said patient state includes kinetic information of at least one biochemical at a temporal resolution of better than 1 second.

There is also provided in accordance with an exemplary embodiment of the invention, a method of acquiring a patient profile, comprising:

providing at least one material to a patient;

scanning an interaction of said material with the patient at a rate of over once a second; and building a complex profile of the patient including one or more of a kinetic profile of a parameter related to said material and a plurality of concurrently measured patient parameters.

In an exemplary embodiment of the invention, said building comprises building based one a previous estimated kinetic profile of the material.

There is also provided in accordance with an exemplary embodiment of the invention, apparatus for carrying out the methods described herein, comprising circuitry for said building.

There is also provided in accordance with an exemplary embodiment of the invention, a method of selecting a material for diagnosis, comprising:

estimating a patient physiological state in the form of a complex profile;

selecting a desired differentiation of patient state; and selecting a material to have an interaction with the patient which provides said differentiation. Optionally, said material is associated with a complex profile which is matched to said patient profile for said selecting.

There is also provided in accordance with an exemplary embodiment of the invention, a database comprising at least 20 substances, each one with a complex substance profile. Optionally, the database comprises at least 50 substances. Optionally, the database comprises at least 150 substances.

An aspect of some embodiments of the invention relates to a complex substance profile. In an exemplary embodiment of the invention, the profile includes intra-body location and/or tissue specific behavior, for example, metabolism and/or uptake. Optionally, the profile is of a time dependent parameter, such as change in metabolic rate over time. Optionally, static parameters, such as "expected effect" are provided and/or determined. In an exemplary embodiment of the invention, the profile includes an interaction of a substance with multiple physiological parameters, for example, parameters measured using methods and apparatus as described herein. In some embodiments, the profile includes an interaction or an effect on the behavior of the substance due to a previous physiological condition or perturbation, for example, the provision of another substance.

In an exemplary embodiment of the invention, the profile includes information on the behavior of a substance in short time frames, for example, tens of seconds, seconds, or fractions of seconds.

An aspect of some embodiments of the invention relates to considering a physiological state of a patient as a complex of multiple physiological parameters. In an exemplary embodiment of the invention, diagnosing a patient comprises identifying a patient's state in an N-space of parameters, optionally in on a relatively continuous scale. Optionally diagnosis is carried out by selecting a material which when applied to the patient will be affected in a noticeable manner dependent on the state of the patient. In an exemplary embodiment of the invention, the scale used for at least 3, at least 5, at least 10 or more or intermediate numbers of dimensions has at least 5, at least 10, at least 20, at least 40 or intermediate or higher numbers of meaningful levels. This is in contrast to typical medicine where usually a small number of threshold values is provided. Optionally, if the patient state is simplified, the simplification misrepresents less than 30%, less than 20%, less than 10%, less than 1% or intermediate percentages of the space, the space being sampled at uniform intervals.

In an exemplary embodiment of the invention, the physiological state of the patient is perturbated, for example by providing a substance, and diagnosis is based, at least in part, on the reaction of the physiological state to the perturbation.

An aspect of some embodiments of the invention relates to acquiring kinetic pharmacological information relating to a substance. In an exemplary embodiment of the invention, a portion of the body is scanned at a rate high enough to acquire kinetic information about the substance, for example, uptake, metabolism and/or physiological effect. In an exemplary embodiment of the invention, the information collected comprises an indication of patient kinetics. In an exemplary embodiment of the invention, the information collected comprises an interaction between the kinetics of a plurality of substances.

In an exemplary embodiment of the invention, the scanning comprises scanning using florescent imaging of fluorescently tagged materials.

Figure 125:
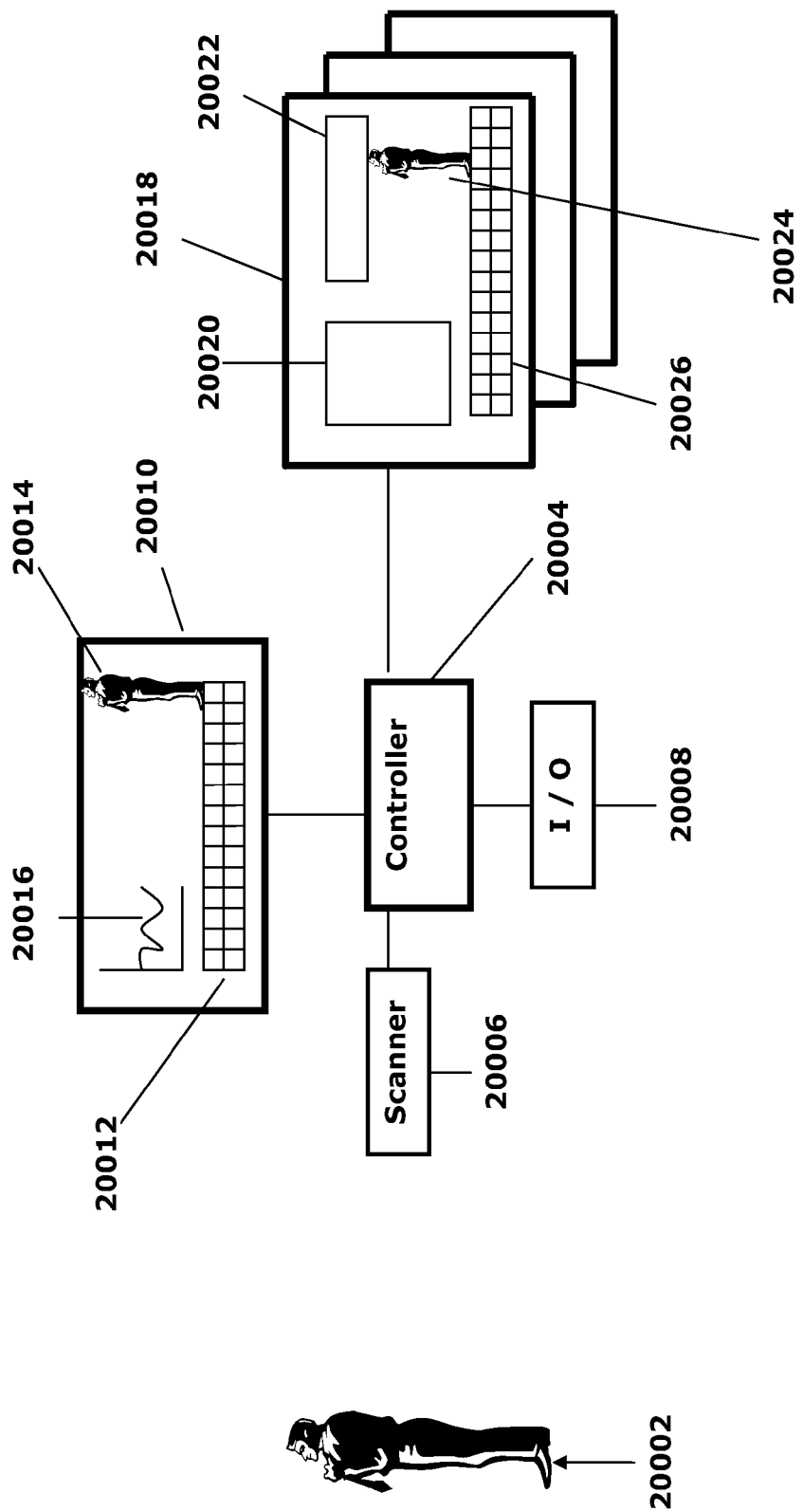
FIG. 125 is a schematic diagram of a configuration for acquiring and/or using multi-parametric information, in accordance with an exemplary embodiment of the invention.
Figure 126:
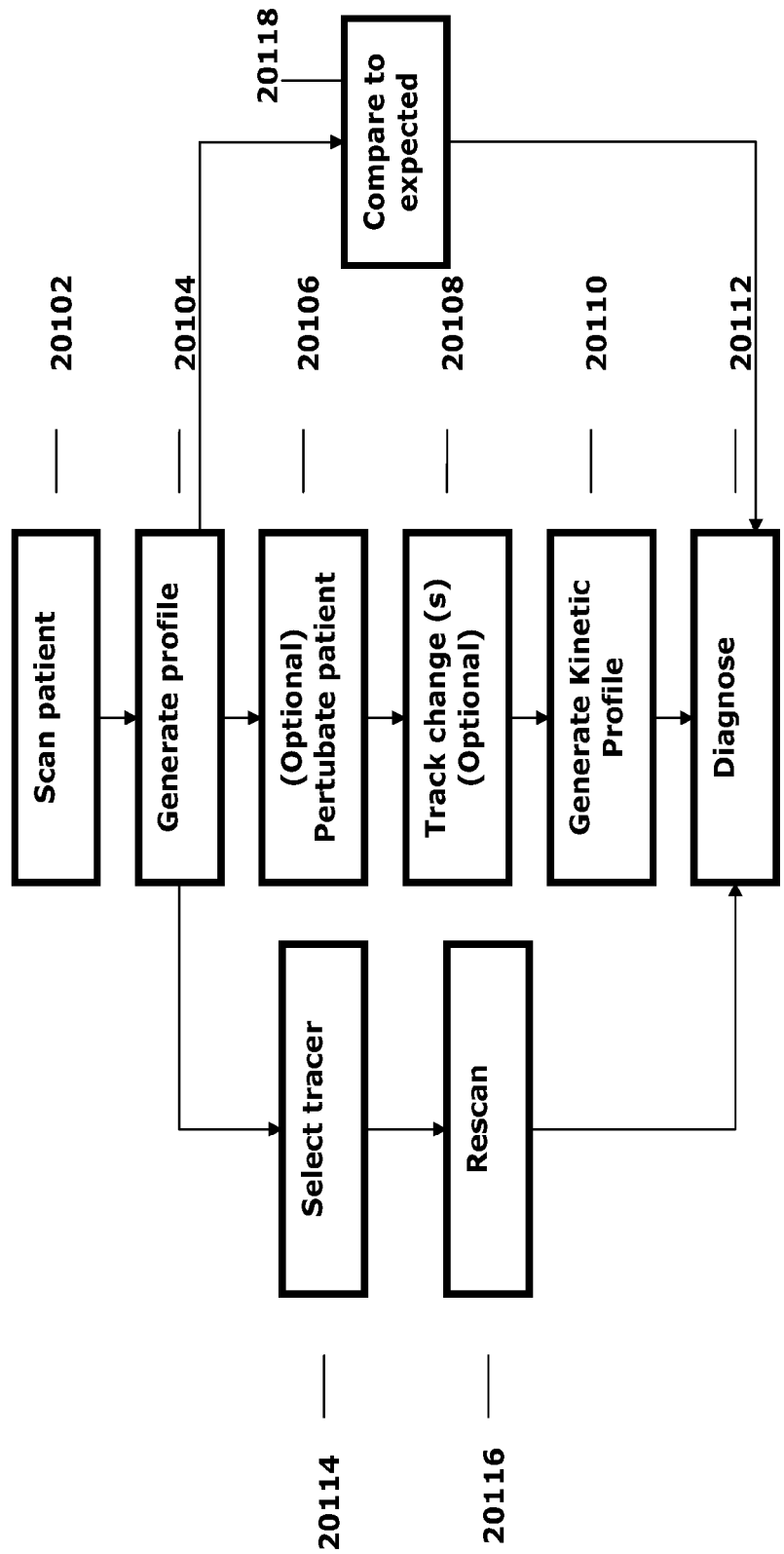
FIG. 126 is a flowchart of a method of acquiring and/or using multi-parametric information, in accordance with an exemplary embodiment of the invention.
Figure 127:
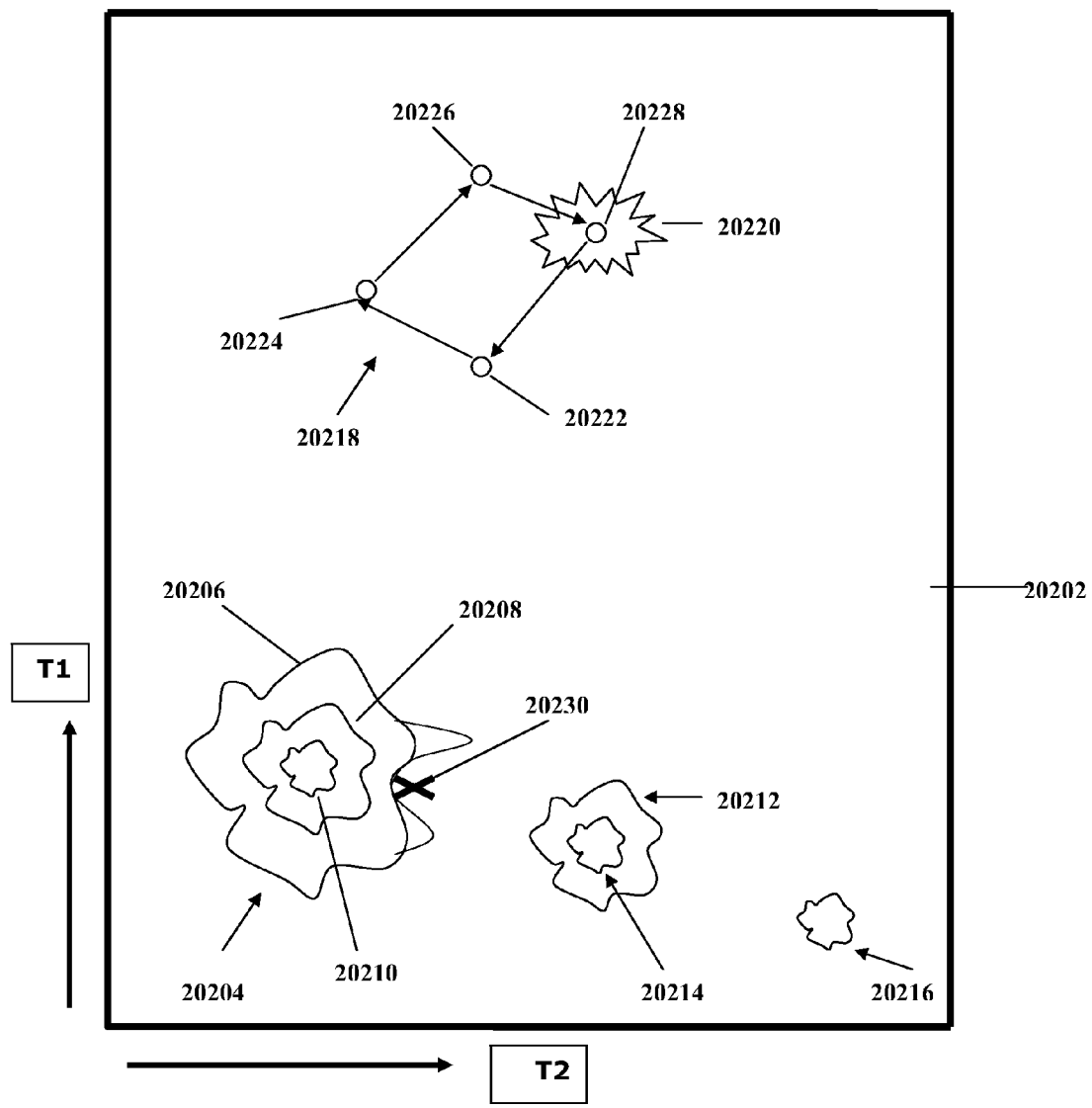
FIG. 127 is a simplified space indicating a diagnosis and a normal physiological state, in accordance with an exemplary embodiment of the invention.
Figure 128:
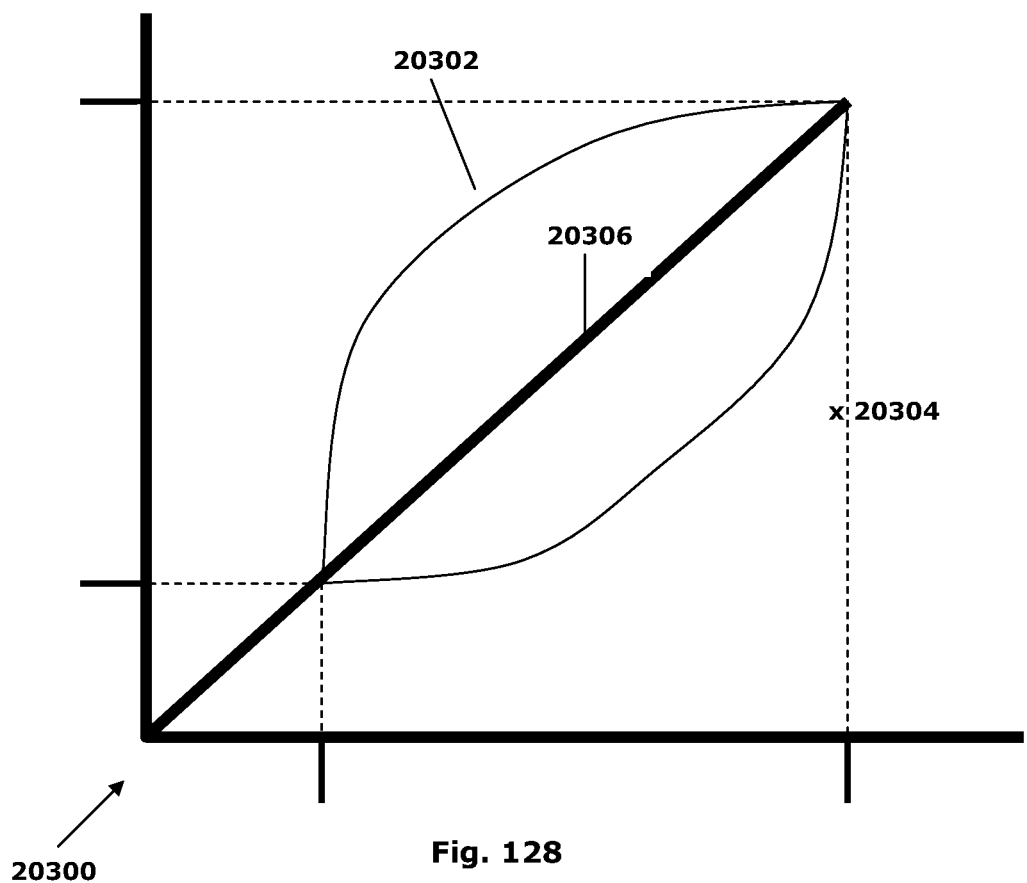
FIG. 128 shows a simplified two dimensional space showing a complex diagnosis, in accordance with an exemplary embodiment of the invention.

FIG. 125 is a schematic diagram of a configuration for acquiring and/or using multi-parametric information, in accordance with an exemplary embodiment of the invention;

FIG. 126 is a flowchart of a method of acquiring and/or using multi-parametric information, in accordance with an exemplary embodiment of the invention;

FIG. 127 is a simplified space indicating a diagnosis and a normal physiological state, in accordance with an exemplary embodiment of the invention;

FIG. 128 shows a simplified two dimensional space showing a complex diagnosis, in accordance with an exemplary embodiment of the invention.

Complex and/or Multi-Parameter Profiles

In the above section on an expert system, the use of some types of multi-parameter profiles has been described. In this section, inter alia, more general uses and/or profile types are described.

In an exemplary embodiment of the invention, the scanning system as described above is used to generate a complex profile of human physiology. Alternatively or additionally, a complex profile of substance is generated and/or used for diagnosis.

In an exemplary embodiment of the invention, the complex profile(s) includes pharmakinetic information at a relatively high temporal and/or tissue type resolution, for example, 10 seconds, 5 seconds, 1 second, 100 milliseconds, 50 milliseconds of faster or intermediate values. In an exemplary embodiment of the invention, the complex profiles are used to generate a diagnosis of patient state and/or define a suitable regime for treatment.

Exemplary Data System

FIG. 125 shows an exemplary configuration which may be useful for acquiring and/or using complex profiles, in accordance with some exemplary embodiments of the invention.

A scanner 20006, for example, as described above or any other type of fast scanner, for example a florescent imaging scanner that images fluorescently tagged materials or other scanners that image tagged materials or devices that track non-tagged materials, such as localized NMR (or other) spectroscopy or infra-red imaging, is used to acquire information about a patient 20002. Alternatively or additionally, genomic information, such as mRNA expression or protein expression is acquired, for example, using a gene chip. Alternatively or additionally to fast scanning, in some embodiments of the invention the scanning is relatively slow and/or maybe invasive, for example, blood tests, blood pressure and oxygenation measurement, mechanical measurements (e.g., ejection fraction) and/or any known physiological measurement. This information can include various physiological parameters of the patient and/or substances introduced therein, for example, substance concentration, metabolism, analyte levels, rates of change and/or fluid flow. Alternatively or additionally, the information comprises dynamic information, for example changes over time or changes in response to an action on the patient. Alternatively or additionally, the information comprises an association with particular body and/or tissue location information.

A controller 20004, optionally connected to scanner 20006, may be used to store, compare, analyze and/or otherwise use multi-parameter profiles and/or other complex profiles. Optionally, controller 20004 builds up a profile based on scanning results. A user input 20008, for example, a display and/or keyboard are optionally used to control controller 20004 and/or display results of controller 20004.

In an exemplary embodiment of the invention, the complex profile data is stored or organized in a tabular form, for example a multi-dimensional data table having, inter alia, some or all of the following dimensions:

(a) intrabody location, including, for example, tissue type and/or tissue location and/or including resolution level (e.g., cellular level, tissue level, organ level, body part level);

(b) diagnostic or body state definition;

(c) measured parameters, for example, biochemical concentrations (including blood analyte levels such as glucose and insulin) or aggregate measurements (e.g., blood pressure), which may include patient information, such as age and weight; and (d) state of patient, for example, at rest, standing, after mechanical stimulation and/or after administration of substance.

Coordinates (discrete or continuous) in the dimensions define cells which can include, for example, values of measured parameters, sets of parameters (e.g., a temporal series) and/or functional and/or statistical definitions of values and distributions.

This inter-relationship between various dimensions may be used to define a parameter space in which searching and/or other activities are carried on.

It should be appreciated that this data structure need not be stored as a table, even if its logical structure is that of a table. In particular, whole portions of the table may be blank (for lack of data and/or meaning), or be defined as a function or statistics. Alternatively or additionally, other data organization methods are used, which may use the above informational items as indexes of some type. In some cases, for at least some of the space, one or more dimensions and/or ranges of coordinates may be collapsed, for example, a range of states may be collapsed into a single meta-state. Such collapsing may also be carried out (e.g., temporarily) while viewing and/or analyzing the data.

It should be noted that a coordinate may include dynamic information, for example a series of absolute or relative changes over time, rather than a single value.

As will be described below, controller 20004 may relate to a patient complex profile 20010 (or more than one, for various situations). In an exemplary embodiment of the invention, complex profile 20010 includes a multi-parameter table 20012, at least one time dependent measurement 20016 and/or at least one location dependent parameter 20014.

As will be described below, controller 20004 may relate to one or more substance complex profiles 20018. In an exemplary embodiment of the invention, complex profile 20018 can include a multi-parameter table 20026, intrabody-location dependent information 20024, substance description 20020 and/or additional information 20022. Optionally, the complex profiles define, for at least some points in the space, a trajectory defining the interaction of the substance (or other stimulus) with a patient located in that point in space. Optionally, the complex profile includes temporal information indicating different interactions at different time delays. Optionally, the complex profile defines cumulative interactions and/or transient interactions of a substance.

In addition, for example as described below, controller 20004 may include or be associated with an additional database defining positive and/or negative areas in the space. While a "goodness" value may be associated with some or all points in space, optionally, a set of areas that are desired patient states are defined as boundaries of areas.

While this description suggests that the controller is located at the scanner and patient, this is not necessarily the case. For example, for diagnosis, a controller may be located at a doctor's office, receive measurements and generate a diagnosis. Any one of the data sources and/or controller may be provided locally and/or remotely, depending on the implementation. In some cases, a simplified database is stored locally and a more complete database and/or processing algorithm is remote. In an exemplary embodiment of the invention, the data comprises one or more of patient data, clinic data, hospital data, healthcare system data, country data and/or international data, which are optionally accesses in a hierarchical manner and/or as slices relating to the patient.

Exemplary Process

FIG. 126 is a flowchart of a process of acquiring and/or using complex profiles in accordance with an exemplary embodiment of the invention. It should be appreciated that some embodiments of the invention involve practicing only parts of this process.

At 20102, a patient is scanned, for example using methods described above and/or using other means, for example invasive and/or non-invasive sensors as known in the art. In an exemplary embodiment of the invention, the scanning measures multiple physiological parameters of the patient, optionally organ and/or tissue specific. In an exemplary embodiment of the invention, at least one of the measured parameters is a biochemical parameter sampled at a high rate, for example, faster than once in ten seconds or once a second. In an exemplary embodiment of the invention, the sampling is made fast enough to provide useful information on a substance having a pharmakinetic behavior at those time scales.

At 20104, a patient profile is optionally generated, for example, by determining coordinates for the patient state in the above space. Optionally, the profile generated for the patient includes an uncertainty factor, which may be represented, for example, by indicating a cloud in the space with the density of the cloud depending on the certainty level of the determination.

In an exemplary embodiment of the invention, the space comprises at least 5, at least 10, at least 20, at least 30 or a smaller, intermediate or larger number of body area and/or tissue types.

In an exemplary embodiment of the invention, the space includes at least 2, at least 4, at least 10, at least 40, at least 100 or a smaller, intermediate or greater number of measured physiological parameters.

In an exemplary embodiment of the invention, the space includes at least 3 at least 10, at least 30 or a greater, smaller or intermediate number of patient classification data, such as height, genomic markers, race and/or age.

In an exemplary embodiment of the invention, time frames for temporal data includes at least 5 data points, at least 10 data points, at least 20 data points or a smaller, intermediate or greater number of points.

In an exemplary embodiment of the invention, a profile comprises a trajectory in space and may include the above number of points for temporal data.

In an exemplary embodiment of the invention, a similar process is used to generate a profile of a substance, by measuring its dynamic behavior in the above space (e.g., after application to the patient). For example, for a body tissue type/location, and other physiological parameters, the values of metabolism or uptake (depending on the measurement method) can be indicated as values in space. In an exemplary embodiment of the invention, the values are measured as a time series for a particular cell in the space. Alternatively or additionally, the correlation between the values and changes in the body state are tracked, for example, a substance may change in measured values as heart rate goes up, wherein each heart rate corresponds to a different point/cell in space. The change in heart rate may be induced. Optionally, for different conditions, different profiles of the substances are achieved, which profiles can be combined into a single complex profile that includes the condition as a dimension (e.g., standing, sleeping, sitting).

FIG. 127 shows a simplified two dimensional space 20202 for illustrating the results of scanning in accordance with an exemplary embodiment of the invention.

An area 20204 indicates a normatively healthy state encompassing a range of sets of values for the two (in practice possibly more) parameters. Optionally, improved health states are indicated by sub areas 20208 (of an area 20206) and 20210. In some cases, a disjoint health area exists, for example an area 20212 with an optional increased health area 20214. Optionally, each point in space is associated with a value indicating "health" that is functionally based on the coordinates and/or on observations.

In an exemplary embodiment of the invention, a non-health state is defined as any point outside of the marked "health areas. Optionally, however, one or more particular dangerous or unacceptable states 20216 are defined as well. In an exemplary embodiment of the invention, a degree of unhealth is defined as a distance between a point in space and a healthy area. Optionally, different diagnoses are associated with different distances and/or relative positions. Alternatively or additionally, diagnoses are associated with trajectories in space. Alternatively or additionally, a composite score is provided. Alternatively or additionally, the score depends on estimated quality of life, pain and/or risk.

A reference 20218 indicates a trajectory of a patient state in space. A plurality of momentary states 20222, 20224, 20226 and 20228 indicate a measurement of the patient state. As can be seen, the patient varies between points, in the example shown in a repetitive manner. In some cases, the behavior of the trajectory is chaotic, for example, with one or more attractors. Optionally, the morphology, position and/or time values for the trajectory are used for diagnosis. It should be noted that also healthy states can be defined as trajectories and/or otherwise be dynamic. Parameter values (e.g., blood glucose levels used as coordinates in space) can also be defined as a single point which indicates a distribution of values, statistical properties, attractors and/or a trajectory between values.

It should be noted that the health values may be obtained in various means, including, for example, based on the patient's own parameters and/or based on normative values collected for a population.

Also shown in FIG. 127 is a point 20230 which is nearly encompassed by a healthy area but is not part of the healthy area. In an exemplary embodiment of the invention, the diagnosis of the patient relates directly to the N-dimensional space (e.g., 20202) and not to dimensions of the space in a piecewise manner. As more specifically shown in a graph 20300 of FIG. 128, it is possible for a point 20304 to be outside of a healthy area 20302, while still being within the range values of projections of the area into lower dimension spaces. In typical diagnosis situations, one of two approaches is normally taken, either processing parameters one at a time or collapsing multiple parameters into a single measure. A BMI (body mass index) is an example of a Xs composite measure which does not capture the intricacies of interaction between weight and height and completely ignores body form, metabolism, exercise level and other important parameters. Further, the "metabolic X syndrome" which is a composite of 5 (or so) measures, also simplifies the real space to avoid complexities. Further, in some cases there is a correlation between measured parameters. Typically, what is done is simply assume a fixed relationship 20306 and squander the information provided in area 20302. In a typical situation, relationship 20306 is realized as an area, for example, a rectangle and not a thin line.

In an exemplary embodiment of the invention, the use of a complex N-dimensional space (and optionally trajectories through space) and diagnosis based on simultaneous attention to multiple parameters enables such inclusions to be correctly identified. In an exemplary embodiment of the invention, the attention is given to at least 2, 3, 4, 5, 7, 10, 20, 50 or more or intermediate numbers of parameters.

In some embodiments, at least some of the dimensions are collapsed, at least for part of the diagnosis, for example, if there is missing measurement information or if the space is not populated with information.

In an exemplary embodiment of the invention, the acquired data is processed to help tease apart dependencies. Optionally, the processing indicates areas where two parameters are possibly less than perfectly correlated, which areas may benefit from additional measurement. While all the measurements are optionally acquired substantially simultaneously (e.g., in a time frame of less than 10 minutes, 1 minute, 10 seconds, 1 second or less), sequential acquisition may be practiced in some embodiments of the invention. In an exemplary embodiment of the invention, new disease states and/or types are defined based on identified points like point 20304 or based on trajectories.

In an exemplary embodiment of the invention, instead of providing a fixed diagnosis, for example "type II diabetes" the diagnosis relates to the actual degree of unhealth, for example, the distance (in some metric) from the nearest or a desirable normatively healthy area.

In an exemplary embodiment of the invention, the diagnosis takes into account not only the distance but also uncertainty factors, for example, uncertainties in measurements. A reference 20220 (FIG. 127) indicates a cloud of uncertainty relating to a measurement of point 20228.

Alternatively or additionally, the diagnosis takes into account the shape of the trajectory of the patient state (or monitored parameter value) and/or a spatial distribution and/or density of states and/or values (e.g., without tracking the ordinal relationship between points).

Referring back to FIG. 126, additional methods are contemplated. In one example, the patient is perturbated (20106), for example, by an impulse (e.g., a short exercise) or by a continuous activity (e.g., vasodilatation materials provision). In an exemplary embodiment of the invention, changes in patient state due to the perturbation and/or caused by the perturbation (e.g., to one or more measured parameters), are tracked (20108). It should be noted that the perturbation will generally cause a change in patient state. Optionally, the trajectory of the change and/or distribution of state points are used to fine tune a diagnosis (20112) of the patient. Alternatively or additionally, the perturbation is used to generate a more complex profile for the substance being tracked, for example by showing values for other conditions. Alternatively or additionally, the perturbation can provide a set of measurements which may reduce the uncertainty of measurement for a single patient state. Alternatively or additionally, the perturbation shows the stability of the patient in his physiological state and/or initiates a trajectory in space, either or both of which may be used as a means for diagnosis, for example by comparing against norms. Alternatively or additionally, the perturbation is used to generate a kinetic profile of the patient and/or a substance (20110).

In a particular example, perturbation comprises administering another substance. The measured values can include, for example, the interaction between the substances (e.g., effect of ability to measure), effect of one or both substances on the physiological state and/or values for one or both substances as the physiological state changes due to the other or both substances.

In another method, once a patient profile is known, a tracer material is selected (20114) so as to provide differentiation for what the profile shows in a later scan (20116). In particular, a tracer which will not be absorbed due to patient state need not be used. Similarly, the tracer is optionally selected and/or formulated so as to meet both data acquisition limitations and need to generate a measurable difference. Optionally, this selection is based on a profile associated with the material. Optionally, a database of materials and complex profiles is stored. In one example, if there is a problem that can be metabolic or absorption based, a tracer affected mainly by metabolism will be useless for absorption problems. Thus by first determining what the underlying problem is, a tracer and/or scanning protocol that will provide useful information on the metabolic (or absorption) problem, can be selected In another method, the patient is scanned with a material having a known complex profile. By comparing (20118) the actual results to anticipated results, a physiological model of the patient may be extracted and/or identified. In an exemplary embodiment of the invention, the model is found by searching the space of patient profile for a profile that acts in a manner similar to the observed manner. In another example, a mathematical model that links the measured parameters to the known profile and/or kinetics is generated and/or tuned.

It should be appreciated that the dimensions of the patient profile space and the material profile space need not match perfectly. Optionally, a mapping function between dimensions is provided by a user.

In an exemplary embodiment of the invention, diagnosis uses an expert system, for example a rule based system or a neural network. In lower-dimension cases, a visual method is optionally used.

In an exemplary embodiment of the invention, the patient profile space is used to store data about all patients and patient types. Optionally, the space is updated continuously as more data is acquired. Optionally, studies, as carried out, are combined into the space to populate empty spaces and/or reduce uncertainty in existing spaces. As new information about studies surfaces, the data may be reintegrated into the space. Optionally, when a patient profile and/or material profile are missing, these may be interpolated from existing data. Optionally, an expert (e.g., human) opinion is provided, for example, to suggest relevant data to be interpolated between and/or weights. In an exemplary embodiment of the invention, a user can input constraints that prevent a diagnosis from extending in the direction of certain coordinate values. Alternatively or additionally, such constrains can be used to guide a diagnosis process, including a step-by-step diagnosis process.

In an exemplary embodiment of the invention, health definitions are provided based on an asymptomatic population and/or time in a patient's life. Alternatively or additionally, health and/or unhealth areas are at least partially defined based on accepted allowed ranges and/or risk-indicating values.

Administrations of Multiple Isotopes

The present embodiments comprise an apparatus and a method for radiation-based imaging of a non-homogenous target area having regions of different material or tissue type or pathology. The imaging uses multi-dimensional data of the target area in order to distinguish the different regions. Typically the multi-dimensional data involves time as one of the dimensions. A radioactive marker has particular time-absorption characteristics which are specific for the different tissues, and the imaging device is programmed to constrain its imaging to a particular characteristic.

The result is not merely an image which concentrates in the tissue of interest but also, because it is constrained to the tissue of interest, is able to concentrate imaging resources on that tissue and thus produce a higher resolution image than the prior art systems which are completely tissue blind.

Figure 129:
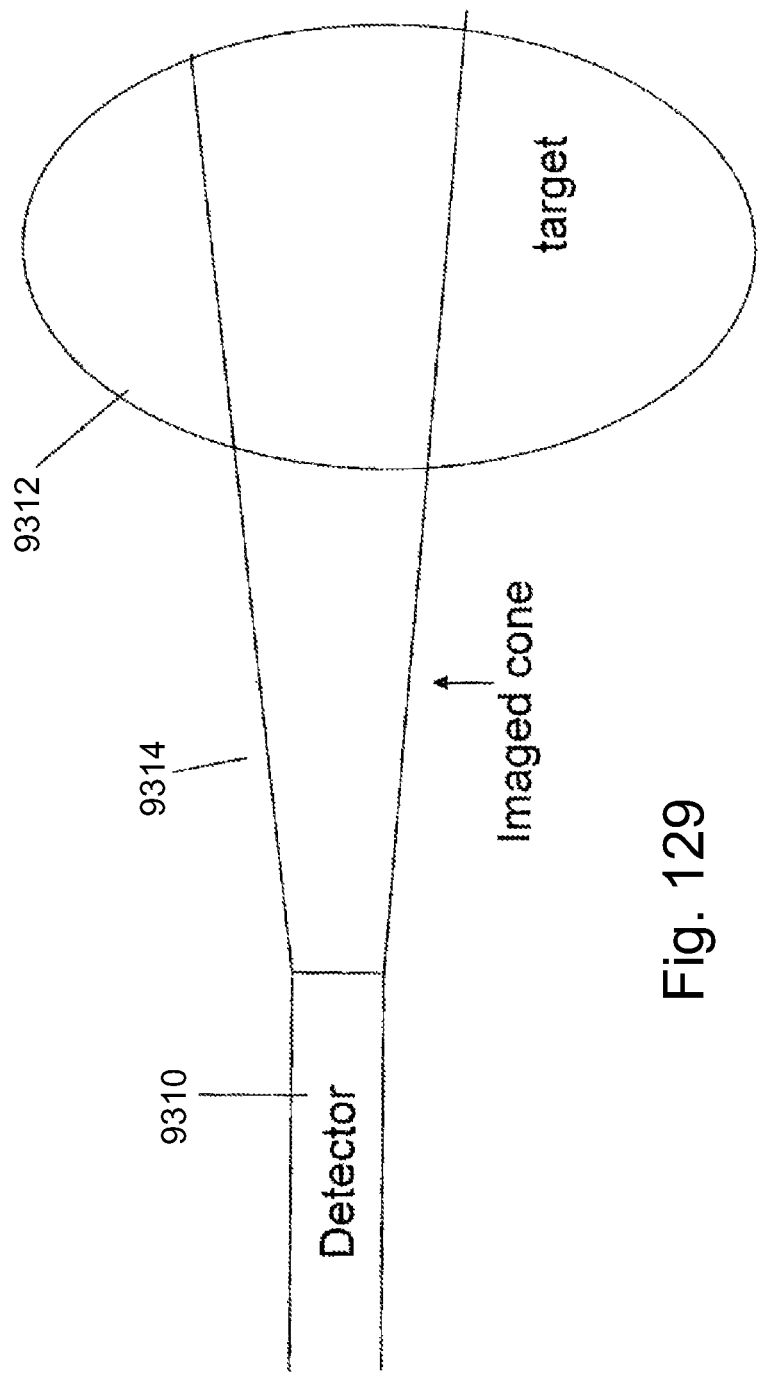

Reference is now made to FIG. 129, which illustrates a simple Geiger counter taking an image of a target according to the prior art. Geiger counter 9310 is placed in association with target 9312 and absorbs any radioactive particles that come its way. In general the radioactive particles arriving at the Geiger counter arrive from somewhere within cone 9314. Geiger counter 9310 has no information as to the depth from which the particle comes and cannot even distinguish between particles arriving from different directions within the cone. Thus in principle prior art Geiger counter 9310 gives low resolution one dimensional information.

If Geiger counter 9310 is now moved to different positions over the surface of the target then the data from the different positions can be built up into a low resolution two-dimensional image.

One way of increasing the resolution of Geiger counter 9310 is to make it smaller. Then cone 9314, whilst retaining the same geometry, gives higher resolution data.

A detector 9310 takes $(y_t)_{t=1}^T$, samples to form a data set, which would typically be a two-dimensional image of the target from a given direction.

Figure 130:
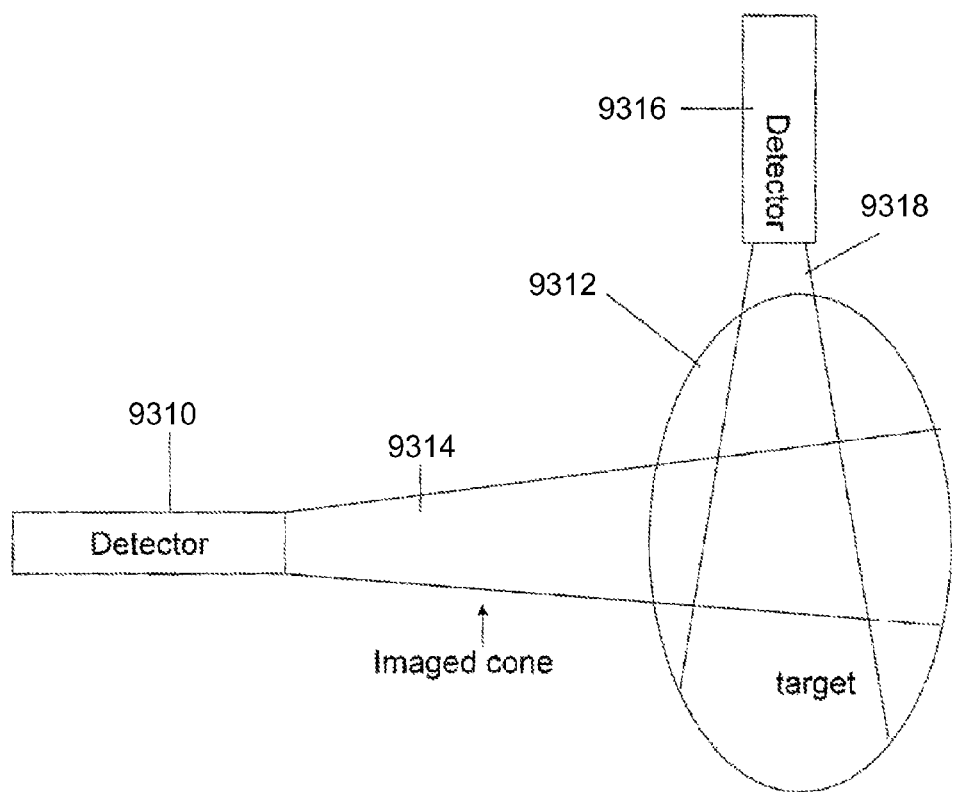

Reference is now made to FIG. 130, which is a simplified diagram showing how three-dimensional information can be obtained from a target 9312. Parts that are the same as in previous figures are given the same reference numerals and are not referred to again except as necessary for understanding the present embodiment. A second Geiger counter 9016 is placed essentially at right angles to first Geiger counter 9310 and obtains a similar kind of image to Geiger counter 9310. However, since the two cones overlap, the images produced can be cross-correlated to infer the presence of hot or cold radiation sources in three dimensions.

Reference is now made to FIG. 131, which is a sequence of graphs illustrating the different absorption characteristics for different tissues of a given radioactive marker. Typical markers that may be considered are thallium 201 and technetium 99. FIG. 131A indicates a typical absorption characteristic of thallium 201 for blood, thallium 201 being a particularly good marker for blood. The marker is generally absorbed by the blood fairly rapidly following digestion and then gradually disappears from circulation as it is taken up by the various tissues and organs including the kidneys. Marker material from the tissues eventually finds its way back into the blood for excretion. That which is absorbed by the kidneys is excreted directly and does not return to the circulation.

Figure 131A:
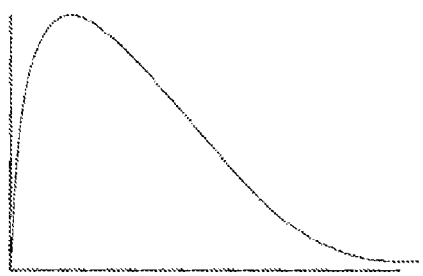
Figure 131B:
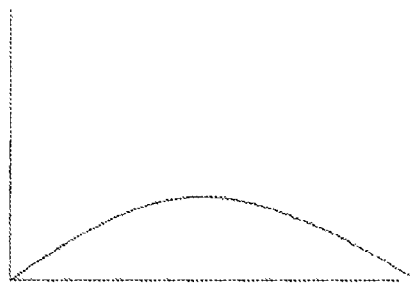
Figure 131C:
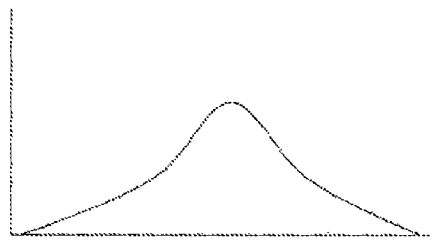
Figure 131D:
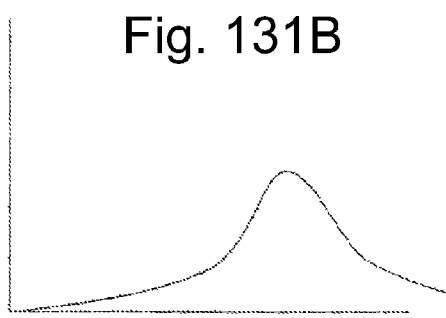

FIGS. 131B, 131C and 131D show time absorption characteristics for technetium 99 for different tissues, and it will be seen that the characteristic tracings are generally curved but peaks at different times for the different tissues.

The principle on which the present embodiments are based is as follows: Considering the graphs in FIG. 131, it will be apparent that a region belonging to a single tissue will behave in a uniform manner as regards signal intensity. That is to say, a given marker will be taken up and then expelled at the same rate from a given tissue, whereas this rate will be different for other tissues. If therefore a series of successive images are taken of the target and the images are analyzed region by region for rates of change of intensity, a particular desired region becomes identified by virtue of having rates of change in intensity that fit with a given characteristic. The regions are distinguishable in this way even if the region of interest is heavily overlapped with other regions.

Figure 132:
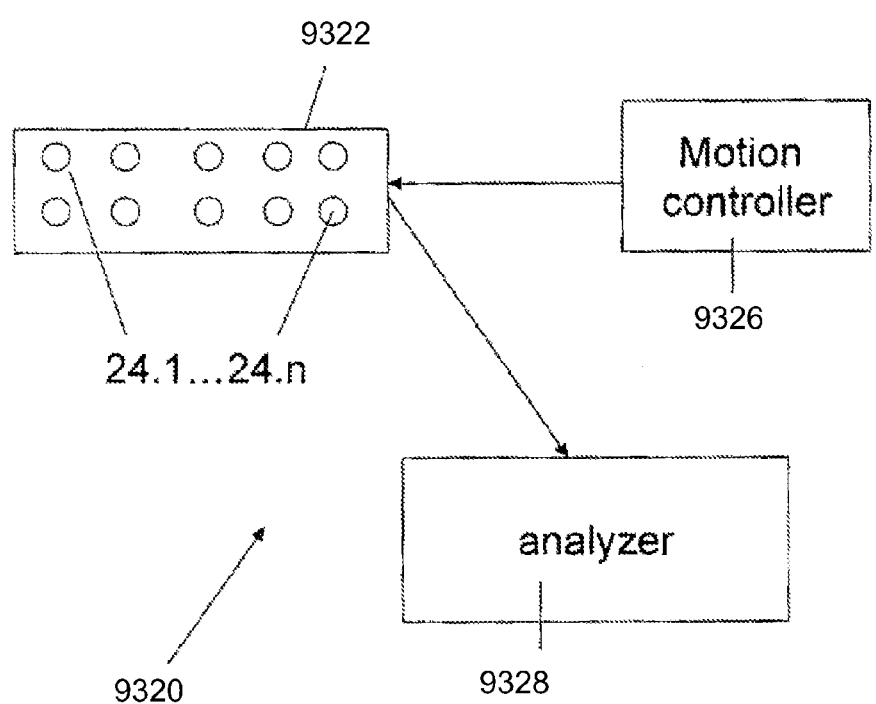

Reference is now made to FIG. 132, which shows apparatus for radiation-based imaging of a non-homogenous target area. Apparatus 9320 comprises an imaging unit 9322 which itself consists of a series of small Geiger counters 24.1 . . . 24.n arranged on an imaging head. The imaging unit is controlled by motion controller 9326 to take readings from different locations around the target area. Preferably, the motion of the imaging head is controlled by software via servo-motors. In addition the motions, either of the individual Geiger counters or of groupings of the Geiger counters, are also controlled by software via servo-motors.

In a preferred embodiment, the signals received from the individual Geiger counters are summed to form a three-dimensional image of the target area. The person skilled in the art will appreciate that the system could also be based on a two-dimensional image. In either case, the signals are fed to an image analyzer 9328, where the signals are analyzed to form images.

In the preferred embodiments, the image analyzer uses the marker uptake characteristics to compare successive images and identify regions of particular interest, and then to concentrate imaging resources on those regions. That is to say the image analyzer is in fact able to control further operation of the imager.

Figure 133:
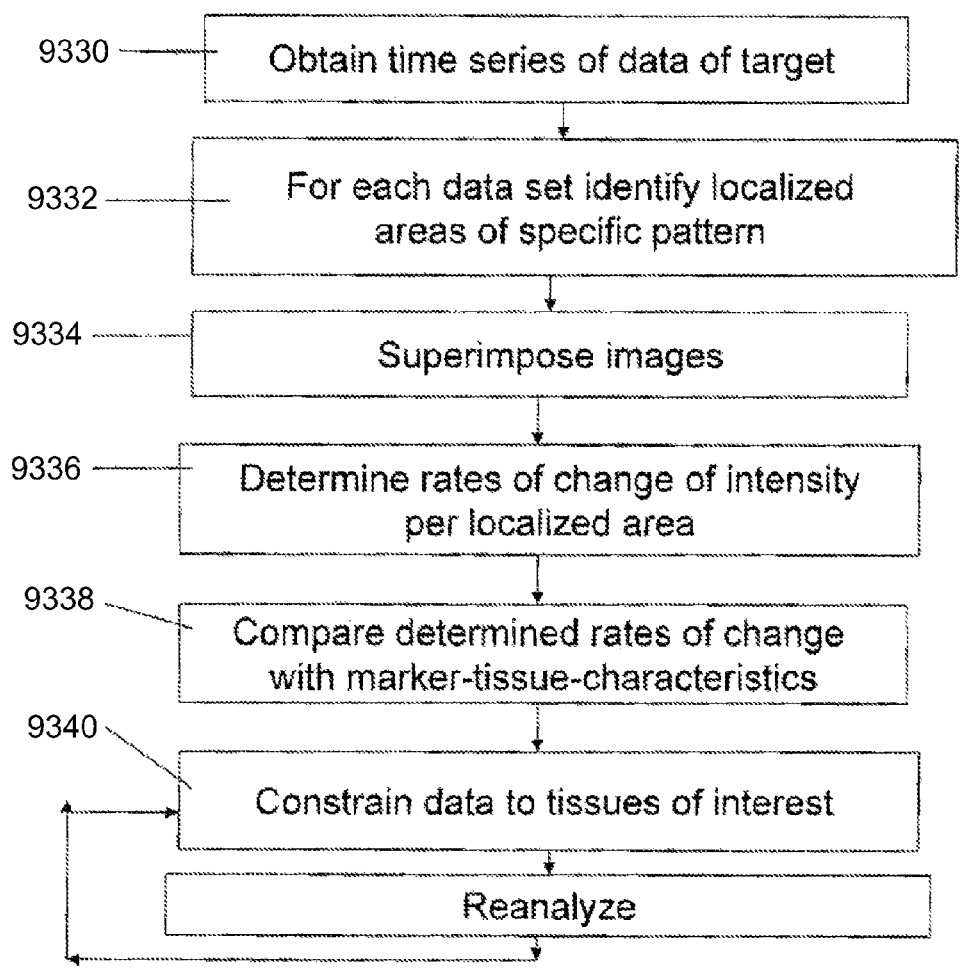

Reference is now made to FIG. 133, which a simplified flow chart illustrates the image analysis process that is carried out by analyzer 9328 in the case of a single marker. Preferably a series of images of the same views are taken at different times, stage 9330, and a three-dimensional overall image of the target is formed for each time. The analyzer then analyzes each of the three-dimensional overall images for local intensities at different locations around the target, stage 9332. The local intensities are noted and the same locations on the different images are superimposed in stage 34. From the superpositioning, local rates of change of intensity between the images may be obtained in stage 9336. The rates of change are compared with the pre-obtained characteristics for the marker with the different tissues in stage 9338, and the data are then constrained to those localities, which conform to the desired predetermined characteristics in stage 9340. As a result the imaging process can be used to identify and concentrate on localities of interest and data from other localities can be jettisoned. Consequently, the image analysis is able to concentrate its resources on the tissues of interest and a higher resolution final image can be produced.

It will be appreciated that in many cases two types of tissue may be superimposed, of which only one of the tissues is of interest. In this case it is of equal importance both to exclude the one tissue that is not of interest and to include the tissue that is of interest. It may be that the best marker for one tissue may not be the best marker for the other tissue. The system as described with respect to FIGS. 132 and 133 may be adapted to use with two or more markers, as will be explained, below, in relation to FIG. 134.

Each marker produces a radioactive particle of different energy level, and therefore the data from the different markers can be collected and summed separately to form different images. Mathematically the different data sets obtained from the different energy level signals may be treated as different dimensions of a multi-dimensional vector. For each of the marker-images the appropriate characteristics are used to identify the tissues of interest, and the results are cross-checked between the different markers. The different tissues are mapped and the image analysis can concentrate on the area of interest. As a result the system uses both time and particle energy as separate dimensions in addition to the spatial dimensions in order to characterize or map the tissues.

As a result the image analysis unit is able to produce a final result treating the various tissue regions as separate entities. Furthermore, as the system is aware of the regions as entities it is able to further direct the imaging process to concentrate on the regions of interest.

An example in which regions at least partially overlap is the heart. Generally, scans of the heart are interested in the muscular walls of the heart. Although the chambers of the heart are filled with blood, any signal coming from the blood is in fact noise to this kind of scan. It is therefore advantageous to carry out an imaging process that is able to positively identify signals from the muscular heart walls and at the same time exclude signals from the blood.

Referring now to FIG. 134, and in a preferred embodiment, the patient ingests two markers, thallium 201 and technetium 99. The first of these is an effective blood marker and two successive thallium images are shown in FIGS. 134A and 134B, and the second is more effective at marking muscle tissue and two successive images thereof are shown in FIGS. 134C and 134D. The heart is imaged at intervals chosen both for the characteristic for thallium 201 in blood and for the characteristic of technetium 99 in muscle. The result is a series of images for each of the markers. The series for thallium 201 may be constrained to show the regions of blood quite clearly, and to filter out other regions.

Figure 134A:
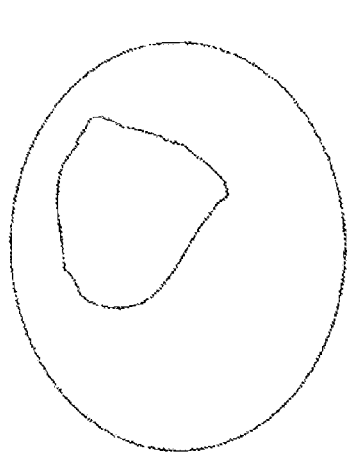
Figure 134B:
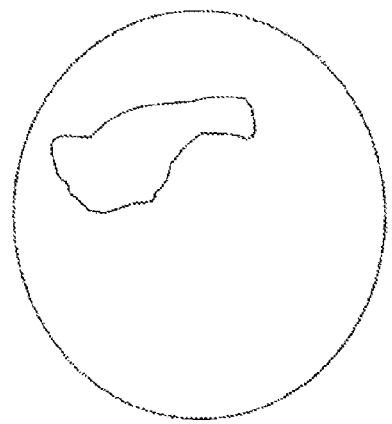
Figure 134C:
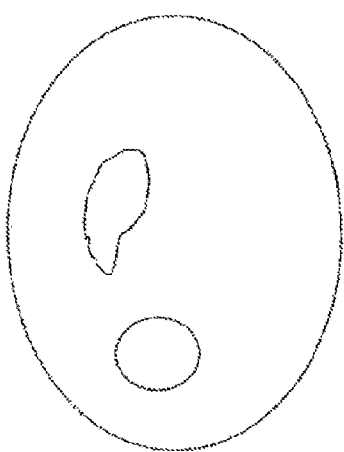
Figure 134D:
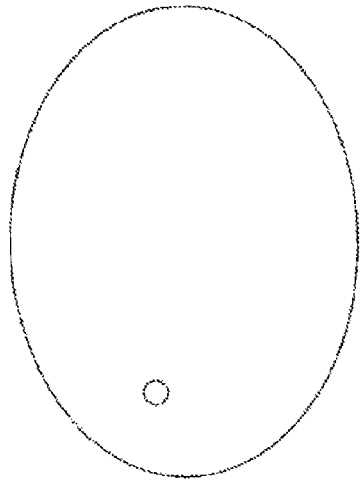

A blood vessel, on the left, is shown clearly in 6A and more faintly in 6B where the thallium has mostly been flushed out. The series for technetium 99, FIGS. 134C and 134D show muscle wall structures. 6A appears to show a larger structure on the right, but in fact all that it is showing is that much technetium has not yet been absorbed in the muscle. The second image 6D may therefore be used to constrain the first image 6C to show only the muscle walls regions. The two series of images may then be superimposed to filter out from the technetium 99 images 6C and 6D anything that appears strongly in the thallium images 6A and 6B. The filtering may additionally remove anything that appears strongly in both images and as coming from outside the region.

In the above example, two regions were of respectively positive and negative interest, meaning one for concentrating on and the other for filtering out. It will be appreciated that several regions or several tissue types may be of positive interest or there may be any combination of regions with just one being of positive interest. Alternatively all regions may be of positive interest but importance may be attached to discriminating between the different signals from the different regions.

The system is able to use the mapping to generate an image comprising the different tissue regions as distinct entities. As a consequence of the mapping process, the system is able to be aware electronically of the different regions and thus control both the imaging head and the analysis unit to concentrate their resources on specific regions. The result is greater resolution for the regions of interest.

The preferred embodiments may be used to expand the information obtained from the markers, using either or both of examining the kinetics of the markets over time and using several markers concurrently.

In order to increase the specificity of the test, additional second substances ("secondary substances"), with reactivity and pharmaco-kinetics differing from those of the first substance can be used in order to enhance the differentiation between the different pathologies, as explained above with respect to FIG. 134. The secondary substance, in this case thallium, ideally marks only a subset of the population marked by the primary substance and does so at different rates. Such a difference exists because of different affinity to various cell types and different participation in metabolic reactions of different tissues. The difference is associated with the rate of marking and/or with the location of the marking.

Upon reading the radioactive signals emanating from the voxels stemming from different substances at different time instances, it is possible to build for every voxel a multi dimensional data matrix $S_{jk}$ whose elements are intensity readings taken at instances K resulting from the interaction of Substance J. Examination of every voxel of tissue in this multi-dimensional space quantifies the temporal and specific reaction of the tissue to different substances and thus increases the probability of specific detection of different pathologies. Furthermore, standard image processing techniques can be used in order to more accurately define the spatial location of different pathologies.

In addition to the method above, spatial properties that reflect typical relationships between neighboring voxels may also be a criteria and represented as part of the pattern of the tissue type.

Figure 135A:
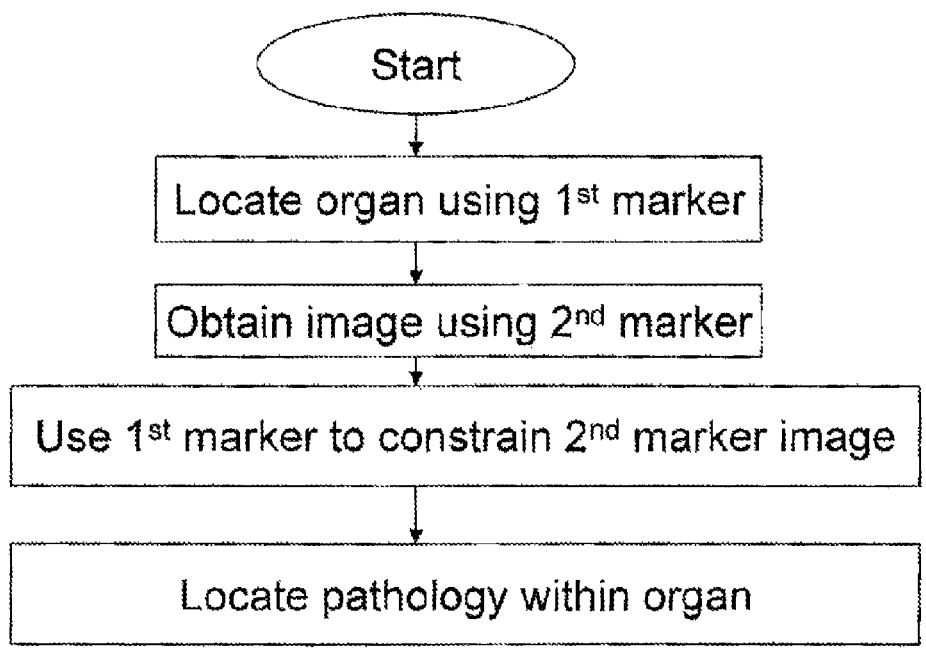
Figure 135B:
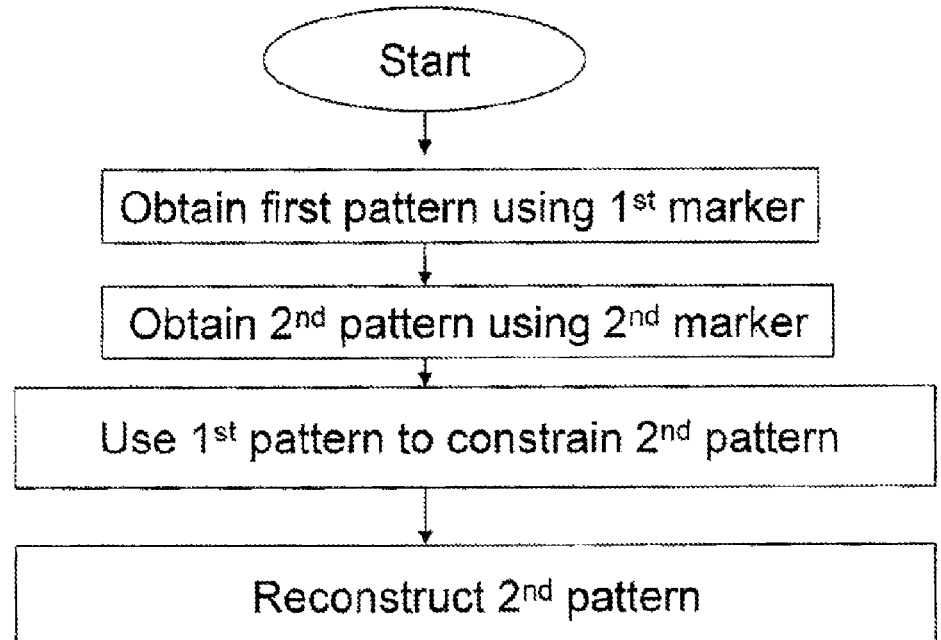

Reference is now made to FIG. 135, which illustrates an additional statistical approach. In FIG. 135, an automatic algorithm based on expected intensities may be used to determine if the entire organ or region is diseased or non-diseased. Once it is possible to become tissue-aware, as explained above, then it is no longer necessary to carry out such analysis on a voxel-by-voxel basis. Rather the system is able to determine where the organ lies say using a first marker and then a second marker may be imaged using the constraint of the organ location, the second marker being able to locate the presence of the pathology.

Figure 136:
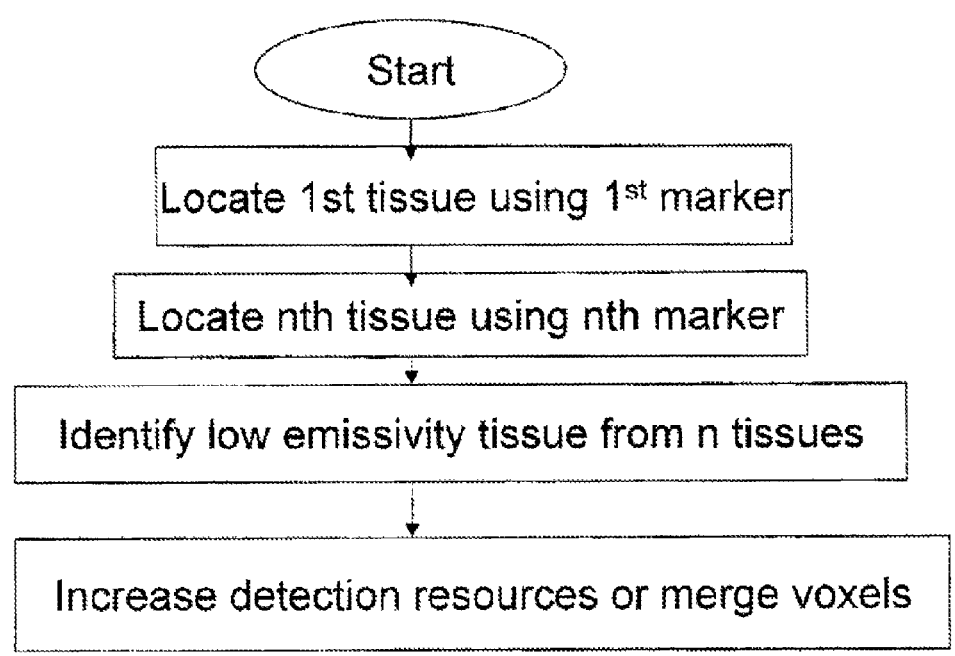
Figure 137A:
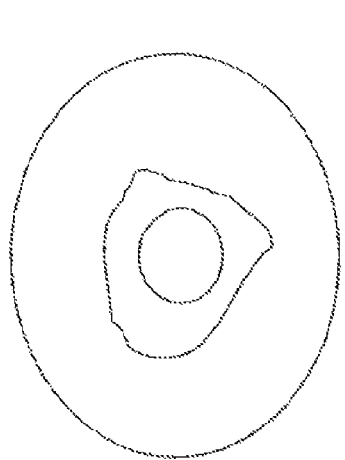
Figure 137C:
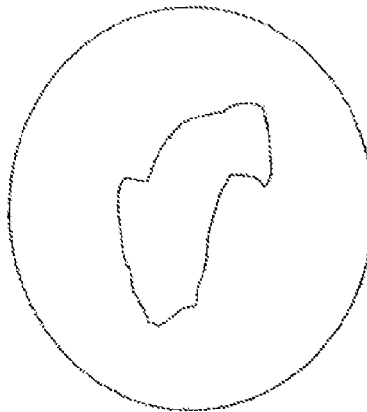
Figure 137B:
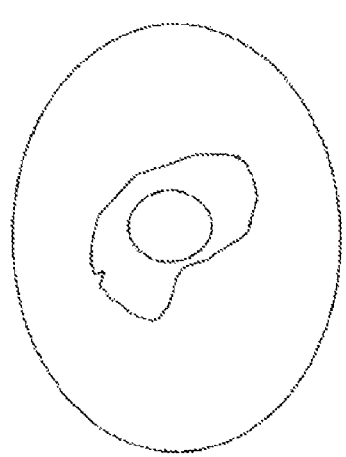
Figure 137D:
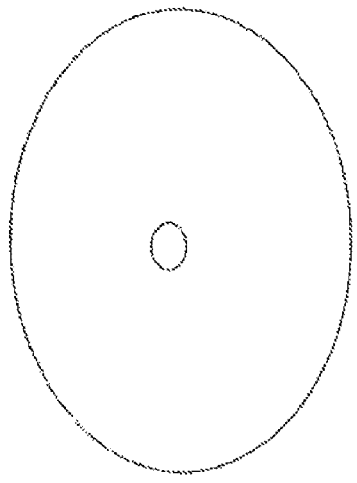

Reference is now made to FIG. 136 that illustrates a method for using the tissue aware properties of the present embodiments in order to tune detection to match tissue or organ emissivities. Generally, any region, no matter how much radiation it produces, can always be imaged sufficiently simply by leaving the measuring device in position for long enough. However, in many cases there may be limited time available. For such cases in which there is limited time for data acquisition, the present embodiments can be used to identify regions that may be expected to produce less emission. The system may then focus imaging resources or resolution onto those tissues according to the number of photons available. Clearly the more photons obtained the more reliable is the data, and therefore a tissue aware system is able to concentrate more detectors on the weaker signaling tissues.

If there are still not enough photons, or there are not enough detectors, then another way of pooling resources is to merge neighboring voxels (or regions). Such a procedure reduces resolution, but increases the overall number of photons for that merged region, and thus enable better classification of that region based on a more reliable photon count. Such a compromise enables analysis of the same collected data by ways that would allow high resolution where there are enough photons and lower resolutions where there are less photons, while maintaining reliability of the analysis.

Again the tissue regions may be identified using multiple markers.

The above-described embodiment may lead to controlled sensitivity levels, currently not available with radioimaging.

The concept of using multiple antibodies can be used for therapy purposes, as in the following:

The specificity of a single antibody carrying a drug (or radioactive therapy) determines the chance for non-target tissue to receive the drug, and thus be subject to any toxicity of the drug. In cases where there are several antibodies, each with limited specificity, but with affinity to different 'background' tissue, a combination of antibodies may be used to improve the overall specificity, and thus to reduce overall toxicity and enable higher efficacy of treatment.

For example, a first antibody (A1) attached to a drug has an affinity (N1) to a first fold on a target tissue and a secondary affinity (B1) for a secondary non-target tissue. A second antibody (A2) attached to a similar drug has an affinity (N2) to a second fold on the target tissue and an affinity (B2) for a different (tertiary) non-target tissue. Using a therapy combining A1 and A2 enables better target vs. non-target specificity in which N1 and N2 both express affinities for the target tissue while B1 and B2 are dispersed between secondary and tertiary tissues.

In a more generalized embodiment, the system may include a signal analysis module, including a library of patterns that are typical for every cell type. Each type of cell has one or more patterns associated with it; the pattern determining how a set of markers, injected according to a specific protocol (dosage, time, etc), is expressed in that cell type. The analysis includes classification of the readings from each voxel based on correlation, or other statistical tools for assessing the most probable tissue classification for each voxel.

Since there may be several cell types for a given disease (e.g. cancer may have several forms), the algorithm may be optimized to determine the exact tissue type per voxel or region. Alternatively, the algorithm may be optimized to determine the general property of diseased/non-diseased, while taking the specific classification only as a factor in the statistical analysis.

It should be noted that the system may allow for various protocols for administering the markers, where injection of the various markets is simultaneous, or at multiple times, for example based upon the different lifetime in the circulation.

The issue of generating imaging using two or more markers is now considered mathematically.

An intensity distribution I, conventionally defined in terms of radioactive emissions per seconds, is now redefined as a vector of distributions over the volume U, forming and input space. Each dimension of the vector is distributions are different in each of the radiopharmaceuticals. The universal set U comprises a set of basic elements u (e.g., pixels in two dimensional spaces, voxels in three dimensional spaces), and I(u) is the intensity in a given basic element u∈U. For j radiopharmaceuticals this becomes $I(u)^{(j,t)}$ An inverse (or reconstruction) problem arises when one cannot sample directly from l, but can sample from a given set of views $\Phi$. A projection $\phi \in \Phi$ is defined by the set of probabilities $\{\phi(u):u \in U\}$, where $\phi(u)$ is the probability of detecting a radioactive emission from a basic element (pixel or voxel) u.

Projection $\phi \in \Phi$ is further defined by viewing parameters, such as the physical and geometrical properties of the detecting unit, attenuation parameters of the viewed volume U, and time parameters. Choosing a view $\phi \in \Phi$, and then sampling according to the parameters of views $\Phi$, yields an optimal measurement.

For j radiopharmaceuticals or markers and k detectors, the probability of seeing a particle becomes $\phi_j^k(u)$ In the following analysis, I is the intensity of a radioactive substance, and the viewing parameters include the geometrical properties of a collimated detecting unit and the detecting unit's position and orientation with respect to volume U. The number of radioactive emissions counted by the detecting unit within a time interval is a Poisson distribution, where $\phi(u)$ is the detection probability of a photon emitted from voxel u∈U and the mean of the distribution is the weighted sum $\Sigma_{u \in U} \phi(u) I(u)$.

For the case of the kth detector a measurement $Y_k = \Sigma_{u \in U} X_t(U)$, where X(U) is a Poisson distribution.

$$X_{(j,k,t)}(u) = I^{(j,t)}(u) \cdot \phi(u)_j^k(u).$$

Where $Y_{(j,k,t)} = \Sigma X_{(j,k,t)}(u)$.

Hence $Y_{(j,k,t)} = Poisson(Y_{(j,k,t)})$

The projection set is thus defined by a matrix $\Phi$, whose rows are the projections of the chosen views. I is a vector of densities (specified per each element in U), and $\Phi$I is a vector of respective effective intensity levels for the views in the set. A vector of measurements y is obtained by a random sample from each view (according to the associated Poisson distribution). As discussed above, there are various known reconstruction methods that provide estimators for I given the projections Φ and the measurements y.

Using the above mathematics the problem is solved (an image created) for a first vector say once an hour. The rates of change are determined. Simultaneously the problem is solved for another a second vector at similar time intervals and the new rates of change are determined. Then a stage of cross-identification is carried out between the two images, so that wanted tissues, as identified by each image minus unwanted tissues identified on each image, are concentrated, forming form a new image. Cross-identification may be an iterative process.

In the example given above of the imaging of the heart using one blood marker and one muscular tissue marker, the areas identified by the blood marker are subtracted. The areas identified by the muscle marker are added, and those tissues not identified by either are likewise ignored as being signals from outside the target region.

The non-homogenous target area is typically a region of living tissue, generally belonging to a patient. The distinguishable regions within can be different tissues, different organs, a mixture of blood and organ tissue as with the above example of the heart, or tissue regions exhibiting differential pathologies.

An alternative to the above described approaches for imaging using two or more radiopharmaceuticals can be realized if one is able to distinguish between emissions of two or more radiopharmaceuticals by using low doses of the radiopharmaceuticals which do not cause spectral interference or masking (e.g. interference caused by Compton scattering). For example, 20 mCi of Tc-99m produces numerous photons in the tissue (due to Compton) that fall within the spectral line of Thallium (1-4 mCi). Reducing the Tc-99m dose to 2 or less mCi, results in minimal interference with Thallium, and enables simultaneous imaging of the two isotopes.

Use of novel low doses of Radiopharmaceuticals, typically Radiopharmaceuticals which result in less than 2.5 mrem EDE per Kg body weight (e.g., less than 2 mCi of Tc-99m) is enabled through the use of more sensitive emission detectors such as those described I, PCT/IL2005/000394, PCT/IL2005/000572, PCT/IL2005/000575, PCT/IL2005/000394 and PCT/IL2005/000048, hereby included in their entirety by reference.

Table 5 below provides typical prior art doses and novel low doses of radiopharmaceuticals that are effectively imaged using the emission detection systems described in the above referenced PCT applications. Table 5A shows the information provided in Table 5 in limited form, showing the radiopharmaceutical and prior art dosage only.

TABLE 5A

Radiopharmaceuticals and prior art dosages

| Radiopharmaceutical | Prior art dose in mCi (range) |
| --- | --- |
| Positron Emission Isotopes | |
| ISOTOPE/Half-Life Time | |
| Ammonia N 13 | 9.96 min 20 |
| Fludeoxyglucose F-18 | 110 min 10 |
| Protein/peptide/antibody + Isotopes | |
| Indium-111 Capromab pendetide (ProstaScint) | 5 |
| Indium In-111 WBCs (non-protein, peptide) | 0.5 |
| Indium In-111 Satumomab Pendetide (OncoScint) | 5 |
| Technetium Tc 99m Arcitumomab (CEA-Scan) | 20-30 |
| Technetium Tc 99m Fanolesomab (Neutrospec) | 75-25 mcg of Fanolesomab is labeled with10-20 mCi |
| Non-peptide/protein based isotopes | |
| Cyanocobalamin Co 57 | 0.001 |
| Gallium Citrate Ga 67 | 5 10 for SPECT |
| Indium In 111 Pentetreotide | 6 |
| Krypton Kr 81m | 10 (as a gas, USED FOR DYNAMIC IMAGING) |
| Iodide 125 Albumin | 0.02 |
| SodiumChromate Cr 51 | 0.15 0.1-0.3 |
| Sodium Iodide I 123 | 0.4, (also 0.1-0.2 as capsules) |
| Sodium Iodide I 131 | 0.004-0.01 |
| (Sodium) Pertechnetate Tc 99m | 10 100-200 micro for eye imaging (1 drop per eye) 1 mCi for cyctogram |
| Technetium Tc 99m Albumin Aggregated | 1-4 2 mCi in each leg |
| Technetium Tc 99m Albumin Colloid | |
| Technetium Tc 99m Erythrocytes (RBCs) | 10-20 20-25 for liver perfusion & SPECT |
| Technetium Tc 99m Depreotide (NeoTect) | 20 |
| Technetium Tc 99m Apcitide (AcuTect) | 20 |
| TechnetiumTc 99m Bicisate (ECD, Neurolite) | 20 |
| Technetium Tc 99m DMSA Dimercaptosuccinic acid (Succimer) | 2-6 (typically 5) |
| Technetium Tc 99m Disofenin (HIDA) | 5 |
| TechnetiumTc 99m Exametazime (HMPAO) | 20 |
| Technetium Tc 99m Mebrofenin | 5 mCi (non-jaundiced) 8 mCi (jaundiced) |
| TechnetiumTc 99m Medronate (MDP) | 20 15 |
| Technetium Tc 99m Mertiatide (MAG3) | 5-10 |
| Chromic Phosphate | 4 |
| SR 89 Chloride (Metastron) | 4 (this is for palliative treatment) |
| Technetium Tc 99m Pentetate (DTPA) | 3-5 (for GFR), 10-20 (for brain, renal perfusion) |
| TechnetiumTc 99m Pyrophosphate | 15 20 for muscle necrosis |
| Technetium Tc 99m Sestamibi (Cardiolite, Miraluma - for breast imaging) | 10-30 (typically 10 for rest and 30 for stress) |
| Technetium Tc 99m Tetrofosmin (MyoView) | 5-33 (typical 8-20) |
| Technetium Tc 99m HDP | 20-25 < 30 years 25-30.30 yrs & obese |

TABLE 5A-continued

Radiopharmaceuticals and prior art dosages

| Radiopharmaceutical | Prior art dose in mCi (range) |
|---|---|
| Technetium Tc 99m Sulpher colloid | 12 mCi/70 kg |
| Thallous Chloride Tl 201 | 0.055 mCi/kg |
| Xenon Xe 127 | 5-10 |
| Xenon Xe 133 | 5-10 |

Use of radiopharmaceutical cocktails yields generations of new products (premixed radiopharmaceutical pairs) and diagnostic procedures that enable multi-dimensional, differential diagnosis and use of one diagnostic procedure for revealing any pathology. Radiopharmaceutical cocktails also require significantly lower radiopharmaceutical dosage and results in several-fold increase in sensitivity as well as a 90% procedure time reduction and significant improvement in spatial and spectral resolution.

Radiopharmaceutical combinations are exemplified in a liver-spleen scan using +RBC+gallium (for cases of liver SOL/hemangioma/abscess/hepatoma). Bone scan+gallium or bone scan+In-WBC (for osteomyelitis). Perfusion rest/stress+MIBG for autonomic system in heart, mapping+BMIPP for heart failure with the addition of FDG for viability.

Assessment of the sentinel lymph node of tumors via Lymphoscintigraphy, (melanoma, breast, etc) with addition of FDG (and optionally MIBI) to assess the presence of tumor in these nodes (typically effected by peri-tumoral injection for lymphoscintigraphy and IV FDG). FIG. 139 provides a table that further exemplifies nuclear scans which can benefit from use of radiopharmaceutical cocktails and simultaneous imaging.

Although low doses are preferred for the reasons set forth hereinabove, higher doses can also be utilized in combinations provided one can effectively isolate the signal resultant from each radiopharmaceutical.

One approach for signal isolation is detailed below. We denote the intensity density of isotope i in voxel u by $I^i(u)$. Detector t, detects $y_{tb}$ photons at energy bin b, detector t comprising a composite of a collimator and a radiation sensor such as CZT, placed at some location. In an actual system, a physical detector that takes snap shots from several locations is regarded as different detectors for the purpose of the following derivations.

We denote by $\phi_{tb}^i(u)$ the probability of a photon emitted from isotope i in voxel it, to be detected by detector t at energy bin b. This probability is determined by the geometrical and physical properties of the detector, its position, orientation, and the reduction of the energy of the photon emitted from isotope I, to the measured energy b. We will refer to $\phi_{tb}^i(u)$ as the functional in the following derivations. The functional can be either, analytically calculated via geometry together with applying the Compton Effect for scattering, measured via experiment, or partly calculated and tuned via experiment.\

The change of angle θ of a photon emitted at energy $E_0$, and scattered to energy E is given by:

$$E(E_0, \theta) = E_0 \left[ \frac{m_e c^2}{m_e c^2 + E_0(1-\cos(\theta))} \right] \Leftrightarrow \cos(\theta) = 1 - \left(\frac{1}{E} - \frac{1}{E_0}\right) m_e c^2,$$

Where $m_e$ represents the rest mass of the electron, and c is the speed of light in a vacuum.

The random count $X_{tb}^i(u)$ of photons that are emitted from voxel u and detected in measurement tb (detector t at energy bin b), is modeled by a Poisson process with mean $\Sigma_i \phi_{tb}^i(u) I^i(u)$. The total count of photons detected in measurement tb is $Y_{tb} = \Sigma_u X_{tb}(u)$, and the problem is to reconstruct the intensities $I^i(u)$ from the measurements $y_{tb}$.

Simultaneous Submission of Multiple Isotopes

The measurements have a Poisson distribution $y_{tb} \sim \text{Poiss}(\Sigma_i \Sigma_u \phi_{tb}^i(u) I^i(u))$.

The log-likelihood is given by:

$$L(y/I^1, I^2, \ldots) = \sum_{tb} \ln \text{Poiss}\left(y_{tb} \Big/ \sum_i \sum_u \phi_{tb}^i(u) I^i(u)\right) = \sum_{tb} \left\{ -\sum_i \sum_u \phi_{tb}^i(u) I^i(u) + y_{tb} \ln\left[\sum_i \sum_u \phi_{tb}^i(u) I^i(u)\right] - \ln(y_{tb}!) \right\}$$

The maximum likelihood is the solution of set of non-linear equations:

$$\sum_{tb} \sum_u \phi_{tb}^i(u) = \sum_{tb} \frac{\phi_{tb}^i y_{tb}}{\hat{y}_{tb}}, \text{ for all } i$$

where $\hat{y}_{tb} \equiv \sum_i \sum_u \phi_{tb}^i(u) I^i(u)$.

The solution may be solved via the EM approach:

$X_{tb}^i(u) \sim \text{Poiss}(\phi_{tb}^i(u) I^i(u))$.

The likelihood of the complete data:

$\ln P(x/I^1, I^2, \ldots) = \Sigma_{tb} \Sigma_i \Sigma_u \{-\phi_{tb}^i(u) I^i(u) + x_{tb}^i(u) \ln [\phi_{tb}^i(u) I^i(u)] - \ln(x_{tb}^i(u)!)\}$ The EM based algorithm:

$$I^i(u) = \frac{1}{\sum_{tb} \phi_{tb}^i(u)} \sum_{tb} \frac{y_{tb}}{\hat{y}_{tb}} \phi_{tb}^i(u) I^i(u), \text{ for all } i$$

where $\hat{y}_{tb} \equiv \sum_i \sum_u \phi_{tb}^i(u) I^i(u)$.

This is the basis for faster Ordered set based algorithms.

Two Separate Submissions of Two Isotopes—Two Step Estimation

We first submit isotope i=1, and scan. We estimate its density distribution $I^1(u)$ using an EM based algorithm. Then we submit isotope i=2, while i=1 is still distributed in the volume. To estimate $I^2(u)$ given the estimated $\hat{I}^1(u)$:

$$I^2(u) = \frac{1}{\sum_{tb} \phi_{tb}^2(u)} \sum_{tb} \frac{y_{tb}}{\hat{y}_{tb}} \phi_{tb}^2(u) I^2(u), \text{ for all } i = 2$$

where $\hat{y}_{tb} \equiv \sum_u \phi_{tb}^2(u) I^2(u) + \sum_u \phi_{tb}^1(u) \hat{I}^1(u)$.

Extension to multiple submissions is straightforward.

2 separate submissions two Isotopes—combined estimation

We first submit isotope i=1, and scan. We denote the measurements of the first scan by $y_{tb}^{(1)}$.

We then submit isotope i=2, and scan. In this scan the two isotopes are distributed. We denote the measurements of the first scan by $y_{tb}^{(2)}$.

We wish to estimate both distributions $I^1(u)$ and $I^2(u)$ using the measurements from both scans $y_{tb}^{(1)}$ and $y_{tb}^{(2)}$.

We discriminate between the functionals of the first scan $\phi_{tb}^{1(1)}$, and those of the second scan $\phi_{tb}^{1(2)}$, $\phi_{tb}^{2(2)}$.

The measurements have the Poisson distributions:

$$y_{tb}^{(1)} \sim \text{Poiss}(\Sigma_u \phi_{tb}^{1(1)}(u) I^1(u))$$

$$y_{tb}^{(2)} \sim \text{Poiss}(\Sigma_u \phi_{tb}^{1(2)}(u) I^1(u) + \phi_{tb}^{2(2)}(u) I^2(u))$$

The solution based on the EM approach:

$$I^1(u) = \frac{1}{\sum_{tb} \phi_{tb}^{1(1)}(u) + \phi_{tb}^{1(2)}(u) + \phi_{tb}^{2(2)}(u)}$$

$$\sum_{tb} \left( \frac{y_{tb}^{(1)} \phi_{tb}^{1(1)}(u)}{\hat{y}_{tb}^{(1)}} + \frac{y_{tb}^{(2)} \phi_{tb}^{1(2)}(u)}{\hat{y}_{tb}^{(2)}} \right) I^1(u), \text{ for all}$$

$$I^2(u) = \frac{1}{\sum_{tb} \phi_{tb}^{1(1)}(u) + \phi_{tb}^{1(2)}(u) + \phi_{tb}^{2(2)}(u)} \sum_{tb} \left( \frac{y_{tb}^{(2)} \phi_{tb}^{2(2)}(u)}{\hat{y}_{tb}^{(2)}} \right) I^2(u)$$

$i = 2$

Where $$\hat{y}_{tb}^{(1)} \equiv \sum_u \phi_{tb}^{1(1)}(u) I^1(u)$$

$$\hat{y}_{tb}^{(2)} \sum_u \phi_{tb}^{1(2)}(u) I^1(u) + \phi_{tb}^{2(2)}(u) I^2(u)$$

The above described algorithm enables identification of the different energy level photons (energy signature) emitted from a radioisotope (produced from directly collected photons as well as photons generated from Compton scattering), or a plurality of radioisotopes (e.g. cocktail) administered to a body and detected by a scintillation camera. Thus, such an algorithm enables association between various energy level photons and an isotope source. In essence, this algorithm produces for every radioisotope an energy signature that is composed of the various energy photons produced thereby in a body as a function of a voxel imaged by the camera.

The above-described algorithm can serve as a basis for more advanced imaging which enables specific tissue imaging by accounting for time distribution of radiopharmaceuticals (especially radiotracers).

The prior art disclosed a plurality of radiotracers with varying affinities for various pathological or normal tissues. Table 5 above provides several examples of such radiotracers. Each radiotracer is characterized by a unique distribution kinetics following administration with peak levels reached at specific time points in specific tissues. By monitoring distribution of each such radiotracer as a function of energy intensity emitted therefrom and a function of time; and by using the above-described algorithm, one can associate each voxel imaged with a tissue and a radiotracer signal signature.

Such association provides numerous benefits in imaging since the association enables identification of specific pathologies, confirmation of pathologies via multi-tracer comparison and use of radiopharmaceuticals which include the same radioisotope attached to a different tracer.

It will be appreciated that time dependent distribution of radiotracers can be generated on the fly or derived from data provided by the manufacturer. In any case, such data is used to correlate Voxel photons to a tissue and radiotracer thereby enabling accurate imaging even in cases where several radiotracers having the same isotope or in cases where Compton scattering of one radiotracer generates photons which are naturally produced by another radiotracer.

Kinetics of radiotracer distribution and derivation of data from such distribution is exemplified by the following equation.

Suppose one tracer has uptake over time curve C1(t), and a second tracer has uptake over the time-curve C2(t). Both use the same isotope (e.g. Tc-99m). If both are injected at the same time (or separate time dT), the reading will be:

$$\text{Reading}(t) = A*C1(t) + B*C2(t-dT)$$

A and B relate to the response of the specific tissue location to the presence of tracers 1 and 2 in the blood. C1 and C2 are known in the literature as used for various body organs, in various injected doses, in various patient conditions (e.g. blood pressure, blood flow, . . . ), etc.

Therefore, a de-convolution process may enable separation of the Reading(t) into its components A*C1(t) and b*C2(t), and A and B represent the tissue response.

By looking at the absolute values of A and B (compared with literature), their relative values (e.g. A/B), or their values vs. other organ locations, abnormalities can be detected.

Clearly, many more than just 2 tracers can be used, and injection does not have to be at once or at only two instances, but rather there may be any injection time plan P(t), and thus an expected level in the organ is a convolution of C1(t) with P1(t). The injection time plan is controlled and adjusted in response to the voxel readings, so as to emphasize specific time points of interest.

For example, the time in which one radiotracer is expected to peak and the other to diminish, etc. In particular, the injection time plan can detect the best timing to begin/increase/decrease/stop injections.

Another equation can be used to generate a tissue probability index for an imaged voxel as a function of time.

$$\text{Intensity(voxel)}^{(t)} = \Sigma_i P_i(t) C_{i,k,n}^{(t)}$$

Wherein:
P=injected dose
i=intensity
k=tissue type
n=state
C=function of tracer
(t)=time Thus, $C_{i,k,n}^{(t)}$ expression curve of a radiotracer 'i' in tissue 'k' (e.g. heart, liver muscle blood) having a pathological state 'n' (e.g. normal, ischemic, tumor, abnormal physiology, scar). $C_i$ is a vector that expresses the level of emission of each energy level of a radiotracer. It is possible that several tracers 'i' would produce the same energy spectra lines, for example when different tracers are bound to the same isotope.

P can further depend on the location of injection, in case of non-systemic injection (e.g. in cases of direct organ injection).

C is typically provided by the tracer manufacturer or by researchers that have mapped the uptake of the radiotracer in various tissues and pathologies. C may further be expressed by using a parametric model, for example by using commonly acceptable bioavailability coefficients of the tracer; for example, uptake and clearance coefficients, interaction coefficients and the like.

C can also be expressed in various patient populations (grouped by gender, age, medical history) and under various physiological conditions (rest, stress, stimulation, drugs).

The above described equation can be utilized to reconstruct the 'k' and 'n' per voxel, which are most likely to match the reconstructed voxel intensity.

'k' and 'n' can also be constrained by prior knowledge, such as expectation of presence of a specific type of tissue at a voxel or voxels, and expected specific type of pathologies (prior knowledge of a suspected pathology). 'k' and 'n' can also be constrained by information relating to neighboring voxels or reference voxels which have been previously determined, using for example, x-ray imaging.

Reconstruction of the bioavailability of a radiotracer for each voxel can also be effected by reconstructing the kinetics of each tracer for each voxel followed by matching the parameters rather than the time series of the intensities at each voxel.

Following the above described processing, the present system can represent data to the operator (for example a physician) as intensity over time, at each voxel, parametric representation (ratios between different radiotracers and the like which can be color coded) and finally assigning a probability to the classification, e.g., 95% normal, 3% typed pathology etc.

Reconstruction of the 'k', 'n' or the parametric representation of the Ci may be utilized for further iteration and refinement of voxel intensity over time. It can be further improved and provide a method for the direct recovery of the parametric representation or the classification of a voxel ('k', 'n') without necessitating recovery of the voxel intensity over time. In this case, the kinetics equation are incorporated into the 3-D reconstruction model which is based upon camera readings.

Table 6 below provides an example that illustrates the benefits of associating radiotracer information to generate a differential diagnosis that cannot be derived from each radiotracer alone.

TABLE 6 differential diagnosis of heart ischemia using Thallium and mibiTc-99m

| | Injection Thallium | Rest imaging | Stress injection mibiTc-99m | Post stress imaging | Late imaging (4-24 hrs) thallium |
|---|---|---|---|---|---|
| Normal | | ++ | | ++ | ++ |
| ischemic | | + | | NC | ++ |
| Scar (dead tissue) | | NC | | NC | NC |

NC—no counts
+ low counts
++ high counts

The table above illustrates the uptake profiles of normal ischemic and scar tissue using two separately injected and imaged radiopharmaceuticals, thallium and mibiTc-99m. Normal tissue and scar tissue are easily differentiated since they present contrasting uptake profiles. Ischemic tissue however, shows low rest imaging counts and higher Counts 4-24 hours post injection for thallium, which indicates that this tissue is still capable of uptaking thallium over time and indicates possible loss of viability. However, post stress injection of mibiTc-99m provides no counts for ischemic tissue, supporting the fact that that the tissue is ischemic, as normal tissue uptakes mibiTc-99m as efficiently as it does thallium.

FIGS. 138A-B illustrate simultaneous imaging of two different co-injected radiopharmaceuticals, Tc-99m DMCA and Ga67 and Tc-99m Sestamibi/Tc-99mHDP and Ga67. In both cases anatomical imaging (CT, US or Echo) is concomitantly utilized in order to visualize the tissue. As is illustrated by FIGS. 138A-B, use of the present invention enables efficient co-imaging of both administered radiopharmaceuticals and accurate differential diagnosis.

Thus, according to another aspect of the present invention there is provided a system which enables time dependent analysis of voxel spectral information from one or more radioisotopes to thereby enable more accurate tissue mapping and pathology diagnosis.

The system according to this aspect of the present invention performs three main functions, acquisition of photons, association of each photon to a radioisotope source and a voxel as a function of time and image reconstruction from voxels (association of each voxel to a tissue or pathology)

Thus, the system not only measures the accumulated level at a given time, but also recovers kinetics parameter, thus enabling differentiation between multiple tracers. The differentiation is accomplished (even if they have similar isotope) according to their time behavior profile (which can be derived from, or verified against, their profile as generated by the manufacturer). Further, the differentiation is used to further verify the location of a voxel in the body and associate other adjacent voxels to adjacent tissues and body regions.

Result of such imaging can denote probability of a diagnosis for a given tissue imaged and state of the tissue. For example, a single voxel, or a collection of voxels associated with a specific tissue region (e.g. heart) can be used to generate a probability of diagnosis as follows: 87%—normal, 9%—ischemic, 3% scar, 1%—tumor; the probability being derived from radioisotope mapping as a function of time and photon signature and, additionally, as a function of radiotracer association.

Where a tissue is not known, a probability distribution can also be generated. For example, blood pool imaging (by dynamic flow imaging) can help the algorithms know where blood is and where muscle is, thus the reconstruction algorithm described herein can take that into account by subtracting from voxel maps of radiotracers which attach only to muscle the blood pool imaging maps.

A higher-level analysis determines disease diagnosis, not per voxel, but rather by providing to the system information on the disease and how it is typically manifested in patients. This embodiment of the present system (which includes a large database) can support diagnostic decision-making.

It will be appreciated that the availability of the information described above also enables tailoring of the exact injection profile (boluses, drips, etc) of each radiopharmaceutical.

In addition to the advantages described above (e.g. tissue mapping and differential diagnosis) use of radiopharmaceutical cocktails and simultaneous dual imaging is also advantageous in that administration of two or more radiopharmaceuticals via a single injection shortens patient cycle time since there is now one imaging phase rather than two.

It is expected that during the life of this patent many relevant markers, radiological imaging devices and two and three dimensional imaging systems will be developed and the scopes of the corresponding terms herein, are intended to include all such new technologies a priori.

Simplified Scatter Correction in the Administration of Dual Isotopes

The present embodiment provides a method and apparatus for radioisotope that address shortcomings of present radioisotope imaging from subjects containing two imaging isotopes. Specifically, the present invention provides methods, and gamma probes for two imaging isotopes, X1 and X2, wherein each isotope has a gamma energy, for example, Y1 and Y2, respectively; wherein the energy state of Y1 is greater than the energy state of Y2 and Y1 scatter interferes with measurements of Y2.

In accordance with embodiments of the present invention, imaging is performed with fast gamma probes wherein two complete scans are taken, each is of a short duration, for example, 2-5 minutes.

In and exemplary embodiment, a radiopharmaceutical of X1 is administered and an image of X1 is taken. The scatter at and around the region of Y2, ie., the cross talk of X1 at and around Y2, is obtained.

Following imaging X1, radiopharmaceutical of X2 is administered and an image of X1+X2 is taken. The scatter of X1 in the region of Y2, the cross talk of X1 at and around Y2, is then subtracted from the image of X1+X2.

In an exemplary embodiment, $Tl^{201}$ and $Tc^{99m}$ are administered in a myocardial perfusion study; $Tc^{99m}$ having a photon emission at 140 KeV, and $Tl^{201}$ having a photon emission energy 70 KeV; resulting in cross talk around the 70 KeV region of $Tl^{201}$ photon emission.

In another exemplary embodiment, $Tc^{99m}$ and $In^{111}$ are administered for pelvic SPECT imaging; $Tl^{201}$ having a photon emission energy 70 KeV as noted above and $In^{111}$ has a photon emission of 170 KeV; resulting in cross talk around the 140 KeV region of $Tc^{99m}$ photon emission.

FIG. 140 is a flowchart 9400 for an imaging method of two isotopes, such as X1 and X2, having distinct gamma energies, for example, Y1 and Y2, respectively. In an exemplary embodiment, the energy of Y1 is greater than the energy of Y2 and scatter from Y1 may interfere with measurements of Y2.

An imaging method 100 includes the following steps:

at 9402 radiopharmaceutical X1 is administered;

at 9404 a first shot duration image of X1 is obtained using a fast probe at and around the energy region of Y2;

at 9406 radiopharmaceutical X2 is administered while the patient remains under the imager;

at 9408, a second short duration image is obtained using a fast probe, the image including includes energy at and around Y1 and Y2; and at 9410 the image of X1 at and around the energy region of Y2, (at 9404) is subtracted from the image of X1+X2 (at 9410) substantially eliminating cross talk of X1 from Y2.

Myocardial Perfusion

In an exemplary embodiment, the following procedure is used for imaging myocardial perfusion:

A patient undergoes a stress test and is injected at peak exercise with a standard dose of $Tc^{99m}$ sestamibi. The dose could be reduced due to the high sensitivity of the DynaQ™ cardiac scanner thus minimizing scattered $Tc^{99m}$ photons and patient radiation exposure.

After a recovery of approximately 60 minutes, the patient is positioned under a DynaQ™ Cardiac or DynaQ™ CVCT Scanner. A brief pre-scan image of the $Tc^{99m}$ sestamibi distribution is obtained at and around 70 KeV; an energy associated with imaging of $Tl^{201}$. This scan is typically performed in under 2 minutes due to the sensitivity of the DynaQ™ scanner and is used to subtract $Tc^{99m}$ sestamibi cross-talk from the $Tl^{201}$ energy window in final image processing. While still under the DynaQ™ scanner, the patient is injected with a standard dose of $Tl^{201}$.

Simultaneous dual isotope data is then acquired, typically in less than 3 minutes. Utilization of the above-noted $Tc^{99m}$ sestamibi scan, herein a "pre-scan", the resultant image can be resolved on a pixel by pixel basis. Execution of the pre-scan image is enabled by the rapid acquisition of the DynaQ™ system, for example, as taught by commonly owned PCT/IL2005/000575, hereby incorporated in its entirety by reference.

It will be appreciated that the procedure would not be practical in absence of the high speed of the DynaQ™ scanner.

It will be appreciated that similar performance can be achieved substituting one or more isotopes for $Tc^{99m}$ sestamibi and/or $Tl^{201}$, providing that the speed of acquisition is much higher than today's standard.

Referring further to the drawings, FIG. 141 schematically represents a time line for myocardial perfusion, in accordance with embodiments of the present invention.

Accordingly, at time zero, the patient begins physical exercise, represented as A. The exercise optionally lasts 10-15 minutes, and after about 7 minutes $Tc^{99m}$ is administered, for example, by injection. The patient continues to exercise 1-3 minutes longer.

At 50 to 60 minutes later, a $Tc^{99m}$ scan, lasting about 2-3 minutes, is obtained.

Preferably, while the patient remains under the scanner, $Tl^{201}$ is administered, for example, by injection.

Some 2-3 minutes after the second administration, a dual isotope scan, also lasting about 2-3 minutes is obtained.

Referring further to the drawings, FIGS. 142a-142c are schematic representations of a $Tc^{99m}$ photopeak (FIG. 142a), a $Tl^{201}$ photopeak (FIG. 142b), and $Tc^{99m}$ cross talk contribution to at and around the $Tl^{201}$ main energy window (FIG. 142c).

Pelvic Scans

In accordance with a second example, the DynaQ system is used for obtaining a pelvic SPECT, in two scans of rapid acquisitions, as follows:

i. administering $In^{111}$, having an energy of 170 Kev gamma;

ii. allowing distribution of $In^{111}$ and performing a first scan for the $In^{111}$ at and around the 140 KeV energy window of $Tc^{99m}$, iii. administering the $Tc^{99m}$, of 140 Kev gamma;

iv. allowing distribution of $Tc^{99m}$ and performing a second scan of both $Tc^{99m}$ and $In^{111}$; and v. subtracting the cross talk of $In^{111}$ at and around the 140 KeV energy window of $Tc^{99m}$ from the second scan of both $Tc^{99m}$ and $In^{111}$, wherein both the first and second scans are of short durations of about 2-4 minutes each.

The present embodiment is possible with a fast gamma camera, for example as taught by the present invention.

The aforementioned description is based on Okudan B, Smitherman T C. The value and throughput of rest Thallium-201/stress Technetium-99m sestamibi dual-isotope myocardial SPECT. Anadolu Kardiyol Derg. 2004 June; 4(2):161-8; Weinmann P, Faraggi M, Moretti J L, Hannequin P. Clinical validation of simultaneous dual-isotope myocardial scintigraphy. Eur J Nucl Med Mol Imaging. 2003 January; 30(1): 25-31; Hannequin P, Weinmanin P, Mas J, Vinot S. Preliminary clinical results of photon energy recovery in simultaneous rest Tl-201/stress Tc-99m sestamibi myocardial SPECT. J Nucl Cardiol. 2001 March-April; 8(2):144-51; Unlu M, Gunaydin S, Ilgin N, Inanir S, Gokcora N, Gokgoz L. Dual isotope myocardial perfusion SPECT in the detection of coronary artery disease: comparison of separate and simultaneous acquisition protocols. J Nucl Biol Med. 1993 December; 37(4):233-7; Lowe V J, Greer K L, Hanson M W, Jaszczak R J, Coleman R E. Cardiac phantom evaluation of simultaneously acquired dual-isotope rest thallium-201/stress technetium-99m SPECT images. J Nucl Med. 1993

November; 34(11):1998-2006; Knesaurek K, Machac J. Comparison of correction techniques for simultaneous 201Tl/99mTc myocardial perfusion SPECT imaging: a dog study. Phys Med Biol. 2000 November; 45(11):N167-76; Yang D C, Ragasa E, Gould L, Huang M, Reddy C V, Saul B, Schifter D, Rainaldi D, Feld C, Tank R A. Radionuclide simultaneous dual-isotope stress myocardial perfusion study using the "three window technique". Clin Nucl Med. 1993 October; 18(10):852-7; Nakamura M, Takeda K, Ichihara T, Motomura N, Shimizu H, Saito Y, Nomura Y, Isaka N, Konishi T, Nakano T. Feasibility of simultaneous stress 99mTc-sestamibi/rest 201Tl dual-isotope myocardial perfusion SPECT in the detection of coronary artery disease. J Nucl Med. 1999 June; 40(6):895-903; and Hannequin P, Mas J, Germano G. Photon energy recovery for crosstalk correction in simultaneous 99mTc/201Tl imaging. J Nucl Med. 2000 April; 41(4):728-36.

Diagnostic Protocols

Protocols for Fast Cardiac Imaging

The following cardiac imaging protocols include two imaging stages, at rest and after stress. Generally, they are performed with gating and attenuation corrections, as illustrated in the Tables of FIGS. 148A-V.

1. A fast, dual-isotope, imaging protocol: For imaging at rest, a patient is injected with about 3 mCi of Th-201-thallous chloride, some time prior to the imaging, while remaining substantially at rest. After a waiting period of 10-15 minutes, a rest imaging of about 2 minutes is taken. The patient is then subject to a physical stress, for example by exercising on a treadmill. At the peak stress level, the patient is injected with about 20-30 mCi of Tc-99m-sestamibi. After a waiting period of about 30-60 minutes, during which the patient is advised to remain in motion, for example, by walking, a post-stress imaging of about 2 minutes is taken. The total imaging time of this protocol is about 4 minutes, and the total patient time is about 60-90 minutes. The advantage of this protocol is in the fast imaging time, of about 2 minutes per image, when compared to standard imaging methods.

2. A fast, single-isotope, imaging protocol: For imaging at rest, the patient is injected with about 8-10 mCi of Tc-99m-sestamibi, some time prior to the imaging, while remaining substantially at rest. After a waiting period of about 30 minutes, a rest imaging of about 2 minutes is taken. The patient is then subject to a physical stress, for example by exercising on a treadmill. At the peak stress level, the patient is injected with about 20-30 mCi of Tc-99m-sestamibi. After a waiting period of about 30-60 minutes, during which the patient is advised to remain in motion, for example, by walking, a post-stress imaging of about 2 minutes is taken. The total imaging time of this protocol is about 4 minutes, and the total patient time is about 60-90 minutes. The advantage of this protocol is in the fast imaging time, of about 2 minutes per image, when compared to standard imaging methods.

3. An ultra fast, dual-isotope, imaging protocol: For imaging at rest, the patient is injected with about 3 mCi of Th-201-thallous chloride, some time prior to the imaging, while remaining substantially at rest. After a waiting period of about 2 minutes, a rest imaging of about 2 minutes is taken. The patient is then subject to a pharmacological stress, for example, for example, by the administration of adenosine. At the peak stress level, the patient is injected with about 20-30 mCi of Tc-99m-sestamibi, while positioned under the camera. Substantially immediately after the second injection, a post-stress imaging of about 2 minutes is taken. The total imaging time of this protocol is about 4 minutes, and the total patient time is about 20-30 minutes. The advantage of this protocol is in the fast imaging time, of about two minutes, and in the avoidance of liver radioactivity, since imaging takes place substantially immediately after injection, before buildup of radioactivity in the liver takes place.

4. An ultra fast, single-isotope, imaging protocol: For imaging at rest, the patient is injected with about 8-10 mCi of Tc-99m-sestamibi, some time prior to the imaging, while remaining substantially at rest. After a waiting period of about 0-2 minutes, a rest imaging of about 2 minutes is taken. The patient is then subject to a pharmacological stress, for example, by the administration of adenosine. At the peak stress level, the patient is injected with about 20-30 mCi of Tc-99m-sestamibi, while positioned under the camera. Substantially immediately after the second injection, a post-stress imaging of about 2 minutes is taken. The total imaging time of this protocol is about 4 minutes, and the total patient time is about 20-30 minutes. The advantage of this protocol is in the fast imaging time, of about two minutes, and in the avoidance of liver radioactivity, as in protocol 3.

5. A dual-isotope, simultaneous imaging protocol: The patient is injected with about 3 mCi of Th-201-thallous chloride, and proceeds to a treadmill. At the peak stress level, the patient is injected with about 20-30 mCi of Tc-99m-sestamibi. After a waiting period of about 30-60 minutes, during which the patient is advised to remain in motion, for example, by walking, a simultaneous imaging of about 2 minutes is taken. The total imaging time of this protocol is about 2 minutes, and the total patient time is about 40-90 minutes. The advantage of this protocol is in the fast imaging time, of about 2 minutes of single acquisition, and more important, in the dual registration of the two isotopes, when imaged simultaneously.

6. A fast, dual-isotope, thallium-stress-perfusion, imaging protocol: For imaging at rest, the patient is injected with about 3 mCi of Tc-99m-sestamibi, some time prior to the imaging, while remaining substantially at rest. After a waiting period of about 30 minutes, a rest imaging of about 2 minutes is taken. The patient is then subject to a physical stress, for example by exercising on a treadmill. At the peak stress level, the patient is injected with about 3 mCi of Th-201-thallous chloride. After a waiting period of about 10-15 minutes, during which the patient is advised to remain in motion, for example, by walking, a post-stress imaging of about 4 minutes is taken. The total imaging time of this protocol is about 6 minutes, and the total patient time is about 45-60 minutes. The advantage of this protocol is in the fast imaging time, of about 2-4 minutes per image, and in the better flow linearity, the ability to detect small lesions, and the relatively high viability.

7. A fast, dual-isotope, thallium-stress-perfusion, imaging protocol: For imaging at rest, the patient is injected with about 3 mCi of Tc-99m-sestamibi, some time prior to the imaging, while remaining substantially at rest. After a waiting period of about 30 minutes, a rest imaging of about 2 minutes is taken. The patient is then subject to a pharmacological stress, for example, by the administration of adenosine. At the peak stress level, the patient is injected with about 3 mCi of Th-201-thallous chloride, while positioned under the camera. Substantially immediately after the second injection, a post-stress imaging of about 4 minutes is taken. The total imaging time of this protocol is about 6 minutes, and the total patient time is about 20-30 minutes. The advantage of this protocol is in the fast imaging time, of about 6 minutes per image, and in the better flow linearity, the ability to detect small lesions, and the relatively high viability.

8. An ultra fast, dual-isotope, thallium-stress-perfusion, imaging protocol: For imaging at rest, the patient is injected with about 3 mCi of Tc-99m-sestamibi, and rest imaging of about 2 minutes is taken, with substantially no waiting period.

The patient is then subject to a pharmacological stress, for example, by the administration of adenosine. At the peak stress level, the patient is injected with about 3 mCi of Th-201-thallous chloride, while positioned under the camera. Substantially immediately after the second injection, a post-stress imaging of about 4 minutes is taken. The total imaging time of this protocol is about 6 minutes, and the total patient time is about 10-20 minutes. The advantage of this protocol is in the fast imaging time, of about 6 minutes per image, in the better flow linearity, the ability to detect small lesions, the relatively high viability, the single acquisition, and more important, the dual registration of the two isotopes, when imaged simultaneously.

9. A fast, dual-isotope, simultaneous imaging protocol: For imaging at rest, the patient is injected with about 3 mCi of Tc-99m-sestamibi, some time prior to the imaging, while remaining substantially at rest. After a waiting period of about 30 minutes, a rest imaging of about 2 minutes is taken. The patient is then subject to a pharmacological stress, for example, by the administration of adenosine. At the peak stress level, the patient is injected with about 3 mCi of Th-201-thallous chloride. After a waiting period of about 2 minutes, a post-stress imaging of about 4 minutes is taken. The total imaging time of this protocol is about 6 minutes, and the total patient time is about 10-20 minutes. The advantage of this protocol is in the single imaging time, of about 6 minutes per image, and in the better flow linearity, the ability to detect small lesions, and the relatively high viability.

10. A fast, single-isotope, Tc-99m-teboroxime imaging protocol: For imaging at rest, a patient is injected with about 8-10 mCi of Tc-99m-teboroxime, while the patient is under the camera, and a rest imaging of about 10 minutes is taken. The patient is then subject to a pharmacological stress, for example, by the administration of adenosine. At the peak stress level, the patient is injected with about 20-30 mCi of teboroxime, while positioned under the camera. Substantially immediately after the second injection, a post-stress imaging of about 2 minutes is taken. The total imaging time of this protocol is about 12 minutes, and the total patient time is about 20 minutes.

Protocols for Fast General Imaging

The following fast imaging protocols are illustrated in Tables of FIGS. 148A-V.

11. Lung V/P-DTPA aerosol and macro-aggregated albumin (lung perfusion agent) protocol, for studying lung perfusion by quantitative parameters, such as ml/mini/gr. A patient is injected with Tc-99m-diethylene triamine pentaacetate (DTPA), up to about 5 mCi (up to 1M particles) Tc-99m-macro-aggregated albumin (MAA), I-123 while positioned under the camera. Substantially immediately after injection, an imaging of up to about 6 minutes is taken, with an energy window of between 3 and 15%. The advantage of this protocol is that it is fast.

12. Fast MDP-bone scan-whole body scan protocol, routinely performed to look for bone tumors or inflammatory processes of the bone (e.g. osteomyelitis), with an acquisition time of up to 6 minutes, using Tc-99m-MDP, at 20-30 mCi total dose, with a waiting period of 0-60 minutes, energy window—anywhere between 3-15%, advantage—fast.

Protocols for Low-Dose Cardiac Imaging

The following cardiac imaging protocols include two imaging stages, at rest and after stress. Generally, they are performed with gating and attenuation corrections, as illustrated in the Tables of FIGS. 148A-V.

14. A low-dose, dual-isotope, imaging protocol: For imaging at rest, a patient is injected with about 0.3 mCi of Th-201-thallous chloride, some time prior to the imaging, while remaining substantially at rest. After a waiting period of 10-15 minutes, a rest imaging of about 15 minutes is taken. The patient is then subject to a physical stress, for example by exercising on a treadmill. At the peak stress level, the patient is injected with about 3 mCi of Tc-99m-sestamibi. After a waiting period of about 30-60 minutes, during which the patient is advised to remain in motion, for example, by walking, a post-stress imaging of about 15 minutes is taken. The total imaging time of this protocol is about 25-30 minutes, and the total patient time is about 90 minutes. The energy window is between 3 and 15%. The advantage of this protocol is in the low dose, and the better spectral resolution that results from it.

15. A low-dose, single-isotope, imaging protocol: For imaging at rest, a patient is injected with about 0.3 mCi of Tc-99m-sestamibi, some time prior to the imaging, while remaining substantially at rest. After a waiting period of about 30 minutes, a rest imaging of about 15 minutes is taken. The patient is then subject to a physical stress, for example by exercising on a treadmill. At the peak stress level, the patient is injected with about 3 mCi of Tc-99m-sestamibi. After a waiting period of about 30-60 minutes, during which the patient is advised to remain in motion, for example, by walking, a post-stress imaging of about 15 minutes is taken. The total imaging time of this protocol is about 25-30 minutes, and the total patient time is about 90 minutes. The energy window is between 3 and 15%. The advantage of this protocol is in the low dose, and the better spectral resolution that results from it.

16. A low-dose, dual-isotope, simultaneous imaging protocol: The patient is injected with about 0.3 mCi of Th-201-thallous chloride and then subject to a physical stress, for example by exercising on a treadmill. At the peak stress level, the patient is injected with about 3-5 mCi of Tc-99m-sestamibi. After a waiting period of about 30-60 minutes, during which the patient is advised to remain in motion, for example, by walking, a simultaneous rest and post-stress imaging of about 5-15 minutes is taken. The total imaging time of this protocol is about 20-30 minutes, and the total patient time is about 90 minutes. The energy window is between 3 and 15%. The advantage of this protocol is in the low dose, better image registration, and better spectral resolution.

17. A low-dose, dual-isotope, fast imaging protocol: For imaging at rest, the patient is injected with about 0.3 mCi of Th-201-thallous chloride, while under the camera. After a waiting period of about 2 minutes, a rest imaging of about 15 minutes is taken. The patient is then subject to a pharmacological stress, for example, by the administration of adenosine. At the peak stress level, the patient is injected with about 20-30 mCi of Tc-99m-sestamibi, while under the camera, and a post-stress imaging of about 2 minutes is taken, immediately. The total imaging time of this protocol is about 17 minutes, and the total patient time is about 45 minutes. The energy window is about 3-15%. The advantage of this protocol is that it is fast, and low dose.

18. A low-dose, single-isotope, fast imaging protocol: For imaging at rest, the patient is injected with about 0.3 mCi of Tc-99m-sestamibi, while under the camera. Immediately, a rest imaging of about 15 minutes is taken. The patient is then subject to a pharmacological stress, for example, by the administration of adenosine. At the peak stress level, the patient is injected with about 3 mCi of Tc-99m-sestamibi, while under the camera, and a post-stress imaging of about 15 minutes is taken, immediately. The total imaging time of this protocol is about 30 minutes, and the total patient time is about 45 minutes. The energy window is about 3-15%. The advantage of this protocol is that it is fast, and low dose.

Protocols for Low-Dose General Imaging

The following low-dose imaging protocols are illustrated in the Tables of FIGS. 148A-V.

19. Brain perfusion mapping protocol: used for mapping of perfusion described by quantitative parameters (mg/min/gr); measurement of cerebral flow reserve in stress protocols using pharmacological stress agents; parametric quantitation; and identification of disease signature, for example in Alzheimer's, depression, schizophrenia, and similar conditions. A patient is injected with up to about 20 mCi Tc-99m-exametazine (HMPAO), up to about 20 mCi Tc-99m N,N'(1,2-ethenediyl)bis-L-cysteine diethyl ester (Tc-99m-ECD), and up to about 5 mCi of I-123 iofetamine hydrochloride. After a waiting period of up to one hour, imaging is taken, with an energy window of between 3 and 15%. The advantage of this protocol is that it can show stroke at an early stage.

20. Hepatobiliary imaging: for studying the structure of the liver, including identification of hemangiomas, abscesses, and liver enlargement. A patient is injected with up to about 0.5 mCi Tc-99m-mebrofenin while under the camera, and imaging is begun immediately. The acquisition time is up to about 30 minutes, with an energy window of between 3 and 15%. This protocol studies fluid flow, rate of tracer uptake (passive or active), accumulation and redistribution of tracer, tracer metabolism, and secretion and/or washout of tracer or metabolite (passive or active).

21. Lung V/P—DTPA aerosol and macro-aggregated albumin (lung perfusion agent) protocol, for studying lung perfusion by quantitative parameters, such as ml/mini/gr. A patient is injected with Tc-99m-diethylene triamine pentaacetate (DTPA), up to about 5 mCi (up to 1M particles) Tc-99m-macro-aggregated albumin (MAA), I-123 while positioned under the camera. Substantially immediately after injection, an imaging of up to about 6 minutes is taken, with an energy window of between 3 and 15%. The advantage of this protocol is that it is fast.

Protocols for Imaging of Dynamic Processes

22. Cardiac perfusion (thallium rest) protocol: this protocol is used for imaging of cardiac perfusion under rest conditions. The perfusion is described by quantitative parameters (ml/mini/gr), coronary flow reserve and parametric quantitation. A patient is injected with up to about 4 mCi Tl-201 thallous chloride, with the camera running, and imaging is begun immediately. Imaging is taken for a time of from about 2 to about 20 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

23. Cardiac perfusion (thallium stress) protocol: this protocol is used for imaging of cardiac perfusion under stress conditions. The perfusion is described by quantitative parameters (ml/mini/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 4 mCi Tl-201 thallous chloride, with the camera running, and imaging is begun immediately. Imaging is taken for a time of from about 2 to about 20 minutes, with an energy window of between 3 and 15%. This protocol enables the study of fluid flow, rate of tracer uptake (passive or active), tracer accumulation and redistribution, tracer metabolism, and is secretion and/or washout (active or passive) of tracer/metabolites.

24. Cardiac perfusion (teboroxime rest) protocol: this protocol is used for imaging of cardiac perfusion under rest conditions. The perfusion is described by quantitative parameters (ml/mini/gr), coronary flow reserve and parametric quantitation. A patient is injected with up to about 30 mCi teboroxime, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

25. Cardiac perfusion (teboroxime stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 4 mCi teboroxime, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

26. Cardiac perfusion (sestamibi rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

27. Cardiac perfusion (sestamibi stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

28. Cardiac perfusion (tetrofosmin rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi tetrofosmin, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

29. Cardiac perfusion (tetrofosmin stress) protocol: this protocol is used for imaging of cardiac perfusion tinder stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi tetrofosmin, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

30. Cardiac perfusion (Q12 NAME FROM SHANKAR rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

31. Cardiac perfusion (Q12 NAME FROM SHANKAR stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi Tc-99m-sestamibi, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

32. BMIPP (rest) protocol: this protocol is used for imaging of cardiac perfusion under rest conditions. The perfusion is described by quantitative parameters (ml/min/gr), coronary flow reserve and parametric quantitation. A patient is injected with up to about 30 mCi Tc-99m-sestamibi, with the camera running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

33. BMIPP (stress) protocol: this protocol is used for imaging of cardiac perfusion under stress conditions. The perfusion is described by quantitative parameters (ml/min/gr), coronary flow reserve and parametric quantitation. A patient subjected to a pharmacological stress, for example, for example, by the administration of adenosine or to a physical stress, for example by exercising on a treadmill. At the peak stress level, the patient is injected with up to about 30 mCi Tc-99m-sestamibi, with the camera to running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

34. A protocol utilizing any of the above combinations: this protocol is used for imaging of cardiac perfusion under either stress or rest conditions. The perfusion is described by quantitative parameters (ml/min/gr), coronary flow reserve and parametric quantitation. A patient is injected with any of the above radiopharmaceuticals, with the camera running, and imaging is begun immediately. Imaging is taken for a time of up to 10 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

35. A protocol utilizing all PET radiopharmaceuticals within the currently used PET protocols used with our SPECT camera: this protocol is used for imaging of cardiac perfusion under stress or rest conditions. The perfusion is described by quantitative parameters (ml/min/gr), coronary flow reserve and parametric quantitation. A patient is injected with any PET radiopharmaceutical, as discussed above, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

36. Cancer—tumor perfusion protocol—evaluation of tumors by single isotope (need to expand on the breast) SPECT with Teboroxime TC-99m or Tc-99m-sestamibi: this protocol is used for imaging of cardiac perfusion under rest or stress conditions. Image tumor blood supply with Tl-201 thallous chloride in combination with Tc-99m-sestamibi uptake and washout which is affected by the MDR complex showing therapeutic response to chemo. The perfusion is described by quantitative parameters (ml/min/gr) and parametric quantitation. A patient is injected with up to about 30 mCi Tc-99m-sestamibi, with the camera running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

37. Cancer—tumor perfusion protocol—evaluation of tumors by simultaneous dual isotope SPECT with Tl-201 thallous chloride and Tc-99m-sestamibi: this protocol is used for imaging of cardiac perfusion under rest or stress conditions. Tumor imaging; Image tumor blood supply with Tl-201 thallous chloride in combination with Tc-99m-sestamibi washout which is affected by the MDR complex showing therapeutic response to chemo. The perfusion is described by quantitative parameters (ml/min/gr) and parametric quantitation. A patient subjected to a pharmacological stress, for example, for example, by the administration of adenosine or physical stress, for example by exercising on a treadmill. At the peak stress level, the patient is injected, simultaneously, with up to about 4 mCi Tl-201 thallous chloride and up to 30 mCi Tc-99m-sestamibi, with the camera running, and imaging is begun immediately. Imaging is taken for a time of up to 5 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

38. Kidney—renal function (111-In-DTPA and oomTc-MAG3) protocol: this protocol is used for assessment of filtration and tubular secretion, perfusion described by quantitative parameters (ml/min/gr), coronary flow reserve and parametric quantitation, under stress or rest conditions. A patient is injected with up to about 1 mCi of 111-In-DTPA and 0.2 mCi of Tc-MAG3, with the camera running, and imaging is begun immediately. Imaging is taken for a time of up to 10 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

39. Kidney—renal function (111-In-DTPA and Hippuran I-123) protocol: this protocol is used for assessment of filtration and tubular secretion, under rest or stress conditions. The perfusion is described by quantitative parameters (ml/min/gr) and parametric quantitation. A patient subjected to a pharmacological stress, for example, for example, by the administration of adenosine or to a physical stress, for example by exercising on a treadmill. At the peak stress level, the patient is injected with 0.3 mCi of 111-In-DTPA and up to 10 mCi of Hippuran I-123, with the camera running, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

40. Brain perfusion protocol: this protocol is used for perfusion mapping under rest or stress conditions. The perfusion is described by quantitative parameters (ml/min/gr), cerebral flow reserve (in stress protocols using pharmacological stress agents), parametric quantitation, and disease signature (Alzheimer's, depression, schizophrenia, etc.). A patient is injected with up to about 20 mCi HMPAO, 99m labeled Tc-99m ECD (neurolite), and up to 5 mCi I-123, with the camera running, and imaging is begun immediately. Imaging is taken for a time of up to 30 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

41. Brain perfusion protocol: this protocol is used for perfusion mapping under rest or stress conditions. The perfusion is described by quantitative parameters (ml/min/gr), cerebral flow reserve (in stress protocols using pharmacological stress agents), parametric quantitation, and disease signature (Alzheimer's, depression, schizophrenia, etc.). A patient subjected to a pharmacological stress, for example, for example, by the administration of adenosine or to a physical stress, for example by exercising on a treadmill. At the peak stress level, the patient is injected with up to about 20 mCi Tc-99m and up to about 5 mCi teboroxime, with the camera running, and imaging is begun immediately. Imaging is taken for a time of up to 30 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

42. Hepatobiliary Tc-99m sulfur colloid protocol: this protocol is used for looking at the liver structure (hemangiomas, abscesses, liver enlargement, etc.) under rest or stress conditions. A patient is injected with up to about 5 mCi Tc-99m sulfur colloid, with the camera running, and imaging is begun immediately. Imaging is taken for a time of up to 10 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

43. Liver function study protocol: this protocol is used for imaging under rest or stress conditions. A patient subjected to a pharmacological stress, for example, for example, by the administration of adenosine or to a physical stress, for example by exercising on a treadmill. At the peak stress level, the patient is injected with up to about 10 mCi Tc-99m disida (disulfenine), choletec, HIDA, (all bind to bilirubin sites) teboroxime, with the camera running, and imaging is begun immediately. Imaging is taken every 5 minutes, for a time of 5 minutes, for up to an hour, with an energy window of between 3 and 15%. If no activity is seen in the intestine, a pharmacological agent is used for gall bladder contraction. This protocol enables the study of fluid flow, rate of tracer uptake (passive or active), tracer accumulation and redistribution, tracer metabolism, and secretion and/or washout (active or passive) of tracer/metabolites.

44. Dual phase gastric emptying study protocol: this protocol is used for determining the rate that the stomach empties of food. With the camera running, imaging is begun immediately before the patient injects solid food that is labeled with Tc99m-S-colloid or liquid food that is labeled with In-111-DTPA labeled. The study continues until the stomach is approximately empty of all tracer.

45. Cardiac vulnerable plaque study protocol: this protocol is used for finding plaques that may be a nidus for initiating a CVA. A patient is injected with up to 5 mCi of Annexin radiopharmaceutical containing 111-In-DTPA imaging isotope and up to 5 mCi of AcuTec radiopharmaceutical containing Tc-99m-sestamibi and waits for 24 hours and imaging begins. AcuTec attaches to activated platelets and shows thrombus. Annexin attaches to apoptotic cells; apoptotic cells being human neutrophils that have died and broken up, demonstrating inflammatory infiltrate. This protocol enables the study of dynamic plaques that are associated with cardiac plaque tissue damage and repair.

46. Prostate imaging study protocol: this protocol is used for determining the presence and/or extent of metastatic and/or primary cancer in the prostate. A patient is injected with up to 5 mCi of Prostascint radiopharmaceutical, containing 111-In-DTPA imaging isotope and waits for 24-72 hours and imaging begins. This protocol enables the study of dynamic plaques that are associated with tissue damage and repair.

47. SST-receptor imaging study protocol: this protocol is used for determining the presence and/or extent of SST-receptor expressing tumors, whether metastatic and/or primary cancerous tumors. A patient is injected with up to 5 mCi of Octreotide radiopharmaceutical, containing 111-In-DTPA imaging isotope and waits for 24-72 hours and imaging begins. This protocol enables the study of SST-receptor expressing tumors metastatic and/or primary cancerous tumors.

48. Neuroendocrine tumors imaging study protocol: this protocol is used for determining the presence and/or extent of metastatic and/or primary Neuroendocrine tumors by binding to associated Somatostatin receptors. A patient is injected with up to 20 mCi of Neotec radiopharmaceutical, containing Tc-99m-sestamibi imaging isotope and waits for 24 hours and imaging begins. This protocol enables the study of Neuroendocrine tumors.

49. Thrombus detection imaging study protocol: this protocol is used for imaging DVT and intratererial thromus in coronary and carotid arteries, by binding to GP IIb/IIIa receptors on platelets. A patient is injected with up to 20 mCi of Acutect radiopharmaceutical, containing Tc-99m-sestamibi imaging isotope and waits for 0-20 minutes and imaging begins. This protocol enables the study of Thrombus detection, including DVT and intratererial thromus in coronary and carotid arteries.

50. Pheochromocytoma and or Myocardial failure imaging study protocol: this protocol is used for imaging pancreatic adrenergic tissue uptake and presynaptic adrenergic receptors, adrenergic being associated with adrenaline, by binding to GP IIb/IIIa receptors on platelets. A patient is injected with up to 5 mCi of MIBG Radiopharmaceutical, containing I-123 iofetamine hydrochloride imaging isotope and waits for 24 hours and imaging begins. This protocol enables the study of tissue and receptors that are associated with adrenergic uptake.

51. A gated cardiac stress imaging protocol: a dynamic study to investigate the effects of stress, for example adenosine, ice-water, and/or vasodilatation agents, on blood flow kinetics. A patient is injected with about 4 mCi of Th-201-thallous chloride, some time prior to the imaging. After a waiting period of 0-2 minutes, a rest imaging of about 2-5 minutes is taken. The patient is then administered adenosine, ice-water, and/or vasodilatation agents. After a waiting period of about 0-5 minutes an imaging of about 2-10 minutes is taken.

52. A Kidney function imaging protocol: a dynamic study to investigate the effects of stress on blood flow kinetics (captopril; fusides etc) of the kidneys. A patient is injected with about 2-4 mCi Indium and/or Tc-MAG3, while remaining substantially at rest. A rest imaging of about 10-30 minutes is taken. After a waiting period of about 10-30 minutes, imaging of about 2 minutes is taken.

53. A Bexaar dosimetry imaging protocol: a study to determine the dose required to inject in order to administer an effective dose of 75 REM. A patient is injected with about 5 mCi/35 mg protein of, I-123 iofetamine hydrochloride, some time prior to each scan; each scan having an energy window anywhere between 3-15% and lasting approximately five minutes. Three acquisitions are acquired during the week to produce a graph of metabolism.

Protocols for Multiple Radiopharmaceuticals

A combination of at least two radiopharmaceuticals may be used for specific imaging protocols. Such a combination may be used, for example, to obtain information regarding both a pathology and an anatomy, such that the location of an imaged pathology within the body is identified; or to identify multiple pathologies in different sections of the body of a subject; or to study different pathological processes within a single organ of a subject.

The individual radiopharmaceuticals may be administered sequentially or substantially simultaneously. Preferably, the radiopharmaceuticals are administered as a single composition.

Combinations for the Study of a Pathology and an Anatomy:

1. Thallium-201-thallous chloride (a parathyroid avid agent) and Tc-99m-pertechnetate (a thyroid agent) may be administered in combination for parathyroid adenoma imaging, and anatomical differentiation of the parathyroid from the thyroid. A patient is injected up to about 1 mCi Thallium-201-thallous chloride, and up to about 15 mCi a dose of Tc-99m. After a waiting time of about 10 minutes, imaging is taken for a period of about 5 minutes, with an energy window of between 2 and 10 percent.

2. Tc-99m-methoxyisobutylisonitrile (sestamibi) (a parathyroid avid agent) and I-123 (a thyroid agent) may be administered in combination for parathyroid adenoma imaging, and anatomical differentiation of the parathyroid from the thyroid. A patient is injected with up to about 15 mCi Tc-99m-sestamibi and up to about 100 mCi I-123. After a waiting time of about 10 minutes, imaging is taken for a period of about 5 minutes, with an energy window of between 2 and 10 percent.

3. I-123 and Tc-99m-labeled red blood cells or Tc-99m-dihydrogen methylenediphosphate (medronate MDP) may be administered in combination for imaging of thyroid cancer and identification of the location of the cancer. Tc99m -MDP is a bone-imaging agent, which enables visualization of the skeleton to provide anatomical landmarks. Tc99m-labeling of red blood cells enables the larger blood vessels to be visualized to provide anatomical landmarks.

A patient is injected with up to about 4 mCi thallium-201-thallous chloride, and up to about 10 mCi of MDP. After a waiting time of up to about 2 hours, imaging is taken for a period of up to about 30 minutes, with an energy window of between 2 and 10 percent.

4. In-111-L-Cysteinamide, D-phenylalanyl-L-cysteinyl-L-phenylalanyl-D-tryptophyl-L-lysyl-L-threonyl-N-[2-hydroxy-1-(hydroxy-methyl) propyl]-, cyclic 7)-disulfide (In-111-octreotide) and Tc-99m-MDP may be administered in combination to optimally localize certain endocrine tumors. In-111-Octreotide is a tumor imaging agent for somastatin-receptor expressing tumors. Tc99m-MDP is a bone-imaging agent, which enables visualization of the skeleton to provide anatomical landmarks.

A patient is injected with up to about 4 mCi In-111-octreotide, and up to about 15 mCi of Tc-99m-MDP. Within 3 days of injection of In-111-octreotide, but not more than 2 hours after injection of Tc-99m-MDP, imaging is taken for a period of up to about 30 minutes, with an energy window of between 2 and 10 percent. Hence, for example, the two radiopharmaceuticals may be administered substantially simultaneously, and imaging taken within 2 hours of injection. Alternatively, In-111-octreotide may be injected first, and imaging taken within 3 days of this injection, with Tc-99m-MDP injected at a later time point, no more than 2 hours prior to imaging.

5. In-111-capromab pendetide and Tc-99m-labeled red blood cells (RBCs) may be administered for delineating vascular structures of the pelvis or abdomen, and enabling the clinician to distinguish the blood vessels from the lymph nodes by pathologic uptake of antibodies. In-111-capromab pendetide is a monoclonal anti-tumor antibody to prostate specific membrane antigen (PMSA).

A patient is injected with up to about 3 mCi In-111-capromab pendetide, and up to about 15 mCi of Tc-99m-RBCs. Within 3 days of injection of In-111-capromab pendetide, but not more than 2 hours after injection of Tc-99m-RBCs, imaging is taken for a period of up to about 30 minutes, with an energy window of between 2 and 10 percent.

6. Tc-99m-colloid and In-111-white blood cells (WBCs) may be administered in combination for the identification and localization of bone infection. A patient is injected with up to about 15 mCi Tc-99m-colloid, and up to about 3 mCi of In-111-WBCs. Within 3 days of injection of In-111-WBC, but not more than 2 hours after injection of Tc Tc-99m-colloid, imaging is taken for a period of up to about 30 minutes, with an energy window of between 2 and 10 percent.

7. Tl-201-thallous chloride (a tumor imaging agent) and Tc-99m-MDP (a bone scan agent) may be administered in combination to evaluate the invasion of bone or cartilage by head or neck cancer. A patient is injected with up to about 2 mCi thallium-201-thallous chloride, and up to about 15 mCi of MDP. After a waiting time of up to about 2 hours, imaging is taken for a period of up to about 30 minutes, with an energy window of between 2 and 10 percent.

Combinations for the Study of Multiple Pathologies:

8. Tl-201-thallous chloride, Te-99-m-sestamibi, and In-111-white blood cells may be administered in combination for the assessment of various pathological conditions, including cardiac conditions, tumors, and infection. A patient is injected with up to about up to about 1 mCi Tl-201-thallous chloride, tip to about 10 mCi of Te-99-m-sestamibi, and up to about 2 mCi In-111-WBCs. After a waiting time of up to about 24 hours, imaging is taken for a period of up to about 30 minutes, with an energy window of between 2 and 10 percent.

9. Tl-201-thallous chloride, Te-99-m-MDP, and In-111-white blood cells may be administered in combination for the assessment of various pathological conditions, including cardiac conditions, tumors, and infection. A patient is injected with up to about 1 mCi Tl-201-thallous chloride, up to about 10 mCi of Te-99-m-MDP, and up to about 2 mCi In-111-WBCs. After a waiting time of up to about 24 hours, imaging is taken for a period of up to about 30 minutes, with an energy window of between 2 and 10 percent.

Combinations for the Study of Different Pathological Processes of the Same Organ:

10. Tl-201-thallous chloride, Tc-99 in-teboroxime or Tc-99m-sestamibi, and I-123-beta-methyl-p-iodophenylpentadecanoic acid (BMIPP) may be administered in combination for the study of acute myocardial ischemia. A patient is injected with up to about 1 mCi Tl-201-thallous chloride, up to about 10 mCi Tc-99m-teboroxime or Tc-99m-sestamibi, and up to about 2 mCi I-123-beta-methyl-p-iodophenylpentadecanoic acid (BMIPP). After a waiting time of up to about 48 hours, imaging is taken for a period of up to about 30 minutes, with an energy window of between 2 and 10 percent.

11. Tc-99m-Fanoselomab and In-111-white blood cells may be administered in combination to study fever of unknown origin. A patient is injected with up to about 15 mCi 99m-Fanioselomab and up to about 2 mCi In-111-white blood cells. After a waiting time of up to about 24 hours, imaging is taken for a period of up to about 30 minutes, with an energy window of between 2 and 10 percent.

12. I-123-iodobenzamide (IBZM) and Tc-99m-Exametazine (HMPAO) may be administered in combination to study schizophrenia or Parkinson's disease. A patient is injected with up to 2 mCi I-123-iodobenzamide (IBZM) and up to about 15 mCi Tc-99m-Exametazine (HMPAO). After a waiting time of up to about 48 hours, imaging is taken for a period of up to about 30 minutes, with an energy window of between 2 and 10 percent.

13. In-111-labeled antibody, Tc-99m-sestamibi or Tc-99m-Arcitumomab and Tl-201-thallous chloride may be administered in combination for tumor identification and characterization by perfusion studies. A patient is injected with up to about 1 mCi I-111-labeled antibody, up to about 10 mCi Tc-99m-sestamibi or Tc-99m-Arcitumomab, and up to about 1 mCi Tl-201-thallous chloride. After a waiting time of up to about 24 hours, imaging is taken for a period of up to about 30 minutes, with an energy window of between 2 and 10 percent.

14. In-111-diethylene triamine pentaacetate (DTPA) and Tc-99m-mercaptoacetyltriglycine (MAG3) may be administered in combination for dynamic flow studies for the investigation of renal function. A patient is injected with up to about 2 mCi In-111-diethylene triamine pentaacetate (DTPA) and up to about 15 mCi Tc-99m-mercaptoacetyltriglycine (MAG3). After a waiting time of up to about 24 hours, imaging is taken for a period of up to about 30 minutes, with an energy window of between 2 and 10 percent.

15. Tl-201-thallous chloride and Tc-99m-teboroxime or Tc-99m-sestamibi may be administered in combination for the study of tumor perfusion and therapeutic response. A patient is injected with up to about 1 mCi Tl-201-thallous chloride and up to about 15 mCi Tc-99m-teboroxime or Tc-99m-sestamibi. After a waiting time of up to about 1 hour, imaging is taken for a period of up to about 30 minutes, with an energy window of between 2 and 10 percent.

16. Tc-99m-sulfur colloid and In-111-WBCs may be administered in combination to differentiate between infection and bone marrow activation. A patient is injected with up to about 15 mCi Tc-99m-sulfur colloid and up to about 2 mCi In-111-WBCs. After a waiting time of up to about 24 hours, imaging is taken for a period of up to about 30 minutes, with an energy window of between 2 and 10 percent.

17. Tc-99m-MDP and In-111-WBCs may be administered in combination to differentiate between acute and chronic acute osteomyelitis. A patient is injected with up to about 15 mCi Tc-99m-MDP and up to about 2 mCi In-111-WBCs. After a waiting time of up to about 24 hours, imaging is taken for a period of tip to about 30 minutes, with an energy window of between 2 and 10 percent.

18. Gallium-67 and In-111-WBCs may be administered in combination to differentiate between acute and chronic inflammation. A patient is injected with up to about 5 mCi gallium-67 and up to about 2 mCi In-111-WBCs. After a waiting time of up to about 72 hours, imaging is taken for a period of up to about 30 minutes, with an energy window of between 2 and 10 percent.

19. Tc-99m-teboroxime or Tl-201-thallous chloride and In-111-annexin may be administered in combination to study myocardial perfusion and apoptosis. A patient is injected with up to about 15 mCi Tc-99m-teboroxime or up to about 2 mCi Tl-201-thallous chloride and up to about 2 mCi In-111-annexin. After a waiting time of up to about 24 hours, imaging is taken for a period of up to about 30 minutes, with an energy window of between 2 and 10 percent.

20. Tl-201-thallous chloride and Tc-99m-pyrophosphate may be administered in combination to investigate myocardial perfusion and infarct. A patient is injected with up to about 2 mCi Tl-201-thallous chloride and tip to about 15 mCi Tc-99m-pyrophosphate. After a waiting time of up to about 1 hour, imaging is taken for a period of up to about 30 minutes, with an energy window of between 2 and 10 percent.

Protocols for Non-Coincidence Imaging Using Pet Radiopharmaceuticals

The following imaging protocols use non-coincidence imaging using PET radiopharmaceuticals, as is further described in the Tables shown in FIGS. 148 A-V:

1. Use of F-18-Fluorodeoxyglucose (FDG), as a substrate for hexokinase in glucose metabolism, for the study of glucose metabolism of cells including tumor, heart and brain cells.

2. Use of F-18-Fluoromisonidazole for imaging of hypoxia and oxidative metabolism, with the clinical application of radiotherapy treatment planning.

3. Use of F-18-3'-Fluoro-3'-deoxythymidine (FLT) for the study of DNA synthesis.

4. Use of F-18-Fluoromethyl choline (FCH) as a choline precursor for cell membrane synthesis, for the study of choline metabolism of tumors.

5. Use of F-18-4-Fluoro-m-tyrosine (FMT) as a precursor for dopamine synthesis and as a substrate for aromatic amino acid decarboxylase (AAAD), with the clinical application of imaging brain tumors.

6. Use of F-18-6-Fluoro-L-DOPA as a precursor for dopamine synthesis and as a precursor for AAAD, with the clinical applications of imaging and grading Parkinson's disease and imaging neuroendocrine tumors.

7. Use of F-18-FP-β-CIT for binding to the dopamine transporter in dopaminergic axons, with the clinical application of imaging and grading Parkinson's disease and imaging neuroendocrine tumors.

8. Use of F-18-Pencyclovir (FHBG) to target thymidine kinase, with the clinical application of imaging reporter gene expression.

9. Use of F-18-Fluoroestradiol (FES) to target estrogen receptors, with the clinical application of breast tumor imaging.

10. Use of C-11-Methionine to target amino acid synthesis, with the clinical application of imaging brain tumors.

11. Use of In-111-Pentetreotide (Octreoscan®) to target somatostatin receptors, with the clinical application of imaging neuroendocrine tumors.

12. Use of Tc-99m-P829, (Neotec®) to target somatostatin receptors, with the clinical application of imaging neuroendocrine tumors.

13. Use of Tc-99m-P280, Acutect® to target GP IIb/IIIa receptors on platelets, with the clinical applications of detection of thrombosis, such as deep vein thrombosis (DVT) and intratererial thrombosis in coronary and carotid arteries.

14. Use of I-123-vasoactive intestinal peptide (VIP) to target VIP receptors, with the clinical application of imaging gastrointestinal tumors.

15. Use of I-123-MIBG (meta-iodo benzyl guanidine) to target adrenergic tissue uptake and presynaptic adrenergic receptors, with the clinical application of tumor imaging (Pheochromocytoma) and myocardial failure imaging.

16. Use of I-123-NP-59 to target the low-density lipoprotein (LDL) receptor and cholesterol metabolism, with the clinical application of imaging of adrenal carcinoma, adenoma, and Cushing's syndrome.

17. Use of C-11-Raclopride to target dopamine D2 receptors, for brain imaging of dopamine D2 receptors in schizophrenia, and assessment of dose for neuroleptics.

18. Use of I-123-iodobenzamide (IBZM) to target dopamine D2 receptors, for brain imaging of dopamine D2 receptors in schizophrenia, and assessment of dose for neuroleptics.

19. C-11-carfentanil to target Mu opioid receptors in brain, with the clinical application of imaging drug addiction.

20. Use of C-11-α-methyl-L-tryptophan as a precursor for (X-methyl serotonin synthesis and as a substrate for AAAD enzyme, with the clinical application of imaging depression.

21. Use of C-115-Hydroxytryptophan as a precursor for serotonin synthesis with the clinical application of imaging neuroendocrine tumors.

22. Use of F-18-MPPF to bind to 5-HT1A (5-hydroxytryptamine-1A) serotonin receptors, with the clinical application of imaging depression and epilepsy.

23. Use of F-18-Altanserin to bind to 5-HT2A serotonin receptors with the clinical application of imaging depression and epilepsy.

24. Use of C-11-Acetate for the study of tricarboxylic acid cycle activity and oxidative metabolism with the clinical application of studying myocardial oxygen metabolism.

25. Use of C-11-Palmitate as a precursor for fatty acid metabolism with the clinical application of imaging myocardial metabolism.

26. F-18-Fluorodopamine to target presynaptic adrenergic receptors

Protocols for Beta Emitting Radiopharmaceuticals

The following beta emitting radionuclides may be used for diagnostic studies, using a dose of about 1 mCi, using the camera of the present invention: Sm-153 ($T_{1/2}$ 1.95 days), I-131 ($T_{1/2}$ 8.04 days), Cu-67 ($T_{1/2}$ 2.58 days), Lu-177 ($T_{1/2}$ 6.7 days), and Sn-117m ($T_{1/2}$ 13.6 days). These include both long-lived radiopharmaceuticals and radiopharmaceuticals with low abundance gamma.

Protocols for Long-Lived Radiopharmaceuticals

Long-lived radiopharmaceuticals suitable for use with the camera of the present invention include I-131 and Sn-117m.

Protocols for Radiopharmaceuticals with Low Abundance Gamma

Cu-67, Lu-177 and Sm-153

Section I: Technetium-Labeled Radiopharmaceuticals

Technetium exists only in the form of radioactive isotopes. Tc-99 has a half life of 21000 years. The widely used Tc-99m is an isomer of Tc-99, which decays to Tc-99, and has a half life of 6.02 hours, emitting a gamma ray of 141 KeV.

The short half-life makes storing impractical, even for a weekly supply. Therefore, a Tc-99m radionuclide generator is employed, on site, using the parent, Mo-99, which has a half-life of 67 hours. In the radionuclide generator, the parent is retained in such a way that the daughter can be easily separated for clinical use.

A decay curve of Mo-99 to Tc-99m and to Tc-99 is seen in FIG. 144, while a build-up and decay graph for both Tc-99m and Tc-99 is seen in FIG. 145. The buildup of Tc-99 occurs both by decay of the isomeric Tc-99m to Tc-99 and by the direct decay of Mo-99 to Tc-99, so the total Tc-99, from a chemical standpoint is the sum of Tc-99m and Tc-99, at any point in time.

In general, a Mo-99 to Tc-99m generator uses an alumina ($Al_2O_3$) column, such as $(NH_4)2\ ^{99}MoO_4$ (ammonium molybdate). The Mo-99 decays to Tc-99m and Tc-99, which exist in a $TcO_4^-$ form (pertechnetate), weakly bound to the alumina column.

Elution takes place by an isotonic saline, replacing the weakly bound $TcO4^-$ with $Cl^-$. The chemical form of Tc in the eluant is $NaTcO_4$, known as sodium pertechnetate, which includes both Tc-99m-sodium pertechnetate and Tc-99-sodium pertechnetate.

A normal elution cycle is 24 hours, as described in FIG. 145.

A recommended low-dose elution cycle will take place every 23 hours, then again an hour later, to provide low dose Tc-99m, as seen in FIG. 146.

A. Tc-99m-Teboroxime for Myocardial Perfusion Imaging, at Rest

Tc-99m-teboroxime is a natural boronic acid adduct of technetium dioxime complexes, which is highly lipophilic. Therefore it crosses cell membranes easily, with no involvement of active metabolic processes. Excretion is primarily enterohepatic, with peak hepatic uptake at about 6 minutes following injection.

In myocardial perfusion imaging protocols, separate rest and stress injections are given. Tc-99m-teboroxime has a high myocardial extraction fraction, of about 90%, and rapid myocardial washout, greater than about 70%. The myocardial biological half-life is between 10 and 11 minutes, and most of the administered Tc-99m-Teboroxime is undetectable after about 20 to 22 minutes.

Teboxime Labeling Kit and Technique:

U.S. Pat. No. 6,056,941, to Schramm, et al., issued on May 2, 2000, describes a tebroxime labeling kit, by Cardiotec®, Bracco Diagnostics. The kit is provided as a reaction vial, containing a sterile, nonpyrogenic, lyophilized formulation of:
- 2 mg cyclohexanedione dioxime
- 2 mg methyl boronic acid;
- 2 mg pentetic acid;
- 9 mg citric acid;
- 100 mg sodium chloride;
- 50 mg 2-hydroxypropyl gamma cyclodextrin; and
- 0.02-0.058 mg tin as stannous chloride $SnCl_2$.

For labeling, 1 ml sodium pertechnetate, containing Tc-99m, is added to the vial at a desired dose of between 10 and 100 mCi, in physiological saline, to provide Tc-99-teboroxime.

Standard-Dose Example:

For cardiac perfusion, a standard-dose of imaging at stress may be 30 mCi. For practical reasons, the injection solution is preferably between 1 ml and 3 ml. In other words, the solution should be prepared so as to avoid situations, where an injection of 0.1 ml or of 80 ml is required in order to meet the required dose, since this would be technically impractical.

Standard-Dose Preparation:

Assume the sodium pertechnetate, has been assayed and found to have a Tc-99m radioactivity of 90 mCi per ml.

Example 1 Standard-Dose Preparation Proceeds as Follows:

Combine:
1 ml of the sodium pertechnetate, having a total Tc-99m radioactivity of 90 mCi; and
the contents of a reaction vial, containing a sterile, nonpyrogenic, lyophilized formulation as described above,
to form:
about 1 ml injection solution, having the total Tc-99m radiation dose of 90 mCi,
dilute:
the injection solution by a ratio of 1:3 by addition of 2 ml saline solution to give a total volume of 3 ml; and
inject:
1 ml of the diluted solution, for a total Tc-99m radiation dose of 30 mCi.

Low-Dose Example:

For cardiac perfusion, a low dose of imaging at stress may be 3 mCi, about a tenth of the standard-dose. Again, for practical reasons, the injection solution is preferably between 1 ml and 3 ml.

Low-Dose Preparation, Example 1:

In this example, a low dose of 3 mCi, is achieved by a standard-and-low dose elution process, where elution takes place every 23 hours for the standard dose, and an hour later, for the low dose.

Assume the sodium pertechnetate from a low-dose elution, has been assayed and found to have a Tc-99m radioactivity of 10 mCi per ml. The solution may be diluted to provide an injection solution having a radioactivity dose of about 3 mCi per ml by dilution by a factor of about 1:3 using standard methods. 1 mCi diluted solution is added to the lyophilized formulation described above, and the full 0.1 ml injected to provide a total dose of about 3 mCi.

It will be appreciated that two generators, one for low dose and one for standard dose may be employed.

Low Dose Preparation, Example 2:

A low dose injection solution may be prepared by diluting a standard solution of Tc-99m-sodium pertechnetate by known methods.

Assume the sodium pertechnetate, has been assayed and found to have a Tc-99m radioactivity of 90 mCi per ml. This solution may be diluted by a factor of about 1:30, for example by withdrawing 1 ml of the standard solution and adding 29 ml saline solution to produce a diluted injection solution containing about 3 mCi per ml. 1 ml of the diluted injection solution is then withdrawn and added to the to the lyophilized formulation described above, and the full 1 ml injected to provide a total dose of about 3 mCi.

Low-Dose Preparation, Example 3:

A low dose injection may be prepared by withdrawing a volume providing the required dose of radioactivity from a standard preparation of Tc-99m-sodium pertechnetate, using specialized measuring instruments of high accuracy. Such instruments are known in the art, and may be used for measuring of a volume of up to 0.5 ml. The instruments are graduated at intervals of 0.05 ml, and are provided with a radiation shield.

Assume the sodium pertechnetate, has been assayed and found to have a Tc-99m radioactivity of 90 mCi per ml. A radiation dose of about 9 mCi will be provided by 0.1 ml. A volume of 0.1 ml is withdrawn, the solution is then diluted by addition of 0.2 ml saline solution to provide a solution having a total radiation dose of 3 mCi in 0.3 ml. This solution may then be brought to a final volume of at least 1 ml for injection.

B. Sestamibi for Breast Tumor Imaging

Sestamibi (methoxyisobutylisonitrile) is a lipophilic monovalent cation, which enters the cell via passive diffusion across plasma and mitochondrial membranes. Blood clearing occurs with a half life of 4.3 minutes at rest, and 1.6 minutes under exercise conditions. At 5 minutes post injection, about 8% of the injected dose remains in circulation. There is less than 1% Tc-99m-sestamibi protein binding in plasma. The myocardial biological half-life is approximately 6 hours after a rest or exercise injection. The major pathway for clearance of Tc-99m-sestamibi is the hepatobiliary system.

Sestamibi Labeling Kit and Technique:

A kit for the preparation of Tc-99m-sestamibi for is supplied by Bristol Myers Squibb, containing a sterile non-pyrogenic, lyophilized mixture of:
- 1 mg of 2-methoxy isobutyl isonitrile copper (I) tetrafluoroborate
- 2.6 mg of sodium citrate dihydrate
- 1 mg of L-cysteine hydrochloride monohydrate
- 20 mg mannitol
- 0.025-0.075 stannous chloride dihydrate
- up to 0.086 mg tin chloride Sodium pertechnetate, containing Tc-99m, at a dose of between 25-150 mCi, in physiological saline at a volume of 1-3 ml is added, to provide Tc-99-sestamibi.

Standard-Dose Example:

For breast tumor imaging, a standard dose used is 20-30 mC, in a volume of between 1 ml and 3 ml.

Standard-Dose Preparation

A standard dose may be prepared by addition of a standard preparation of Tc-99m-sodium pertechnetate to a vial containing the lyophilized formulation as described above, and diluted as necessary, by methods known in the art, as described above for Tc-99m-Teboroxime.

Low-Dose Example:

For breast tumor imaging, a low dose of imaging at stress may be 2-3 mCi, about a tenth of the standard-dose. Again, for practical reasons, the injection solution is preferably between 1 ml and 3 ml.

Low-Dose Preparation:

A low dose may be prepared as for any of the examples described above for Tc-99m-Teboroxime.

C. Tc-99m-Tetrofosmin for Myocardial Perfusion Imaging

Tetrofosmin is [6,9-bis(2-ethoxyethyl)-3,12-dioxa-6,9-diphosphatetradecane], which is labeled with Tc-99m to form a lipophilic, cationic complex, used for myocardial perfusion imaging. The heart uptake of Tc-99m-tetrofosmin is rapid and retention good, with approximately 1% of the injected dose remaining at 120 minutes post-injection. Clearance from lungs and liver is rapid, with activity practically undetectable within 4 or 8 hours, respectively, of injection. Blood and plasma clearance are also rapid, such that less than 5% of the injected dose remains in blood by 10 minutes post-injection, and less than 3.5% remain in plasma.

Tetrofosmin Labeling Kit and Technique:

A kit for the preparation of Te-99m-tetrofosmin for injection is produced by Amersham Health. The kit comprises a sterile, non-pyrogenic, lyophilized mixture of:

0.23 mg tetrofosmin;
0.03 mg stannous chloride dihydrate;
0.32 disodium sulphosalicyclate;
1 mg sodium D-gluconate; and
1.8 mg sodium hydrogen carbonate.

To this mixture is added 4-8 ml Tc-99m-sodium pertechnetate containing 30 mCi/ml in physiological saline, to provide Tc-99m-tetrofosmin of up to 240 mCi.

Standard-Dose Example:

For cardiac imaging, a standard dose used is 20-30 mC, in a volume of between 1 ml and 3 ml.

Standard-Dose Preparation Example:

A standard dose may be prepared by addition of a standard preparation of Tc-99m-sodium pertechnetate to a vial containing the lyophilized formulation as described above, and diluted as necessary, by methods known in the art, as described above for Tc-99m-Teboroxime.

Low-Dose Example:

For cardiac imaging, a low dose of imaging is 2-3 mCi, about a tenth of the standard-dose. Again, for practical reasons, the injection solution is preferably between 1 ml and 3 ml.

Low-Dose Preparation Example:

A low dose may be prepared as for any of the examples described above for Tc-99m-Teboroxime.

D. Tc-99m-medronate (MDP) for Bone Imaging

Tc-99 m-medronate (disodium dihydrogen methylenediphosphate) is used as a skeletal imaging agent to delineate areas of abnormal osteogenesis, such as those that occur with metastatic bone disease, Paget's disease, arthritic disease, osteomyelitis and fractures. It is generally accepted that technetium Tc-9m-medronate localizes on the surface of hydroxyapatite crystals by a process termed chemisorption, with blood flow and/or blood concentration being most important in the delivery of the agent to sites of uptake. Visualization of osseous lesions is possible since skeletal uptake of technetium Tc-99m-medronate is altered in areas of abnormal osteogenesis.

During the initial 24 hours following intravenous injection of Tc-99m-medroniate, about 50 percent of the dose is retained in the skeleton, and about 50% is excreted in the urine. Clearance of radioactivity from the blood is quite rapid, with about 10% of the injected dose remaining at 1 hour, and less than 5 and 2% at 2 and 4 hours, respectively.

Tc-99m-MDP Labeling Kit and Technique:

Kits for the preparation of Tc-99m-MDP are produced by Bracco Diagnostics; Draximage; Amersham Healthcare; and Mallicknrodt.

Standard-Dose Example:

For bone imaging, a standard dose of 20 mCi is used.

Standard-Dose Preparation:

The kit provided by Draximage comprises a vial containing a sterile, non-pyrogenic, non-radioactive lyophilized mixture of:

10 mg medronic acid;
0.8-1.21 mg stannous chloride dihydrate; and
2 mg p-aminobenzoic acid.

The pH is adjusted with sodium hydroxide or hydrochloric acid to 6.5-7.5 prior to lyophilization. The pH of the reconstituted product is 5.4 to 6.8.

For reconstitution, 2-10 ml of Tc-99m-sodium pertechnetate is added, providing up to 500 mCi.

A standard dose may be prepared by addition of a standard preparation of Tc-99m-sodium pertechnetate to a vial containing the lyophilized formulation as described above, and diluted as necessary, by methods known in the art, as described above for Tc-99m-Teboroxime.

Standard-Dose Preparation:

A standard dose may be prepared by addition of a standard preparation of Tc-99m-sodium pertechnetate to a vial containing the lyophilized formulation as described above, and diluted as necessary, by methods known in the art, as described above for Tc-99m-Teboroxime.

Low-Dose Example:

For bone imaging, a low dose may be 2 mCi, about a tenth of the standard-dose. Again, for practical reasons, the injection solution is preferably between 1 ml and 3 ml.

Low-Dose Preparation:

A low dose may be prepared as for any of the examples described above for Tc-99m-Teboroxime.

E. Tc-99m-Mertiatide (MAG3) for Renal Imaging

Technetium-99m-mertiatide ((N—[N—[N-(Mercaptoacetyl)glycyl]glycyl]-glycine benzoate) is indicated as a renal imaging agent to assess renal perfusion, size, position, configuration, function (including differential renal function), upper urinary tract obstruction, and active urinoma. The use of this agent for renal imaging is based on its clearance through the urinary tract predominantly via active tubular secretion (almost exclusively by the proximal renal tubules) and to a small extent by glomerular filtration. The rate of appearance and excretion and the concentration of technetium Tc 99m mertiatide in the kidney can be monitored to assess renal function.

Technetium-99m-mertiatide is rapidly distributed in and cleared from the plasma. Systemic protein binding is between 70-90%, but is reversible. The agent is rapidly excreted by the kidneys via active tubular secretion and glomerular filtration.

Tc-99m-Mertiatide Labeling Kit and Technique:

A kit for the preparation of Tc-99m-mertiatide is produced by Mallicknrodt. The kit comprises a vial containing a sterile, non-pyrogenic, lyophilized powder, comprising 1 mg betiatide (N—[N—[N—[(benxoylthio)acetyl]glycyl]glycyl]glycine)
0.2 mg stannous chloride dihydrate;
40 mg sodium tartrate dihydrate; and
20 mg lactose monohydrate.

For labeling, 4-10 ml of Tc-99m-sodium pertechnetate solution containing 20-100 mCi is added.

Standard-Dose Example:

For renal imaging, a standard dose of 10 mCi is used.

Standard-Dose Preparation:

A standard dose may be prepared by addition of a standard preparation of Tc-99m-sodium pertechnetate to a vial containing the lyophilized formulation as described above, and diluted as necessary, by methods known in the art, as described above for Tc-99m-Teboroxime.

Low-Dose Example:

For renal imaging, a low dose may be 1 mCi, about a tenth of the standard-dose. Again, for practical reasons, the injection solution is preferably between 1 ml and 3 ml.

Low-Dose Preparation:

A low dose may be prepared as for any of the examples described above for Tc-99m-Teboroxime.

F. Tc-99m-Exametazine (HMPAO) for Cerebral Imaging

Examatazine (hexamethylpropylene amine oxime, HMPAO) is [(R,R,S,S)-4,8-diaza-3,6,6,9-tetramethylundecamce-2,10-dione bisoxime]. Tc-99m-HMPAO is commonly used for detection of altered regional cerebral perfusion and for the radiolabeling of autologous leukocytes.

Tc-99m-HMPAO is rapidly cleared from the blood after intravenous injection. Uptake in the brain reaches a maximum of 3.5-7% of the injected dose within 1 minute of injection. Up to 15% of the activity is eliminated from the brain by 2 minutes post injection, after which little activity is lost for the following 24 hours, except by physical decay of Tc-99m. The activity not associated with the brain is widely distributed throughout the body. About 30% of the injected dose is found in the gastrointestinal tract immediately after injection, and about 50% of this is excreted through the intestinal tract over a 48 hour period. About 40% of the injected dose is excreted through the kidneys and urine within 48 hours post injection.

Tc-99m-HMPAO Labeling Kit and Technique:

A kit for the preparation of Tc-99m-HMPAO is produced by Nycomed Amersham. The kit comprises:

a vial containing a sterile, non-pyrogenic, lyophilized powder, comprising
  0.5 mg HMPAO;
  7.6 µg stannous chloride dihydrate; and
  4.5 mg sodium chloride;
a vial containing 10 mg methylene blue in water; and
a vial containing sodium phosphate solution, each ml comprising:
  0.276 mg monobasic sodium phosphate monohydrate;
  0.142 mg dibasic sodium phosphate anhydrous; and
  9 mg sodium chloride in water.

Standard-Dose Example:

For cerebral imaging, a standard dose of 20 mCi is used.

Standard-Dose Preparation:

For preparation of Tc-99m-HMPAO, 0.5 ml methylene blue is added to the vial containing monobasic sodium phosphate and dibasic sodium phosphate. 2 ml of this mixture is withdrawn. HMPAO is reconstituted with 5 ml Tc-99m to provide a dose of 10-54 mCi, and the 2 ml methylene blue/sodium phosphate mixture added.

The injection solution may be diluted as necessary, by methods known in the art, as described above for Tc-99m-Teboroxime.

Low-Dose Example:

For cardiac imaging, a low dose may be 2 mCi, about a tenth of the standard-dose. Again, for practical reasons, the injection solution is preferably between 1 ml and 3 ml.

Low-Dose Preparation:

A low dose may be prepared as for any of the examples described above for Tc-99m-Teboroxime.

G. Tc-99m-Mebrofenin for Hepatobiliary Imaging

Mebrofenin (2,2'-[[2-[(3-bromo-2,4,6-trimethylphenyl)-amino]-2-oxoethyl]imino]bisacetic acid) is an iminodiacetic acid derivative, which binds to plasma proteins (mainly albumin). In the liver, in the space of Disse, Tc-99m-mebrofenin dissociates from the proteins and enters the hepatocyte by a mechanism similar to that of serum bilirubin. Tc-99m-mebrofenin traverses through the hepatocyte unmetabolized and enters the bile canaliculi. Flow beyond the canaliculi is influenced to a large extent by the tone of the sphincter of Oddi and the patency of the bile ducts. Clear visualization of the gallbladder and intestines, usually within 15 to 30 minutes of administration, demonstrates hepatobiliary tract patency.

Tc-99m-HMPAO Labeling Kit and Technique:

A kit for the preparation of Tc-99m-Mebrofenin is manufactured by Bracco Diagnostics (Choletec™). The kit comprises a sterile, non-pyrogenic mixture comprising:
  45 mg mebrofenin;
  0.54-1.03 mg stannous fluoride dihydrate;
  up to 5.2 mg methyl-paraben; and
  0.58 propylparaben.

Standard Dose Example

For hepatobiliary imaging, a standard dose of 10 mCi is used.

Low-Dose Example:

For cardiac imaging, a low dose may be 1 mCi, about a tenth of the standard-dose. Again, for practical reasons, the injection solution is preferably between 1 ml and 3 ml.

H. Tc-99m-Fanoselomab for Infectious Imaging

Fanoselomab is a monoclonal antibody for imaging of infection. Fanoselomab is directed against the carbohydrate moiety 3-fucosyl-N-acetyllactoseamine that defines the cluster of differentiation 15 (CD15) antigen. Tc-99m-fanoselomab radiolabels human white blood cells and myeloid precursors. The CD15 antigen is expressed on the surface of polymorphonuclear neutrophils, eosinophils and monocytes.

Tc-99m-fanoselomab is indicated for imaging of patients with equivocal signs and symptoms of appendicitis.

Tc-99m-Fanoselomab Labeling Kit and Technique:

A kit for the preparation of Tc-99m-Fanoselomab is manufactured by Mallingkrodt (NeutroSpecr™). The kit comprises a sterile, non-pyrogenic mixture comprising:
  0.25 mg lanolesomab;
  12.5 mg maltose monohydrate;
  0.522 mg sodium potassium tartrate tetrahydrate;
  0.221 mg succinic acid;
  54 µg stannous tartrate;
  28 µg glycine; and
  9.3 µg disodium edetate dihydrate.

0.2-0.35 ml Tc-99m-sodium pertechnetate is added to the lyophilized mixture, and ascorbic acid (500 mg/ml) added to make the final preparation volume up to 1 ml.

Standard Dose Example

For imaging of infection, a standard dose of 10-20 mCi is used.

Low-Dose Example:

For imaging of infection, a low dose may be 1-2 mCi, about a tenth of the standard-dose. Again, for practical reasons, the injection solution is preferably between 1 ml and 3 ml.

Section II:

I. Thallium-201 for Tumor Imaging

Thallium is a metal in group IIIA of the periodic table, with biological properties similar to those of potassium. The distribution of the thallous ion following intravenous administration is primarily intracellular. Transport of thallium across the cell membrane has been reported to occur partly via an ouabain inhibitable mechanism, presumed to be the sodium-potassium ATPase pump.

Thallium-201, administered in the form of thallous chloride, is used for myocardial perfusion imaging and for parathyroid and tumor imaging. The normal net myocardial clearance half-life of Tl-201 after intravenous injection is approximately 4 hours when the patient is injected during exercise, and longer when the patient is injected at submaximal exercise heart rate or at rest.

Thallium-201 has a half-life of 73 hours, and emits gamma-4 rays of 135 KeV; gamma-6 rays of 167 KeV and mercury x-rays of 68-80 KeV.

Thallium Labeling Kit and Technique:

Thallium 201 is supplied by Amersham Healthcare, in an isotonic solution as a sterile, non-pyrogenic diagnostic radiopharmaceutical for intravenous administration, comprising 1 mCi per ml, made isotonic with 9 mg sodium chloride and preserved with 0.9% (v/v) benzyl alcohol. The pH is adjusted to between 4.5 and 7.0 with hydrochloric acid and/or sodium hydroxide. Thallium Tl 201 is cyclotron produced.

Standard-Dose Example:

For tumor imaging, a standard dose of up to 3 mCi is used.

Standard-Dose Preparation:

3 ml of the injection solution are injected.

Low-Dose Example:

For tumor imaging, a low dose of 0.3 mCi, about a tenth of the standard-dose may be used. Again, for practical reasons, the injection solution is preferably between 1 ml and 3 ml.

Low-Dose Preparation:

A low dose may be prepared as for any of the examples described above for Tc-99m-Teboroxime.

Section III: Indium In-111-Labeled Radiopharmaceuticals

Indium In-111 has a physical half-life of about 6.2 hours (2.8 days), emitting gamma-2 rays with an energy of 171.3 KeV and gamma-3 rays with an energy of 245.4 KeV.

J: Octreotride for Neuroendocrine Tumor Imaging

Octreotide is the acetate salt of a cyclic octapeptide. It is a long-acting octapeptide with pharmacologic properties mimicking those of the natural hormone somatostatin. Octreotide is known chemically as L-Cysteinamide, D-phenylalanyl-L-cysteinyl-L-phenylalanyl-D-tryptophyl-L-lysyl-L-threonyl-N-[2-hydroxy-1-(hydroxy-methyl) propyl]-, cyclic 7)-disulfide; (2 [R—(R,R)].

In-111-Octreotide Labeling Kit and Technique

A kit for the preparation of In-111-Octreotide is produced by Mallinckrodt (OcteoScan™). The kit comprises a lyophilized mixture of:

10 µg octreotide;
2 mg gentisic acid (2,5-dihydroxybenzoic acid);
4.9 mg trisodium citrate, anhydrous;
0.37 mg citric acid, anhydrous; and
10 mg inositol.

Standard-Dose Example:

For neuroendocrine tumor imaging a standard dose of 6 mCi is used.

Low-Dose Example:

For neuroendocrine tumor imaging, a low dose of 0.6 mCi, about a tenth of the standard-dose may be used.

K: Indium-111-capromab pendetide

Indium-111-capromab pendetide is used for diagnosis of prostatic carcinoma and intra-pelvic metastases.

Capromab is a murine monoclonal antibody of the immunoglobulin subclass IgG-1-K, which localizes or binds specifically to a prostate-specific membrane glycoprotein (PSMA) that is only expressed by prostatic epithelial cells (benign and malignant). The monoclonal antibody is site-specifically labeled with indium In-111-chloride using the linker-chelator, glycyl-tyrosyl-(N,epsilon-diethylenetriaminepentaacetic acid)-lysine hydrochloride or GYK-DTPA-HCl. The resultant radiolabeled monoclonal antibody conjugate, In111-capromab pendetide (CYT-356), retains the immunoreactivity of the unconjugated monoclonal antibody.

Following intravenous administration, In-111-capromab pendetide localizes to the prostate and some primary and metastatic tumor sites. Some non-antigen-dependent localization occurs, probably secondary to catabolism, in normal liver, spleen, and bone marrow. In some individuals, some radioactivity may localize in the bowel, blood pool, kidneys, urinary bladder, and genitalia Indium-111-Capromab Pendetide Labeling Kit and Technique A kit for the preparation of In-111-capromab-pendetide is produced by Cytogen (ProstaScint™). The kit contains a vial of 0.5 mg of capromab pendetide in 1 ml of sodium phosphate buffered saline solution adjusted to pH 6, and a vial of sodium acetate buffer containing 82 mg of sodium acetate in 2 ml of water for injection adjusted to pH 5-7 with glacial acetic acid. The sodium acetate solution must be added to the In-111-chloride solution to buffer it prior to radiolabeling.

Standard-Dose Example:

For prostate metastasis imaging a standard dose of 5 mCi is used.

Low-Dose Example:

For prostate metastasis imaging, a low dose of 0.5 mCi, about a tenth of the standard-dose may be used.

M: Indium-111-Labeled White Blood Cells (WBCs)

WBC scanning is a diagnostic technique that utilises the natural migratory behaviour of WBCs to provide an image of their localisation. By identifying the sites of infection and inflammation to which WBCs naturally migrate, the presence and extent of active disease is revealed. The patient's own WBCs (mixed leucocytes—granulocytes, lymphocytes and monocytes) are isolated from a sample of whole blood and are then radiolabelled with In-111. The radiolabelled WBCs are then reinjected into the patient.

Section IV: Iodine-123-Labeled Radiopharmaceuticals

M. I-123-mIBG

I-123-meta-iodobenzylguanidine (MIBG) is used for diagnostic imaging of the adrenal medulla, for the evaluation and localization of intra- and extra-adrenal pheochromocytomas, paragangliomas, and neuroblastomas, as well as for localization of metastatic lesions from these tumors.

In adrenergic nerves, guanidines are believed to share the same transport pathway as norepinephrine and to accumulate in, and displace norepinephrine from, intraneuronal storage granules. The retention of 123 I- and 131-I-mIBG in the adrenal medulla may be a result of their uptake in adrenergic neurons and subsequent sequestration into chromaffin storage granules. Due to their selective uptake mechanism, 123 I- and 131-I-mIBG allow specific detection and localization of neuroendocrine tumors and adrenal medullary hyperplasia.

After intravenous administration, there is rapid uptake of mIBG mainly in the liver, and in lesser amounts in the lungs, heart, spleen, and salivary glands. Although the uptake in normal adrenal glands is very low, hyperplastic adrenals and tumors such as pheochromocytoma, neuroblastoma, and other tumors with neurosecretory granules have a relatively higher uptake.

Automatic Transfer of Information

Different devices associated with producing, shipping, preparing, administering, identifying radiopharmaceuticals and imaging, analyzing and diagnosing patients administered with radiopharmaceuticals, including, but not limited to, the various devices described herein, such as syringe, pump, IV line, mixer, camera, patient tag, ERP, dispensers, vials and/or pharmaceutical label may include a transceiver or other mechanisms for automatic reception/delivery of data and for storing, analyzing and/or processing, e.g., comparing, data associated with a given radiopharmaceutical, procedure, protocol, producer, patient ID, prescription, source, planned protocol, actual protocol and the like.

Hence, the present invention relates also to a method of automatic communication of data related to a radiopharmaceutical or a patient administered therewith among devices used therewith.

CONCLUDING REMARKS

The present invention embodies many aspects and embodiments, each having many sub embodiments and alternatives, the aspects and embodiments include, but not limited to, radioimaging cameras with unprecedented high resolution, algorithms operable in conjunction with the cameras, low dose radiopharmaceuticals, combinations of radiopharmaceuticals either as compositions and/or kits, administering devices which may include syringes, pumps and IV lines, mixers for mixing different radiopharmaceuticals, an ERP system for controlling and monitoring each one or more of these aspects and embodiments and their sub embodiments and alternatives and diagnostic methods in which one or more of the above aspects and embodiments and/or their sub embodiments and alternatives are used. Each of the aspects and embodiments of the present invention and/or each of their sub embodiments and alternatives may be practiced in itself or in combination with other aspects and embodiments of the present invention and/or each of their sub embodiments and alternatives. Hence, the present invention encompasses as novel and inventive concepts all combinations and sub combinations of each of these embodiments and aspects of the invention as well as combinations and sub combinations of each of the sub embodiments and alternatives of any of these embodiments and aspects of the invention and this application should be read as if each such combination and/or sub combination of each of the embodiments and aspects of the invention and/or their sub embodiments and alternatives is described in particular.

Thus, it is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

As used herein the terms "about" and "substantially" refer to ±20%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

It is expected that during the life of this patent many relevant radioactive-emission-camera systems, cameras and methods will be developed and the scope of these terms is intended to include all such new technologies a priori.

What is claimed is:

1. A method of functional imaging, comprising:
   (a) administering a radiopharmaceutical selected from the group consisting of Tc-99m-sestamibi, Tc 99m Tetrofosmin and Tl-201-thallous chloride to a patient;
   (b) imaging said patient using one or both of a low dose protocol in which dosage of said radiopharmaceutical is lower by at least a factor of 3 from standard dosage of said radiopharmaceutical set forth in Table 5A and a fast protocol in which substantial acquisition time is shorter than 10 minutes,
   wherein imaging is performed with a radiation camera comprising at least one collimator defining an angle from which the radiation camera detects radiation events and wherein the camera is configured to detect at least one out of 1500 photons emitted from the isotope in an imaged area.

2. A method according to claim 1, wherein said imaging comprises dynamic imaging of an organ of the patient.

3. A method according to claim 1, wherein said imaging comprises simultaneous imaging of at least one additional radiopharmaceutical in the patient.

4. A method according to claim 1, wherein said imaging is of a 3D distribution of the radiopharmaceutical.

5. A method according to claim 1 wherein said providing comprises providing at a dose equivalent of 2.5 mrem or less per kg body weight.

6. A method according to claim 1, wherein said administered dosage is at most 10 mCi of Tc-99m.

7. A method according to claim 1, wherein said administered dosage is at most 1 mCi of Tl-201.

8. A method according to claim 1, wherein acquisition time is five minutes or less.

9. A method according to claim 1, wherein said dosage used is 1/10 or less of said standard dosage.

10. A method according to claim 1, wherein said dosage used is 1/5 or less of said standard dosage.

11. A method according to claim 1, wherein imaging comprises imaging said patient using a low dose protocol in which dosage is lower by at least a factor of 3 from standard dosage set forth in Table 5.

12. A method according to claim 11, wherein said isotope labeled radiopharmaceutical comprises Technetium Tc 99m Sestamibi and wherein standard dosage is 30 mCi for stress imaging.

13. A method according to claim 11, wherein said isotope labeled radiopharmaceutical comprises Technetium Tc 99m Sestamibi and wherein standard dosage is 10 mCi for rest imaging.

14. A method according to claim 11, wherein said isotope labeled radiopharmaceutical comprises Tl-201 and wherein administered dosage is no more than 1 mCi.

15. A method according to claim 1, wherein imaging comprises imaging said patient using a fast protocol in which substantial acquisition time is shorter than 10 minutes.

16. A method according to claim 15, wherein imaging comprises imaging said patient using a fast protocol in which substantial acquisition time is shorter than 6 minutes.

17. A method according to claim 15, wherein imaging comprises imaging said patient using a fast protocol in which substantial acquisition time is shorter than 5 minutes.

18. A method according to claim 15, wherein imaging comprises imaging said patient using a fast protocol in which substantial acquisition time is shorter than 4 minutes.

19. A method according to claim 15, wherein imaging comprises imaging said patient using a fast protocol in which substantial acquisition time is shorter than 2 minutes.

20. A method according to claim 15, wherein imaging comprises imaging said patient using a fast protocol in which substantial acquisition time is shorter than 1 minute.

21. A method according to claim 1, wherein said imaging comprises cardiac imaging.

22. A method of imaging, comprising:
   (a) providing an isotope labeled radiopharmaceutical at a dosage in a body of a patient;

(b) receiving radiation generated by said radiopharmaceutical from said body using a radiation camera; and
(c) reconstructing a 3D distribution of said radiopharmaceutical from said received radiation,
wherein the dosage is less than ⅓ of a standard dose set forth in Table 5A, and
wherein the radiation camera comprises at least one collimator defining an angle from which the radiation camera detects radiation events and wherein the camera is configured to detect at least one out of 1500 photons emitted from the isotope in an imaged area.

23. A method according to claim 22, wherein said administering comprises providing a molecule labeled with a positron-emitting nuclide in a body; and wherein imaging comprises receiving radiation from said body using a non-coincident radiation camera; and
reconstructing a 3D distribution of said isotope from said received radiation.

24. A method according to claim 1, wherein said isotope is selected from the group consisting of F-18, C-11, N-13, O-15, Rb-82, Cu-62, and Ga-68.

25. A method according to claim 24, wherein F-18-Fluorodeoxyglucose (FDG) is used as a substrate for hexokinase in glucose metabolism, for the study of glucose metabolism of cells including one or more of tumor, heart and brain cells.

26. A method according to claim 24, wherein F-18-Fluorodeoxyglucose (FDG) is used for imaging of one or both of hypoxia and oxidative metabolism for radiotherapy treatment planning.

27. A method according to claim 26, wherein C-11-Methionine is used to target amino acid synthesis, for imaging brain tumors.

28. A method according to claim 22, wherein said imaging, comprises:
receiving radiation generated by said isotope from said body using a non-coincident radiation camera;
reconstructing a distribution of said isotope from said received radiation; and
investigating the biology of at least one molecular event in a living cell in vivo using said image.

29. A method according to claim 28, wherein said reconstructing comprises reconstructing an image from an isotope concentration of less than 1E-10 Moles in 1 gr of tissue and using said image for a medical procedure.

30. A method according to claim 28, wherein investigating comprises determining a level of one or more of gene expression, mRNA expression and protein expression.

31. A method of imaging according to claim 22, wherein said isotope is a beta emitting isotope; and wherein said receiving comprises receiving radiation generated by said beta emissions from said body using a non-coincident radiation camera.

32. A method according to claim 31, wherein said isotope is selected from a group consisting of Sm-153, I-131, Cu-67, Lu-177, and Sn-117m.

33. A method according to claim 22, wherein the dosage is less than 1/10 of a standard dose set forth in Table 5.

34. A method according to claim 22, wherein the receiving comprises receiving for acquiring data of at least the same quality and type as a standard protocol for the standard dose.

35. A method of imaging according to claim 22, wherein providing an isotope comprises providing an isotope with a gamma decay scheme of low abundance in a body; and wherein receiving comprises receiving radiation generated by said isotope from said body using a non-coincident radiation camera.

36. A method according to claim 35, wherein said abundance is about or less than about 10%.

37. A method according to claim 35, wherein said isotopes are selected from a group consisting of Cu-67, Lu-177 and Sm-153.

38. A method of imaging according to claim 22, wherein providing comprises providing an isotope with a long half-life of greater than 8 days in a body; and wherein receiving comprises receiving radiation generated by said isotope from said body using a non-coincident radiation camera.

39. A method according to claim 38, wherein said isotope is selected from a group consisting of I-131 and Sn-117m.

40. A method of imaging according to claim 22, wherein said camera comprising two or more detecting modules, wherein the position of at least two of said detecting modules can be adjusted relative to each other; and
wherein the method further comprises:
(d) identifying a body contour adjacent to a target area of interest;
(e) adjusting the position of said at least two detecting modules, thereby conforming said camera to said contour, to be within 5 centimeters of said body.

41. A method according to claim 40, comprising selecting at least one view according to which the camera is adjusted.

42. A method according to claim 40, wherein said camera includes an actuator for movement thereof.

43. A method according to claim 40, wherein said camera includes an actuator for said conforming.

44. A method according to claim 40, wherein said camera includes a plurality of detectors that are moved relative to each other for said regulating.

45. A method according to claim 22, wherein imaging comprises acquiring an image and using said image for identifying a cancerous growth.

46. A method according to claim 22, wherein imaging comprises acquiring an image suitable for identifying weakened, diseased or ischemic tissue.

47. A method according to claim 22, wherein said standard dosage is 20 mCi for breast imaging.

48. A method according to claim 22, wherein said standard dosage is 20 mCi for cardiac stress imaging.

49. A method according to claim 22, wherein said standard dosage is 20 mCi for bone imaging.

50. A method according to claim 22, wherein said standard dosage is 10 mCi for renal imaging, hepatobiliary imaging or infection imaging.

51. A method according to claim 22, wherein said standard dosage is 20 mCi for cerebral imaging.

52. A method according to claim 22, wherein said standard dosage is 3 mCi for tumor imaging.

53. A method according to claim 22, wherein said standard dosage is 6 mCi for neuroendocrine tumor imaging.

54. A method according to claim 22, wherein said standard dosage is 5 mCi for prostate metastasis imaging.

55. A method according to claim 22 wherein said providing comprises providing at a dose equivalent of 2.5 mrem or less per kg body weight and wherein said imaging is non-coincidence imaging.

56. A method according to claim 22, wherein said standard dosage is 20 mCi of Tc-99m for cardiac stress imaging.

57. A method according to claim 22, wherein said administered dosage is less than 10 mCi.

58. A method according to claim 22, wherein substantial acquisition time is five minutes or less.

59. A method according to claim 22, wherein said administered dosage is no more than 10 mCi for a Tc-99m radiopharmaceutical and wherein said imaging is performed using a non-coincident camera.

60. A method according to claim 22, wherein said administered dosage is no more than 5 mCi for a Tc-99m radiopharmaceutical and wherein said imaging is performed using a non-coincident camera.

61. A method according to claim 22, wherein said administered dosage is no more than 1 mCi for a Tl-201 radiopharmaceutical and wherein said imaging is performed using a non-coincident camera.

62. A method according to claim 22, wherein said administered dosage is no more than 2 mCi for a In-111 radiopharmaceutical and wherein said imaging is performed using a non-coincident camera.

63. A method according to claim 22, wherein said administered dosage is no more than 5 mCi for a I-123 radiopharmaceutical and wherein said imaging is performed using a non-coincident camera.

64. A method according to claim 22, wherein said administered dosage is no more than 5 mCi for a G-67 radiopharmaceutical and wherein said imaging is performed using a non-coincident camera.

65. A method according to claim 22, wherein said isotope labeled radiopharmaceutical comprises Technetium Tc 99m Sestamibi and wherein said standard dosage is 30 mCi for stress imaging.

66. A method according to claim 22, wherein said isotope labeled radiopharmaceutical comprises Technetium Tc 99m Sestamibi and wherein said standard dosage is 10 mCi for rest imaging.

* * * * *